(12) United States Patent
Taylor

(10) Patent No.: US 10,667,991 B2
(45) Date of Patent: Jun. 2, 2020

(54) FACE SOAKING DEVICE

(71) Applicant: John Richard Taylor, Arp, TX (US)

(72) Inventor: John Richard Taylor, Arp, TX (US)

( * ) Notice: Subject to any disclaimer, the term of this patent is extended or adjusted under 35 U.S.C. 154(b) by 1075 days.

(21) Appl. No.: 14/964,552

(22) Filed: Dec. 9, 2015

(65) Prior Publication Data

US 2016/0175550 A1 Jun. 23, 2016

Related U.S. Application Data

(63) Continuation-in-part of application No. 14/877,856, filed on Oct. 7, 2015, and a continuation-in-part of
(Continued)

(51) Int. Cl.
*A61H 35/00* (2006.01)
*A61N 5/06* (2006.01)
(Continued)

(52) U.S. Cl.
CPC ........... *A61H 35/008* (2013.01); *A61H 33/02* (2013.01); *A61M 35/30* (2019.05); *A61N 5/0616* (2013.01);
(Continued)

(58) Field of Classification Search
CPC ................ A61H 9/0021; A61H 9/0042; A61H 33/0087; A61H 33/02–028; A61H 33/12;
(Continued)

(56) References Cited

U.S. PATENT DOCUMENTS

| 1,446,841 A | 2/1923 | Dietsche |
| 2,194,804 A * | 3/1940 | Mayhew ................ A45D 19/10 4/519 |

(Continued)

FOREIGN PATENT DOCUMENTS

| EP | 0930033 A1 | 7/1999 |
| EP | 2868218 A1 | 6/2015 |

(Continued)

OTHER PUBLICATIONS be26-minimal-circle-blur-art-illusion, posted at androidpapers.co, online URL:http://androidpapers.co/be26-minimal-circle-blur-art-illustration/ (Year: 2019).
(Continued)

*Primary Examiner* — Valerie L Woodward
(74) *Attorney, Agent, or Firm* — Eric Kelly

(57) ABSTRACT

In some embodiments, a face soaking device may have a vessel, a vessel neck gasket, and a breathing apparatus. The vessel may be configured to hold a liquid to submerge a face of a user or a portion thereof. The vessel neck gasket may be (removably) joined to the vessel. The vessel neck gasket may be configured to comfortably accommodate a front portion of the user's neck. The breathing apparatus may be in removable contact with: the vessel, with a head rest subassembly, and/or with the user. The breathing apparatus may be configured to permit the user to breathe while the user's face may be submerged within the liquid. When the vessel may be filled with the liquid to at least a sufficient level, the user may soak the face or the portion thereof, such that the skin being soaked receives a benefit.

28 Claims, 198 Drawing Sheets

Related U.S. Application Data application No. PCT/US2015/054576, filed on Oct. 7, 2015.

(60) Provisional application No. 62/208,325, filed on Aug. 21, 2015, provisional application No. 62/173,204, filed on Jun. 9, 2015, provisional application No. 62/137,799, filed on Mar. 24, 2015, provisional application No. 62/176,754, filed on Feb. 26, 2015, provisional application No. 62/114,962, filed on Feb. 11, 2015, provisional application No. 62/106,138, filed on Jan. 21, 2015, provisional application No. 62/094,036, filed on Dec. 18, 2014.

(51) Int. Cl.
    *A61M 35/00*     (2006.01)
    *A61H 33/02*     (2006.01)

(52) U.S. Cl.
    CPC .  *A61M 2202/02* (2013.01); *A61M 2210/0606* (2013.01); *A61N 2005/0643* (2013.01); *A61N 2005/0652* (2013.01)

(58) Field of Classification Search
    CPC .. A61H 33/6005; A61H 35/008; A61H 35/02; A61H 35/04; A45D 19/06–12; A61F 7/0053; A61F 2007/0002; A61F 2007/0003; A47K 1/04; A47K 1/05; A47K 1/06; A47K 3/001; A47K 3/022; A61M 2210/0606; A61N 5/0616
    See application file for complete search history.

(56) References Cited

U.S. PATENT DOCUMENTS

| | | | |
|---|---|---|---|
| 2,475,259 A | 4/1945 | Singleton | |
| 3,465,370 A | 9/1969 | Chernick | |
| 3,733,620 A | 5/1973 | Glintz | |
| 4,004,302 A * | 1/1977 | Hori | A61H 33/02 261/124 |
| D249,278 S | 9/1978 | Milligan | |
| 4,152,792 A | 5/1979 | Glintz | |
| 4,281,423 A | 8/1981 | Fukunaga | |
| 4,546,504 A * | 10/1985 | Vars | A45D 19/10 4/515 |
| 4,561,979 A | 12/1985 | Harms | |
| 4,649,580 A * | 3/1987 | Bastien | A45D 19/06 4/519 |
| 4,864,667 A | 9/1989 | Adams | |
| 5,245,713 A | 9/1993 | Tickle | |
| 5,328,031 A | 7/1994 | Hendriks | |
| 5,381,562 A * | 1/1995 | Holloway | A45D 19/06 4/516 |
| D396,982 S | 8/1998 | Harris | |
| D398,075 S | 9/1998 | Book | |
| 6,328,031 B1 | 12/2001 | Tischer | |
| 6,405,389 B1 | 6/2002 | Harty | |
| D461,278 S | 8/2002 | Takechi | |
| 6,558,344 B2 | 5/2003 | McKinnon | |
| 6,609,257 B1 | 8/2003 | O'Geary | |
| D483,493 S | 12/2003 | Lie | |
| D491,670 S | 6/2004 | Leung | |
| D495,059 S | 8/2004 | Lie | |
| D500,893 S | 1/2005 | Chang | |
| D522,174 S | 5/2006 | Jackel-Marken | |
| D551,513 S | 9/2007 | Fiorella | |
| D566,246 S | 4/2008 | Cunningham | |
| D573,260 S | 7/2008 | Dunshee | |
| 7,448,093 B1 | 11/2008 | Ruck | |
| D583,958 S | 12/2008 | Usui | |
| 7,641,835 B2 | 1/2010 | Ramsey | |
| D621,927 S | 8/2010 | Dominguez | |
| 7,785,303 B2 | 8/2010 | Tapadiya | |
| D632,798 S | 2/2011 | Tran | |
| 7,931,157 B1 | 4/2011 | Palumbo | |
| D638,170 S | 5/2011 | Chen | |
| D672,086 S | 12/2012 | Tai | |
| 8,375,478 B2 | 2/2013 | Luo | |
| D692,149 S | 10/2013 | Uematsu | |
| D707,997 S | 7/2014 | English | |
| D712,558 S | 9/2014 | Ledbetter | |
| D715,002 S | 10/2014 | Chang | |
| D716,958 S | 11/2014 | Thomas | |
| D736,939 S | 8/2015 | McKay | |
| D736,940 S | 8/2015 | McKay | |
| D757,280 S | 5/2016 | Ogaki | |
| D757,282 S | 5/2016 | Loyd | |
| D767,154 S | 9/2016 | Bromilow | |
| 9,669,519 B2 | 6/2017 | Wunderlich | |
| D809,804 S | 2/2018 | Tai | |
| D831,838 S | 10/2018 | Koifman | |
| D837,542 S | 1/2019 | Nicoll | |
| 2002/0146955 A1 | 10/2002 | Levine | |
| 2004/0025243 A1 * | 2/2004 | Chien | A61H 33/12 4/525 |
| 2004/0225265 A1 | 11/2004 | Tapadiya | |
| 2005/0015873 A1 * | 1/2005 | Hansen | A45D 19/10 4/519 |
| 2008/0234610 A1 * | 9/2008 | Summers | A61H 9/0021 601/46 |
| 2009/0193577 A1 * | 8/2009 | Eiteneer | A61H 35/008 4/650 |
| 2010/0006467 A1 | 1/2010 | Joseph | |
| 2010/0324635 A1 * | 12/2010 | Kreck | A61F 7/12 607/105 |
| 2011/0225726 A1 | 9/2011 | Dominguez | |
| 2012/0222210 A1 | 9/2012 | Wiggins | |
| 2012/0227177 A1 * | 9/2012 | Kiser | A45D 19/10 4/519 |
| 2013/0053737 A1 | 2/2013 | Scerbo | |
| 2014/0073996 A1 * | 3/2014 | Jaguan | A61N 5/0618 601/15 |
| 2015/0305573 A1 | 10/2015 | Stafford | |
| 2015/0328393 A1 | 11/2015 | Stephens | |

FOREIGN PATENT DOCUMENTS

| | | |
|---|---|---|
| FR | 2637180 A1 | 6/1990 |
| JP | 558358 S | 4/1981 |
| JP | 658358 S | 4/1981 |
| JP | 1367329 | 8/2009 |
| JP | 1367331 | 8/2009 |
| WO | 2009094601 A2 | 7/2009 |

OTHER PUBLICATIONS

CNBTR 5PCS 88mm Universal HCS Flat Semicicle Saw Blades Black, posted at aliexpress.com, online, URL:https://www.aliexpress.com/item/CNBTR-5PCS-88mm-Universal-HCS-Flat-Semicircle-Saw-Blades-Black/32777274663.html (Years: 2019).

Find the area of shaded region in Fig. 1248, where arc(APD, AQB, BRC, and CSD) are semicircles, posted Feb. 8, 2018, posted at sarthaks.com, online, URL:https://www.sarthaks.com/32495/tind-the-area-of-the-shaded-region-in-fig-12-48-where-arc-apd-brc-and-csd-are-semicircles (Year: 2018).

* cited by examiner

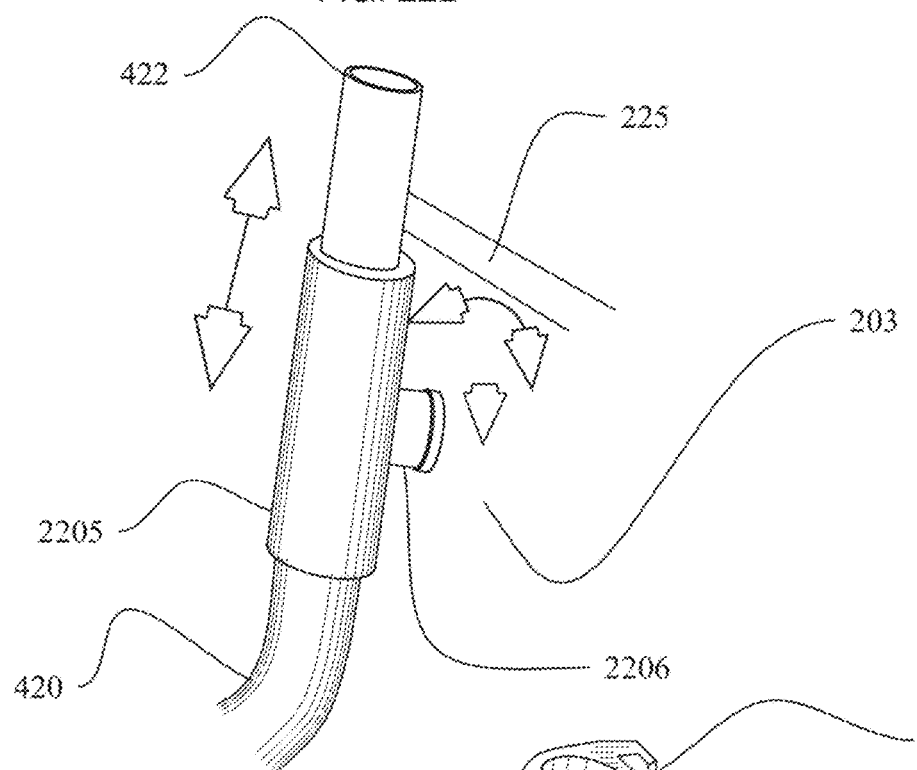
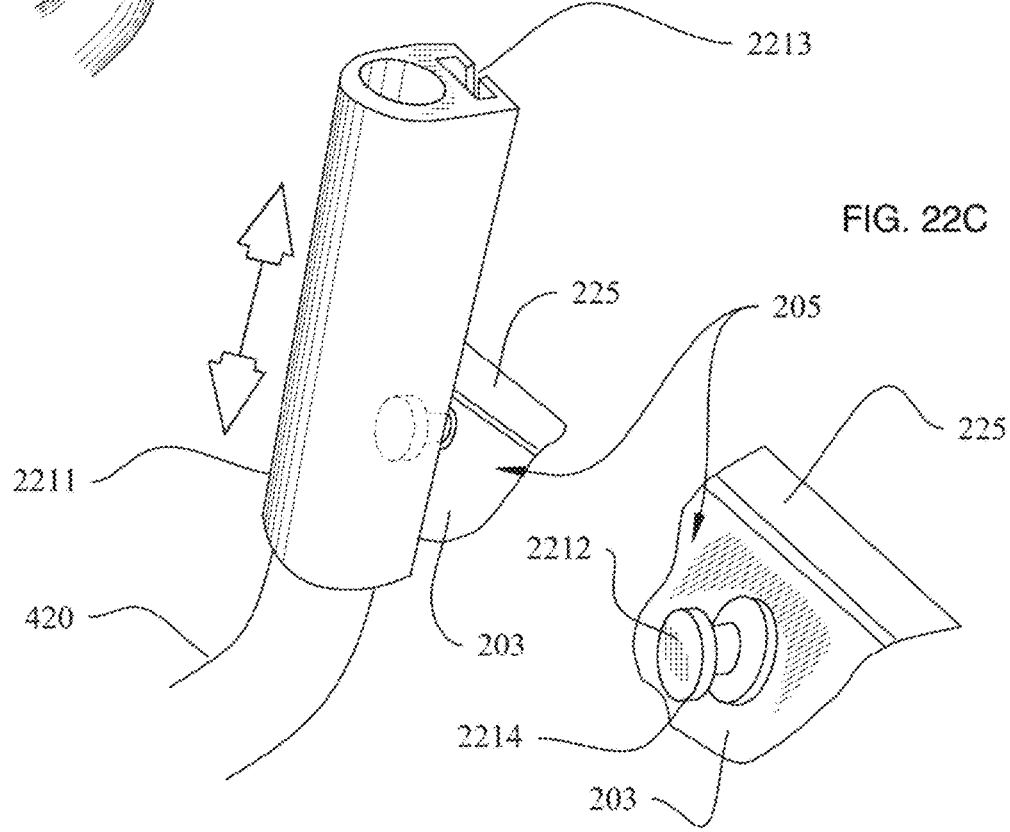

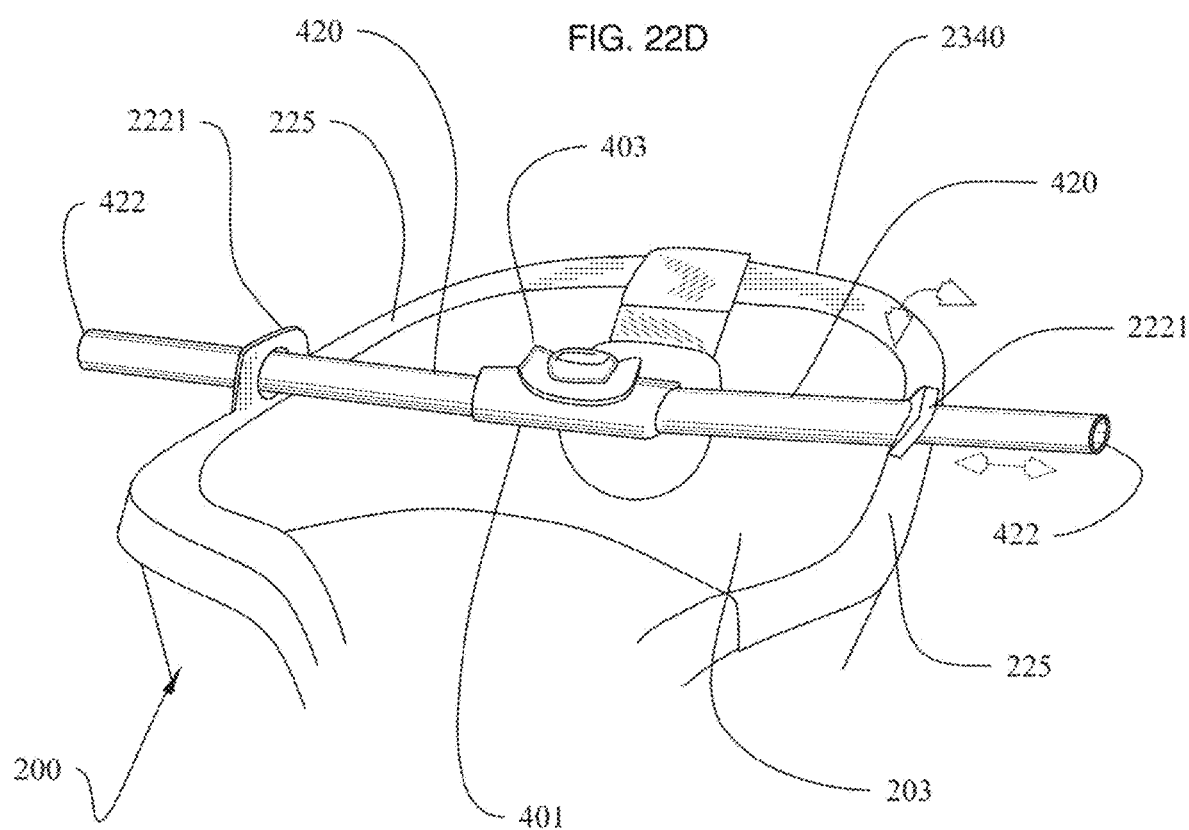

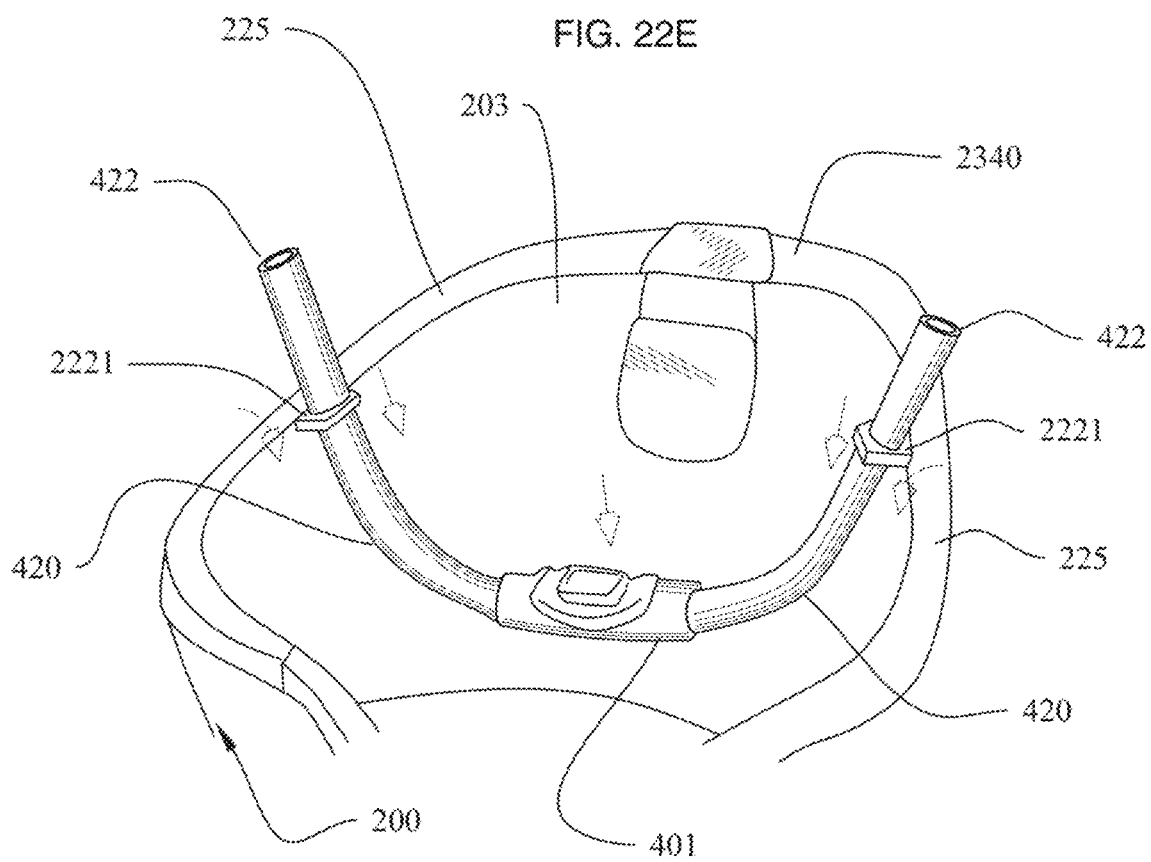

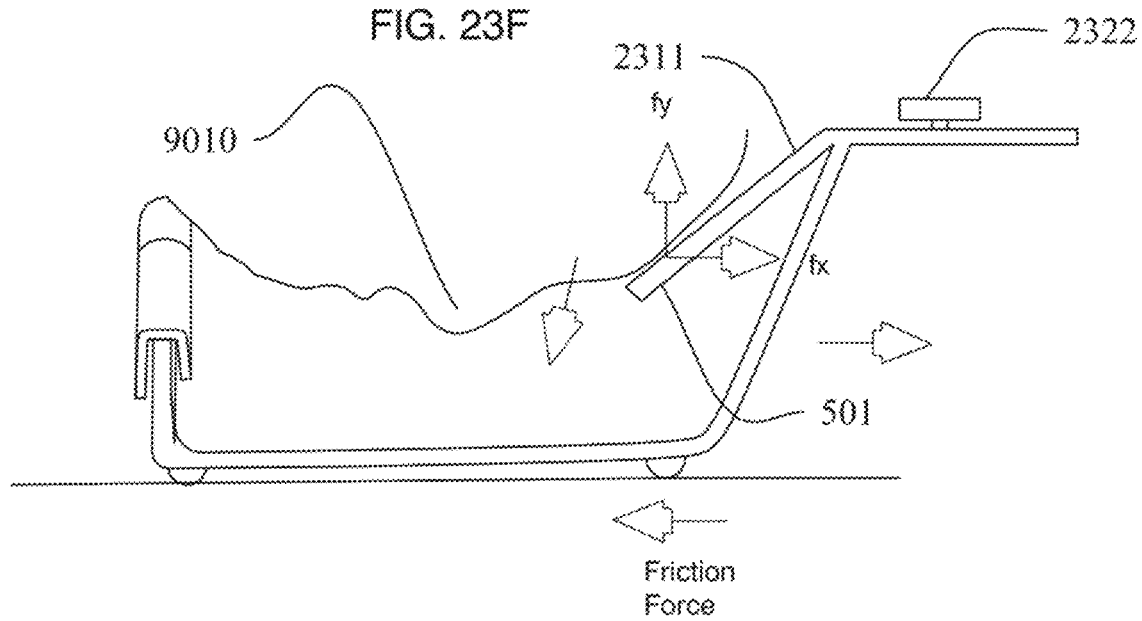

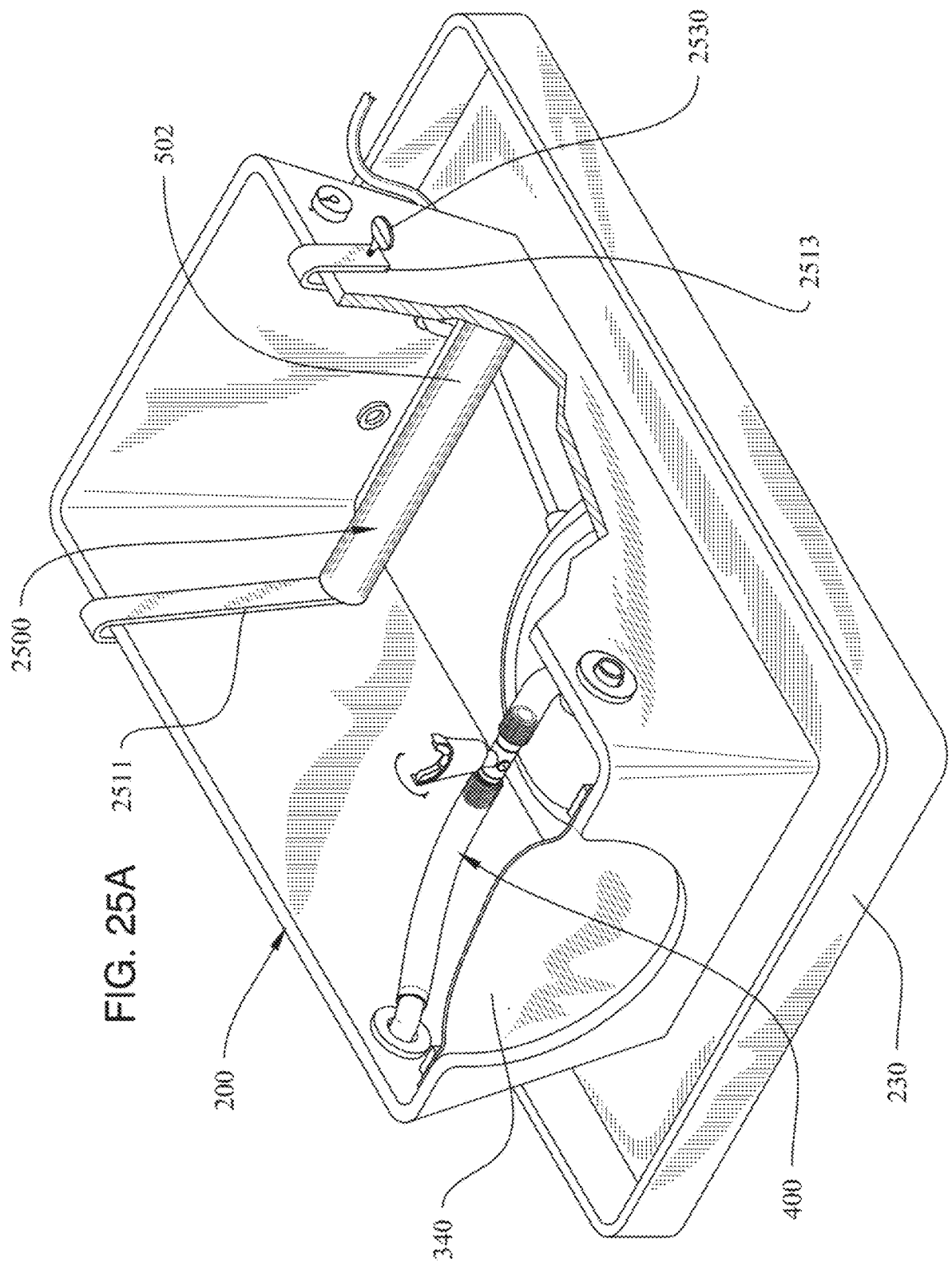

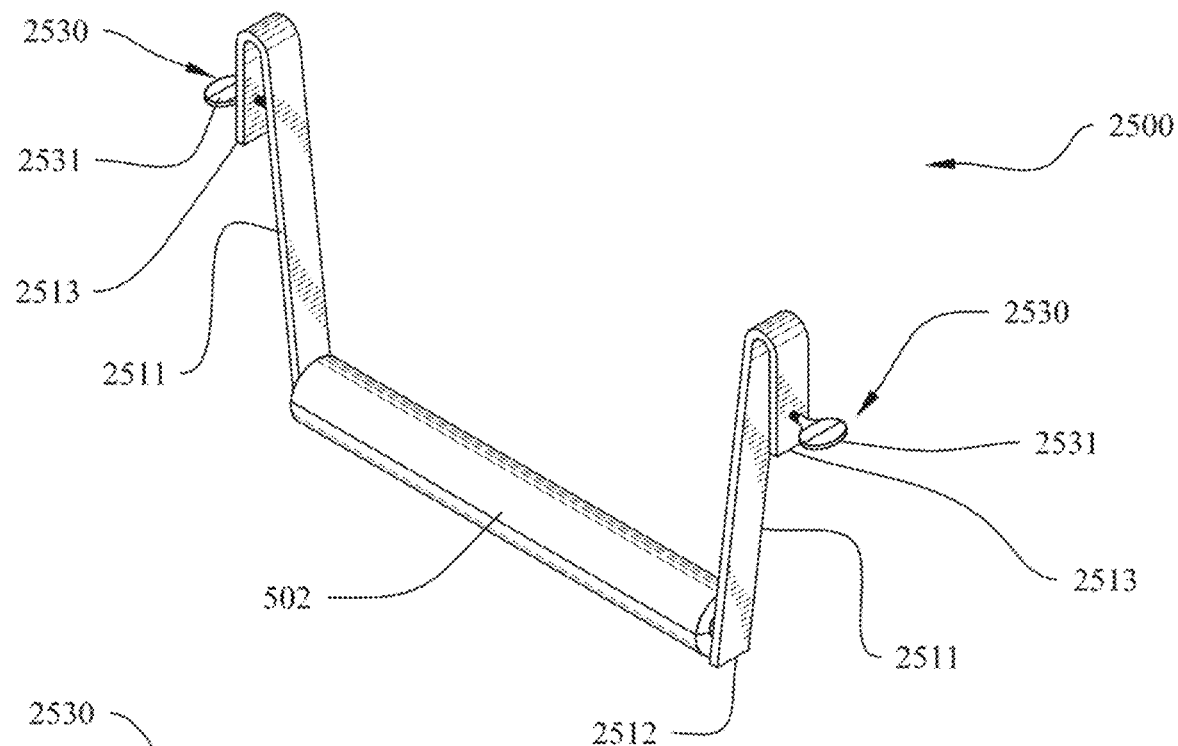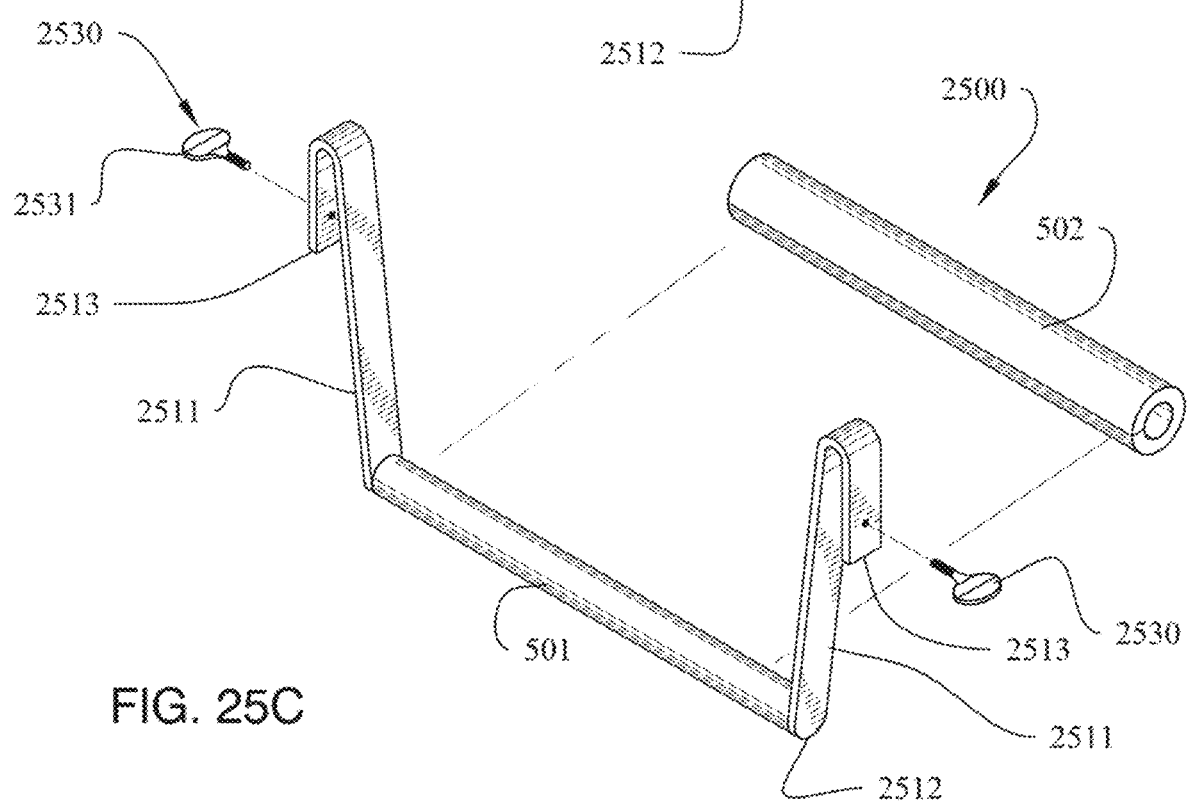

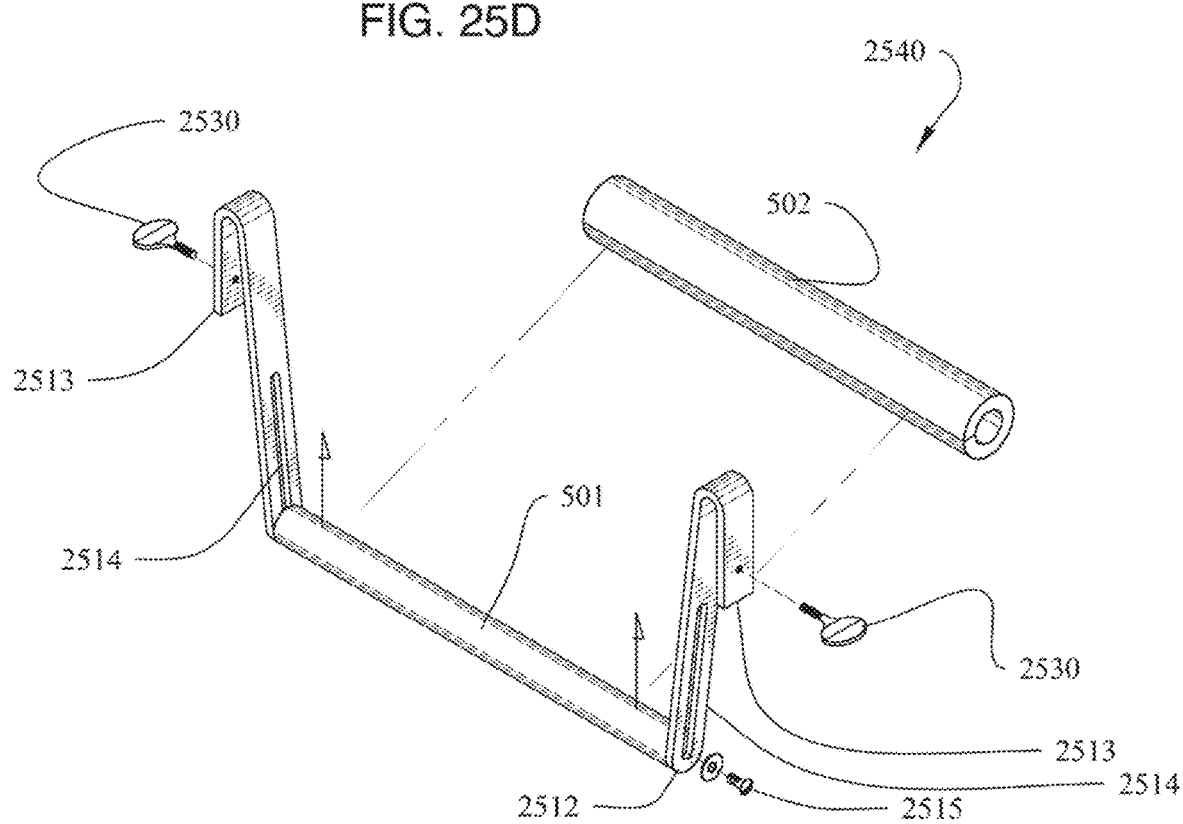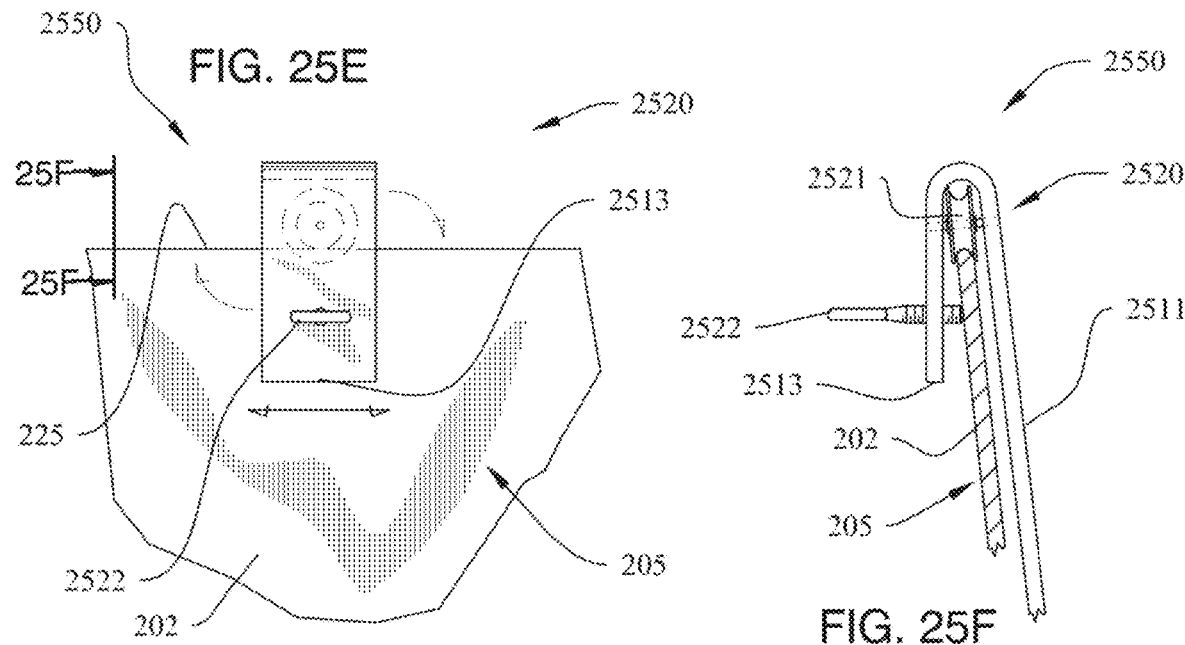

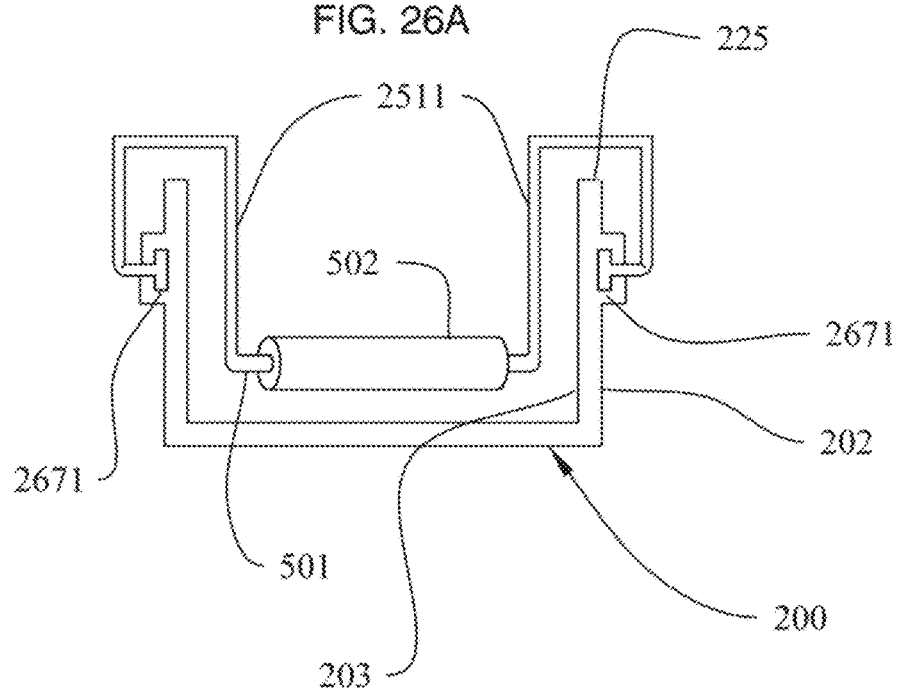
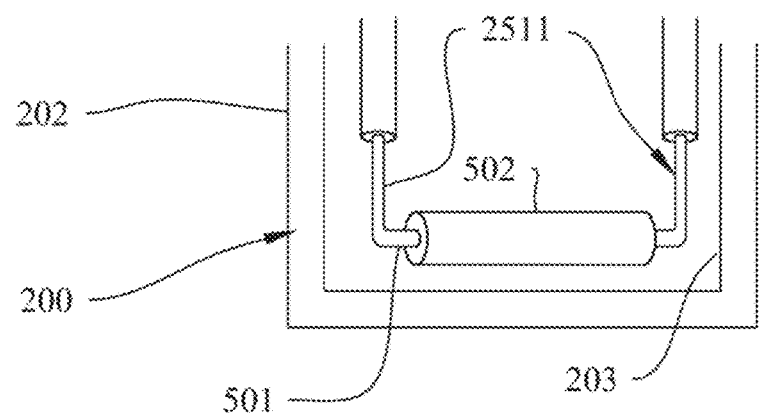

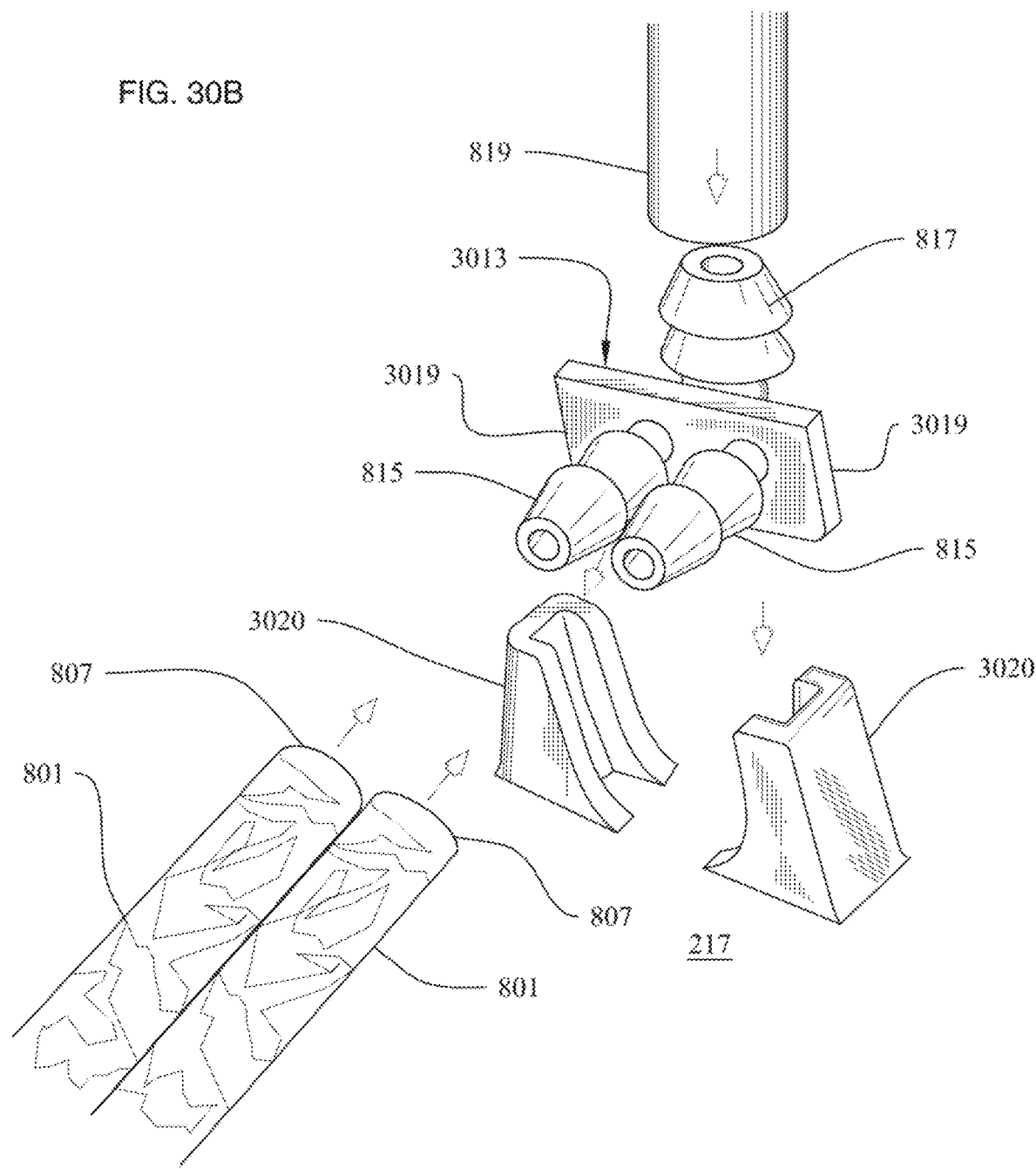

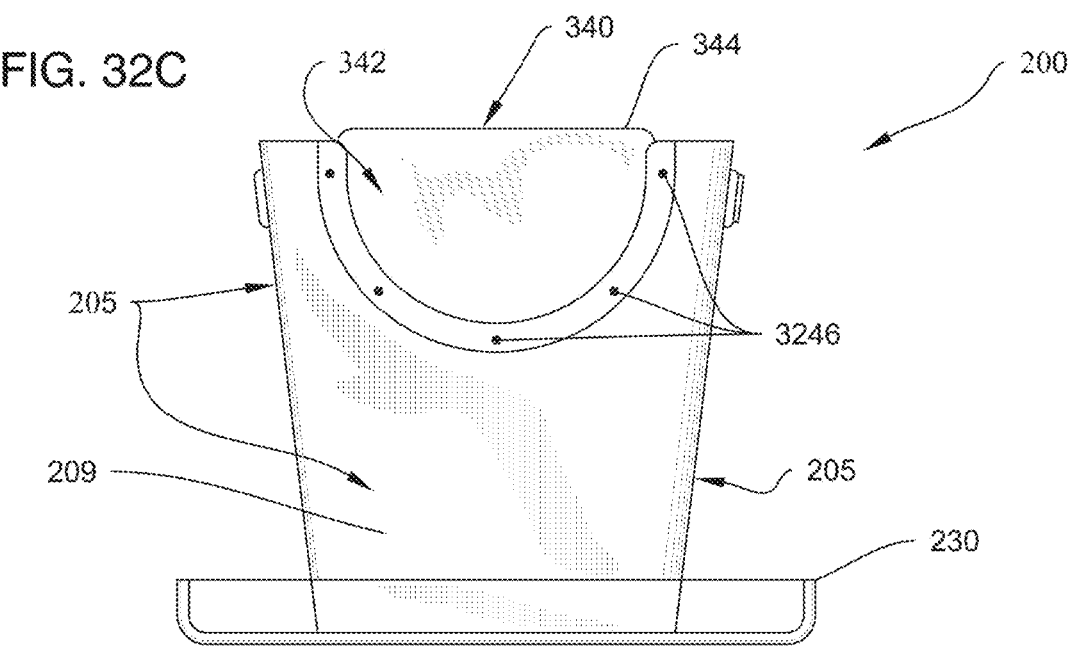
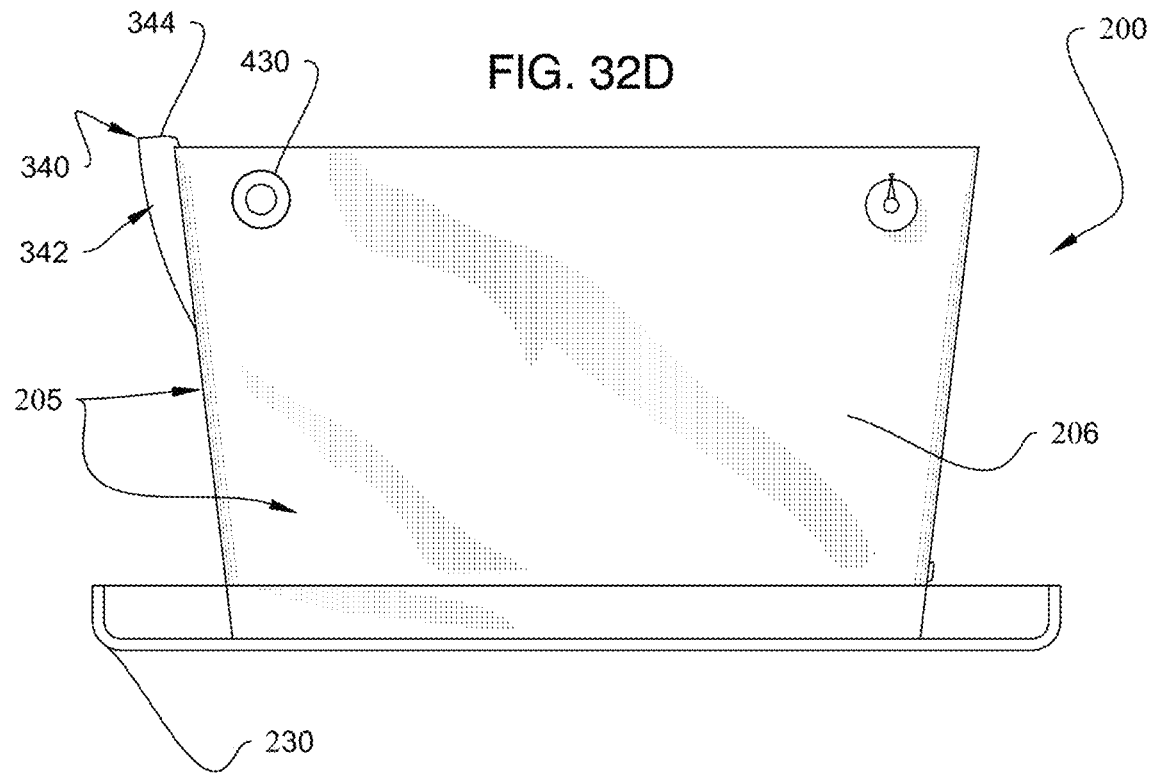

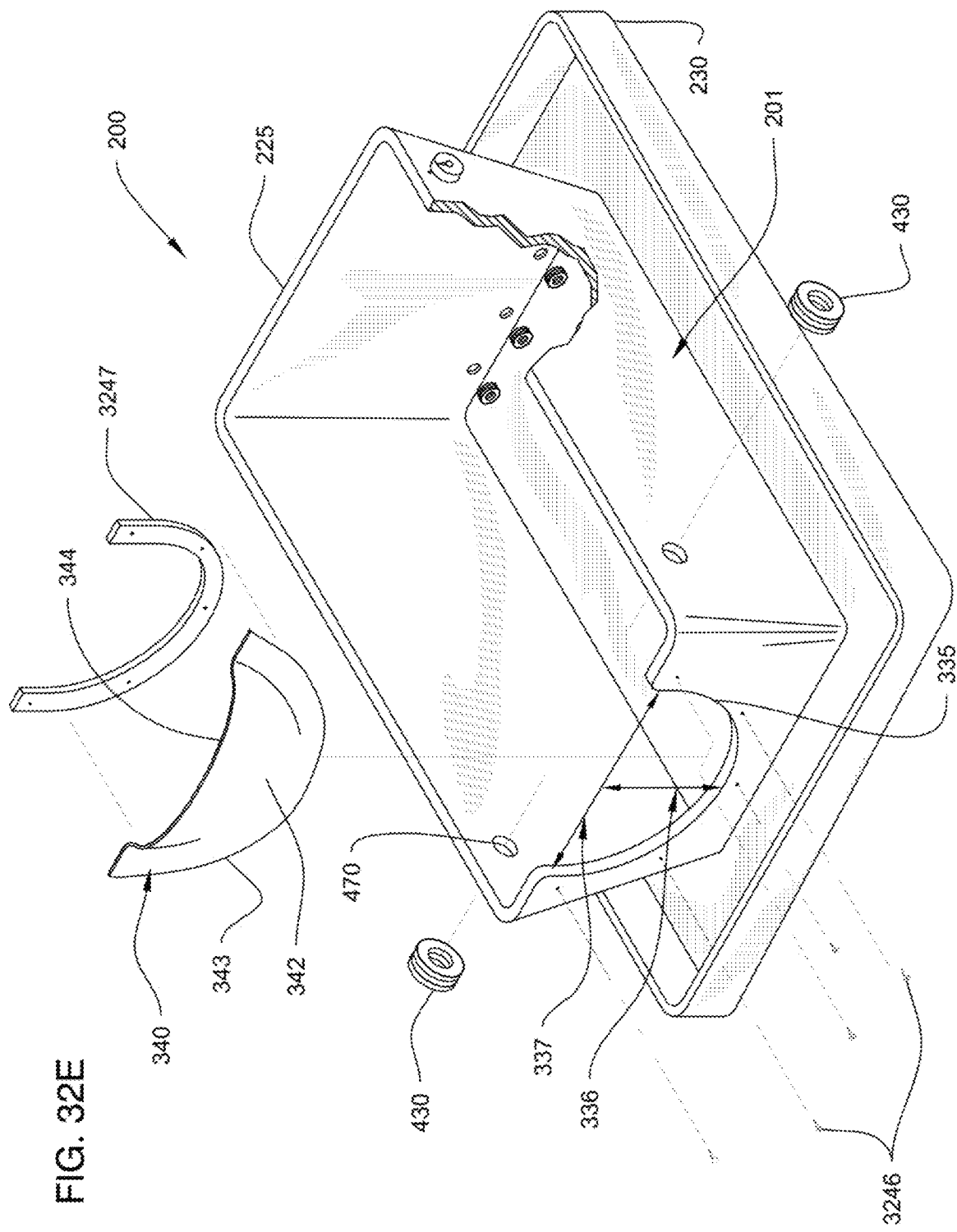

FACE SOAKING DEVICE

The present application is a continuation-in-part (CIP) application that claims priority under 35 U.S.C. § 120 to U.S. Non-Provisional patent application Ser. No. 14/877,856 filed on Oct. 7, 2015; the disclosure of which is incorporated herein by reference in its entirety.

The present application is a CIP application that claims priority under 35 U.S.C. § 120 and/or under 35 U.S.C. § 365 to Patent Cooperation Treaty (PCT) international patent application number PCT/US15/54576 filed on Oct. 7, 2015, in the US Receiving Office; the disclosure of which is incorporated herein by reference in its entirety.

The present application claims priority under 35 U.S.C. § 119(e) to the following seven U.S. Provisional Patent Applications: (1) application Ser. No. 62/094,036 filed on Dec. 18, 2014; (2) application Ser. No. 62/106,138 filed on Jan. 21, 2015; (3) application Ser. No. 62/114,962 filed on Feb. 11, 2015; (4) application Ser. No. 62/176,754 filed on Feb. 26, 2015; (5) application Ser. No. 62/137,799 filed on Mar. 24, 2015; (6) application Ser. No. 62/173,204 filed on Jun. 9, 2015; and (7) application Ser. No. 62/208,325 filed on Aug. 21, 2015; the disclosures of which are all incorporated herein by reference in their entirety.

CROSS REFERENCE TO RELATED PATENT APPLICATIONS

The present application is related to PCT international patent application number PCT/US15/54576 filed on Oct. 7, 2015; the disclosure of which is incorporated herein by reference in its entirety.

TECHNICAL FIELD OF THE INVENTION

The present invention relates in general to skin soaking devices and more specifically to face soaking devices.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

The skin (epidermis) of humans (and of terrestrial vertebrates) may suffer from a number of problems, such as: acne; wrinkles, including age spots; infections; physical damage; various rashes, including *pityriasis rosea*, acne rosacea; and the like. Each of these skin problems may be briefly discussed below.

Acne may result from clogged skin pores, which may be visible as pustules or pimples—i.e., what are commonly called blackheads and whiteheads. Such visible acne may be both visually unpleasant and painful. Severe acne may also result in scaring from the physical damage associated with ruptures of follicle walls, which may also form deep cysts under the skin. The clogged skin pores visible as acne may result from an overproduction of sebum oil, keratin, and/or metabolic byproducts of skin pore bacteria, as well as from the cells of skin pore bacteria. A common skin pore bacterium is *Propionibacterium acnes* (*P. acne*).

Undesirable wrinkles on the skin may result from age, environmental factors, genetic factors, and repeated facial expressions. Age may be a factor in wrinkle formation because as skin ages, it may lose elasticity, in part due to accumulated gravitational pull over time and changes in connective tissues. Additionally with age, sebum production may slow (from the sebaceous glands), which may contribute to skin dryness with age, wherein such skin dryness may enhance visibility of wrinkles. Environmental factors may include sun and wind exposure as well as exposure to smoke, which over time may also contribute to wrinkles. Further, consistent facial expressions over time such as squinting, smiling, and even thinking can result in skin wrinkles. And in addition to wrinkles, age spots, such as liver spots and solar lentigines may also appear on the skin as the skin ages and is exposed to various environmental factors over time.

Additionally, various microorganisms, which may include bacteria, fungi, protozoans, and even some small invertebrates may infect skin, both on the surface and within the skin tissue, with varying levels of severity. For example, the mere presence of some such microorganisms, whether dead or alive, may act as an irritant, causing inflammation. Some microorganism metabolic byproducts may also act as irritants; whereas, some byproducts may actually be toxic. And some microorganisms may actually feed on the skin itself and/or the natural secretions of the skin, such as sebum. Such microorganisms may also infect open wounds on the skin and use such open wounds to gain entry to the body, and pose a larger bodily infectious threat.

Additionally, viruses may cause contagious, painful, and/or unpleasant looking lesions and blisters, e.g., cold sores. Such lesions and blisters if ruptured may result in physical damage to the skin, as well as pain. Such viruses may include herpes and herpes like viruses.

With respect to physical damage to the skin, this may include: various wounds, cuts, abrasions, burns, lesions, blisters, ruptures, and the like. Such physical damage to the skin may result in scarring as the skin heals and prior to healing may increase chances for various microorganism infection.

Such skin problems, particularly when occurring on the face, because of the inherent visibility to others of the face, may result in collateral detrimental effects, such as to one's psychological, social, and occupational wellbeing.

*Pityriasis rosea* may be a type of skin rash. Often, *pityriasis rosea* may begin with a single "herald patch" an oval red lesion of 2 to 10 centimeters (cm), followed in one or two weeks by a generalized body rash of many small (5 to 10 millimeter (mm)) patches of pink and/or red, flaky, oval shaped lesions, which often appear on the torso, but may also appear on the cheeks and/or at the hairline.

Acne rosacea or just rosacea may be a chronic skin rash condition characterized by facial erythema (redness) and sometimes pimples. Rosacea may affect all ages. Rosacea may typically begin as redness on the central face across the cheeks, nose, or forehead, but may also affect the neck, chest, ears, and/or scalp. In some cases, additional signs, such as semipermanent redness, telangiectasia (dilation of superficial blood vessels on the face), red domed papules (small bumps) and pustules, red gritty eyes, burning and stinging sensations, and in some advanced cases, a red lobulated nose (rhinophyma), may be present.

The prior state of the art has responded to such problems with a diversity of technologies. For example, there may be a plethora of various topical ointments and creams for treating various skin problems. However, relevant here, may be the application of soaking the affected skin in an immersion liquid. Regardless of explanation, the prior state of art has shown a positive correlation with improvements to the above noted skin problems with soaking the skin in an appropriate immersion liquid. For example, such a treatment modality may be known in the art generally as hydrotherapy when the immersion liquid in question may be predominantly water. However, such hydrotherapy principles may be applied to other such immersion liquids, such as various oils, various paraffin waxes (typically heated), and oil water mixtures (emulsions). As used herein, hydrotherapy may be a means of treating various skin problems, by immersing the skin in a particular immersion liquid, wherein the immersion liquid may be predominantly water or some other liquid, such as an oil in liquid form at room temperature or an appropriate temperature, such as paraffin wax in liquid form when appropriately heated, or an oil and water mixture.

Such hydrotherapy may involve soaking a target region of skin within the immersion liquid. The immersion liquid may comprise various properties. For example, the immersion liquid may contain various dissolved salts, wherein such a liquid may be known herein as a saline solution. For example, the immersion liquid may contain released oxygen, either as dissolved oxygen and/or as gas bubbles within the immersion liquid. For example, the immersion liquid may contain an increased or decreased temperature with respect to room temperature. And for example, the immersion liquid may be directed via one or more jets, such that a stream of liquid pressure may be directed at the target region of skin.

With respect to saline solutions as the immersion liquid, saline and salts as used herein may refer not only to solutions of sodium chloride, but may also refer to other minerals in solution, e.g. potassium and/or magnesium, that may be dissolved in a solvent, such as predominantly water. Various negative ions, such as chloride, may also be present in solution with the positive mineral ions. For example, sodium and potassium salt solutions may be present with chloride ions and magnesium may be present with sulfate ions, as in Epsom salt. An immersion liquid using various salts may promote different benefits. For example, some such saline solutions may soften the skin and/or others may tend to moisturize the soaked skin.

Benefits to the skin from soaking the skin in saline solutions may predominantly function by osmosis. Osmosis is a random movement of water molecules across partially-permeable membranes (such as cellular membranes, including skin cells), from an area of high water concentration (e.g. within a cell) to an area of low water concentration (e.g. the saline solution). Thus osmosis will function to draw water out of cells, including skin cells, when the saline solution has a salinity that is greater than the salinity within the cells. For example, human blood has an average salinity of about 0.85% by weight, which is often rounded to 0.9%. Thus if the saline solution that the skin may be soaking in is greater than 0.9% by weight, there will be osmotic flow of water molecules from the skin cells into the saline solution.

However, it is from this flow of water molecules across cell membranes that several benefits may result for treating and/or improving the various skin problems noted above.

For example, with respect to acne, skin with acne that is exposed to saline solutions may see a reduction in acne. Such reduction may result from the saline solution reducing sebum oil within pores, by the saline solution reducing the population of skin pore bacteria, and/or by the saline solution encouraging a reduction in skin pore size. The saline solution may help to loosen sebum oil from pores. With respect to skin pore bacteria, which may be adapted for non-saline environments, such bacteria may not be adapted to cope with the osmotic flow of water molecules out of the bacterial cells. Such saline solutions may hinder reproduction of such bacterial cells. Such saline solutions may actually kill such bacterial cells. With respect to the reduction in skin pore size, this may also result from osmotic flow of water molecules.

With respect to a reduction in wrinkles, the saline solution may reduce wrinkles by softening the wrinkled skin tissue and by stimulating the sebaceous glands to produce sebum oil which may combat age associated skin dryness. For example, exposing a face to warm water may soften facial skin in preparation and aiding in shaving whiskers (stubble) from that face. Additionally, depending upon the salinity of the given saline solution, the saline solution may have a hydrating effect upon the immersed skin.

With respect to mitigating against microorganism infection of the skin, as noted above, those microorganisms which may be predominantly present on the skin are not typically adapted to withstand osmotic flow of water molecules from within the bacterial cells. Immersion of skin in such saline solutions may result in microorganism population reduction.

With respect to improving a rate of healing damaged skin, skin immersed into saline solutions may experience an improved rate of healing by reducing the populations of microorganisms which may interfere with healing. And the osmotic flow may also aid healing damaged skin by aiding transport of nutrients and repair proteins from within the cells and tissues below the surface skin to the damaged skin site.

Thus immersion of skin into a saline solution which may have a salinity greater than the skin tissue being immersed, may result in a plurality of benefits to the immersed skin.

Now turning to oxygen treatments for the skin and how oxygen may reduce some of the skin problems identified above. Again, regardless of explanation, the state of the prior art shows a positive correlation with exposing skin to oxygen and improvements in the skin.

Molecular oxygen (atmospheric oxygen), i.e. $O_2$, may be essential for cellular respiration and the basis for how each vertebrate cell derives energy via the Krebs Cycle (Citric Acid Cycle). Without a sufficient supply of consistent oxygen to any vertebrate cell, that cell may be hypoxic and may have a diminished capacity to operate normal cellular activities, including a diminished capacity to reproduce, to fight infection, and/or to heal. By providing oxygen in sufficient concentration directly to the skin, such exposed skin may obtain some of its needed oxygen directly, instead of relying largely upon delivery of oxygen via hemoglobin in red blood cells. Such skin cells having a steady available source of oxygen may allow such skin cells a full range of normal cellular activities. Additionally, immune system cells (e.g. macrophages and phagocytes) which target and kill infectious microorganisms better perform when such cells have an adequate supply of oxygen. And a second mechanism of oxygen reducing infectious microorganism population may be by oxygen's oxidation properties and ability to form reactive oxygen species that may then oxidize bacterial cellular machinery, such as interfering with bacterial cell walls.

Now oxygen may be applied to the skin in gaseous form and/or released as a dissolved gas and/or as gas bubbles within a liquid, including the immersion liquid. For example, atmospheric air will contain atmospheric oxygen, e.g. at approximately 20.95%. A delivered concentration of gaseous oxygen may be increased over the atmospheric percentage by using pure oxygen as a supply source. However, use of gaseous oxygen directed at skin may have the drawback of being difficult to control and manipulate due to the gasses' inherent ability to more freely and disperse. Whereas, release of oxygen in a liquid may provide for better control as the target area of skin may be immersed in the liquid, which then may have oxygen from air or pure oxygen released into the liquid.

The benefits of oxygen and saline solutions may be combined into the same immersion liquid. For example, air (which includes oxygen) and/or oxygen may be pumped or released into an appropriate saline solution. Additionally, such an oxygenated saline solution may be combined with the benefits of controlling a temperature of the oxygenated saline solution.

For example, increasing a temperature of the immersion liquid above room temperature but less than a temperature which may be harmful (e.g. painful), allows for an increase in chemical reactions (kinetics). Thus increasing the immersion liquids temperature in such a range will tend to increase the effectiveness of saline solutions as well as the effectiveness of oxygenation of the skin. Additionally, such increased temperature of the immersion liquid may result in an environment that may be soothing and relaxing to a user. Such a soothing and relaxing result may then release stress and mitigate against headaches. Release of stress may promote lowering of blood pressure, healing of damaged skin, and a stronger immune system. Thus, increasing the temperature of the immersion liquid not only may provide direct improvements to how the saline and the oxygen functions to improve the skin, but by creating the soothing and relaxing environment, a collateral benefit of stress release may be achieved, which may also then include a cascade of additional benefits.

Further, increasing the immersion liquids temperature above room temperature may then permit the immersion liquid to be used for heat therapy. Heat therapy may be used to treat not only skin problems, but also other ailments, such as, but not limited to, arthritis, osteoarthritis, fibromyalgia, joint stiffness, bursitis, tendonitis, sprains and pulled muscles. The heat and immersion liquid which may convey the heat, may increase blood flow, improve joint stiffness and reduce pain. For example, heated paraffin waxes as the immersion liquid may be utilized. Such heated paraffin wax may soften hardened skin caused by scleroderma, a disease in which collagen accumulates on the body.

In addition or alternatively, decreasing the immersion liquids temperature below room temperature may then permit the immersion liquid to be used for cold therapy. Chilling the liquid by use of a chiller, chilling equipment, and/or by introduction of ice, may then permit various cold therapies to be used to treat the face or other body part which may be removably immersed into the chilled liquid. Additionally or alternatively, heat therapy may be alternated with cold therapy; wherein such alternation of warmth and cold may aid in increasing blood flow, facilitating removal of cellular toxins (e.g., but not limited to, lactic acid), and/or promoting healing of burned or traumatized tissue.

Additionally, liquid jets, for example water jets, when directed at the immersed skin may also result in an environment that is soothing and relaxing to the user. Such water jets also may have their benefit increased when the immersion temperature is increased as noted per above.

Light therapy may also be used to impart various benefits to the exposed skin and/or body in general. Light therapy may involve directing a source of light at skin. Some wavelengths of light have found to increase healing rates of damaged skin, such damaging including cuts, scrapes, bruising, lacerations, lesions, and the like. Light such as ultraviolet (UV) light may also be used for skin tanning purposes. However, both existing oxygen therapy and existing light therapy are conducted in a treatment environment of atmospheric air, i.e., not with an article to be treated (e.g. a region of skin) submerged within an immersion liquid.

Additionally, it may be desirable to expand beyond just oxygen, air, or air enriched with oxygen, as treatment gasses for skin.

Additionally, current light therapy devices generally are directed at emitting only a very narrow range of wavelengths, generally within the visible light spectrum, near infrared (IR), and near ultraviolet (UV). It would be desirable to have expanded devices that may be capable of emitting electromagnetic (EM) radiation in various wavelengths that may encompass regions of the entire EM spectrum, i.e. not necessarily a single device capable of emitting across the entire EM spectrum (since different technologies may be required to produce a given range of wavelengths), but rather a multitude of EM emitting devices where each different device may be capable of emitting a particular range of wavelengths, such that these different EM emitting devices may collectively be able to cover the entire EM spectrum.

Conducting oxygen therapy and/or light therapy or other EM therapy within the immersion liquid may be desirable for several reasons. Because the liquid is more dense than atmospheric air, more control over directing oxygen (or other gas) to a target region on the article (e.g., immersed skin region) may be achieved over conducting oxygen therapy in atmospheric air, where expelled oxygen quickly dissipates into the atmospheric air. By using the immersion liquid to removably submerge the target region of the article, useful properties of the liquid may be tailored for specific applications with respect to the target region of the article. For example, liquid water, such as saline solutions, may soften the skin and make such softened skin better able to benefit from exposure to oxygen and/or various wavelengths of light. The additives in the liquid may be used to heal, cleanse, rejuvenate, sanitize, sterilize, and the like. Likewise, controlling a temperature of the liquid may then be able to impart heat or withdraw heat from the target region of the article in a much greater efficiency than may be possible where the treatment environment is atmospheric air and not the liquid. Additionally, controlling the temperature (up, down, or maintaining) of the liquid may increase or decrease the efficacy of the additives, e.g., from a kinetics perspective.

Furthermore, it has been discovered that conducting light therapy or other EM therapy may be enhanced when the EM radiation may be emitted through a plurality of bubbles within the immersion liquid, by providing an increased coverage of the target region of the article receiving EM radiation in comparison to if there were no bubbles. The emitted EM radiation and the bubbles produce an optical chain reaction (OCR) phenomena that provides this enhancement.

However, as noted above, with respect to such skin problems on the face, these problems are exacerbated because the high visibility of the face. Additionally, these skin problems on the face are exacerbated because the current state of the art does not provide a means by which the user may immerse the face to receive hydrotherapy, wherein the hydrotherapy immersion liquid may comprise saline solutions, delivery of oxygen (and/or other gasses), heating means for increasing and/or decreasing immersion liquid temperature, and/or use of liquid jets. The problem that the prior state of the art has failed to address, until this invention, results from two biological facts. One, terrestrial vertebrates breathe from their nose and/or mouth located on the face and thus a hydrotherapy means for the face needs to provide a means by which the user may breathe while the user's face is immersed. Otherwise immersion of the face is limited to how long the user can hold their breath. And two, all pre-existing vessels have no means to accommodate a neck region of the user, particularly the soft tissue regions of the neck (front and sides of the neck), so if the user were to submerge the user's face into a pre-existing vessel, a rim of that vessel would press into the neck region causing discomfort rendering the prior state of the art ineffective for hydrotherapy of the face. Or the user would have to angle their head into the prior art vessel and attempt to hold their head at an uncomfortable angle to soak their face, which if is prolonged may result in neck pain. Additionally, it may be desirable if such a device might, in at least some embodiments, comfortably support the head region of the user, particularly the forehead, to promote facial immersion that may be comfortable and not strain the neck; wherein the user may soak their face, in comfort, for extended periods of time.

There is a need in the art for devices and/or methods that permit treating specifically targeted regions of the articles (e.g., skin) to be removably submerged in the immersion liquid and then treated with various gas bubbles, such as oxygen, treated with various wavelengths of EM radiation, such as visible light, and/or providing for an enhanced EM radiation coverage of the treated region by a synergistic combination of EM radiation and bubbles that may result from directing EM radiation through bubbles in the liquid.

There then is a need in the art for a device which may promote comfortable face immersion into the immersion liquid that both allows the user to breathe while the face is immersed and that may be comfortable to the neck of the user.

It is to these ends that the present invention has been developed.

BRIEF SUMMARY OF THE INVENTION

To minimize the limitations in the prior art, and to minimize other limitations that will be apparent upon reading and understanding the present specification, one or more embodiments of the present invention may describe a face soaking device.

Some embodiments may provide for a device which may be used to place and hold a person's face into a liquid for an extended time while the person conveniently and/or comfortably breathes through a breathing tube (e.g., breathing apparatus). While the person has his or her face immersed in the liquid, the device may aerate the liquid (with various gasses). In some embodiments, the device may be designed to minimize or prevent the spillage of liquid onto the person's clothing or the immediate area around the device.

In some embodiments the face soaking device may comprise a vessel, a vessel neck gasket, and a breathing apparatus. The vessel may be configured to hold a liquid to submerge a face of a user or a portion thereof. The vessel neck gasket may be removably joined to the vessel. The vessel neck gasket may be configured to comfortably accommodate a portion of the user's neck. The breathing apparatus may be in removable contact with: the vessel, with a head support, and/or with the user. The breathing apparatus may be configured to permit the user to breathe while the user's face (in whole or in part) may be submerged within the liquid. When the vessel may be filled with the liquid to at least a sufficient level, the user may soak the face or the portion thereof, such that skin being soaked receives a benefit.

It is an objective of the present invention to provide a face soaking device that may be used to reduce severity of facial acne by immersing the face within the immersion liquid.

It is another objective of the present invention to provide the face soaking device that may be used to reduce severity of facial wrinkles and/or facial age spots by immersing the face within the immersion liquid.

It is another objective of the present invention to provide the face soaking device that may be used to reduce severity of microorganism infection, including, but not limited to viral, bacterial, and/or fungal infections, of facial skin by immersing the face within the immersion liquid.

It is another objective of the present invention to provide the face soaking device that may be used to reduce severity of physical damage to facial skin by immersing the face within the immersion liquid.

It is another objective of the present invention to provide the face soaking device that may permit a user to submerge the user's face within the immersion liquid by the face soaking device comprising a vessel which may be configured to hold the immersion liquid.

It is another objective of the present invention to provide the face soaking device that may permit the user to breath while the user's face may be immersed in the immersion liquid.

It is another objective of the present invention to provide the face soaking device that may permit the user to immerse the user's face within the immersion liquid while maintaining comfort to the neck where the neck may contact the face soaking device, particularly where the soft tissue of the neck may contact the face soaking device.

It is another objective of the present invention to provide the face soaking device that may minimize immersion liquid spillage around the user's neck when the user's face may be immersed within the immersion liquid.

It is another objective of the present invention to provide the face soaking device that may catch spilled immersion liquid from a main vessel (e.g., the vessel) holding the immersion liquid.

It is another objective of the present invention to provide the face soaking device that may permit the user to immerse the user's face within the immersion liquid while maintaining comfort to the neck and mitigating against neck strain, by supporting a portion of the user's head that may be within the vessel, particularly that of the forehead.

It is another objective of the present invention to provide the face soaking device, wherein a head support (e.g., a head rest subassembly) may be adjustable; wherein such adjustments may be in a vertical direction (height direction) and/or in a forwards-backwards direction.

It is another objective of the present invention to provide the face soaking device wherein the immersion liquid may receive various gasses into the immersion liquid.

It is another objective of the present invention to provide the face soaking device wherein the immersion liquid may be oxygenated by a release of air and/or oxygen within the immersion liquid.

It is another objective of the present invention to provide the face soaking device wherein a temperature of the immersion liquid may be increased or decreased with respect to a room temperature of the face soaking device.

It is another objective of the present invention to provide the face soaking device wherein the vessel may be insulated to help control the temperature of the immersion liquid.

It is another objective of the present invention to provide the face soaking device wherein the face soaking device may be used for heat therapy and/or for cold therapy.

It is another objective of the present invention to provide the face soaking device wherein the face soaking device may be used for heat therapy and/or for cold therapy, wherein the heat therapy and/or the cold therapy may be used to treat not only skin problems, but also other ailments, such as, but not limited to, arthritis, osteoarthritis, fibromyalgia, joint stiffness, bursitis, tendonitis, sprains, pulled muscles, and the like.

It is another objective of the present invention to provide the face soaking device wherein the face soaking device may be used for heat therapy and/or for cold therapy, wherein the heat therapy and/or the cold therapy may increase blood flow, improve joint stiffness, reduce pain, and the like.

It is another objective of the present invention to provide the face soaking device wherein the face soaking device may be used for cold therapy, wherein the cold therapy may increase blood flow, improve joint stiffness, reduce pain, reduce swelling, and the like.

It is another objective of the present invention to provide the face soaking device wherein the face soaking device may be used for alternating between heat therapy and cold therapy, wherein the alternating heat and cold therapy may increase blood flow, improve joint stiffness, reduce pain, reduce swelling, improve healing, aid in removing cellular toxins, and the like.

It is another objective of the present invention to provide the face soaking device wherein the face soaking device may be used for soaking facial skin for at least a purpose of softening such facial skin and/or for softening facial hair (e.g., whiskers and/or stubble). For example, such skin softening may be beneficial for facial shaving.

It is another objective of the present invention to provide the face soaking device wherein the face soaking device may be used for treating burns, external and/or internal.

It is another objective of the present invention to provide the face soaking device wherein the face soaking device may be used for lightening skin shading.

It is another objective of the present invention to provide the face soaking device wherein the face soaking device may be used for darkening skin shading (e.g., skin tone or skin hue).

It is another objective of the present invention to provide the face soaking device wherein the immersion liquid may be paraffin wax.

It is another objective of the present invention to provide the face soaking device wherein interior surface of the vessel may be smooth to facilitate draining of the immersion liquid and to facilitate cleaning and sanitation of the face soaking device.

It is another objective of the present invention to provide the face soaking device that may be portable and that may be carried by a single adult user.

It is another objective of the present invention to provide the face soaking device wherein interior surfaces of the vessel may comprise one or more jet nozzles, one or more intakes, and a means for pumping the immersion liquid from the intakes and through the jet nozzles such that a pressure of immersion liquid may be directed to portions of the immersed face.

It is another objective of the present invention to provide the face soaking device wherein jet nozzle positioning may be adjustable.

It is another objective of the present invention to provide the face soaking device wherein facial immersion within the immersion liquid within the vessel may be soothing and relaxing to the user, such stress may be reduced.

It is yet another objective of the present invention that such a stress releasing use of the face soaking device may result in further collateral benefits such as promoting lowering of blood pressure, mitigation against headache severity, and/or strengthening the user's immune system.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

FIG. 4I may depict a partial top perspective view, while showing some exterior of the vessel, of how one of the second terminal ends of the at least one hose or of the at least one tubing may removably engage the some structure proximate to the rim of the vessel.

FIG. 6I may depict a longitudinal cross-sectional view along sectional line 6I-6I through the head rest subassembly.

FIG. 7I may depict at least one heating element of the heater subassembly, shown from a top view.

FIG. 13B may depict a face soaking device that may not comprise a vessel neck gasket nor a neck-gasket-accommodator.

Figure 16A:
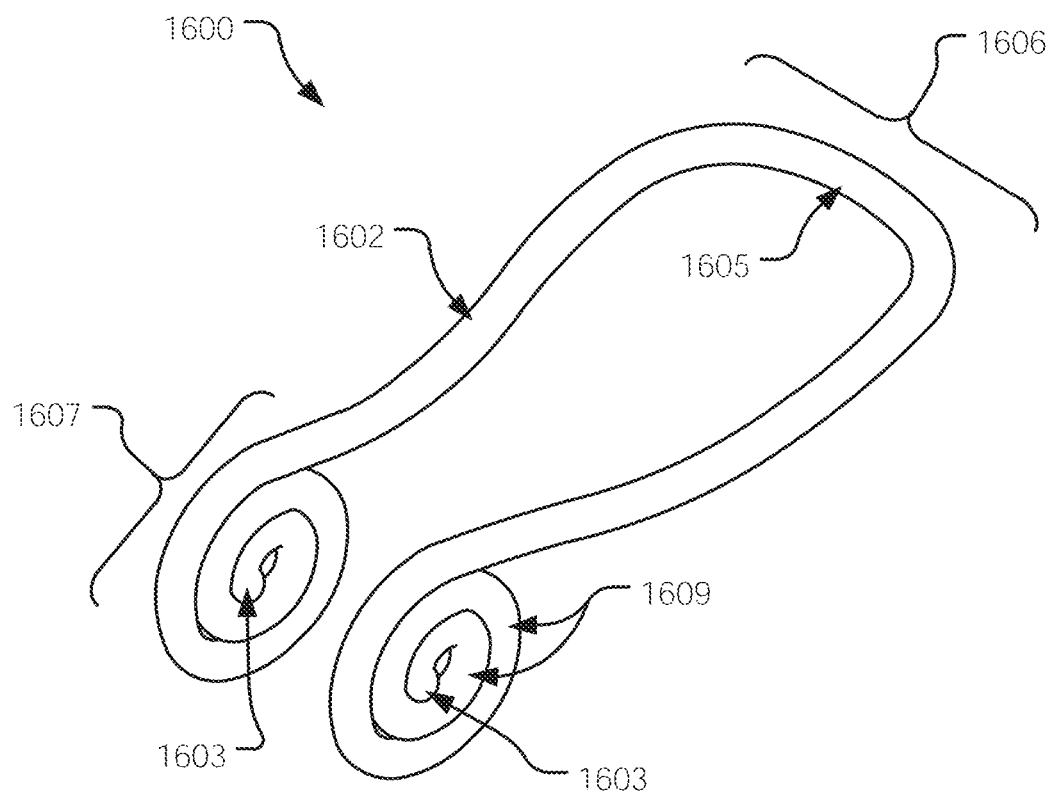

FIG. 16A may depict an exemplary embodiment of a nose-clip, comprising tight coils, shown from a top perspective view.

FIG. 16B may depict the exemplary embodiment of FIG. 16A, shown from a bottom perspective view.

FIG. 16C may depict the exemplary embodiment of FIG. 16A, shown from a front view.

FIG. 16D may depict the exemplary embodiment of FIG. 16A, shown from a side view.

FIG. 16E may depict the exemplary embodiment of FIG. 16A, shown from a back view.

FIG. 16F may depict the exemplary embodiment of FIG. 16A, shown from a top view.

FIG. 16G may depict the exemplary embodiment of FIG. 16A, shown from a bottom view.

Figure 17A:
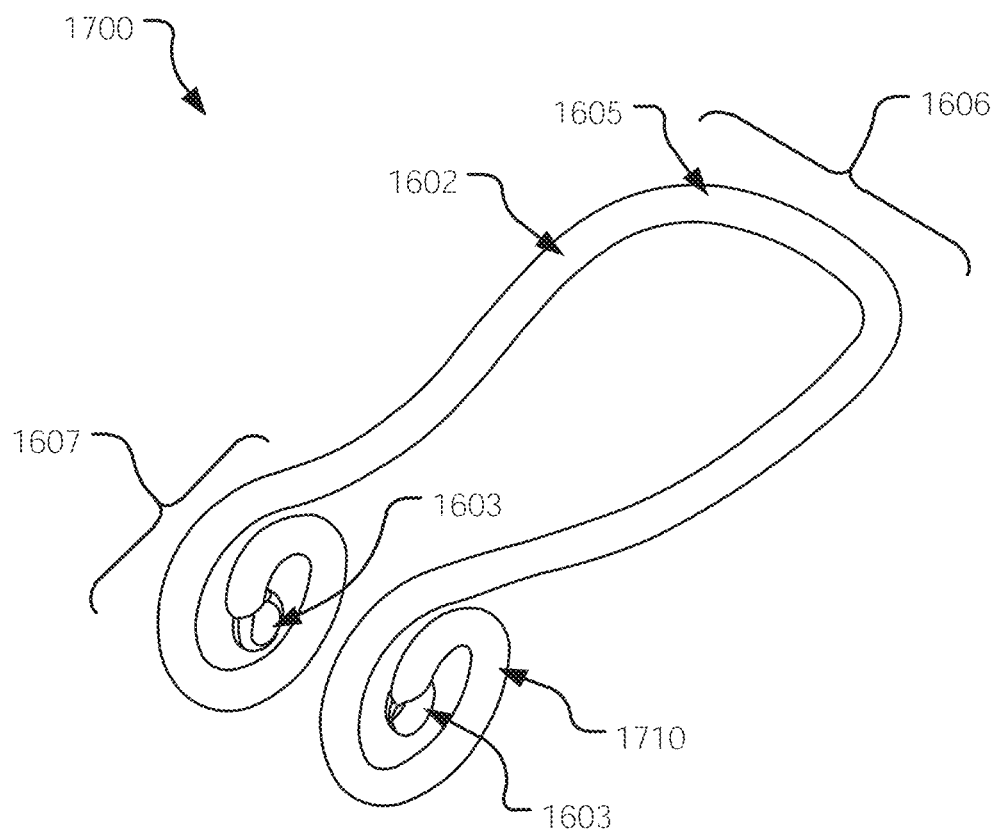

FIG. 17A may depict an exemplary embodiment of a nose-clip, comprising loose coils, shown from a top perspective view.

Figure 17B:
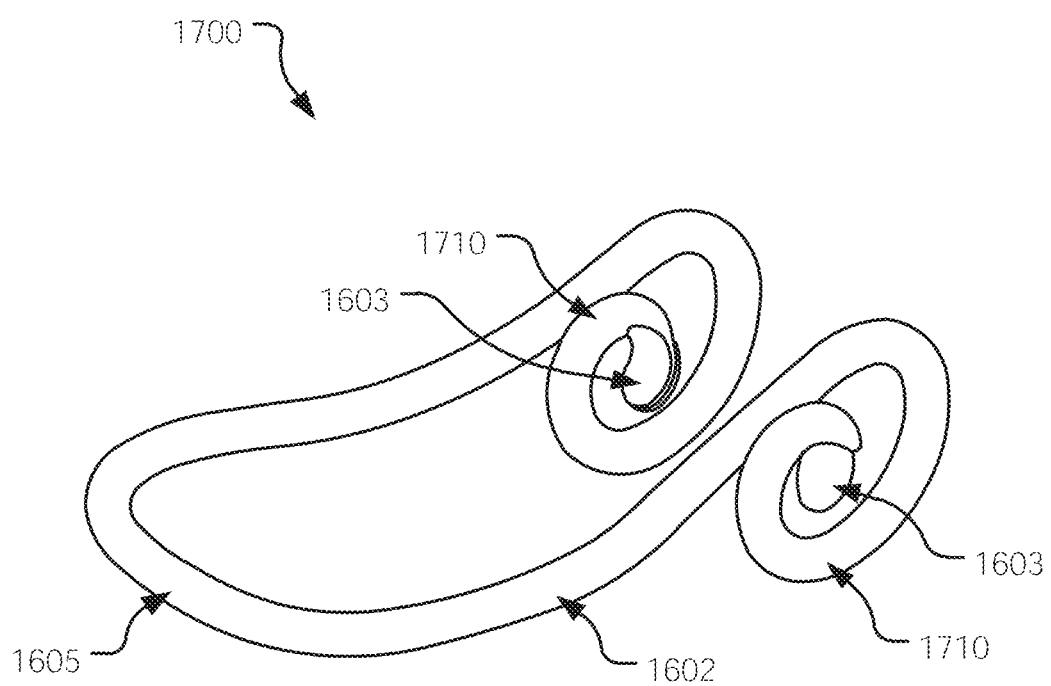

FIG. 17B may depict the exemplary embodiment of FIG. 17A, shown from a bottom perspective view.

Figure 17C:
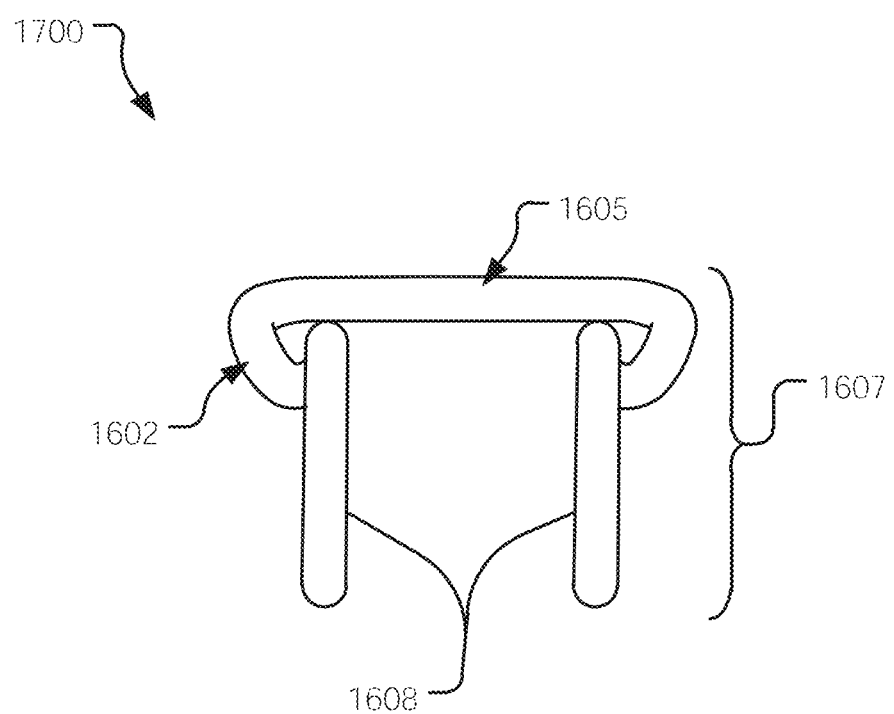

FIG. 17C may depict the exemplary embodiment of FIG. 17A, shown from a front view.

Figure 17D:
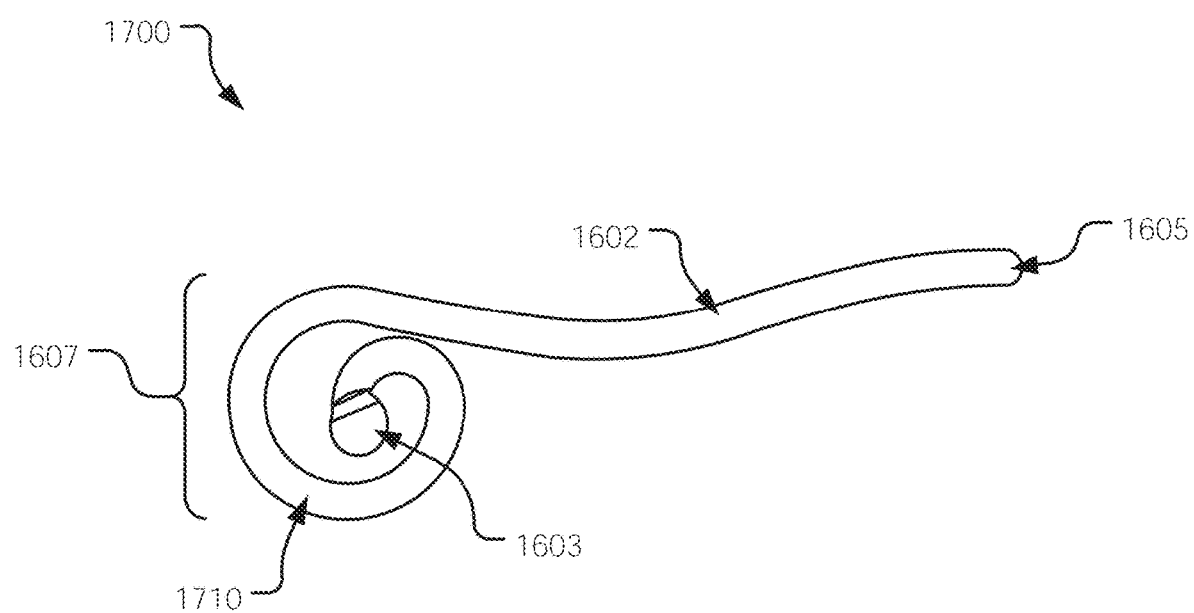

FIG. 17D may depict the exemplary embodiment of FIG. 17A, shown from a side view.

Figure 17E:
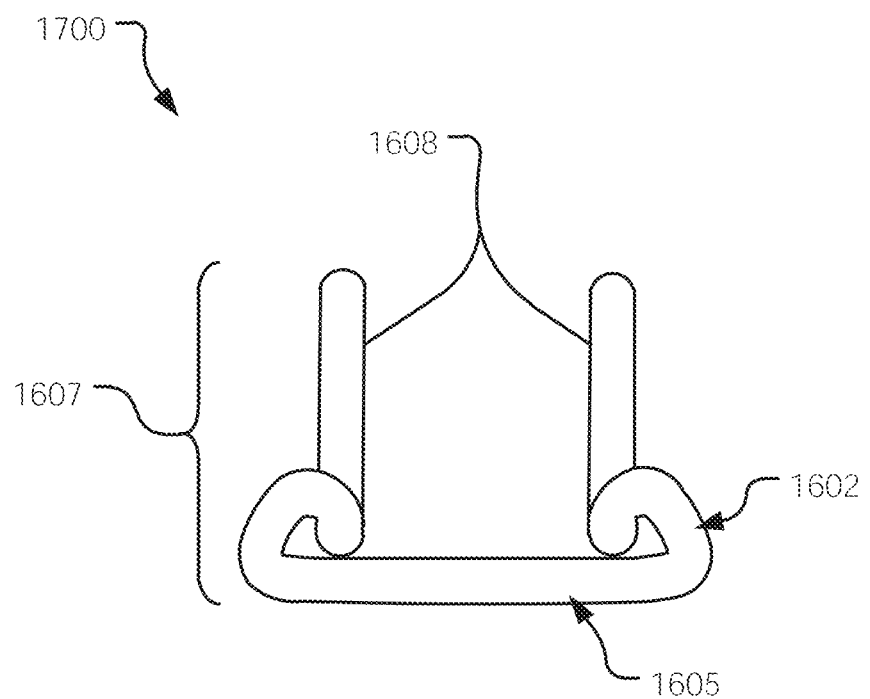

FIG. 17E may depict the exemplary embodiment of FIG. 17A, shown from a back view.

Figure 17F:
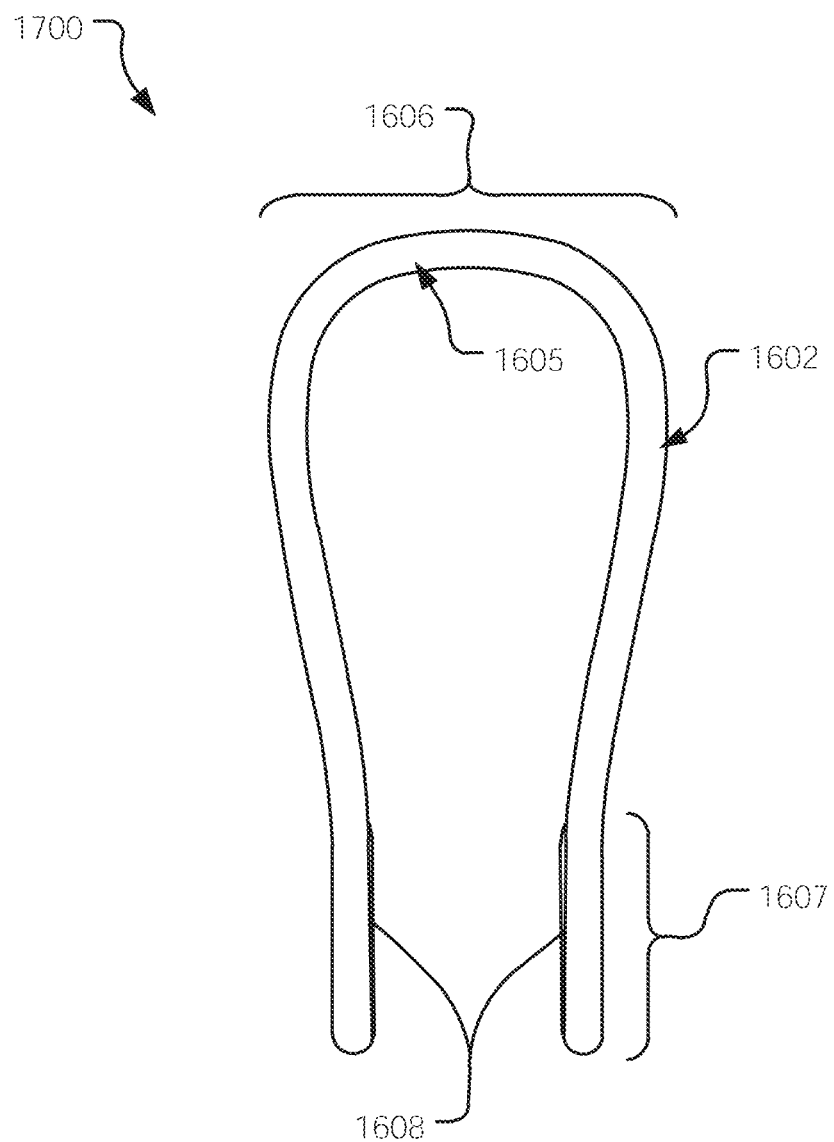

FIG. 17F may depict the exemplary embodiment of FIG. 17A, shown from a top view.

Figure 17G:
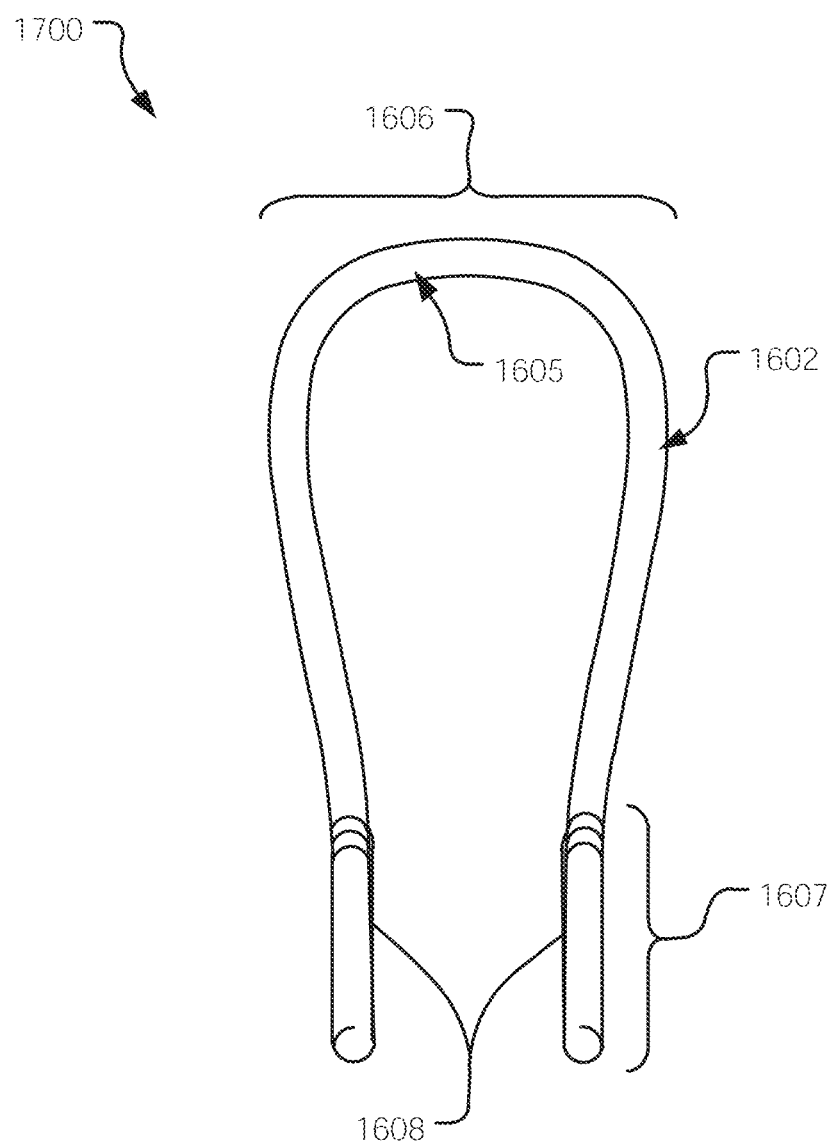

FIG. 17G may depict the exemplary embodiment of FIG. 17A, shown from a bottom view.

Figure 18A:
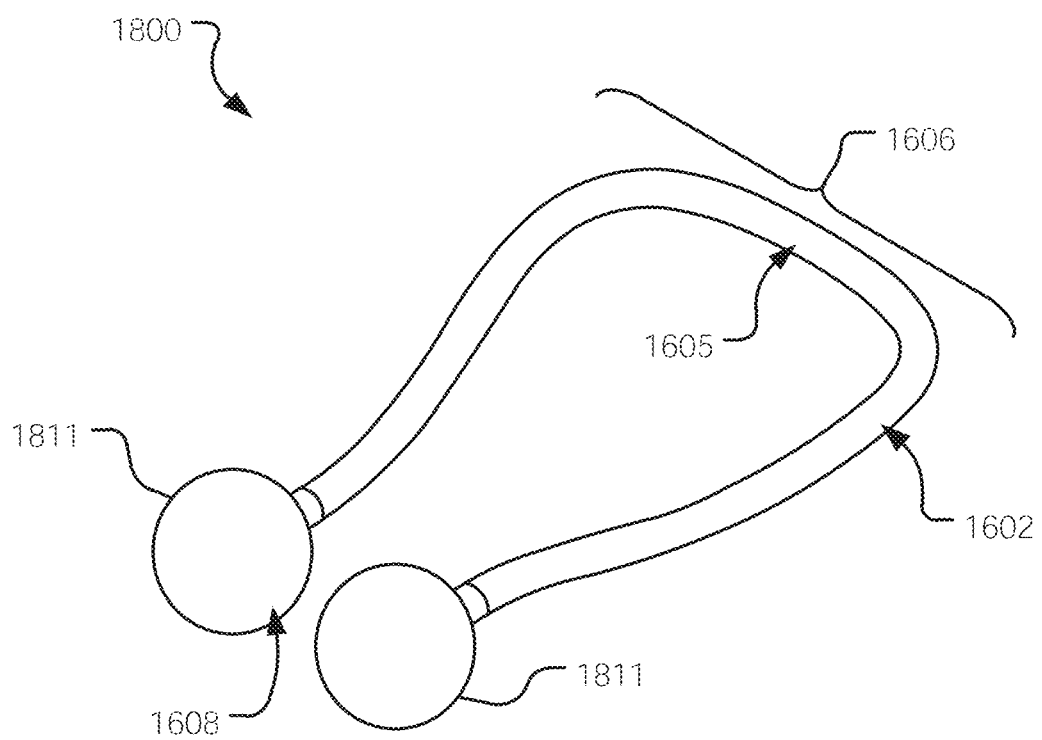

FIG. 18A may depict an exemplary embodiment of a nose-clip, comprising a pair of spherical terminating structures, shown from a top perspective view.

Figure 18B:
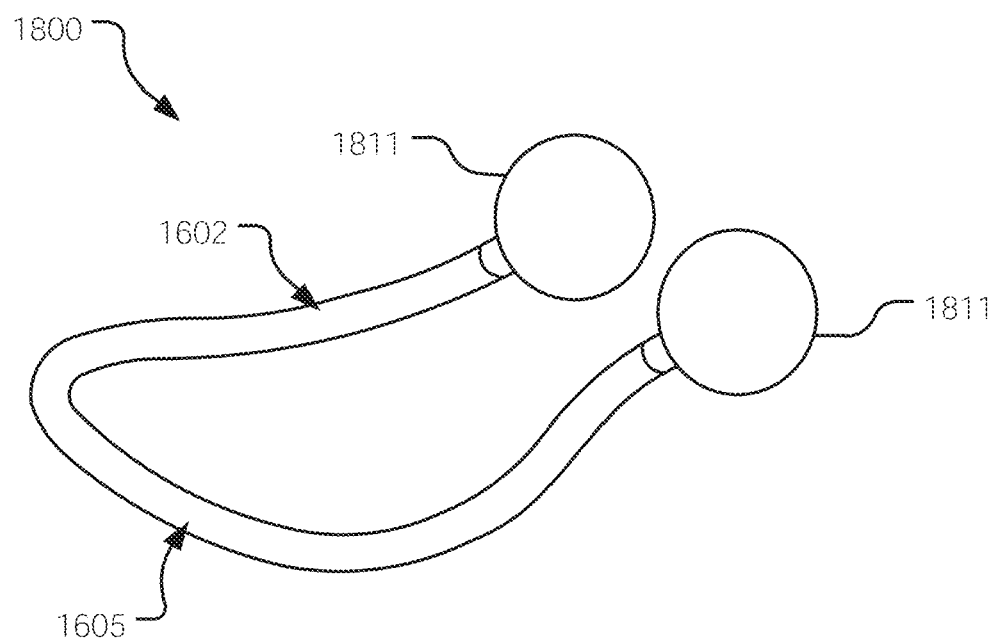

FIG. 18B may depict the exemplary embodiment of FIG. 18A, shown from a bottom perspective view.

Figure 18C:
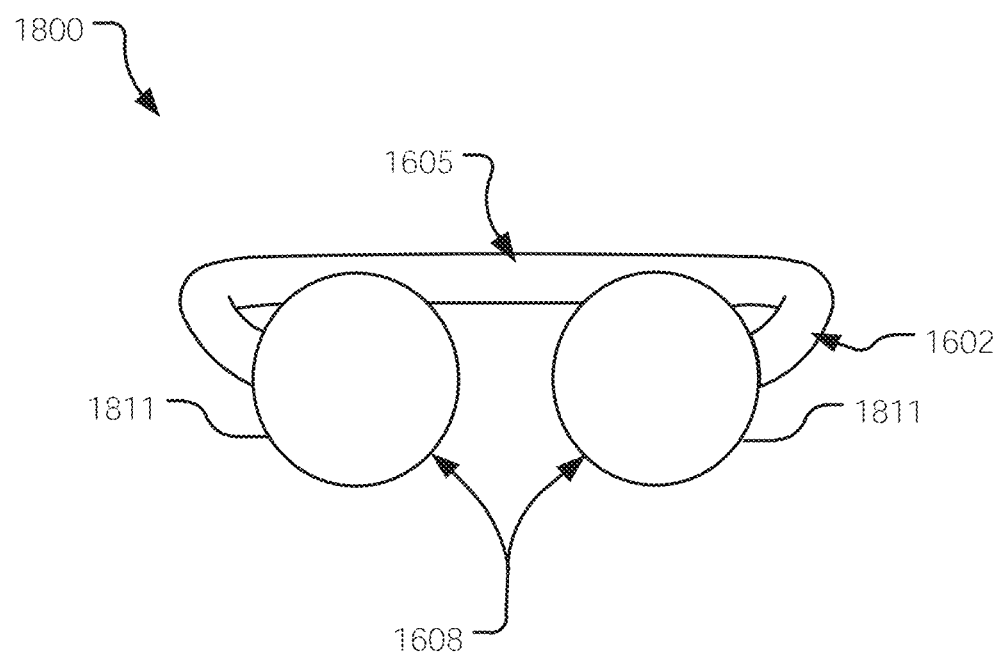

FIG. 18C may depict the exemplary embodiment of FIG. 18A, shown from a front view.

Figure 18D:
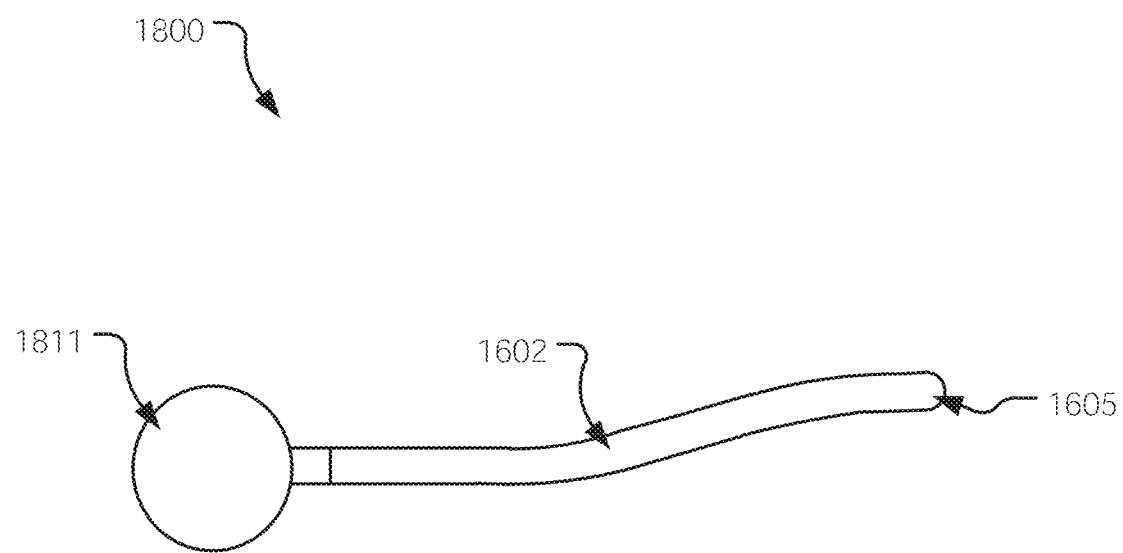

FIG. 18D may depict the exemplary embodiment of FIG. 18A, shown from a side view.

Figure 18E:
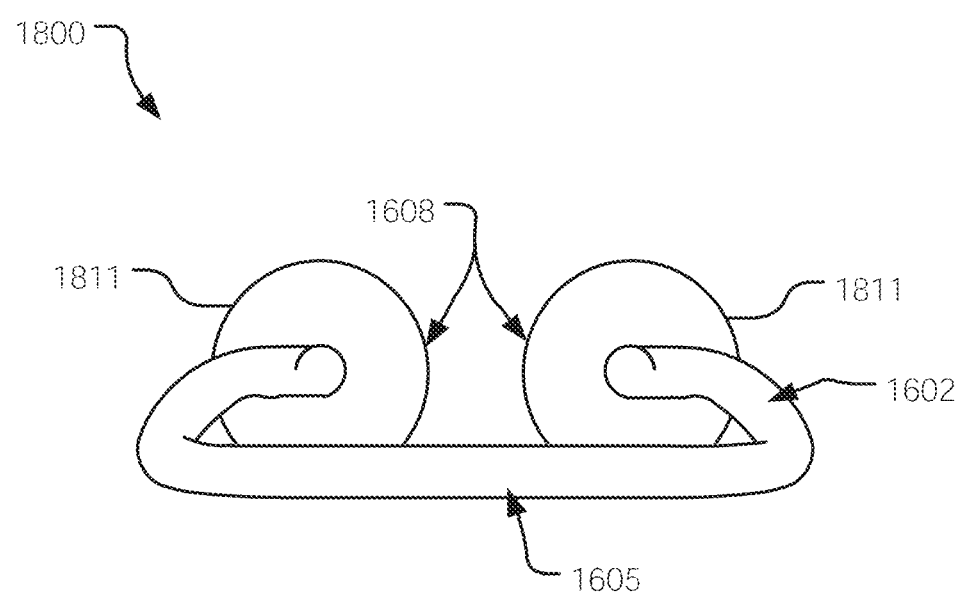

FIG. 18E may depict the exemplary embodiment of FIG. 18A, shown from a back view.

Figure 18F:
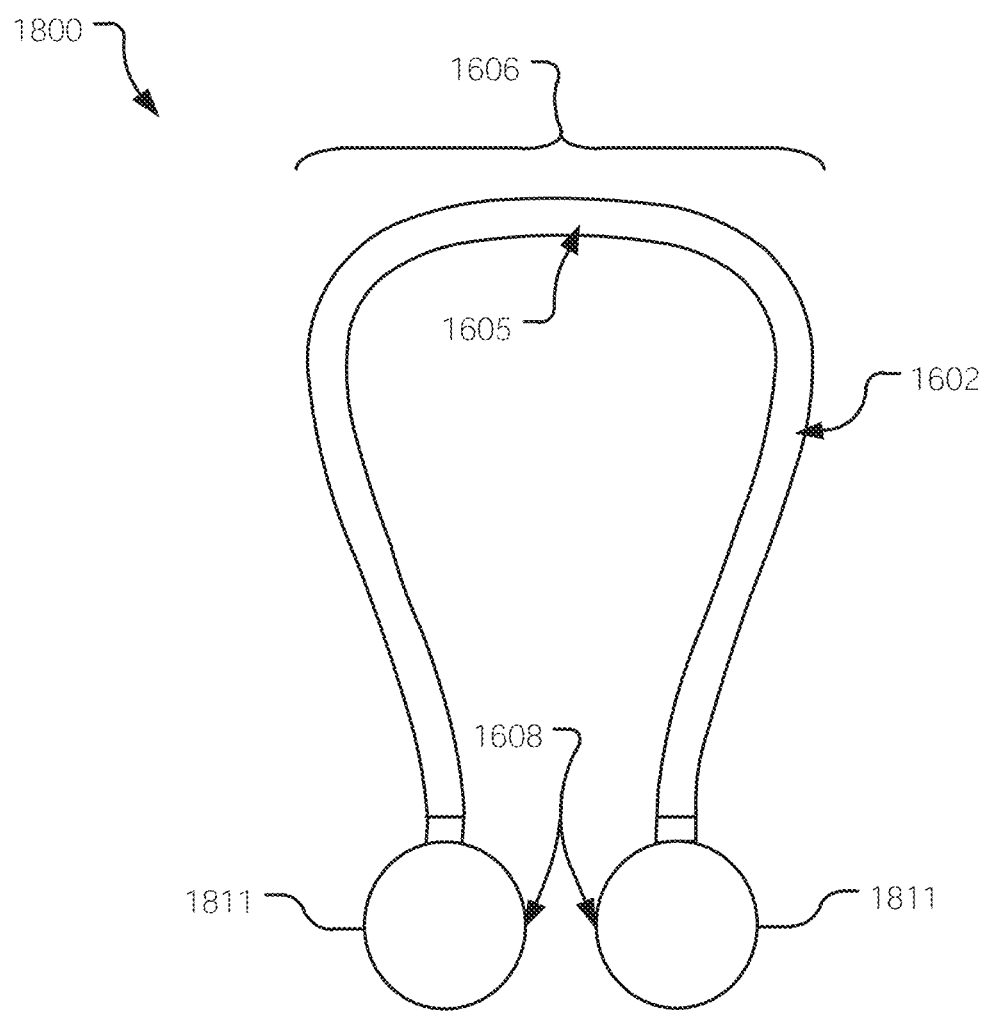

FIG. 18F may depict the exemplary embodiment of FIG. 18A, shown from a top view.

Figure 19A:
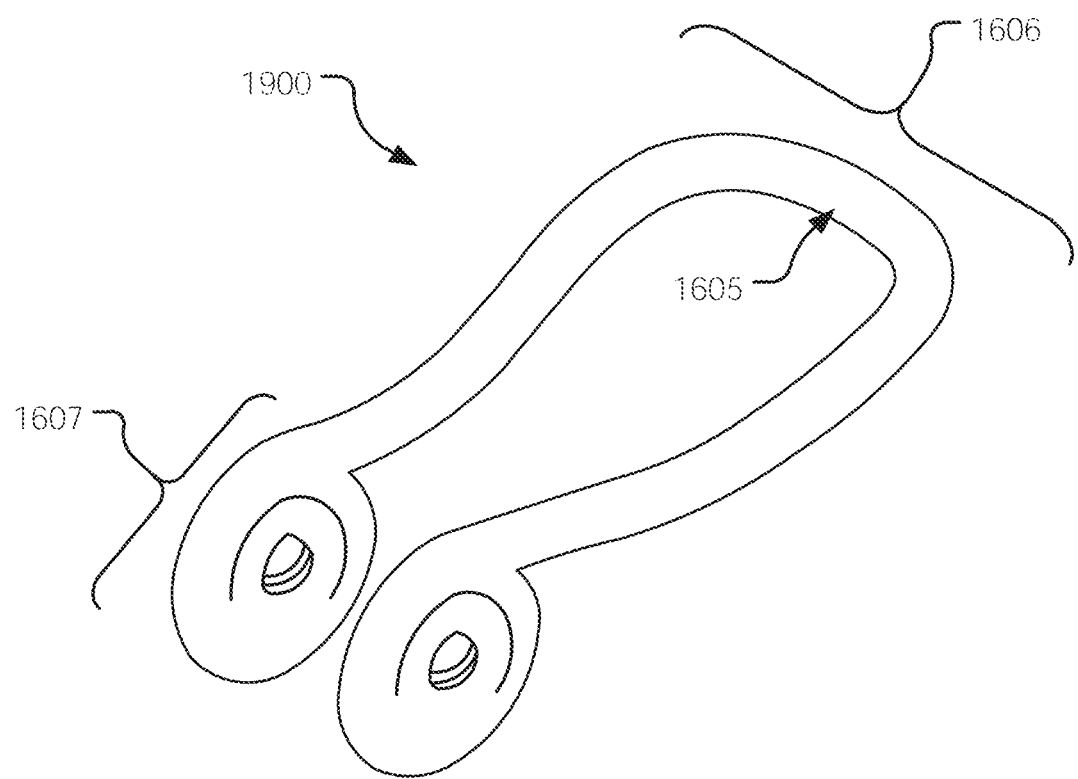

FIG. 19A may depict an exemplary embodiment of a nose-clip, wherein the nose-clip may be coated with a polymer, shown from a top perspective view.

Figure 19B:
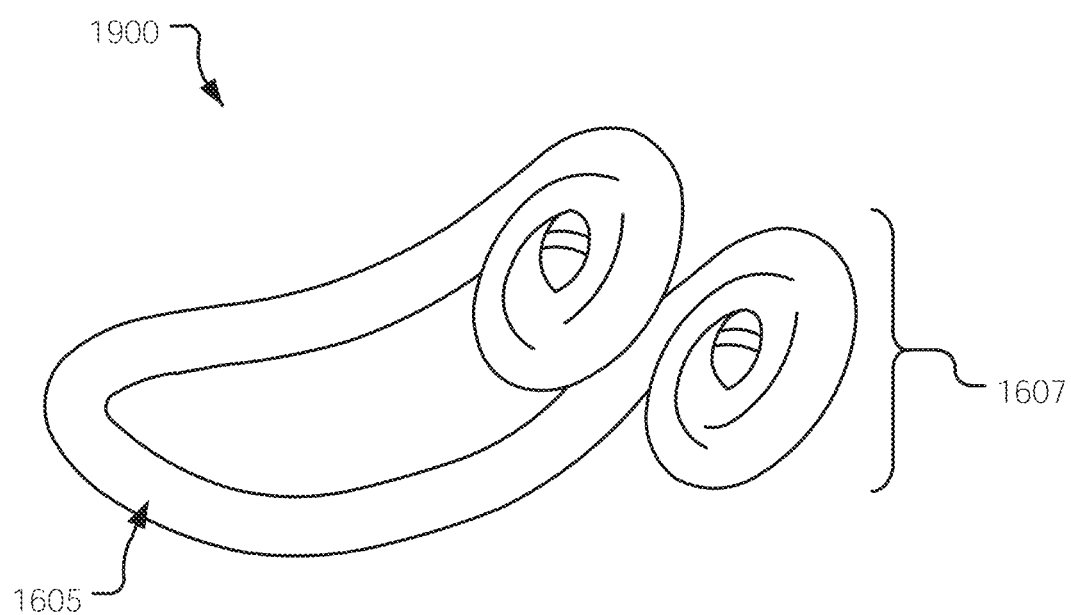

FIG. 19B may depict the exemplary embodiment of FIG. 19A, shown from a bottom perspective view.

Figure 19C:
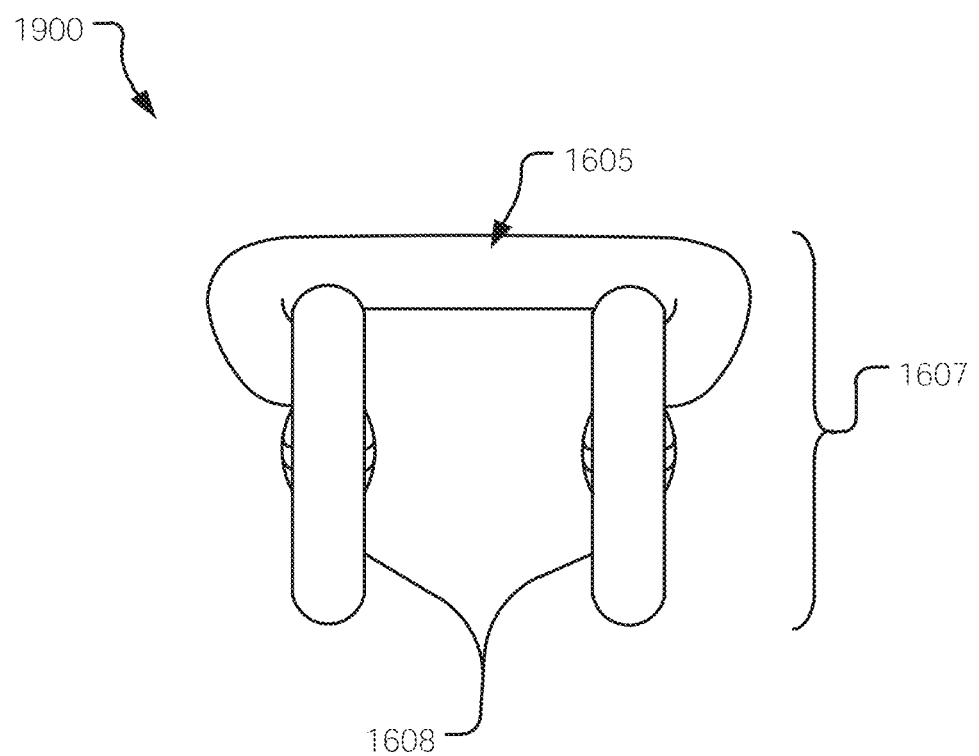

FIG. 19C may depict the exemplary embodiment of FIG. 19A, shown from a front view.

Figure 19D:
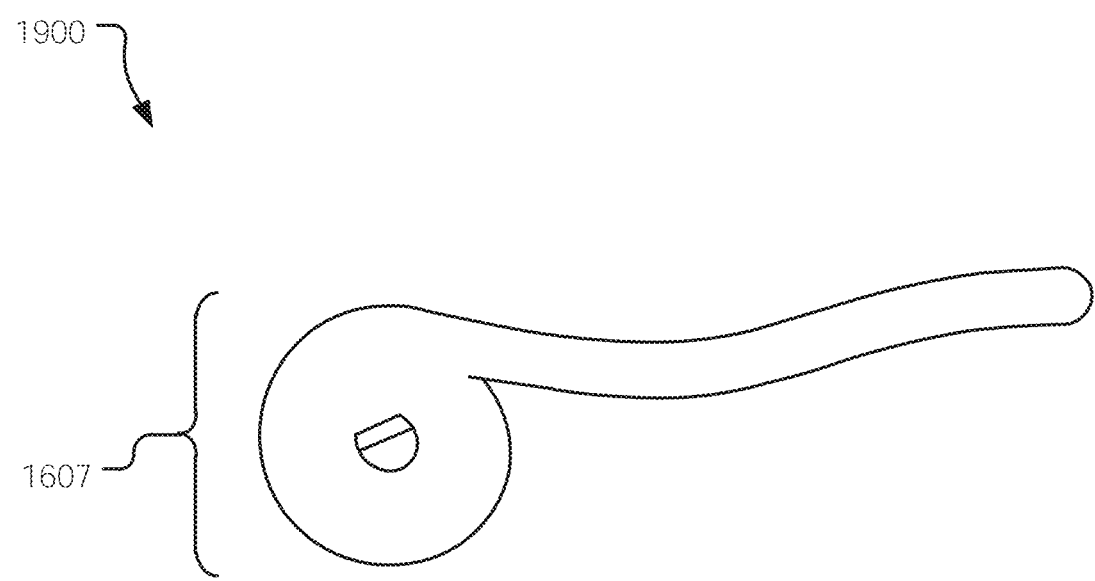

FIG. 19D may depict the exemplary embodiment of FIG. 19A, shown from a side view.

Figure 19E:
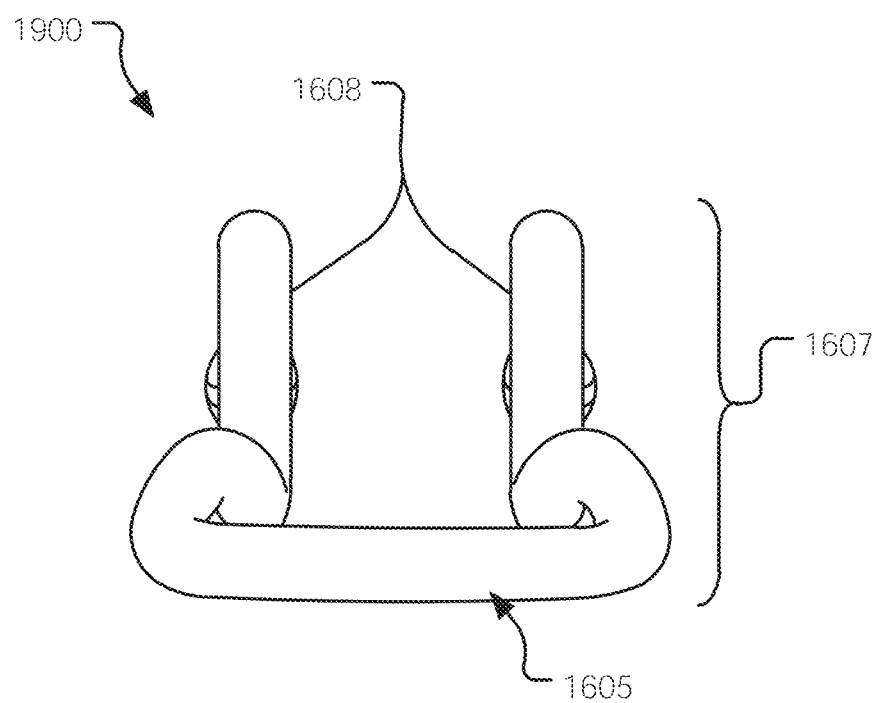

FIG. 19E may depict the exemplary embodiment of FIG. 19A, shown from a back view.

Figure 19F:
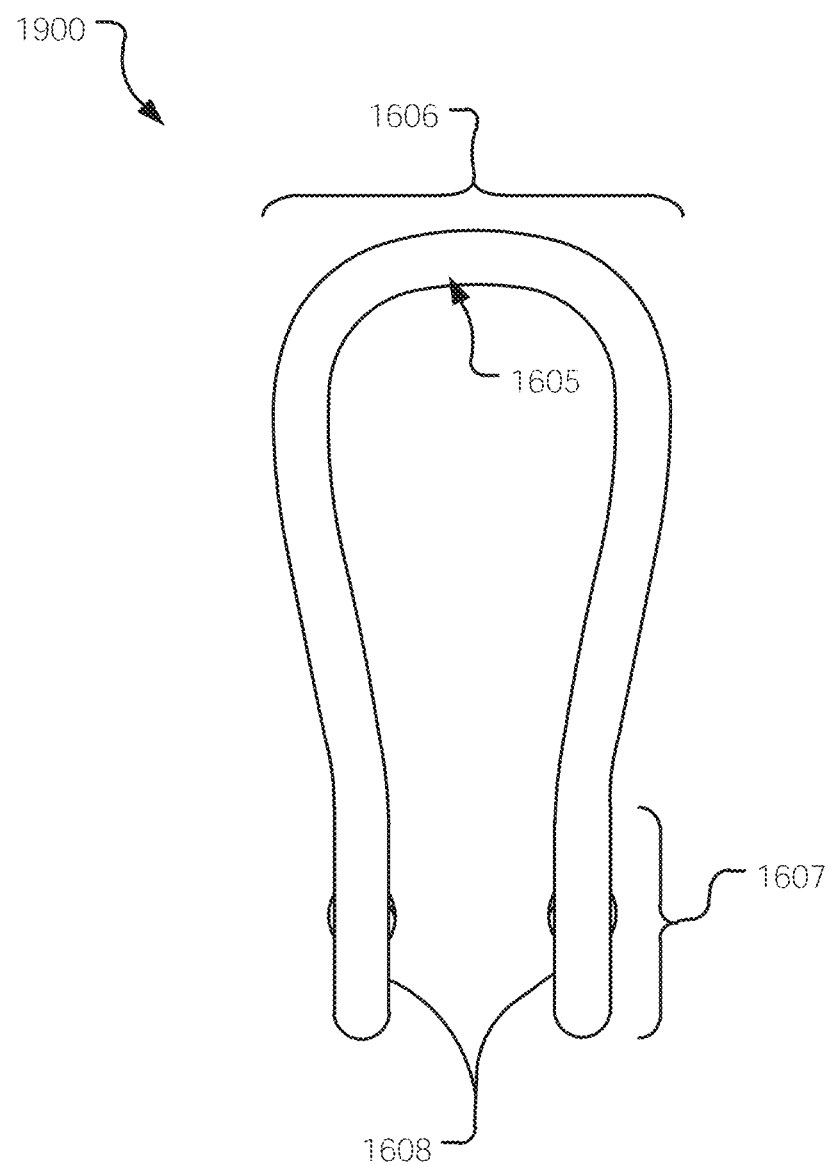

FIG. 19F may depict the exemplary embodiment of FIG. 19A, shown from a top view.

Figure 19G:
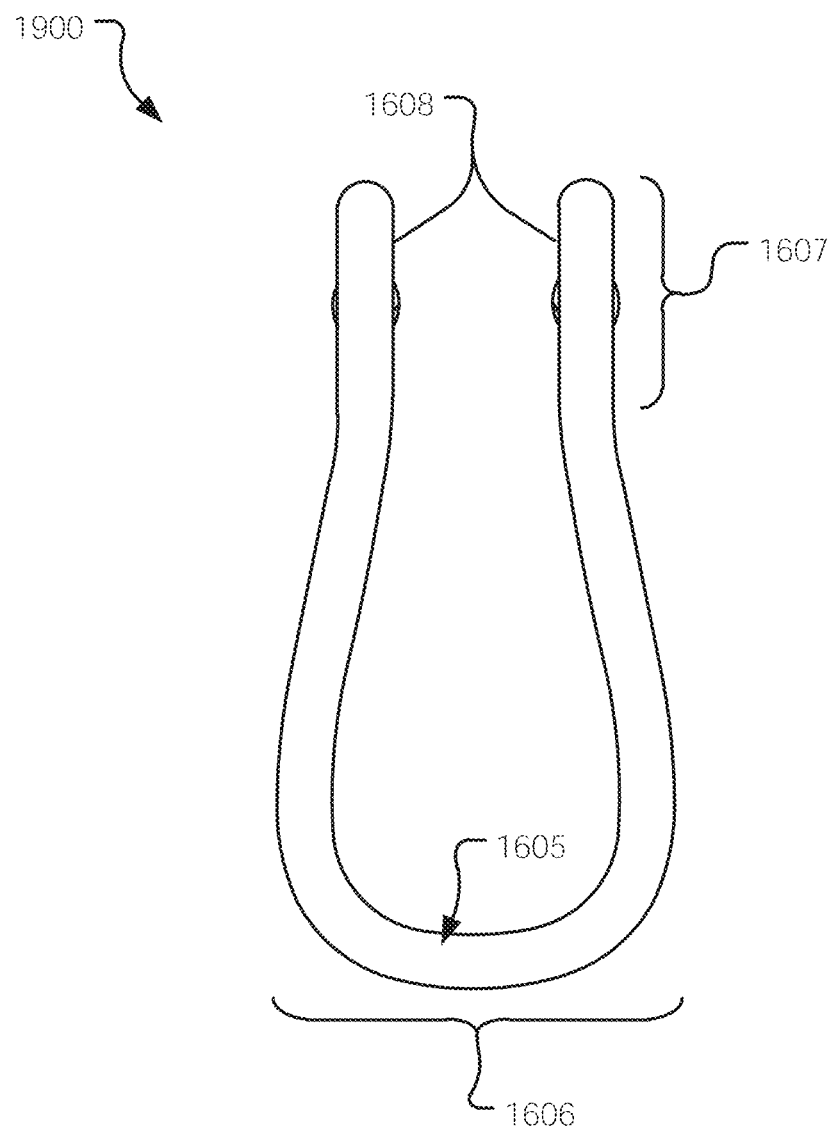

FIG. 19G may depict the exemplary embodiment of FIG. 19A, shown from a bottom view.

Figure 20A:
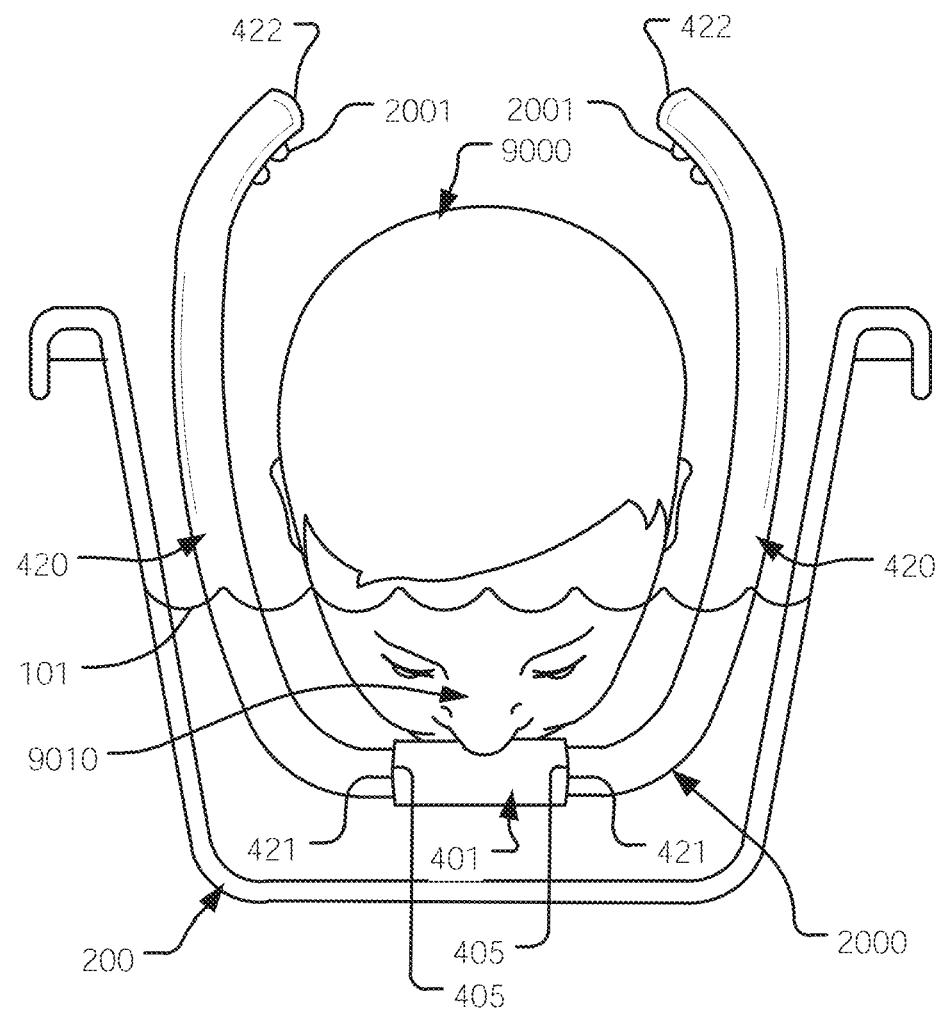

FIG. 20A may depict a cross-sectional view of a face soaking device in use by the user, depicting an independent breathing apparatus.

Figure 20B:
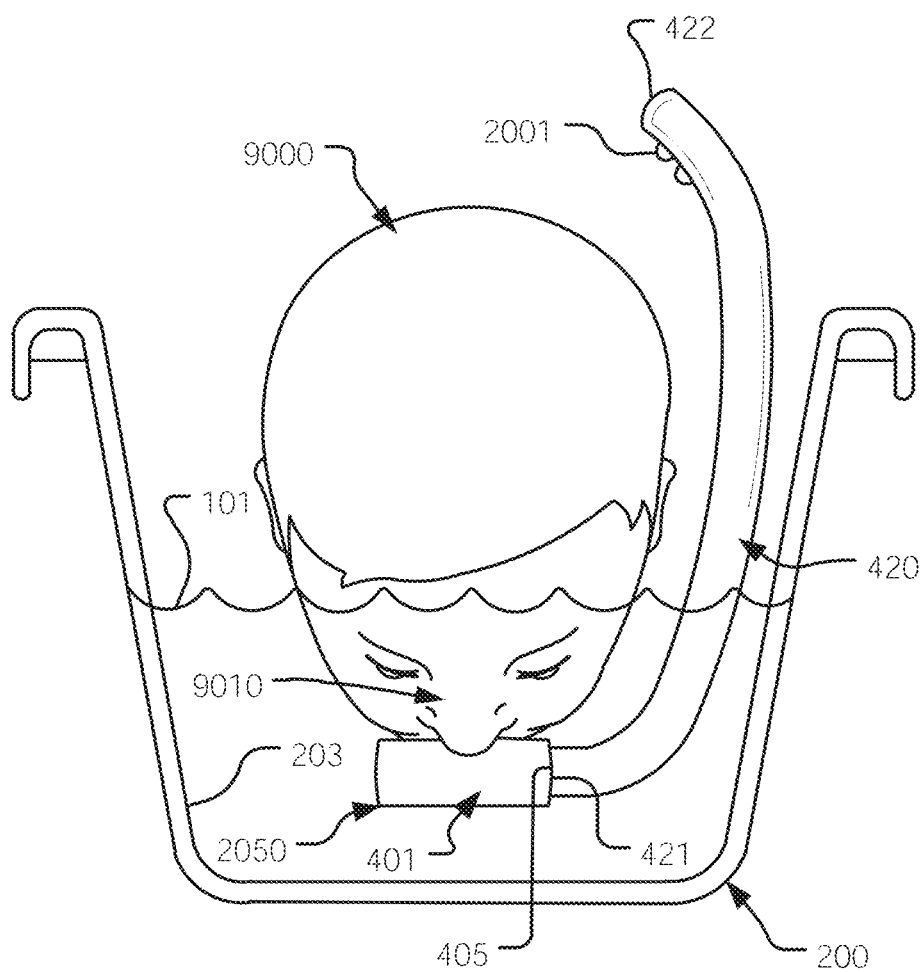

FIG. 20B may depict a cross-sectional view of a face soaking device in use by the user, depicting an independent breathing apparatus.

Figure 21A:
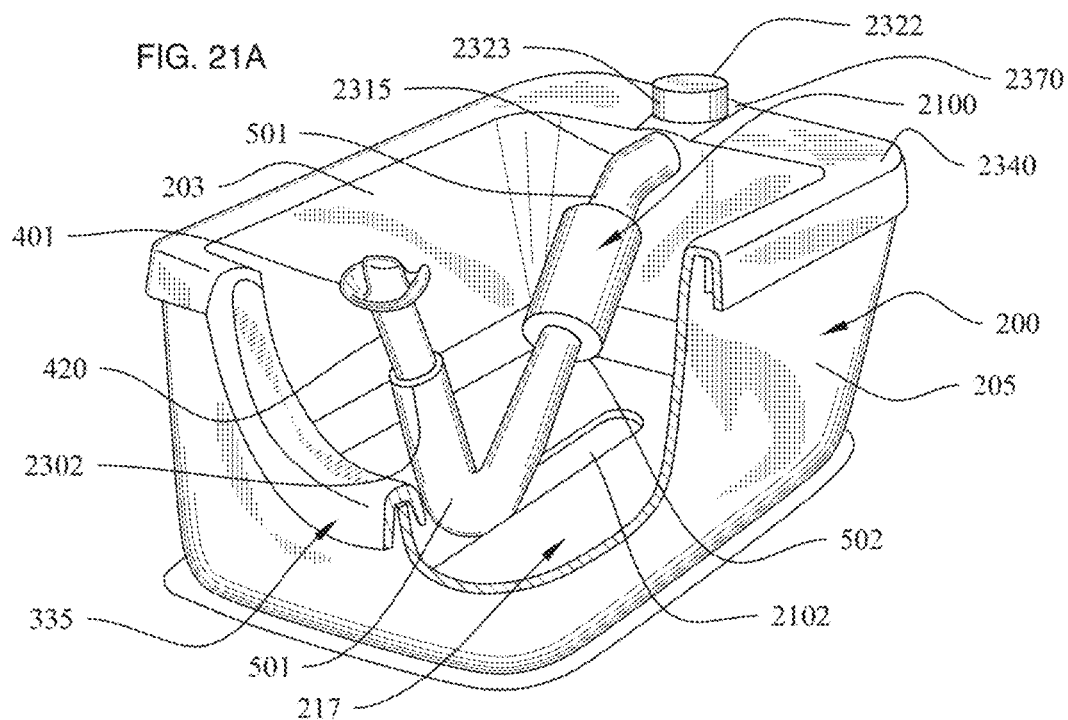

FIG. 21A may depict a face soaking device embodiment, wherein a breathing apparatus may be incorporated (combined) into a head rest subassembly, shown from a perspective view, with a partial cutout view of the vessel.

Figure 21B:
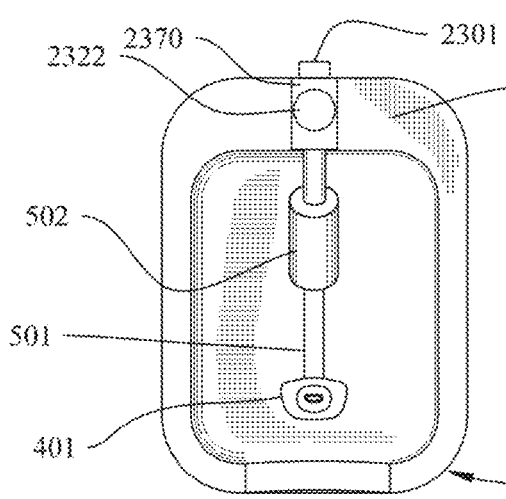

FIG. 21B may depict the embodiment of FIG. 21A, but from a top view.

Figure 21C:
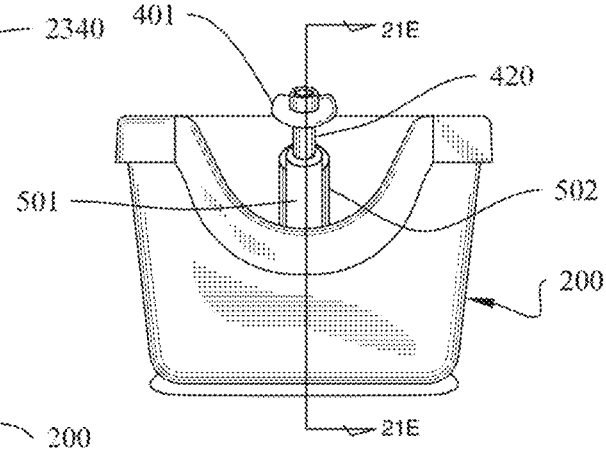

FIG. 21C may depict the embodiment of FIG. 21A, but from a front view. And a sectional line 21E-21E may be shown in FIG. 21C through the combined breathing apparatus with head rest subassembly.

Figure 21D:
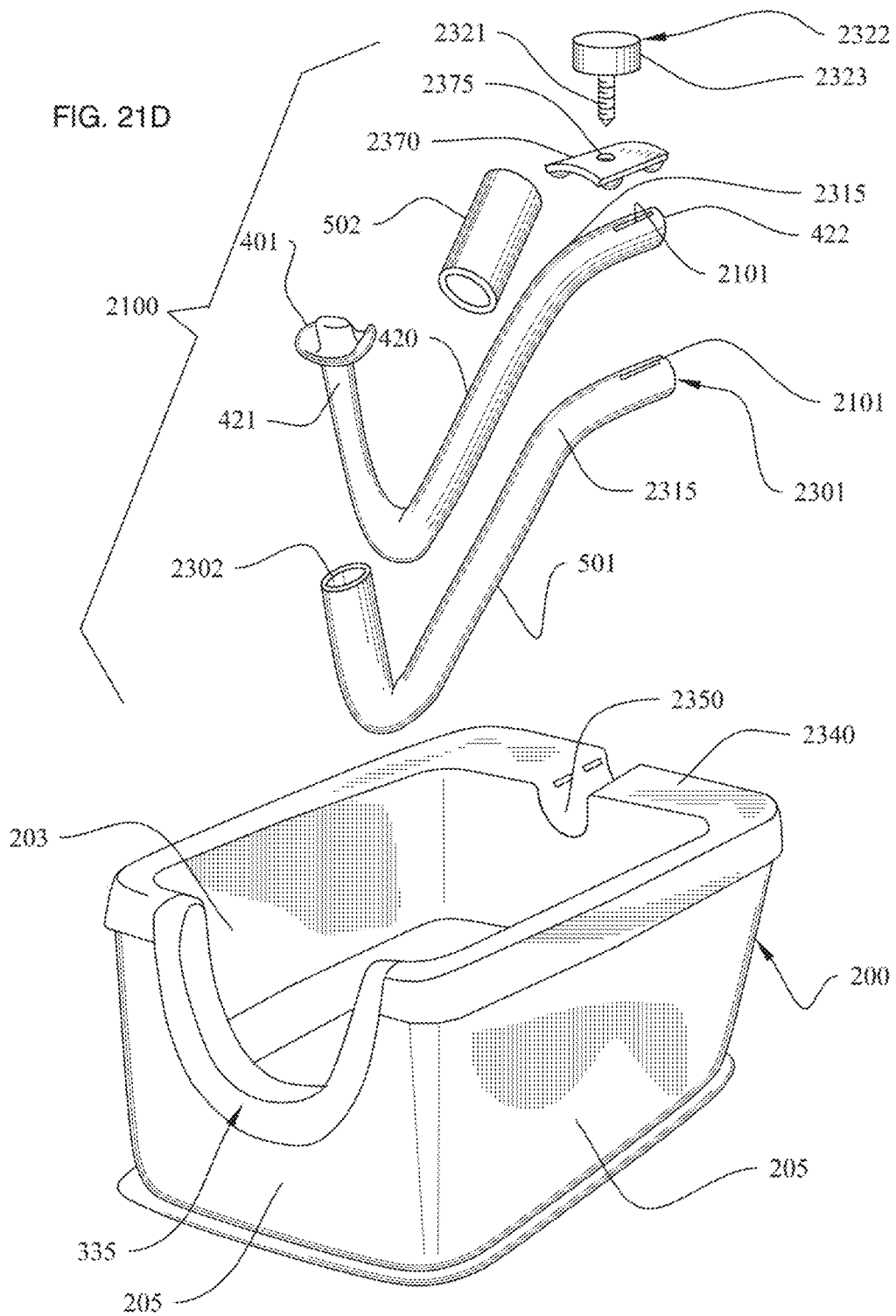

FIG. 21D may depict the embodiment of FIG. 21A, but from an exploded perspective view.

Figure 21E:
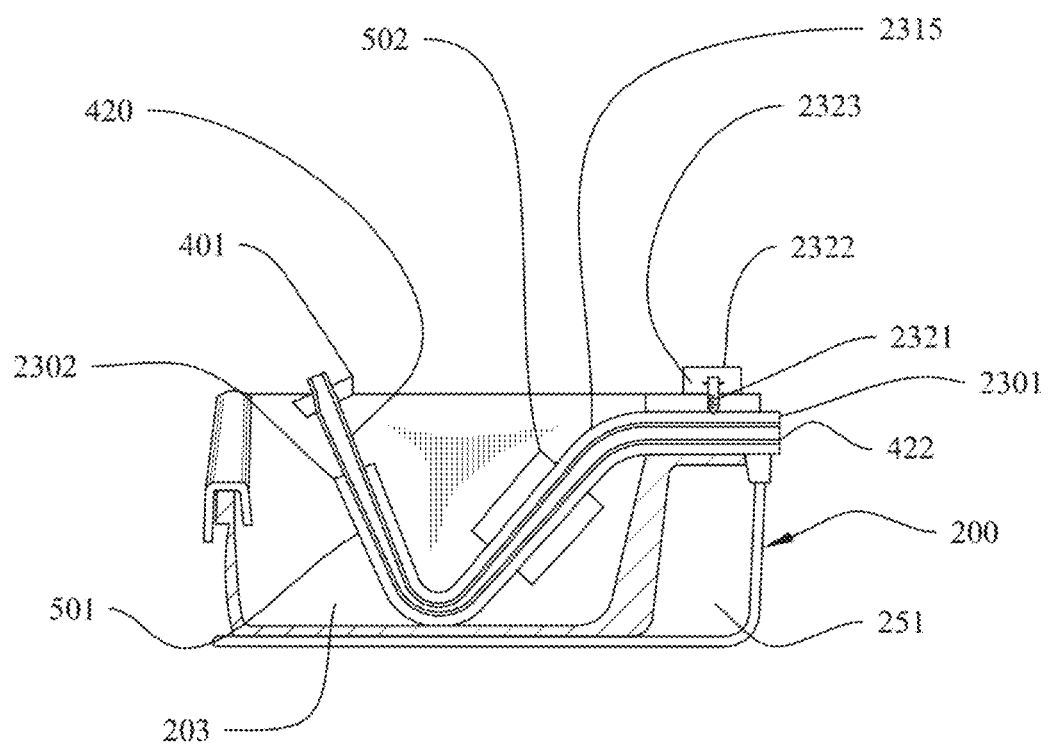

FIG. 21E may depict the embodiment of FIG. 21A, showing the view along sectional line 21E-21E, which may show a longitudinal side cross sectional view.

Figure 22A:
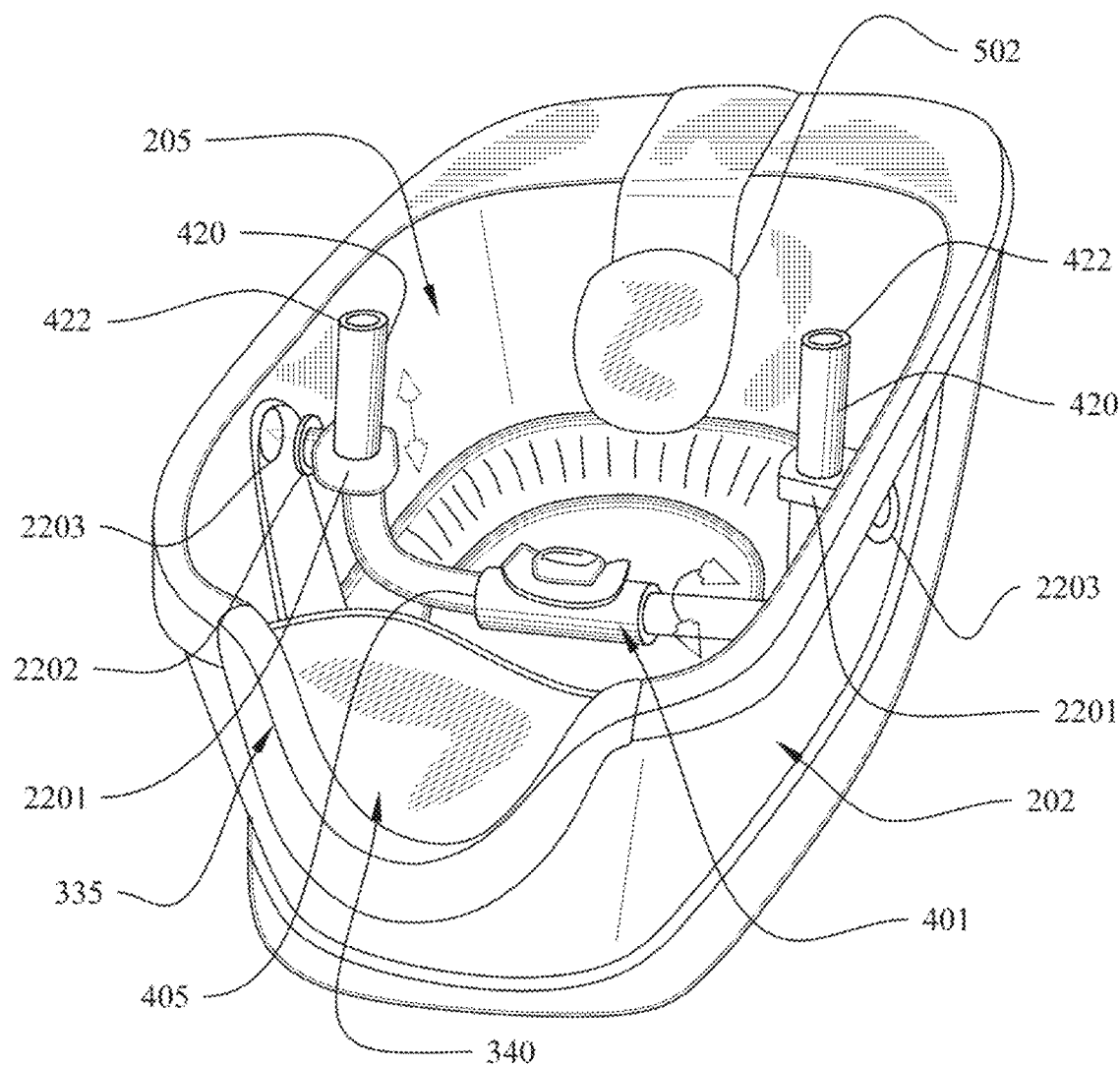

FIG. 22A may depict an embodiment of an adjustable breathing apparatus, shown from a perspective view.

FIG. 22B may depict an embodiment of an adjustable breathing apparatus, shown from a close up perspective view.

FIG. 22C may depict an embodiment of an adjustable breathing apparatus, shown from a close up perspective partial view a side wall tab in a transparent view inside of a channel sleeve and a comparison view without the channel sleeve.

FIG. 22D may depict an embodiment of an adjustable breathing apparatus, shown from a perspective view, while the breathing apparatus may be in a resting configuration.

FIG. 22E may depict an embodiment of an adjustable breathing apparatus, shown from a perspective view, while the breathing apparatus may be in an adjustable loaded configuration.

Figure 22F:
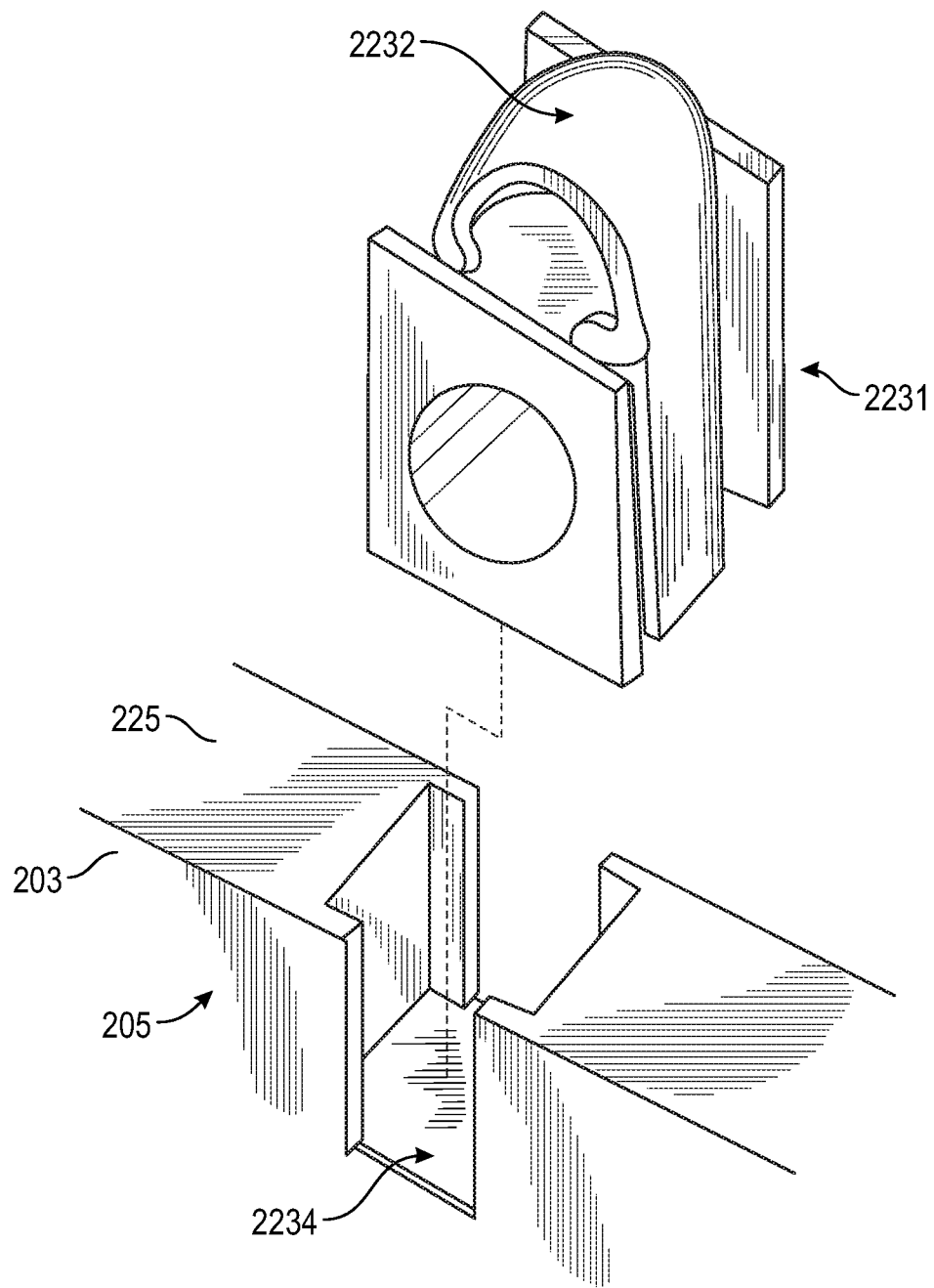

FIG. 22F may depict a top perspective view of another embodiment of at least one vessel-tube-hose-connector.

Figure 23A:
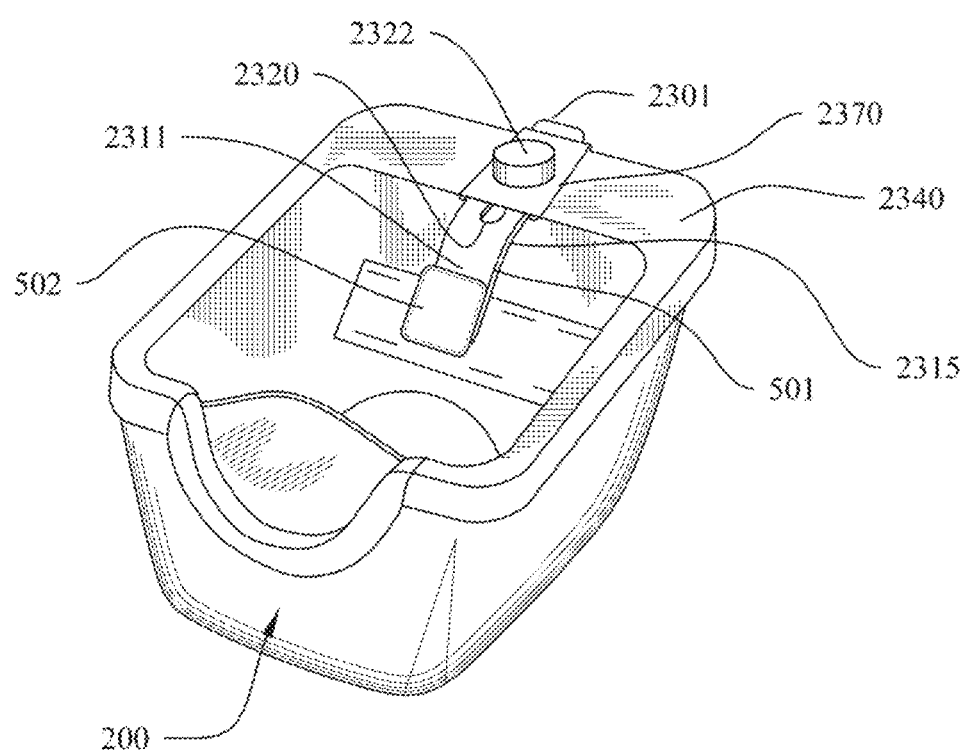

FIG. 23A may depict an exemplary embodiment of a head rest subassembly, shown from a perspective view.

Figure 23B:
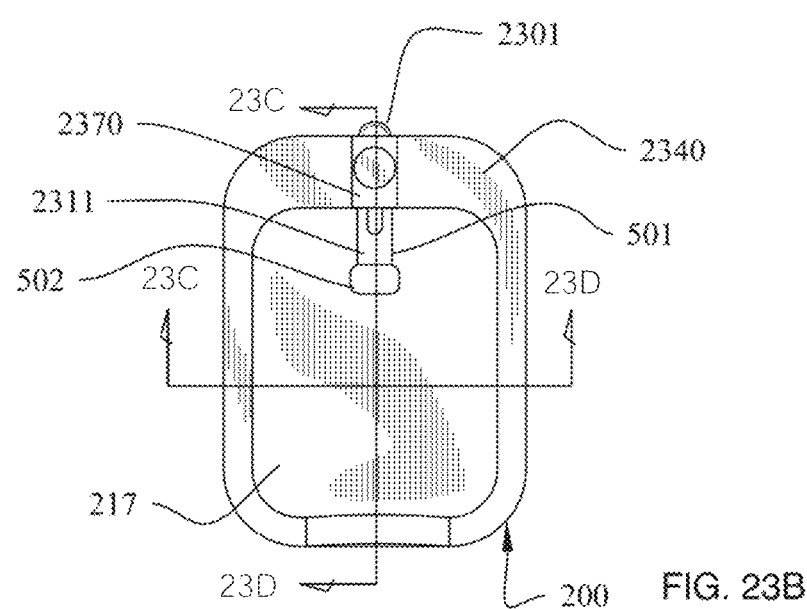

FIG. 23B may depict the exemplary embodiment of FIG. 23A, but shown from a top view. Two sectionals lines may be shown in FIG. 23B, sectional line 23C-23C and sectional line 23D-23D. Sectional line 23C-23C may be transverse-width sectional line and sectional line 23D-23D may be a longitudinal sectional-line through the head rest subassembly.

Figure 23C:
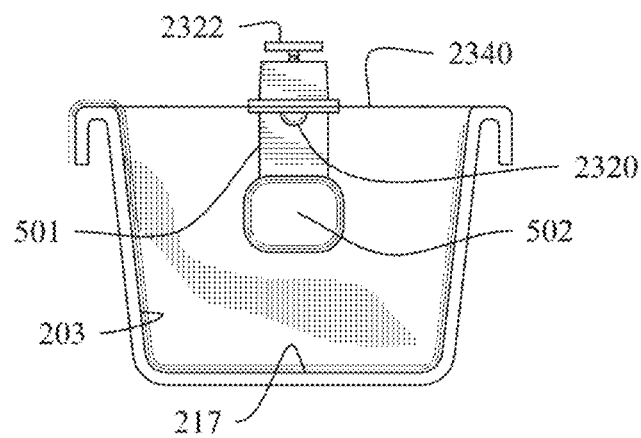

FIG. 23C may depict a transverse-width cross-sectional front view along sectional line 23C-23C from FIG. 23B.

Figure 23D:
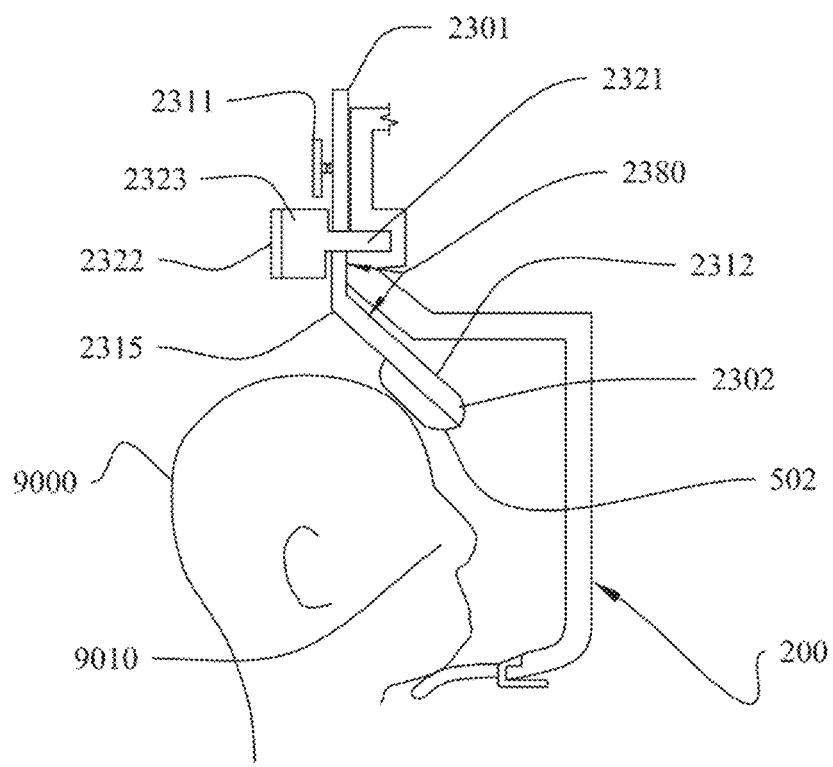

FIG. 23D may depict a longitudinal cross-sectional side view along sectional line 23D-23D from FIG. 23B. A cross-section of the head of the user may also be shown in FIG. 23D, while resting upon a portion of a comfortable exterior surface of a support member of the head rest subassembly.

Figure 23E:
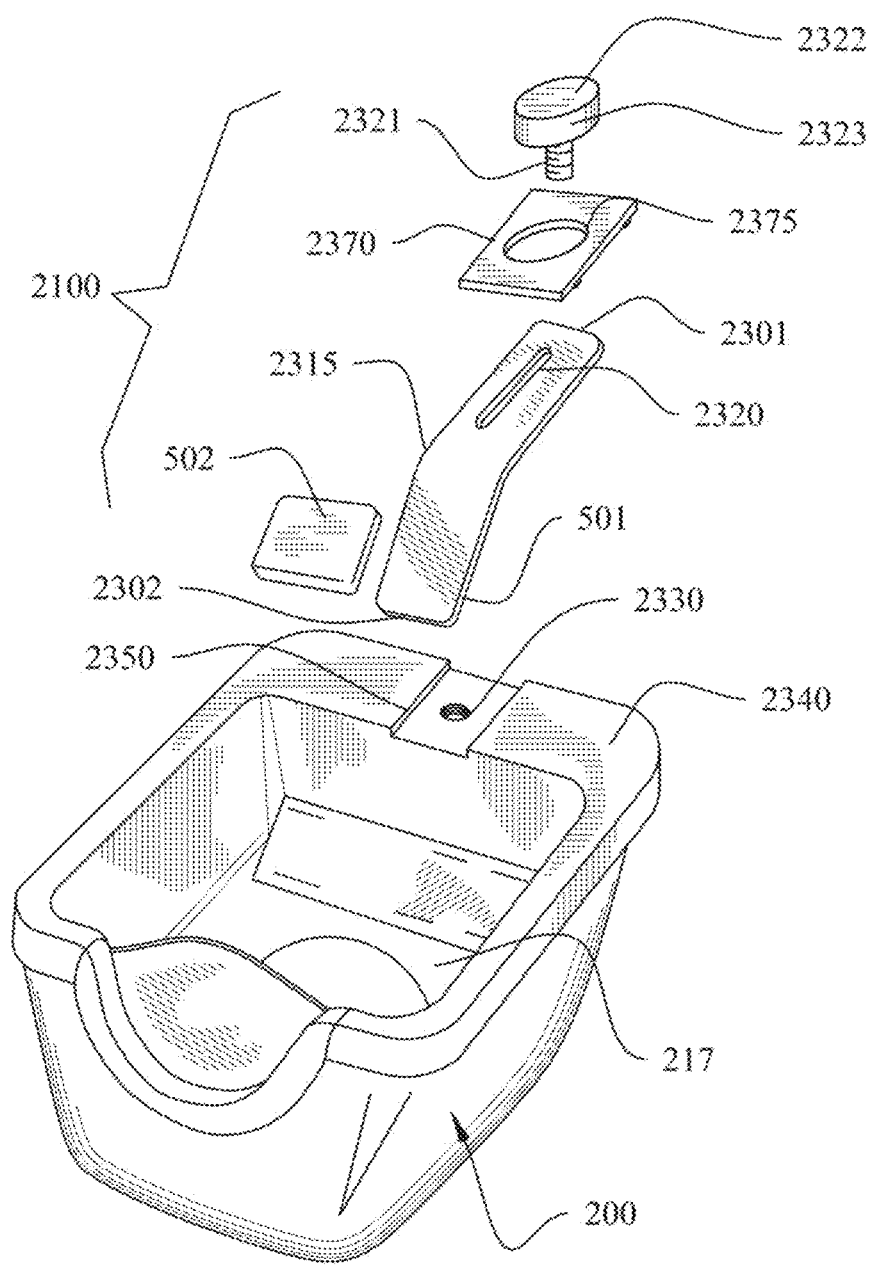

FIG. 23E may depict the exemplary embodiment of FIG. 23A, but shown from an exploded perspective view.

FIG. 23F may depict a longitudinal side cross-sectional view that may illustrate a potential backwards sliding problem of a certain head rest subassembly.

Figure 24A:
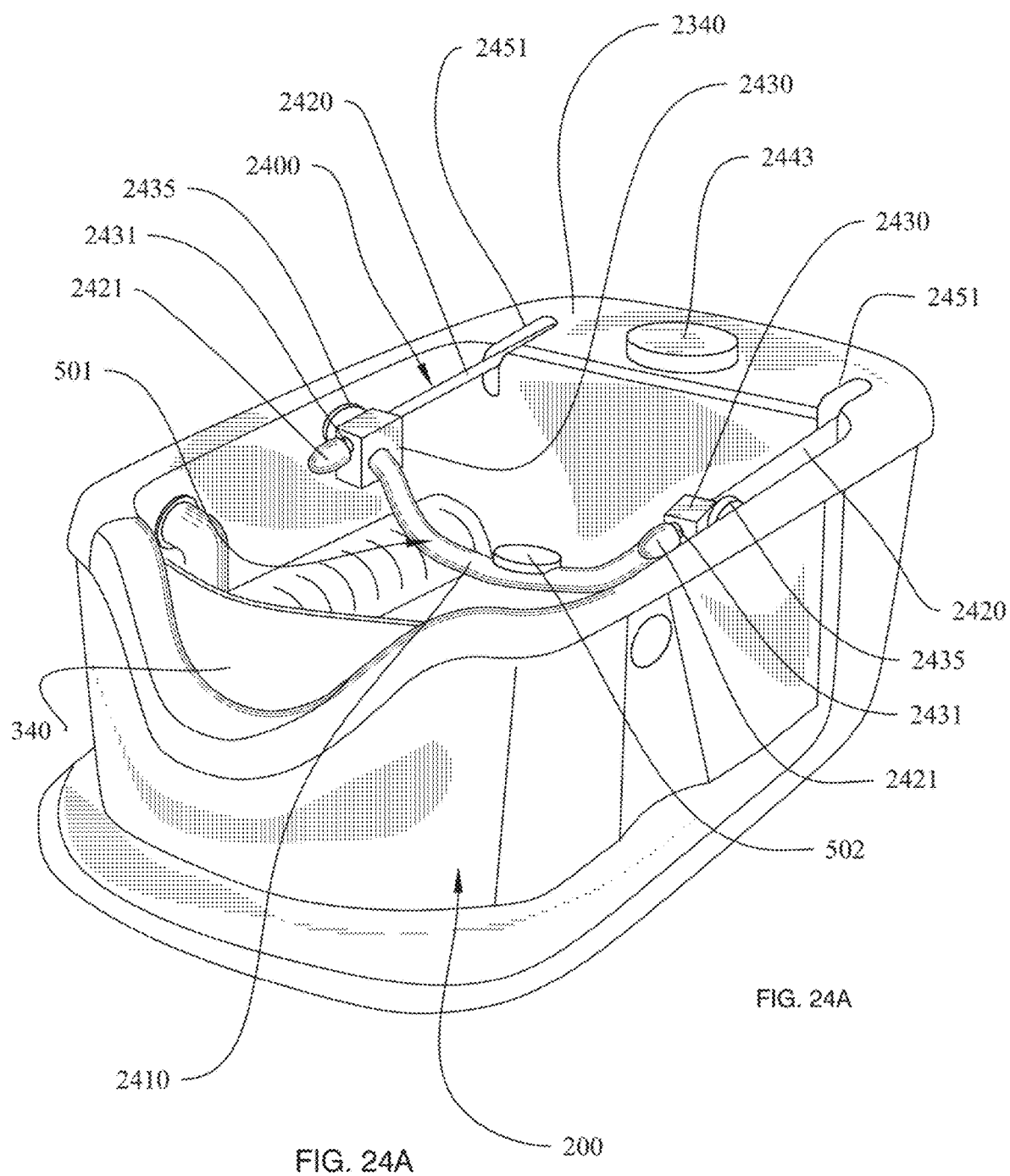

FIG. 24A may depict an assembled overall perspective view of a face soaking device with a head rest subassembly embodiment that may alleviate the problem identified in FIG. 23F.

Figure 24B:
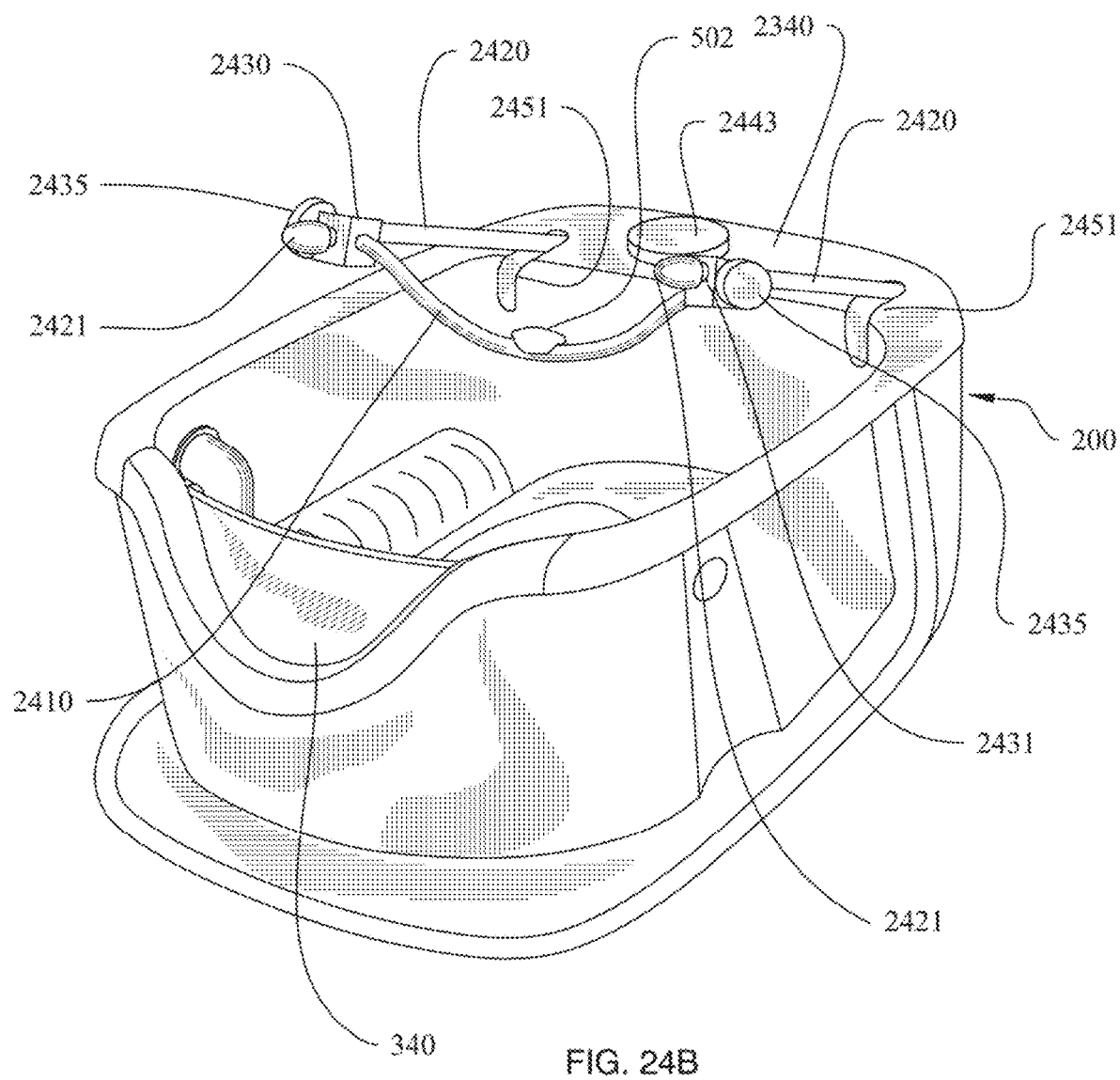

FIG. 24B may depict the head rest subassembly embodiment of FIG. 24A, but with a portion of the head rest subassembly tilted upwards.

Figure 24C:
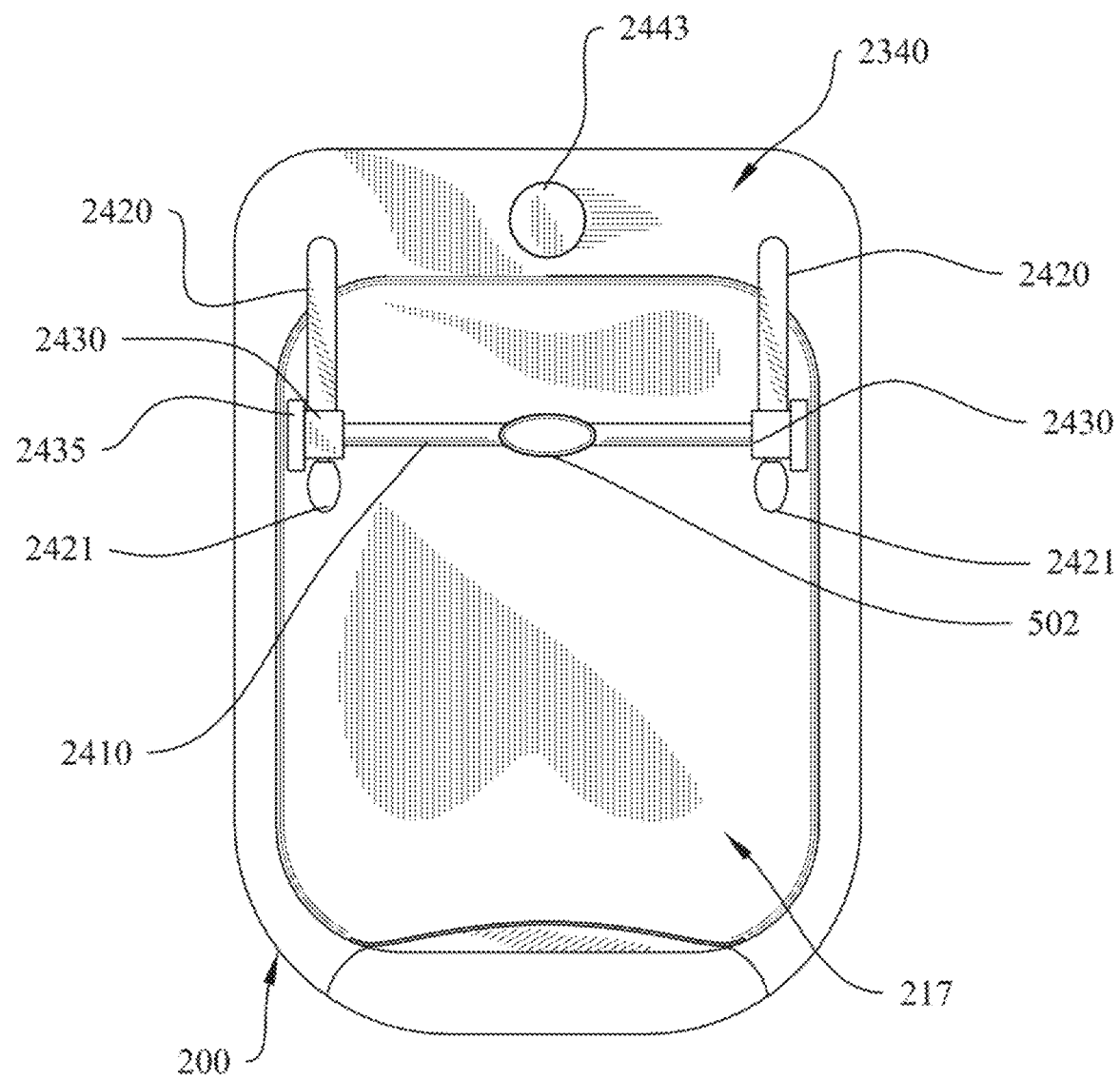

FIG. 24C may depict the head rest subassembly embodiment of FIG. 24A, but from a top view.

Figure 24D:
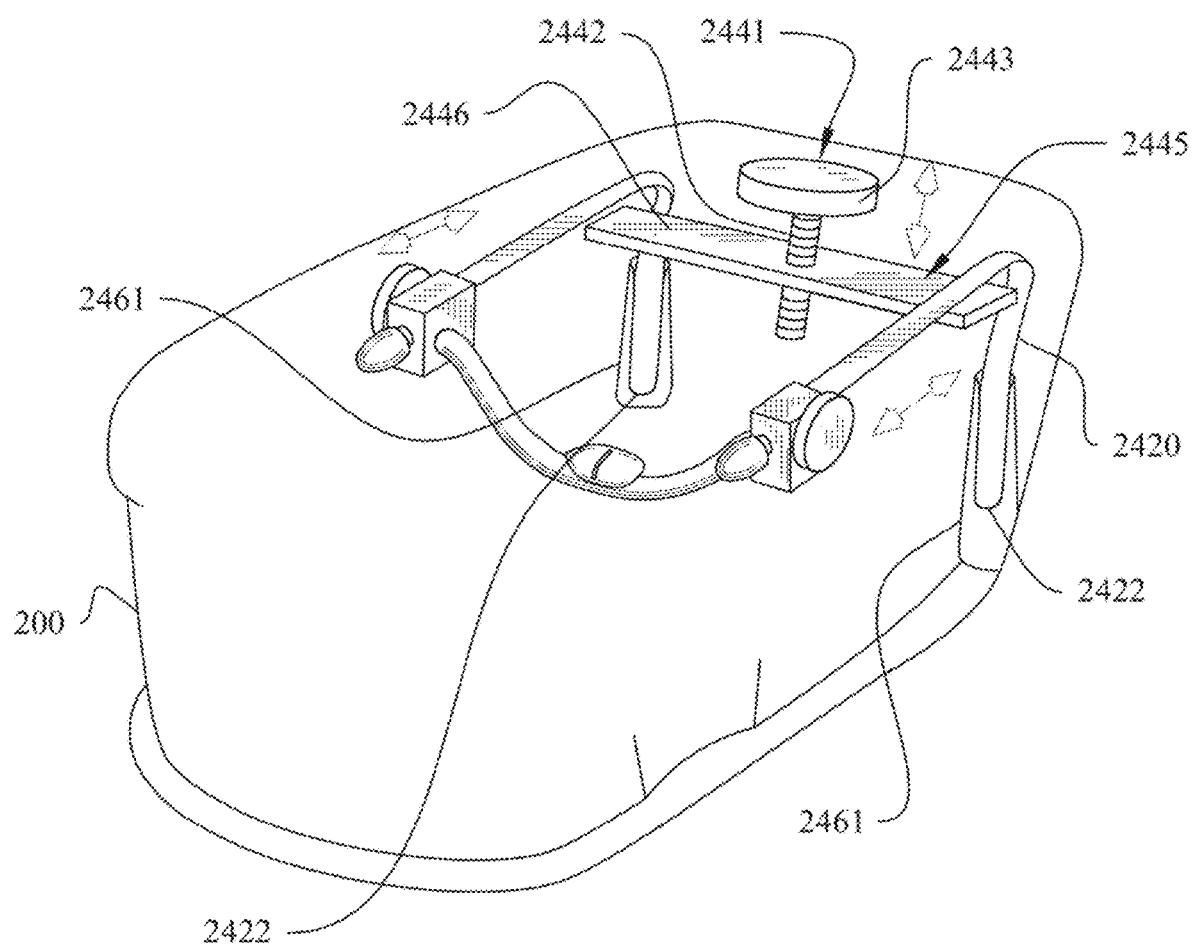

FIG. 24D may depict the head rest subassembly embodiment of FIG. 24A, but showing a transparent view within a mechanical compartment.

FIG. 25A may depict a face soaking device with an alternative embodiment head rest subassembly; shown from a top perspective view.

FIG. 25B may depict the head rest subassembly of FIG. 25A, shown from a top perspective view.

FIG. 25C may depict the head rest subassembly of FIG. 25A, but shown from an exploded top perspective view.

FIG. 25D may depict an alternative embodiment of a head rest subassembly, shown from an exploded top perspective view. A support member may be adjusted vertically, wherein the support member may a component of the head rest subassembly.

FIG. 25E may depict an alternative embodiment of a head rest subassembly, shown from side (right and left) view. A support member may be adjusted vertically and/or adjusted in a forwards or backwards direction with respect to a front of the face soaking device.

FIG. 25F may depict the embodiment of FIG. 25E, but shown as a cross-sectional view along sectional line 25F-25F shown in FIG. 25E. This cross-sectional view may depict how the support member may be pivoted to achieve vertical adjustment and/or forwards or backwards adjustment.

Figure 25G:
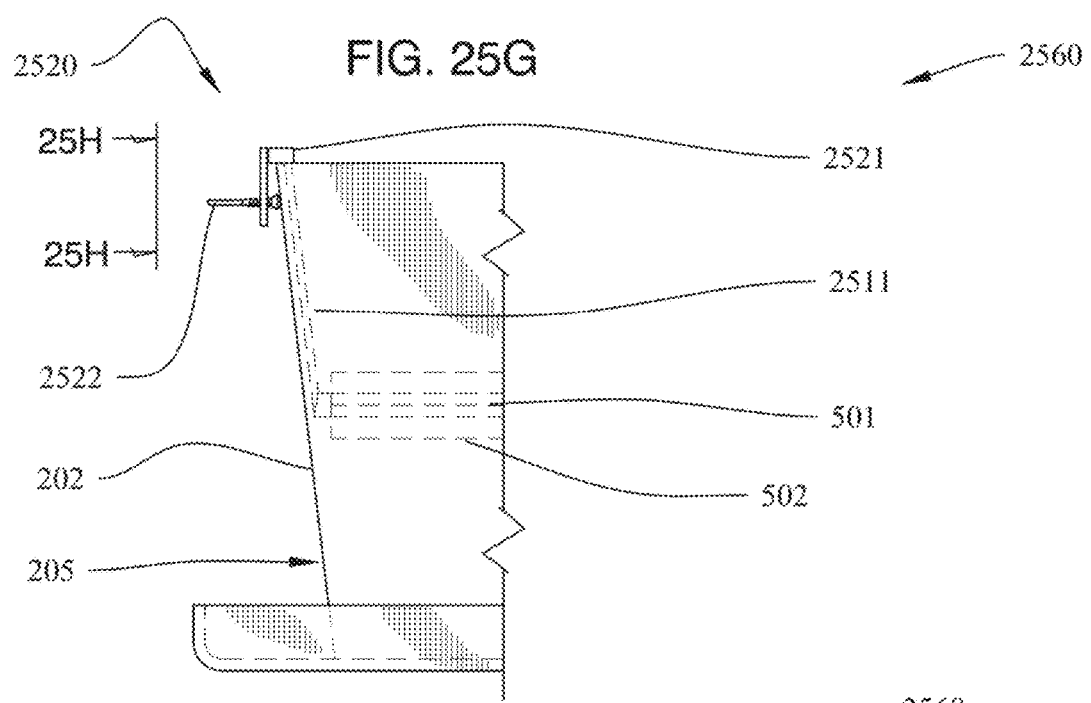

FIG. 25G may depict an alternative embodiment of a head rest subassembly, shown from side rear view. A support member may be adjusted vertically and/or adjusted in a forwards or backwards direction with respect to the front of the face soaking device. FIG. 25G may also depict sectional line 25H-25H.

Figure 25H:
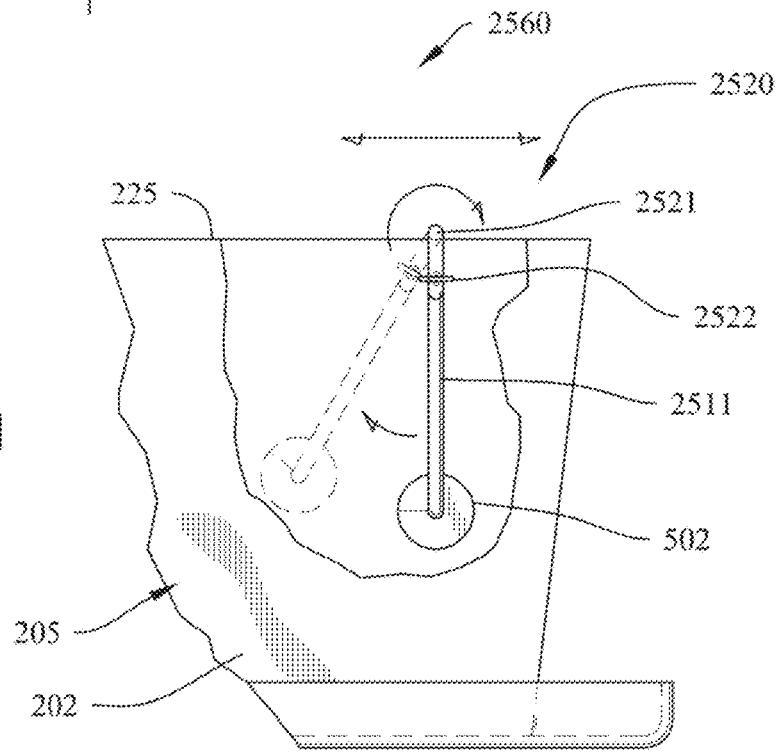

FIG. 25H may depict the embodiment of FIG. 25G, but shown as a cross-sectional view along sectional line 25H-25H. This cross-sectional view may depict how the support member may be pivoted to achieve vertical adjustment and/or forwards or backwards adjustment.

FIG. 26A may depict one or more of a forwards-backwards adjust means and/or a height adjust means for the support member, using a track and flange embodiment, shown from a cross-sectional view from right to left.

FIG. 26B may depict a height adjust means for the support member, using a telescoping strut embodiment, shown from a cross-sectional view from right to left.

Figure 26C:
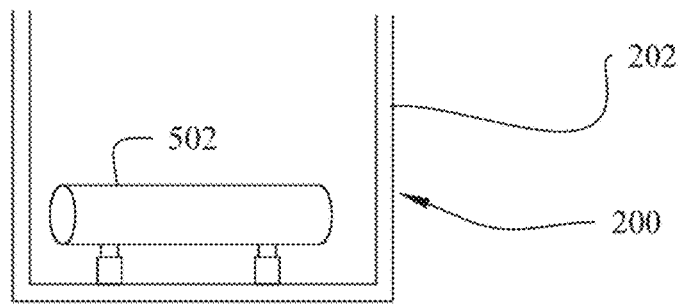

FIG. 26C may depict a height adjust means for the support member, using a telescoping strut embodiment, shown from a cross-sectional view from right to left.

Figure 26D:
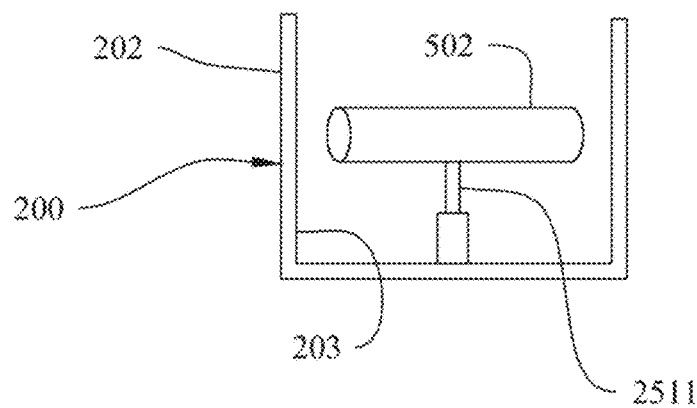

FIG. 26D may depict a height adjust means for the support member, using a telescoping strut embodiment, shown from a cross-sectional view from right to left.

Figure 26E:
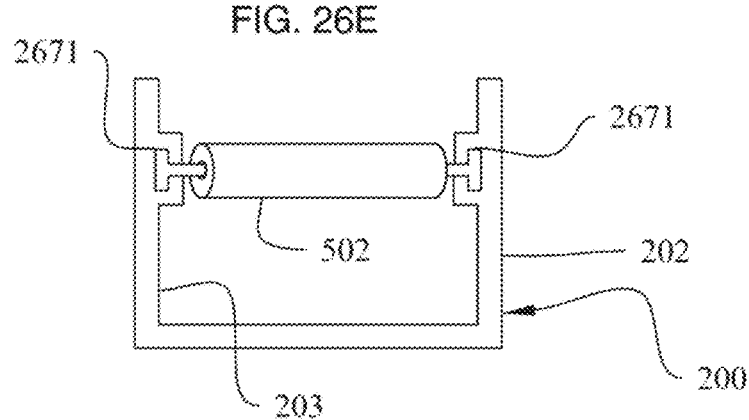

FIG. 26E may depict one or more of a forwards-backwards adjust means and/or a height adjust means for the support member, using a track and flange embodiment, shown from a cross-sectional view from right to left.

Figure 26F:
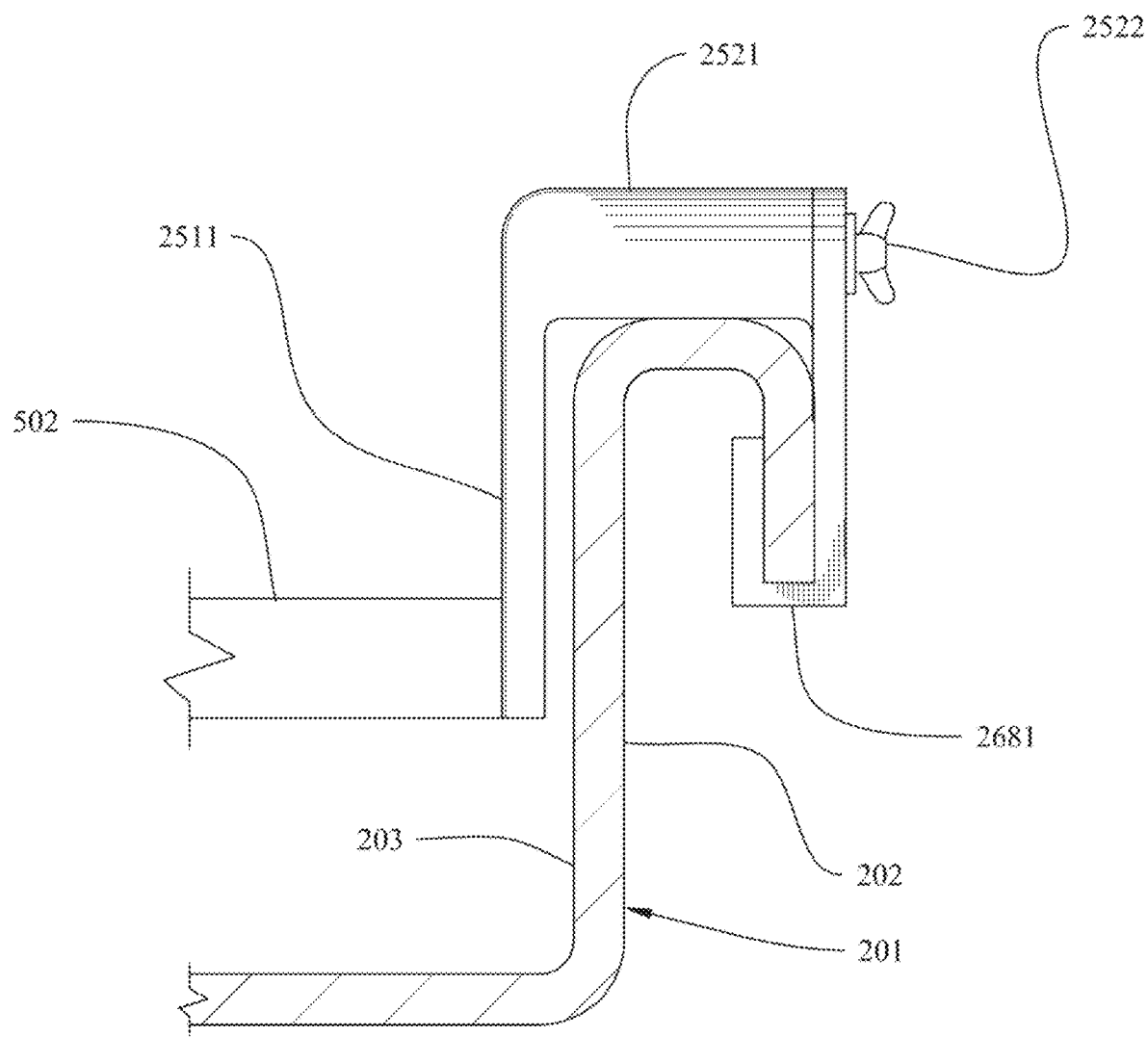

FIG. 26F may depict a height adjust means and a forwards-backwards adjust means for the support member, using a pivotable locking means, shown from a cross-sectional view from right to left.

Figure 27A:
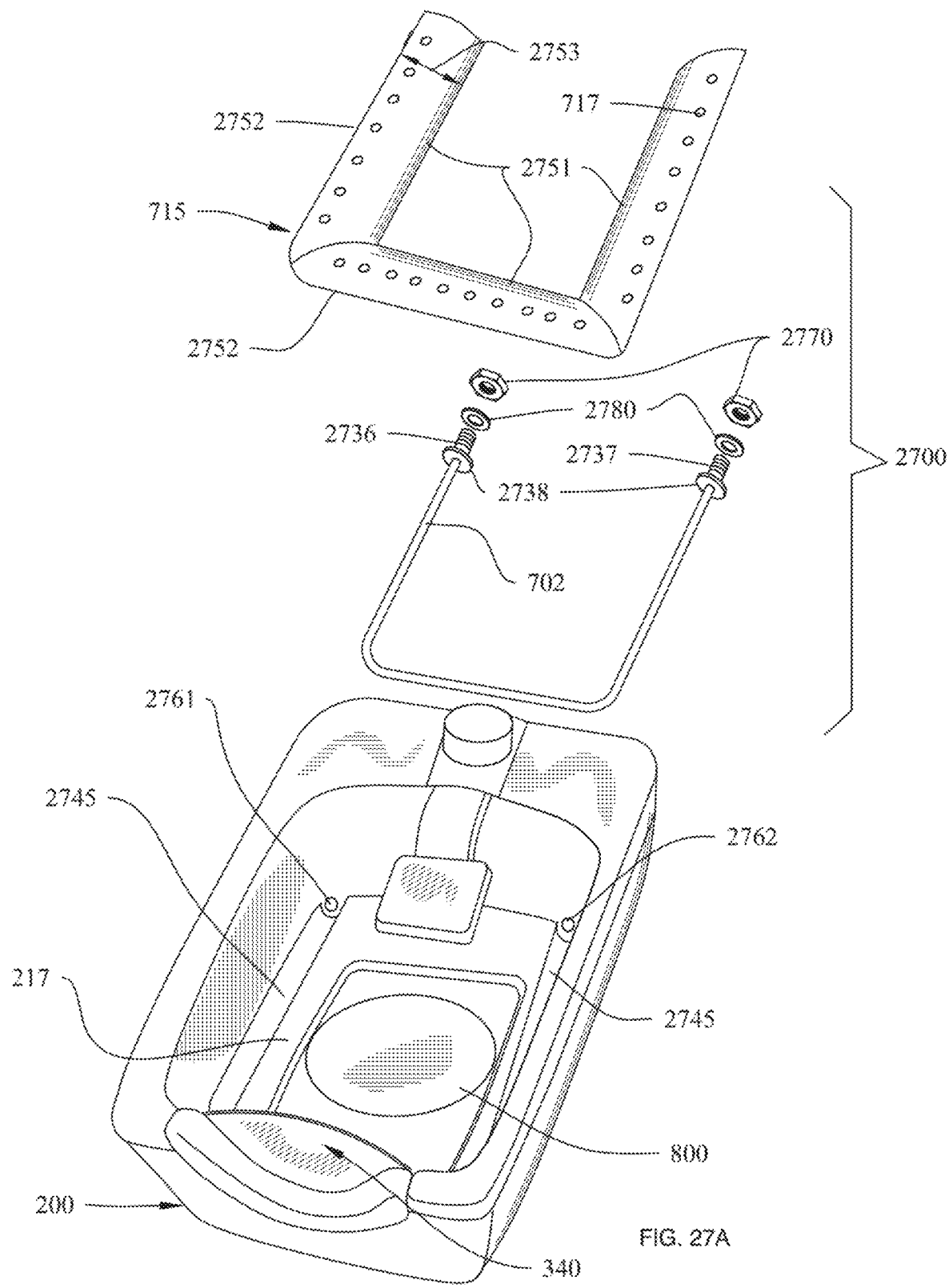

FIG. 27A may depict an embodiment of a U-shaped heating element heater subassembly for a face soaking device, shown from a top perspective exploded view.

Figure 27B:
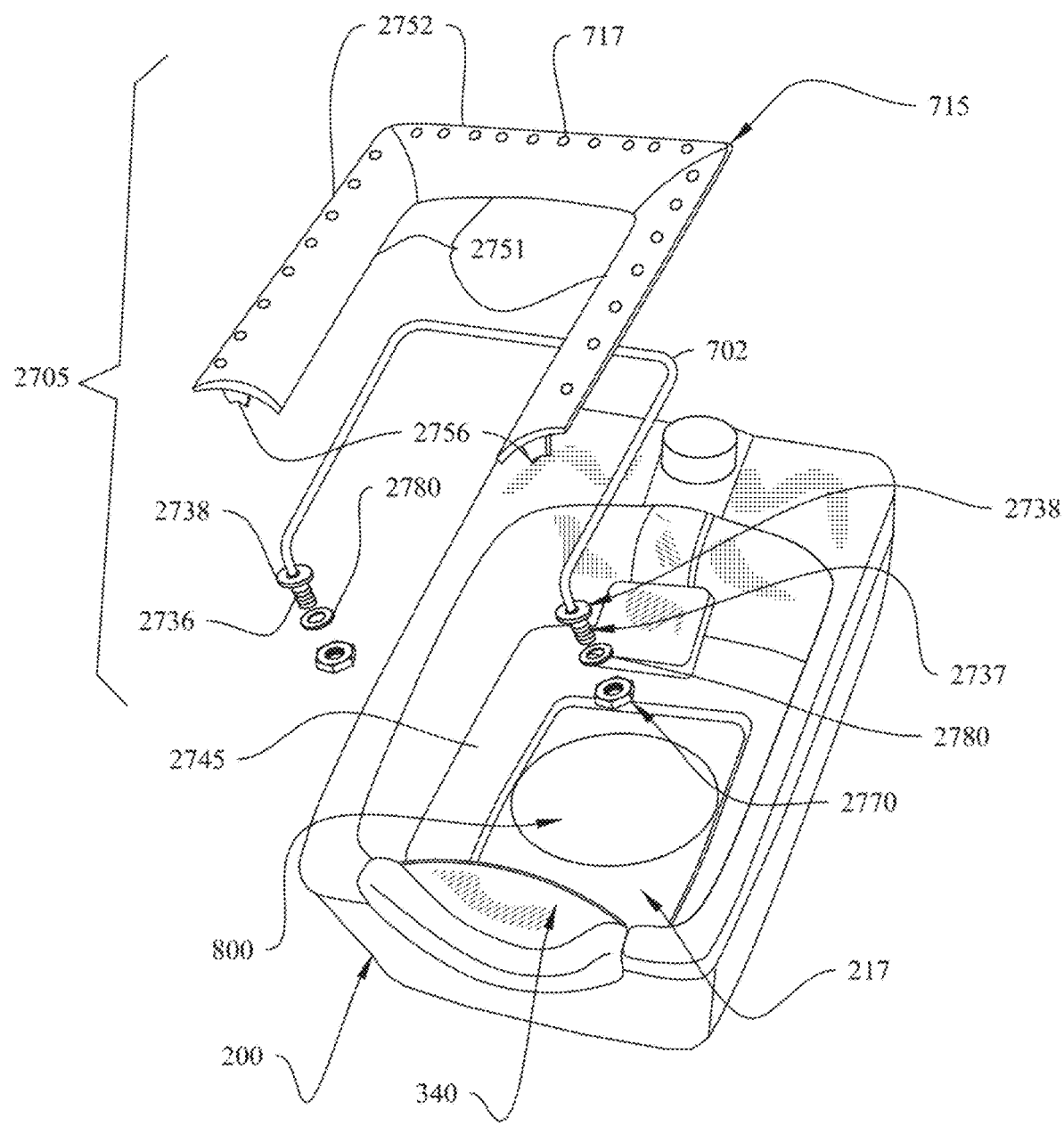

FIG. 27B may depict another embodiment of a U-shaped heating element heater subassembly for a face soaking device, shown from a top perspective exploded view.

Figure 27C:
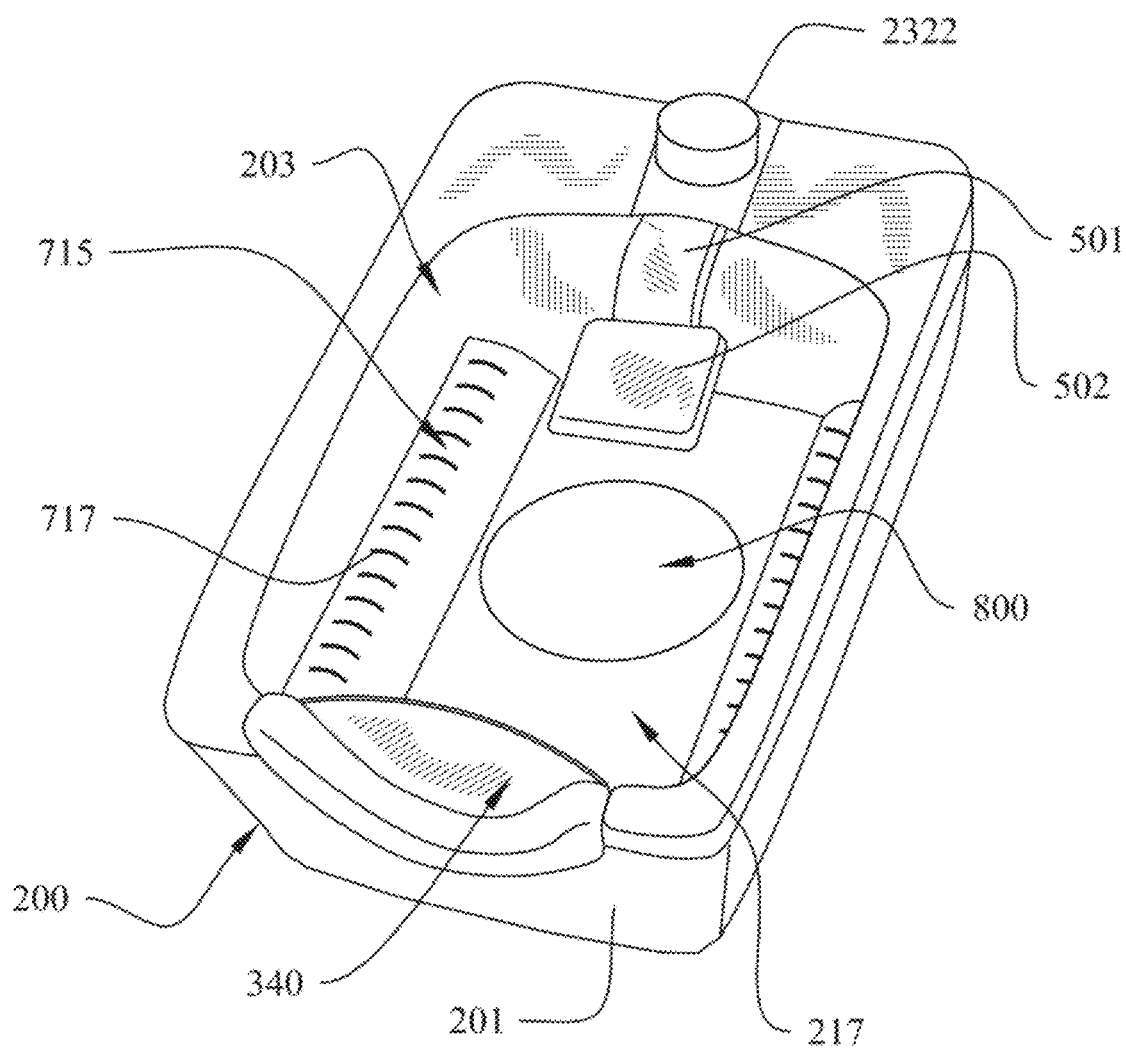

FIG. 27C may depict the U-shaped heater subassembly, assembled, of either FIG. 27A or FIG. 27B, shown from a top perspective view.

Figure 27D:
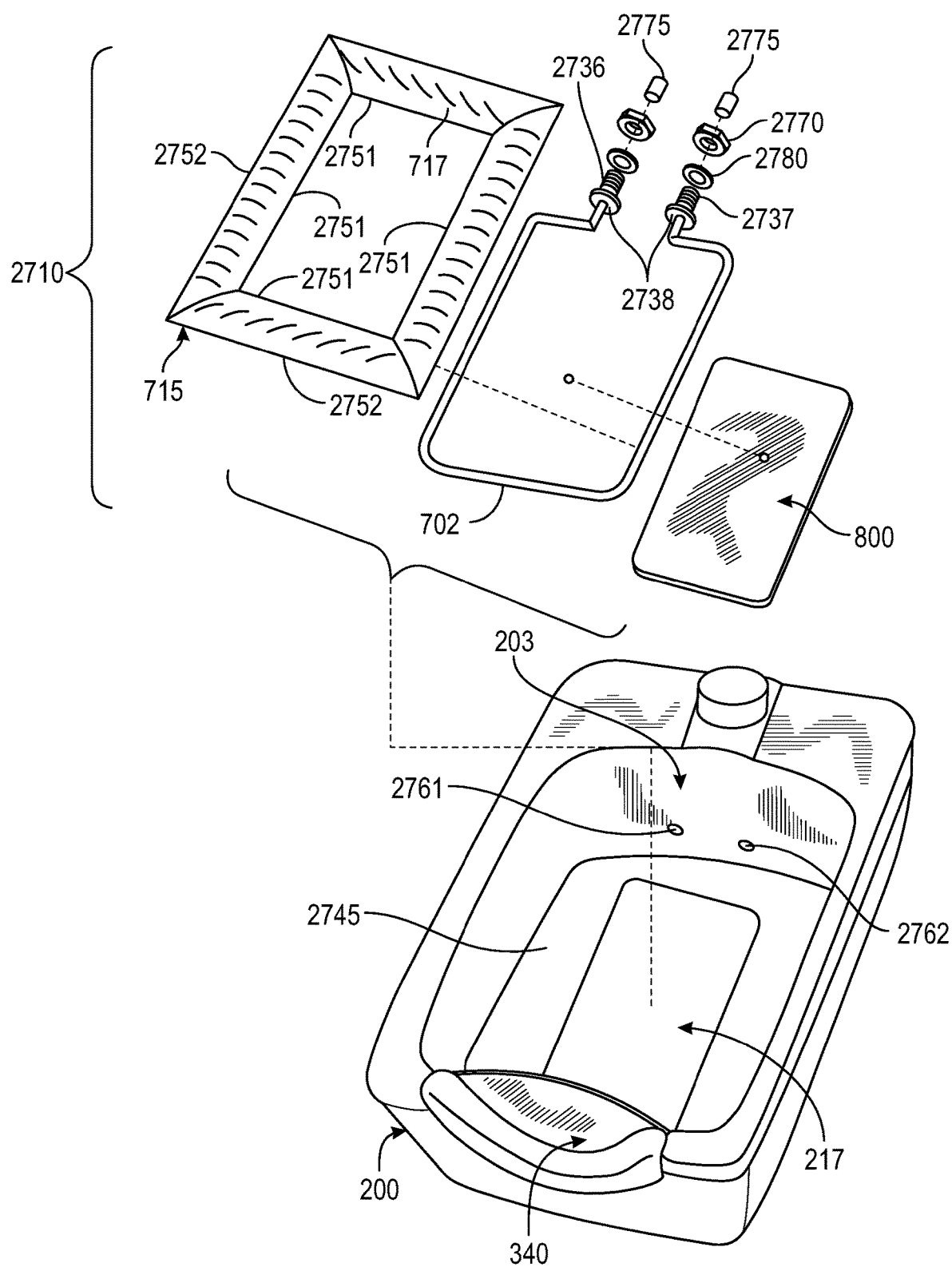

FIG. 27D may depict an embodiment of an approximate O-shaped heating element heater subassembly for a face soaking device, shown from a top perspective exploded view.

Figure 27E:
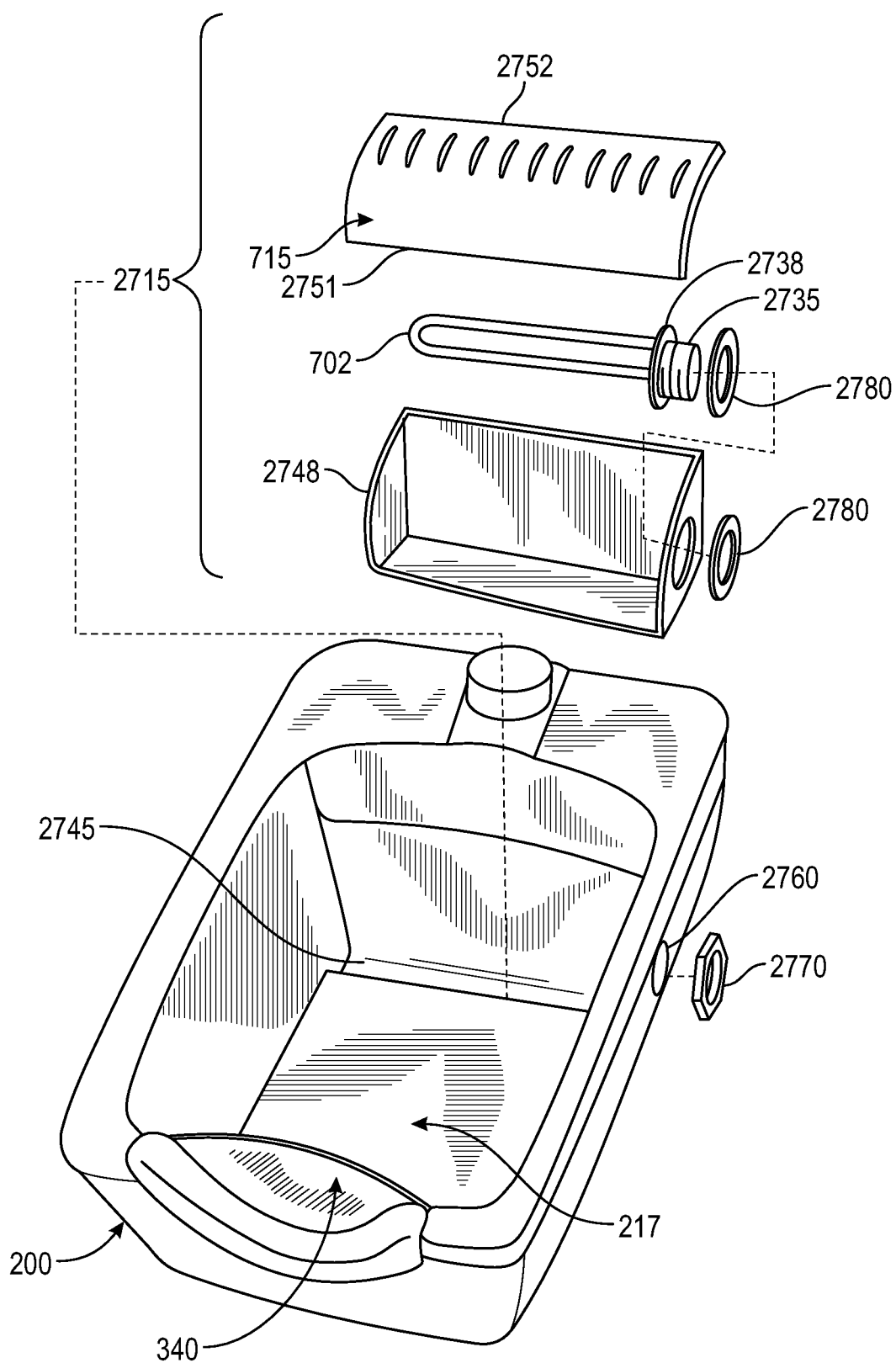

FIG. 27E may depict an embodiment of a back heater subassembly for a face soaking device, shown from a top perspective exploded view.

Figure 27F:
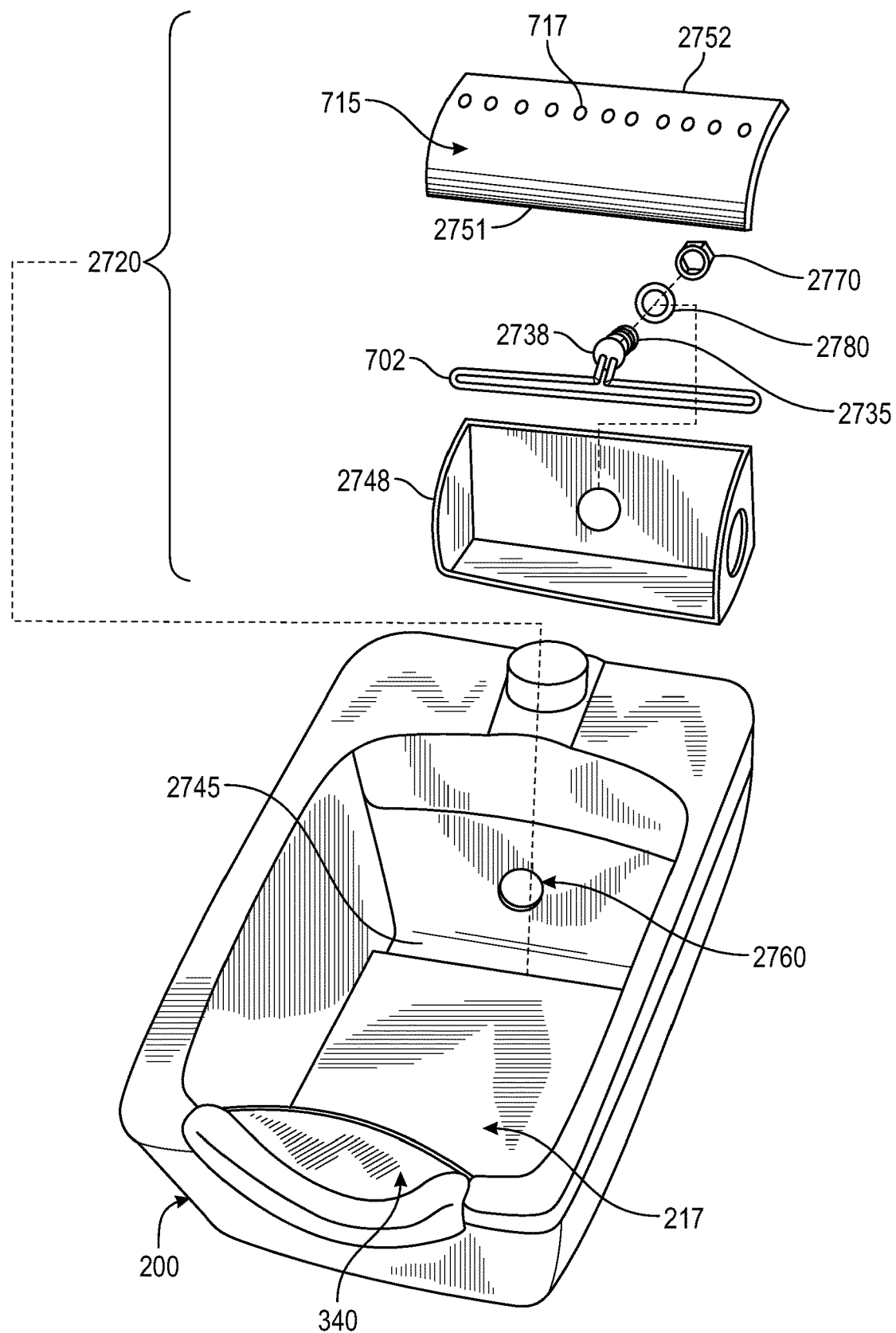

FIG. 27F may depict an embodiment of a T-shaped heating element back heater subassembly for a face soaking device, shown from a top perspective exploded view.

Figure 27G:
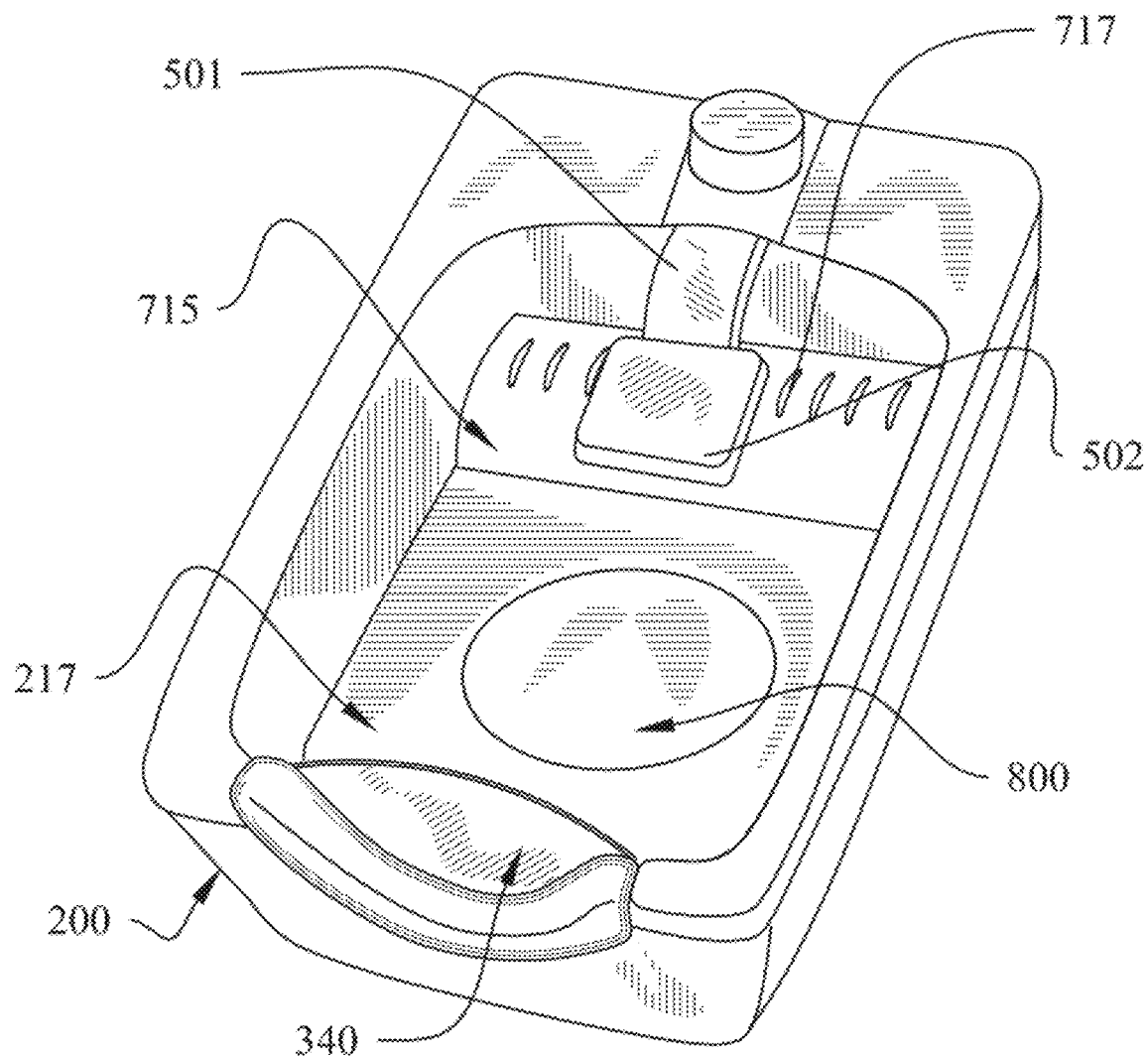

FIG. 27G may depict the back heater subassembly, assembled, of either FIG. 27E or FIG. 27F, shown from a top perspective view.

Figure 27H:
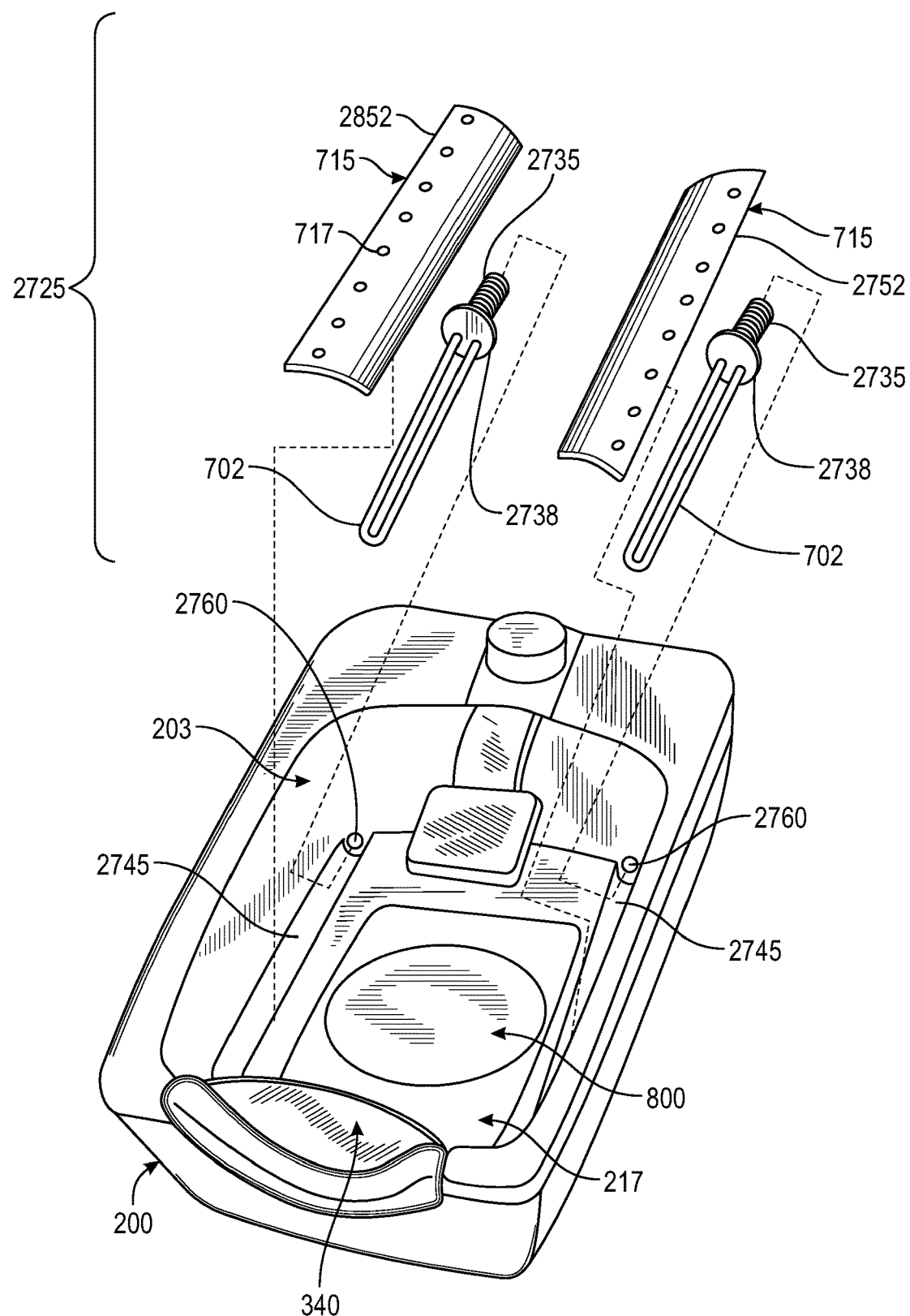
Figure 271:
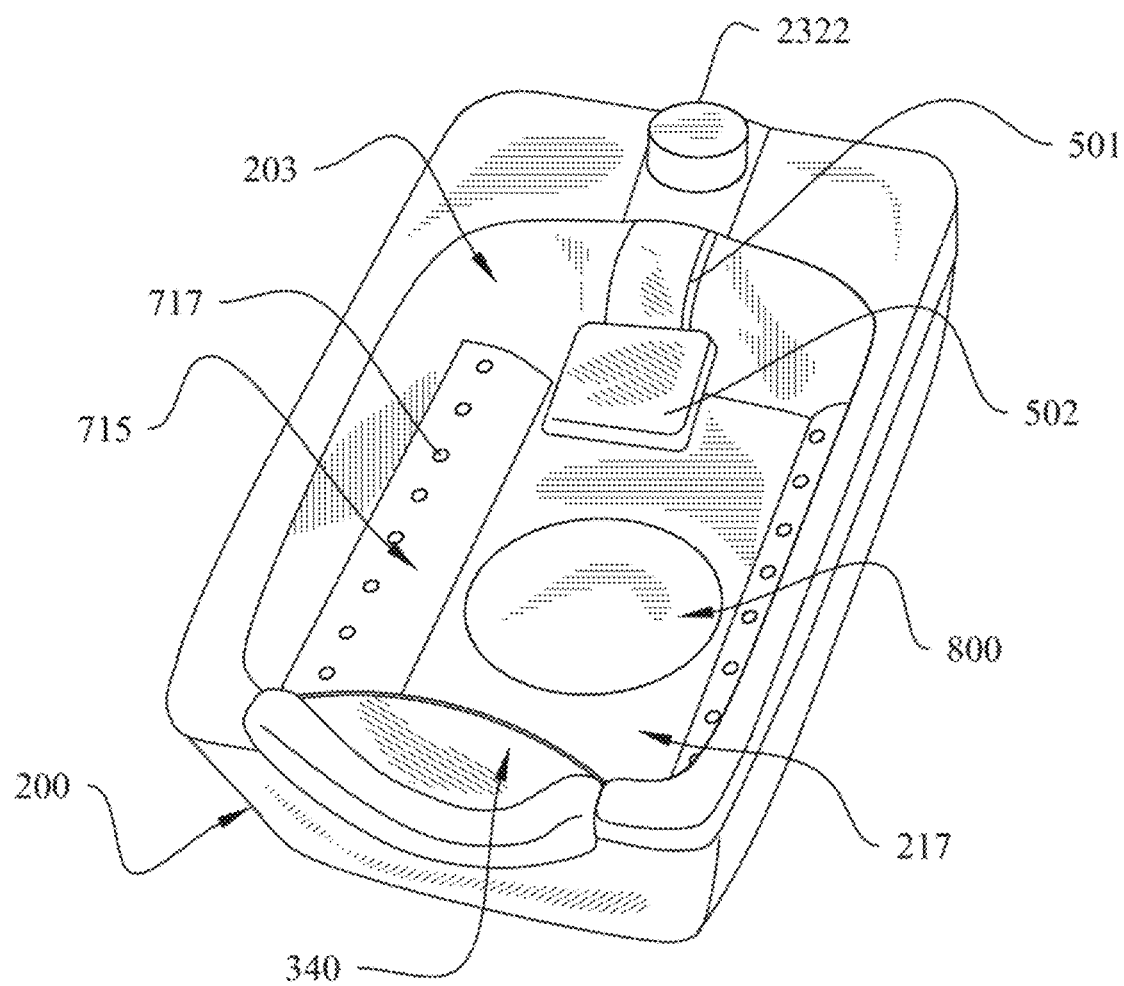

FIG. 27H may depict an embodiment of a double side wall heater subassembly for a face soaking device, shown from a top perspective exploded view.

FIG. 27I may depict the double side wall heater subassembly, assembled, of FIG. 27H, shown from a top perspective view.

FIG. 28A through FIG. 28H may depict various heating element layout configurations, as shown from a top view, depicting various overall shapes of heating elements.

Figure 28A:
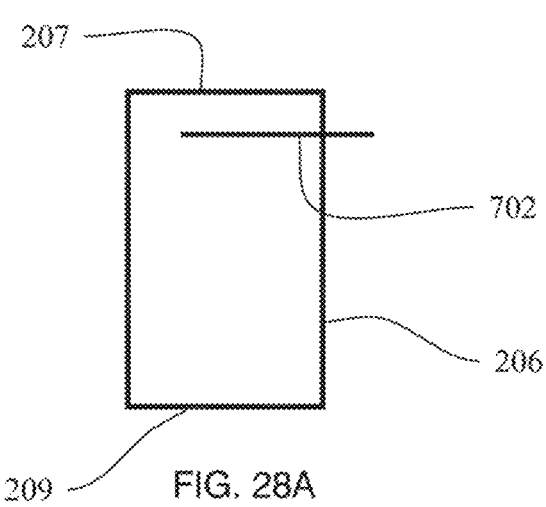

FIG. 28A may depict a linear heating element proximate to a back of a vessel, with the heating element entering the vessel from a side wall of the vessel.

Figure 28B:
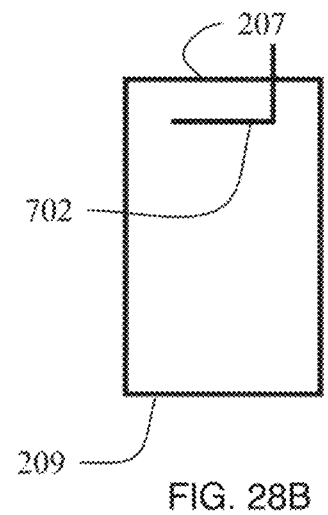

FIG. 28B may depict a L-shaped heating element proximate to a back of a vessel, with the heating element entering the vessel from the back.

Figure 28C:
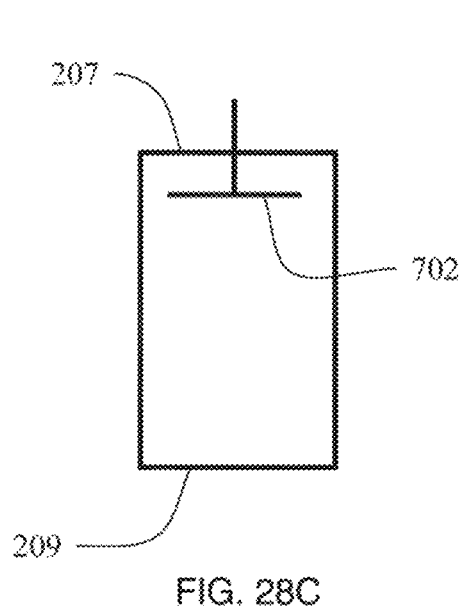

FIG. 28C may depict a T-shaped heating element proximate to a back of a vessel, with the heating element entering the vessel from the back.

Figure 28D:
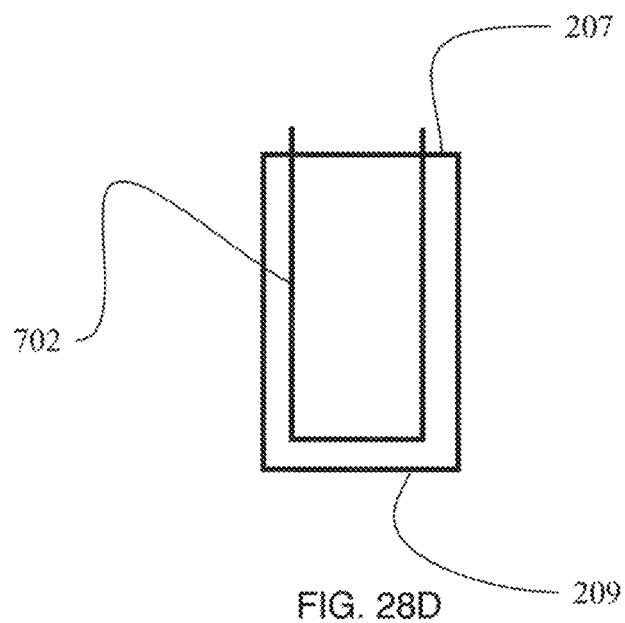

FIG. 28D may depict a U-shaped heating element, with the heating element entering a vessel from a back of the vessel.

Figure 28E:
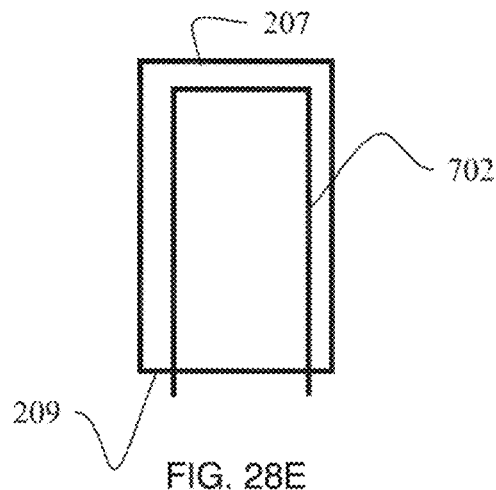

FIG. 28E may depict a U-shaped heating element, with the heating element entering a vessel from a front of the vessel.

Figure 28F:
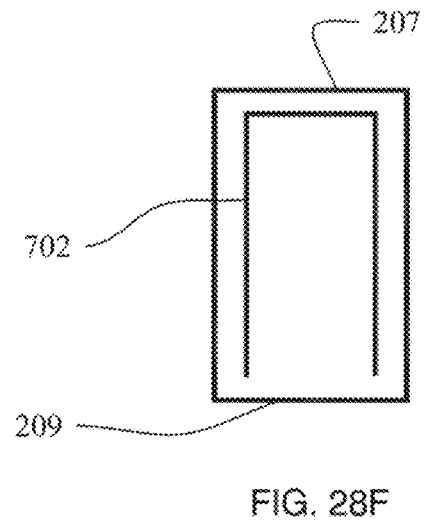

FIG. 28F may depict a U-shaped heating element, with the heating element entering a vessel from a bottom of the vessel.

Figure 28G:
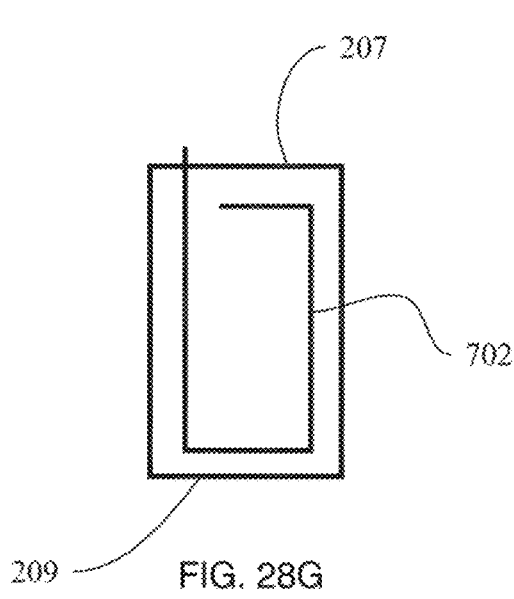

FIG. 28G may depict an approximate O-shaped heating element, with the heating element entering a vessel from a back of the vessel.

Figure 28H:
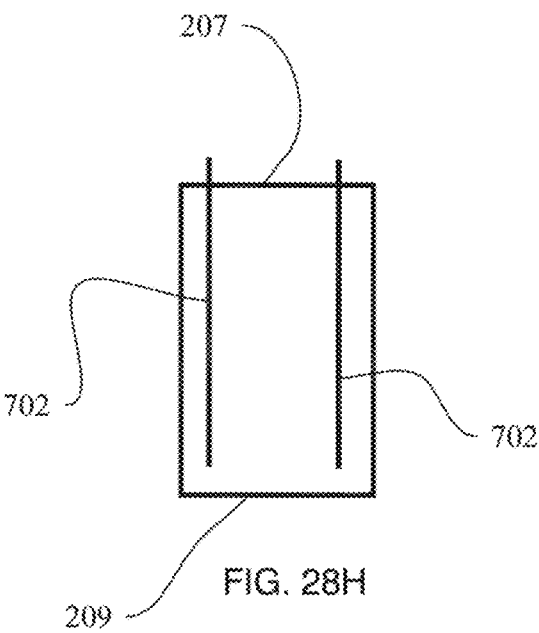

FIG. 28H may depict a pair of linear heating elements, with each proximate to an opposing but parallel side wall, with the heating elements entering a vessel from a back of the vessel.

Figure 29A:
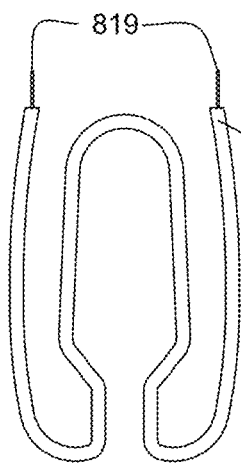

FIG. 29A may depict a layout configuration for one or more gas-diffuser-tubings within a given vessel, shown from a top view.

Figure 29B:
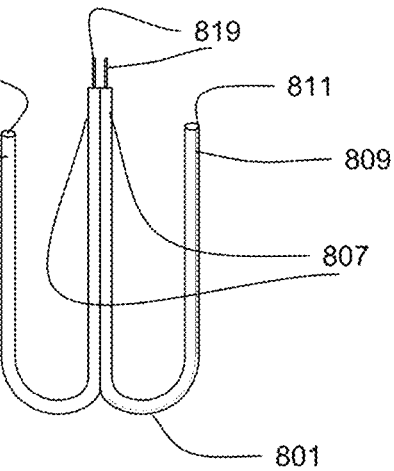

FIG. 29B may depict a layout configuration for one or more gas-diffuser-tubings within a given vessel, shown from a top view.

Figure 29C:
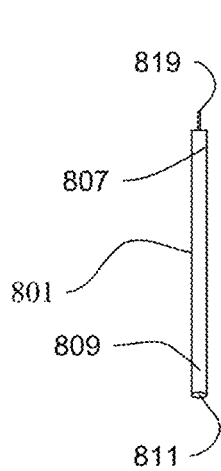

FIG. 29C may depict a layout configuration for one or more gas-diffuser-tubings within a given vessel, shown from a top view.

Figure 29D:
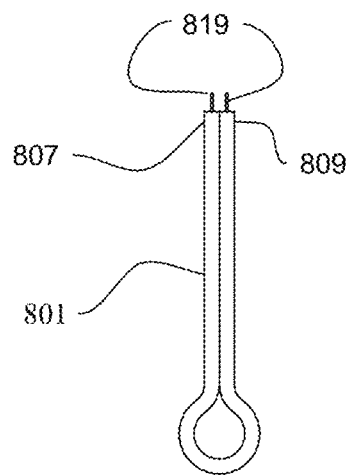

FIG. 29D may depict a layout configuration for one or more gas-diffuser-tubings within a given vessel, shown from a top view.

Figure 29E:
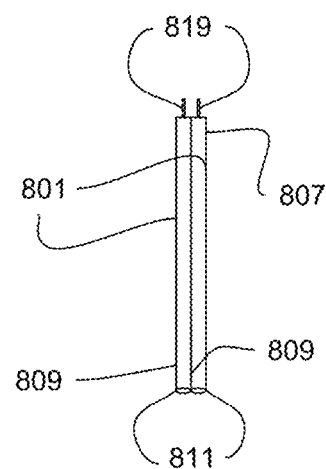

FIG. 29E may depict a layout configuration for one or more gas-diffuser-tubings within a given vessel, shown from a top view.

Figure 30A:
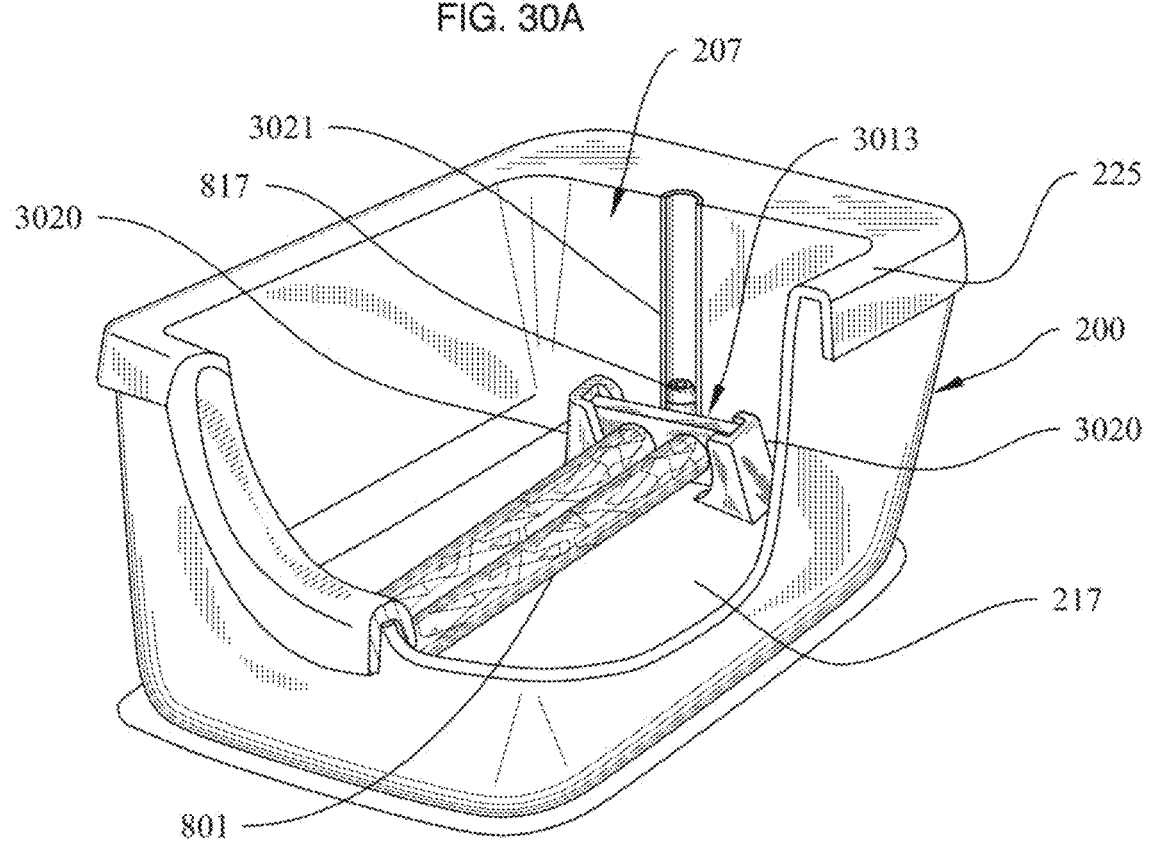

FIG. 30A may depict an up and over manner of securing one or more gas-diffuser-tubings located within an internal volume of the vessel to an airline tubing; wherein a portion of the airline tubing may be located outside of the internal volume; wherein, "up and over" may be with respect to a rim of the vessel.

FIG. 30B may depict a close up detailed view of a connection region of FIG. 30A where the one or more gas-diffuser-tubings may be removably coupled to the airline tubing via a connector.

Figure 31A:
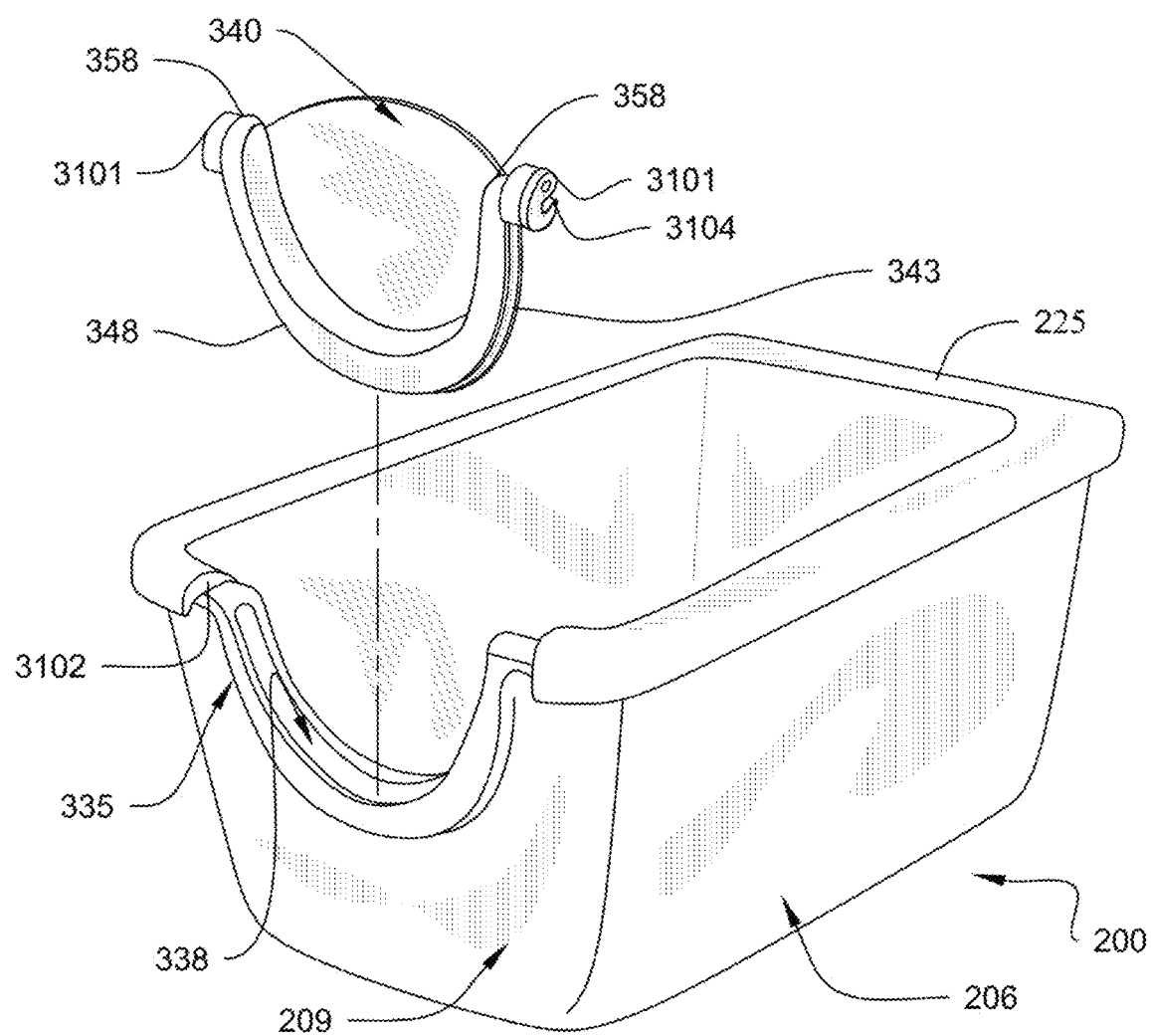

FIG. 31A may depict a push down press fit embodiment for a clamp with the vessel neck gasket to be received by the neck-gasket-accommodator of the vessel, shown in a perspective view with the clamp and the vessel neck gasket exploded from the neck-gasket-accommodator.

Figure 31B:
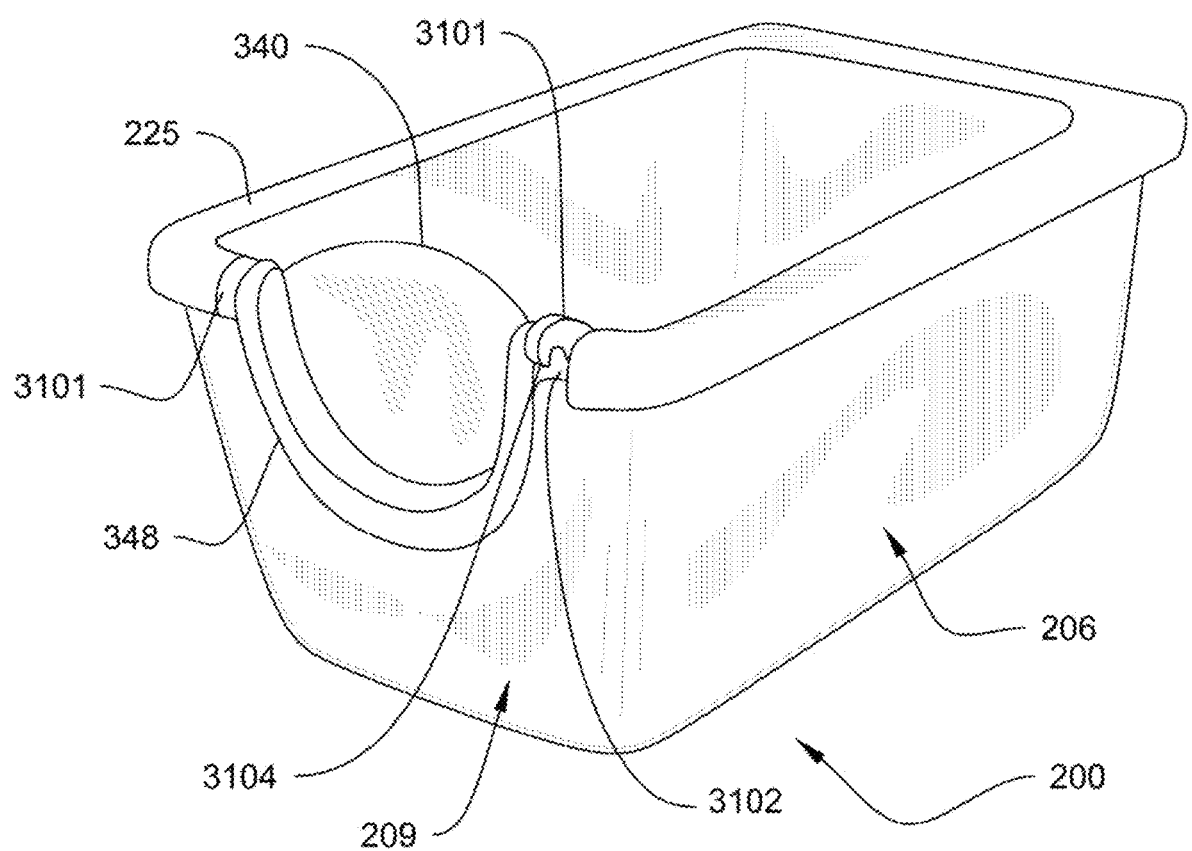

FIG. 31B may depict the embodiment of FIG. 31A, but with the clamp and the vessel neck gasket removably attached to the vessel and received at the neck-gasket-accommodator, shown from a perspective view.

Figure 31C:
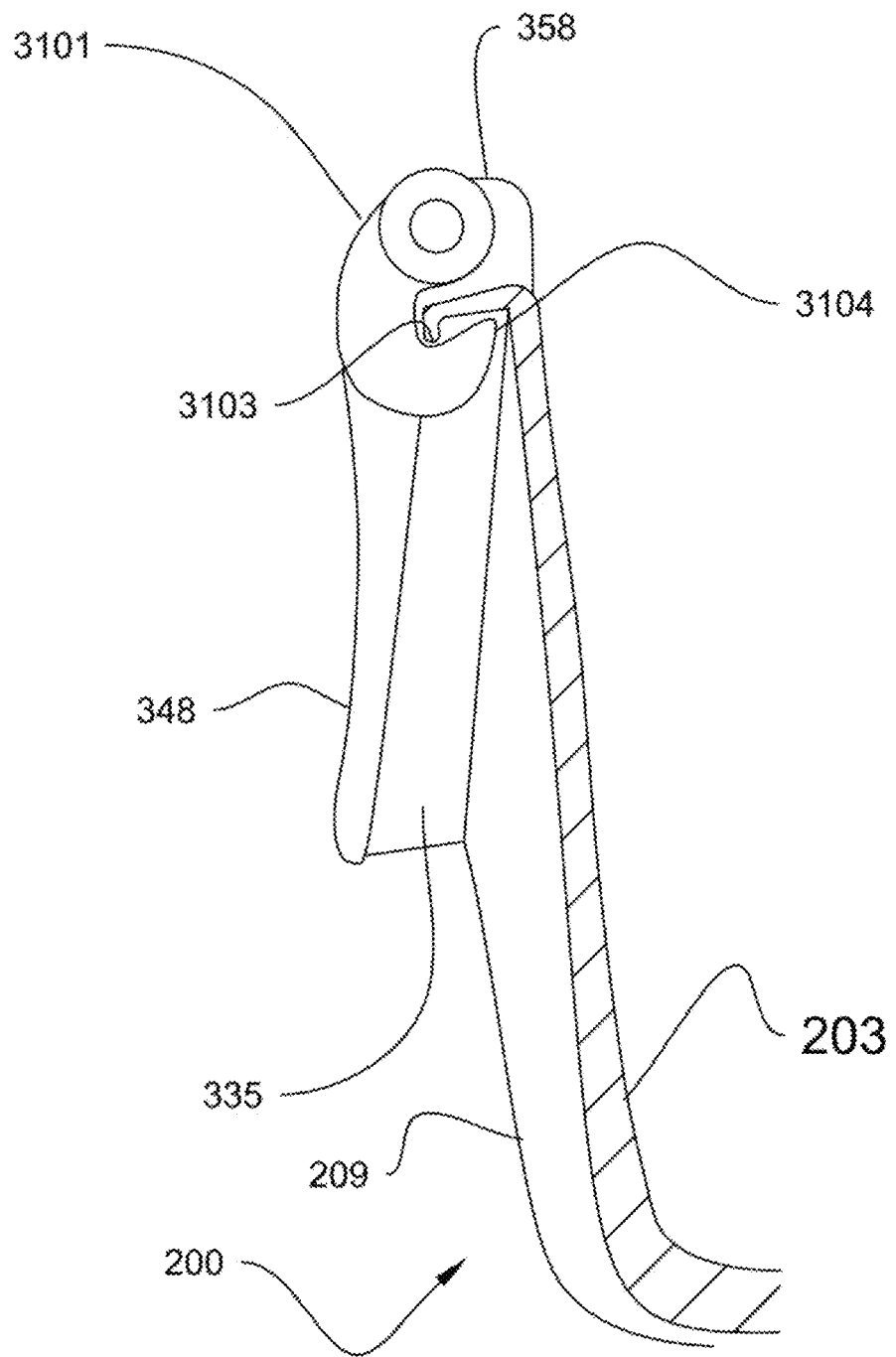

FIG. 31C may depict the push down clamp with the vessel neck gasket embodiment of FIG. 31A, but shown from a longitudinal cross-section with respect to the vessel, showing how a hook lock of the clamp may be removably latch onto a tab of the vessel.

Figure 31D:
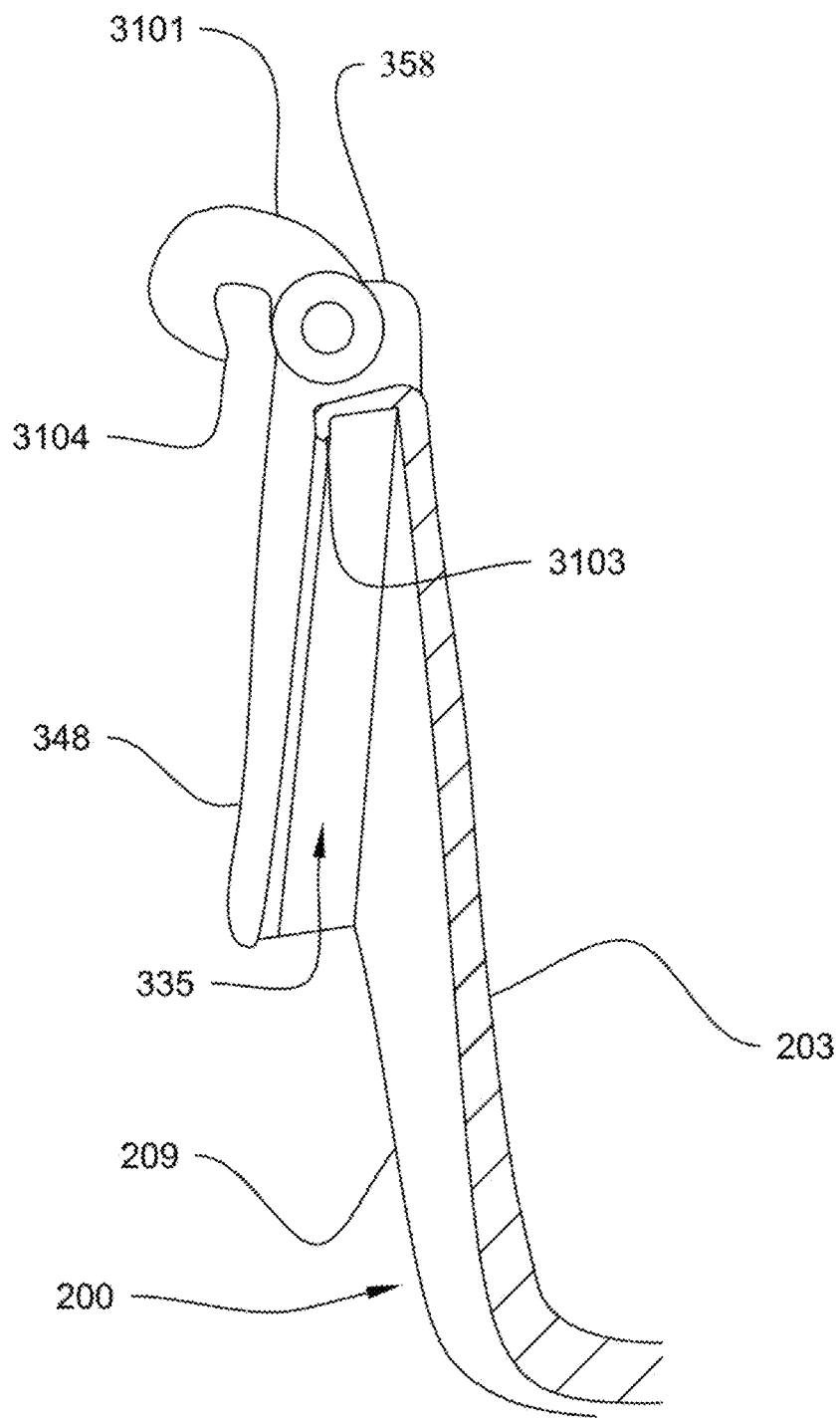

FIG. 31D may depict the same view and embodiment of FIG. 31C, except the hook lock may be rotate such that the hook lock may not be removably engaging the tab.

Figure 32A:
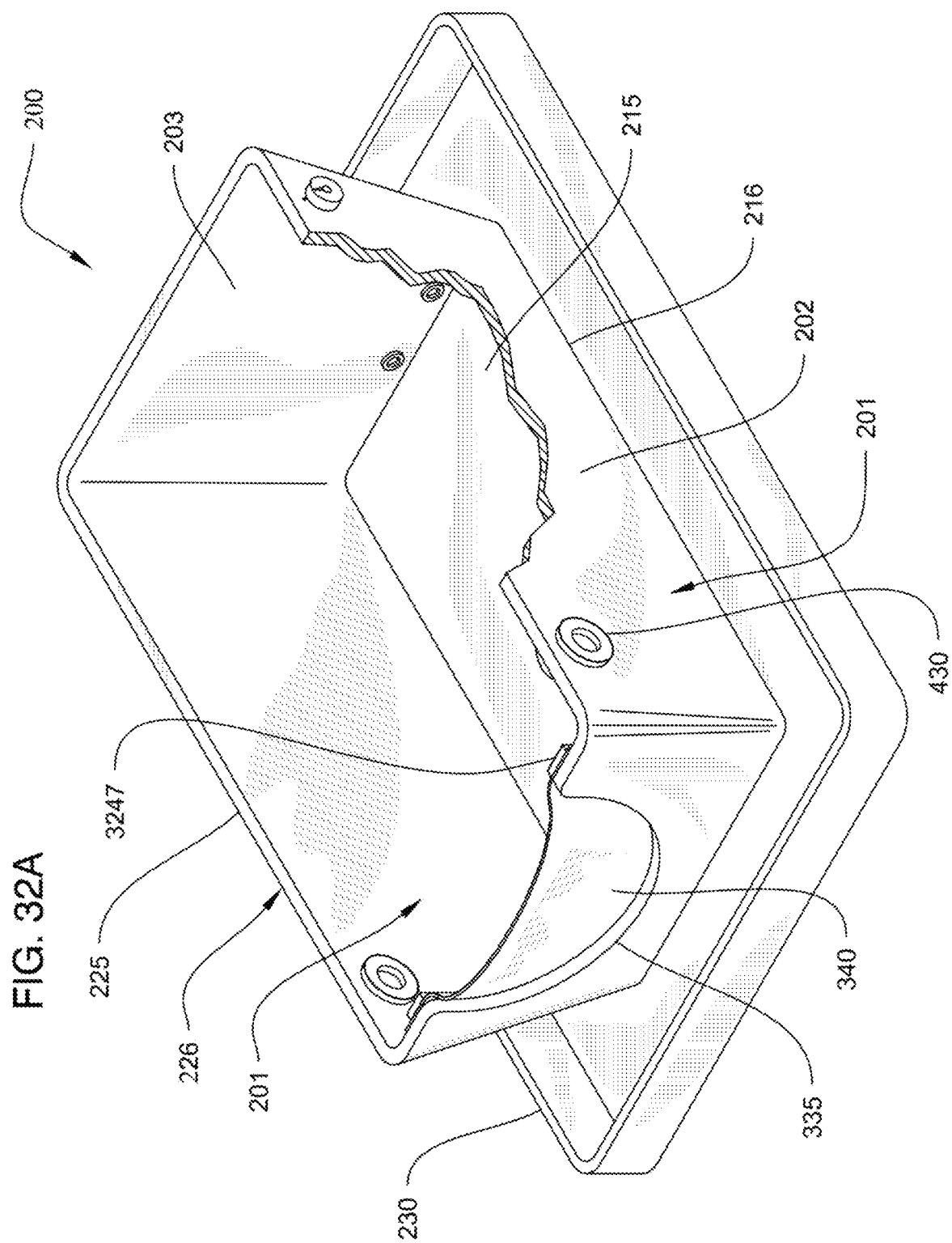

FIG. 32A may depict a mounting block embodiment for attaching the vessel neck gasket to the vessel, shown from a perspective view.

Figure 32B:
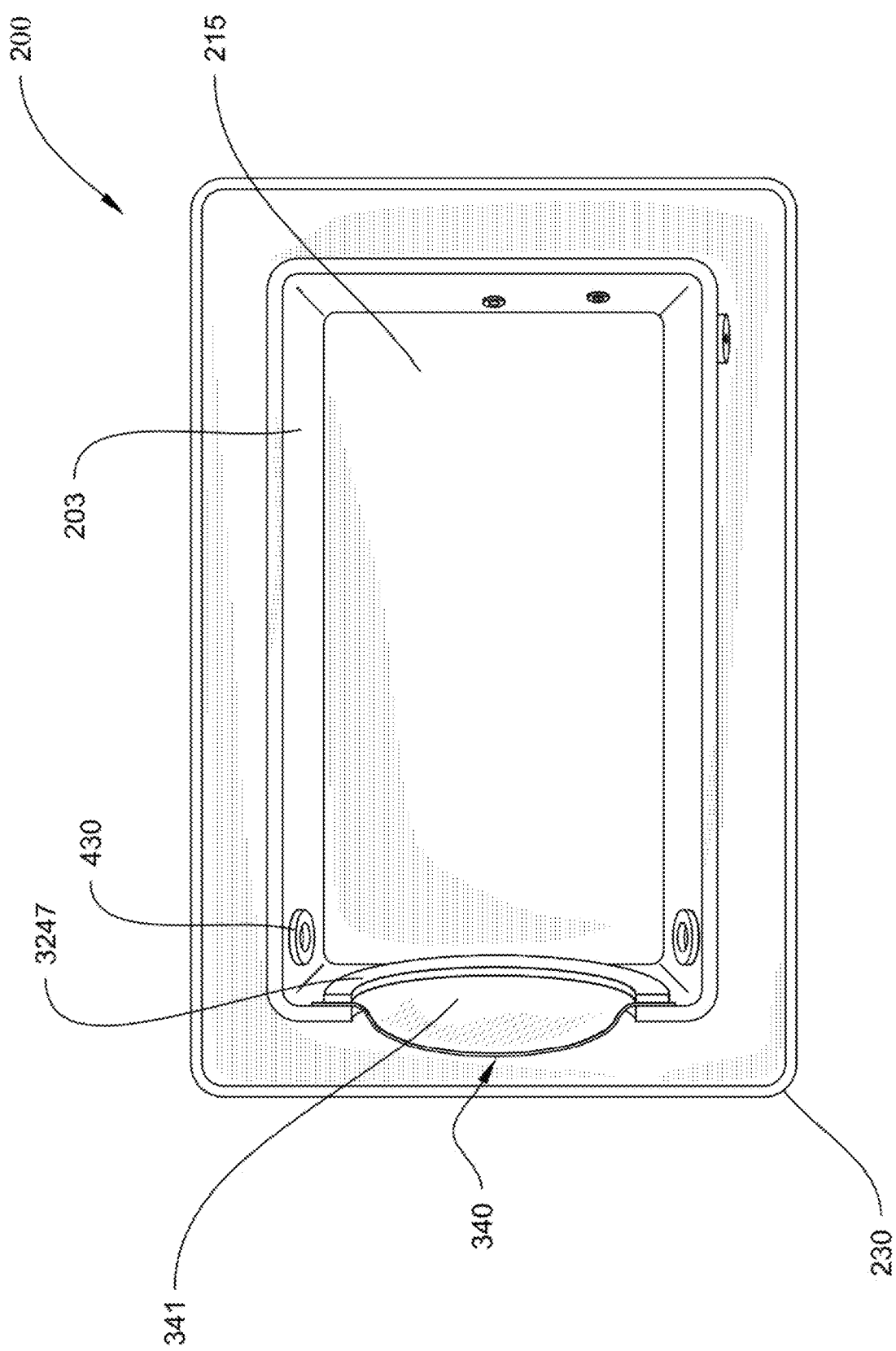

FIG. 32B may depict the embodiment of FIG. 32A, but shown from a top view.

FIG. 32C may depict the embodiment of FIG. 32A, but shown from a front view. The front view may also be known as a vessel neck gasket view.

FIG. 32D may depict the embodiment of FIG. 32A, but shown from a right view. The right view may be with respect to an observer looking upon the front view, i.e. the right view may be with respect to the observer's right.

FIG. 32E may depict the embodiment of FIG. 32A, but shown from an exploded perspective view.

Figure 33A:
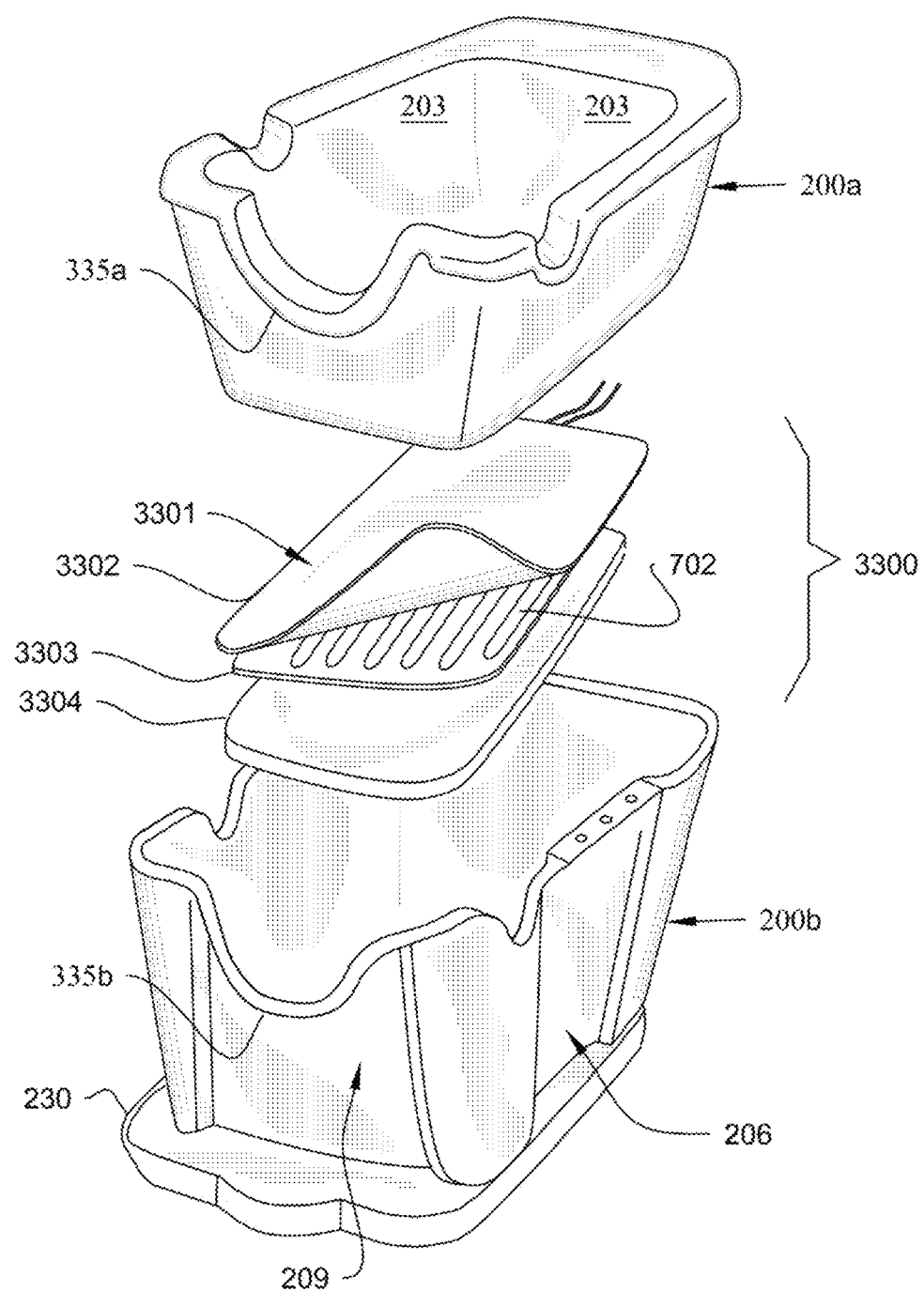

FIG. 33A may depict an embodiment of a heating pad heater subassembly for a face soaking device, shown from a top perspective exploded view.

Figure 33B:
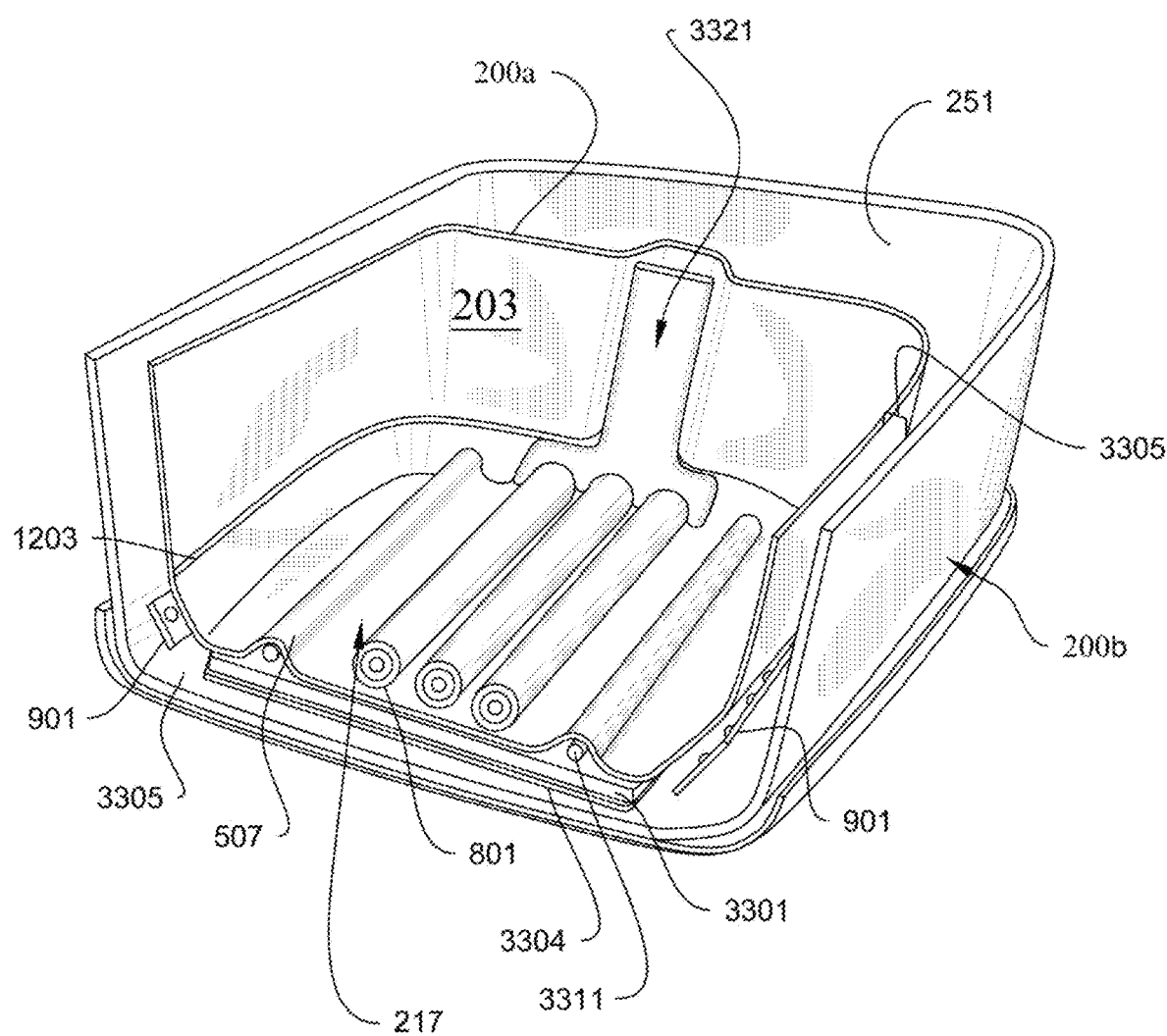

FIG. 33B may depict the embodiment of FIG. 33A, but shown with from two orthogonal sections, a transverse with cross-section being depicted and a bottom perspective section being depicted.

Figure 33C:
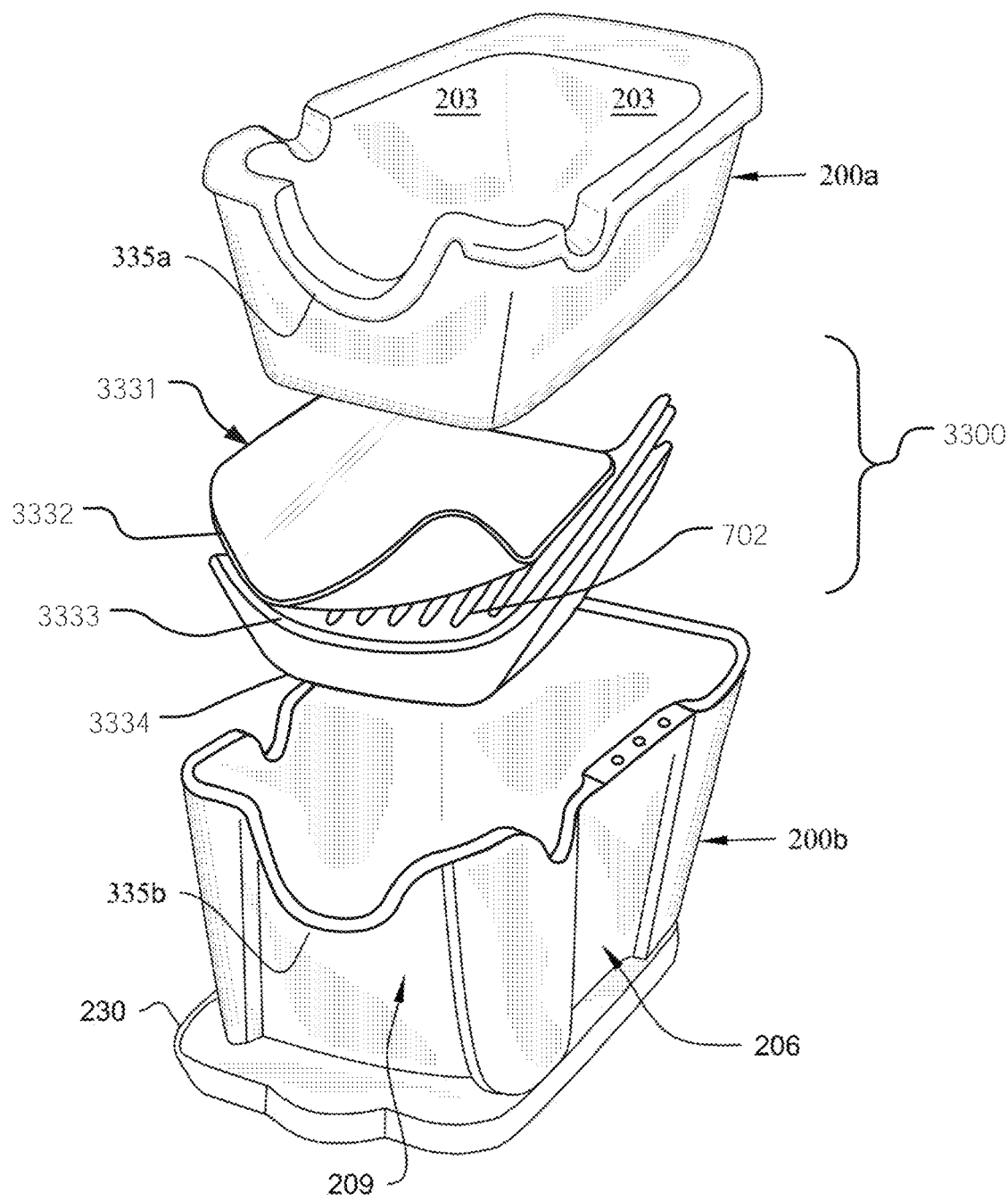

FIG. 33C may depict an embodiment of a heating pad heater subassembly for a face soaking device, shown from a top perspective exploded view; wherein at least some portions of a heating pad may be disposed between a vessel lining and a vessel cover in at least some side wall portions of the vessel.

Figure 33D:
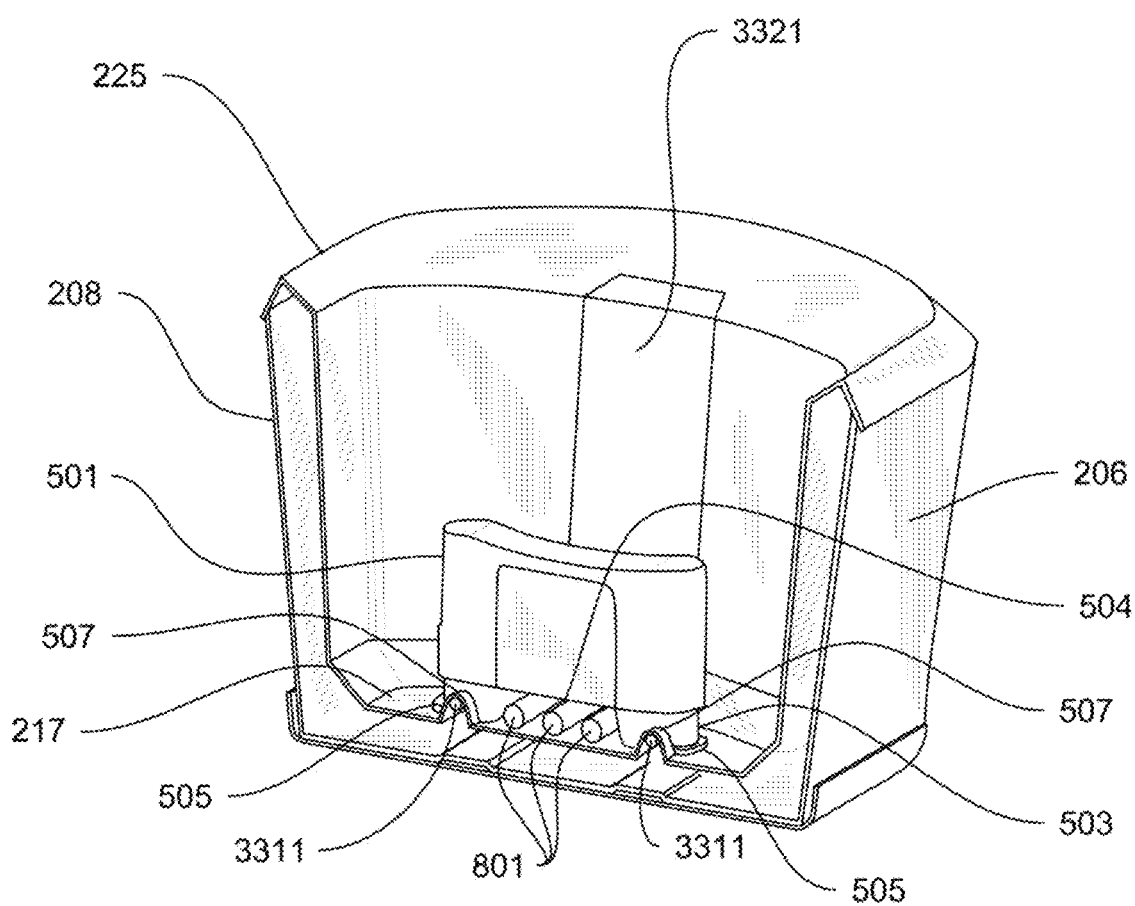

FIG. 33D may depict a transverse width cross section of a face soaking device embodiment, showing a support member of a headrest subassembly removably riding two guides (i.e., rails).

Figure 34:
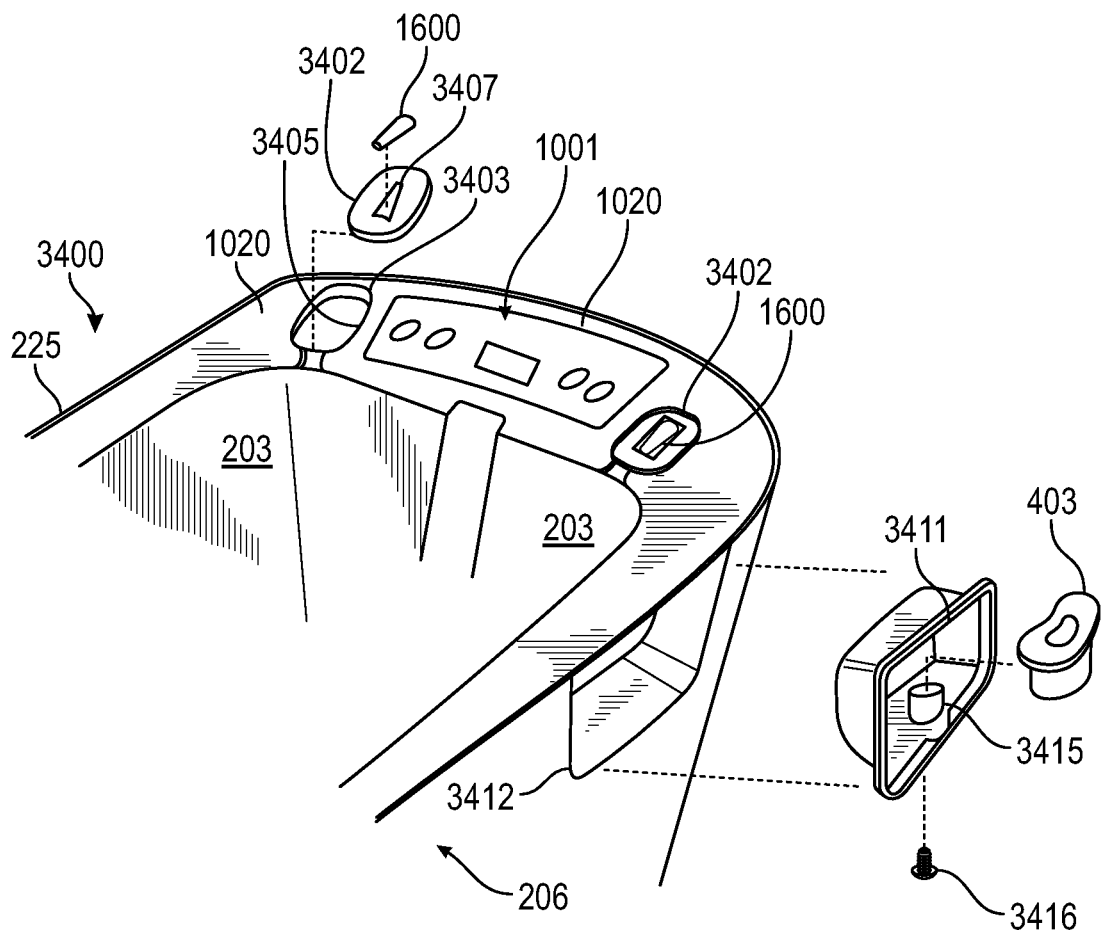

FIG. 34 may depict a partial perspective and partial exploded view of a vessel embodiment showing storage means for nose-clips and storage means for a mouthing portion.

REFERENCE NUMERAL KEY 100 face soaking device 100
101 liquid 101
125 bubbles 125 (plurality of bubbles 125)
126 at least one bubble 126
200 vessel 200
200a vessel lining 200a
200b vessel cover 200b
201 at least one wall 201
202 exterior wall surface 202
203 interior wall surface 203
205 at least one side wall 205
206 first side wall 206
207 second side wall 207
208 third side wall 208
209 fourth side wall 209
210 at least one port 210
215 at least one base 215
216 perimeter of base 216
217 bottom interior surface 217
220 internal volume 220
225 rim 225
226 top opening 226
230 catch basin 230
251 mechanical compartment 251
335 neck-gasket-accommodator 335
335a neck-gasket-accommodator 335a
335b neck-gasket-accommodator 335b
336 maximum vertical length 336
337 horizontal width 337
338 contour 338
339 at least one pinch point 339
340 vessel neck gasket 340
341 internal surface 341
342 external surface 342
343 mating edge 343
344 top edge 344
345 stretched region 345 (region of stretch 345)
348 clamp 348
350 at least one sealing fin 350
351 complimentary pinch point 351
352 lip 352
353 first complimentary sealing fin 353
354 second complimentary sealing fin 354
355 tab 355
356 upper exterior surface 356
357 lateral exterior surface 357
358 clamp terminal ends 358
364 pull 364
367 channel 367
371 opening wall-edge 371
372 edge-lip 372
380 mating-wall-edge 380
381 snap latch 381
391 press-in-fit-part 391
400 breathing apparatus 400
401 mouth piece 401
403 mouthing portion 403
405 at least one connection end 405
420 at least one hose 420 or at least one tubing 420
421 first terminal end 421
422 second terminal end 422
430 at least one vessel-tube-hose-connector 430
431 opening 431
433 interior side 433
435 exterior side 435
437 butting-ring 437
439 interior-butting-ring 439
441 connector-rim 441
470 at least one grommet-accommodating-contour 470
471 exterior side containment lip 471
473 interior side containment lip 473
475 weep-hole 475
477 drain-channel 477
500 head rest subassembly 500
501 support member 501
502 at least one comfortable exterior surface 502)
503 at least one post 503
504 gas-diffuser-tubing-groove 504
505 two legs 505
506 at least one magnet 506
507 at least one guide 507
508 slot 508
510 tab 510
509 cap 509
511 at least one plate 511
512 pad 512
513 defined channel 513
600 head rest subassembly 600
650 head rest subassembly 650
700 heater subassembly 700 (heater 700)
701 at least one heating element 701
702 element 702
703 bushing 703
704 connection bushing 704
705 flange 705
706 electrical terminals 706
707 electrical wiring 707
708 bushing hole 708
709 gasket/washer 709
710 at least one nut 710
711 element receiving channel 711

715 shield 715
716 upper planar surface 716
717 liquid passage means 717
718 shield-attachment-means 718
719 shield-legs 719
720 complimentary and supportive structure 720
721 shield-back-panel 721
800 gas diffuser 800
801 one or more gas-diffuser-tubings 801
803 porous-elongate-member 803
805 central-elongate-member 805
807 first end 807
809 second end 809
811 end-cap 811
812 flange 812
813 connector 813
815 hose barbs 815
817 airline tubing connector 817 (hose barbs 817) (threading 817)
819 airline tubing 819
820 flange-receiver 820
831 gasket 831
832 nut 832
900 at least one electromagnetic (EM) emitter 900
901 at least one LED array 901
902 at least one LED 902
950 LED-housing 950
951 LED-housing-cavity 951
952 opening 952
1000 membrane switch subassembly 1000
1001 membrane switch cover 1001
1002 one or more area of engagement 1002
1003 at least one status indicator 1003
1005 area of engagement and/or status indicator 1005
1007 membrane switch electronics 1007
1008 one or more sensors 1008
1009 wiring 1009
1020 roof 1020
1021 membrane-switch-receiving-recess 1021
1022 passage 1022
1100 controller 1100
1101 processor 1101
1102 memory 1102
1103 output means 1103
1104 network adapter 1104
1105 level indicator 1105
1106 temperature sensor 1106
1107 thermostat 1107
1110 compressor 1110
1115 power source 1115
1116 electrical power cord 1116
1117 fan 1117
1150 one or more mobile computing devices 1150
1160 network 1160
1200 device 1200
1203 window 1203
1211 first beam 1211
1212 first reflected beam 1212
1213 first refracted beam 1213
1214 second reflected beam 1214
1215 second refracted beam 1215
1216 $n^{th}$ reflected beam 1216
1217 $n^{th}$ refracted beam 1217
1218 n+1 reflected beam 1218
1219 n+1 refracted beam 1219
1227 surface 1227 (of bubble 126 or bubble 128)
1228 another bubble 1228
1241 emitted electromagnetic radiation 1241 (EM radiation 1241)
1244 at least one electromagnetic emitter 1244 (EM emitter 1244)
1245 at least one electromagnetic emitter 1245 (EM emitter 1245)
1246 at least one electromagnetic emitter 1246 (EM emitter 1246)
1247 at least one electromagnetic emitter 1247 (EM emitter 1247)
1248 at least one electromagnetic emitter 1248 (EM emitter 1248)
1249 at least one electromagnetic emitter 1249 (EM emitter 1249)
1251 proximate distance 1251
1252 proximate distance 1252
1260 at least one jet 1260
1300 face soaking device 1300 (with a curved wall vessel)
1301 curved wall 1301
1303 interior wall surface 1303
1310 at least one vessel-tube-hose-vent 1310
1315 at least one base 1315
1320 internal volume 1320
1350 bottom interior surface 1350
1351 face soaking device 1351
1360 vessel 1360
1361 at least one wall 1361
1385 at least one horizontal hose 1385 or at least one horizontal tube 1385
1370 face soaking device 1370
1371 region of flexible side wall 1371
1372 vessel 1372
1373 at least one wall 1373
1374 first wall thickness 1374
1375 second wall thickness 1375
1449 carrier 1449
1559 pin 1559
1560 pin receptacle 1560
1561 receiving channel 1561
1563 tooth 1563
1565 micro fins 1565
1566 micro fins 1566
1567 molded region 1567
1600 nose-clip 1600
1602 elongate member 1602
1603 two terminal ends 1603
1605 central bend region 1605
1606 major radius 1606
1607 terminating structure 1607
1608 pad 1608
1609 tight coils 1609
1700 nose-clip 1700
1710 loose coils 1710
1800 nose-clip 1800
1811 spherical structure 1811
1900 coated nose-clip 1900
2000 independent breathing apparatus 2000
2001 exit port 2001
2050 independent breathing apparatus 2050
2100 combination breathing apparatus and head rest subassembly 2100
2101 common slot 2101
2102 channel 2102
2201 collar 2201
2202 collar tab 2202
2203 side wall tab receiver 2203
2205 sleeve 2205

2206 sleeve tab 2206'
2211 channel sleeve 2211
2212 side wall tab 2212
2213 channel 2213
2214 flange 2214
2221 collar hinge 2221
2231 at least one vessel-tube-hose-connector 2231
2232 independent finger pull 2232
2234 at least one grommet-accommodating-contour 2234
2300 head rest subassembly 2300
2301 fifth terminal end 2301
2302 sixth terminal end 2302
2311 upper surface 2311
2312 lower surface 2312
2315 bend 2315
2320 slot 2320
2321 threaded bolt/threaded screw 2321
2322 friction clamp 2322
2323 user engagement flange 2323
2330 threaded hole 2330
2340 roof 2340
2350 recessed channel 2350
2370 cover 2370
2375 center hole 2375
2380 angle 2380
2400 head rest subassembly 2400
2410 transverse-head-support-member 2410
2420 at least one longitudinal-support 2420
2421 first-end 2421
2422 second-end 2422
2430 coupling 2430
2431 receiving-hole 2431
2435 set screw 2435
2441 set-bolt 2441
2442 threaded portion 2442
2443 knob 2443
2445 head-rest-brake 2445
2446 upper surface 2446
2451 vertical slot 2451
2461 cavity 2461
2500 head rest subassembly 2500
2511 at least one strut 2511
2512 third terminal end 2512
2513 fourth terminal end 2513
2514 height adjustment slot 2514
2515 height adjust pin 2515
2520 pivotable locking means 2520
2521 rotatable axle member 2521
2522 friction clamp 2522
2530 strut attachment means 2530
2531 wing bolt 2531
2540 head rest subassembly 2540
2550 head rest subassembly 2550
2560 head rest subassembly 2560
2671 at least one track 2671
2681 "J" hook 2681
2700 U-shaped heater 2700
2705 U-shaped heater 2705
2710 O-shaped heater 2710
2715 back heater 2715
2720 T-shaped heater 2720
2725 double heater 2725
2735 at least one connection bushing 2735
2736 first connection bushing 2736
2737 second connection bushing 2737
2738 flange 1638
2745 element receiving channel 2745
2748 element receiving tray 2748
2751 first edge 2751
2752 second edge 2752
2753 shield transverse width 2753
2756 shield attachment 2756
2760 at least one bushing hole 2760
2761 first bushing hole 2761
2762 second bushing hole 2762
2770 at least one nut 2770
2775 adapter 2775
2780 washer/gasket 2780
3013 connector 3013
3019 flange 3019
3020 flange-receiver 3020
3021 airline tubing channel 3021
3101 hook lock 3101
3102 receiving groove 3102
3103 tab 3103
3104 latch structure 3104
3246 plurality of screws or bolts 3246
3247 mounting block 3247
3300 heater subassembly 3300
3301 heating pad 3301
3302 upper pad 3302
3303 lower pad 3303
3304 insulator 3304
3305 insulation 3305
3311 at least one magnetically attractable member 3311
3321 cover 3321
3330 heater subassembly 3330
3331 heating pad 3331
3332 upper pad 3332
3333 lower pad 3333
3334 insulator 3334
3400 vessel 3400
3402 nose-clip holder 3402
3403 nose-clip holder recessed cavity 3403
3405 friction means 3405
3407 nose-clip cavity 3407
3411 recess pocket 3411
3412 recessed cavity 3412
3415 stem 3415
3416 stem attachment means 3416
9000 user 9000
9010 face 9010
9020 neck 9020

DETAILED DESCRIPTION OF THE INVENTION

Embodiments of face soaking devices, article soaking devices, and flexible detachable vessel covers are described and disclosed; as well as methods of use. In some exemplary embodiments these face soaking devices may comprise a vessel with gasket-accommodator, a vessel neck gasket, and a breathing apparatus. The vessel may be configured to hold an immersion liquid (liquid) to submerge a face of a user or a portion thereof. The vessel neck gasket may be removably joined to the vessel. The vessel neck gasket may be configured to comfortably accommodate a portion of the user's neck. The breathing apparatus may be in removable contact with: the vessel, with a head rest subassembly, and/or with the user. The breathing apparatus may be configured to permit the user to breathe while the user's face may be submerged within the liquid. When the vessel may be filled with the liquid to at least a sufficient level, the user may soak the face or the portion thereof, such that skin being soaked may receive a benefit.

Note, the term, "removably" as used within this disclosure may mean the two or more components being referenced in the sentence with "removably" may be in some embodiments be removable from each other. However, such use of "removably" is not intended to eliminate embodiments wherein the two components may not be removable. For example, as used above, in "the vessel neck gasket may be removably joined to the vessel" may mean in some embodiments the vessel neck gasket may be removed from the vessel (e.g. to effect repairs or replacement of the vessel neck gasket); whereas in other embodiments, the vessel neck gasket may not be removed from the vessel.

The benefits the user may derive from such face soaking may depend upon a number of factors. Some of these factors may include, but are not limited to, how long the user submerges their face in the liquid in any given use of the face soaking device, how often the user may use the face soaking device, and/or of characteristics the liquid.

For example, and without limiting the scope of the present invention, the characteristics of the liquid may comprise: the predominant chemical species of the liquid (e.g. water, oil, paraffin wax, water oil mixture, etc.) (which may be functioning as a solvent and/or carrier); an amount of air, oxygen, and/or gas present in the liquid (whether dissolved or not); a temperature of the liquid; whether or not the liquid may be circulated; and/or whether or not the liquid may be directed at a portion of the immersed face via a jet nozzle (or some other forced movement means). In some embodiments, the predominant chemical species may also comprise further additives, to provide various treatments. In some embodiments, these further additives to the liquid may comprise one or more of: salts, mineral salts, organic salts, minerals, active pharmaceutical ingredients, dyes, oxidizers, bleaching agents, lightening agents, cleansers, sanitizers, spices, fragrances, essential oils (e.g., in the context of the cosmetics industry), herbs, homeopathic ingredients, and/or medicinal ingredients. For example, and without limiting the scope of the present invention, such herbs may include herbs found in one or more of traditional Chinese medicine, traditional Japanese medicine, traditional Indian medicine, traditional Native American medicine, and the like. For example, and without limiting the scope of the present invention, such herbs may include various teas, including herbal teas and/or teas from the tea plant (tree). Some of these characteristics of the liquid may be inherent with the liquid and/or some of these characteristics of the liquid may be imparted to the liquid from the face soaking device.

For example, and without limiting the scope of the present invention, some such inherent properties may be chemical properties derived from the chemical composition of the liquid. In some embodiments, the liquid may be a saline solution, derived from dissolving various salts within water, oil, and/or an oil and water mixture. Such salts may comprise various positive ionic minerals with complimentary negative ions. Such minerals may include sodium, potassium, magnesium, and the like. Such negative ions may include chloride, sulfate, and the like. For example, such salts may be sodium chloride, potassium chloride, magnesium sulfate (Epsom salt), and the like. Different positive mineral ions may provide different benefits to the skin being soaked within the face soaking device. For example, some such positive mineral ions may tend to soften the skin, while others may tend to moisturize the skin. For example, Epsom salt baths tend to both soften and moisturize immersed skin.

Note, the term "saline," and/or "saline solution" may often be used to denote a salt solution comprising sodium chloride dissolved in water. Within this disclosure, the terms "saline" and/or "saline solution" may refer to any salt solutions, such as sodium chloride, potassium chloride, magnesium sulfate, and the like.

Such chemical properties, such as osmotic pressure, may be a function of salt concentration. In some embodiments, where it may be desirable for there to be an osmotic flow from within the immersed skin tissue towards the liquid, the liquid should have a salt concentration greater than 0.9% by weight.

In some embodiments, the liquid may be provided by the user. In such embodiments, the user may be free to formulate the liquid in any number of different ways. For example, the user may determine which salts to employ, or a mixture of salts. The user may set the salt concentration. The user may also add other additives and/or ingredients for other desired effects. For example, the user may use their own home-remedy recipes that may rely upon various herbal, mineral, homeopathic, and/or medicinal ingredients. Additionally, various licensed medical practitioners, may provide prescriptions for various formulations of liquid to be used within the face soaking device.

In some embodiments, a supplier of a face soaking device may provide various packets to be mixed with water, oils, paraffin waxes, and/or oil and water mixtures to formulate a given desired liquid for use within the face soaking device. These packets may comprise the various additives as noted above.

In some embodiments, the supplier of a face soaking device may provide recipes so that the user may mix and formulate the given desired liquid for use within the face soaking device.

For example, and without limiting the scope of the present invention, some such imparted characteristics of the liquid may be the amount of air, oxygen, and/or gas present in the liquid (whether dissolved or otherwise); the temperature of the liquid, whether or not the liquid may be circulated; and/or whether or not the liquid may be directed at a portion of the immersed face via the jet nozzle.

For example, and without limiting the scope of the present invention, the temperature of the liquid may be controlled with various heaters, chillers, and/or with ice. Chilling the liquid by use of the chiller, chilling equipment, and/or by introduction of ice, may then permit various cold therapy to be used to treat the face or other body part which may be removably immersed into the chilled liquid. In some embodiments, the liquid may be substantially ice. Additionally or alternatively, warm (or hot) therapy may be alternated with cold therapy; wherein such alternation of warmth and cold may aid in increasing blood flow, facilitating removal of cellular toxins (e.g., but not limited to, lactic acid), and/or promoting healing of burned or traumatized tissue.

Additionally, such face soaking devices may also be used for other purposes. For example and without limiting the scope of the present invention, face soaking devices may also be used: to relax, to facilitate face washing, to facilitate face soaking in preparation of facial shaving, as a wash for eyes, as a means to soak hands and/or feet, lower arms, lower legs, and the like.

In some uses, such face soaking devices may be used to lighten skin shading of the user, for example, by adding one or more oxidizers or bleaching agents to the liquid. For example, and without limiting the scope of the present invention, various concentrations of hydrogen peroxide may be used in the liquid as an oxidizer. In some uses, such face soaking devices may be used to lighten skin shading of the user, for example, by adding one or more lightening agents which may disrupt melanin production to the liquid. For example, and without limiting the scope of the present invention, various concentrations of hydroquinone may be used as a skin lightening agent. In some embodiments, one or more other skin lightening agent may be used with various embodiments of face soaking devices, such as, but not limited to, deoxyarbutin, glycolic acid, kojic acid, corticosteroids, niacinamide, retinol, soy, licorice extract, arbutin, and the like.

Conversely, in some uses, such face soaking devices may be used to darken skin shading of the user, for example, by imparting ultraviolet energy to the liquid to then tan the exposed skin. For example, and without limiting the scope of the present invention, ultraviolet light sources may be directed to impart ultraviolet electromagnetic (EM) energy into the liquid with sufficient intensity to provide an effect upon the user's skin. Or alternatively (or in addition) to ultraviolet treatment, one or more dyes (permanent or temporary) may be added to the liquid to change the hue (shade) of the user's skin. For example, and without limiting the scope of the present invention, one or more of dihydroxyacetone (DHA), erythrulose, melatonin (including derivatives and synthetic derivatives such as Melatonin II), and the like may be added to the liquid to darken (tan) the skin.

That is, various embodiments of face soaking devices may be used to lighten and/or darken hues, tones, and/or shades of skin.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

Figure 1A:
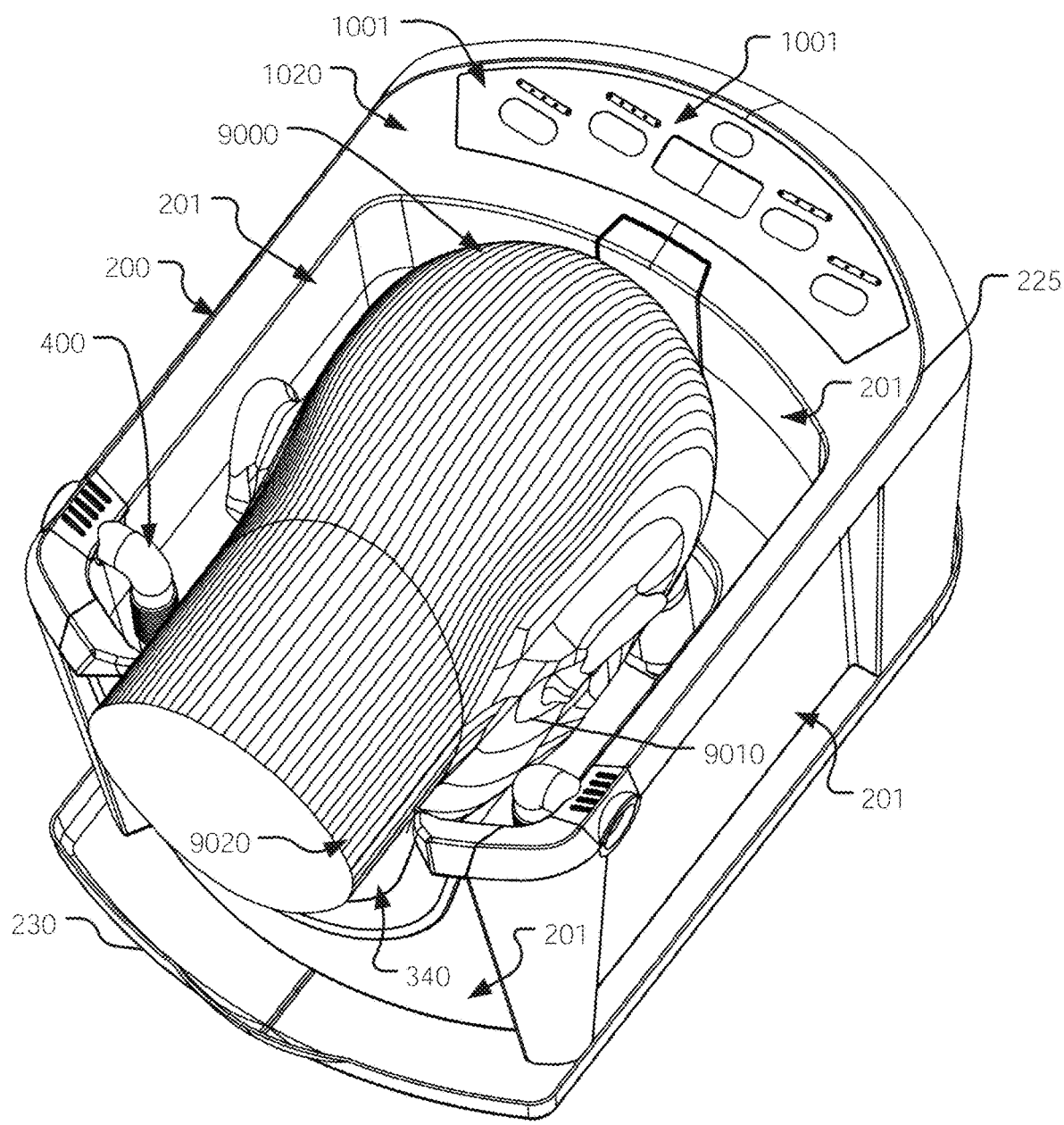
FIG. 1A may depict an exemplary embodiment of an overall assembled face soaking device, shown from a top perspective view, wherein at least a portion of a face of a user may be substantially immersed in an immersion liquid (liquid) removably contained within a vessel of the face soaking device.
Figure 1B:
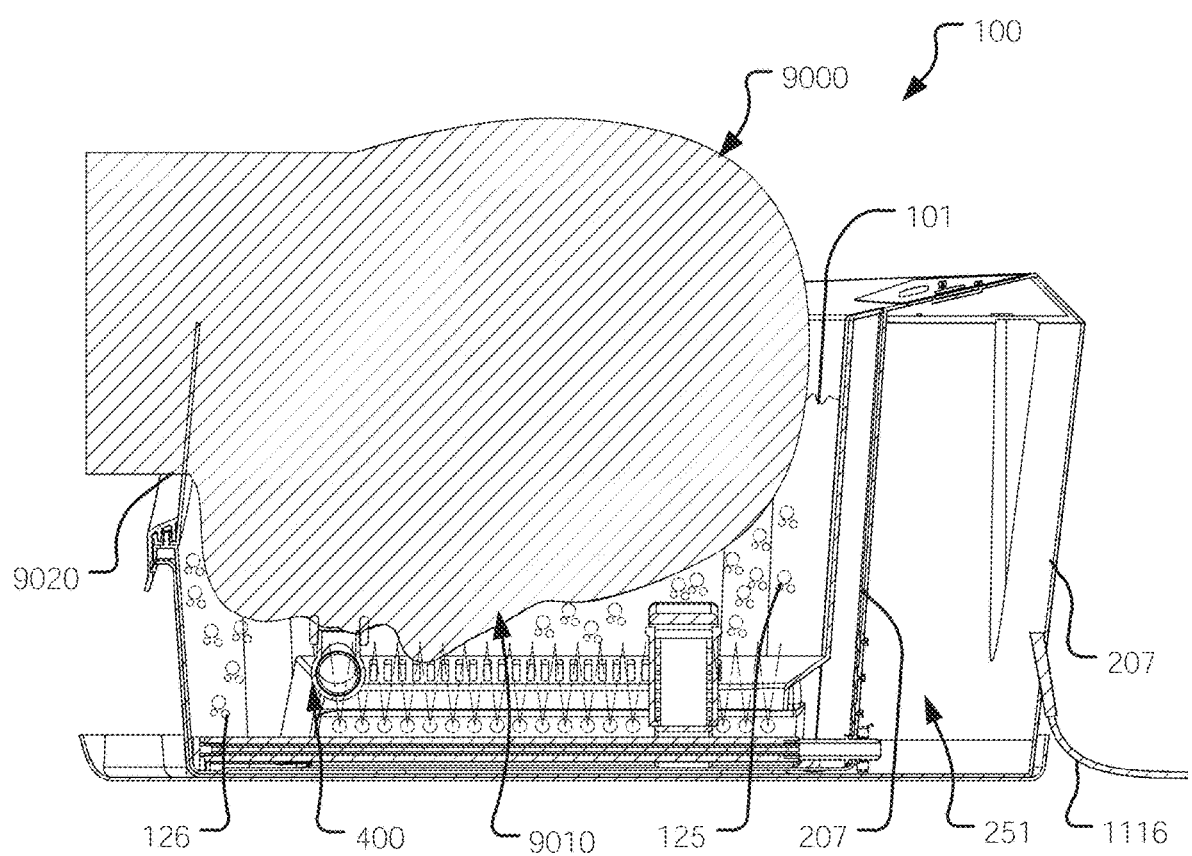
FIG. 1B may depict a longitudinal cross-section of face soaking device of FIG. 1A, wherein the at least the portion of the face of the user may be substantially immersed in the liquid removably contained within the vessel of the face soaking device.

FIG. 1A may depict an exemplary embodiment of an overall assembled face soaking device 100, shown from a top perspective view, wherein at least a portion of a face 9010 of a user 9000 may be substantially immersed in a liquid 101 (see FIG. 1B); that may be removably contained within a vessel 200 of face soaking device 100. FIG. 1B may depict a longitudinal cross-section of face soaking device 100 of FIG. 1A, wherein the at least the portion of face 9010 of user 9000 may be substantially immersed in liquid 101 removably contained within vessel 200 of face soaking device 100.

In some exemplary embodiments, as may be depicted in FIG. 1A and FIG. 1B, face soaking device 100 may comprise: vessel 200, a vessel neck gasket 340, and a breathing apparatus 400.

Continuing discussing FIG. 1A and FIG. 1B, in some embodiments, vessel 200 may be configured to hold liquid 101 in a sufficient volume to submerge a whole face 9010 of user 9000 or a portion thereof. It is obvious to one of ordinary skill in the art, that vessel 200 may be configured to hold liquid 101 at a sufficient level to permit user 9000 to submerge (immerse) the whole of face 9010, or a portion thereof within liquid 101, while liquid 101 may be held within vessel 200. This sufficient level may be a liquid level where when user 9000 inserts face 9010 into internal volume 220 and rests a first portion of neck 9020 upon vessel neck gasket 340, such that face 9010 may be completely immersed in the liquid. The maximum liquid level of vessel 200 may be greater (higher) than this sufficient level.

In some embodiments, vessel 200 may comprise at least one wall 201 and at least one base 215. At least one wall 201 and at least one base 215 may be in physical contact with each other. (See e.g., FIG. 2AG for at least one base 215.) At least one wall 201 may comprise a neck-gasket-accommodator 335. (See e.g., FIG. 3G for neck-gasket-accommodator 335.) Neck-gasket-accommodator 335 may be configured to accommodate vessel neck gasket 340. In some embodiments, neck-gasket-accommodator 335 may be formed as a cutout into a region of at least one wall 201, from a top of vessel 200. In some embodiments, neck-gasket-accommodator 335 may be formed as an integral molded structure of a region of at least one wall 201. Vessel neck gasket 340 may be removably joined to vessel 200. Where vessel neck gasket 340 may join vessel 200, i.e., along such surfaces of physical contact, a primary water tight seal may be formed in or at the vicinity of neck-gasket-accommodator 335. For example, and without limiting the scope of the present invention, in some embodiments, this vicinity of neck-gasket-accommodator 335 may be two inches or less. In other embodiments, other distances may be used for "the vicinity of neck-gasket-accommodator 335." Vessel neck gasket 340 may be configured to receive a first portion of a neck 9020 region of user 9000 when the whole face 9010 or the first portion thereof may be submerged in liquid 101. The first portion of the neck 9020 region of user 9000 may be where neck 9020 physically contacts vessel neck gasket 340. Note, the nature of the physical contact between the first portion of the neck 9020 region of user 9000 and vessel neck gasket 340 may be removable. When vessel neck gasket 340 may receive the first portion of the neck 9020 region, a secondary water tight seal may be formed between this first portion of the neck 9020 region and vessel neck gasket 340. Note, vessel 200 may be further detailed in the FIG. 2 series of figures and discussed below in the FIG. 2 series of figures discussion. Note, vessel neck gasket 340 and neck-gasket-accommodator 335 may be further detailed in the FIG. 3 series of figures and discussed below in the FIG. 3 series of figures discussion. (Note, this paragraph may in general refer to FIG. 1A and FIG. 1B, but with some of the references to structures and/or components being discussed in greater details below.)

In some embodiments, breathing apparatus 400 may be in physical contact with vessel 200, as may be shown in FIG. 1A and FIG. 1B (and focused on in the FIG. 4 series of figures). In some embodiments, a breathing apparatus embodiment may be in physical contact with a head rest subassembly 2100 (see e.g. FIG. 21 series of figures). In both embodiments, the nature of the physical contact between breathing apparatus embodiments (e.g., 400) and vessel 200; or between breathing embodiments and a head rest subassembly (e.g., 2100), may be removable in some embodiments; while non-removable in other embodiments.

In some embodiments, user 9000 may be able to breathe using breathing apparatus 400 when a mouth of user 9000 may be holding a mouth piece 401 of breathing apparatus 400. (See e.g., FIG. 4A for mouth piece 401.) Note, breathing apparatus 400 may be further detailed in the FIG. 4 series of figures and discussed below in the FIG. 4 series of figures discussion. (And other breathing apparatus embodiments may be addressed in a FIG. 20 series of figures, a FIG. 21 series of figures, and a FIG. 22 series of figures.)

When vessel 200 may be filled with liquid 101 to a level at or less than a maximum liquid level of vessel 200, user 9000 may soak the whole face 9010 or the portion thereof for a time period. The skin being soaked in liquid 101 for the time period may receive a health, an aesthetic, and/or a soothing benefit.

In some embodiments, the benefit may comprise one or more of a reduction in acne, a reduction in wrinkle severity, a softening of skin, moisturizing of skin, promotion of relaxation, promotion of healing of damaged skin, promotion of healing of infected skin, reduction in rash severity, reduction and/or elimination of headaches (including migraine), promotion of healing of traumatized tissue (including burned tissue), lightening skin shades, darkening skin shades (tone, hue), reduction in swelling, and the like. Such benefits may derive from facial skin exposure to liquid 101 where characteristics of liquid 101 may comprise one or more of liquid 101 being a saline solution, liquid 101 being a saline solution with a salt concentration greater than 0.9% by weight, presence of air and/or oxygen within liquid 101, temperature of liquid 101 being less than or greater than ambient room temperature, circulation of liquid 101 within vessel 200, and/or liquid 101 being directed against a portion of the skin in the form of stream or jet of liquid 101 pressure.

Now turning to a discussion of the FIG. 2 series of figures. The FIG. 2 series of figures may comprise FIG. 2A through FIG. 2H. These FIG. 2 series of figures may focus on depicting an overall assembled face soaking device 100, with the exception of FIG. 2G and FIG. 2H which may show exploded views. These FIG. 2 series of figures may focus on showing some structure and geometry of vessel 200.

Figure 2A:
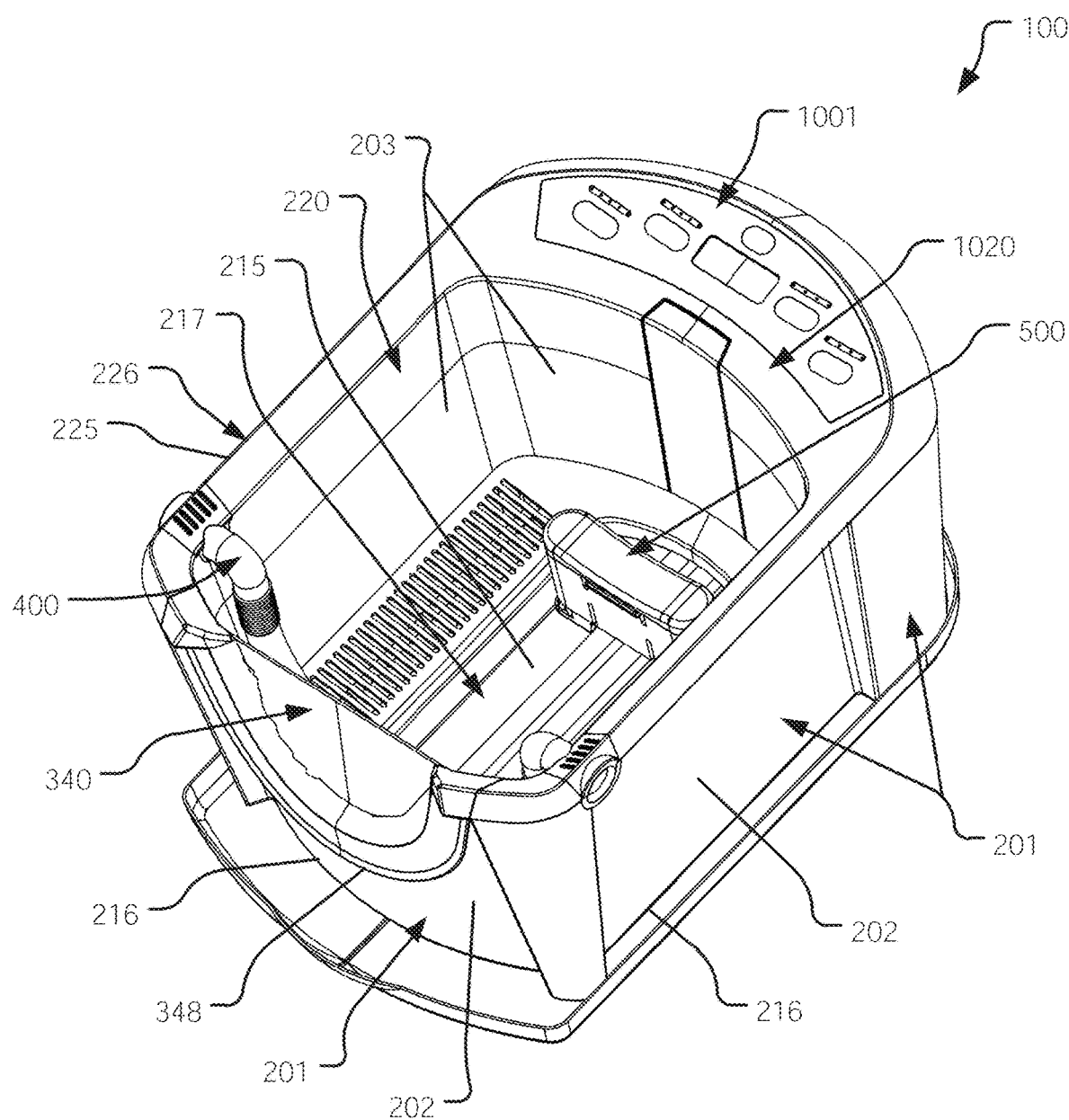
FIG. 2A may depict may depict an exemplary embodiment of an overall assembled face soaking device, shown from a top perspective view. The user may not be depicted in the FIG. 2 series of figures.
Figure 2B:
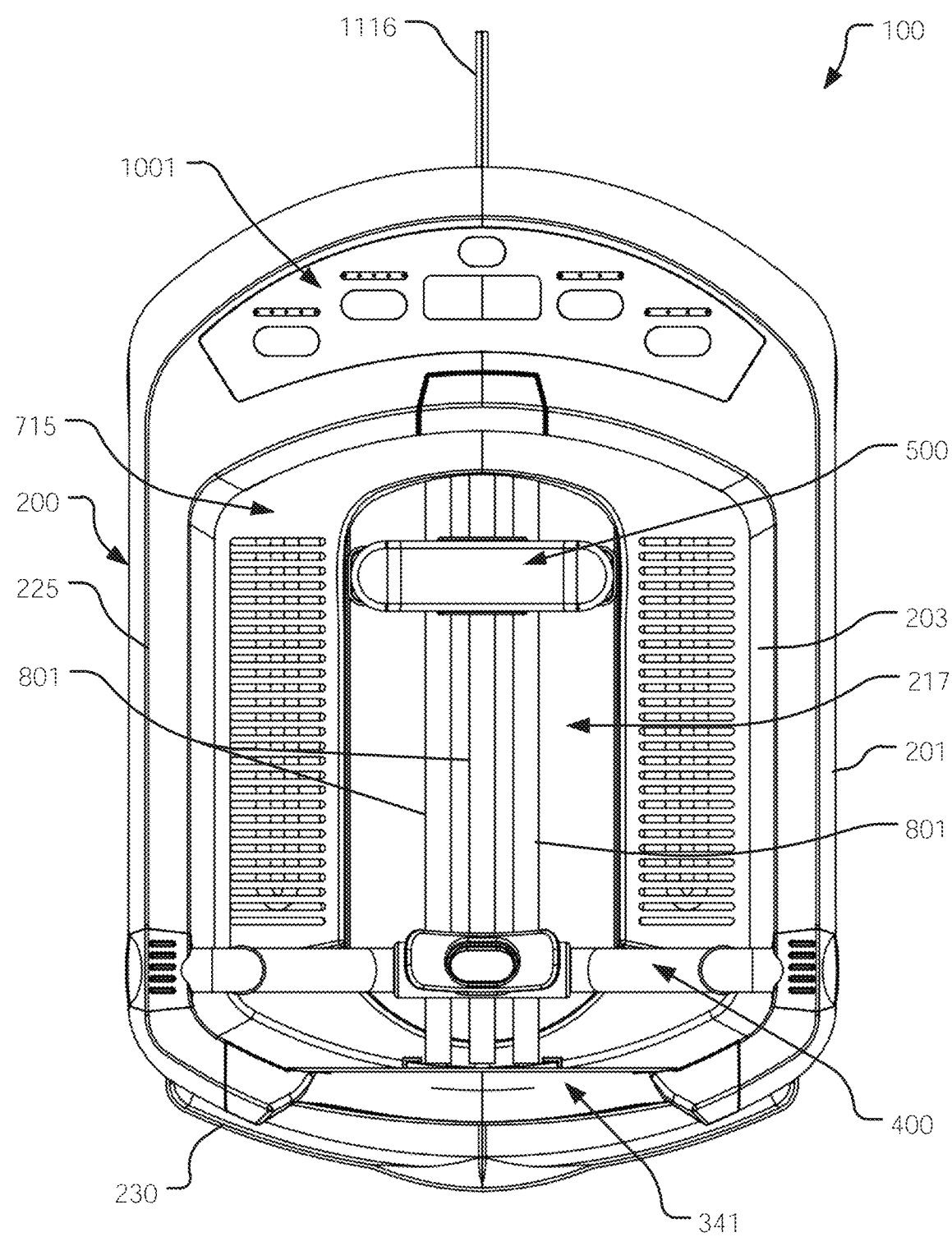
FIG. 2B may depict a top view of the face soaking device of FIG. 2A.
Figure 2C:
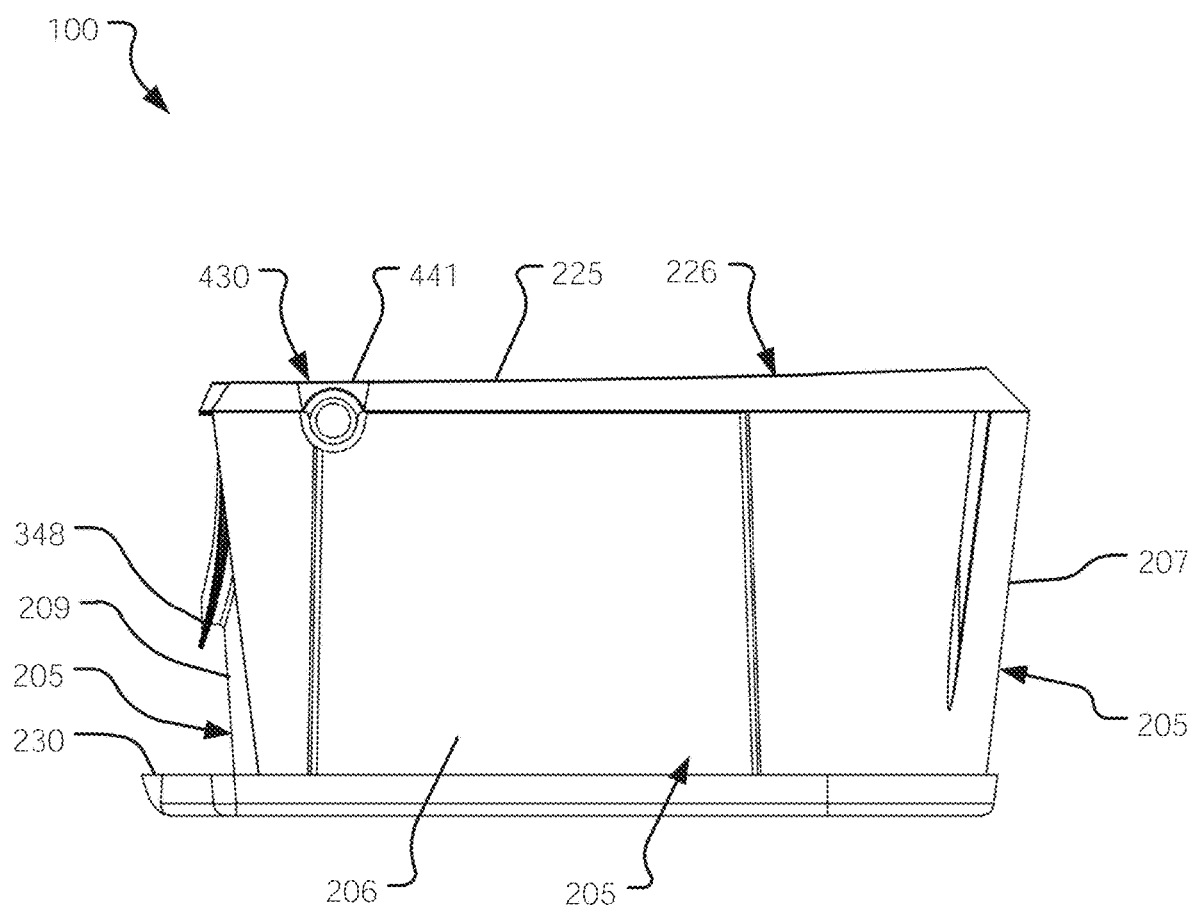
FIG. 2C may depict a longitudinal (exterior) side view of the face soaking device of FIG. 2A.
Figure 2D:
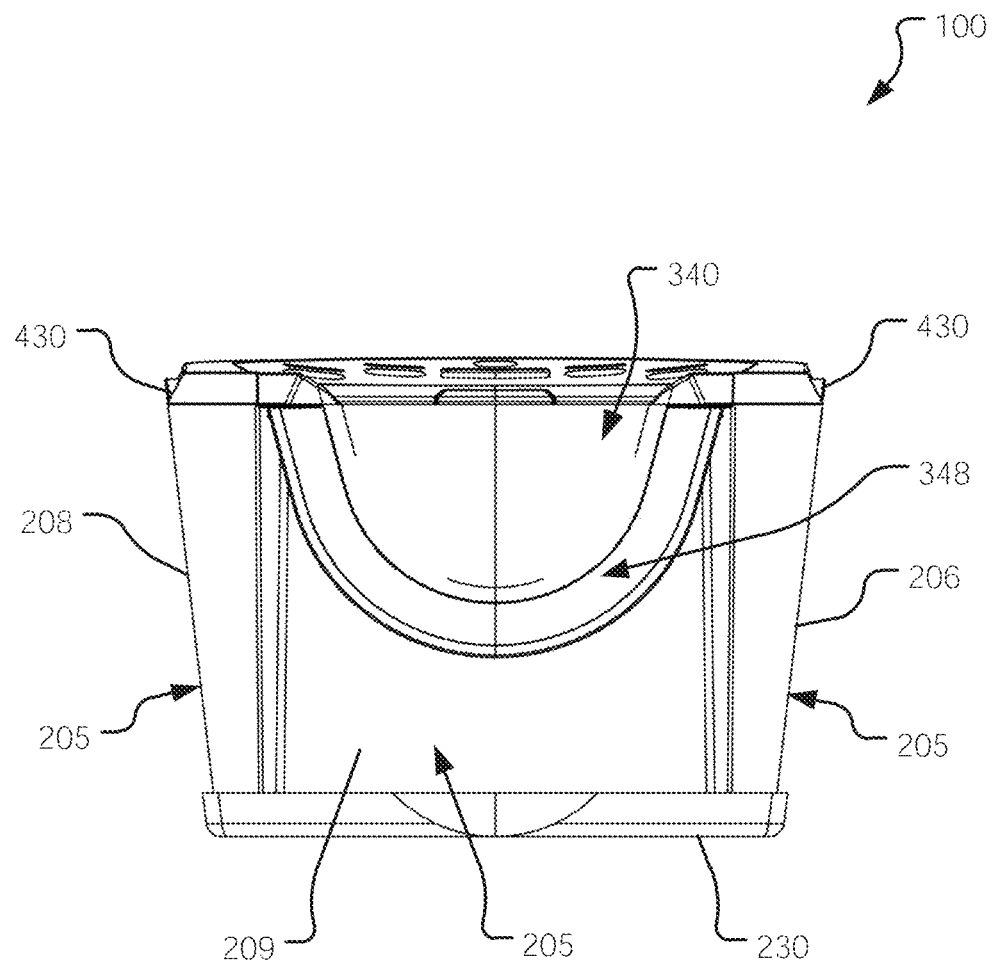
FIG. 2D may depict a front view of the face soaking device of FIG. 2A, which may depict a front of a vessel neck gasket of the face soaking device.
Figure 2E:
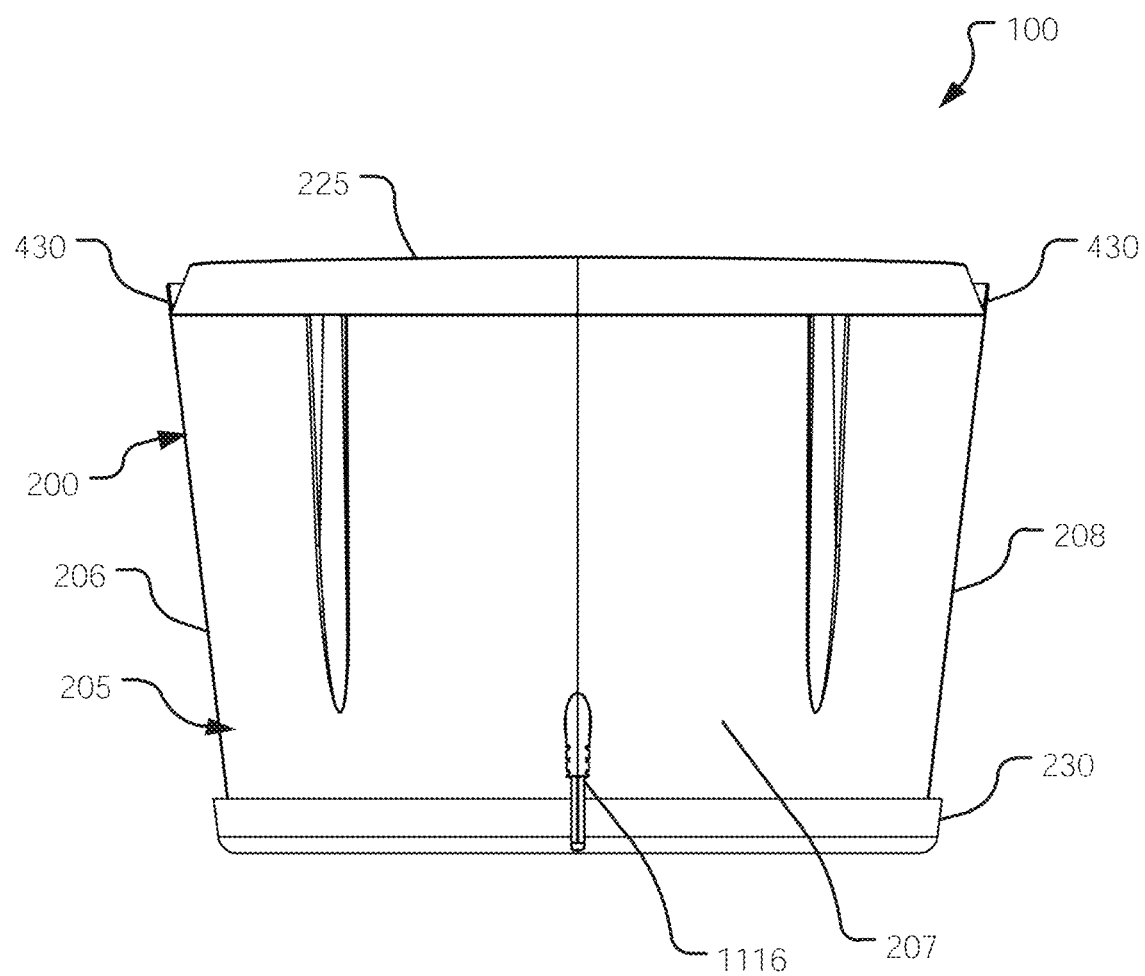
FIG. 2E may depict a back view of the face soaking device of FIG. 2A.
Figure 2F:
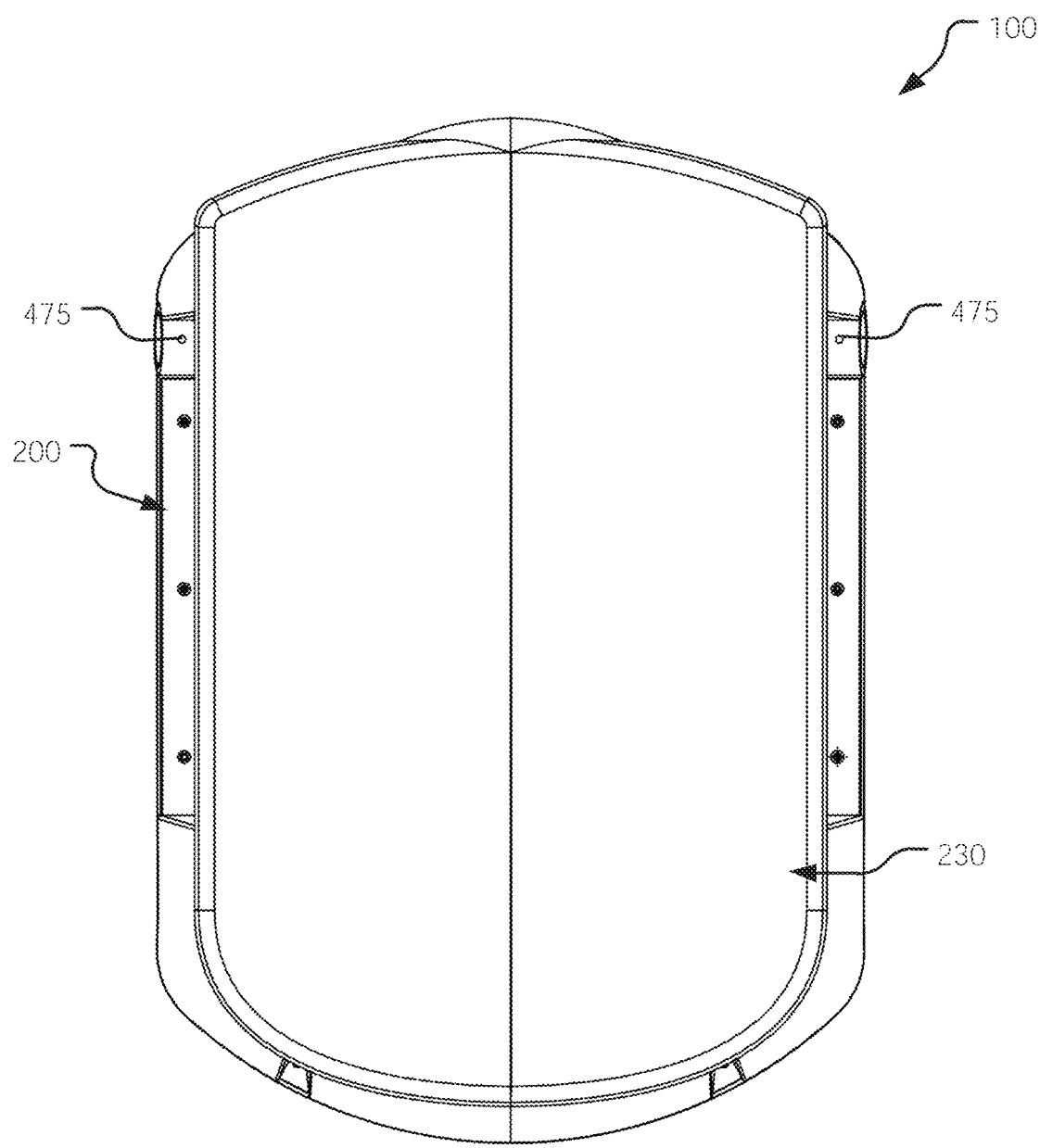
FIG. 2F may depict a bottom view of the face soaking device of FIG. 2A.
Figure 2G:
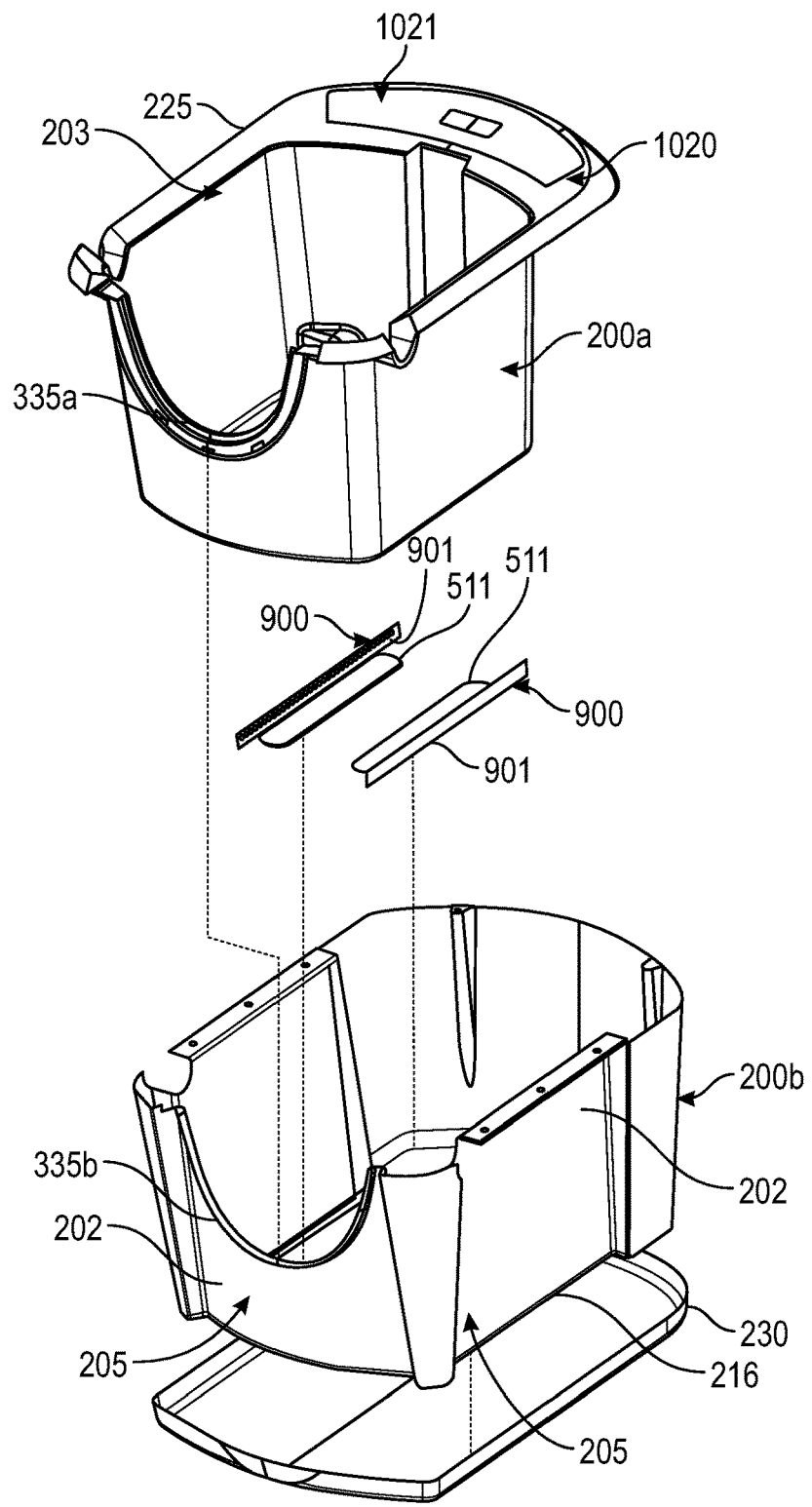
FIG. 2G and FIG. 2H together may depict an exploded top perspective view of the face soaking device of FIG. 2A; wherein this exploded view is shown across two drawing sheets.
Figure 2H:
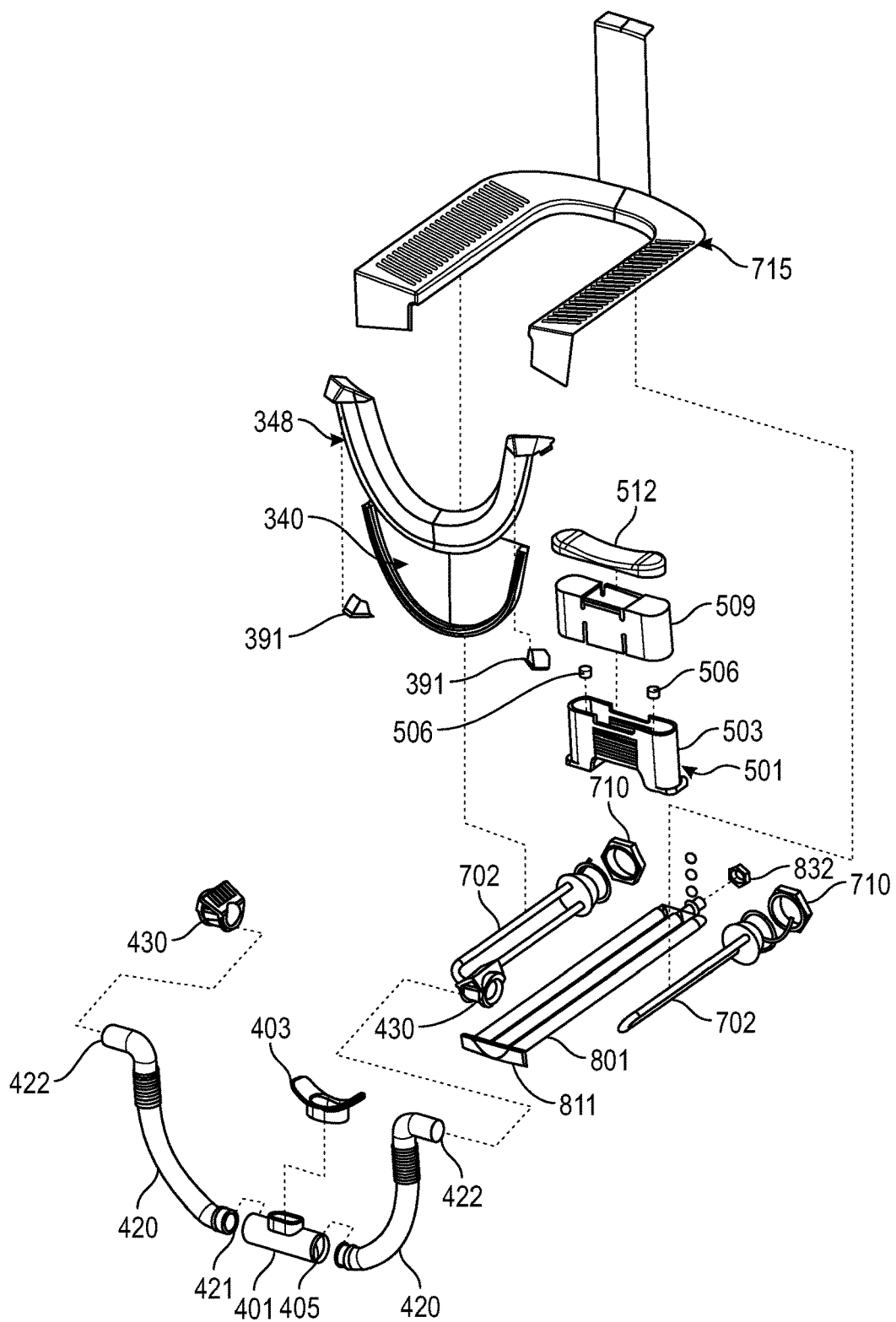

FIG. 2A may depict may depict an exemplary embodiment of an overall assembled face soaking device 100, shown from a top perspective view. User 9000 may not be depicted in the FIG. 2 series of figures. Liquid 101 may not be depicted in the FIG. 2 series of figures; see FIG. 1B for a depiction of liquid 101. FIG. 2B may depict a top view of face soaking device 100. FIG. 2C may depict a longitudinal (exterior) side view of face soaking device 100. Technically FIG. 2C may be a right longitudinal (exterior) side view of face soaking device 100; although in some embodiments, the right longitudinal (exterior) side view of face soaking device 100 may be substantially similar to a left longitudinal (exterior) side view of face soaking device 100, which may not be depicted in the figures. FIG. 2D may depict a front view of face soaking device 100, which may depict a front of a vessel neck gasket 340 of face soaking device 100. The front view may also be known as a vessel neck gasket view. The right view may be with respect to an observer looking upon the front view, wherein the right view may be with respect to the observer's right, i.e., the right side of face soaking device 100 when viewed from the front view. FIG. 2E may then depict a back view of face soaking device 100 (i.e., an opposing view from FIG. 2D). FIG. 2F may depict a bottom view of face soaking device 100. FIG. 2G and FIG. 2H together may depict an exploded top perspective view of the face soaking device 100; wherein this exploded view is shown across two drawing sheets.

In FIG. 2A, in some embodiments, vessel 200 may comprise at least one wall 201 and at least one base 215. At least one wall 201 and at least one base 215 may be in physical contact with each other. In some embodiments, the nature of the physical contact between at least one wall 201 and at least one base 215 may be that of permanent connection, where all points of contact may be water tight. In some embodiments, at least one base 215 may be conceptualized as a bottom of a given face soaking device embodiment. See e.g., FIG. 2A.

In some embodiments, at least one wall 201 may comprise an exterior wall surface 202 and an interior wall surface 203 disposed opposite of each other separated by a wall thickness. Interior wall surface 203 may circumscribe an internal volume 220 of vessel 200. Internal volume 200 of vessel 200 may be configured to hold liquid 101. That is, all interior wall surfaces 203, including the interior surfaces of at least one base 215 may all be water tight. See e.g. FIG. 2A.

In some embodiments, at least one base 215 may comprise bottom interior surface 217. References to at least one base 215, could include exterior or interior surfaces of at least one base 215; whereas, references to bottom interior surface 217 may be respect to interior surfaces of at least one base 215. In some embodiments, interior wall surface 203 and bottom interior surface 217 may together circumscribe internal volume 220, with an upper main opening noted as top opening 226. See e.g., FIG. 2A.

For example, and without limiting the scope of the present invention, in some embodiments, internal volume 220 may be from a half gallon to five and half gallons or any other volume suitable for submerging face 9010. In other embodiments, other volumes may be used for internal volume 220.

In some embodiments, at least one wall 201 and/or at least one base 215 may be constructed of semi-rigid to rigid materials of construction. The semi-rigid to the rigid materials of construction may be selected from one or more of the group comprising: thermo formed plastics, glass, fiberglass, metals, wood, ceramics, composites thereof, and any other semi-rigid to rigid materials suitable for holding liquid 101 within internal volume 220.

For example, and without limiting the scope of the present invention, thermo formed plastics may comprise one or more of the group of: acrylic; vinyl, including polyvinyl chloride (PVC); acrylonitrile butadiene styrene (ABS); polycarbonate, polyethylene, polypropylene, and any other thermo formed plastic suitable for holding liquid 101 within internal volume 220.

In some embodiments, at least one wall 201 and/or at least one base 215 may be constructed of a flexible material of construction such that vessel 200 may be formed by inflating a space between exterior wall surface 202 and interior wall surface 203 with a gas, such as air. When this space may be filled with the gas, the gas may exert sufficient pressure against exterior wall surface 202 and interior wall surface 203 to provide at least a semi-rigid structure to vessel 200. In some such embodiments, a valve may be attached to exterior wall surface 202 (and/or interior wall surface 203) to permit inflating of vessel 200 and/or deflating of vessel 200. In some embodiments, such a valve may be openable and removably closeable. Such an inflatable vessel 200 may facilitate portability of vessel 200.

In some embodiments, at least one wall 201 of vessel 200 may comprise an upper portion (upper boundary), i.e., a rim 225. Rim 225 may circumscribe top opening 226 to internal volume 220 of vessel 200. Rim 225 may substantially circumscribe top opening 226 to internal volume 220 of vessel 200. Rim 225 may be disposed opposite from at least one base 215 (or bottom interior surface 217). See e.g., FIG. 2A. Top opening 226 may permit internal volume 220 of vessel 200 to be filled with liquid 101 to the level at or less than the maximum liquid level of vessel 200. Top opening 226 may permit internal volume 220 of vessel 200 to be drained of liquid 101. That is, top opening 226 may permit access to internal volume 220.

Figure 13A:
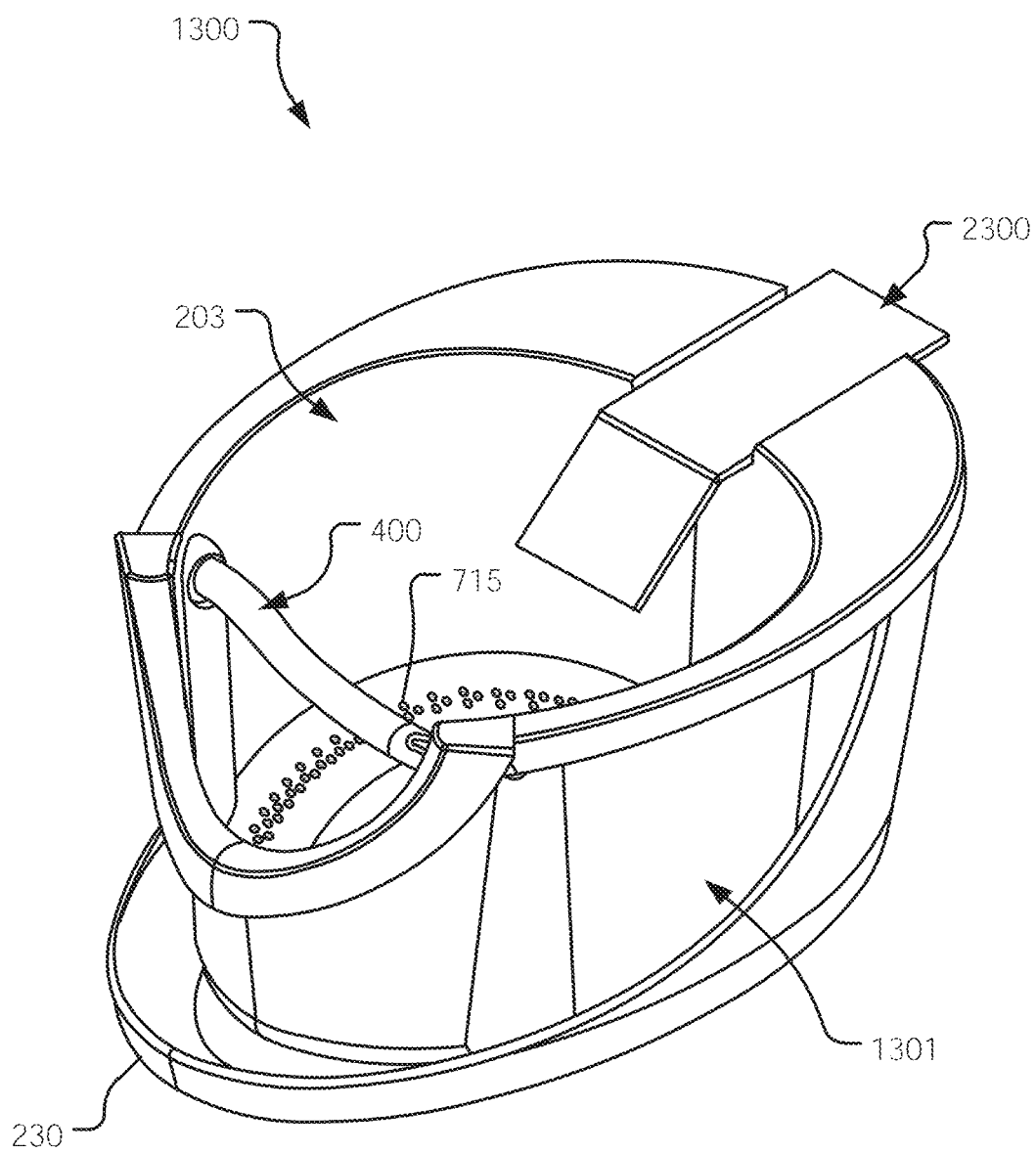
FIG. 13A may depict a face soaking device with curved vessel wall, shown a top perspective view.

In some embodiments there may be one continuous wall 201, such as curved wall 1301. In such embodiments, an overall shape of the vessel may be hemispherical, such as a bowl shape, wherein top opening 226 may be ovoid (e.g.

oval and/or elliptical), including circular, as viewed from above. See e.g., FIG. 13A which may depicted curved wall 1301.

Continuing discussing the FIG. 2 series of figures. In some embodiments, vessel 200 may comprise a catch basin 230. Catch basin 230 may be in physical contact with vessel 200. In some embodiments, the nature of the physical contact may be removable; whereas, in other embodiments the nature of the physical contact may be removable. Catch basin 230 may be configured to catch liquid 101 spilled from internal volume 220 of vessel 200. Catch basin 230 may be in physical contact with portions of at least one wall 201 of vessel 200. Catch basin 230 may be in physical contact with at least some portion of exterior wall surface 202 of at least one wall 201 of vessel 200. Catch basin 230 may be in physical contact with perimeter 216 of base 215. Catch basin 230 may circumscribe a perimeter greater than or less than, of at least one wall 201 of vessel 200 or of perimeter 216 of at least one base 215. See e.g., FIG. 2A.

In some embodiments, a location of catch basin 230 may be at at least one base 215 of vessel 200, where exterior wall surface 202 of at least one wall 201 may meet an exterior surface of at least one base 215. In some embodiments, the nature of the physical contact between catch basin 230 and some portions of exterior wall surface 202 of at least one wall 201 may be integral, such that two may be one article of manufacture. In some embodiments, catch basin 230 may be removable from vessel 200. In some embodiments, catch basin 230 may be located at and/or attached to a bottom of at least one base 215. See e.g., FIG. 2A. See also FIG. 2F, which may be a bottom view of face soaking device 100, wherein a bottom of catch basin 230 may be depicted.

In some embodiments, catch basin 230 may be constructed of semi-rigid to rigid materials of construction. The semi-rigid to rigid materials of construction may be selected from one or more of the group comprising: thermo formed plastics, glass, fiberglass, metals, wood, ceramics, composites thereof, and any other semi-rigid to rigid materials suitable for its intended purpose of catching spilled liquid 101 from internal volume 220. In some embodiments, catch basin 230 may be constructed of the same materials as at least one wall 201 and at least one base 215 may be constructed of. In some embodiments, vessel 200 and/or catch basin 230 may be injection molded, 3D printed, machines, and/or a combination thereof.

In some embodiments, between exterior wall surface 202 and interior wall surface 203 may enclose an insulation space within at least one wall 201. (See e.g., insulation 3305 in FIG. 33B.) This insulation space may comprise a form of thermal insulation. The form of thermal insulation may be selected from one or more of the group comprising: liquids, air, foams, gels, batting, fibers, wools, vacuum, any other form of thermal insulation, and/or combinations thereof. A purpose of this insulating space may be to provide insulation to liquid 101 removably occupying internal volume 220 of vessel 200. For example, and without limiting the scope of the present invention, in some embodiments, this insulating liquid may be water or some other insulating liquid.

Now turning to FIG. 2C which may depict vessel 200 from a longitudinal (exterior) side view. In some embodiments, the at least one wall 201 may comprise at least one side wall 205. Note, at least one wall 201 may be a broader structural element than at least one side wall 205. At least one side wall 205 may refer to walls of vessel 200 that may be at least partially vertically (or substantially vertically) oriented with respect to at least one base 215, which may be substantially horizontally oriented, when in use. Thus, any reference to at least one wall 201 in the figures may be replaced with at least one side wall 205, if that at least one wall 201 depicted is at least partially vertically oriented. Note at least one base 215 may not be depicted in FIG. 2C. In some embodiments, at least one side wall 205 may comprise exterior wall surface 202 and interior wall surface 203 disposed opposite of each other separated by the wall thickness (which may be variable). In some embodiments, interior wall surface 203 and bottom interior surface 217 may form internal volume 220. In some embodiments, figures labeled with at least one side wall 205 may be replaced with at least one wall 201.

In some embodiments, at least one side wall 205 and at least one base 215 may be in physical contact with each other. A point of contact between at least one side wall 205 and at least one base 215 may form a perimeter of base 216 of base 215. See e.g. FIG. 2A for perimeter of base 216. At least a portion of the base 215 within the perimeter of base 216 may be flat such that face soaking device 100 may rest with stability upon a flat substrate. At least a portion of a bottom of catch basin 230 may be flat such that face soaking device 100 may rest with stability upon the flat substrate. See e.g., FIG. 2F. For example, and without limiting the scope of the present invention, the flat substrate may be a tabletop, a countertop, a desktop, a floor, a ground surface, and/or the like.

In some embodiments, at least one side wall 205 may have some curvature, such as a bowl shaped side wall. See e.g., the FIG. 13 series of figures. Continuing discussing the FIG. 2 series of figures, in some embodiments, exterior wall surface 202 of at least one side wall 205 and the flat portion of base 215 may be substantially perpendicular to each other for some part of at least one side wall 205, because other parts of at least one side wall 205 may be curved. "Substantially perpendicular" as used herein may note that such relationship need not be perfect true geometric perpendicular relationship, but rather such corresponding surfaces diverge from each at approximately 90 degrees, e.g., within plus or minus 11 degrees from 90 degrees. In other embodiments, exterior wall surface 202 of at least one side wall 205 and the flat portion of base 215 may not be true geometric perpendicular to each other. For example, in embodiments where at least one side wall 205 tends to flare outwards away from internal volume 220.

In some embodiments, at least one side wall 205 may comprise four side walls, a first side wall 206, a second side wall 207, a third side wall 208, and a fourth side wall 209. See e.g., FIG. 2C for first side wall 206, second side wall 207, and fourth side wall 209; and see FIG. 2D for first side wall 206, third side wall 208, and fourth side wall 209. First side wall 206 and third side wall 208 may be substantially parallel to each other. First side wall 206 and third side wall 208 may be oppose each other. Second side wall 207 and fourth side wall 209 may be substantially parallel to each other. Second side wall 207 and fourth side wall 209 may oppose each other. First side wall 206 may be in physical contact with second side wall 207, fourth side wall 209, and at least one base 215. Second side wall 207 may be in physical contact with first side wall 206, third side wall 208 and at least one base 215. Third side wall 208 may be in physical contact with second side wall 207, fourth side wall 209, and at least one base 215. Fourth side wall 209 may be in physical contact with first side wall 206, third side wall 208, and at least one base 215. See FIG. 2C for first side wall 206. See FIG. 2E for second side wall 207. See FIG. 2D for fourth side wall 209. An exterior wall surface 202 view of third side wall 208 is not depicted from a straight on view in the figures because a left view of face soaking device 100 was not included as such a view may be largely redundant with the right view of FIG. 2C. However, third side wall 208 (and first side wall 206) may be depicted in FIG. 2D as side walls that may be substantially perpendicular or abutting walls with fourth side wall 209. Interior wall surface 203 of third side wall 208 may be depicted in FIG. 2A and FIG. 2B. FIG. 2B may depict interior wall surfaces 203 of all four side walls.

In some embodiments, fourth side wall 209 may be a front wall. In some embodiments, first side wall 206 and third side wall 208 may be side walls (right and left, respectively). In some embodiments, second side wall 207 may be a back wall. These front wall and back wall may be opposing walls.

In some embodiments, where each side wall 205 may join (i.e. meet) another side wall 205 and/or where each side wall 205 may join (i.e. meet) at least one base 215, an integral seam (i.e. watertight) may be formed. In some embodiments, such seams and the transitions to such seams may be smooth and continuous to facilitate cleaning of the internal volume, to reduce a likelihood debris accumulating, and/or the like.

Now turning to FIG. 2G and FIG. 2H. FIG. 2G and FIG. 2H together may depict an exploded top perspective view of the face soaking device 100. In FIG. 2G, vessel 200, portions of at least one electromagnetic (EM) emitter 900, portions of a head rest subassembly 500, and catch basin 230 may be depicted. In FIG. 2H, vessel neck gasket 340, clamp 348, breathing apparatus 400, remaining portions of head rest subassembly 500, heater subassembly 700, and a gas diffuser 800 may be depicted. Vessel neck gasket 340, clamp 348, and neck-gasket-accommodator 335 may be addressed further in the FIG. 3 series of figures and its corresponding discussion. Breathing apparatus 400 may be addressed further in the FIG. 4 series of figures and its corresponding discussion. Head rest subassembly 500 may be addressed further in the FIG. 5 series of figures and its corresponding discussion. Heater subassembly 700 may be addressed further in the FIG. 7 series of figures and its corresponding discussion. Gas diffuser 800 may be addressed further in the FIG. 8 series of figures and its corresponding discussion. At least one EM emitter 900 may be addressed further in the FIG. 9 series of figures and its corresponding discussion.

In some embodiments, vessel 200 may comprise two complimentary fitting hull shells, vessel lining 200a and vessel cover 200b. In some embodiments, vessel 200 may be comprised of a double hulled structured. See e.g., FIG. 2G. In some embodiments, vessel lining 200a may be inserted into vessel cover 200b to form vessel 200. In some embodiments, such an insertion may be designed to be permanent; whereas in other embodiments such an insertion may be removable. In some embodiments, bottom exterior portions of vessel cover 200b may be integral with catch basin 230. In some embodiments, substantially all of the interior surfaces of vessel lining 200a may comprise interior wall surfaces 203 and bottom interior surface 217. In some embodiments, substantially all of vertically oriented exterior surfaces of vessel cover 200b may comprise exterior wall surfaces 202.

In some embodiments, at least one plate 511 may be disposed between vessel lining 200a and vessel cover 200b. See e.g., FIG. 2G. At least one plate 511 may be a component of head rest subassembly 500. In some embodiments, portions of at least one EM emitter 900 may be disposed between vessel lining 200a and vessel cover 200b. See e.g., FIG. 2G.

Note, although not visible in FIG. 2G, in some embodiments, disposed between vessel lining 200a and vessel cover 200b at or proximate to second side wall 207 (i.e., the back wall) may a mechanical compartment 251. In some embodiments, this mechanical compartment 251 may house at least some portions of electronics (e.g., controller 1100 and compressor 1110) and some portions of airline tubing 819 of face soaking device 100. That is, mechanical compartment 251 may be formed between exterior portions of second side wall 207 of vessel cover 200b and interior portions of second side wall 207 of vessel lining 200a. See e.g., FIG. 1B and FIG. 5G.

In some embodiments, vessel 200 may comprise at least one port 210. At least one port 210 may be configured to permit passage, insertion, or attachment of various articles, through, in, or on at least one port 210 in at least one wall 201. In some embodiments, at least one port 210 may be a small opening for the controlled passage of the various articles from an exterior to an interior of vessel 200. Small opening as used herein may mean a diameter of at least one port 210 that may be small enough to permit passage of the various articles in a manner where such passage may be water tight. In some embodiments, at least one port 210 may provide passage from internal volume 220 to mechanical compartment 251. In some embodiments, at least one port 210 may provide passage from exteriorly of face soaking device 100 to mechanical compartment 251. The various articles may be selected from one or more of the group comprising: fiber optics, wiring, electrical cords (e.g., electrical power cord 1116), hoses, tubing, airline tubing 819, a drain valve, a drain plug, gaskets, O-rings, grommets, fittings, at least one vessel-tube-hose-connector, or any other suitable article to achieve its intended purpose. See e.g., FIG. 8G, which may show at least one port 210, which may be for receiving airline tubing connector 817 of connector 813. See also FIG. 9B and FIG. 9C, which may show a back side of where this at least one port 210 may be, where in FIG. 9B and FIG. 9C nut 832 may be shown (connected to airline tubing connector 817).

In some embodiments, each such port 210 may comprise a port gasket, a port grommet, and/or a port O-ring to provide a water tight seal between a port surface and the article that may be passing through port 210. Such port gaskets, port grommets, and/or port O-rings may be constructed of various elastomers (e.g. silicones, rubbers, and the link) with different durometers to achieve the water tight seal. For example, and without limiting the scope of the present invention, such port gaskets may be gasket 831. Gasket 831 may be used to seal airline tubing 819 to a given port 210.

In some embodiments, face soaking device 100 may comprise a drain. The drain may be configured to permit user 9000 to remove at least a majority of liquid 101 from internal volume 220. In some embodiments, the drain may be located at, or near, at least one base 215 of vessel 200. For example, and without limiting the scope of the present invention, in some embodiments, near at least one base 215 may be at or less than two inches. In other embodiments, near at least one base 215 may be other distances. In some embodiments, the drain may be either a drain valve or a removable plug.

In some embodiments, the interior surface of at least one base 215 may be sloped to mitigate against undesirable pooling of residual liquid and to encourage proper drainage of the liquid 101 from the drain.

At least one interior wall surface 203 may comprise at least one liquid fill indicator. The at least one liquid fill indicator may comprise structural geometry on interior wall surface 203 that may be visible to user 9000. The at least one liquid fill indicator 620 may indicate a volume of liquid 101 that may be held within internal volume 220 when the liquid level touches the at least one liquid fill indicator. The at least one liquid fill indicator may comprise a plurality of graduated markings arranged in a vertical fashion on interior wall surface 203. These graduated markings, may or may not, have associated numerical markings indicating different fill volumes of liquid 101.

In some embodiments, the at least one liquid fill indicator may designate the maximum liquid level. In some embodiments, the at least one liquid fill indicator may comprise a horizontal, a vertical, and/or raised line(s) from interior wall surface 203. Such a raised line may be integral and molded during manufacturing. In some embodiments, the at least one liquid fill indicator may comprise raised lettering and/or numbering.

In some embodiments, a 2D overall external shape of a vessel of a given face soaking device as viewed from above may be selected from the group comprising: regular polygons (with or without rounded corners), irregular polygons (with or without rounded corners), square (with or without rounded corners), rectangular (with or without rounded corners), trapezoidal (with or without rounded corners), circles, ellipses, and/or ovals. See example, FIG. 13A which may depict a face soaking device 1300 with curved vessel wall 1301, shown a top perspective view, such that the 2D overall external shape may be oval and/or elliptical. Curved vessel wall 1301 may replace at least one wall 201 in such embodiments. See also, FIG. 13B, wherein the 2D overall external shape may be oval and/or elliptical.

Figure 13B:
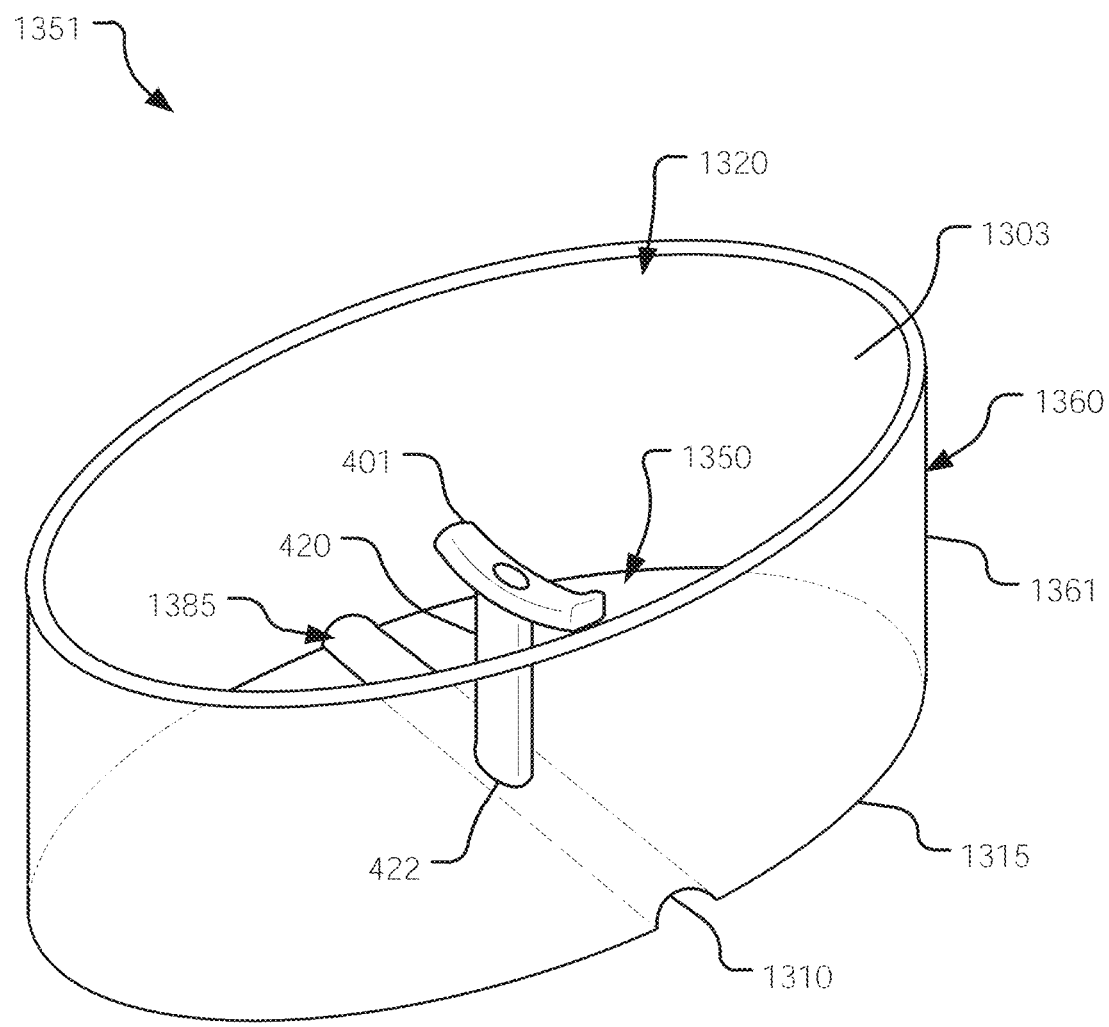
FIG. 13B may depict a face soaking device, wherein portions of a breathing apparatus may emerge from a bottom of a vessel of the face soaking device, shown from a top perspective view.

FIG. 13B may depict a face soaking device 1351, wherein portions of a breathing apparatus (e.g., variations of breathing apparatus 400) may emerge from a bottom 1350 of a vessel 1360 of face soaking device 1351, shown a top perspective view. FIG. 13B may depict face soaking device 1351 that may not comprise a vessel neck gasket nor a neck-gasket-accommodator.

In some embodiments, face soaking device 1351 may comprise vessel 1360 and the breathing apparatus. Vessel 1360 may be configured to hold liquid 101 in a sufficient volume to submerge whole face 9010 of user 9000 or a portion thereof. Vessel 1360 may comprise at least one wall 1361 and at least one base 1315. At least one wall 1361 and the at least one base 1315 may be in physical contact with each other. At least one wall 1361 and the at least one base 1315 may together form vessel 1360, which may substantially bound internal volume 1320.

When internal volume 1320 of vessel 1360 may be filled with the liquid 101 to a level at or less than a maximum liquid level of the vessel, user 9000 may soak whole face 9010 or the portion thereof for a time period, such that skin being soaked in liquid 101 for the time period may receive health, aesthetic, and/or soothing benefits.

In some embodiments, portions of the breathing apparatus may extend from a bottom interior surface 1350 of internal volume 1320 (depicted in FIG. 13B) and/or from interior wall surface 1303 (where that embodiment is not depicted in FIG. 13B). The breathing apparatus may comprise a mouth piece 401, at least one vessel-tube-hose-vent 1310, and at least one hose 420 or at least one tubing 420. At least one hose 420 or the at least one tubing 420 may connect mouth piece 401 to at least one vessel-tube-hose-vent 1310. Mouth piece 401 may be configured to be held by the mouth of user 9000. At least one vessel-tube-hose-vent 1310 may be in gas communication with air and may be configured for respiratory gas movement. At least one vessel-tube-hose-vent 1310 may be located at a bottom exterior of vessel 1360. User 9000 may be able to breathe using breathing apparatus 400 when the mouth of the user may holding mouth piece 401. See e.g., FIG. 13B.

In some embodiments, breathing apparatus 400 may comprise at least one horizontal hose 1385 or at least one horizontal tube 1385. A second terminal end 422 of at least one hose 420 or at least one tubing 420 may removably attach to at least one horizontal hose 1385 or at least one horizontal tube 1385. Such an attachment may be configured to permit respiratory gasses to move freely between an opening of mouthpiece 401 and at least one vessel-tube-hose-vent 1310. In some embodiments, at least one hose 420 or at least one tubing 420 may be flexible; while, at least one horizontal hose 1385 or at least one horizontal tube 1385 may be semi-rigid to rigid. In some embodiments, at least one horizontal hose 1385 or at least one horizontal tube 1385 may be integral and formed from a portion of at least one base 1315. For example, and without limiting the scope of the present invention, at least one horizontal hose 1385 or at least one horizontal tube 1385 and at least one base 1315 may be constructed of the same materials of construction. For example, and without limiting the scope of the present invention, at least one horizontal hose 1385 or at least one horizontal tube 1385 and at least one base 1315 may be molded (e.g. injection molded) as one article of manufacturing.

Figure 13C:
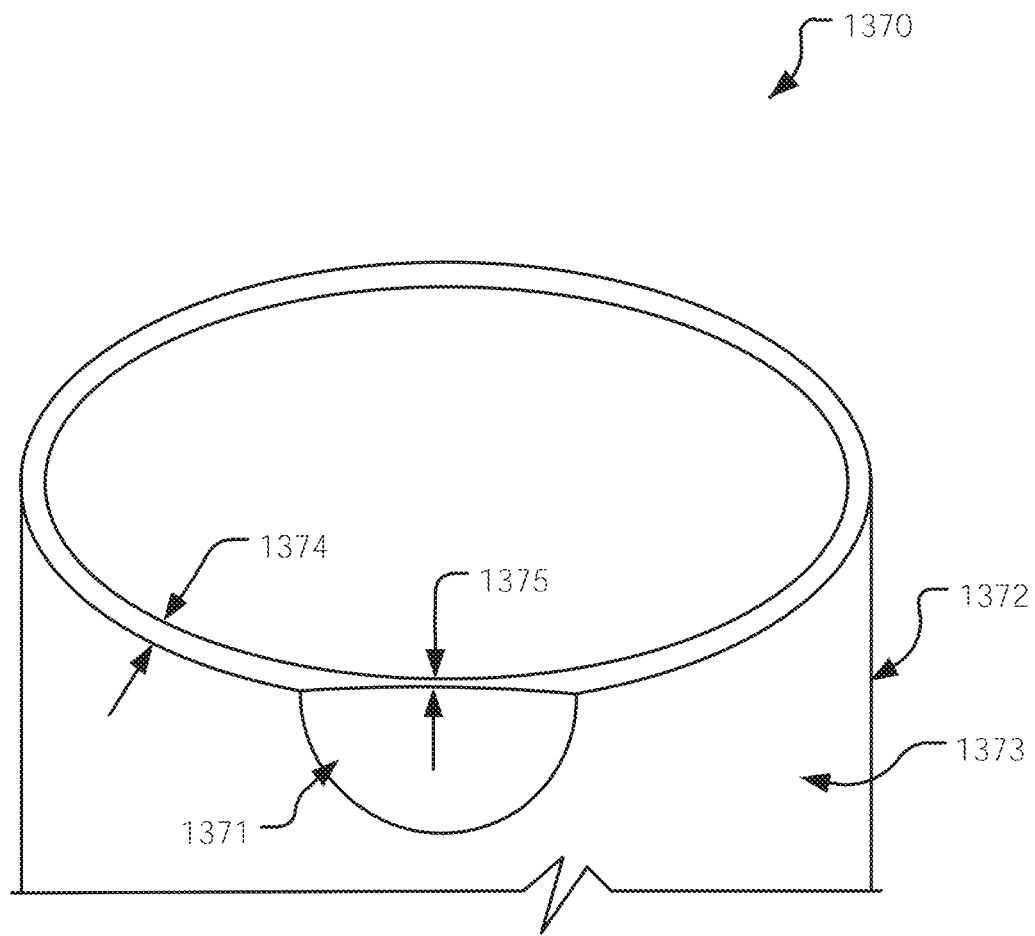
FIG. 13C may depict a face soaking device, wherein a vessel neck gasket may be formed from a region of flexible side wall configured to conform to the user's neck.

FIG. 13C may depict a face soaking device 1370, wherein a vessel neck gasket may be formed from a region of flexible side wall 1371 configured to conform to the user's 9000 neck 9020.

In some embodiments, face soaking device 1370 may comprise vessel 1372 and a breathing apparatus (e.g., breathing apparatus 400). Note such a breathing apparatus is not depicted in FIG. 13C. Vessel 1372 may be configured to hold liquid 101 in a sufficient volume to submerge whole face 9010 of user 9000 or a portion thereof. Vessel 1372 may comprise at least one wall 1373 and at least one base. At least one wall 1373 and the at least one base may be in physical contact with each other. At least one wall 1373 and the at least one base may together form vessel 1372, which may substantially bound an internal volume of vessel 1372. At least one wall 1373 may comprise region of flexible side wall 1371. Region of flexible side wall 1371 may be configured to accommodate a neck region of user 9000 when whole face 9010 or the portion thereof may be submerged in liquid 101. The breathing apparatus in use with face soaking device 1370 and/or vessel 1372 may be as depicted in the FIG. 4 series of figures, FIG. 20 series of figures, FIG. 21 series of figures, or FIG. 22 series of figures.

Continuing discussing FIG. 13C, in some embodiments, region of flexible side wall 1371 may be formed during a molding process by a mold cavity resulting in two different wall thicknesses, a first wall thickness 1374 and a second wall thickness 1375. First wall thickness 1374 may be greater than second wall thickness 1375. First wall thickness 1374 may be a wall thickness for a majority of at least one wall 1373. First wall thickness 954 may be such that the majority of at least one wall 1373 may be semi-rigid to rigid. Second wall thickness 1375 may be such that region of flexible side wall 1371 may be flexible. Such flexibility may conform to the neck region of user 9000 that may be in contact with region of flexible side wall 1371.

In some embodiments, region of flexible side wall 1371 may be concave or convex with a semi-round, a semi-oval, a U-shape or any other similar semicircular or semi-ovoid contour suitable to receive the portion of the neck region of user 9000 when in use. In some embodiments, region of flexible side wall 1371 may be a regular or an irregular polygon or semi-polygon contour suitable to receive the portion of the neck region of user 9000 when in use.

A FIG. 3 series of figures may comprise FIG. 3A through FIG. 3L. The FIG. 3 series of figures may focus on exemplary embodiments of a vessel neck gasket 340, a clamp 348, and a neck-gasket-accommodator 335, which may all communicate together forming both the primary and the secondary water tight seals.

Figure 3A:
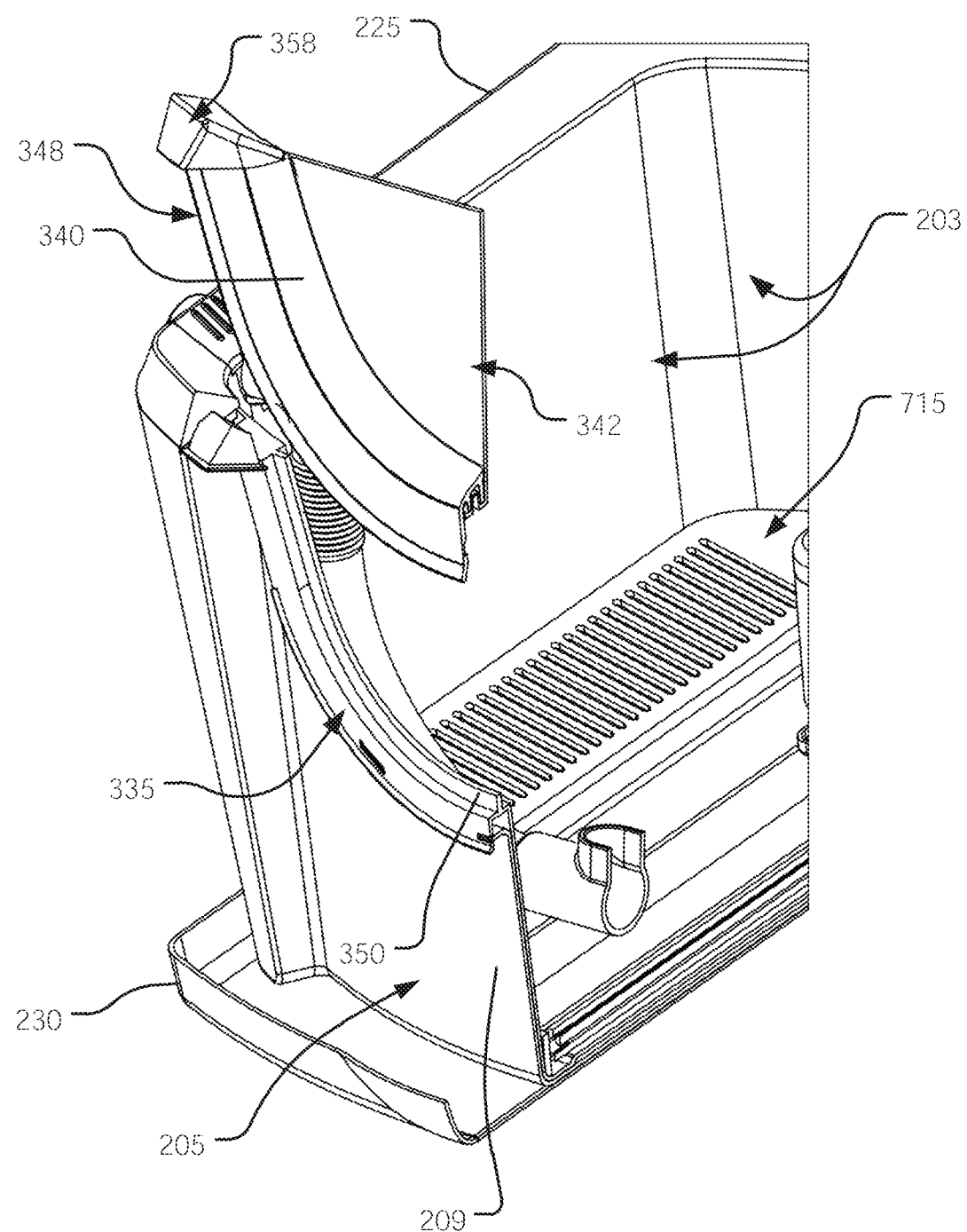
FIG. 3A may depict a vessel neck gasket and a clamp, in communication together, but exploded from a neck-gasketaccommodator of the vessel, shown from a partial perspective longitudinal cross-sectional view.

FIG. 3A may depict vessel neck gasket 340 and clamp 348, in communication together, but exploded from neck-gasket-accommodator 335 of vessel 200, shown from a partial perspective longitudinal cross-sectional view.

Figure 3B:
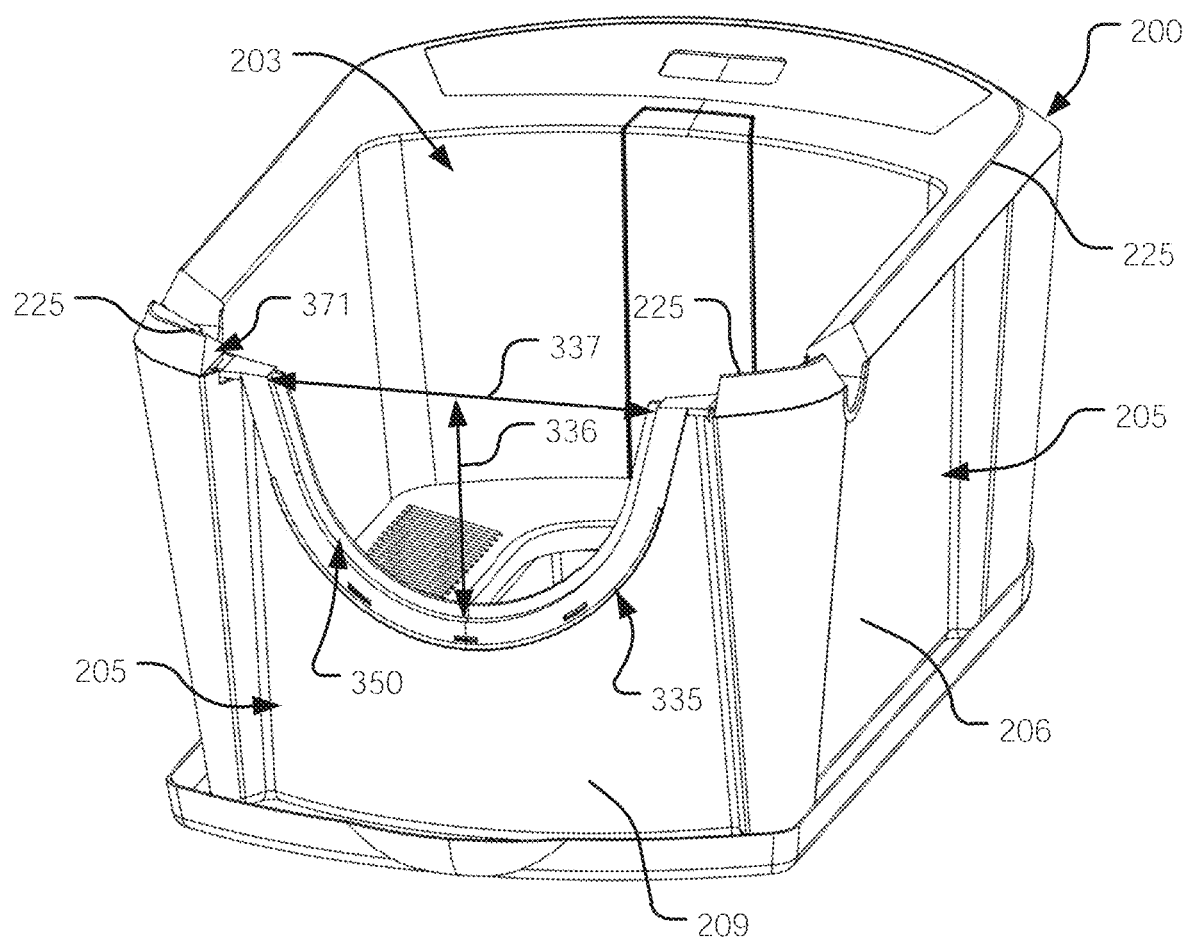
FIG. 3B may depict a front perspective view of the vessel, with the vessel neck gasket and the clamp removed, wherein a focus of FIG. 3B may be the neck-gasket-accommodator.

FIG. 3B may depict a front perspective view of vessel 200, with vessel neck gasket 340 and clamp 348 removed, wherein a focus of FIG. 3B may be neck-gasket-accommodator 335.

Figure 3C:
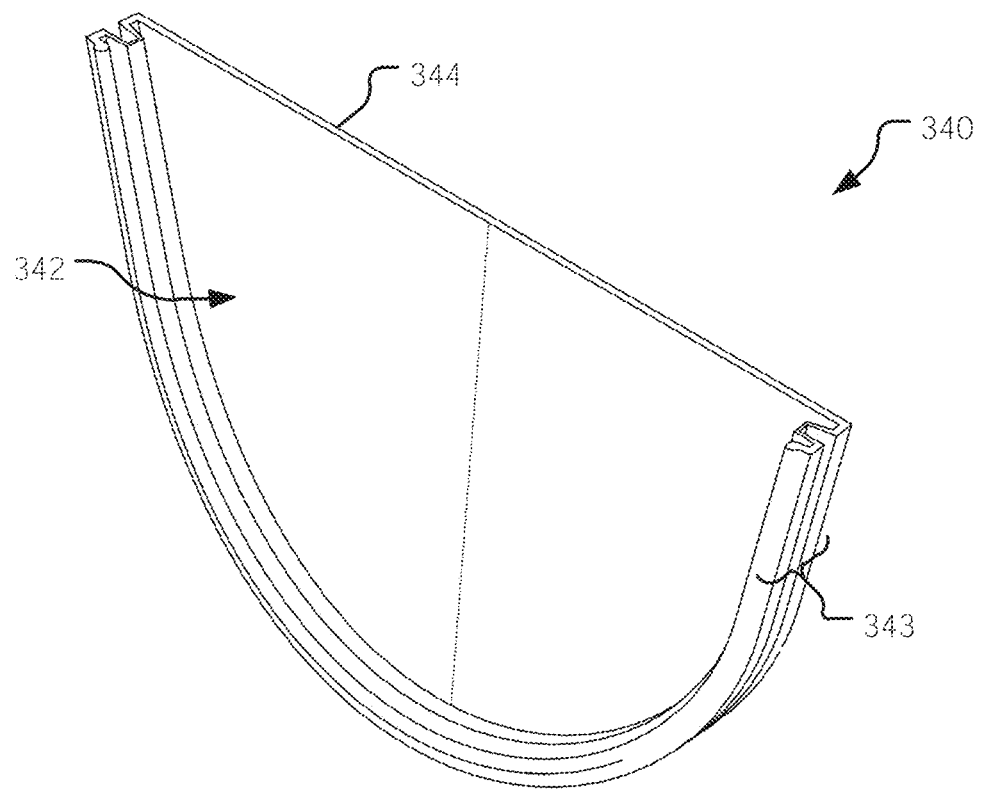
FIG. 3C may depict an exemplary embodiment of the vessel neck gasket, a component of some embodiments of face soaking devices, shown from a top front perspective view.
Figure 3D:
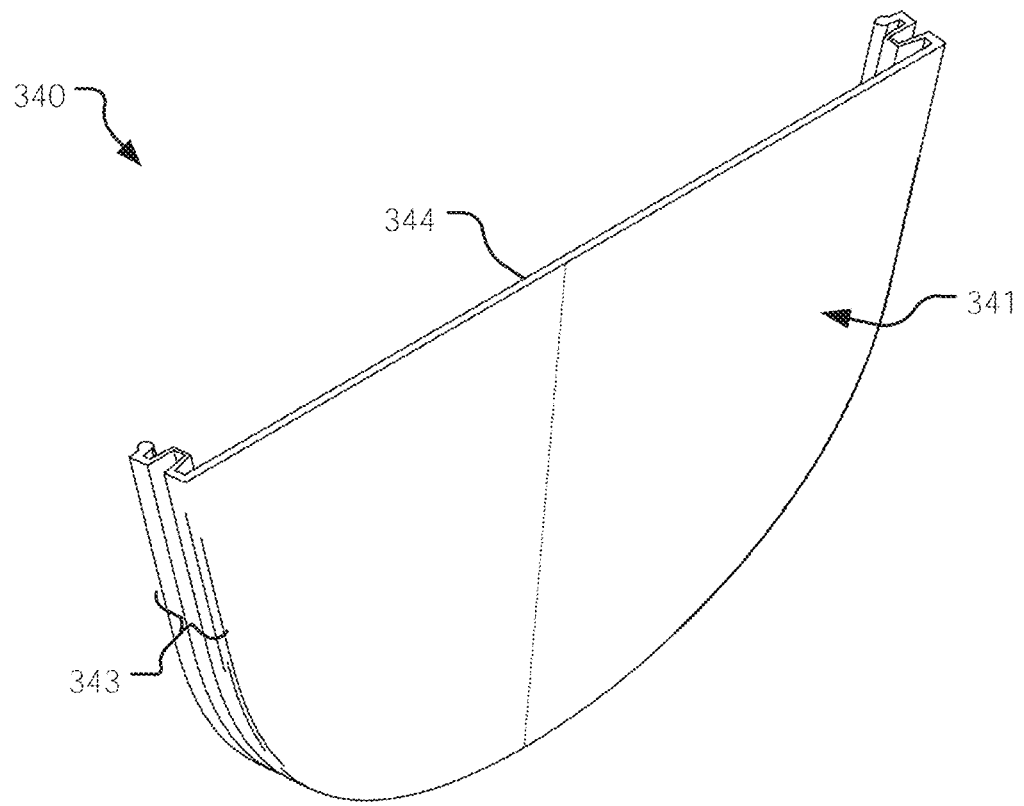
FIG. 3D may depict the vessel neck gasket of FIG. 3C, shown from a top back perspective view.

FIG. 3C may depict an exemplary embodiment of vessel neck gasket 340, a component of some embodiments of face soaking devices (e.g., face soaking devices 100), shown from a top front perspective view. FIG. 3D may depict vessel neck gasket 340, shown from a top back perspective view.

Figure 3E:
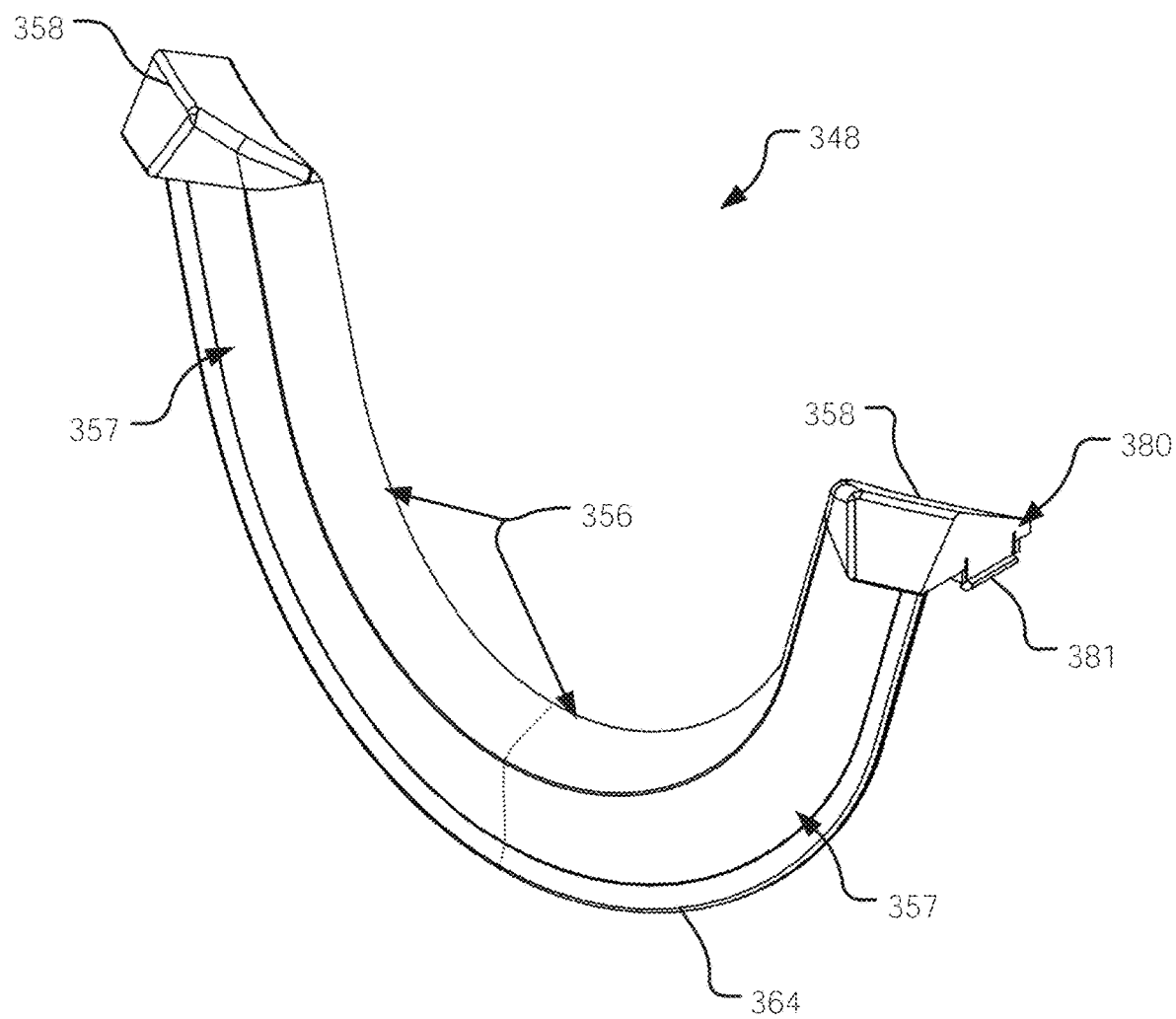
FIG. 3E may depict an exemplary embodiment of the clamp, a component of some embodiments of face soaking devices, shown from a top front perspective view.
Figure 3F:
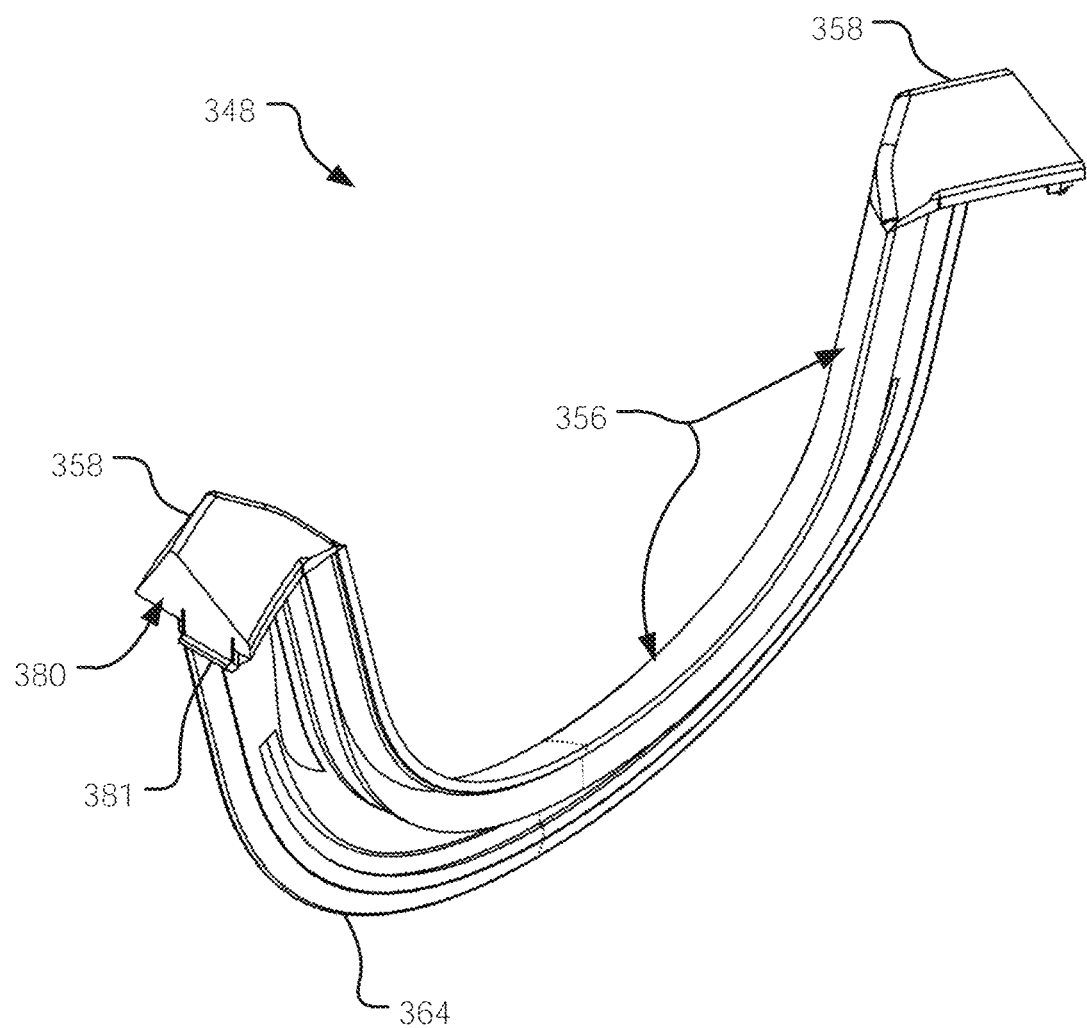
FIG. 3F may depict the clamp of FIG. 3E, shown from a top back perspective view.

FIG. 3E may depict an exemplary embodiment of clamp 348, a component of some embodiments of face soaking devices (e.g., face soaking devices 100), shown from a top front perspective view. FIG. 3F may depict clamp 348, shown from a top back perspective view.

Figure 3G:
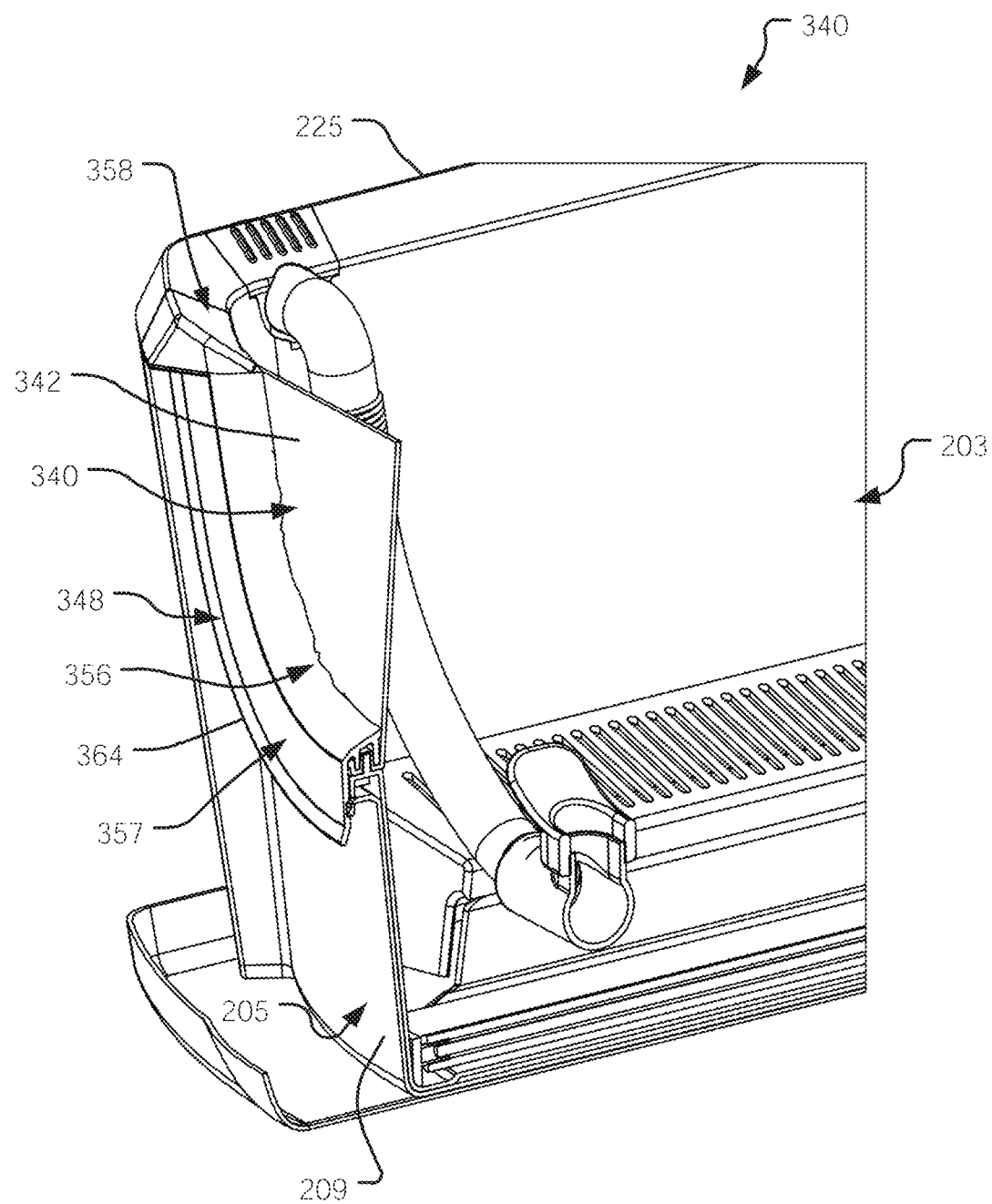
FIG. 3G may depict the vessel neck gasket of FIG. 3A and the clamp of FIG. 3C, assembled together, from a partial perspective longitudinal cross-sectional view.
Figure 3H:
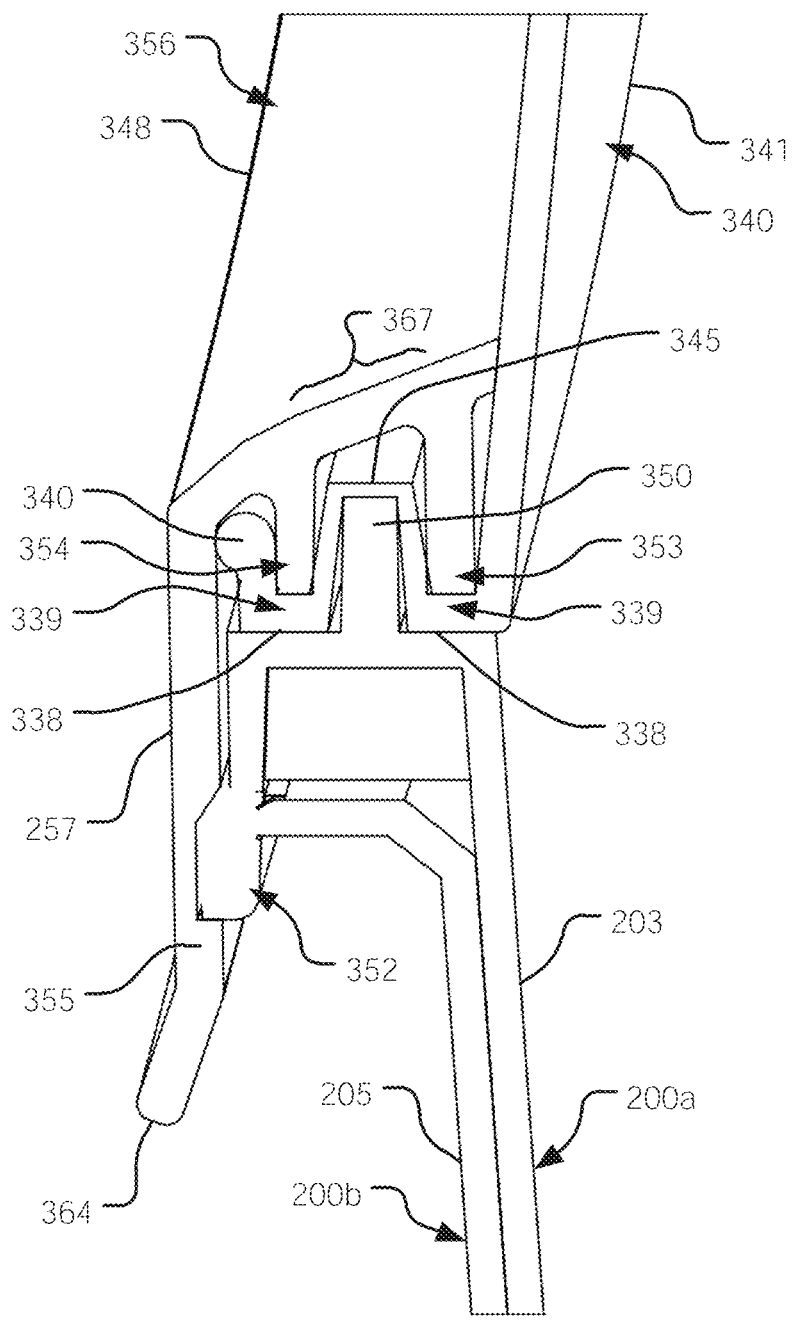
FIG. 3H may depict the vessel neck gasket of FIG. 3C and the clamp of FIG. 3E, assembled together, from a partial longitudinal cross-sectional view.

FIG. 3G may depict vessel neck gasket 340 and clamp 348, assembled together, from a partial perspective longitudinal cross-sectional view. FIG. 3H may depict vessel neck gasket 340 and clamp 348, assembled together, from a partial longitudinal cross-sectional view, but closer view as compared against FIG. 3G.

Figure 3I:
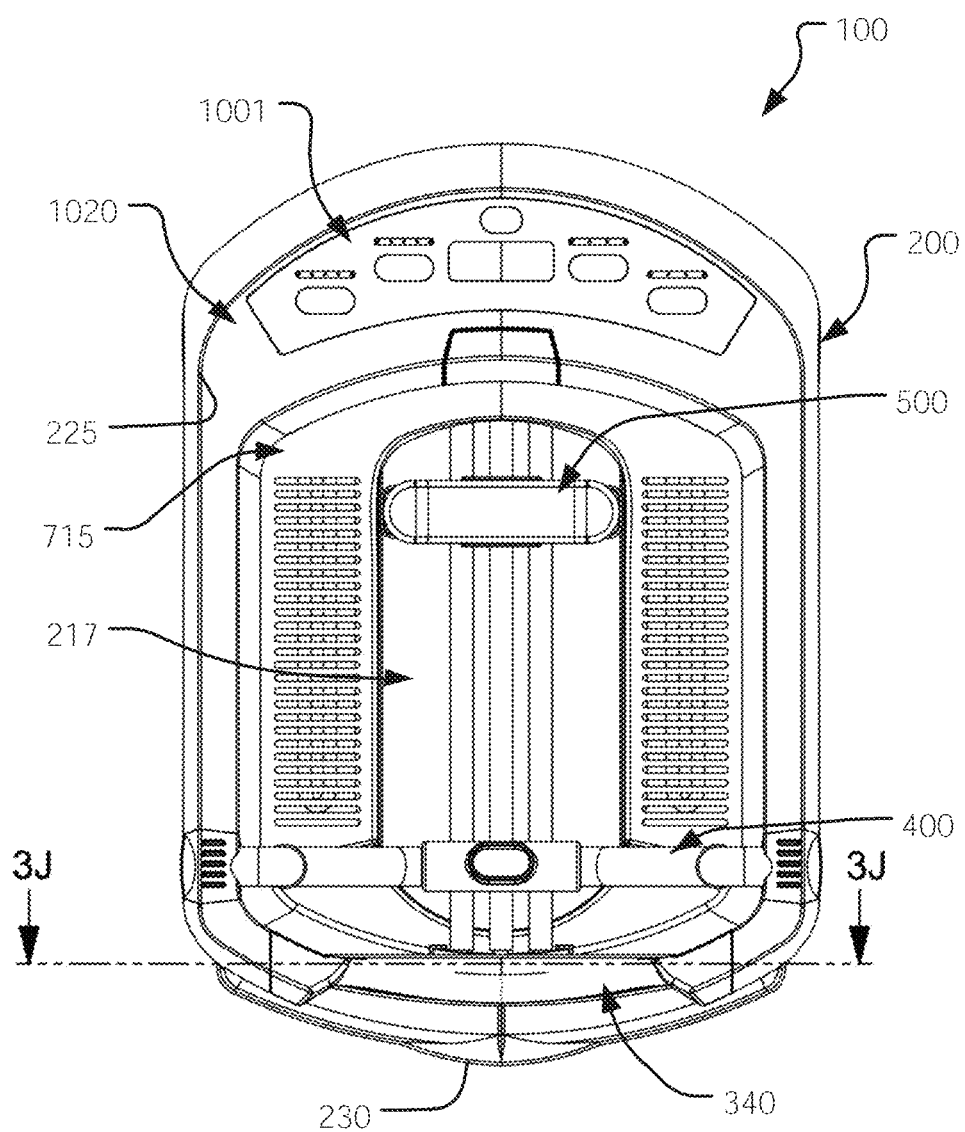
FIG. 3I may depict a top view of the face soaking device of FIG. 2A, including a transverse-width sectional line 3J-3J across a front portion of the face soaking device.
Figure 3J:
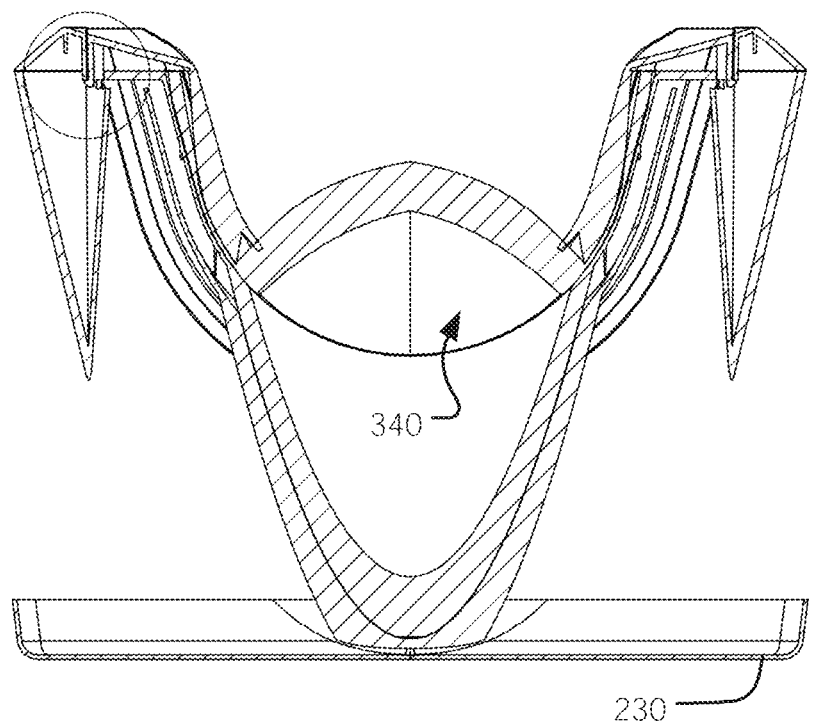
FIG. 3J may depict a front view from the sectional line 3J-3J of FIG. 3I; wherein in FIG. 3J a region of DETAIL 3K may be shown, which may depict how clamp terminal ends of the clamp may removably engage a rim of the vessel or structure proximate to the rim.
Figure 3K:
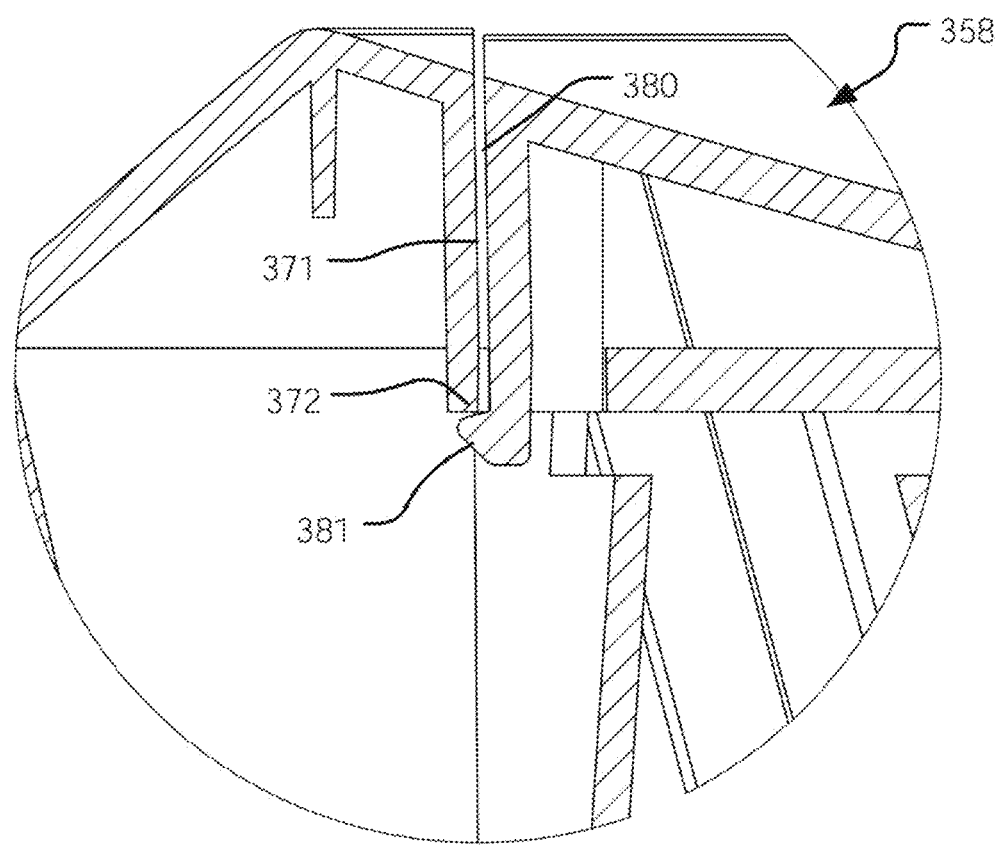
FIG. 3K may depict a close-up of DETAIL 3K, which may depict how the clamp terminal ends of the clamp may removably engage the rim or the structure proximate to the rim.

FIG. 3I may depict a top view of face soaking device 100, including a transverse-width sectional line 3J-3J across a front portion of face soaking device 100. FIG. 3J may depict a front view from the sectional line 3J-3J of FIG. 3I; wherein in FIG. 3J a region of Detail 3K may be shown, which may depict how clamp terminal ends 358 of clamp 348 may removably engage rim 225 of the vessel 200 or structure proximate to rim 225. FIG. 3K may depict a close-up of DETAIL 3K, which may depict how clamp terminal ends 358 of clamp 348 may removably engage the rim 225 or the structure proximate to the rim 225.

Figure 3L:
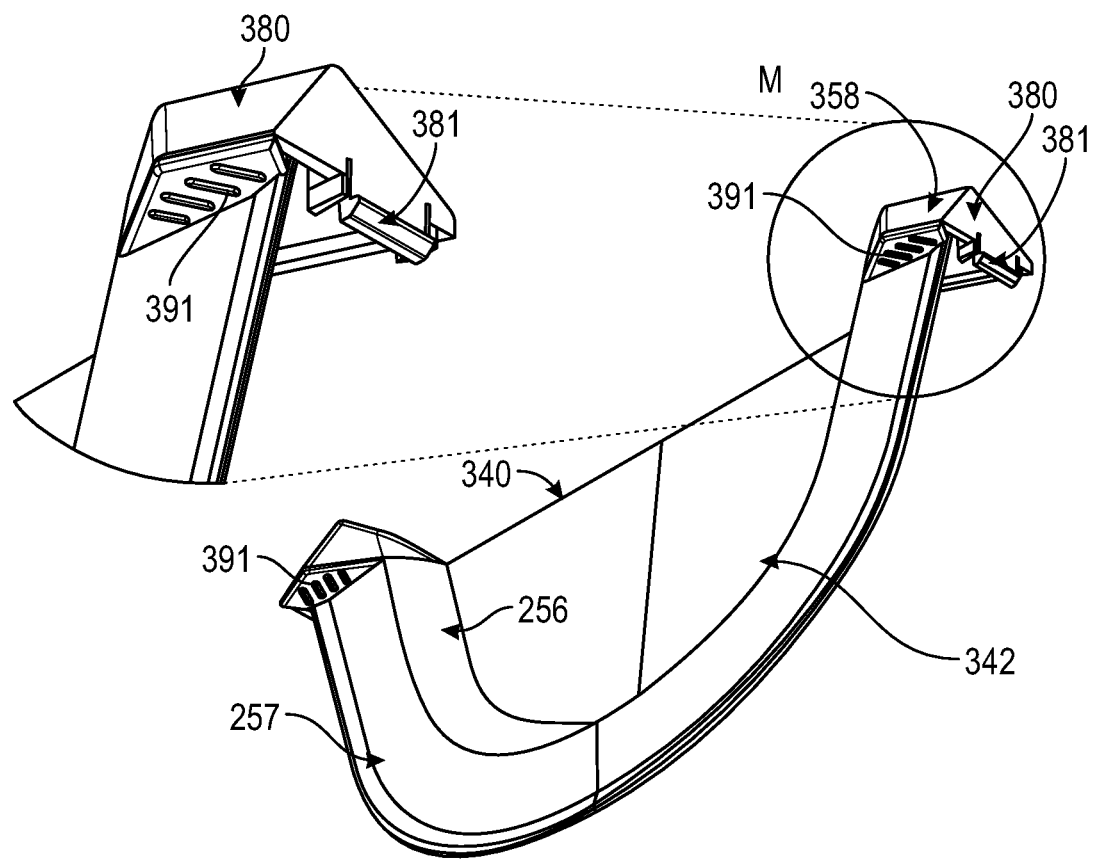
FIG. 3L may depict a perspective view of the vessel neck gasket together with the clamp, and further depicting a press-in-fit-part.

FIG. 3L may depict a perspective view of the vessel neck gasket 340 together with the clamp 348, depicting a press-fit-part 391.

In some embodiments, in at least one side wall 205 (or in at least one wall 201) of vessel 200 may be neck-gasket-accommodator 335. In some embodiments, at least one side wall 205 (or at least one wall 201) of vessel 200 may comprise neck-gasket-accommodator 335. Many figures show neck-gasket-accommodator 335 located in fourth side wall 209, i.e., the front wall. See e.g., FIG. 3A. In some embodiments, neck-gasket-accommodator 335 may be formed in fourth side wall 209 and/or the front wall of vessel 200. In some embodiments, neck-gasket-accommodator 335 may be formed from each of two respective and complimentary portions of vessel 200, i.e. from vessel ling 200a and vessel cover 200b. See e.g., FIG. 2G. In such embodiments, neck-gasket-accommodator 335 may comprise neck-gasket-accommodator 335a and neck-gasket-accommodator 335b; wherein neck-gasket-accommodator 335a may be formed from vessel ling 200a and neck-gasket-accommodator 335b may be formed from vessel cover 200b. That is, together, neck-gasket-accommodator 335a and neck-gasket-accommodator 335b may form neck-gasket-accommodator 335.

Neck-gasket-accommodator 335 may comprise a maximum vertical length 336 greater than a second portion of the neck region of user 9000 extending from rim 225 towards at least one base 215 of vessel 200, extending to a bottom most portion of neck-gasket-accommodator 335. See e.g., FIG. 3B. The second portion of the neck region may be a vertical area of a front of neck 9020, i.e. the soft tissue side of neck 9020, where neck 9020 may contact vessel neck gasket 340. Neck-gasket-accommodator 335 may have a horizontal width 337 greater than a third portion of the neck region of user 9000 centered in a horizontal width (e.g., transverse-width or from right to left) of vessel 200, extending from rim 225 to opposing rim 225 across an opening that neck-gasket-accommodator 335 creates. See e.g., FIG. 3B. The third portion of the neck region may be a horizontal area of a front of neck 9020, i.e. the soft tissue side of neck 9020, where neck 9020 may contact vessel neck gasket 340.

Note with respect, to the first portion, the second portion, and the third portion of the neck region of user 9000, the first portion may comprise the second portion and the third portion. That is, the second portion may define a vertical dimension of the first portion and the third portion may define a horizontal dimension of the first portion. For example, and without limiting the scope of the present invention, this first portion of the neck region may be a portion of neck 9020 what may correspond to where an Adam's Apple of a neck may be located; and including up two inches from that Adam's Apple region or a corresponding region on a neck with no Adam's Apple.

In some embodiments, neck-gasket-accommodator 335 may comprise a contour 338. Contour 338 may generally track an overall shape of neck-gasket-accommodator 335. Contour 338 may comprise one or more surfaces. In some embodiments, such surfaces may face one or more of: each other, face the front of a face soaking device, face the back of a face soaking device, and/or face away from an upper surface of bottom interior surface 217 of vessel 200.

In some embodiments, neck-gasket-accommodator 335 may comprise contour 338 in at least one wall 201 (or in at least one side wall 205) that runs below rim 225 of vessel 200. In some embodiments, contour 338 begins where a surface of contour 338 first runs below rim 225 and contour 338 continues until ending where the surface of contour 338 runs back up to rim 225. In some embodiments, where contour 338 begins and where contour 338 ends may be separated by horizontal width 337. In some embodiments, contour 338 has maximum vertical length 336 from a height of rim 225 to a lowest point on contour 338. See e.g., FIG. 3B.

In some embodiments, horizontal width 337 may be greater than or equal to a diameter of neck 9020 of user 9000. In some embodiments, maximum vertical length 336 may be greater than or equal to half of a diameter of neck 9020 of user 9000. For example, some large adult men may have a neck circumference of about 21 inches, which results in a neck diameter of about 6.69 inches. For example, and without limiting the scope of the present invention, in some embodiments, horizontal width 337 may be 7 to 11 inches. For example, and without limiting the scope of the present invention, in some embodiments, maximum vertical length 336 may be 3.5 to 7 inches.

In some embodiments, neck-gasket-accommodator 335, in terms of an overall shape, may be concave or convex with a semi-round (with respect to at least one base 215), a semi-oval, a U-shape or any other similar semicircular, semi-elliptical, semi-oval contour 338 suitable to receive vessel neck gasket 340 and the first portion of the neck region of user 9000 when in use in a given face soaking device embodiment (e.g., face soaking device 100). See e.g., FIG. 3B wherein the overall shape of contour 338 of neck-gasket-accommodator 335 may be semicircular, semi-elliptical, and/or semi-oval.

In some embodiments, a shape (i.e., the overall shape) of contour 338 as viewed from a front of face soaking device 100 may be selected from the group comprising: one third to three thirds of a circle, one third to three thirds of an oval, one third to three thirds of an ellipse, a "U" shape, a horseshoe shape, a regular polygon, an irregular polygon, a semi-polygon, and/or the like; with an arc of the partial circle, partial oval, partial ellipse, or the horseshoe shape oriented downwards towards at least one base 215. See e.g., FIG. 3B.

In some embodiments, neck-gasket-accommodator 335 may be a regular or an irregular polygon or semi-polygon contour 338 suitable to receive vessel neck gasket 340 and the first portion of the neck region of user 9000 when in use. This embodiment is not shown in the figures; however, it should be obvious to one of ordinary skill in the art that overall shape semi-circular neck-gasket-accommodator 335 shown FIG. 3B may be modified into the regular or the irregular polygon or the semi-polygon contour 338 and that such a contour may continue to be within the scope of this invention.

Note, in some embodiments, neck-gasket-accommodator 335 may be a gasket-accommodator.

In some embodiments, vessel neck gasket 340 may be configured to fit contour 338 of neck-gasket-accommodator 335 in at least one side wall 205 of vessel 200. Vessel neck gasket 340 may be equal to, greater than, or less than, a size of neck-gasket-accommodator 335. Vessel neck gasket 340 may comprise a mating edge 343 complimentary to at least some surfaces of contour 338 of neck-gasket-accommodator 335 in at least one side wall 205 of vessel 200. Vessel neck gasket 340 may comprise a top edge 344 accommodative to receiving the first portion of the neck region of user 9000. See e.g., FIG. 3C. In some embodiments, mating edge 343 of vessel neck gasket 340 may be attached to contour 338 of neck-gasket-accommodator 335 by a vessel neck gasket attachment means. In some embodiments, the vessel neck gasket attachment means may comprise clamp 348. Or in some embodiments, mating edge 343 of vessel neck gasket 340 may be attached to either exterior wall surface 202 or interior wall surface 203 of at least side one wall 205, at a fixed distance from contour 338 of neck-gasket-accommodator 335 by the vessel neck gasket attachment means. For example, and without limiting the scope of the present invention, in some embodiments, the fixed distance may be one inch or less. In other embodiments, the fixed distance may be other distances.

In some embodiments, vessel neck gasket 340 may be removable from vessel 200. Such embodiments may facilitate switching out vessel neck gasket 340 in the event of wear and tear and/or damage to an installed vessel neck gasket 340. In some other embodiments, vessel neck gasket 340 may not be removed from vessel 200 once installed.

In some embodiments, vessel neck gasket 340 may be a flexible member. Vessel neck gasket 340 may be planar with an internal surface 341 (see FIG. 3D) and an external surface 342 (see FIG. 3C) disposed opposite of internal surface 341. External surface 342 or internal surface 341 may be configured to form the secondary water tight seal with the neck region, when user 9000 rests neck 9020 against vessel neck gasket 340. In some embodiments, a portion of internal surface 341 may physically contact liquid 101 when liquid 101 may be held within internal volume 220.

In some embodiments, vessel neck gasket 340 may be a flexible sheet. The flexible sheet may be shaped generally to cover the gasket-accommodator (i.e., neck-gasket-accommodator 335) of vessel 200. This flexible sheet may comprise a gasket along the bottom of the sheet. In some embodiments, this gasket may be mating edge 343.

In some embodiments, vessel neck gasket 340 may be substantially constructed of one or more materials (i.e., materials of construction) suitable for forming water tight seals against human skin (or against an exterior portion of a terrestrial vertebrates body) and/or against the vessel (e.g. vessel 200), and/or suitable for being comfortable when touching human skin. In some embodiments, vessel neck gasket 340 may be constructed of one or more of elastomers comprising silicone, rubber, neoprene, nitrile, vinyl, polyethylene, polypropylene, and/or any other material suitable for forming water tight seals against human skin and/or against the vessel (e.g. vessel 200), and/or suitable for being comfortable when touching human skin. In some embodiments, the rubber may be natural rubber. In some embodiments, the rubber may be synthetic, including latex free.

In some embodiments, internal surface 341 and external surface 342 may be constructed of different elastomers. Internal surface 341 may be constructed of an elastomer with a focus on water impermeability. External surface 342 may be constructed of an elastomer with a focus on comfort to user 9000, i.e. an elastomer with a soft outer surface and/or a nontacky outer surface. Such two different elastomers may be joined into a single flexible composite member of vessel neck gasket 340. The means for joining internal surface 341 to external surface 342 may be by solvent bonding, heat welding, ultrasonic welding, chemical adhesive/sealant, and/or the like.

In some embodiments, the vessel neck gasket attachment means may be selected from one or more of: a friction fit, heat welding, ultrasonic welding, solvent bonding, chemical adhesives and/or sealants, mechanical fasteners, and/or the like. Use of clamp 348 may an example of a frictional fit and/or a type of mechanical fastener.

For example, and without limiting the scope of the present invention, the mechanical fasteners may comprise a plurality of screws or bolts 3246 and a mounting block 3247. A FIG. 32 series of figures may comprise FIG. 32A through FIG. 32E. These FIG. 32 series of figures may depict mounting block 3247 embodiments for attaching vessel neck gasket 340 to vessel 200. FIG. 32A may depict an embodiment utilizing mounting block 3247 for attaching vessel neck gasket 340 to the vessel 200, shown from a perspective view. FIG. 32B may depict the embodiment of FIG. 32A, but shown from a top view. FIG. 32C may depict the embodiment of FIG. 32A, but shown from a front view. In FIG. 32C, a broken line may indicate an outline of mounting block 3247 may be mounted within interior volume 220 of vessel 200. The front view may also be known as a vessel neck gasket view. FIG. 32D may depict the embodiment of FIG. 32A, but shown from a right view. The right view may be with respect to an observer looking upon the front view, i.e., the right view may be with respect to the observer's right. FIG. 32E may depict the embodiment of FIG. 32A, but shown from an exploded perspective view.

In some embodiments, mounting block 3247 may be configured with a plurality of complimentary threaded female holes for receiving screws or bolts 3246. See e.g., FIG. 32E. Vessel neck gasket 340 mating edge 343 may be secured between exterior wall surface 203 and mounting block 3247 with the screws or the bolts 3246 providing the clamping force, sufficient to create the primary water tight seal. See e.g., the FIG. 32 series of figures. Or alternatively, vessel neck gasket 340 mating edge 343 may be secured between exterior wall surface 202 and mounting block 3247 with screws or bolts 3246 providing the clamping force, sufficient to create the primary water tight seal (this embodiment may not be depicted). In either embodiment, plurality of screws or bolts 3246 may pass through a complimentary number of ports (may be threaded ports) through vessel 200 (such as at least one wall 201). In addition, to such mechanical fasteners, heat welding, ultrasonic welding, solvent bonding, and chemical adhesives and/or sealants may be used in conjunction with the mechanical fasteners.

In some embodiments, a shape of mounting block 3247 may be complimentary to a shape of neck-gasket-accommodator 335 and/or contour 338. For example, in the FIG. 32 series of figures, mounting block 3247 may have a "U" shape and/or a horseshoe shape.

In some embodiments, one end of mounting block 3247 may be permanently and pivotally attached to at least one wall 201, such that mounting block 3247 may be pivoted; which may allow for replacing vessel neck gasket 340.

In some embodiments, an exemplary embodiment of face soaking device 100 may comprise at least three elements: vessel neck gasket 340, clamp 348, and neck-gasket-accommodator 335. In some embodiments, an exemplary vessel neck gasket subassembly may comprise at least three parts: vessel neck gasket 340, clamp 348, and neck-gasket-accommodator 335. Neck-gasket-accommodator 335 may be a portion or region of a given vessel embodiment, such as vessel 200 embodiments. Note, vessel neck gasket 340, clamp 348, and neck-gasket-accommodator 335 of the exemplary vessel neck gasket subassembly of the FIG. 3 series of figures may be different structurally from such similar elements depicted in the FIG. 14 series of figures, the FIG. 15 series of figures, the FIG. 3I series of figures, and the FIG. 32 series of figures.

In some embodiments vessel neck gasket 340 may be attached to neck-gasket-accommodator 335 by use of clamp 348. See e.g., FIG. 3G. In some embodiments such an attachment may form the primary water tight seal. In some embodiments clamp 348 may be shaped to complimentary fit neck-gasket-accommodator 335, with a portion of vessel neck gasket 340 sandwiched between clamp 240 and contour 338 of neck-gasket-accommodator 335, forming the primary water tight seal. See e.g., FIG. 3H. In some embodiments, contour 338 may comprise at least one surface facing away from an upper surface of a bottom interior surface 217 of vessel 200. Bottom interior surface 217 may be an interior space of vessel 200. In some embodiments, bottom interior surface 217 may be a largest interior space of vessel 200 by volume.

In some embodiments, clamp 348 fit attachment to contour 338 of neck-gasket-accommodator 335 may be removable. In some embodiments, clamp 348 fit attachment to contour 338 of neck-gasket-accommodator 335 may be a frictional fit. In some embodiments, clamp 348 fit attachment to contour 338 of neck-gasket-accommodator 335 may be from one or more snap fits.

In some embodiments, contour 338 of the neck-gasket-accommodator 335 may comprise at least one sealing fin 350. See e.g., FIG. 3H. In some embodiments, at least one sealing fin 350 may be a protrusion extending away from one on more surfaces of contour 338. For example, and without limiting the scope of the present invention, in some embodiments, at least one sealing fin 350 may protrude and extend from such one or more surfaces for one inch or less. In some embodiments, at least one sealing fin 350 may be a protrusion extending in a direction away from the upper surface of the bottom interior surface 217 of vessel 200.

In some embodiments, when clamp 348 may be removably coupled to neck-gasket-accommodator 335, with the portion of vessel neck gasket 340 disposed between clamp 348 and neck-gasket-accommodator 335, at least one sealing fin 350 may push into some of the portion of vessel neck gasket 340 stretching regions 345 of vessel neck gasket 340 to both sides of at least one sealing fin 350. In some embodiments, stretched region 345 of vessel neck gasket 340 may form the primary water tight seal. In some embodiments, at least one sealing fin 350 may provide some sealing surface area where the at least one sealing fin contacts vessel neck gasket 340, minimizing leakage of liquid 101. See e.g., FIG. 3H.

In some embodiments, contour 338 of neck-gasket-accommodator 335 may comprise at least two pinch points 339. See e.g., FIG. 3H. In some embodiments, at least one sealing fin 350 may be disposed between at least two pinch points 339. See e.g., FIG. 3H. In some embodiments, one of the at least two pinch points 339 may be located beneath a termination end of a first complimentary sealing fin 353 and above contour 338, when clamp 348 may be removably coupled to neck-gasket-accommodator 335. In some embodiments, the remaining pinch point of at least two pinch points 339 may be located beneath a termination end of a second complimentary sealing fin 354 and above contour 338, when clamp 348 may be removably coupled to neck-gasket-accommodator 335. In some embodiments, first complimentary sealing fin 353 and secondary complimentary sealing fin 354 may each be protrusions of clamp 348, extending away from upper exterior surface 356 of clamp 348. In some embodiments, first complimentary sealing fin 353 and secondary complimentary sealing fin 354 may be separated by a width of a channel 367 in clamp 348. See e.g., FIG. 3H. In some embodiments, this width of channel 367 may be sized to accommodate a width of at least one sealing fin 350 of contour 338 with the some of the portion of vessel neck gasket 340 disposed between at least one sealing fin 350 and channel 367 with first complimentary sealing fin 353 and second complimentary sealing fin 354 to either side of channel 367. In some embodiments, first complimentary sealing fin 353 and second complimentary sealing fin 354 may removably push the some of the portion of vessel neck gasket down 340, while at least one sealing fin 350 may removably push the some of the portion of vessel neck gasket 340 up into channel 367, stretching regions 345 of vessel neck gasket 340 into a shape that in cross section may resemble a "W." See e.g., FIG. 3H. In some embodiments, stretched regions 345 of vessel neck gasket 340 may form the primary water tight seal when clamp 348 may be removably coupled to neck-gasket-accommodator 335 and the portion of the vessel neck gasket 340 may be disposed between clamp 348 and neck-gasket-accommodator 335 (e.g., contour 338).

In some embodiments, clamp 348 may be constructed (or substantially) of a semi-rigid to rigid material of construction. For example, and without limiting the scope of the present invention, clamp 348 may be substantially constructed of one or more of a thermoformed plastic, metal, wood, composite, laminate, and/or the like.

In some embodiments, clamp 348 may comprise two exterior surfaces, upper exterior surface 356 and lateral exterior surface 357. See e.g., FIG. 3E and FIG. 3H. In some embodiments, upper exterior surface 356 and lateral exterior surface 357 may be integrally attached to each other along a common and continuous vertex.

In some embodiments, clamp 348 may comprise first complimentary sealing fin 353 and second complimentary sealing fin 354. See e.g., FIG. 3H. In some embodiments, first complimentary sealing fin 353 and second complimentary sealing fin 354 may each extend away from upper exterior surface 356. In some embodiments, clamp 348 may comprise channel 367. In some embodiments, channel 367 may be disposed between first complimentary sealing fin 353 and second complimentary sealing fin 354.

In some embodiments, channel 367 may be sized to accommodate the width of the at least one sealing fin 350 of contour 338 with the some of the portion of vessel neck gasket 340 disposed between at least one sealing fin 350 and channel 367 with first complimentary sealing fin 253 and second complimentary sealing fin 254 to either side of channel 367. In some embodiments, clamp 348 may be sized (configured) to accommodate a thickness of at least one sealing fin 350 of neck-gasket-accommodator 335 in a space (e.g., channel 367) disposed between first complimentary sealing fin 353 and second complimentary sealing fin 354. See e.g., FIG. 3H.

In some embodiments, neck-gasket-accommodator 335 may comprise at least one lip 352. See e.g., FIG. 3H. In some embodiments, at least one lip 352 may extend in an opposite direction from at least one sealing fin 350, on a distal portion of neck-gasket-accommodator 335 from the internal volume 220. In some embodiments, at least one lip 352 may provide structure for a tab 355 of clamp 348 to be engaged by. In some embodiments, at least one lip 352 and tab 355 may have complimentary geometry for forming a removable snap fit. See e.g., FIG. 3H. In some embodiments, removable coupling (attachment) of tab 355 to lip 352 may increase frictional fit of clamp 348 to neck-gasket-accommodator 335.

In some embodiments, lateral exterior surface 357 (of clamp 348) terminates in pull 364. See e.g., FIG. 3H. In some embodiments, pull 364 may be distal from the common and continuous vertex where upper exterior surface 256 and the lateral exterior surface 257 may integrally attach to each other. In some embodiments, pull 364 may be pulled by user 9000 to release clamp 348 from neck-gasket-accommodator 335 by pull 364 comprising structure to function as a lever arm. In some embodiments, lateral exterior surface 357 terminating in pull 364 may extend beyond at least one lip 352 of neck-gasket-accommodator 335 when clamp 348 may be removably attached to the neck-gasket-accommodator 335. See e.g., FIG. 3H.

In some embodiments, clamp 348 may comprises at least one tab 355. See e.g., FIG. 3H. In some embodiments, at least one tab 355 may protrude out from an interior surface side of the lateral exterior surface 257. In some embodiments, tab 355 may removably engage at least one lip 352 of neck-gasket-accommodator 335 when the clamp 348 may be removably attached to neck-gasket-accommodator 335. In some embodiments, such engagement of at least one tab 355 to the at least one lip 352 may be one or more of a snap fit or a friction fit. That is, at least one tab 355 may (removably) hook onto at least one lip 352.

A FIG. 3J (which may be a cross-sectional view along line sectional line 3J-3J in FIG. 3I) and FIG. 3K (which may be a close-up of DETAIL 3K from FIG. 3J) may depict additional snap latch structure illustrating how clamp 348 (of the FIG. 3 series) may removably couple with neck-gasket-accommodator 335. FIG. 3I may depict a top view of face soaking device 100. FIG. 3I may depict sectional line 3J-3J, wherein sectional line 3J-3J is a cross-section across a portion of the front of face soaking device 100. FIG. 3J may depict the cross-sectional view along sectional line 3J-3J. And FIG. 3J may comprise a region of highlighted Detail 3K. FIG. 3K may depict a close up of Detail 3K, which may depict how one of two snap latch connections may work to assist in removably coupling clamp 348 to neck-gasket-accommodator 335.

In some embodiments, neck-gasket-accommodator 335 may comprises two opposing opening wall-edges 371. In some embodiments, the two opposing opening wall-edges 371 may define where neck-gasket-accommodator 335 begins. See e.g., FIG. 3K and FIG. 3B which may depict one such opening wall-edge 371; e.g., a left opening wall-edge 371 from the perspective of user 9000 looking at the front of face soaking device 100; wherein a right opening wall-edge 371 may be a mirror image of the left opening wall-edge 371. In some embodiments, each opening wall-edge 371 (e.g., left and right) may be separated from the other by at least the at least horizontal width 337 of neck-gasket-accommodator 335 (see e.g., FIG. 3B for horizontal width 337). In some embodiments, each opening wall-edge 371 may descend downwards direction towards at least one base 215 from rim 225. In some embodiments, each opening wall-edge 371 may be substantially flat (i.e., a substantially flat surface). See e.g., FIG. 3K and FIG. 3B.

For example, and without limiting the scope of the present invention, in some embodiments, each opening wall-edge 371 may descend downwards for less than two inches but greater than one thirty second (1/32) of an inch.

In some embodiments, clamp 348 may comprise two terminal ends 358 disposed opposite of each other. See e.g., FIG. 3E and FIG. 3F. In some embodiments, each terminal end 358 may comprise a mating-wall-edge 380. See e.g., FIG. 3K which may depict one such mating-wall-edge 380; e.g., a left mating-wall-edge 380 from the perspective of user 9000 looking at the front of face soaking device 100; wherein a right mating-wall-edge 380 may be a mirror image of the left mating-wall-edge 380. A left and right designation of clamp 348 may be with respect to lateral exterior surface 257 facing away from internal volume 220 and facing user 9000 who may be viewing the front of face soaking device 100.

In some embodiments, each mating-wall-edge 380 may be paired with a respective opening wall-edge 371, such that mating-wall-edge 380 paired to a given opening wall-edge 371 may be complimentary to each other, when clamp 348 may be removably coupled to neck-gasket-accommodator 335. See e.g., FIG. 3K. In some embodiments, each mating-wall-edge 380 may be paired with a respective opening wall-edge 371, such that mating-wall-edge 380 paired to the respective opening wall-edge 371 may be substantially parallel to each other, when clamp 348 may be removably coupled to neck-gasket-accommodator 335 such that lateral exterior surface 257 may be facing away from internal volume 220. For example, and without limiting the scope of the present invention, left opening wall-edge 371 may be paired with left mating-wall-edge 380 as shown in FIG. 3K. For example, and without limiting the scope of the present invention, right opening wall-edge 371 may be paired with right mating-wall-edge 380 which may be a mirror image of FIG. 3K. In some embodiments, each mating-wall-edge 380 may be substantially flat to compliment a substantially flat region on corresponding (paired) opening wall-edge 371.

In some embodiments, when left opening wall-edge 271 may be paired with left mating-wall-edge 380 and right opening wall-edge 371 may be paired with right mating-wall-edge 380 each respective pairing may be a friction fit between the paired and complimentary surfaces.

In some embodiments, each mating-wall-edge 380 may terminate in a snap latch 381. See e.g., FIG. 3E, FIG. 3F, and FIG. 3K. In some embodiments, each opening wall-edge 371 may terminate in an edge-lip 372. See e.g., FIG. 3K which may depict a left edge-lip 372 at the termination of left opening wall-edge 371. Note, corresponding right structures (e.g., right edge-lip 372 and right snap latch 381) may be mirror images of respective left structures. In some embodiments, each snap latch 381 may be paired with a respective edge-clip 372 such that the paired snap latch 381 may removably snap over paired edge-lip 372 to form a removable snap latch connection at each of the two respective pairings. See e.g., FIG. 3K which may depict such a left snap latch connection. In some embodiments, a paired snap latch 381 may comprise a protrusion that may be removably engage a surface of the paired edge-lip 372. See e.g., FIG. 3K.

In some embodiments, release of each removable snap latch connection (left and right) may be accomplished by user 9000 squeezing each mating-wall-edge 380 towards each other, which may disengage a given paired snap latch 381 from the paired edge-lip 372. In some embodiments, release of clamp 348 from neck-gasket-accommodator may also require user 9000 to pull (or lift) pull 364.

FIG. 3L may depict a perspective view of vessel neck gasket 340 together with clamp 348, and further depicting a press-in-fit-part 391. Press-in-fit-part 391 may be first depicted in FIG. 2H. In some embodiments, a single press-in-fit-part 391 may attach to each clamp terminal end 358 (e.g., to an underside of each clamp terminal end 358). In some embodiments, clamp 348 may comprise press-in-fit-parts 391. In some embodiments, each clamp terminal end 358 may comprise a single press-in-fit-part 391. In some embodiments, a single press-in-fit-part 391 may attach to an underside of each clamp terminal end 358. See e.g., FIG. 3L. Each press-in-fit-part 391 may provide a comfortable material of construction for user 9000 to engage, by pressing against. In some embodiments, press-in-fit-part 391 may be substantially constructed of one or more of: an elastomer and/or a plastic. The elastomer may be a silicone and/or a rubber, including synthetic rubbers. The plastic may be a thermoplastic, such as, but not necessarily, a thermoplastic polyurethane (TPU) and the like. When a user may be removing clamp 348 (along with vessel neck gasket 340) from neck-gasket-accommodator 335, user 9000 may press (squeeze) each opposing press-in-fit-part 391 towards each other to help release clamp 348 (along with vessel neck gasket 340) from neck-gasket-accommodator 335. Note, press-in-fit-part 391 may not be included in all face soaking device 100 embodiments.

Some embodiments may be characterized as a flexible detachable vessel cover that may comprise: (1) vessel 200 having top opening 226 and capable of holding liquid 101; wherein vessel 200 has gasket-accommodator 335; and (2) a flexible sheet (e.g., vessel neck gasket 340); wherein the flexible sheet that may be shaped generally to cover gasket-accommodator 335 of vessel 200; wherein the flexible sheet has a gasket (e.g., mating edge 343) along the bottom of the flexible sheet; and wherein the bottom of the gasket and a top of gasket-accommodator 335 of vessel 200 are arranged to mate tightly with one another to form the primary water tight seal.

Figure 14A:
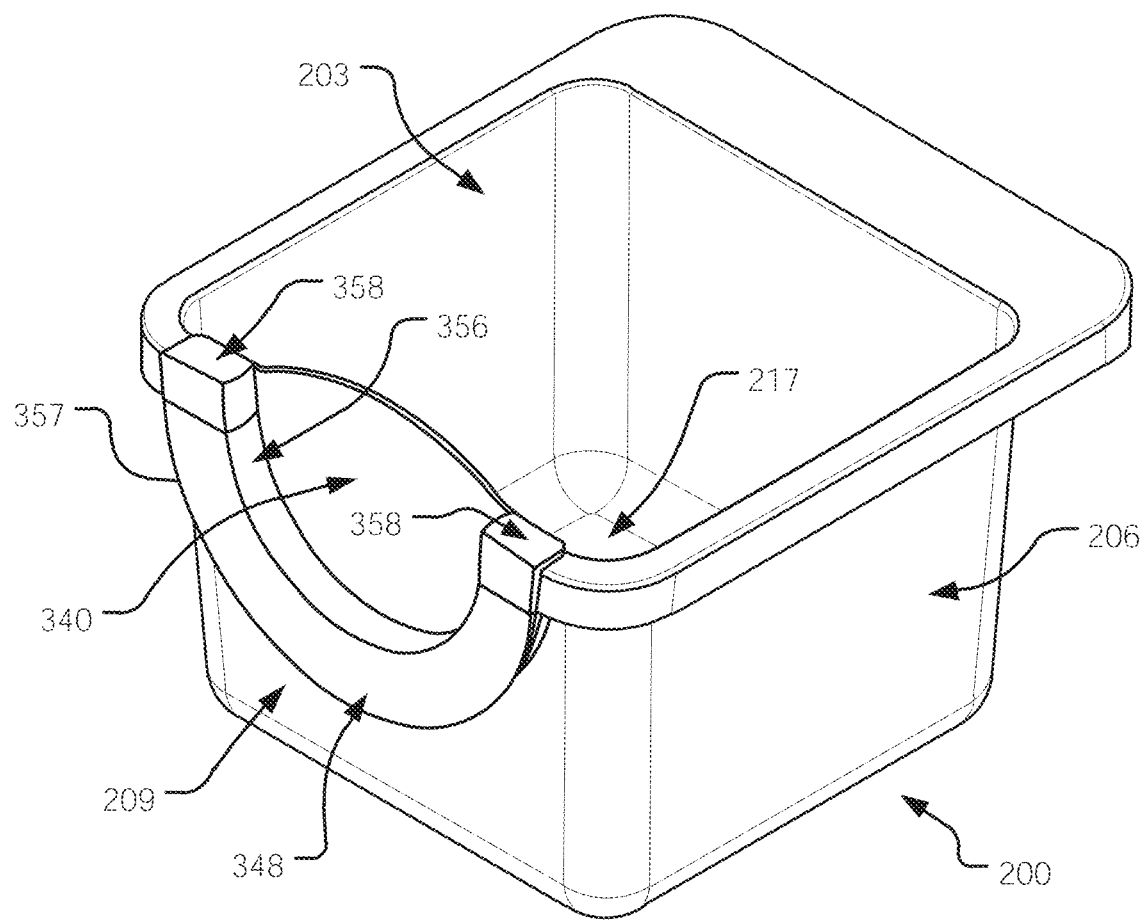
FIG. 14A may depict a face soaking device with an alternative embodiment vessel neck gasket, shown from a perspective view. (A breathing apparatus, a head rest subassembly, a heater subassembly, and a gas diffuser may be removed.)
Figure 14B:
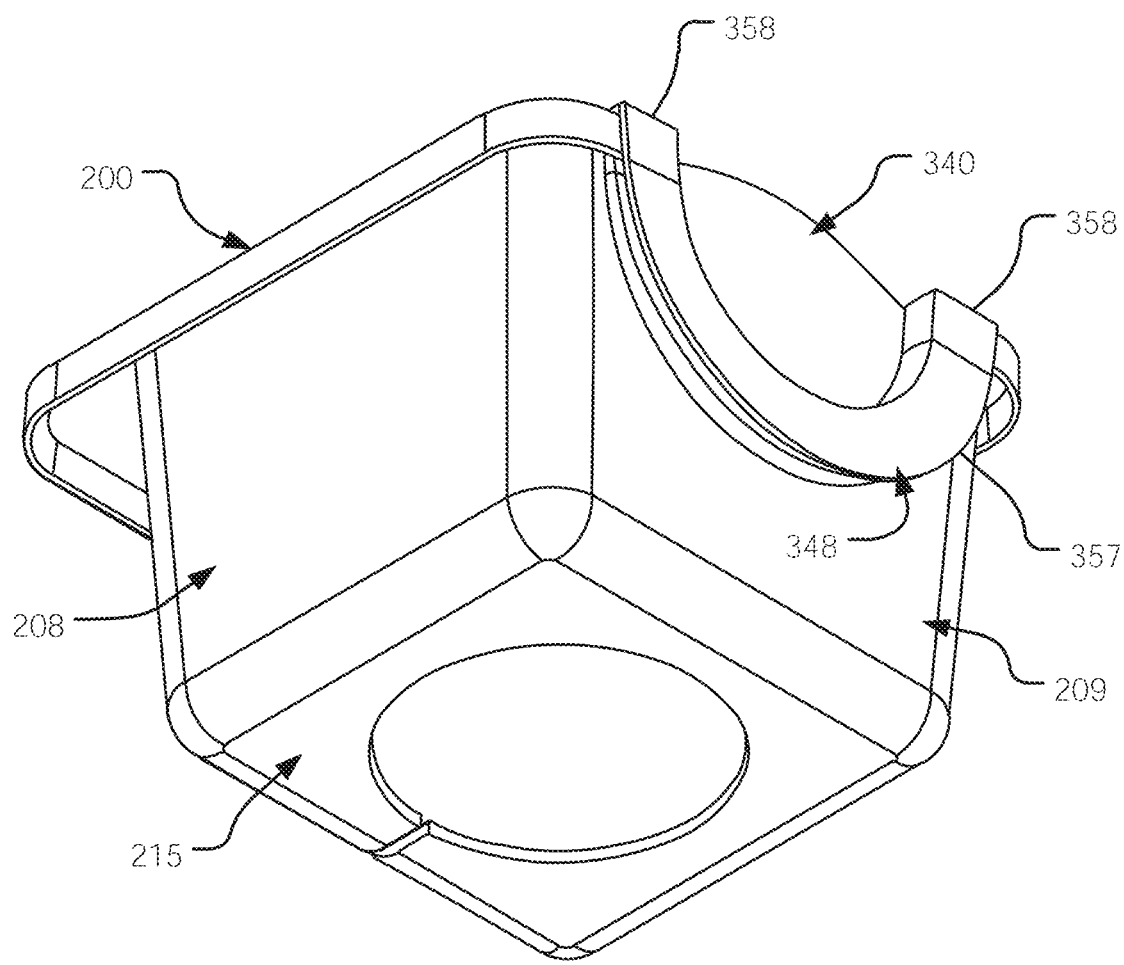
FIG. 14B may depict the face soaking device of FIG. 14A, but shown from a bottom perspective view.
Figure 14C:
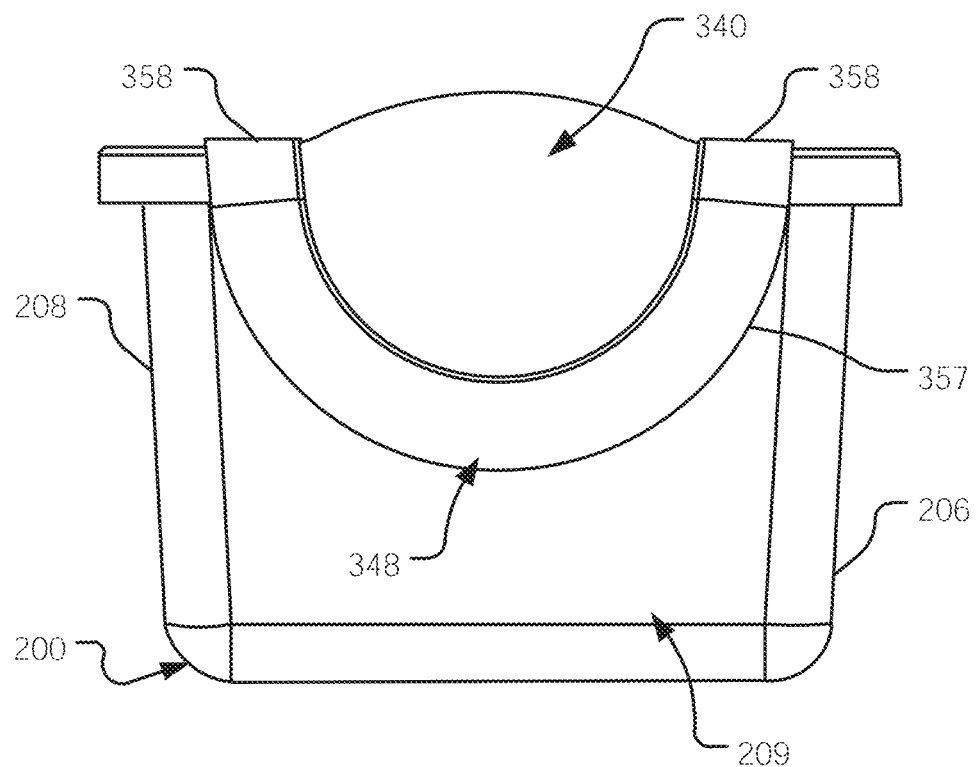
FIG. 14C may depict the face soaking device of FIG. 14A, but shown from a front view.
Figure 14D:
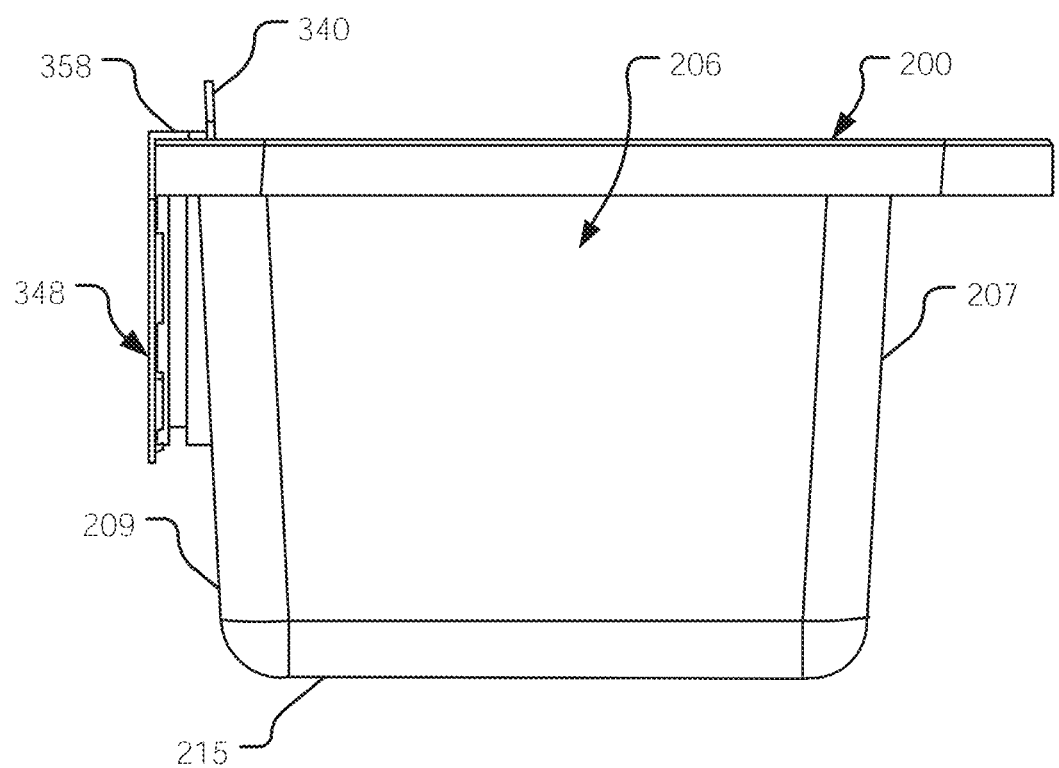
FIG. 14D may depict the face soaking device of FIG. 14A, but shown from a side (right) view.
Figure 14E:
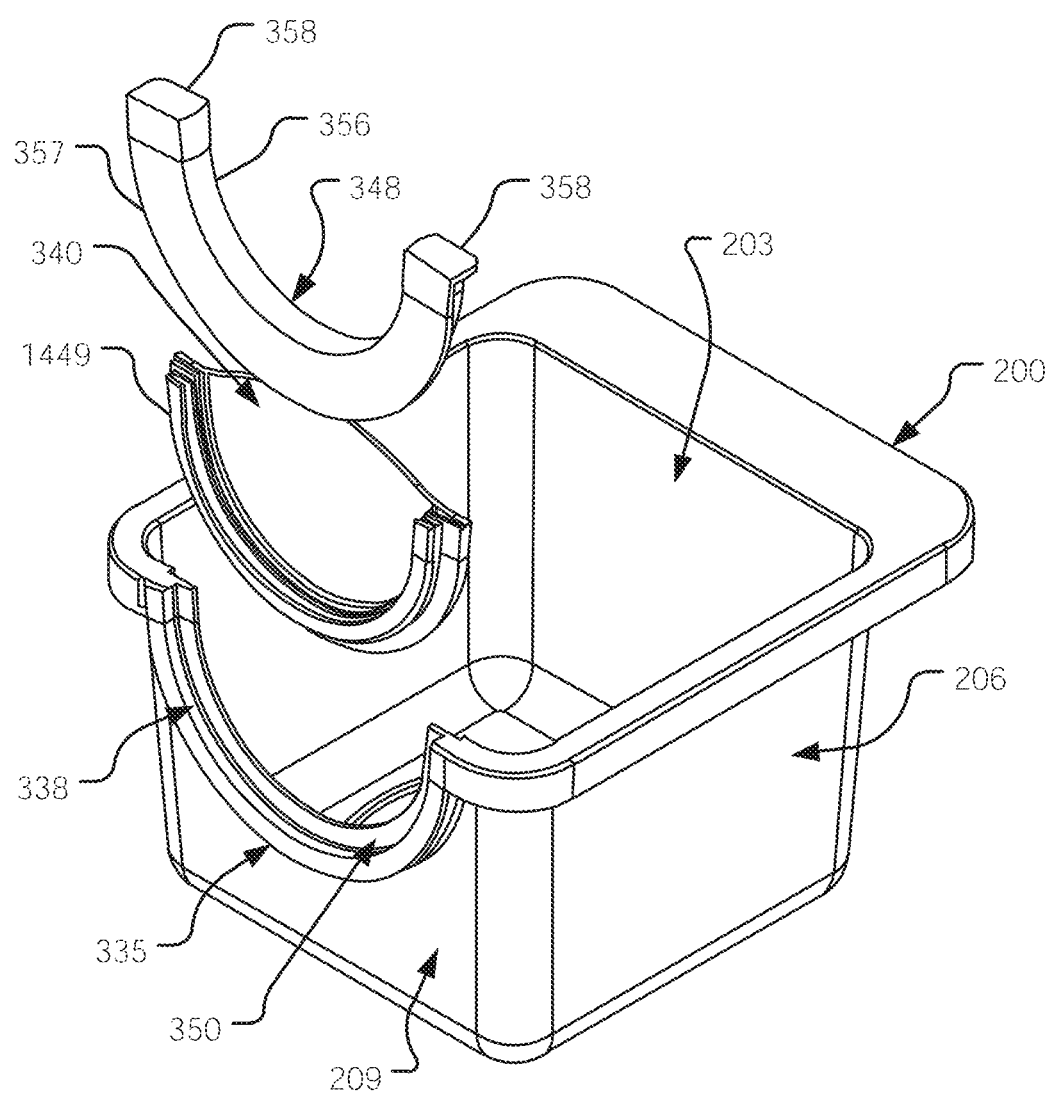
FIG. 14E may depict the face soaking device of FIG. 14A, but shown in a top perspective exploded view.
Figure 14F:
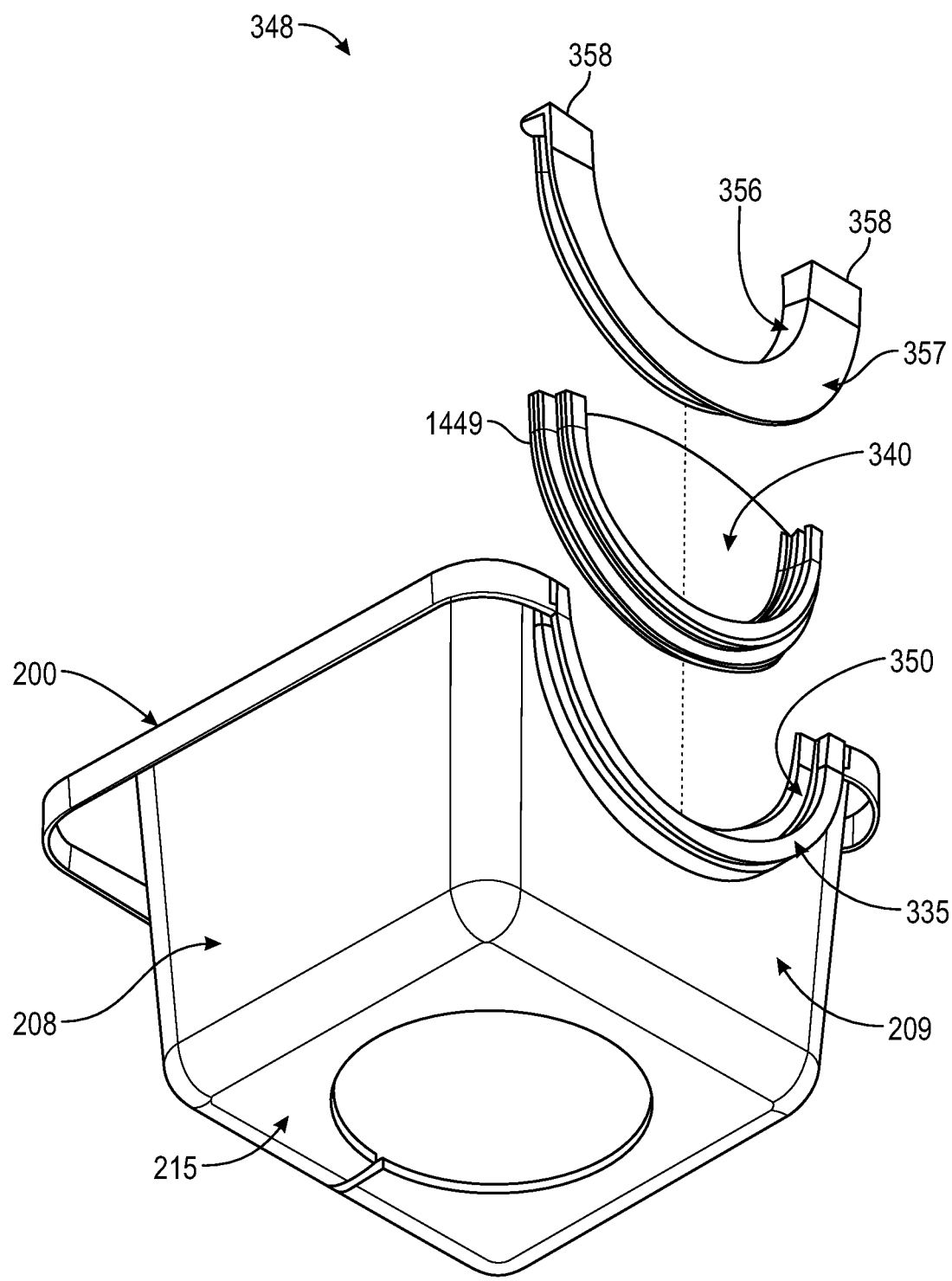
FIG. 14F may depict the face soaking device of FIG. 14A, but shown in a bottom perspective exploded view.
Figure 14G:
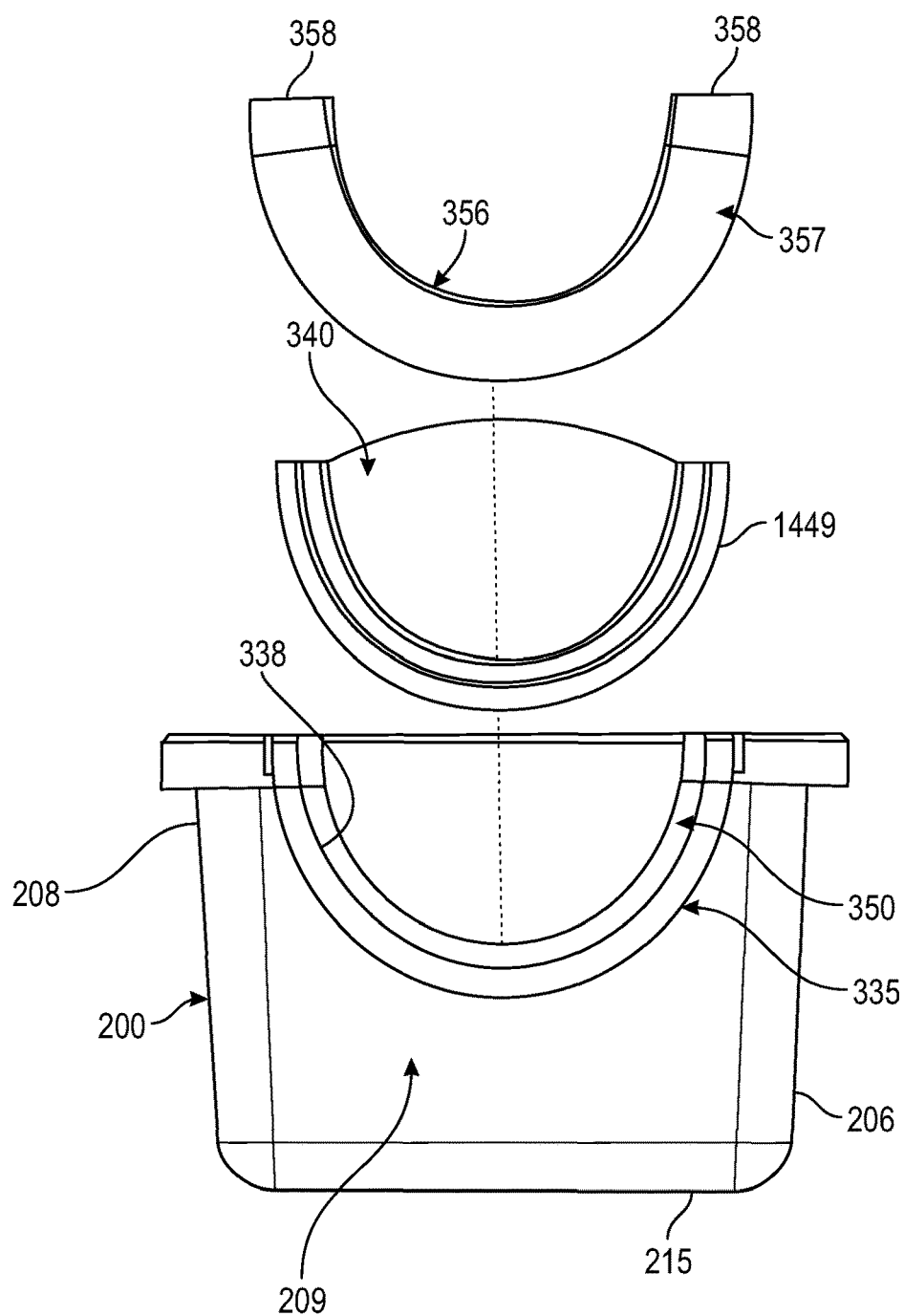
FIG. 14G may depict the face soaking device of FIG. 14A, but shown in a front exploded view.
Figure 14H:
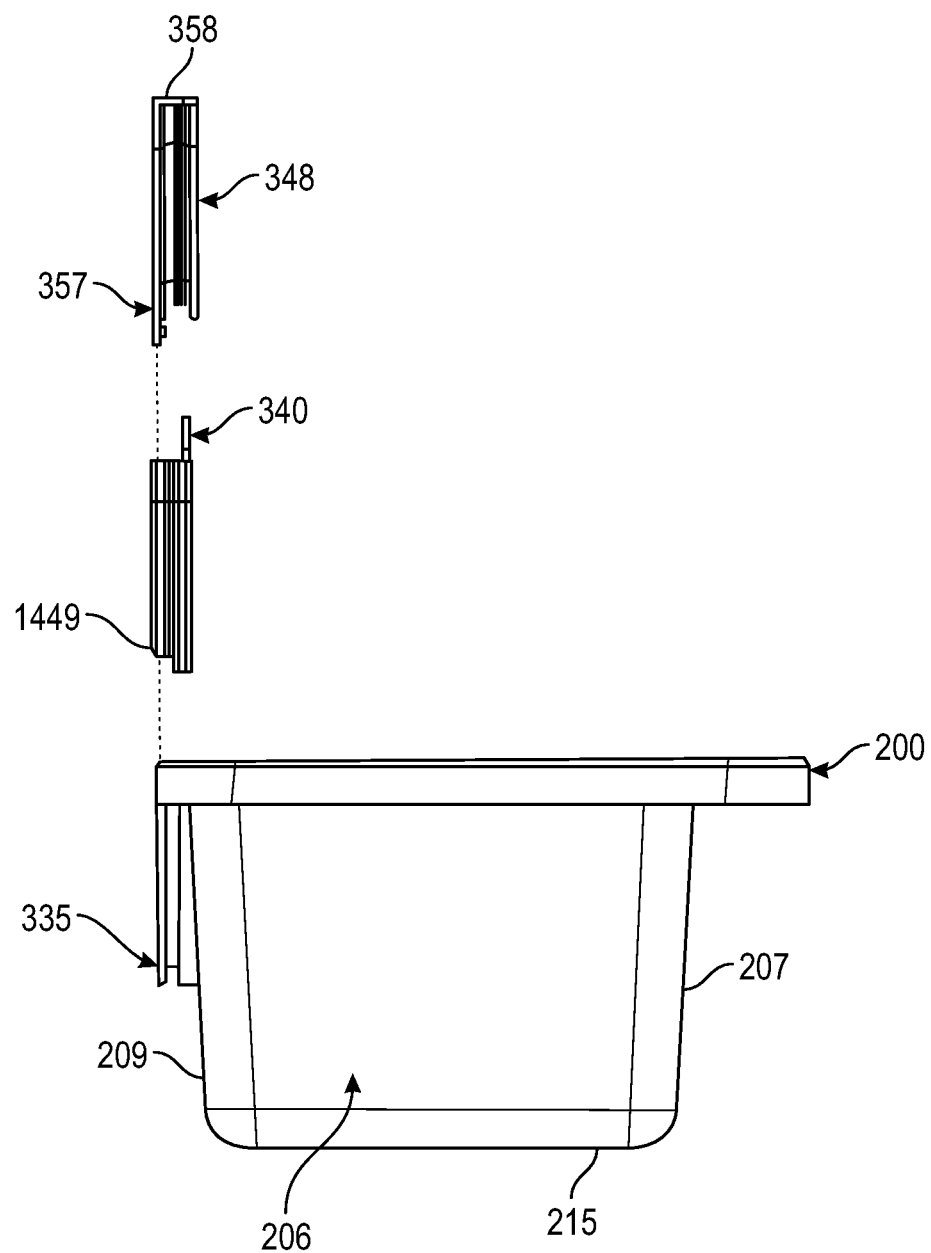
FIG. 14H may depict the face soaking device of FIG. 14A, but shown in a side (right) exploded view.
Figure 14I:
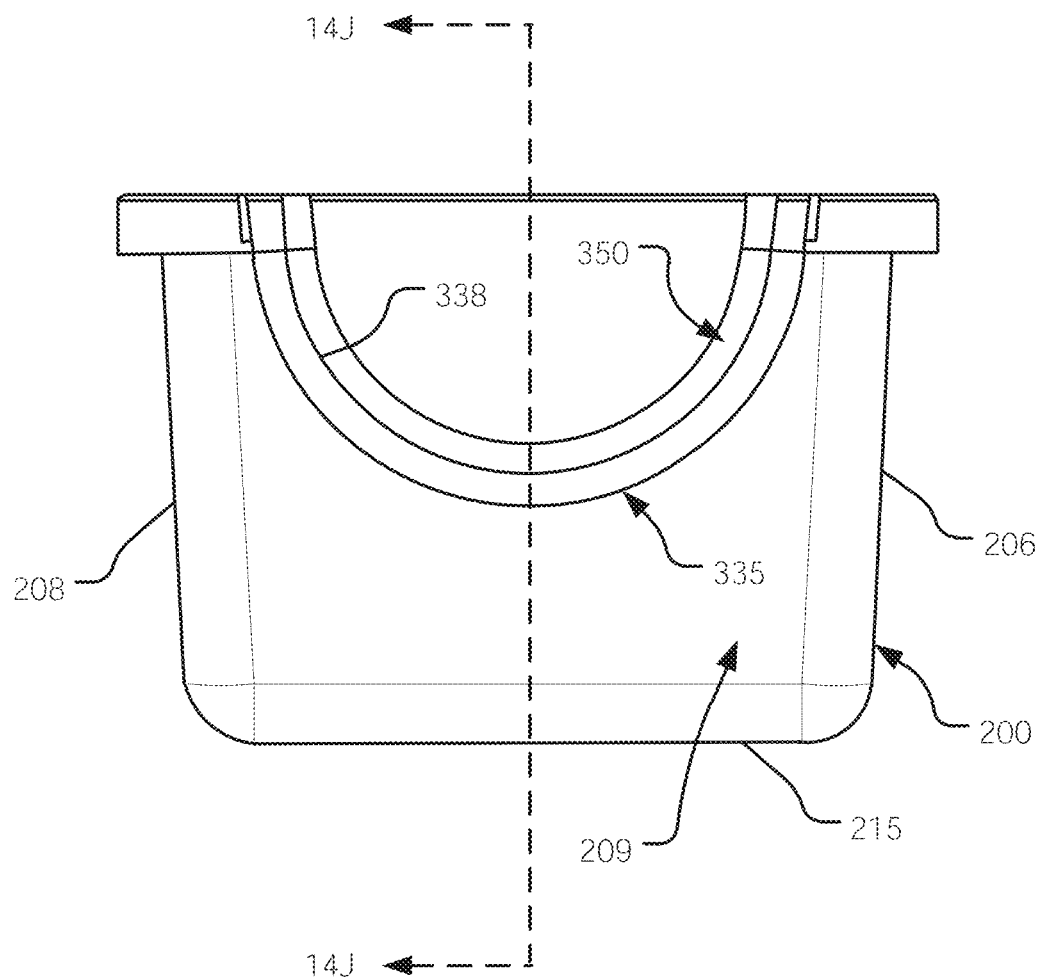
FIG. 14I may depict the face soaking device of FIG. 14A, but shown in a front view, with a sectional line 14J-14J through the neck-gasket-accommodator; wherein the vessel neck gasket and the clamp may be removed.
Figure 14J:
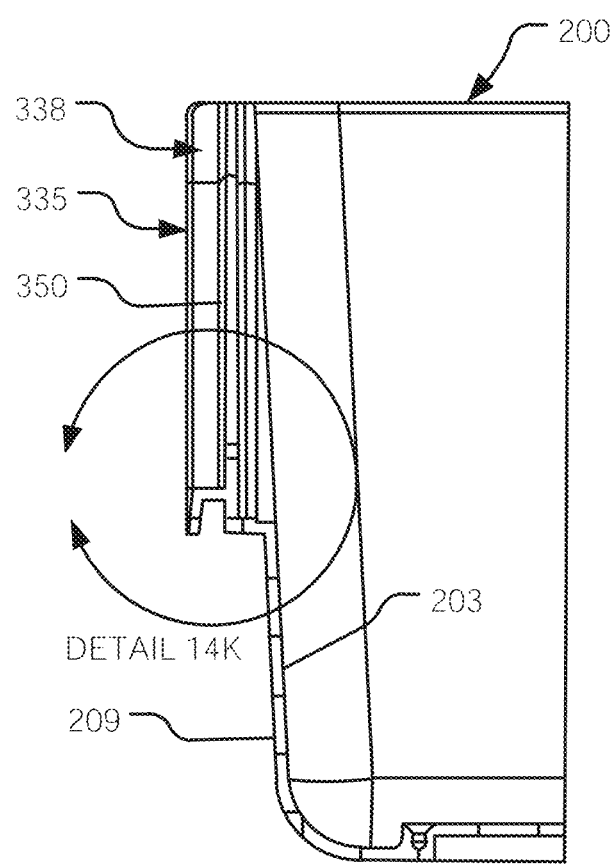
FIG. 14J may depict a cross-sectional side view along sectional line 14J-14J; wherein FIG. 14J may also depict a region of Detail 14K.
Figure 14K:
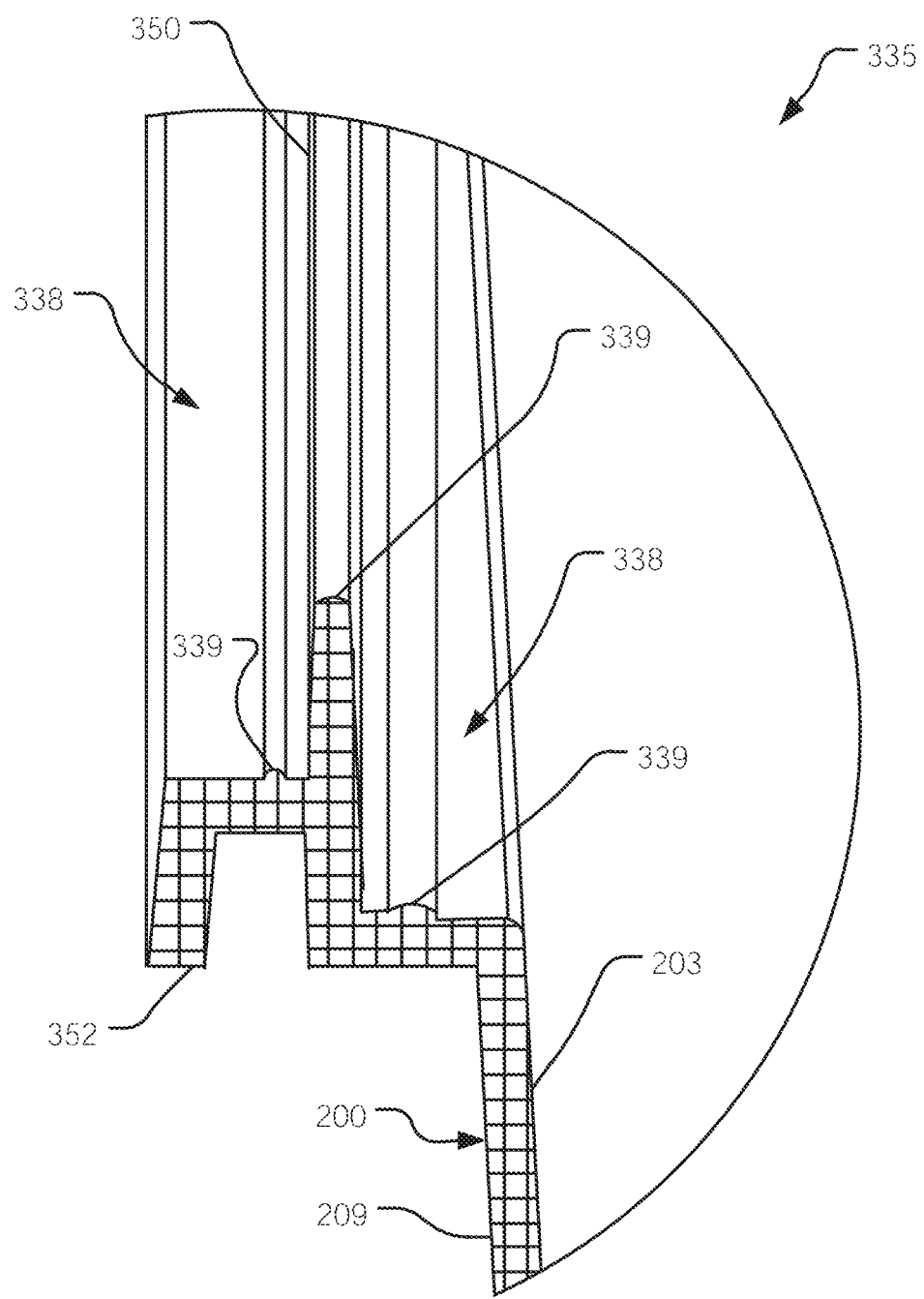
FIG. 14K may depict a close-up of Detail K.
Figure 14L:
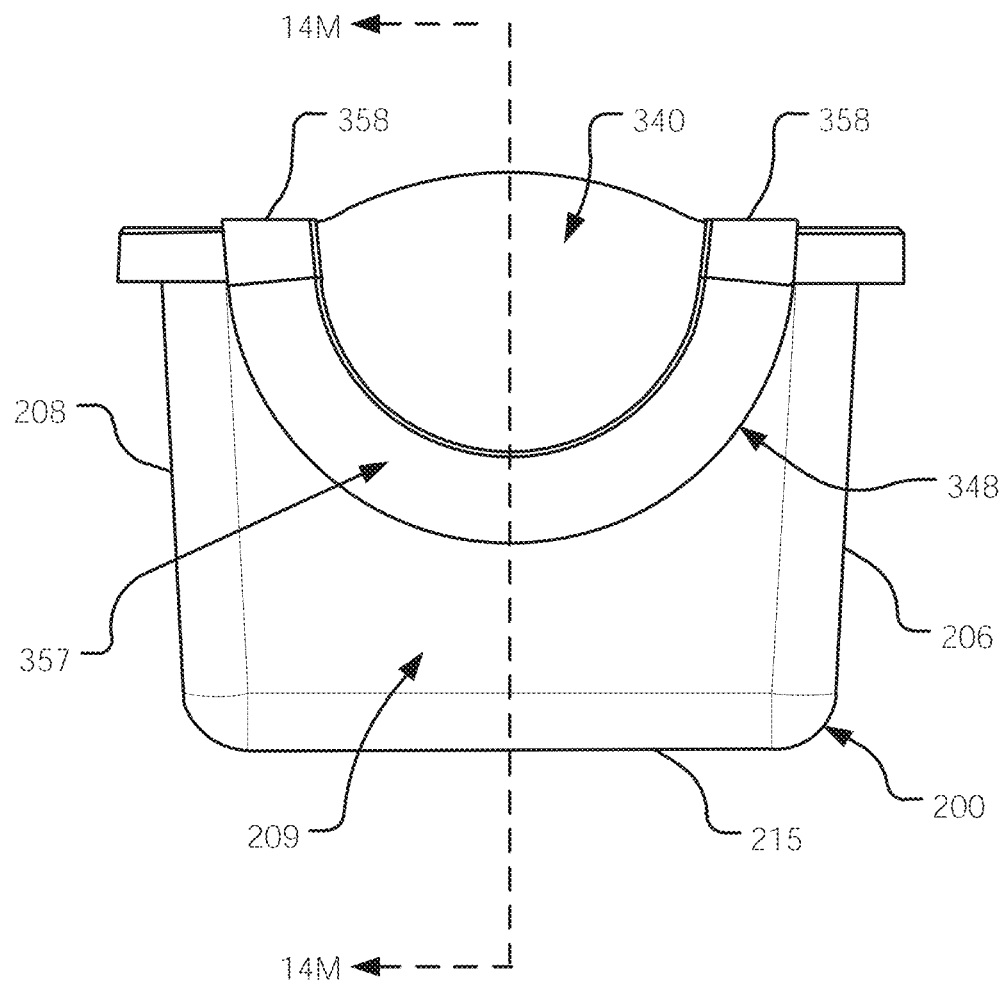
FIG. 14L may depict the face soaking device of FIG. 14A, but shown in a front view, with a sectional line 14M-14M through the vessel neck gasket, the clamp, and the neck-gasket-accommodator.
Figure 14M:
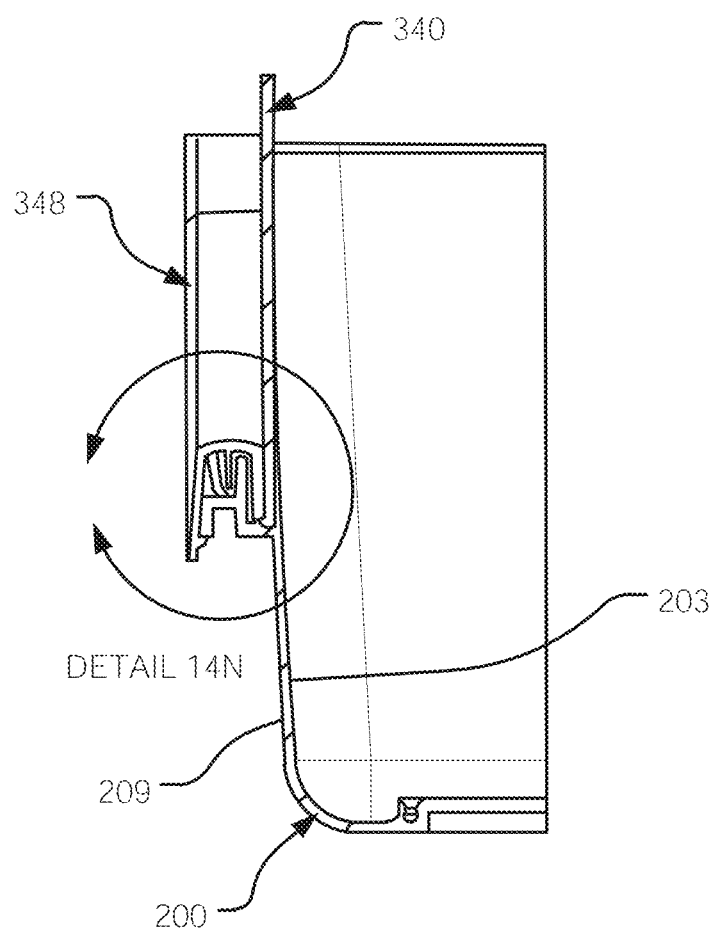
FIG. 14M may depict a cross-sectional side view along sectional line 14M-14M; wherein FIG. 14M may also depict a region of Detail 14N.
Figure 14N:
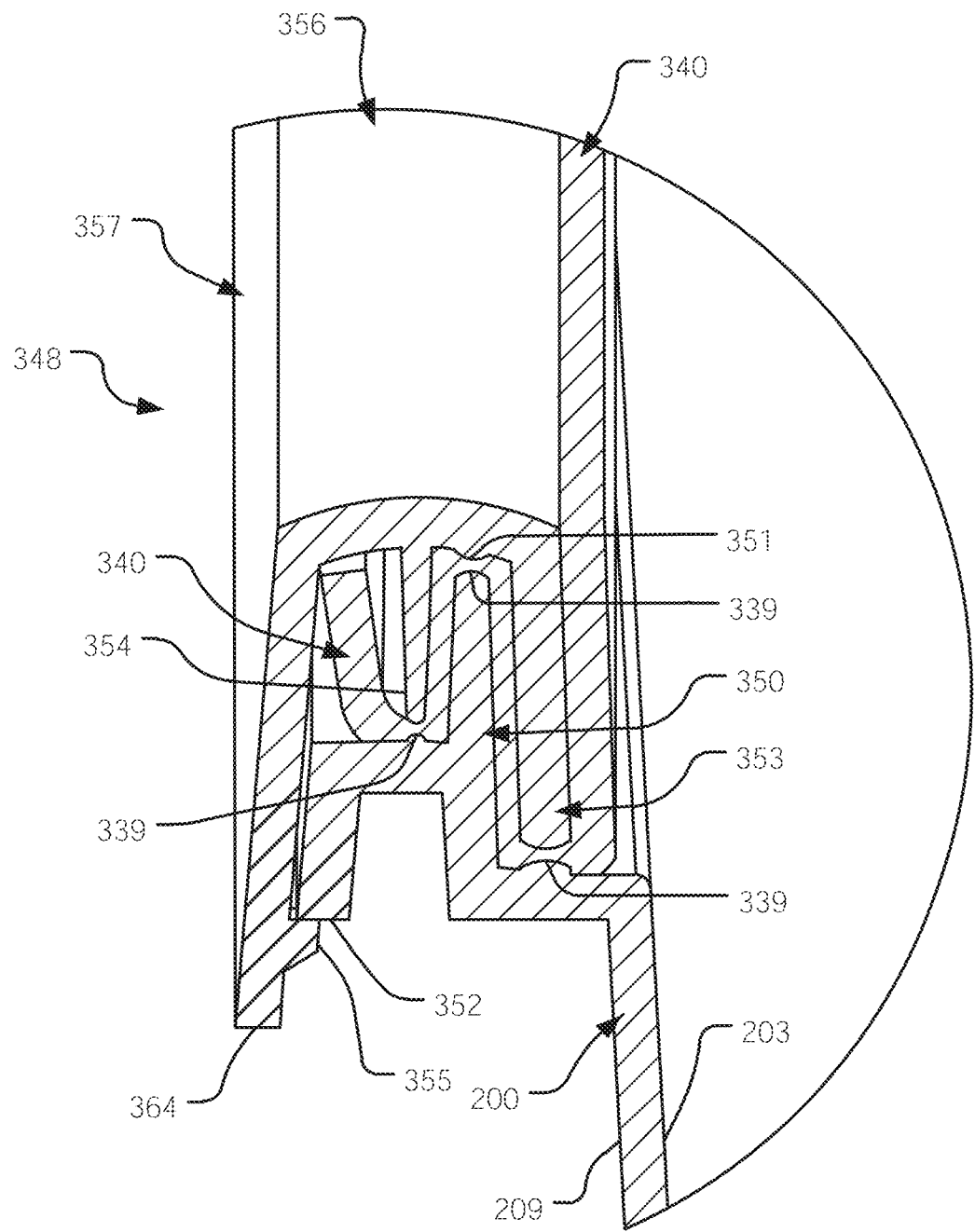
FIG. 14N may depict a close-up view of Detail 14N.

A FIG. 14 series of figures may comprise FIG. 14A through FIG. 14N. This FIG. 14 series of figures may focus on depicting an alternative embodiment of vessel neck gasket subassembly (alternative to the FIG. 3 series of figures). FIG. 14A may depict a face soaking device with the alternative embodiment vessel neck gasket subassembly, shown from a perspective view. (A breathing apparatus, a head rest subassembly, a heater subassembly, and a gas diffuser may be removed.) FIG. 14B may depict the face soaking device of FIG. 14A, but shown from a bottom perspective view. FIG. 14C may depict the face soaking device of FIG. 14A, but shown from a front view. FIG. 14D may depict the face soaking device of FIG. 14A, but shown from a side (right) view. FIG. 14E may depict the face soaking device of FIG. 14A, but shown in a top perspective exploded view. FIG. 14F may depict the face soaking device of FIG. 14A, but shown in a bottom perspective exploded view. FIG. 14G may depict the face soaking device of FIG. 14A, but shown in a front exploded view. FIG. 14H may depict the face soaking device of FIG. 14A, but shown in a side (right) exploded view. FIG. 14I may depict the face soaking device of FIG. 14A, but shown in a front view, with a sectional line 14J-14J through neck-gasket-accommodator 335; wherein vessel neck gasket 340 and clamp 348 may be removed. FIG. 14J may depict a cross-sectional side view along sectional line 14J-14J; wherein FIG. 14J may also depict a region of Detail 14K. FIG. 14K may depict a close-up of Detail K. FIG. 14L may depict the face soaking device of FIG. 14A, but shown in a front view, with a sectional line 14M-14M through vessel neck gasket 340, clamp 348, and neck-gasket-accommodator 335. FIG. 14M may depict a cross-sectional side view along sectional line 14M-14M; wherein FIG. 14M may also depict a region of Detail 14N. FIG. 14N may depict a close-up view of Detail 14N.

In some embodiments, contour 338 may comprise at least one sealing fin 350, and at least one pinch point 339. See e.g., FIG. 14K. At least one sealing fin 350 may be a wall like or dam like protrusion extending away from one or more of the surfaces of contour 338. At least one sealing fin 350 may comprise a function of providing additional sealing surface area for a complimentary frictional fit of some embodiments of vessel neck gasket 340, wherein elastomeric regions of vessel neck gasket 340 may be pressed against flat surfaces of at least one sealing fin 350. In the FIG. 14 series of figures, at least one pinch point 339 may comprise a projection extending away from one or more surfaces of contour 338. At least one pinch point 339 may extend away from the one or more surfaces of contour 338 less than how far at least one sealing fin 350 may extend away from the one or more surfaces of contour 338. See e.g., FIG. 14K. At least one pinch point 339 may comprise a function of providing an increased compression space for squeezing a portion of vessel neck gasket 340 material against complimentary pinch point(es) located on clamp 348. In some embodiments, contour 338 may comprise three pinch points 339. See e.g., FIG. 14K. In some embodiments, at least one sealing fin 350 may have a thickness, wherein a top (distal from contour 338 surfaces) of at least one sealing fin 350 may comprise one of the at least one pinch point 339. The two other pinch points 339, may be located one to each side of the pinch point 339 located at the top of at least one sealing fin 350. In some embodiments, these three pinch points may be termed first pinch point, second pinch point, and third pinch point, with the first pinch point being closest to internal volume 220, with the third pinch point being furthest from internal volume 220, and the second pinch point being disposed between the first and the second pinch points.

In some embodiments, at least one sealing fin 350 may be replaced with a channel embodiment (or at least one sealing fin 350 may be used in conjunction with a channel embodiment), wherein the channel may extend into contour 338, rather than away from contour 338 surfaces as with at least one sealing fin 350. However, without other modifications, such as a channel drainage means, at least one sealing fin 350 may be exemplary over sole channel embodiments because channels may accumulate liquid and debris, providing a source of possible contamination and sanitation issues.

In some such embodiments, neck-gasket-accommodator 335 may further comprise at least one lip 352. At least one lip 352 may extend in an opposite direction of at least one sealing fin 350 and on a distal portion of neck-gasket-accommodator 335 from internal volume 220. In some embodiments, at least one lip 352 may comprise a function of providing additional surface area to complimentary mate with a tab 355 of clamp 348. In some embodiments, at least one lip 352 may be provided with structural support from molded ribs or similar structures. In some embodiments, such ribs or similar support structures may be located on a bottom (ventral) side of neck-gasket-accommodator 335, exterior to internal volume 220. See e.g., FIG. 14K and FIG. 14N.

In some embodiments, attachment of vessel neck gasket 340 to a given vessel (e.g., vessel 200) may comprise the following structure and elements: vessel neck gasket 340, neck-gasket-accommodator 335 (a region of a given vessel), and the vessel neck gasket attachment means. See e.g., the FIG. 14 series of figures.

In some embodiments, vessel neck gasket 340 may comprise carrier 1449. Or alternatively, a given face soaking device may comprise carrier 1449. See e.g., FIG. 14E and/or FIG. 14F. Carrier 1449 may function to provide some rigidity and/or some mating structure to vessel neck gasket 340, wherein such provided rigidity and/or provided mating structures may assist in attaching vessel neck gasket 340 to neck-gasket-accommodator 335 (or to the vessel proximate to neck-gasket-accommodator 335). Carrier 1449 may be semi-rigid to rigid. In some embodiments, carrier 1449 may have a geometric structure which may generally approximate the overall shape of neck-gasket-accommodator 338 and may be complimentary to contour 338. For example, and without limiting the scope of the present invention, carrier 1449 may comprise an overall shape which may be may be concave or convex with a semi-round, a semi-oval, a U-shape, any other similar semicircular, semi-elliptical, or semi-oval shape, a regular or an irregular polygon or a semi-polygon shape that may approximate a complimentary overall shape of neck-gasket-accommodator 335 (e.g. contour 338).

In some embodiments, carrier 1449 may be integral with vessel neck gasket 340, in which carrier 1449 and vessel neck gasket 340 may be a single article of manufacture. In other embodiments, carrier 1449 may be a separate part from vessel neck gasket 340, wherein carrier 1449 may be attached to vessel neck gasket 340. Regardless of whether carrier 1449 and vessel neck gasket 340 may be integral or a subassembly, a union of carrier 1449 to vessel neck gasket 340 may form mating edge 343.

In some embodiments, such attachment of carrier 1449 to vessel neck gasket 340 may be removable, while in other embodiments, such attachment may be permanent. Such attachment may be by one or more of: solvent bonding, heat welding, ultrasonic welding, chemical adhesives/sealants, mechanical fasteners, and/or the like.

As noted, the union of vessel neck gasket 340 to carrier 1449 may result in mating edge 343. That is, a portion of the flexible, compressible, and/or elastomeric component of vessel neck gasket 340 may cover a portion of carrier 1449, wherein the interior surfaces of such physical contact between vessel neck gasket 340 and carrier 1449 may be attached to each other (either integrally or by the above noted attachment methods) and the exterior surface of that portion of vessel neck gasket 340 may then form mating edge 343. Thus, when the union of carrier 1449 and vessel neck gasket 340 may be placed (and pushed) into or onto contour 338, the flexible, compressible, and/or elastomeric component of vessel neck gasket 340 in physical contact with contour 338 may be compressed to form the primary water tight seal, wherein such compression may be increased by at the at least one pinch point and/or the additional surface area may be provided by at least one sealing fin 350. See e.g., FIG. 14N.

In some embodiments, the union of carrier 1449 and vessel neck gasket 340 may comprise an outside diameter which may be complimentary to inside diameters of contour 338, such that placement of the union of carrier 1449 and vessel neck gasket 340 into contour 338 may result in a frictional fit, wherein friction may hold the union of carrier 1449 and vessel neck gasket 340 in place to contour 338.

In some embodiments, the vessel neck gasket attachment means may comprise clamp 348. See e.g., FIG. 14E or FIG. 14F. In the FIG. 14 series of figures, clamp 348 may comprise a function of attaching the union of carrier 1449 and vessel neck gasket 340 to contour 338 of neck-gasket-accommodator 335. In some embodiments, such an attachment may be removable; while in other embodiments, such attachment may be permanent. In some exemplary embodiments, such an attachment may be by a frictional fit. In some embodiments, such a frictional attachment means may be removable; while in other embodiments, such a frictional attachment means may be permanent.

In some embodiments, clamp 348 may be constructed of a semi-rigid to rigid material of construction, such as a thermoformed plastic. In some embodiments, clamp 348 may have a geometric structure which may generally approximate the overall shape of neck-gasket-accommodator 338 and may be complimentary to contour 338. For example, and without limiting the scope of the present invention, clamp 348 may comprise an overall shape which may be may be concave or convex with a semi-round, a semi-oval, a U-shape, any other similar semicircular, semi-elliptical, or semi-oval shape, a regular or an irregular polygon or a semi-polygon shape that may approximate a complimentary overall shape of neck-gasket-accommodator 335 (e.g. contour 338). In some embodiments, clamp 348 may comprise two clamp terminal ends 358. See e.g., FIG. 14G or FIG. 14E.

In some embodiments, clamp 348 may comprise two exterior surfaces, an upper exterior surface 356, and a lateral exterior surface 357. See e.g., FIG. 14N. Upper exterior surface 356 and lateral exterior surface 357 may attach to each other at a common and continuous vertex. In some embodiments, upper exterior surface 356 and lateral exterior surface 357 may diverge from each other at an angle of 60 degrees to 110 degrees. In other embodiments, other angles of divergence may be measured between upper exterior surface 356 and lateral exterior surface 357. In some embodiments, clamp 348 may comprise a first complimentary sealing fin 353, a second complimentary sealing fin 354, and a complimentary pinch point 351. See e.g., FIG. 14N. First complimentary sealing fin 353, second complimentary sealing fin 354, and complimentary pinch point 351 may each extend away from upper exterior surface 356. First complimentary sealing fin 353, second complimentary sealing fin 354, and complimentary pinch point 351 may each extend away from upper exterior surface 356 by a different distance. In some embodiments, first complimentary sealing fin 353 may be longer than second complimentary sealing fin 354, and second complimentary sealing fin 354 may be longer than complimentary pinch point 351. Between first complimentary sealing fin 353 and second complimentary sealing fin 354 may be sufficient space to accommodate the thickness of at least one sealing fin 350. Between second complimentary sealing fin 354 and lateral external surface 357 may be sufficient space to accommodate a thickness of vessel neck gasket 340, which may be compressed and/or stretched when sandwiched between clamp 248 and neck-gasket-accommodator 335. See e.g., FIG. 14N.

In some embodiments, lateral exterior surface 357 may terminate in pull 364. See e.g., FIG. 14N. That is, pull 364 may be distal from the common and continuous vertex where upper exterior surface 356 and lateral exterior surface 357 may attach to each other. In some embodiments, pull 364 may be configured to be pulled on by user 9000 to release clamp 348 from neck-gasket-accommodator 335. In some embodiments, a portion of lateral exterior surface 357 and pull 364 may extend beyond at least one lip 352. In some embodiments, lateral exterior surface 357 may comprise tab 355. Tab 355 may protrude from an interior surface side of lateral exterior surface 357. Tab 355 may be configured to engage (e.g. hook onto) at least one lip 352 of neck-gasket-accommodator 335. See e.g., FIG. 14N.

When clamp 348 may be attached over the union of carrier 1449 and vessel neck gasket 340 to contour 338, first complimentary sealing fin 253 may directly oppose the first pinch point, complimentary pinch point 251 may directly oppose the second pinch point formed by the top of at least one sealing fin 350, and second sealing fin 254 may directly oppose the third pinch point. See e.g., FIG. 14N. Each of these three pairings may form regions for compressing portions of vessel neck gasket 340. Compressing portions of vessel neck gasket 340 between clamp 348 and contour 338 may form the primary water tight seal.

In some embodiments, clamp 348 may comprise an outside diameter which may be complimentary to inside diameters of contour 338, such that placement of clamp 348 into contour 338 may result in a frictional fit, wherein friction may hold clamp 348, as well as the union of carrier 1449 and vessel neck gasket 340, in place to contour 338. In some embodiments, installing clamp 348 over the union of carrier 1449 and vessel neck gasket 340 and into contour 338 may require squeezing each clamp terminal end 358 towards each other to place clamp 348 into place over the union of carrier 1449 and vessel neck gasket 340 and into contour 338, wherein release of the two clamp terminal ends 358 may then yield the frictional fit.

Figure 15A:
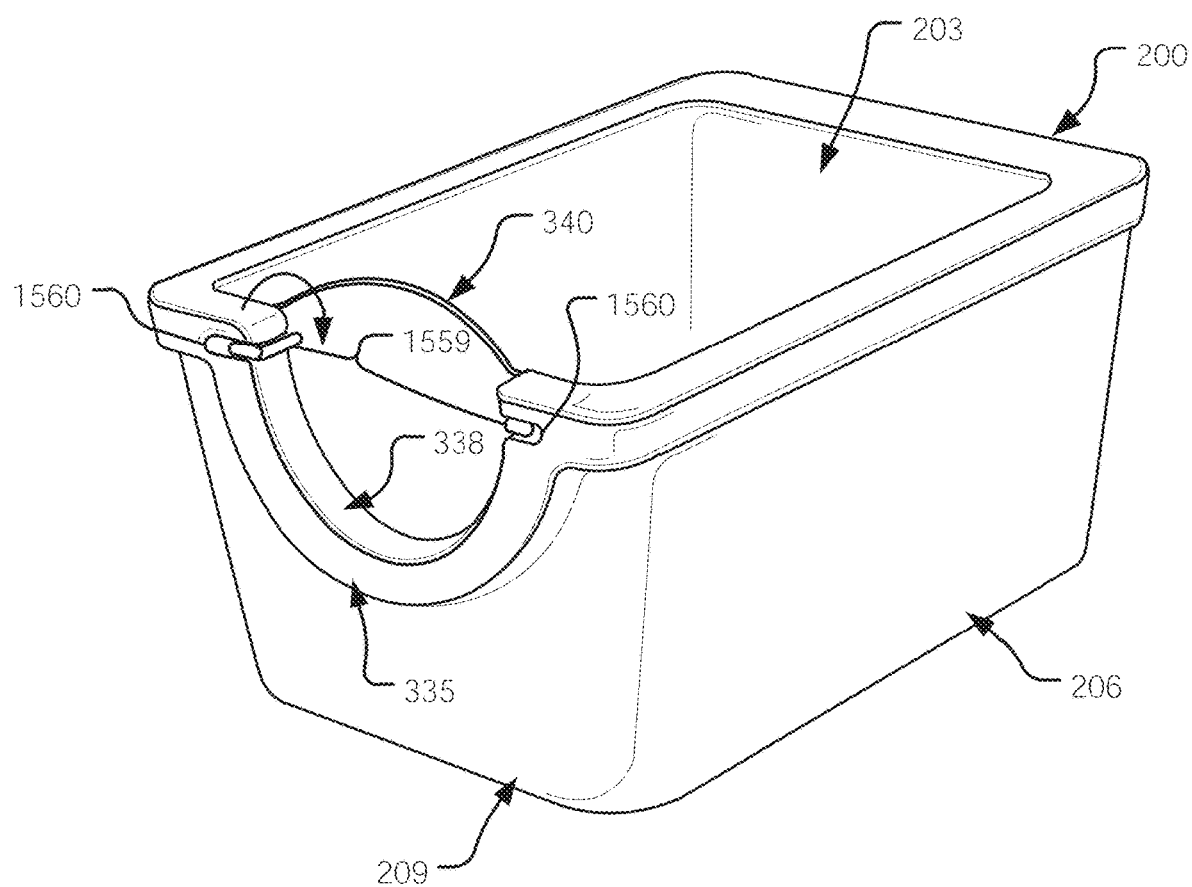
FIG. 15A may depict a face soaking device with an alternative embodiment vessel neck gasket, wherein a clamp may swivel, shown from a perspective view. (A breathing apparatus, a head rest subassembly, a heater subassembly, and a gas diffuser may be removed.)
Figure 15B:
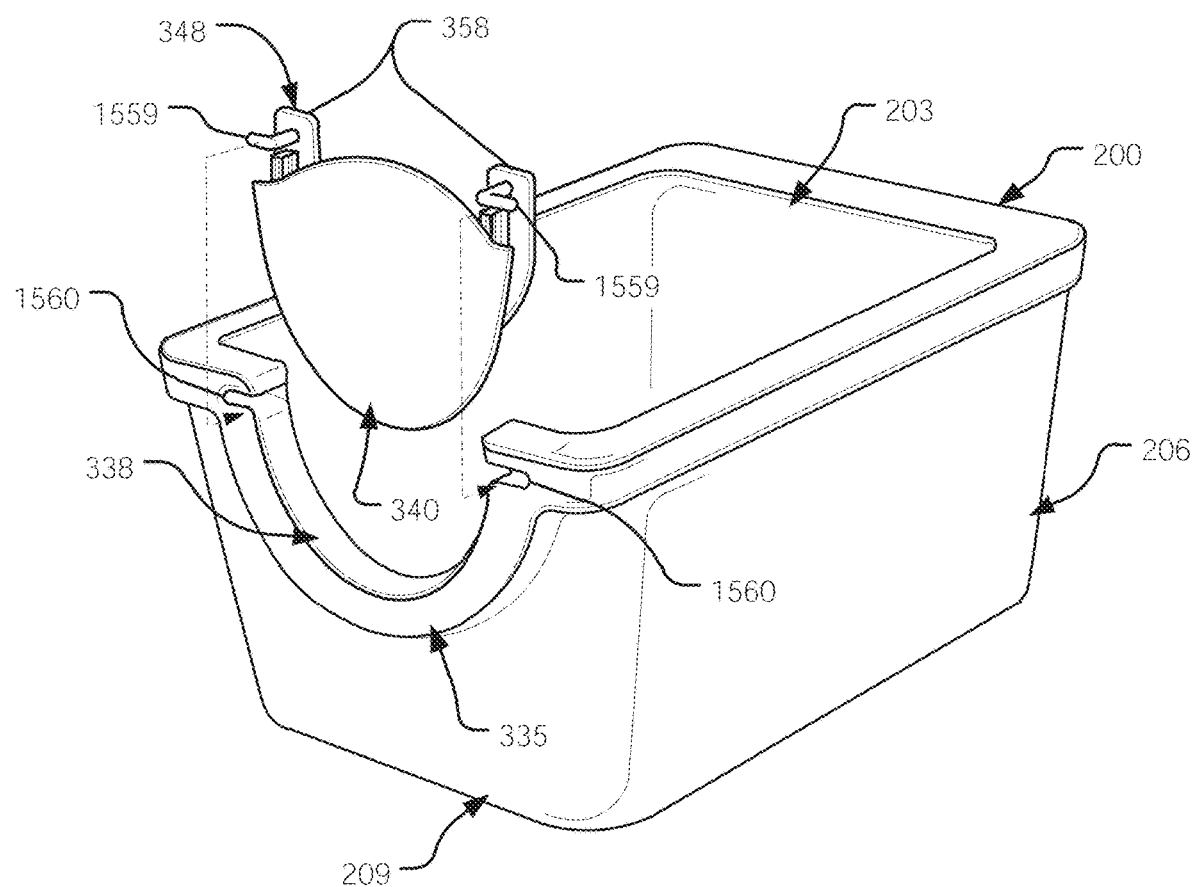
FIG. 15B may depict the face soaking device from FIG. 15A, but wherein the vessel neck gasket and the clamp may be exploded from the vessel.
Figure 15C:
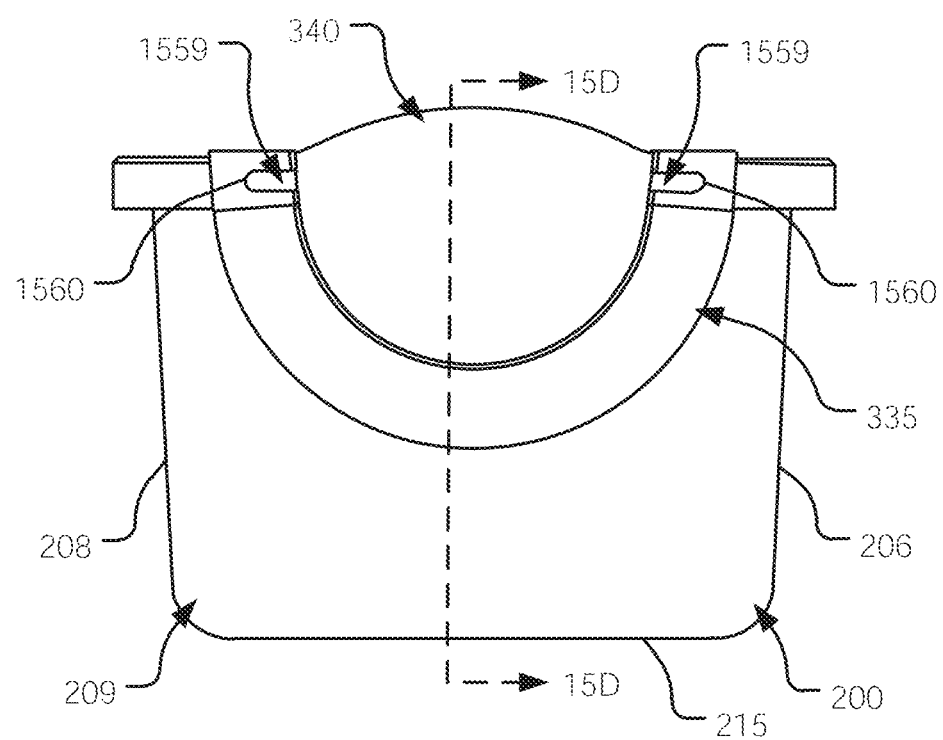
FIG. 15C may depict the face soaking device from FIG. 15A, but shown from a front view, with a sectional line 15D-15D through the vessel neck gasket and the clamp.
Figure 15D:
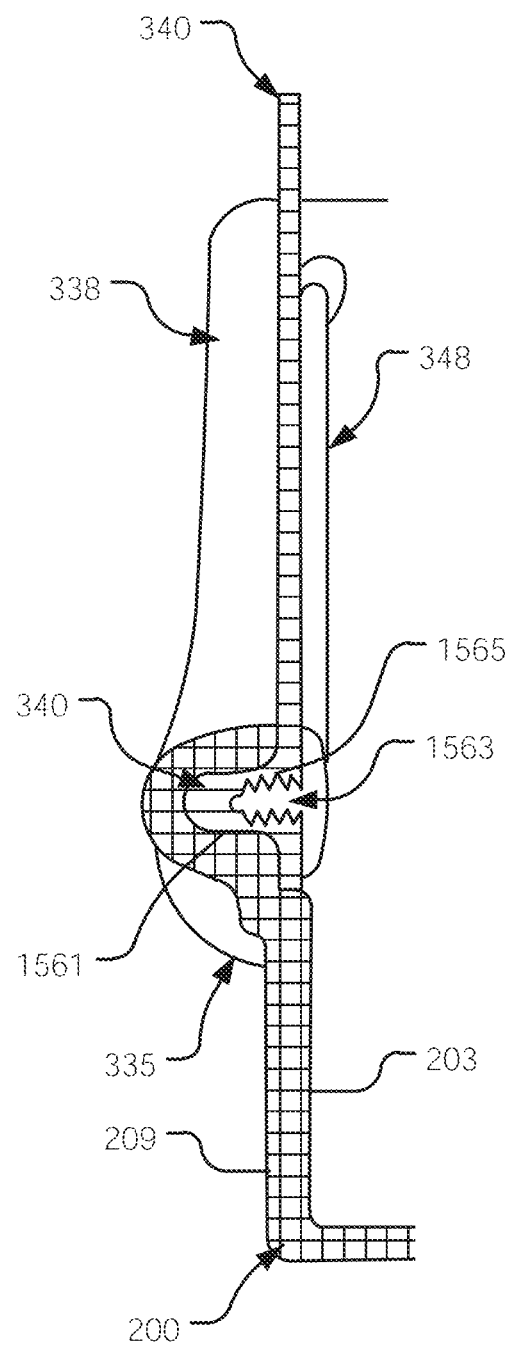
FIG. 15D may depict a partial cross-sectional side view along sectional line 15D-15D.
Figure 15E:
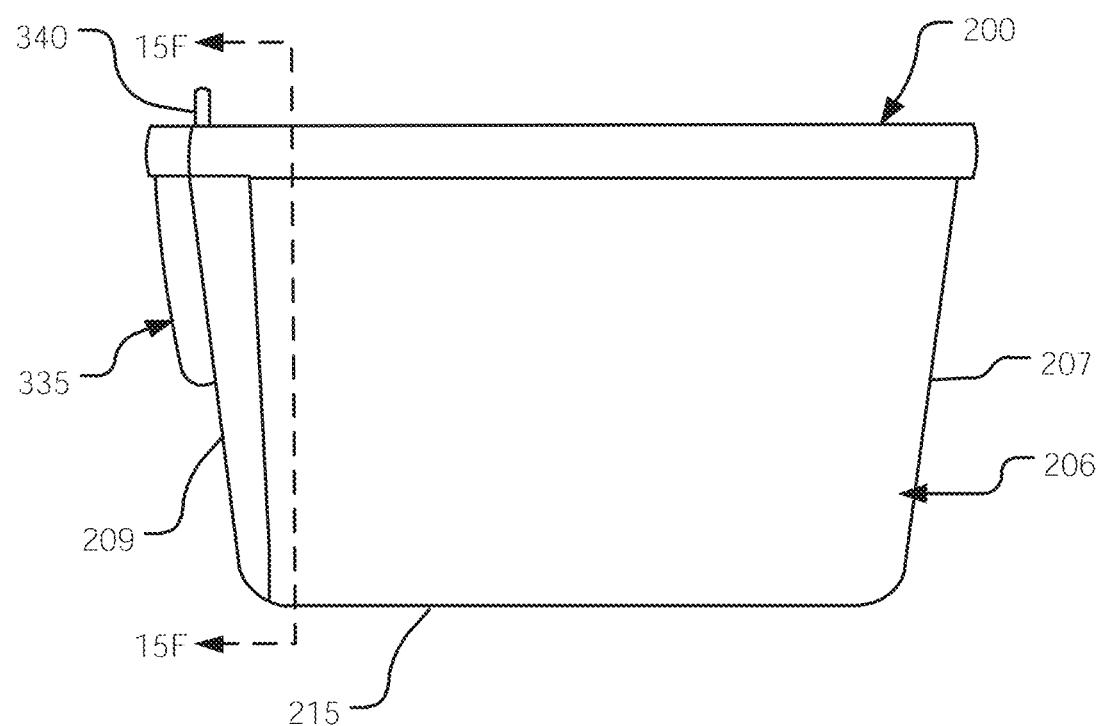
FIG. 15E may depict the face soaking device from FIG. 15A, but shown from a side (right) view, with a sectional line 15F-15F through the vessel.
Figure 15F:
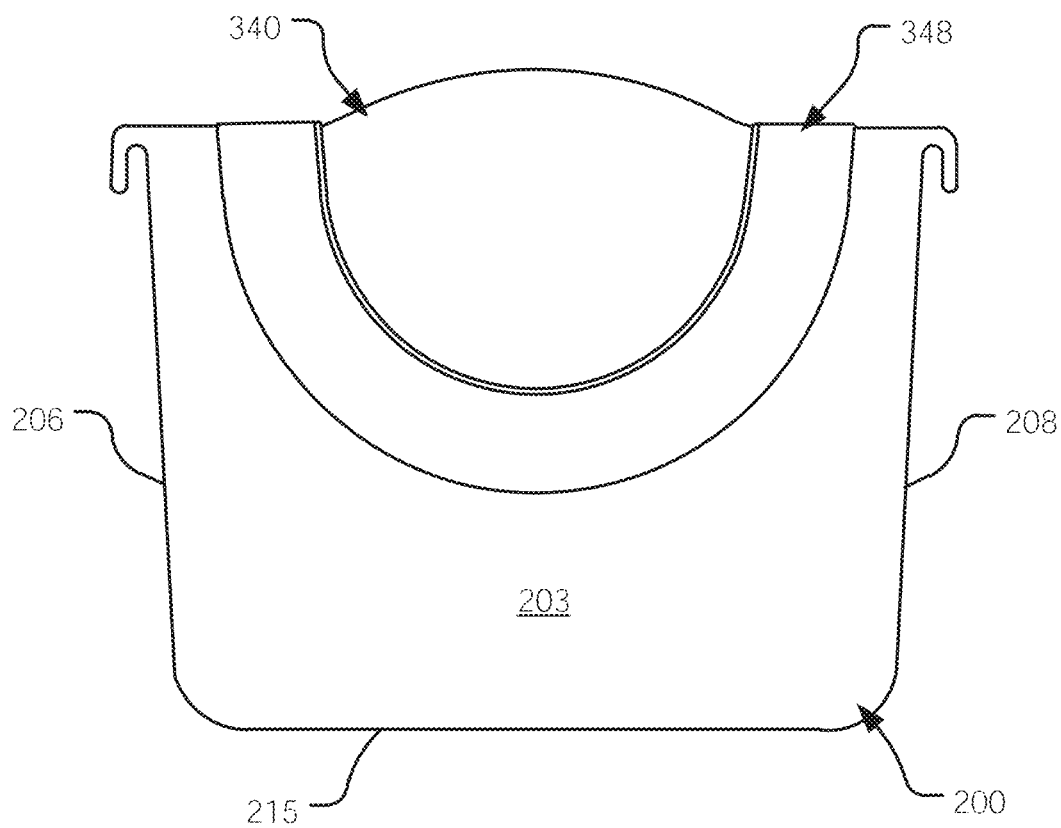
FIG. 15F may depict a transverse-width cross-sectional view along sectional line 15F-15F.
Figure 15G:
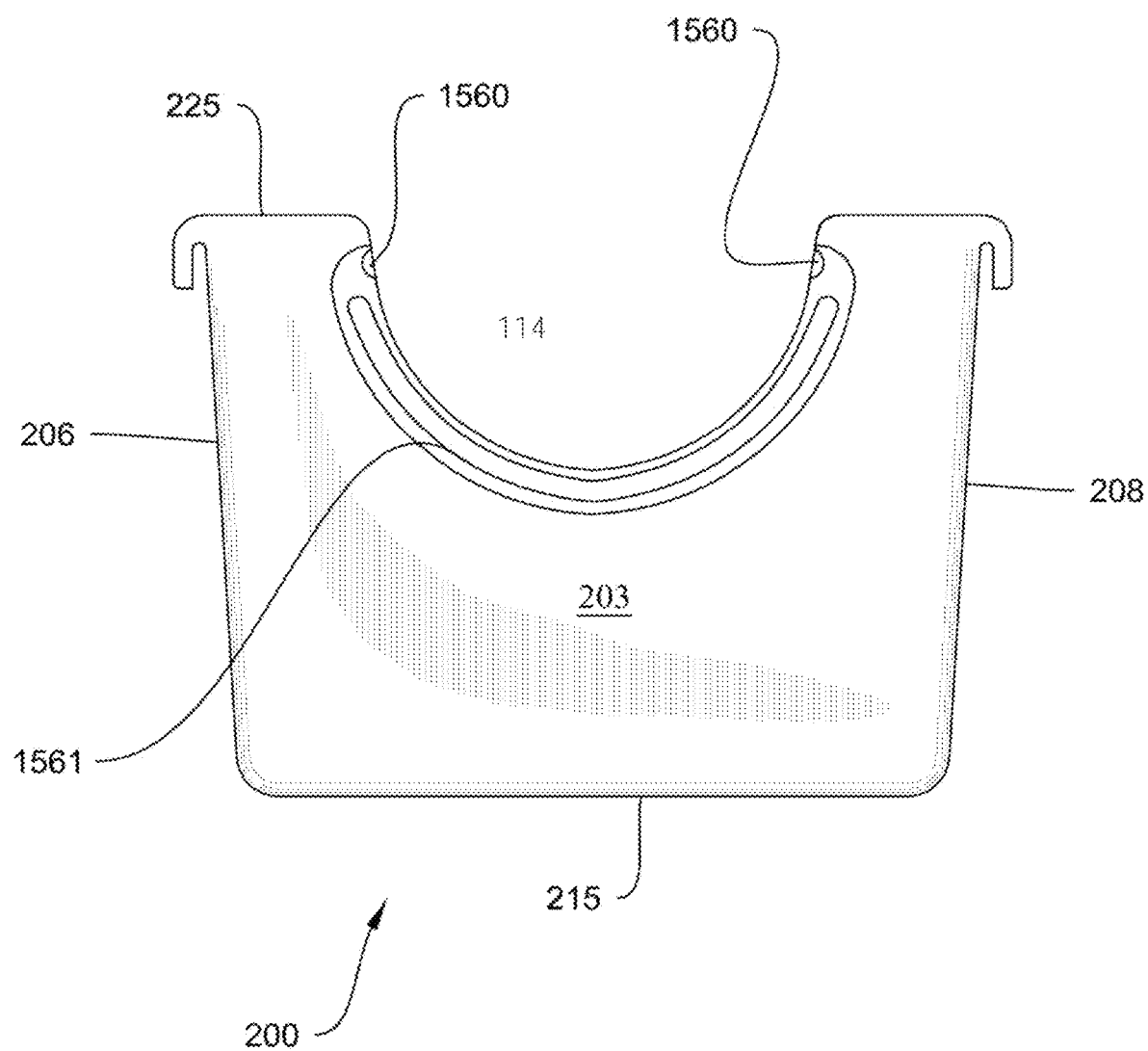
FIG. 15G may depict a similar view as of FIG. 15F, i.e., a cross-sectional view along sectional line 15F-15F; however, in FIG. 15G, the clamp may be removed to show a receiving channel.
Figure 15H:
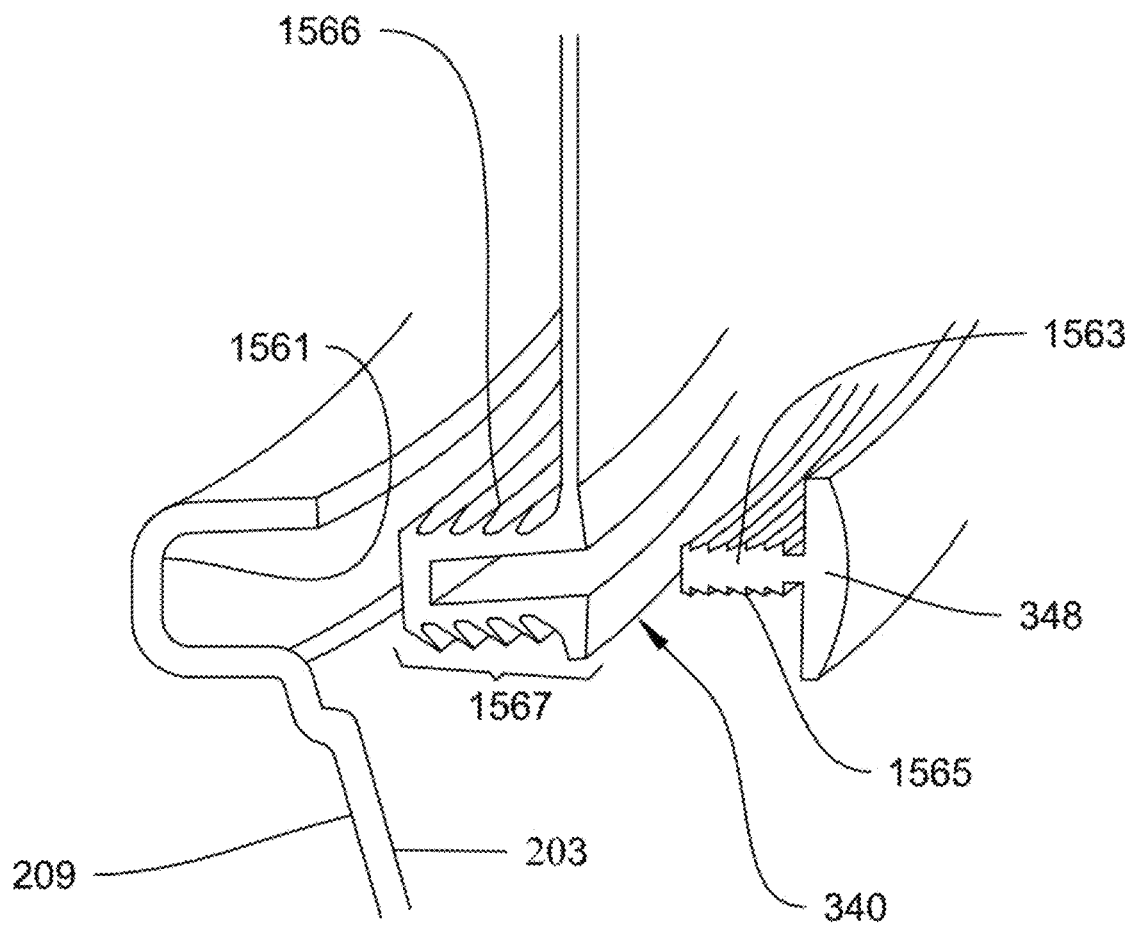
FIG. 15H may depict an alternative embodiment from that depicted in FIG. 15D from a cross-sectional perspective view; wherein in FIG. 15H the vessel neck gasket may comprise micro fins at a location where the vessel neck gasket may frictionally compression fit into the receiving channel.
Figure 15I:
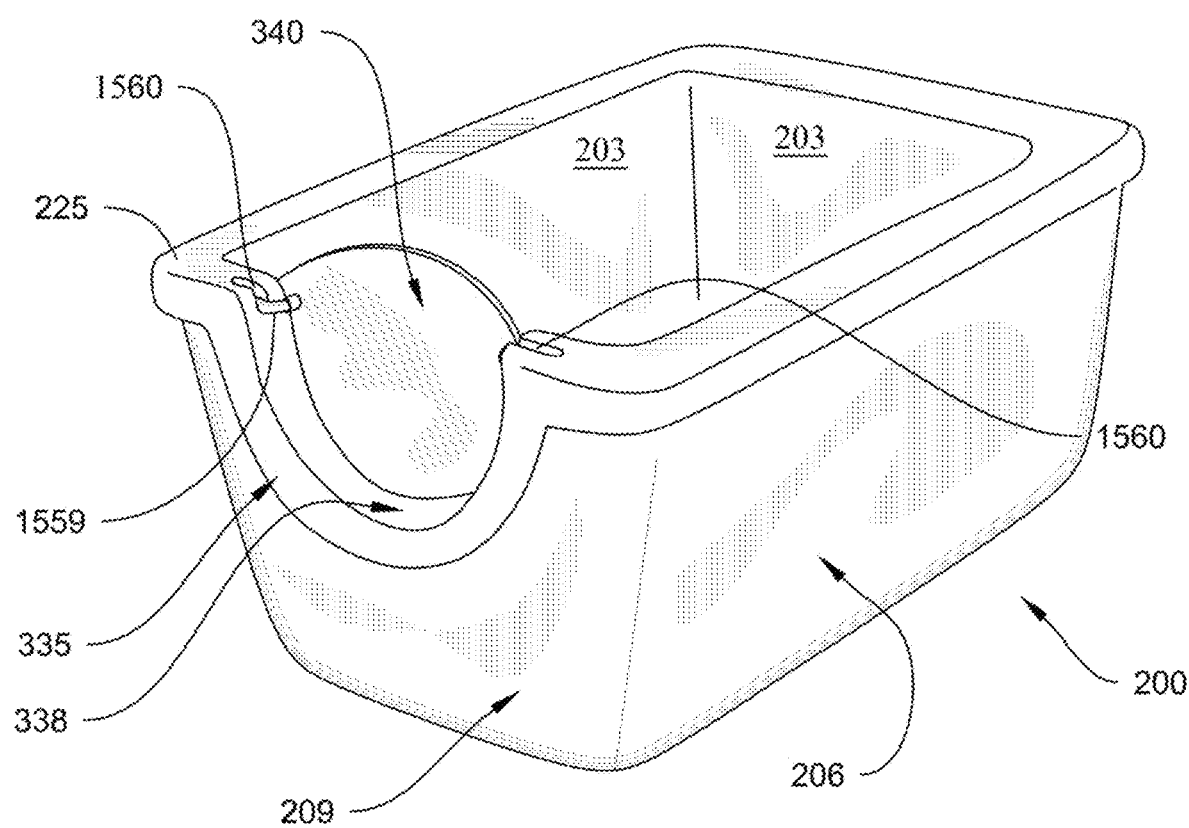
FIG. 15I may depict an alternative embodiment from that depicted in FIG. 15A; wherein in FIG. 15I, access to opposing pin receptacles (which may receive opposing pins of the clamp) may be from the rim of the vessel, as opposed from an exterior side of the vessel as in FIG. 15A.
Figure 15J:
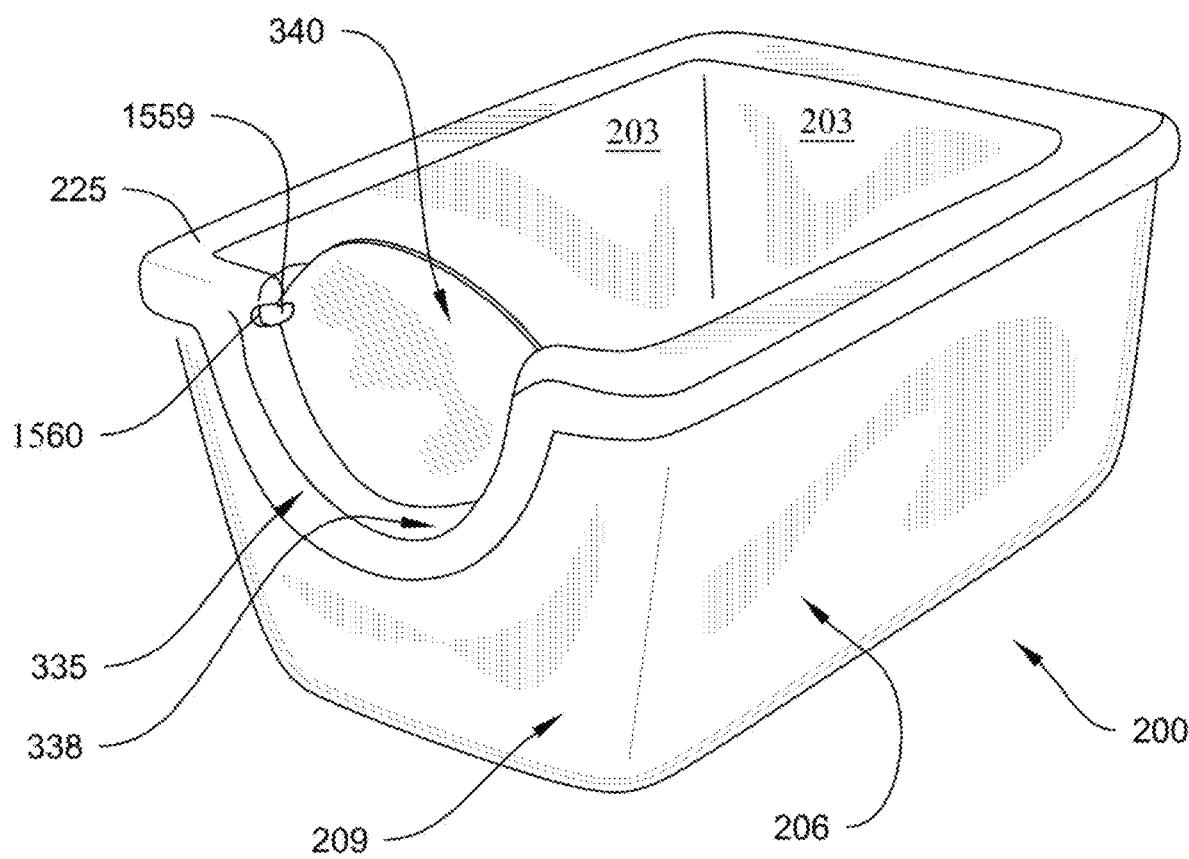
FIG. 15J may depict an alternative embodiment from that depicted in FIG. 15A; wherein in FIG. 15J, access to the opposing pin receptacles may be from a contour of the neck-gasket-accommodator, as opposed from the exterior side of the vessel as in FIG. 15A.
Figure 15K:
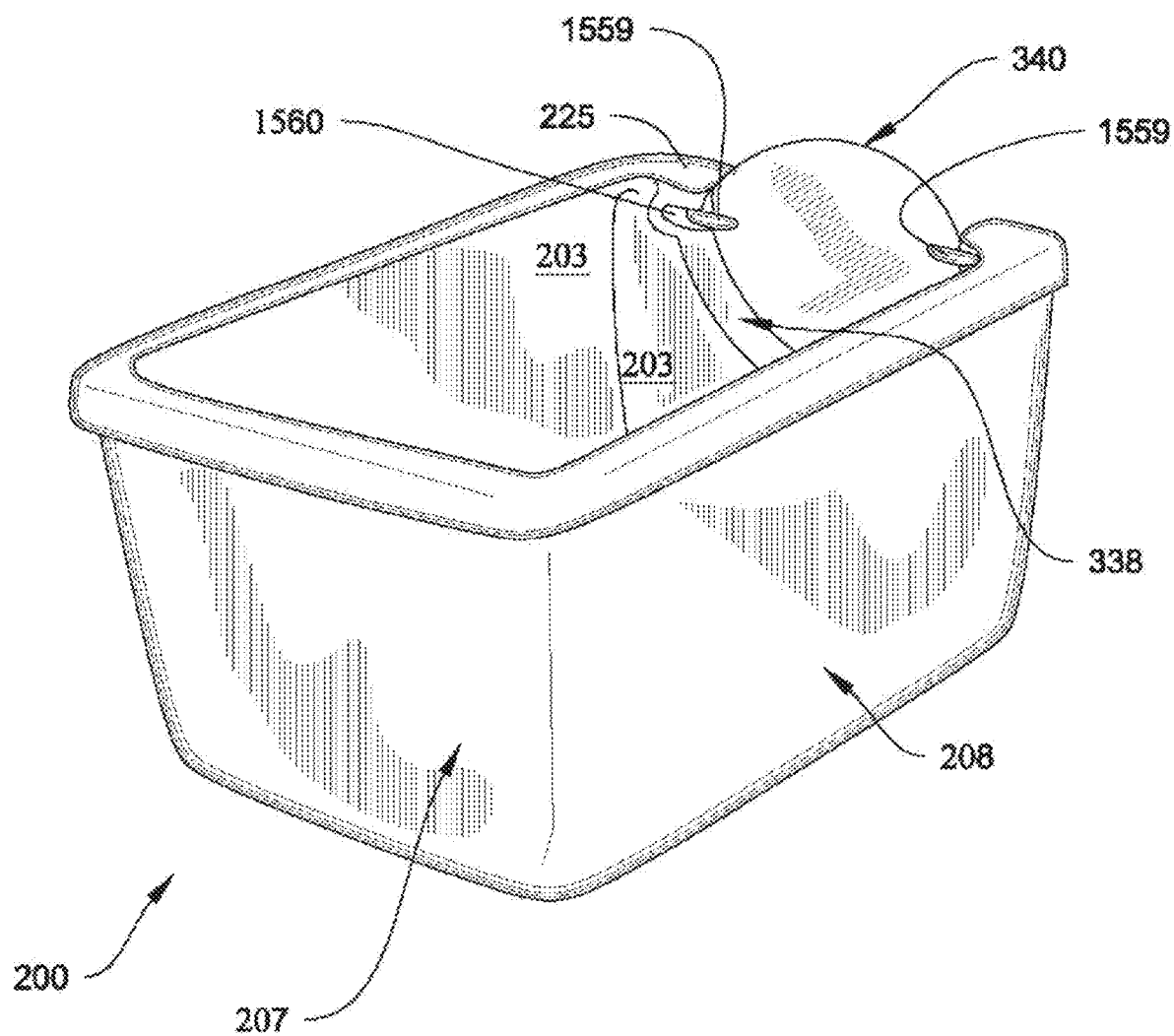
FIG. 15K may depict an alternative embodiment from that depicted in FIG. 15A; wherein in FIG. 15K, access to the opposing pin receptacles may be from an interior side of the vessel, as opposed from the exterior side of the vessel as in FIG. 15A.

A FIG. 15 series of figures may comprise FIG. 15A through FIG. 15K. The FIG. 15 series of figures may depict a hinge embodiment how vessel neck gasket 340 may rotationally translate with respect to the vessel (e.g., vessel 200). FIG. 15A may depict a face soaking device with an alternative embodiment vessel neck gasket 340, wherein clamp 348 may swivel (pivot), shown from a perspective view. (A breathing apparatus, a head rest subassembly, a heater subassembly, and a gas diffuser may be removed.) FIG. 15B may depict the face soaking device from FIG. 15A, but wherein the vessel neck gasket 340 and the clamp 348 may be exploded from the vessel. FIG. 15C may depict the face soaking device from FIG. 15A, but shown from a front view, with a sectional line 15D-15D through vessel neck gasket 340 and clamp 348. FIG. 15D may depict a partial cross-sectional side view along sectional line 15D-15D. FIG. 15E may depict the face soaking device from FIG. 15A, but shown from a side (right) view, with a sectional line 15F-15F through the vessel. FIG. 15F may depict a transverse-width cross-sectional view along sectional line 15F-15F. FIG. 15G may depict a similar view as of FIG. 15F, i.e., a cross-sectional view along sectional line 15F-15F; however, in FIG. 15G, clamp 348 may be removed to show a receiving channel 1561. FIG. 15H may depict an alternative embodiment from that depicted in FIG. 15D from a cross-sectional perspective view; wherein in FIG. 15H vessel neck gasket 340 may comprise micro fins 1566 at a location on vessel neck gasket 340 wherein portions of vessel neck gasket 340 may frictionally compression fit into receiving channel 1561. FIG. 15I may depict an alternative embodiment from that depicted in FIG. 15A; wherein in FIG. 15I access to opposing pin receptacles 1560 (which may receive opposing pins 1559 of clamp 348) may be from rim 225 of vessel 200, as opposed from an exterior side (e.g., exterior wall surface 202) of vessel 200 as in FIG. 15A. FIG. 15J may depict an alternative embodiment from that depicted in FIG. 15A; wherein in FIG. 15J access to the opposing pin receptacles 1560 may be from contour 338 of neck-gasket-accommodator 335, as opposed from the exterior side (e.g., exterior wall surface 202) of vessel 200 as in FIG. 15A. FIG. 15K may depict an alternative embodiment from that depicted in FIG. 15A; wherein in FIG. 15K access to the opposing pin receptacles 1560 may be from an interior side (e.g., interior wall surface 203) of vessel 200, as opposed from the exterior side (e.g., exterior wall surface 202) of vessel 200 as in FIG. 15A.

In some FIG. 15 series embodiments, clamp 348 may be attached to the vessel in a manner which permits rotational (i.e., pivot or hinge) movement at a place of attaching clamp 348 to the vessel, such as hinge motion. See e.g., FIG. 15B. In some embodiments, each terminal end 358 of this clamp 358 may comprise a pin 1559, i.e. clamp 348 may comprise two pins 1559. Each pin 1559 may point away from each other, i.e. each pin 1559 may extend from each terminal end 358, such that each pin 1559 may be disposed opposite of each other. Each pin 1559 may be captured by a pin receptacle 1560. Each pin receptacle 1560 may be located at a top of neck-gasket-accommodator 335, at each end of horizontal width 337. See e.g., FIG. 15B. At this top location, the pair of pin receptacles 1560 may be located in at least one of three regions of this top location: (1) extending into a wall thickness of at least one side wall 205 (depicted in FIG. 15B, FIG. 15I, FIG. J, and in FIG. 15K); (2) on exterior wall surface 202 (not depicted, but similar to FIG. 15A and FIG. 15B); or (3) on interior wall surface 203 (not depicted, but similar to FIG. 15K). When the pair of pin receptacles 1560 may be located at an exterior top location, clamp 348 may open towards the exterior of the vessel. When the pair of pin receptacles 1560 may be located at an interior top location, clamp 348 may open towards the interior of the vessel. When the pair of pin receptacles 1560 may be located a top location of within the wall thickness (e.g., as shown in FIG. 15B, FIG. 15I, FIG. J, and in FIG. 15K) of at least one side wall 205, clamp 348 may open towards the interior of vessel 200 or clamp 348 may open towards the exterior of vessel 200. (When clamp 348 may be configured to open and/or close in the interior of vessel 200, lateral exterior surface 357 of clamp 348 may be deemed "lateral interior surface 357*a*." See e.g., FIG. 15F.)

In some embodiments, pin receptacles 1560 may be accessible via openings from (1) contour 338 (see e.g., FIG. 15J); (2) from exterior wall surface 202 (see e.g., FIG. 15F); (3) from interior wall surface 203 (see e.g., FIG. 15K); and/or (4) from rim 225 (see e.g., FIG. 15I).

In some embodiments, such a pivotable clamp 348 may then pivot downwards (from pins 1559 and pin receptacles 1560) to form the primary water tight seal by pressing vessel neck gasket 340 against interior wall surface 203 of vessel 200, proximate to neck-gasket-accommodator 335. See e.g., FIG. 15D. In some embodiments, parallel and proximate to neck-gasket-accommodator 335 may be a channel, as in receiving channel 1561. See e.g., FIG. 15D, FIG. 15G, and FIG. 15H. Receiving channel 1561 may be configured to receive a portion of vessel neck gasket 340, to create both a frictional fit and the primary water tight seal. In some embodiments, vessel neck gasket 340 may comprise a molded region 1567 (see e.g., FIG. 15H) to be complimentary with fitting into receiving channel 1561. In some embodiments, such a molded region 1567 of vessel neck gasket 340 may comprise at least one micro fin 1566 protrusion to enhance friction and the primary water tight seal. See e.g., FIG. 15H. In some exemplary embodiments, receiving channel 1561 may be located on interior wall surface 203 side versus exterior wall surface 202, which may facilitate proper liquid 101 drainage towards internal volume 220. See e.g., FIG. 15D, FIG. 15G, and FIG. 15H. In some embodiments, receiving channel 1561 may be located on exterior wall surface 202 side (this embodiment not depicted).

In some embodiments, receiving channel 1561 may be configured to receive the portion of vessel neck gasket 340 (which may be molded, e.g., molded region 1567) and a portion of clamp 348, to create both a frictional fit and the primary water tight seal. See e.g., FIG. 15D and FIG. 15H. The portion of clamp 348 may be tooth 1563. In some embodiments, tooth 1563 may comprise at least one micro fin protrusion 1565 to enhance friction and the primary water tight seal. See e.g., FIG. 15D and FIG. 15H.

A FIG. 31 series of figures may comprise FIG. 31A through FIG. 31D. These FIG. 31 series of figures may focus on depicting another embodiment for vessel neck gasket 340, clamp 348 and neck-gasket-accommodator 335; wherein clamp 340 that may be combined with vessel neck gasket 340 may be press fit into contour 338 of neck-gasket-accommodator 335, forming a friction and/or compression fit, that may form the primary water tight seal. FIG. 31A may depict such a push down press fit embodiment for clamp 348 combined with vessel neck gasket 340 to be received by neck-gasket-accommodator 335 of vessel 200, shown in a perspective view with clamp 348 and vessel neck gasket 340 exploded from the neck-gasket-accommodator 335. FIG. 31B may depict the embodiment of FIG. 31A, but with clamp 348 and the vessel neck gasket 340 removably attached to vessel 200 and received at neck-gasket-accommodator 335, shown from a perspective view.

FIG. 31C may depict the push down clamp 348 with the vessel neck gasket 340 embodiment of FIG. 31A, but shown from a longitudinal cross-section with respect to vessel 200, showing how a hook lock 3101 of clamp 348 may be removably latch onto a tab 3103 of vessel 200. FIG. 31D may depict the same view and embodiment of FIG. 31C, except hook lock 3101 may be rotated such that hook lock 3101 may not be removably engaging tab 3103.

In some embodiments, clamp 348 may be a subassembly with vessel neck gasket 340. See e.g., FIG. 31A. In this embodiment, this subassembly of clamp 348 and vessel neck gasket 340 may be press fit into contour 338 of neck-gasket-accommodator 335. Mating edge 343 may run around (or along) bottom and/or side edges of clamp 348 and with a remainder of gasket 340 being disposed in an inside diameter arc of clamp 348. See e.g., FIG. 31A and FIG. 31B. Clamp 348 may be rigid to semi-rigid. Vessel neck gasket 340 and mating edge 343 may be elastomeric materials, such as, but not limited to neoprene. Each clamp terminal end 358 (which may be opposing as depicted in FIG. 31A) may comprise, and/or terminate in a freely rotating hook lock 3101, which may be received into a respective receiving groove 3102, such that clamp 348 with vessel neck gasket 340 may be pressed down into contour 338, such that mating edge 343 is forming the primary water tight seal with contour 338, and then hook locks 3101 may be rotated into place within receiving groove 3102 to lock clamp 348 and vessel neck gasket 340 into place. Each hook lock 3101 may rotate freely with respect to the clamp terminal end 358 that the hook lock 3101 may be attached to. See e.g., FIG. 31A and FIG. 31B. Note, in FIG. 31B, one of the hook locks 3101, a right hook lock 3101, may be shown in a configuration wherein this right hook lock 3101 is not removably engaging tab 3103 that may be located in a right receiving groove 3102. Whereas, a left hook lock 3101 in FIG. 31B may be shown such this left hook lock 3101 may be rotated into a configuration wherein this left hook lock 3101 may be removably engaging tab 3103 of a left receiving groove 3102. Note, tabs 3103 may not be shown in FIG. 31B. And the left receiving groove 3102 may not be explicitly called out in FIG. 31B as the left hook lock 3101 may be substantially occupying the left receiving groove 3102. Each receiving groove 3102 may comprise a tab 3103 (e.g., right and left) to removably engage a latch structure 3104 of each hook lock 3101. The pair of receiving grooves 3102 may bound horizontal width 337. In some embodiments, to either upper end of neck-gasket-accommodator 335 may be receiving groove 3102. In some embodiments, each receiving groove 3102 may bound an upper end of contour 338. See e.g., FIG. 31A for receiving groove 3102 and see FIG. 31C and FIG. 31D for tab 3103. In some embodiments, each hook lock 3101 may comprise latch structure 3104. In some embodiments, each latch structure 3104 may be disposed from a location on hook lock 3101 that permits pivoting with a respective clamp terminal end 358. Each latch structure 3104 and each tab 3103 may have complimentary geometry for forming removable frictional attachments with each other. See e.g., FIG. 31C and FIG. 31D.

Note, in some embodiments, the push down frictional and compression fit of clamp 348 combined with vessel neck gasket 340 depicted in the FIG. 31 series of figures may not need hook lock 3101 in order for clamp 348 combined with vessel neck gasket 340 to frictionally attach to contour 338 to form the primary water tight seal. The sizing of contour 338 and the sizing of mating edge 343, particularly with respect to each other, as well as the materials of constructions may be sufficient to form the primary water tight seal. That is, in some embodiments, addition of hook locks 3101 may be redundant and/or provide for back up in the removable attachment of clamp 348 combined with vessel neck gasket 340 to vessel 200.

Figure 4A:
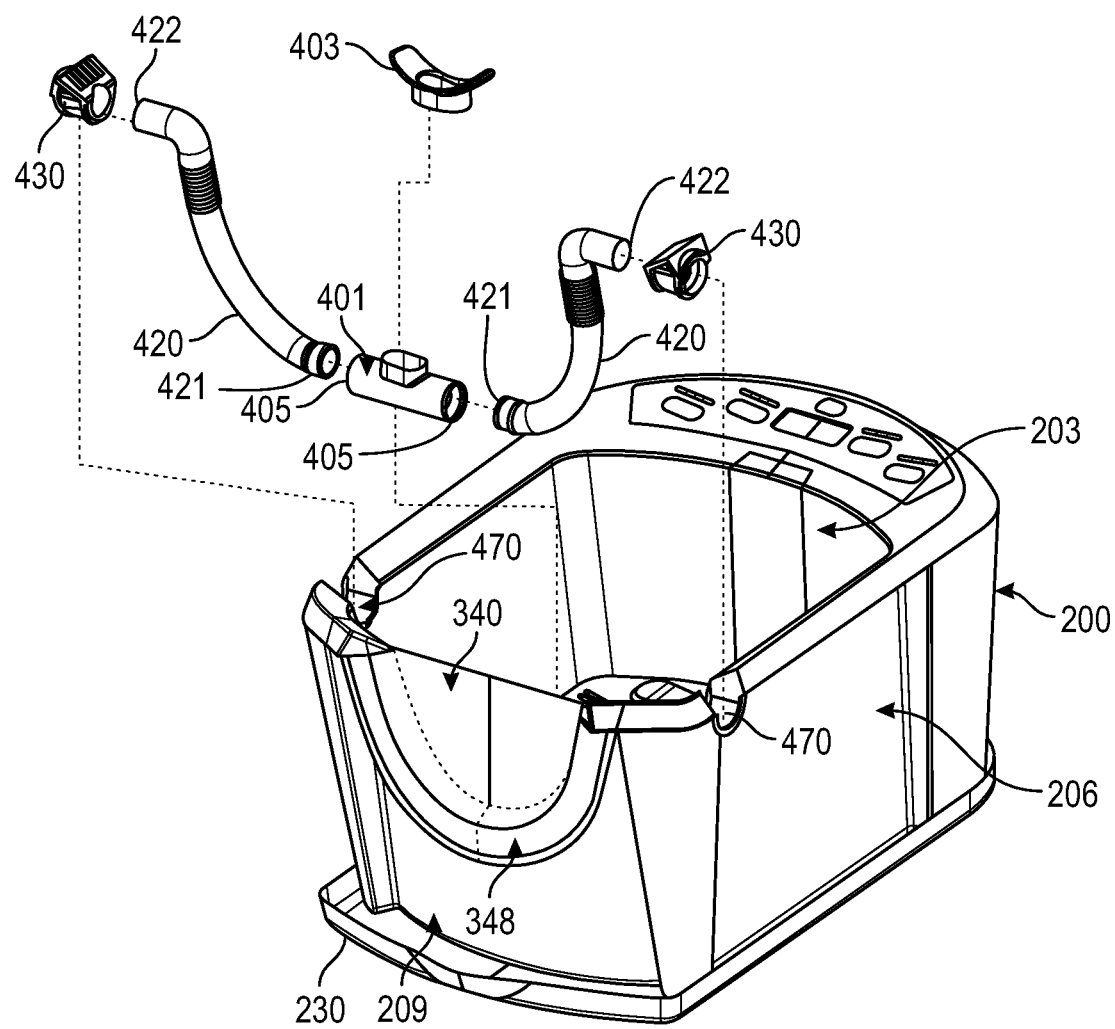
FIG. 4A may depict a top perspective exploded view of a breathing apparatus of the face soaking device of FIG. 2A, wherein the breathing apparatus may be exploded from the vessel.
Figure 4B:
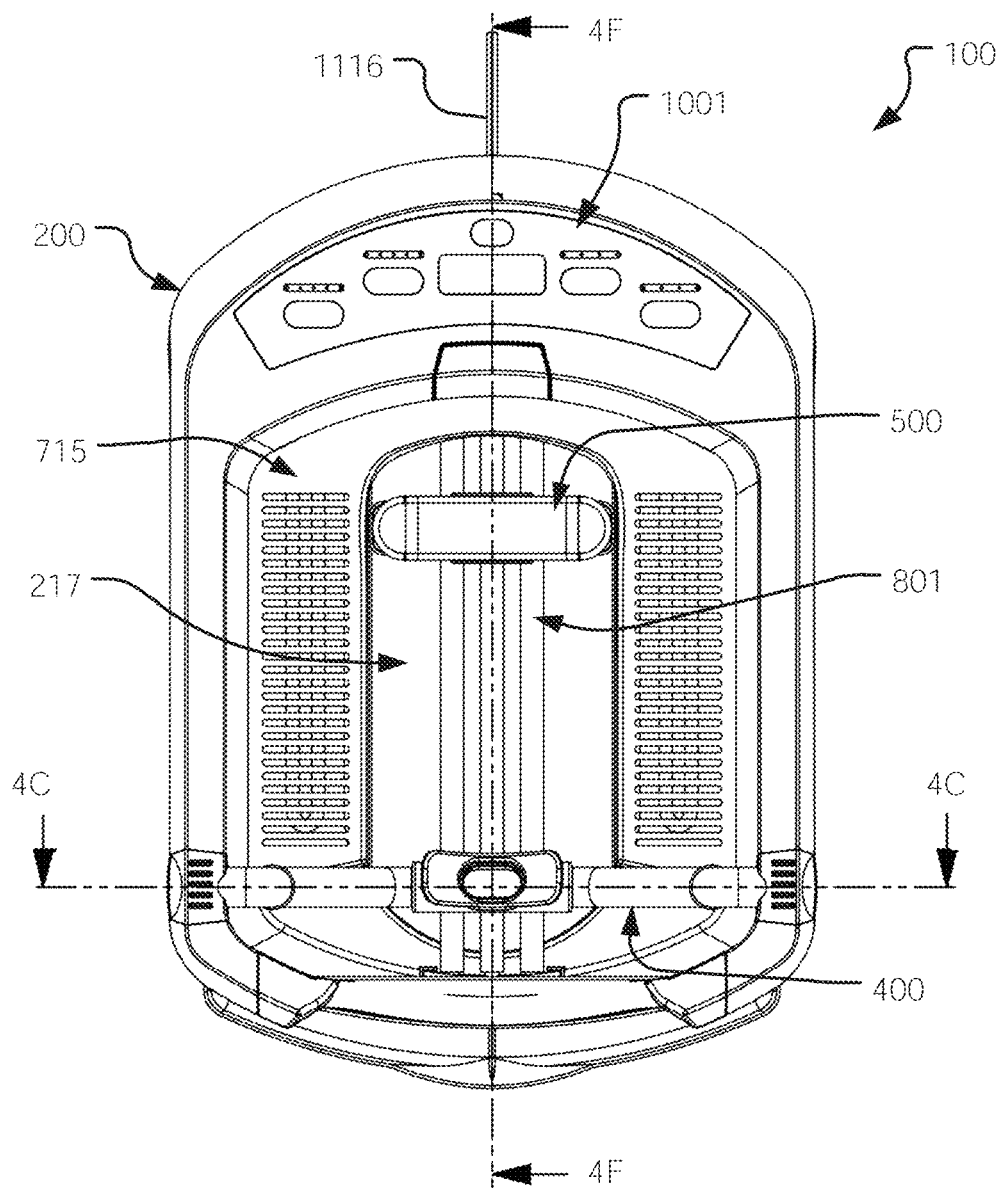
FIG. 4B may depict a top view of the face soaking device of FIG. 2A, wherein FIG. 4B may further depict two sectional lines, sectional line 4C-4C and sectional line 4F-4F; wherein sectional line 4C-4C may be a transverse-width sectional line through the breathing apparatus, and sectional line 4F-4F may be a longitudinal sectional line through the breathing apparatus.
Figure 4C:
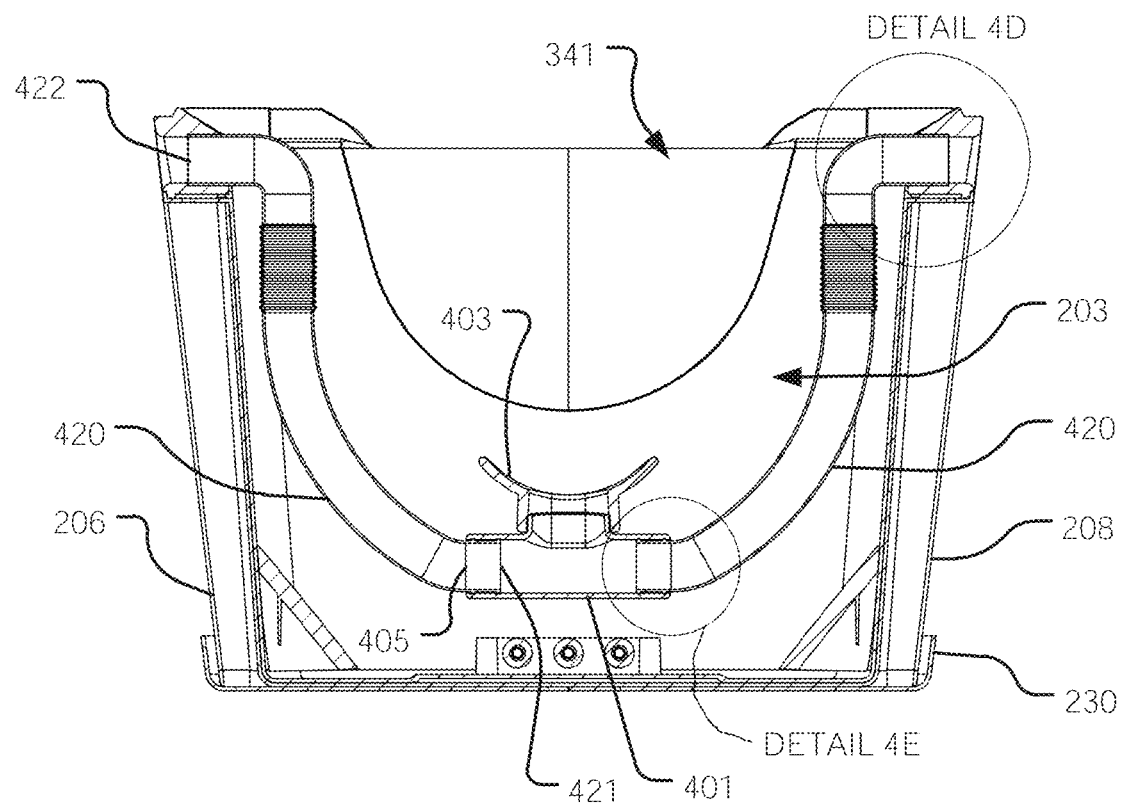
FIG. 4C may depict a transverse-width cross-sectional view along sectional line 4C-4C; wherein FIG. 4C may depict two regions of detail, Detail 4D and Detail 4E; wherein Detail 4D may depict how a second terminal end of at least one hose or of at least one tubing may removably engage some structure proximate to the rim of the vessel; wherein Detail 4E may depict how a first terminal end of the at least one hose or of the at least one tubing may engage a mouth piece.
Figure 4D:
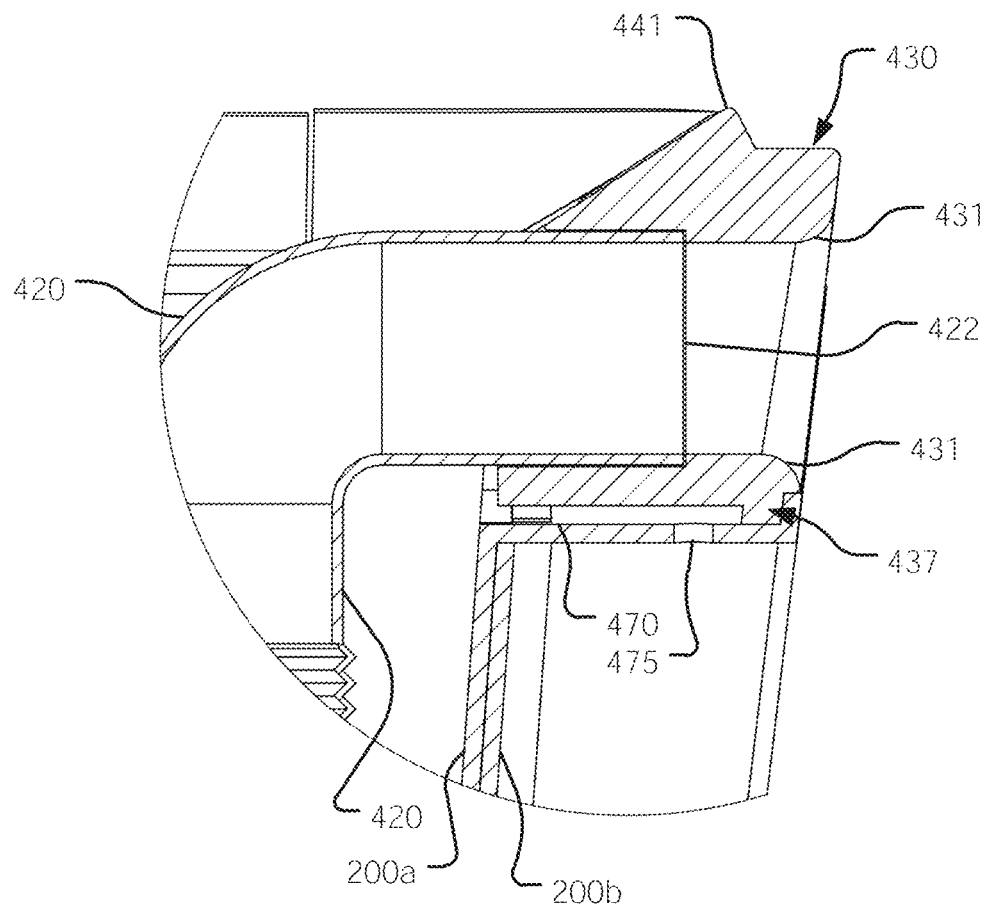
FIG. 4D may depict a close-up of Detail 4D which may depict how the second terminal end of the at least one hose or of the at least one tubing may removably engage the some structure (e.g., at least one vessel-tube-hose-connector) proximate to the rim of the vessel.
Figure 4E:
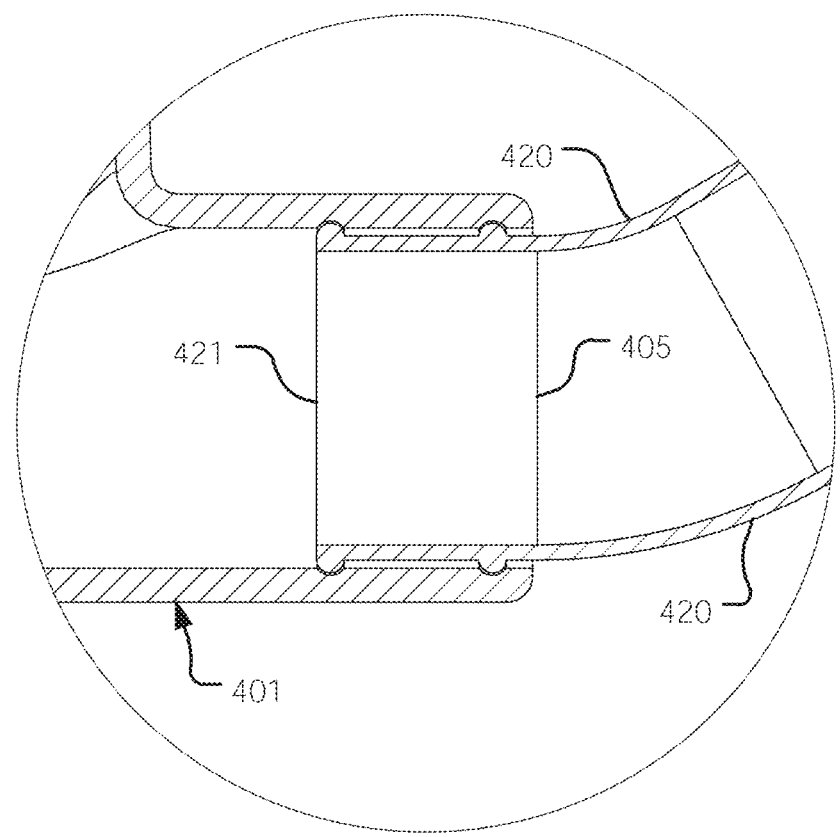
FIG. 4E may depict a close-up of Detail 4E which may depict how the first terminal end of the at least one hose or of the at least one tubing may engage the mouth piece.
Figure 4F:
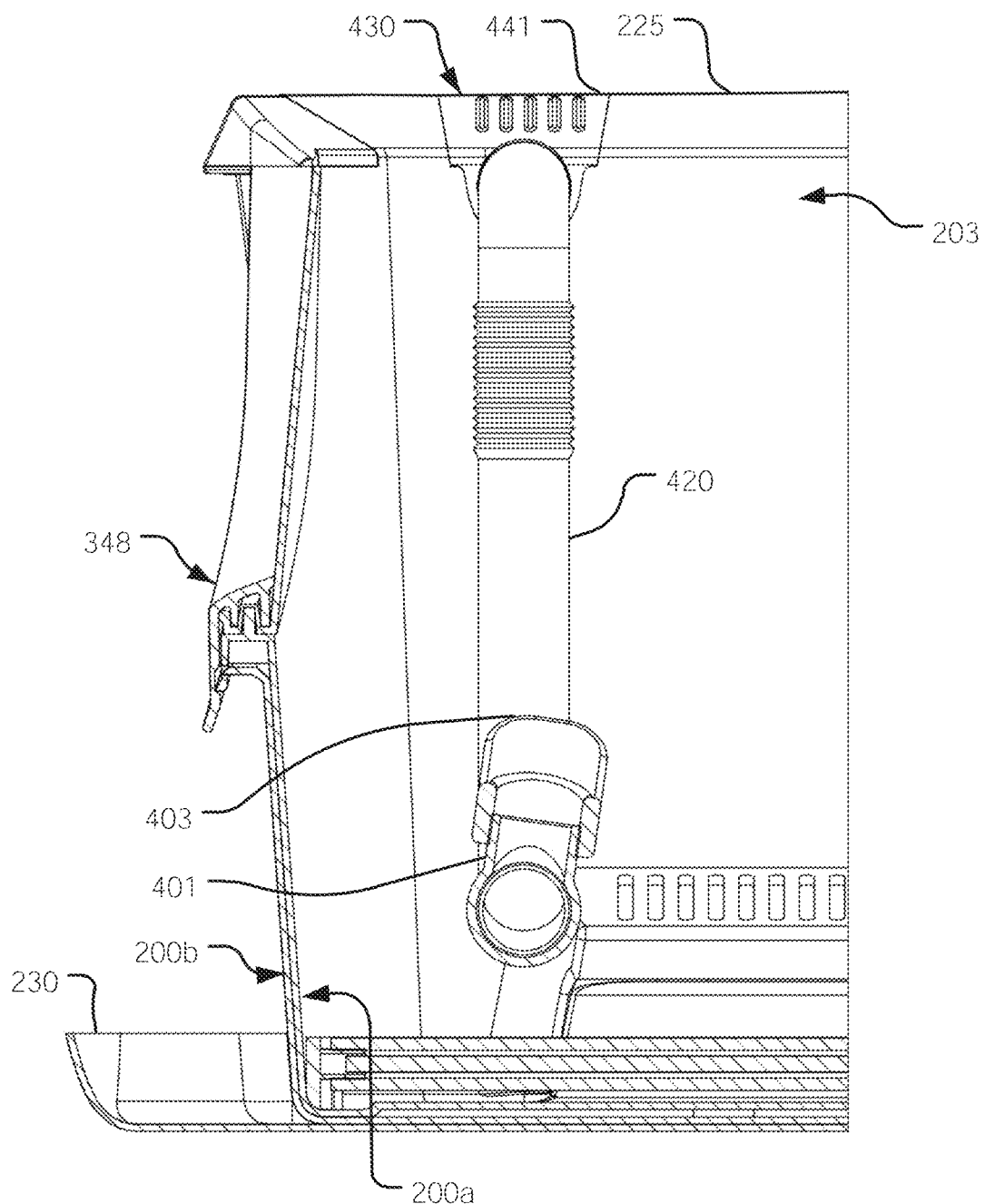
FIG. 4F may depict a partial longitudinal cross-sectional view along sectional line 4F-4F through the breathing apparatus.
Figure 4G:
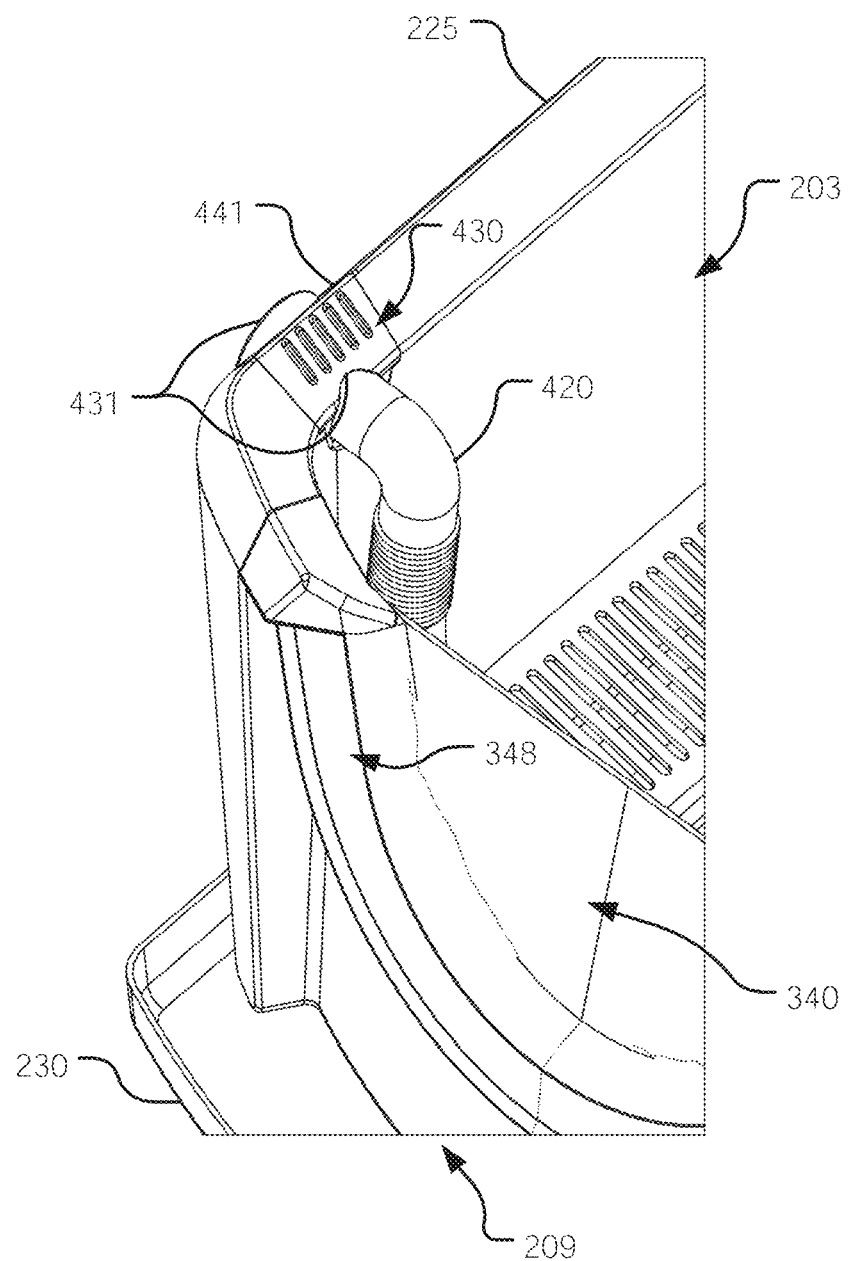
FIG. 4G may depict a partial top perspective view, while showing some interior of the vessel, of how one of the second terminal ends of the at least one hose or of the at least one tubing may removably engage the some structure proximate to the rim of the vessel.
Figure 4H:
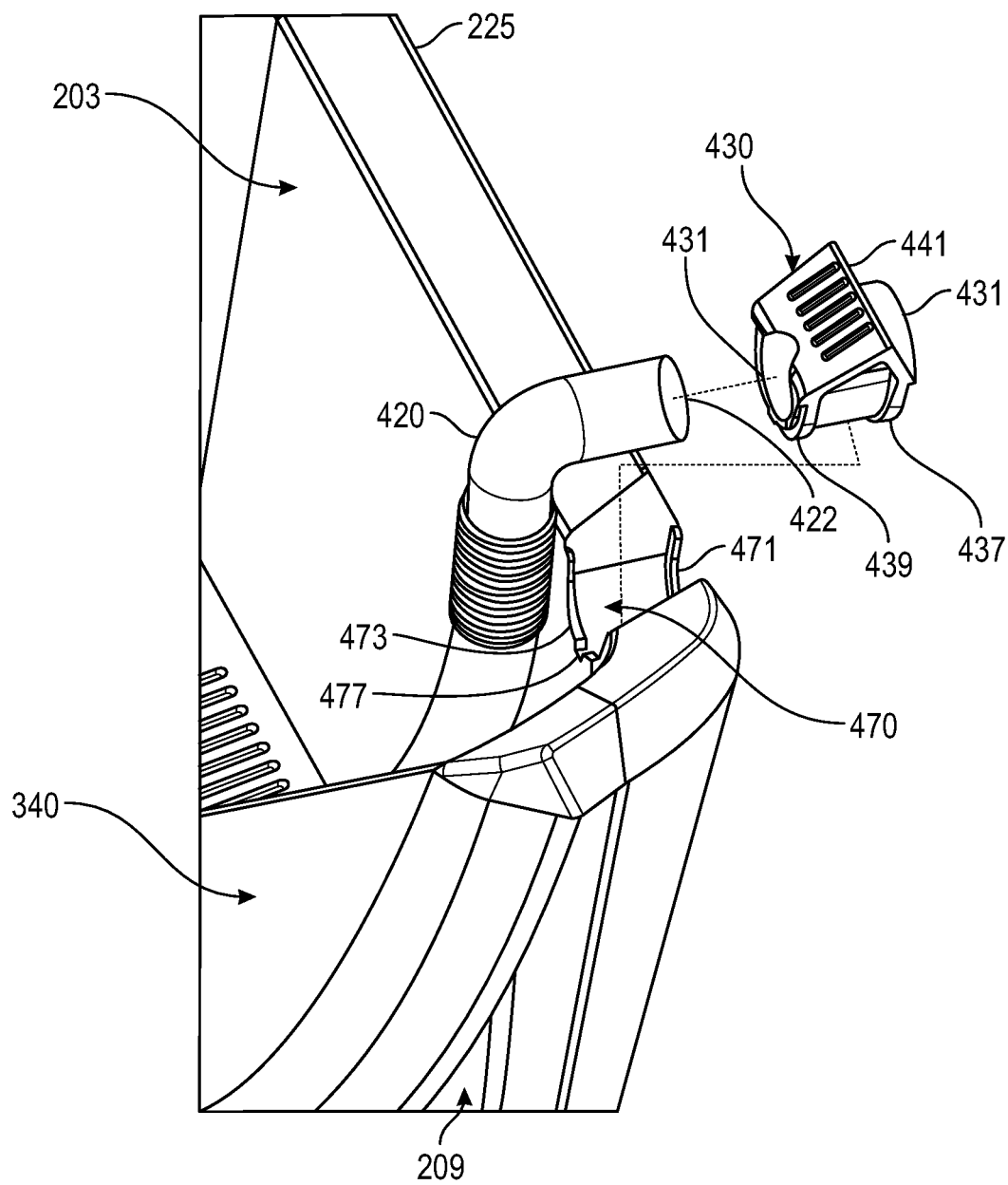
FIG. 4H may depict a partial top perspective exploded view, while showing some interior of the vessel, of how one of the second terminal ends of the at least one hose or of the at least one tubing may removably engage the some structure (e.g., the at least one vessel-tube-hose-connector) proximate to the rim of the vessel.
Figure 41:
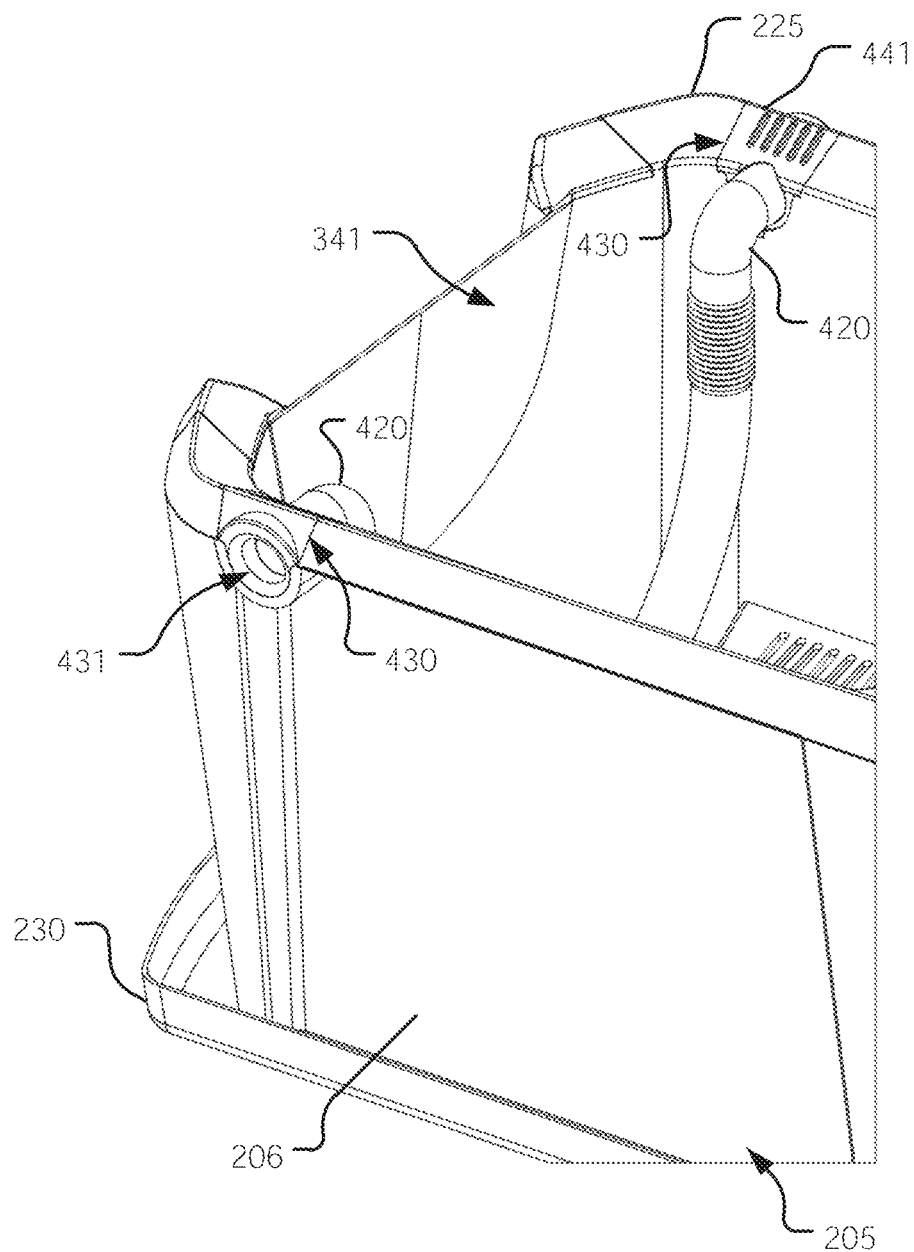
Figure 4J:
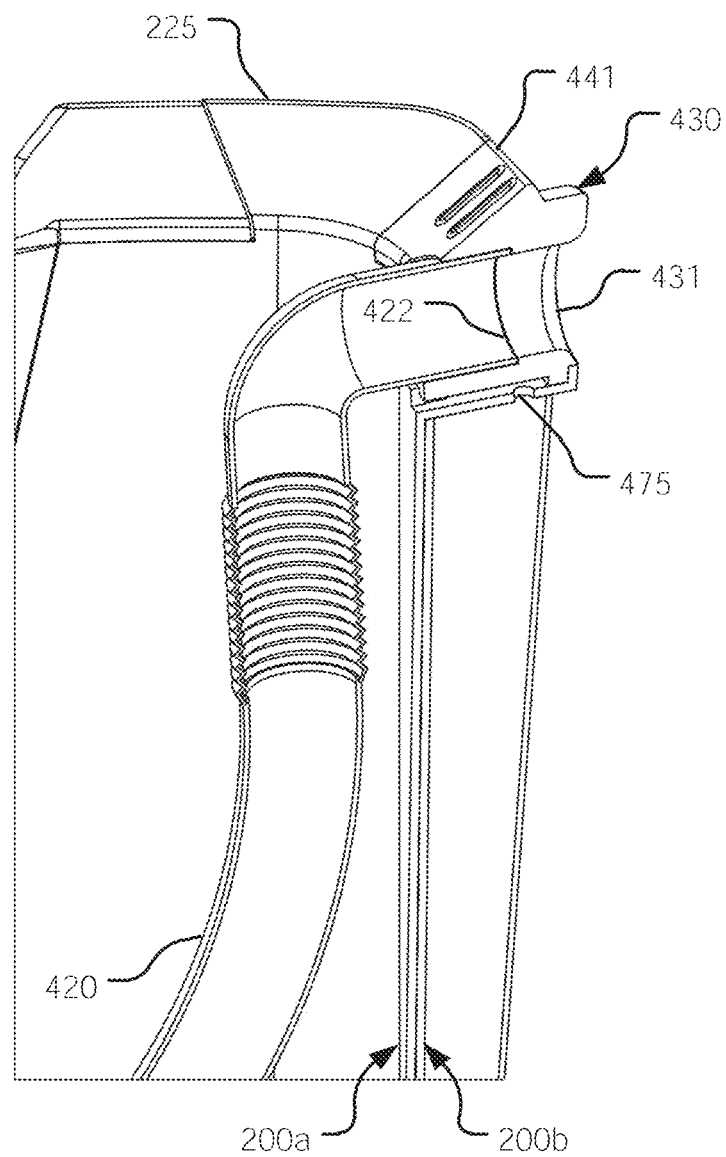
FIG. 4J may depict a partial top perspective cross-sectional view, while showing some interior of the vessel, of how one of the second terminal ends of the at least one hose or of the at least one tubing may removably engage the some structure proximate to the rim of the vessel.
Figure 4K:
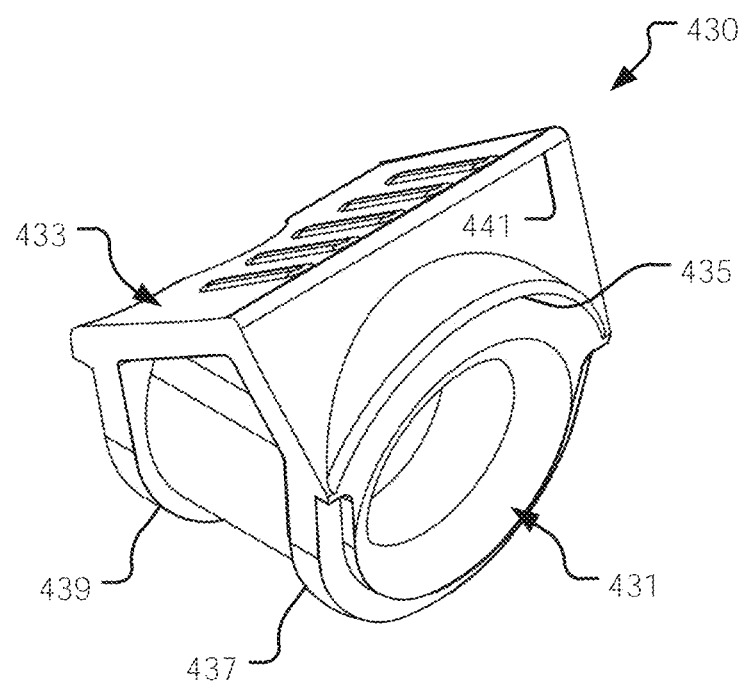
FIG. 4K may depict a top perspective view of a vessel-tube-hose-connector.
Figure 4L:
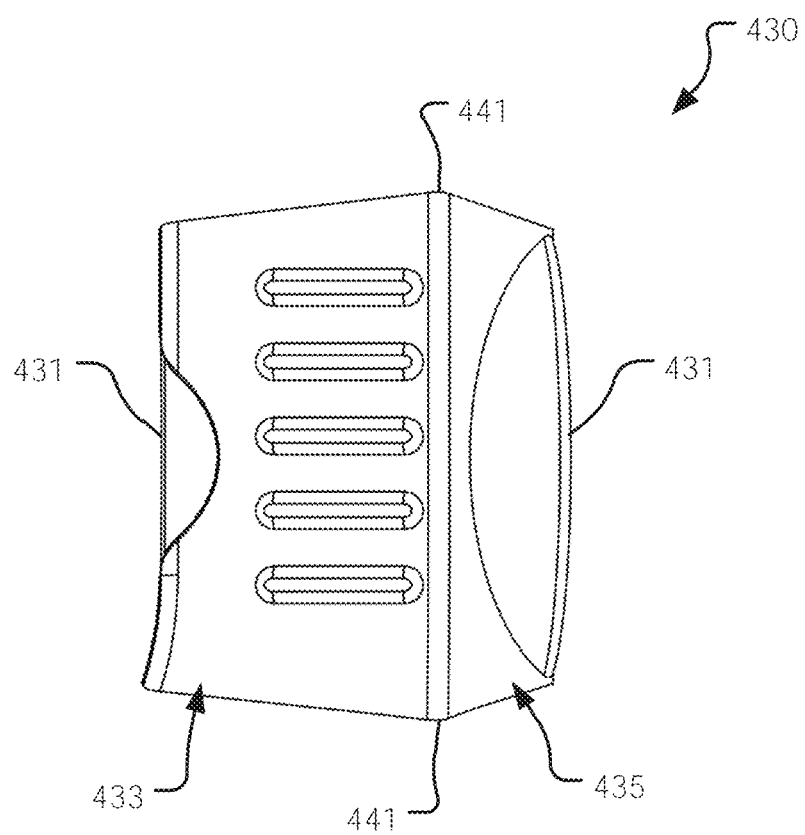
FIG. 4L may depict the vessel-tube-hose-connector of FIG. 4K, shown from a top view.
Figure 4M:
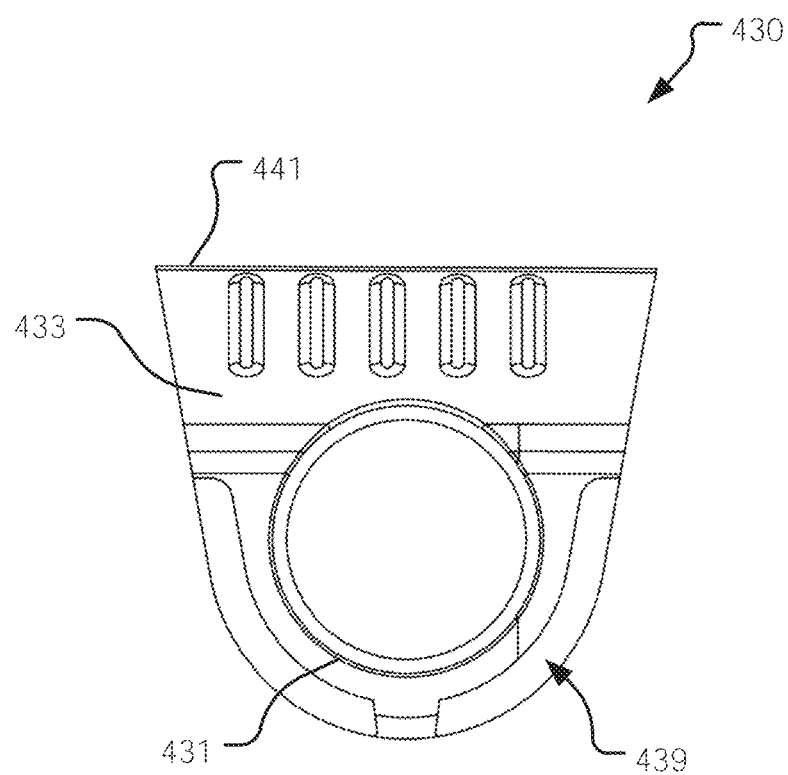
FIG. 4M may depict the vessel-tube-hose-connector of FIG. 4K, shown from an interior side view.
Figure 4N:
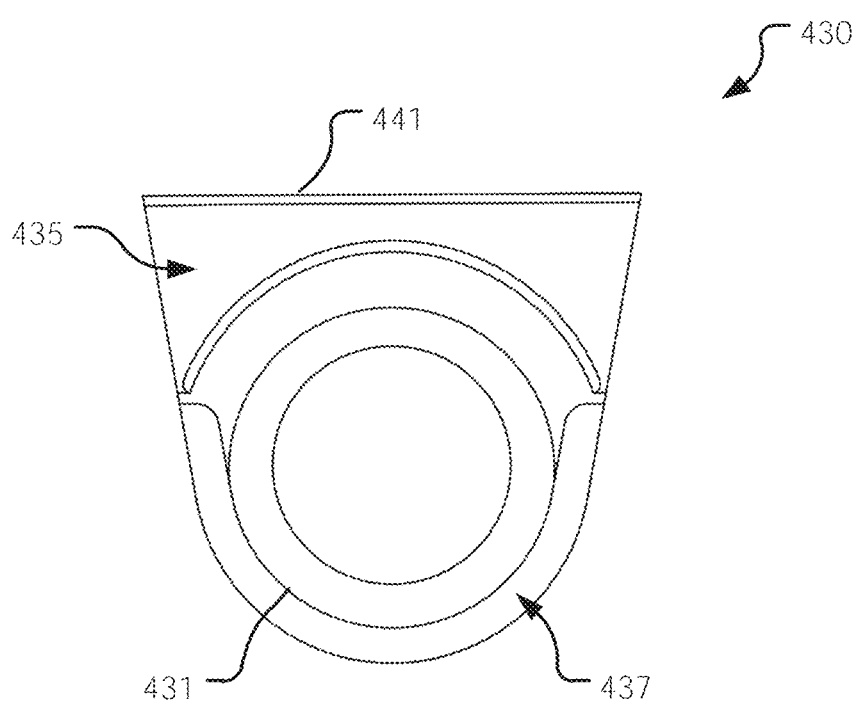
FIG. 4N may depict the vessel-tube-hose-connector of FIG. 4K, shown from an exterior side view.
Figure 4O:
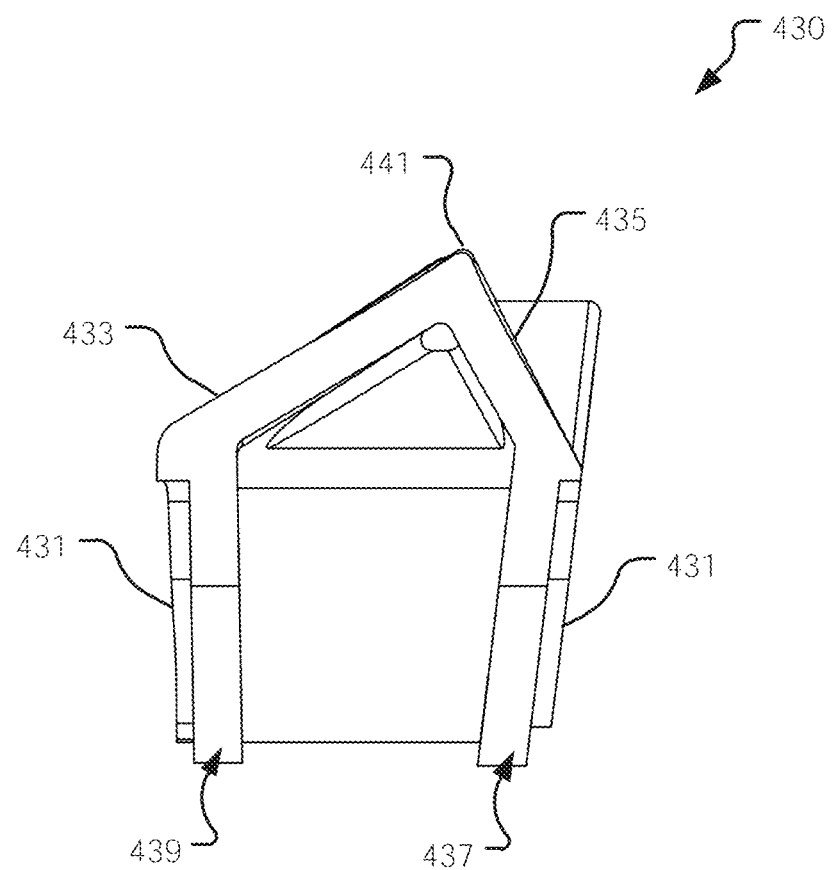
FIG. 4O may depict the vessel-tube-hose-connector of FIG. 4K, shown from a front view.
Figure 4P:
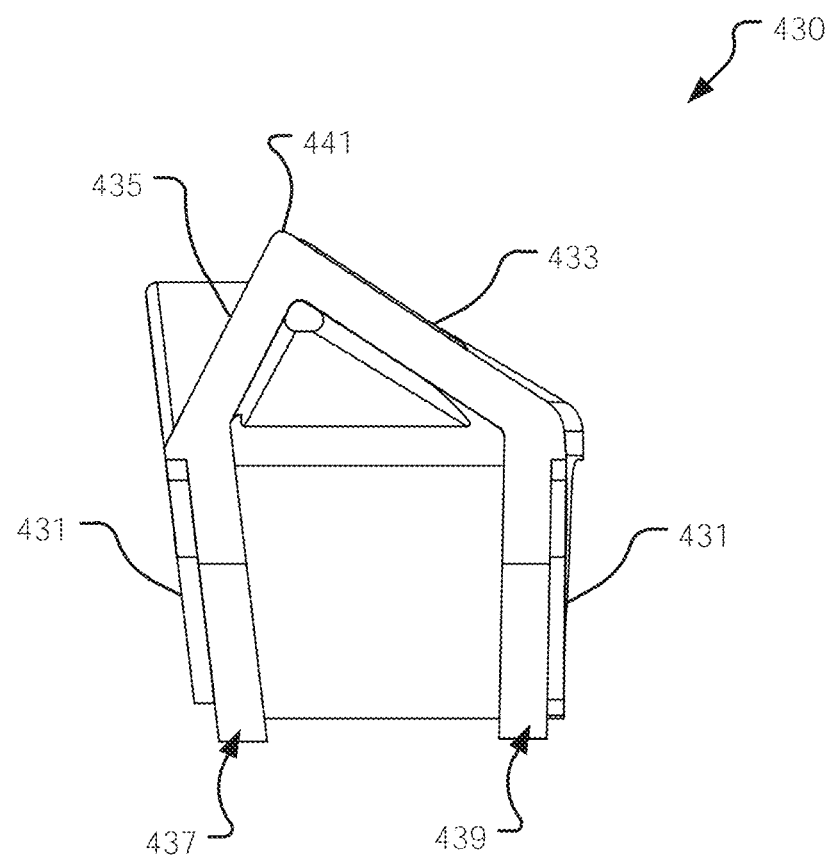
FIG. 4P may depict the vessel-tube-hose-connector of FIG. 4K, shown from a back view.
Figure 4Q:
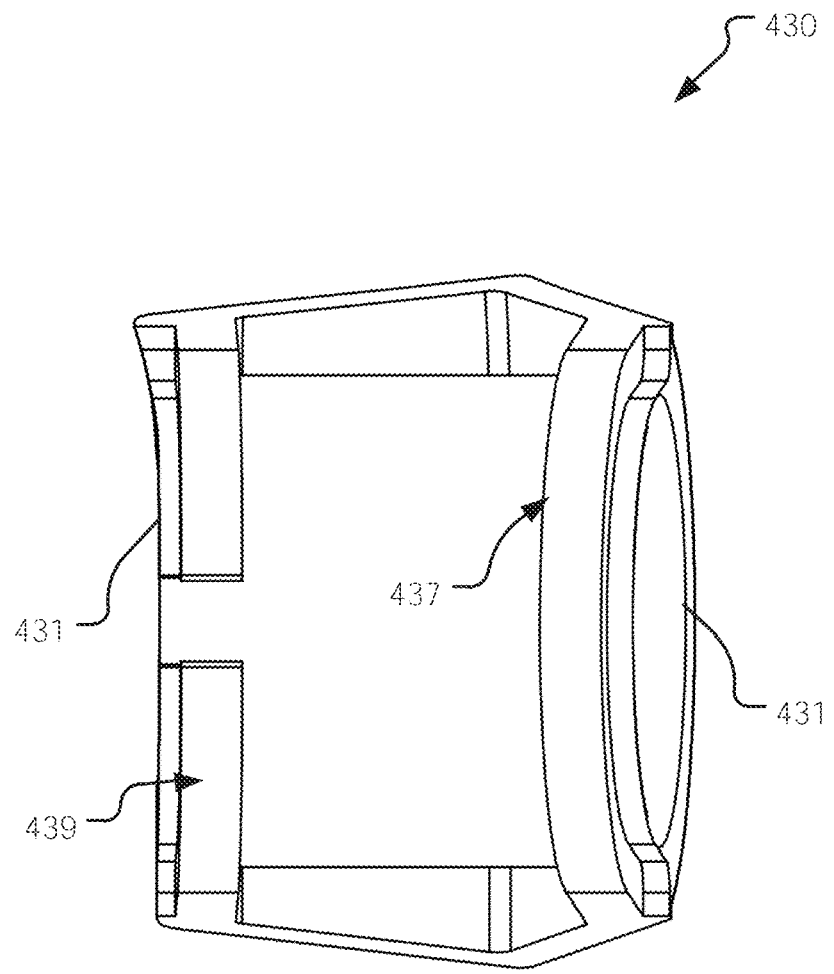
FIG. 4Q may depict the vessel-tube-hose-connector of FIG. 4K, shown from a bottom view.

A FIG. 4 series of figures may comprise FIG. 4A through FIG. 4Q. These FIG. 4 series of figures may focus on depicting an exemplary breathing apparatus 400 and its component parts and structures. FIG. 4A may depict a top perspective exploded view of breathing apparatus 400 of face soaking device 100, wherein breathing apparatus 400 may be exploded from the vessel 200. FIG. 4B may depict a top view of face soaking device 100, wherein FIG. 4B may further depict two sectional lines, sectional line 4C-4C and sectional line 4F-4F; wherein sectional line 4C-4C may be a transverse-width sectional line through breathing apparatus 400, and sectional line 4F-4F may be a longitudinal sectional line through breathing apparatus 400.

FIG. 4C may depict a transverse-width cross-sectional view along sectional line 4C-4C; wherein FIG. 4C may depict two regions of detail, Detail 4D and Detail 4E; wherein Detail 4D may depict how second terminal end 422 of at least one hose 420 or of at least one tubing 420 may removably engage some structure proximate to rim 225 of vessel 200; wherein Detail 4E may depict how a first terminal end 421 of at least one hose 420 or of at least one tubing 420 may engage mouth piece 401.

FIG. 4D may depict a close-up of Detail 4D which may depict how second terminal end 422 of at least one hose 420 or of at least one tubing 420 may removably engage the some structure proximate to rim 225 of vessel 200. FIG. 4E may depict a close-up of Detail 4E which may depict how the first terminal end 421 of at least one hose 420 or of at least one tubing 421 may engage mouth piece 401. FIG. 4F may depict a partial longitudinal cross-sectional view along sectional line 4F-4F through breathing apparatus 400.

FIG. 4G may depict a partial top perspective view, while showing some interior of vessel 200, of how one of the second terminal ends 422 of at least one hose 420 or of at least one tubing 420 may removably engage the some structure proximate to rim 225 of vessel 200. FIG. 4H may depict a partial top perspective exploded view, while showing some interior of vessel 200, of how one of second terminal ends 422 of at least one hose 420 or of at least one tubing 420 may removably engage the some structure proximate to rim 225 of vessel 200. FIG. 4I may depict a partial top perspective view, while showing some exterior of vessel 200, of how one of second terminal ends 422 of at least one hose 420 or of at least one tubing 420 may removably engage the some structure proximate to rim 225 of vessel 200. FIG. 4J may depict a partial top perspective cross-sectional view, while showing some interior of vessel 200, of how one of second terminal ends 422 of at least one hose 420 or of at least one tubing 420 may removably engage the some structure proximate to rim 225 of vessel 200.

FIG. 4K through FIG. 4Q may various view of a vessel-tube-hose-connector 430. The some structure proximate to rim 225 of vessel 200 noted above, may be vessel-tube-hose-connector 430 in some embodiments. FIG. 4K may depict a top perspective view of essel-tube-hose-connector 430. FIG. 4L may depict vessel-tube-hose-connector 430, shown from a top view. FIG. 4M may depict vessel-tube-hose-connector 430, shown from an interior side view. FIG. 4N may depict vessel-tube-hose-connector 430, shown from an exterior side view. FIG. 4O may depict vessel-tube-hose-connector 430, shown from a front view. FIG. 4P may depict vessel-tube-hose-connector 430, shown from a back view. FIG. 4Q may depict vessel-tube-hose-connector 430, shown from a bottom view.

In some embodiments, breathing apparatus 400 may be physically removably contacting portions of vessel 200. In the FIG. 4 series of figures, in some embodiments, breathing apparatus 400 may comprise mouth piece 401, at least one vessel-tube-hose-connector 430, and at least one hose 420 or at least one tubing 420. At least one hose 420 or at least one tubing 420 may connect mouth piece 401 to at least one vessel-tube-hose-connector 430. Mouth piece 401 may be configured to be held by the mouth of user 9000. In some embodiments, at least one vessel-tube-hose-connector 430 may provide a physical link between breathing apparatus 400 and vessel 200 and/or a head rest subassembly. That in, in some embodiments, at least one vessel-tube-hose-connector 430 may be a component that may removably couple to structure of a given vessel (e.g., vessel 200) and/or to some structure of a given head rest subassembly. At least one vessel-tube-hose-connector 430 may be in gas communication with air and may be configured for respiratory gas movement. In some embodiments, at least one vessel-tube-hose-connector 430 may function as a gas vent. As shown in FIG. 4A, at least one hose 420 or at least one tubing 420 may be two hoses 420 or two tubes 420. As shown in FIG. 4A, at least one vessel-tube-hose-connector 430 may be two vessel-tube-hose-connectors 430, i.e. one associated with each hose 420 or tube 420. See e.g., FIG. 4A.

In some embodiments, mouth piece 401 may comprise a mouthing portion 403. See e.g., FIG. 4A. Mouthing portion 403 may be configured to be held by the mouth of user 9000, such that a watertight seal between lips of user 9000 and mouthing portion 403 may be formed when user 9000 may hold mouthing portion 403 within the mouth. In some embodiments, mouthing portion 403 may comprise at least one protrusion. The at least one protrusion may be configured to be held by teeth of user 9000. In some embodiments, mouthing portion 403 may be constructed of a soft elastomer. In some embodiments, mouthing portion 403 of mouth piece 401 may be constructed of silicone, rubber (either natural or synthetic), and/or the like.

In some embodiments, mouth piece 401 may comprise a purge valve. The purge valve may be configured to operate as a one way check valve. The purge valve may allow liquid 101 (and/or saliva) to leave mouth piece 401 but may not permit liquid 101 to enter mouth piece 401 by way of the purge valve.

In some embodiments, the purge valve may be of a typical one way check valve used in various human breathing devices, such as flapper valves or spring loaded check valves. A natural or resting state of the purge valve may be closed. The purge valve may only open to release liquid 101 (and/or saliva) upon a sufficiently strong exhale from user 9000 to overcome the means used for maintaining the valve closed. In some embodiments, the purge valve may be located on a ventral (bottom) portion of mouth piece 401, i.e. facing base 215 of vessel 200. In some embodiments, the purge valve may be located at other locations on mouth piece 401.

Note, a hose 420 and/or a tubing 420 as used herein, may refer to hose 420 or tubing 420 that may be capable of permitting user 9000 to breathe while hose 420 or tubing 420 may be subjected to liquid 101 pressure upon an outside diameter of hose 420 or tubing 420, without hose 420 or tubing 420 kinking or collapsing under that pressure. Such a hose 420 and/or tubing 420 may be known in the art as breathing hosing, as breathing tubing, and/or the like.

In some embodiments, mouth piece 401 may comprise at least one connection end 405. At least one hose 420 or the at least one tubing 420 may comprise first terminal end 421 and second terminal end 422 disposed opposite of the first terminal end 421. At least one connection end 405 may be configured to connect to first terminal end 421 forming a coupling. This coupling may be configured to permit swivel rotational movement between at least one connection end 405 and first terminal end 421 that may be connected to at least one connection end 405. Such swivel rotational movement may provide increased comfort to user 9000. This coupling may be water tight. See e.g., FIG. 4A, FIG. 4C, and FIG. 4E.

In some embodiments, this swivel capacity that may be shown in Detail 4E and in FIG. 4E, and this water tight capacity of this coupling may be facilitated by a snap fit, a friction fit, a tongue (i.e. flange) and groove fit, and by use of O-rings, washers, and/or gaskets. Such O-rings, washers, and/or gaskets may be separate or integral with at least one hose 420 or the at least one tubing 420. Such O-rings, washers, and/or gaskets may be proximate to first terminal end 421. For example, and without limiting the scope of the present invention, in some embodiments, this may be three inches or less; or three inches or less down to 1/32 of an inch.

In some embodiments the connection of at least one connection end 405 to first terminal end 421 may be a removable connection. In some embodiments the connection of at least one connection end 405 to first terminal end 421 may be a non-removable connection.

In some embodiments, second terminal end 422 may connect to at least one vessel-tube-hose-connector 430. See e.g., Detail 4D of FIG. 4C and FIG. 4D. At least one vessel-tube-hose-connector 430 may be substantially constructed from one or more elastomeric materials, such as, but not limited to various rubbers and/or silicones. In some embodiments, at least one vessel-tube-hose-connector 430 may be substantially constructed from a thermoformed plastic. At least one vessel-tube-hose-connector 430 may connect to at least one grommet-accommodating-contour 470 of vessel 200. See e.g., FIG. 4G, FIG. 4H, FIG. 4I, and FIG. 4J. In some embodiments, a portion of at least one vessel-tube-hose-connector 430 may be configured to be captured and held in place by at least one grommet-accommodating-contour 470. In some embodiments, at least one vessel-tube-hose-connector 430 may be configured to permit swivel rotational movement between second terminal end 422 and at least one vessel-tube-hose-connector 430. In some embodiments, this portion of at least one vessel-tube-hose-connector 430 that may accommodate such rotational movement may be an opening 431. In exemplary embodiments, opening 431 to at least one end of at least one vessel-tube-hose-connector 430 may be in gaseous communication with air. Where at least one vessel-tube-hose-connector 430 may be captured by at least one grommet-accommodating-contour 470, a water tight seal may be formed. See e.g., FIG. 4H.

In some embodiments, this swivel capacity and/or the water tight capacity of where second terminal end 422 in at least one vessel-tube-hose-connector 430 may be captured, may be facilitated by a snap fit, a friction fit, a tongue and groove fit, and by use of grommets, O-rings, washers, and/or gaskets.

In some embodiments the connection of at least one vessel-tube-hose-connector 430 to second terminal end 422 may be a removable connection. In some embodiments the connection of at least one vessel-tube-hose-connector 430 to second terminal end 422 may be a non-removable connection.

In some embodiments, second terminal end 422 of at least one hose 420 or at least one tubing 420 may be inserted (or at least partially inserted) into opening 431 of at least one vessel-tube-hose-connector 430. Such an insertion may be facilitated by second terminal end 422 tapering. Such an insertion may form a frictional fit between second terminal end 422 and at least one vessel-tube-hose-connector 430, and in particular with at least portions of opening 431. Such an insertion may be removable or may be permanent in various embodiments.

In some embodiments, opening 431 may run from an interior side 433 (see e.g., FIG. 4M) of at least one vessel-tube-hose-connector 430 to an exterior side 435 (see e.g., FIG. 4N) of at least one vessel-tube-hose-connector 430. See e.g., FIG. 4L.

In some embodiments, opening 431 may be a cavity. See e.g., FIG. 4M and FIG. 4N. In some embodiments, this cavity may comprise at least some surface area that may be complimentary to at least some surface area of second terminal end 422. Such complimentary surfaces areas (or portions thereof) may permit a frictional fit between the at least some surface area of second terminal end 422 and the at least some surface area of the cavity of opening 431. Such complimentary surfaces areas (or portions thereof) may permit rotational movement between the at least some surface area of second terminal end 422 and the at least some surface area of the cavity of opening 431. The surface area of opening 431 may form a shape that may substantially match a shape of the surface area of second terminal end 422, such that a frictional fit between the at least some surface area of second terminal end 422 and the at least some surface area of the cavity of opening 431 may be formed. See e.g., FIG. 4J.

In some embodiments, opening 431 may be a cylindrical cavity. See e.g., FIG. 4M and FIG. 4N. In such embodiments, this cylindrical cavity may comprise at least some surface area that may be complimentary to at least some surface area of second terminal end 422, permitting a frictional fit between the at least some surface area of second terminal end 422 and the at least some surface area of the cylindrical cavity of opening 431. See e.g., FIG. 4J.

In some embodiments, this cavity of opening 431 may be tapered to facilitate the frictional fit between the at least some surface area of second terminal end 422 and the at least some surface area of the cylindrical cavity of opening 431.

In some embodiments, second terminal end 422 may be inserted through opening 431 such that second terminal end 422 may protrude beyond exterior side 435. This embodiment is not shown in the FIG. 4 figures.

In some embodiments, a bottom of this cavity of opening 431 may be sloped such that liquid 101 in this cavity may gravity drain into internal volume 220 when at least one vessel-tube-hose-connector 430 may be attached to at least one grommet-accommodating-contour 470. In some embodiments, a bottom of this cavity of opening 431 may be sloped such that liquid 101 in this cavity may gravity drain into catch basin 230 when at least one vessel-tube-hose-connector 430 may be attached to at least one grommet-accommodating-contour 470.

In some embodiments, at least one vessel-tube-hose-connector 430 may connect to at least one grommet-accommodating-contour 470 of vessel 200. Such a connection may be how breathing apparatus 400 may be (removably) connected to vessel 200. See e.g., FIG. 4B, FIG. 4C, FIG. 4D, FIG. 4G, FIG. 4I, and FIG. 4J. In some embodiments, at least one vessel-tube-hose-connector 430 may be an elastomeric grommet with a shape that may be complimentary for a frictional fit into at least one grommet-accommodating-contour 470. In some embodiments, at least one vessel-tube-hose-connector 430 may be a thermoformed plastic grommet with a shape that may be complimentary for a frictional fit into at least one grommet-accommodating-contour 470. See e.g., FIG. 4K through FIG. 4Q for an example shape of at least one vessel-tube-hose-connector 430.

In some embodiments, at least one grommet-accommodating-contour 470 may be a contour of complimentary surface area sized to frictionally grip at least a portion of at least one vessel-tube-hose-connector 430. See e.g., FIG. 4A and FIG. 4H for an example contour of at least one grommet-accommodating-contour 470. In some embodiments, at least one grommet-accommodating-contour 470 may be a contour of complimentary surface area sized to frictionally grip at least a bottom portion of the at least one vessel-tube-hose-connector 430. See e.g., FIG. 4A and FIG. 4H for the contour of at least one grommet-accommodating-contour 470.

In some embodiments, at least one grommet-accommodating-contour 470 may be a cutout in rim 225 of vessel 200 or in top opening 226 of vessel 200. Or in some embodiments, the contour of may be formed from a cutout in rim 225 of vessel 200 or in top opening 226 of vessel 200. See e.g., FIG. 4A and FIG. 4H for the contour of at least one grommet-accommodating-contour 470.

That is, in some embodiments, at least one grommet-accommodating-contour 470 may extend from rim 225 of vessel 200 or from top opening 226 of vessel 200 downwards into at least one wall 201 for some proximate distance, forming a shape of this contour. For example, and without limiting the scope of the present invention, this proximate distance may be three inches or less in some embodiments. While this shape of this contour of at least one grommet-accommodating-contour 470 as shown in FIG. 4A and FIG. 4H may be curved approximating a cylindrical or conical shape, this shape may actually be determined from a complimentary shape of at least one vessel-tube-hose-connector 430 (or at least a portion thereof) such that at least some portion of at least one vessel-tube-hose-connector 430 may be inserted into at least one grommet-accommodating-contour 470 and forming a frictional fit.

In some embodiments, this cutout or this contour of at least one grommet-accommodating-contour 470 may be sloped such that liquid 101 may tend to drain towards internal volume 220. In some embodiments, this cutout or this contour of at least one grommet-accommodating-contour 470 may be sloped such that liquid 101 may tend to drain towards catch basin 230.

In some embodiments, at least one grommet-accommodating-contour 470 may be formed from at least one wall 201 in a region proximate to rim 225, such that inner vessel wall (e.g., interior wall surface 203) may be continuous with an outer vessel wall (e.g. exterior wall surface 202) or such that the inner vessel wall may extend beyond the outer vessel wall to minimize the liquid entering between such vessel walls. See e.g., FIG. 4D.

It should be noted that use of the word "cutout" in this context may be a reference to surface geometry of at least one grommet-accommodating-contour 470 depicted in FIG. 4A and FIG. 4H and not necessarily a reference to actually cutting out material from at least one wall 201. Rather in some embodiments, this cutout or this contour of at least one grommet-accommodating-contour 470 may be molded.

In some embodiments, this cutout or this contour of at least one grommet-accommodating-contour 470 may be exteriorly bounded by an exterior side containment lip 471 that may extend substantially perpendicular from a surface area of this cutout or this contour. See e.g., FIG. 4J. That is, this exterior side containment lip 471 may be located closer to exterior wall surface 202 than to interior wall surface 203.

In some embodiments, at least one vessel-tube-hose-connector 430 may comprise a butting-ring 437 that may be complimentary to exterior side containment lip 471. See e.g., FIG. 4K. In some embodiments, butting-ring 437 may be a partial ridge or a partial ring of material, circumscribing a bottom of at least one vessel-tube-hose-connector 430. See e.g., FIG. 4Q. In some embodiments, butting-ring 437 may be closer to exterior side 435 than to interior side 433. See e.g., FIG. 4Q. In some embodiments, butting-ring 437 may contact an interior portion of exterior side containment lip 471, when at least one vessel-tube-hose-connector 430 may be inserted into the at least one grommet-accommodating-contour 470. See e.g., FIG. 4J. That is, in some embodiments, when at least one vessel-tube-hose-connector 430 may be inserted into the at least one grommet-accommodating-contour 470, exterior side containment lip 471 may help to frictionally hold at least one vessel-tube-hose-connector 430 by exterior side containment lip 471 removably mating with butting-ring 437 and/or trapping butting-ring 437.

In some embodiments, this cutout or this contour of at least one grommet-accommodating-contour 470 may be interiorly bounded by an interior side containment lip 473 that may extend substantially perpendicular from the surface area of this cutout or this contour. See e.g., FIG. 4A and FIG. 4H. That is, this interior side containment lip 473 may be located closer to interior wall surface 203 than to exterior wall surface 202.

In some embodiments, at least one vessel-tube-hose-connector 430 may comprise an interior-butting-ring 439 that may be complimentary to interior side containment lip 473. See e.g., FIG. 4K. In some embodiments, interior-butting-ring 439 may be a partial ridge or a partial ring of material, circumscribing the bottom of at least one vessel-tube-hose-connector 430. See e.g., FIG. 4Q. In some embodiments, interior-butting-ring 439 may be closer to interior side 433 than to exterior side 435. See e.g., FIG. 4Q. In some embodiments, interior-butting-ring 439 may contact an interior portion of interior side containment lip 473, when at least one vessel-tube-hose-connector 430 may be inserted into the at least one grommet-accommodating-contour 470. That is, in some embodiments, when at least one vessel-tube-hose-connector 430 may be inserted into the at least one grommet-accommodating-contour 470, interior side containment lip 473 may help to frictionally hold at least one vessel-tube-hose-connector 430 by interior side containment lip 473 removably mating with interior-butting-ring 439 and/or trapping interior-butting-ring 439.

In some embodiments, this cutout of at least one grommet-accommodating-contour 470 may comprise a surface area. In some embodiments, this surface area may comprise a bottom. In some embodiments, located on this bottom may comprise at least one weep-hole 475. In some embodiments, at least one weep-hole 475 may pass entirely through at least one wall 201 from which at least one grommet-accommodating-contour 470 may be formed. In some embodiments, this at least one weep-hole 475 may permit liquid 101 on the surface area (of at least one grommet-accommodating-contour 470) to gravity drain through the at least one weep-hole 475. In some embodiments, such liquid 101 may drain into catch basin 230. See e.g., FIG. 4D and FIG. 4J.

In some embodiments, this bottom of the surface area of the cutout of at least one grommet-accommodating-contour 470 may comprise at least one drain-channel 477. In some embodiments, at least one drain-channel 477 may permit liquid 101 on the surface area to gravity drain from the at least one drain-channel 477 (into internal volume 220). In some embodiments, at least one drain-channel 477 may be closer to interior wall surface 203 than to exterior wall surface 202. In some embodiments, such liquid 101 may drain into internal volume 220. See e.g., FIG. 4H and FIG. 4A. In some embodiments, at least one drain-channel 477 may cut through interior side containment lip 473 of this cutout of at least one grommet-accommodating-contour 470. See e.g., FIG. 4H and FIG. 4A.

In some embodiments, at least one vessel-tube-hose-connector 430 may comprise a connector-rim 441. In some embodiments, connector-rim 441 may run along a top of at least one vessel-tube-hose-connector 430. See e.g., FIG. 4K and FIG. 4L. In some embodiments, when at least one vessel-tube-hose-connector 430 may be (removably) inserted into at least one grommet-accommodating-contour 470, then connector-rim 441 may be substantially even with rim 225 of vessel 200. See e.g., FIG. 4G, FIG. 4I, and FIG. 4J. In some embodiments, when at least one vessel-tube-hose-connector 430 may be (removably) inserted into at least one grommet-accommodating-contour 470, then connector-rim 441 may be below rim 225 of vessel 200 (not depicted). In some embodiments, when at least one vessel-tube-hose-connector 430 may be (removably) inserted into at least one grommet-accommodating-contour 470, then connector-rim 441 may be above rim 225 of vessel 200 (not depicted).

In some embodiments, user 9000 may insert a portion of at least one finger into opening 431 to pull at least one vessel-tube-hose-connector 430 from at least one grommet-accommodating-contour 470 (e.g., by pulling upwards away from at least one base 215). When at least one vessel-tube-hose-connector 430 may be connected to at least one tubing 420 or at least one hose 420, then removing at least one vessel-tube-hose-connector 430 may also remove at least one tubing 420 or at least one hose 420 from at least one grommet-accommodating-contour 470.

In FIG. 22F an alternative embodiment of at least one vessel-tube-hose-connector 430 may be shown, where here in FIG. 22F the at least one vessel-tube-hose-connector may be denoted with reference numeral 2231. In some embodiments, at least one vessel-tube-hose-connector 2231 may comprise an independent (separate) finger pull ring 2232 for lifting at least one vessel-tube-hose-connector 2231 out of at least one grommet-accommodating-contour 2234. At least one grommet-accommodating-contour 2234 of FIG. 22F may be the equivalent to at least one grommet-accommodating-contour 470 of the FIG. 4 series. That is, with at least one vessel-tube-hose-connector 2231, rather than using opening 431 as a finger pull, the independent (separate) finger pull ring 2232 may be used.

Turning back to the FIG. 4 series of figures, in some embodiments, a mounting location for at least one vessel-tube-hose-connector 430 may be at least one grommet-accommodating-contour 470 of vessel 200. In some embodiments, the mounting location may be above the maximum liquid level of vessel 200. In some embodiments, the mounting location for at least one vessel-tube-hose-connector 430 may be below the maximum liquid level of vessel 200. In both embodiments, at least one vessel-tube-hose-connector 430 may be still in gas communication with the air and how at least one vessel-tube-hose-connector 430 may be captured by at least one grommet-accommodating-contour 470 may be water tight.

In some embodiments, breathing apparatus 400 may comprise two vessel-tube-hose-connectors 430 and two hoses 420 or two tubes 420, in addition to a single mouth piece 401. See e.g., FIG. 4A and FIG. 4B. Each such hose 420 or each such tube 420 may comprise two terminal ends, first terminal end 421 and second terminal end 422 disposed opposite of first terminal end 421. Mouth piece 401 may comprise two connection ends 405. First terminal end 421 of each hose 420 or each tube 420 may connect to one respective connection end 405. Second terminal end 422 of each hose 420 or each tube 420 may connect to each respective vessel-tube-hose-connector 430. Each vessel-tube-hose-connector 430 may mount to a location on vessel 200. In some embodiments, this mounting location may be at least one grommet-accommodating-contour 470; wherein in some embodiments, there may be two grommet-accommodating-contours 470. In some embodiments, these two at least one grommet-accommodating-contours 470 may be located on opposing side walls 205 (e.g., first side wall 206 and third side wall 208). See e.g., FIG. 4A. Having two hoses 420 or tubes 420, two vessel-tube-hose-connectors 430, and two grommet-accommodating-contours 470 may provide a safety redundancy.

In some embodiments, each connection end 405 of mouth piece 401 may be disposed opposite of each other on mouth piece 405. See e.g., FIG. 4A. In some embodiments, each connection 405 and mouthing portion 403 may be about 120 degrees apart from each other, i.e. about equally oriented from each other (this embodiment may not be depicted).

In some embodiments, mounting second terminal end 422 of each hose 420 or each tube 420 to each vessel-tube-hose-connector 430, to some structure of vessel 200, and/or to a given head rest subassembly may be accomplished by a snap fit, a friction fit, a tongue (flange) and groove fit, use of grommets, O-rings, washers, and/or gaskets, solvent bonding, heat welding, ultrasonic welding, chemical adhesives/sealants, and the like. In some embodiments, second terminal end 422 of each hose 420 or each tube 420 may be mounted to a given port in a given vessel embodiment (e.g., vessel 200).

In some embodiments, at least one hose 420 or the at least one tubing 420 may be flexible, kink resistant, and sufficiently strong to not collapse under pressure from liquid 101 in internal volume 220. In some embodiments, such hose 420 and/or tubing 420 flexibility may permit user 9000 to place mouth piece 401 (e.g., mouthing portion 403) into the mouth of user 9000 while the mouth may be in the air and then user 9000 may insert the held mouth piece 401 into liquid 101 and then to breathe through breathing apparatus 400.

In some embodiments, at least one hose 420 or the at least one tubing 420 may be corrugated or non-corrugated in other embodiments. Corrugated hose 420 or corrugated tubing 420 may be both flexible and kink resistant. Kink resistance may also be achieved with reinforcement to hose 420 or to tubing 420, such as with textile braiding or polymer braiding. Kink resistance may also be achieved by: increasing the durometer of hose 420 material formulation or of tubing 420 material formulation; by having a star shaped inside diameter cross section of hose 420 or tubing 420; and/or by increasing a thickness of hose 420 material or tubing 420 material (i.e., a distance between an outside diameter and an inside diameter of hose 420 or tubing 420).

In some embodiments, the pressure exerted by liquid 101 upon hose 420 or the tubing 420 may be governed by a height (i.e. head) of liquid 101 within internal volume 220 and the local atmospheric pressure which may press upon liquid 101 within internal volume 220. For example, and without limiting the scope of the present invention, in some embodiments, the head may be 24 inches of liquid or less. In some embodiments, liquid 101 may be water, oil, combinations thereof; and with varying degrees of salinity, i.e. saline solutions. In other embodiments liquid 101 pressure may be greater or less.

In some embodiments, at least one hose 420 or the at least one tubing 420 may be substantially extruded and/or molded. In some embodiments, at least one hose 420 or the at least one tubing 420 may be constructed of one or more of the group selected from: PVC, rubber, fluor polymers, neoprene, polypropylene, polyethylene, and/or any other material suitable for use at allowing the user to breathe while the material may be submerged and under liquid 101 pressure. In some embodiments, a polymeric and/or elastomeric material used for at least one hose 420 or the at least one tubing 420 may be of a food grade or of a medical grade. Such a hose 420 or a tubing 420 before use by user 9000 may be cured to a point where offensive, smelly, and potentially harmful outgassing may be minimized.

Note, in some embodiments, breathing apparatus 400 may be rotated and/or articulated into a raised configuration, wherein mouth piece 401 may be higher than any second terminal end 422. When breathing apparatus 400 may be rotated into such a raised configuration, liquids 101 (and/or saliva) within breathing apparatus 400 may drain naturally via gravity and out of at least one vessel-tube-hose-connector 430 and into catch basin 230. Such rotation may be about each at least one vessel-tube-hose-connector 430 that may be removably coupled to a given at least one grommet-accommodating-contour 470.

In some embodiments, a breathing apparatus may comprise a hollow conduit having a first end and a second end. At least one of the first and second ends may be open (e.g. the second end). An third opening into the conduit may be disposed between the first open end and the second end of the conduit. A mouthpiece may be connected to the third opening such that user 9000 may place the person's mouth on the mouthpiece and breathe through the conduit with air passing between the mouthpiece and at least one of the first and second open ends of the conduit. The conduit may be otherwise sealed tight so that no liquid 101 may enter the conduit other than through the mouthpiece and at least one of the first and second ends of the conduit. The conduit of the apparatus may be shaped in such a manner that the first and second ends are generally co-axial, but where at least some of the conduit between the first and second ends may not be co-axial with the first and second ends. In an exemplary embodiment, the conduit will be shaped as shown in FIG. 4A and FIG. 4C. However, different shapes that accomplish the purpose of the shape shown in FIG. 4A and FIG. 4C are within the scope of some embodiments of this invention. For example, instead of the conduit curving, the conduit may be bent at sharp angles. The first and second ends of the conduit may be attached to the vessel (e.g., vessel 200) such that the conduit, as a whole, may swivel around the axis of the first and second ends, and such that the at least one open end may be completely above any liquid contained in the vessel. The mouthpiece may be arranged such that the mouthpiece and the part of the conduit to which the mouthpiece may be connected is not co-axial with the first and second ends of the conduit, but may offset a predetermined distance from that axis. Thus, when the conduit may be rotated about the axis through the first and second ends of the conduit, the resulting rotation of the mouthpiece may describe a circle about the axis of the first and second ends of the conduit. The offset of the mouthpiece from the axis of the first and second ends may allow user 9000 to place the user's 9000 mouth on the mouthpiece with the mouthpiece out of liquid 101 in the vessel, and then move the user's 9000 head such that the face 9010 and/or head of user 9000 may be at least partially submerged into liquid 101 in the vessel while user 9000 may be able to breathe through the mouthpiece and conduit. Other elements and features recited in this specification can be added to the breathing apparatus as desired.

Alternatively, the breathing apparatus may comprise a hollow conduit between the mouthpiece and the first open end such that there may be continuous open conduit between the mouthpiece and the first open end, and a guide that may not necessarily be hollow between the mouthpiece and the second end of the breathing device. Since breathing may be accomplished through only one side, it is not required that the other side be hollow. Instead, one side may simply be a shaped guide that need not be open for breathing. The first end of the breathing apparatus (which is open) and the second end of the breathing apparatus (which may be a simple guide) may be coaxial. This simple guide may be a rigid to semi-rigid elongate member, and may be insulated when this simple guide may be a metal.

FIG. 20A and FIG. 20B may depict independent breathing apparatus (2000 and 2050, respectively) that might not be coupled to (i.e., attached to or connected to) a given vessel (e.g., vessel 200); nor to any other given face soaking device component. Note in such embodiments, a system may comprise a given face soaking device along with an independent breathing apparatus (e.g., 2000 and 2050). FIG. 20A may depict a cross-sectional view of a face soaking device in use by user 9000, depicting an independent breathing apparatus 2000. FIG. 20B may depict a cross-sectional view of a face soaking device in use by user 9000, depicting an independent breathing apparatus 2050. Independent breathing apparatus 2000 may differ from independent breathing apparatus 2050, in that independent breathing apparatus 2000 may comprise two hoses 420 or tubes 420; while independent breathing apparatus 2050 may comprise one hose 420 or tube 420.

In FIG. 20A and FIG. 20B, in some embodiments, independent breathing apparatus 2000 and 2050 may comprise mouth piece 401, at least one exit port 2001, and at least one hose 420 or at least one tubing 420. At least one hose 420 or at least one tubing 420 may connect to mouth piece 401. Mouth piece 401 may be configured to be held by the mouth of user 9000. At least one exit port 2001 may be in gas communication with air and may be configured for respiratory gas movement. In some embodiments, at least one exit port 2001 may function as the gas vent. As shown in FIG. 20A, at least one hose 420 or at least one tubing 420 may be two hoses 420 or two tubes 420, with two exit ports 2001. As shown in FIG. 20B, at least one hose 420 or at least one tubing 420 may be one hose 420 or one tube 420; and with one exit port 2001.

In some embodiments, mouth piece 401 may comprise at least one connection end 405. At least one hose 420 or the at least one tubing 420 may comprise first terminal end 421 and second terminal end 422 disposed opposite of the first terminal end 421. At least one connection end 405 may be configured to connect to first terminal end 421 forming the coupling. This coupling may be configured to permit swivel rotational movement between at least one connection end 405 and first terminal end 421 that may be connected to at least one connection end 405. Such swivel rotational movement may provide increased comfort to user 9000. This coupling may be water tight.

In some embodiments, at least one exit port 2001 may be located at or proximate to second terminal end 422. For example, and without limiting the scope of the present invention, such a proximate distance may be within three inches of second terminal end 422. In other embodiments, this proximate distance may be greater than three inches. In some embodiments, second terminal end 422 may terminate in at least one exit port 2001.

In some embodiments, a length of at least one hose 420 or at least one tubing 420 may be such, that when independent breathing apparatus 2000 or 2050 may be in use by user 9000, as depicted in FIG. 20A and FIG. 20B, that at least exit port 2001 may be located above rim 225 and/or above the maximum liquid level, such that at least exit port 2001 may be located in the atmospheric environmental air.

In some embodiments, at least one hose 420 or at least one tubing 420 may be semi-rigid to rigid, such that second terminal end 422 may not bend back towards first terminal end 421 under the weight of at least one hose 420 or at least one tubing 420.

In some embodiments, independent breathing apparatus 2000 and/or 2050 might not be attached to vessel 200 (nor to other vessel embodiments), nor to head rest subassembly 500 (nor to other head rest subassembly embodiments). In some embodiments, independent breathing apparatus 2000 and/or 2050 might not be attached to user 9000, aside from the removable holding of mouth piece 401 by user's 9000 mouth. In some embodiments, independent breathing apparatus 2000 and/or 2050 may be removably attached to user 9000 and/or to vessel 200 (or to other vessel embodiments). For example, and without limiting the scope of the present invention, such removable attachment may be accomplished by straps and/or clips.

Aside from differences noted above, in some embodiments, independent breathing apparatus 2000 and independent breathing apparatus 2050 may be substantially similar to breathing apparatus 400 embodiments, in terms of functionality (e.g. facilitating respiratory gas movement of user 9000) and/or in terms of structure (e.g. hollow tubes or hollow hoses, mouthpiece 401, inclusion of the purge valve in some embodiments, and/or the like).

A FIG. 21 series of figures may comprise FIG. 21A through FIG. 21E. This FIG. 21 series of figures may depict embodiments of a breathing apparatus that may be combined with a head rest subassembly. FIG. 21A may depict a face soaking device embodiment, wherein a breathing apparatus may be incorporated (combined) into a head rest subassembly, shown from a perspective view, with a partial cutout view of the vessel. This may be combination breathing apparatus and head rest subassembly 2100.

FIG. 21B may depict combination breathing apparatus and head rest subassembly 2100, but from a top view. FIG. 21C may depict combination breathing apparatus and head rest subassembly 2100, but from a front view. And a sectional line 21E-21E may be shown in FIG. 21C through combination breathing apparatus and head rest subassembly 2100. FIG. 21D may depict combination breathing apparatus and head rest subassembly 2100, but from an exploded perspective view.

FIG. 21E may depict combination breathing apparatus and head rest subassembly 2100, showing the view along sectional line 21E-21E, which may show a longitudinal side cross sectional view of combination breathing apparatus and head rest subassembly 2100.

In some embodiments, combination breathing apparatus and head rest subassembly 2100 may comprise a breathing apparatus and a head rest subassembly into a single subassembly. The breathing apparatus may comprise: mouth piece 401 and at least one hose 420 or at least one tubing 420. In some embodiments, mouth piece 401 and at least one hose 420 or at least one tubing 420 may be as discussed above in the FIG. 4 series of figures discussion. The head rest subassembly may comprise support member 501, comfortable exterior surface 502, a height adjust means, and a forwards-backwards adjust means. In some embodiments, support member 501, comfortable exterior surface 502, the height adjust means, and the forwards-backwards adjust means may be as described and discussed below in the FIG. 5 series of figures discussion (discussed below) and in the FIG. 23 series of figures discussion (discussed after the FIG. 6 series of figures discussion below).

In combination breathing apparatus and head rest subassembly 2100 embodiments, support member 501 may be hollow elongate member. See e.g., FIG. 21D. A substantial portion of a length of at least one hose 420 or at least one tubing 420 may be housed within the hollow elongate member of support member 501. In some embodiments, mouth piece 401 may protrude from sixth terminal end 2302 of the hollow elongate member of support member 501. In some embodiments, an outside diameter of at least one hose 420 or at least one tubing 420 may be small enough as compared against an inside diameter of the hollow elongate member of support member 501, that at least one hose 420 or at least one tubing 420 may be housed and/or slide within the hollow elongate member of support member 501. Such sliding may permit vertical adjustments in a height of mouth piece 401 with respect to at least one base 215 (or bottom interior surface 217).

In some embodiments a length of at least one hose 420 or at least one tubing 420 may be less than a length of the hollow elongate member of support member 501. In such embodiments, second terminal end 422 of at least one hose 420 or at least one tubing 420 may not protrude beyond fifth terminal end 2301 of the hollow elongate member of support member 501. In some such embodiments, at least one hose 420 or at least one tubing 420 may not comprise common slots 2101. See e.g., FIG. 21D.

In some embodiments the length of at least one hose 420 or at least one tubing 420 may be longer than the length of the hollow elongate member of support member 501. In such embodiments, second terminal end 422 of at least one hose 420 or at least one tubing 420 may protrude beyond fifth terminal end 2301 of the hollow elongate member of support member 501. In some such embodiments, at least one hose 420 or at least one tubing 420 may comprise common slots 2101.

In some embodiments, the hollow elongate member of support member 501 may comprise two bends (with two angles) an upper bend (and upper angle) along with a lower bend (and lower angle). In some embodiments, at least one hose 420 or at least one tubing 420 may comprise at least one bend, a complimentary lower bend (lower angle). In some embodiments, at least one hose 420 or at least one tubing 420 may comprise at least one bend, a complimentary upper bend (upper angle). In some embodiments, the upper bend may be bend 2315. In some embodiments, the upper angle may be angle 2380 (see e.g., FIG. 23D).

Regions closer to fifth terminal end 2301 of the hollow elongate member of support member 501 and closer to second terminal end 422 of at least one hose 420 or at least one tubing 420 may be secured and/or attached to a given vessel (e.g., vessel 200). Such attachment may be as described in the FIG. 23 series of figures discussion below relating to head rest subassembly 2300. Such attachment may comprise, in some embodiments, friction clamp 2322, cover 2370, common slots 2101, and recessed channel 2350. In combination breathing apparatus and head rest subassembly 2100 common slots 2101 may replace slot 2320 from head rest subassembly 2300 in support member 501, but may serve a same function and with a same general structure as slot 2320. However, common slots 2101 may be present in two opposing locations on at least one hose 420 or at least one tubing 420 and in two opposing locations on the hollow elongate member of support member 501. Common slots 2101 in at least one hose 420 or at least one tubing 420 may be located closer to second terminal end 422 than to first terminal end 421. Common slots 2101 in the hollow elongate member of support member 501 may be located closer to fifth terminal end 2301 than to sixth terminal end 2302. The common slots 2101 may run substantially parallel with a longitude of at least one hose 420 or at least one tubing 420 and of the hollow elongate member of support member 501. All the common slots 2101 (e.g., four common slots 2101) may be sized to accept passage of portions of threaded bolt/threaded screw 2321 of friction clamp 2322. Portions of threaded bolt/threaded screw 2321 may pass through center hole 2375 of cover 2370, and then through the four common slots 2101, and lastly into threaded hole 2330 (not shown in FIG. 21D, but is shown in FIG. 23E) of recessed channel 2350. See e.g., FIG. 21D.

In combination breathing apparatus and head rest subassembly 2100 common slots 2101 the height adjust means and the forwards-backwards adjust means may be as described in the FIG. 23 series of figures discussion below relating to head rest subassembly 2300. Such height adjust means and forwards-backwards adjust means may comprise, in some embodiments, friction clamp 2322, cover 2370, common slots 2101, the upper bend and/or the upper angle, recessed channel 2350, and channel 2102. Channel 2102 may be a groove in bottom interior surface 217 of the vessel. See e.g., FIG. 21A. A longitude of channel 2102 may be substantially parallel with the forwards-backwards direction, i.e., with a line running center from a center of neck-gasket-accommodator 335 to a center of the back wall (or to a center of recessed channel 2350). A transverse width of channel 2102 may be sized to accommodate an outside diameter of the hollow elongate member of support member 501. Channel 2102 may provide a means for the hollow elongate member of support member 501 to translationally (e.g., slidingly) track in the forward-backwards direction.

When the hollow elongate member of support member 501 may be attached to recessed channel 2350 by threaded bolt 2321 passing through center hole 2375 of cover 2370, and then through common slot 2101, and then finally threaded into threaded hole 2330 (not shown in FIG. 21D, but is shown in FIG. 23E) at a bottom of recessed channel 2350, the hollow elongate member of support member 501 may be slid either forwards or backwards to the desired position of user 9000, with the bottom bend sliding in channel 2102. When friction clamp 2322 may be loose, the hollow elongate member of support member 501 may be adjustable in the forwards-backwards directions. Because of the upper bend (e.g., bend 2315) and/or the upper angle (e.g., angle 2380) in the hollow elongate member of support member 501, adjustments in the forwards-backwards directions may also function to adjust for head height preferences of user 9000. User 9000 may make a single adjustment (e.g. with friction clamp 2322 and sliding) that may result in both a forwards-backwards adjustment and a height adjustment, that may allow different sized heads of various user 9000s to support and/or rest their respective different sized heads onto various locations of comfortable exterior surface 502, as well as to vary locations of mouth piece 401. When friction clamp 2322 may be tightened, the hollow elongate member of support member 501 may be secured in place in the desired position. In some embodiments, tightening or loosening of friction clamp 2322 may be accomplished by user 9000 turning (rotating) user engagement flange 2323 of friction clamp 2322. In some embodiments, turning user engagement flange 2323 one direction may tighten friction clamp 2322, while turning user engagement flange 2323 an opposite direction may loosen friction clamp 2322.

In some embodiments there may be no common slots 2101; no threaded hole 2330 in a bottom of recessed channel 2350 (see e.g., FIG. 23E for recessed channel 2350 and threaded hole 2330); center hole 2375 may be complimentary inside threaded, cover 2370 may be secured against roof 2340 and/or against recessed channel 2350; and threaded bolt/threaded screw 2321 may be used to press against a top outside of the hollow elongate member of support member 501 closer to fifth terminal end 2301.

FIG. 22A may depict an embodiment of an adjustable breathing apparatus, shown from a perspective view. In some embodiments, an at least one vessel-tube-hose-connector may comprise at least one collar 2201. In FIG. 22A, at least one collar 2201 may replace at least one vessel-tube-hose-connector 430; otherwise this breathing apparatus may comprise mouth piece 401, at least one hose 420 or at least one tubing 420, and at least one collar 2201. Collar 2201 may comprise a central hole with an inside diameter sized to receive an outside diameter of a portion of at least one hose 420 or at least one tube 420. Such sizing of the inside diameter in relation to the outside diameter may permit linear and/or rotational translational movement between collar 2201 and the portion of at least one hose 420 or at least one tube 420 inserted into the central hole.

In some embodiments, when the portion of at least one hose 420 or at least one tube 420 may be inserted into the central hole of collar 2201, the breathing apparatus may be adjustable in a direction of the translational movement. For example, and without limiting the scope of the present invention, this direction of translational movement, may be in a vertical direction (i.e. up-down direction).

In some embodiments, collar 2201 may comprise a means to attach to the vessel (e.g. 200) or a given head rest subassembly. In some embodiments, the means to attach of collar 2201 may comprise a collar-tab 2202. Collar-tab 2202 may protrude from an exterior of collar 2201. See e.g., FIG. 22A. For example, and without limiting the scope of the present invention, in some embodiments, collar-tab 2202 may protrude greater than zero inches and less than two inches from the exterior of collar 2201. In some embodiments, collar-tab 2202 may comprise a terminal flange. Collar-tab 2202 may be received by a side wall tab receiver 2203 located on an interior of at least one side wall 205, e.g. interior wall surface 203. See e.g., FIG. 22A. Side wall tab receiver 2203 may be an indentation, a cavity, or a hole in the side wall 205 (e.g. a hole passing from interior wall surface 203 to exterior wall surface 202). Such a hole may be a port in the vessel. In some embodiments, side wall tab receiver 2203 may be located at or above the liquid (fluid) fill level (e.g. maximum liquid level). Side wall tab receiver 2203 may be sized (via an inside diameter for example) to permit rotational movement between the vessel (e.g. 200) and collar 2201. When collar-tab 2202 may be inserted into side wall tab receiver 2203, the breathing apparatus may be adjustable in a rotational direction with respect to at least one side wall 205 with side wall tab receiver 2203; and also adjustable in the direction of the translational movement (if the portion of at least one hose 420 or at least one tube 420 may be inserted into the central hole of collar 2201). Such adjustments of the breathing apparatus may permit users 9000 of different sizes (and/or ages) to utilize one breathing apparatus which may be adjustable to accommodate differences in the user's 9000 sizes.

In some embodiments, at least one hose 420 or at least one tube 420 may comprise a cap (not depicted in FIG. 22A). The cap may be located at a terminal end (e.g. 422) protruding from collar 2201. The cap may prevent the terminal end (e.g. 422) from slipping through the central hole of collar 2201, once the portion of at least one hose 420 or at least one tube 420 may have been inserted through the central hole. In some embodiments, the cap may comprise a wrapping of tape sufficient to increase the outside diameter of the portion of at least one hose 420 or at least one tube 420 such that the outside diameter is larger than the central hole's inside diameter. In some embodiments, the cap may comprise at least one protrusion (from an exterior of hose 420 or tube 420) which may be large enough to prevent passage through the central hole of collar 2201.

In some embodiments, the cap may be structured so as to not interfere with respiratory gas movement. In some adjustable breathing apparatus embodiments, there may no cap, because in some embodiments, tubes 420 or hoses 420 may be sufficiently long to minimize slippage out of collar 2201.

FIG. 22B may depict an embodiment of an adjustable breathing apparatus, shown from a close up perspective view. In some embodiments, an at least one vessel-tube-hose-connector may comprise a sleeve 2205. In FIG. 22B, sleeve 2205 may replace at least one vessel-tube-hose-connector 430; otherwise this breathing apparatus may comprise mouth piece 401, at least one hose 420 or at least one tubing 420, and sleeve 2205. Sleeve 2205 may comprise a central hole with an inside diameter sized to receive an outside diameter of a portion of at least one hose 420 or at least one tube 420. Such sizing of the inside diameter in relation to the outside diameter may permit linear and/or rotational translational movement between sleeve 2205 and the portion of at least one hose 420 or at least one tube 420 inserted into the central hole. In some embodiments, sleeve 2205 may be structurally similar to collar 2201, except sleeve 2205 may comprise a longer length.

In some embodiments, when the portion of at least one hose 420 or at least one tube 420 may be inserted into the central hole of sleeve 2205, the breathing apparatus may be adjustable in a direction of the translational movement. For example, and without limiting the scope of the present invention, this direction of translational movement, may be in a vertical direction (i.e. up-down direction). See e.g., FIG. 22B.

In some embodiments, sleeve 2205 may comprise a means to attach to the vessel (e.g. 200) or to a given head rest subassembly. In some embodiments, the means to attach of sleeve 2205 may comprise a sleeve-tab 2206. Sleeve-tab 2206 may protrude from an exterior of sleeve 2205. For example, and without limiting the scope of the present invention, in some embodiments, sleeve-tab 2206 may protrude greater than zero inches and less than two inches from the exterior of sleeve 2205. In some embodiments, sleeve-tab 2206 may comprise a terminal flange. See e.g., FIG. 22B. Sleeve-tab 2206 may be received by a side wall tab receiver 2203 (not depicted clearly in FIG. 22B, instead see FIG. 22A for side wall tab receiver 2203) located on an interior of at least one side wall 205, e.g. interior wall surface 203. In some embodiments, side wall tab receiver 2203 may be located at or above the liquid (fluid) fill level (e.g. maximum liquid level). Side wall tab receiver 2203 may be an indentation, a cavity, or a hole in the side wall 205 (e.g. a hole passing from interior wall surface 203 to exterior wall surface 202). Such a hole may be a port in the vessel. Side wall tab receiver 2203 may be sized (via an inside diameter for example) to permit rotational movement between the vessel (e.g. 200) and collar sleeve 2205. When sleeve-tab 2206 may be inserted into side wall tab receiver 2203, the breathing apparatus may be adjustable in a rotational direction with respect to at least one side wall 205 with side wall tab receiver 2203; and also adjustable in the direction of the translational movement (if the portion of at least one hose 420 or at least one tube 420 may be inserted into the central hole of sleeve 2205). Such adjustments of the breathing apparatus may permit users 9000 of different sizes (and/or ages) to utilize one breathing apparatus which may be adjustable to accommodate differences in the user's 9000 sizes.

In some embodiments, at least one hose 420 or at least one tube 420 may comprise a cap (not depicted in FIG. 22B). The cap may be located at a terminal end (e.g. 422) protruding from sleeve 2205. The cap may prevent the terminal end (e.g. 422) from slipping through the central hole of sleeve 2205, once the portion of at least one hose 420 or at least one tube 420 may have been inserted through the central hole. In some embodiments, the cap may comprise a wrapping of tape sufficient to increase the outside diameter of the portion of at least one hose 420 or at least one tube 420 such that the outside diameter may be larger than the central hole's inside diameter. In some embodiments, the cap may comprise at least one protrusion (from an exterior of hose 420 or tube 420) which may be large enough to prevent passage through the central hole of sleeve 2205.

In some embodiments, the cap may be structured so as to not interfere with respiratory gas movement. In some adjustable breathing apparatus embodiments, there may no cap, because in some embodiments, tubes 420 or hoses 420 may be sufficiently long to minimize slippage out of sleeve 2205.

FIG. 22C may depict an embodiment of an adjustable breathing apparatus, shown from a close up perspective partial view a side wall tab 2212 in a transparent view inside of channel sleeve 2211 and a comparison view without channel sleeve 2211. In some embodiments, the at least one vessel-tube-hose-connector may comprise a channel sleeve 2211. In FIG. 22C, channel sleeve 2211 may replace at least one vessel-tube-hose-connector 430; otherwise this breathing apparatus may comprise mouth piece 401, at least one hose 420 or at least one tubing 420, and channel sleeve 2211. Channel sleeve 2211 may be connected to a terminal end (e.g., 422) of at least one hose 420 or at least one tube 420. In some embodiments, such a connection may be removable and in other embodiments such a connection may be permanent. In some embodiments, such a connection may be a friction fit between channel sleeve 2211 and the terminal end (e.g., 422) of at least one hose 420 or at least one tube 420.

In some embodiments, channel sleeve 2211 may comprise a central hole in gas communication with an interior of at least one hose 420 or at least one tube 420 connected to the channel sleeve 2211. This connection between channel sleeve 2211 and the terminal end (e.g., 422) of at least one hose 420 or at least one tube 420 may facilitate respiratory gas movement between channel sleeve 2211 and the terminal end (e.g. 422) of at least one hose 420 or at least one tube 420.

In some embodiments, channel sleeve 2211 may comprise a channel 2213 on an exterior surface of channel sleeve 2211 that may face interior wall surface 203. Channel 2213 may run longitudinally along an exterior of channel sleeve 2211. Channel 2213 may be sized to receive a side wall tab 2212. In some embodiments, side wall tab 2212 may be a projection protruding into internal volume 220 of the vessel (e.g.

200) by a proximate distance from a fixed position on at least one side wall 205, e.g. interior wall surface 203. See e.g., FIG. 22C. For example, and without limiting the scope of the present invention, in some embodiments, side wall tab 2212 may protrude greater than zero inches and less than two inches from interior wall surface 203. In some embodiments, side wall tab 2212 may be located at or above the liquid (fluid) fill level (e.g. maximum liquid level). In some embodiments, side wall tab 2212 may comprise a terminal flange 2214.

In some embodiments, when side wall tab 2212 may be held by channel 2213, both linear translational movement, between channel sleeve 2211 and at least one side wall 205 from which side wall tab 2212 may protrude, and rotational movement, between channel sleeve 2211 and a same at least one side wall 205, may be permitted. Such linear translational movement and rotational movement may permit linear translational and rotational adjustments of the breathing apparatus with respect to at least one side wall 205 from which side wall tab 2102 may protrude. Such adjustments of the breathing apparatus may permit users 9000 of different sizes (and/or ages) to utilize one breathing apparatus which may be adjustable to accommodate differences in the user's 9000 sizes.

FIG. 22D may depict an embodiment of an adjustable breathing apparatus, shown from a perspective view, while the breathing apparatus may be in a resting configuration. FIG. 22E may depict the embodiment of FIG. 22D, shown from a perspective view, but while the breathing apparatus may be in an adjustable loaded configuration (i.e., an operational configuration).

In some embodiments, the at least one vessel-tube-hose-connector may comprise two collar hinges 2221. In FIG. 22D and FIG. 22E, two collar hinges 2221 may replace at least one vessel-tube-hose-connector 430; otherwise this breathing apparatus may comprise mouth piece 401, at least one hose 420 or at least one tubing 420, and the two collar hinges 2221. Each collar hinges 2221 may comprise a central hole with an inside diameter sized to receive an outside diameter of a portion of at least one hose 420 or at least one tube 420. When the portion of at least one hose 420 or at least one tube 420 may be inserted into the central hole of collar hinge 2221, linear and/or rotational translational movement may be permitted between collar hinge 2221 and the inserted portion of at least one hose 420 or at least one tube 420. Each collar hinge 2221 may be attached to opposing side walls 205 or opposing rims (e.g. 225) of the vessel (e.g. 200). Each such point of attachment may be a hinged connection permitting swivel movement between collar hinge 2201 and respective side wall 205. See e.g., FIG. 22D and FIG. 22E. Such a hinge may be integral molded hinge.

In some embodiments, the breathing apparatus may comprise two tubes 420 or two hoses 420. Mouthpiece 401 may be disposed between and connected to these comprise two tubes 420 or two hoses 420. In some embodiments, the breathing apparatus may exist in at least one of two configurations, the resting configuration of FIG. 22D and the adjustable loaded configuration of FIG. 22E. In some embodiments, in the resting configuration there may be no user 9000 applied load to the breathing apparatus. In such a configuration, the two tubes 420 or two hoses 420 may remain substantially straight with one portion of each tube 420 or hose 420 passing through one of the central holes of each collar hinge 2201. See e.g., FIG. 22D. "Substantially" as used in the proceeding sentence may mean the two tubes 420 or two hoses 420 may not be geometrically perfectly straight, but rather may have some bend.

In some embodiments, in the adjustable loaded configuration, the user 9000 may be removably holding (engaging) mouthpiece 401 in the user's 9000 mouth and pushing the breathing apparatus down into internal volume 200 of the vessel (e.g. 200). Such pushing may place a load upon the breathing apparatus. Such a load may overcome the resting configuration and cause a shift into the adjustable loaded configuration; which may be a configuration usable by user 9000 for using the face soaking device as intended. In some embodiments, due to inherent flexibility of the two tubes 420 or two hoses 420, the linear translational movement through the central holes of collar hinge 2221, and the swivel movement of collar hinge 2221, the breathing apparatus may be adjustable by user 9000. When user 9000 may be done applying the load to the breathing apparatus, the breathing apparatus may then return to the resting configuration depicted in FIG. 22D, due to inherent elasticity of the two tubes 420 or two hoses 420.

In some embodiments, at least one of the two hoses 420 or two tubes 420 may comprise a cap (not depicted in FIG. 22D nor FIG. 22E). The cap may be located at least one of terminal ends 422. The cap may prevent terminal end 422 from slipping through the central hole of collar hinge 2221, once the portion of the hose 420 or the tube 420 may have been inserted through the central hole. In some embodiments, the cap may comprise a wrapping of tape sufficient to increase the outside diameter of the portion of at least one hose 420 or at least one tube 420 such that the outside diameter may be larger than the central hole's inside diameter. In some embodiments, the cap may comprise at least one protrusion (from an exterior of hose 420 or tube 420) which may be large enough to prevent passage through the central hole of collar hinge 2221.

In some embodiments, the cap may be structured so as to not interfere with respiratory gas movement. In some adjustable breathing apparatus embodiments, there may no cap, because in some embodiments, tubes 420 or hoses 420 may be sufficiently long to minimize slippage out of collar hinge 2221.

Figure 16:
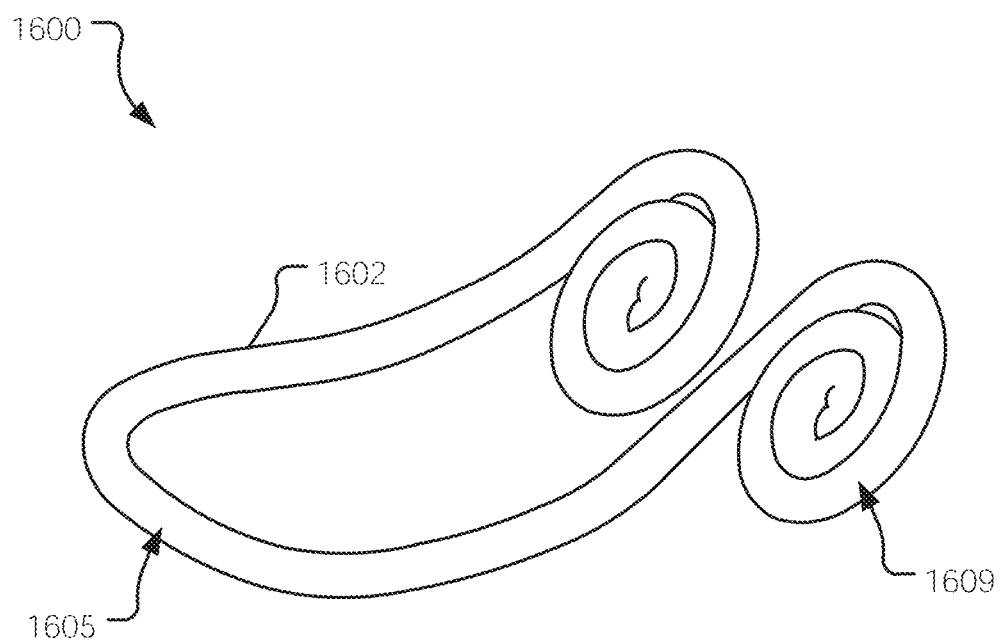
Figure 16:
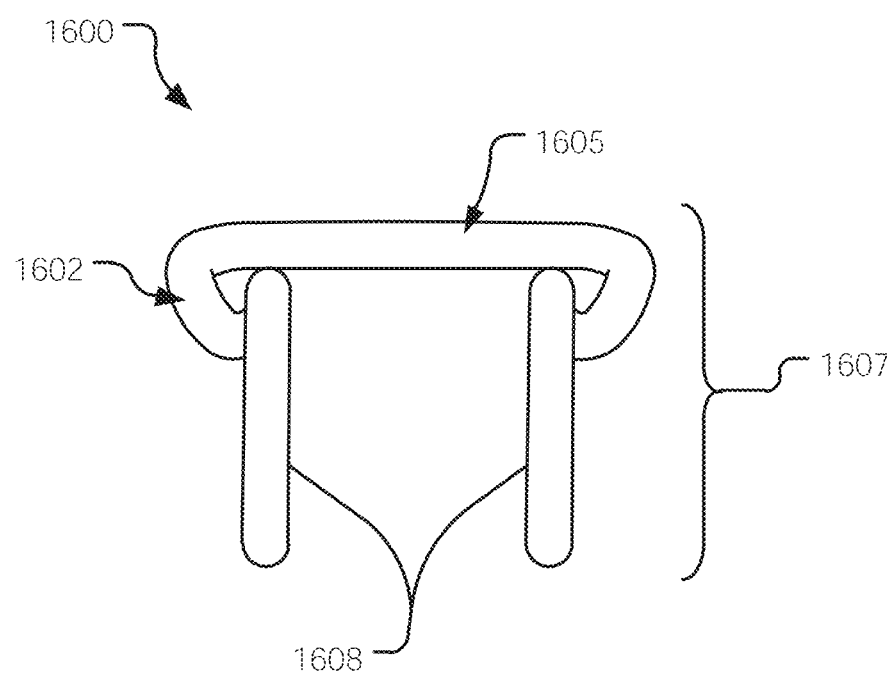
Figure 16:
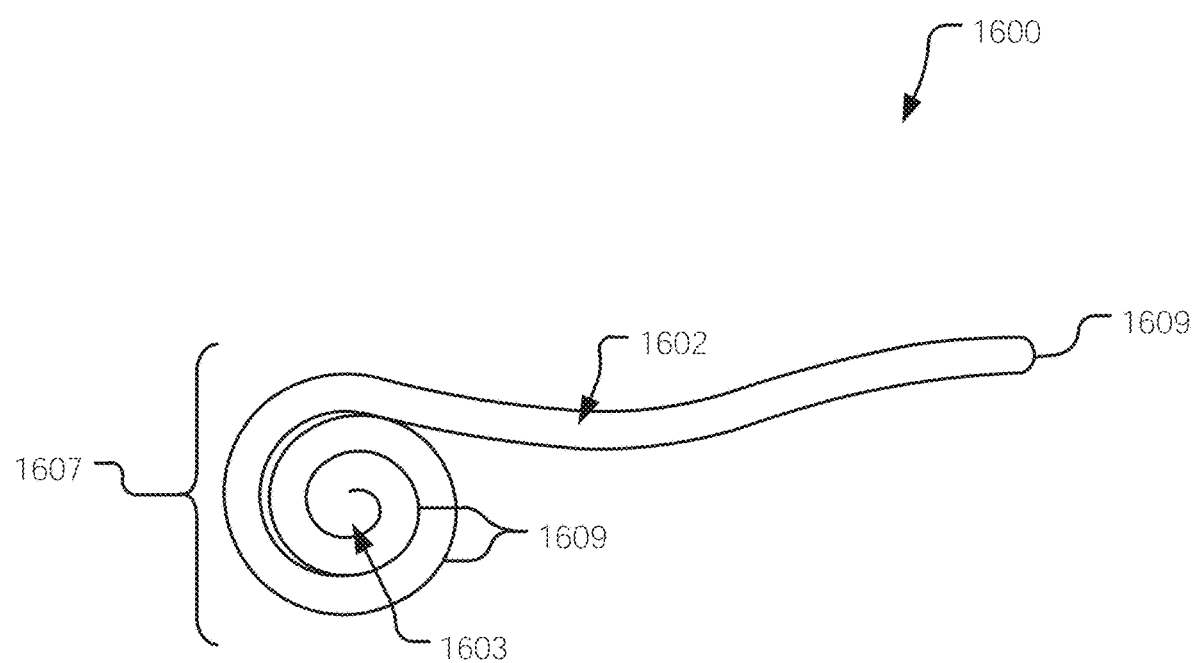
Figure 16:
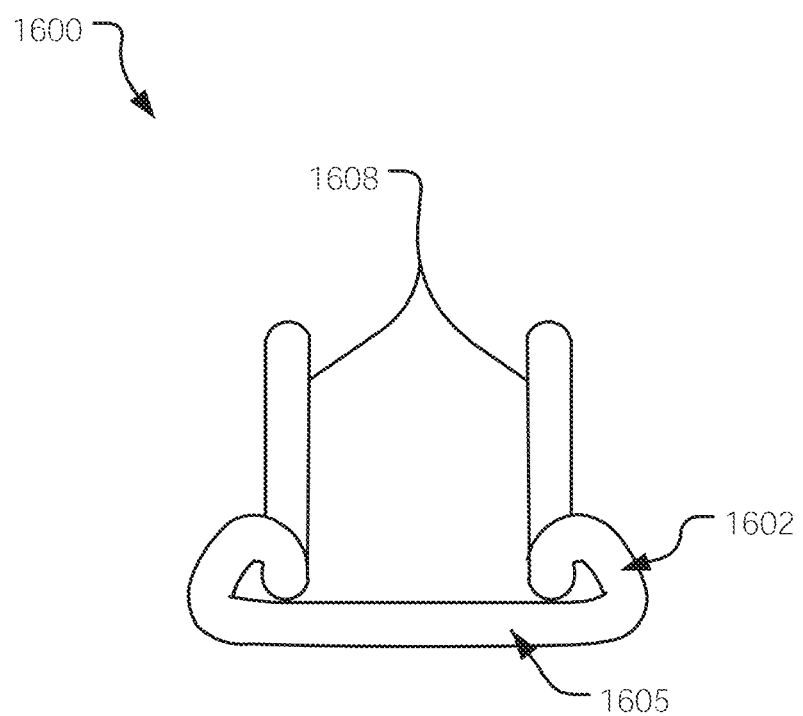
Figure 16:
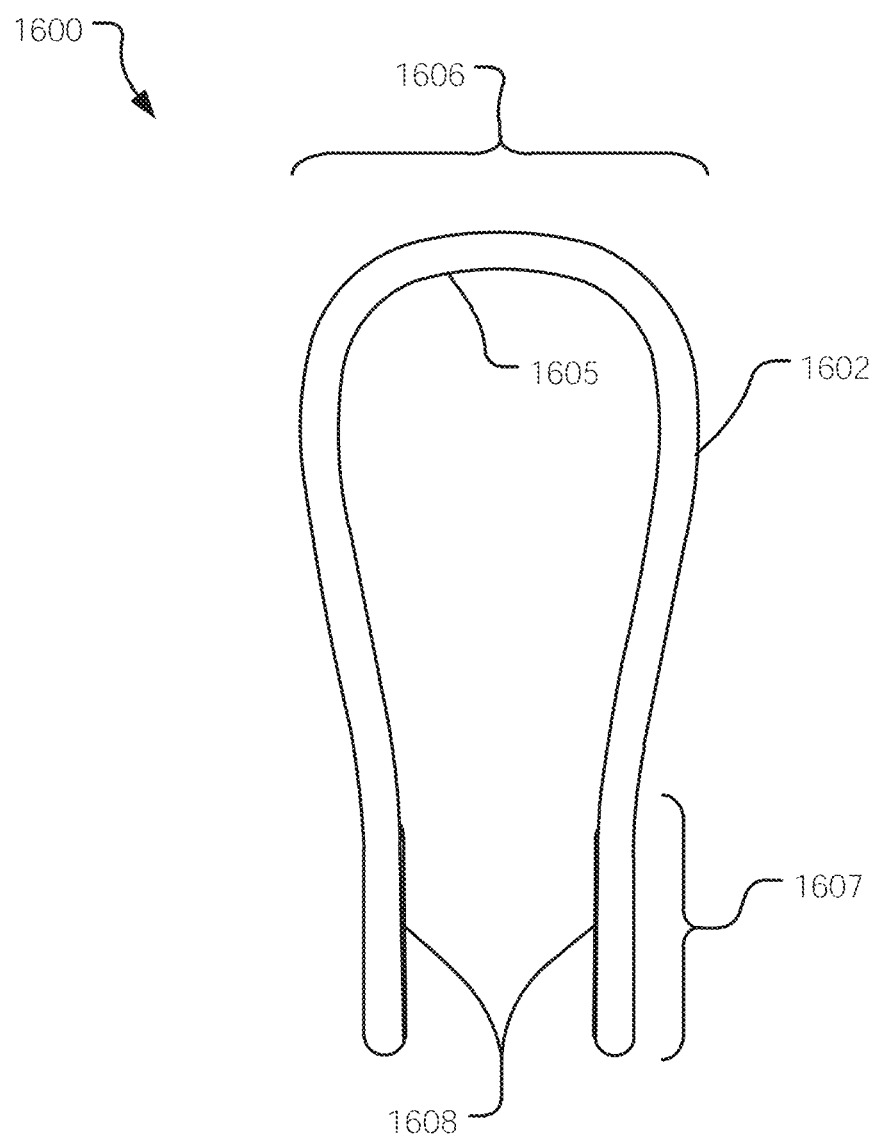
Figure 16:
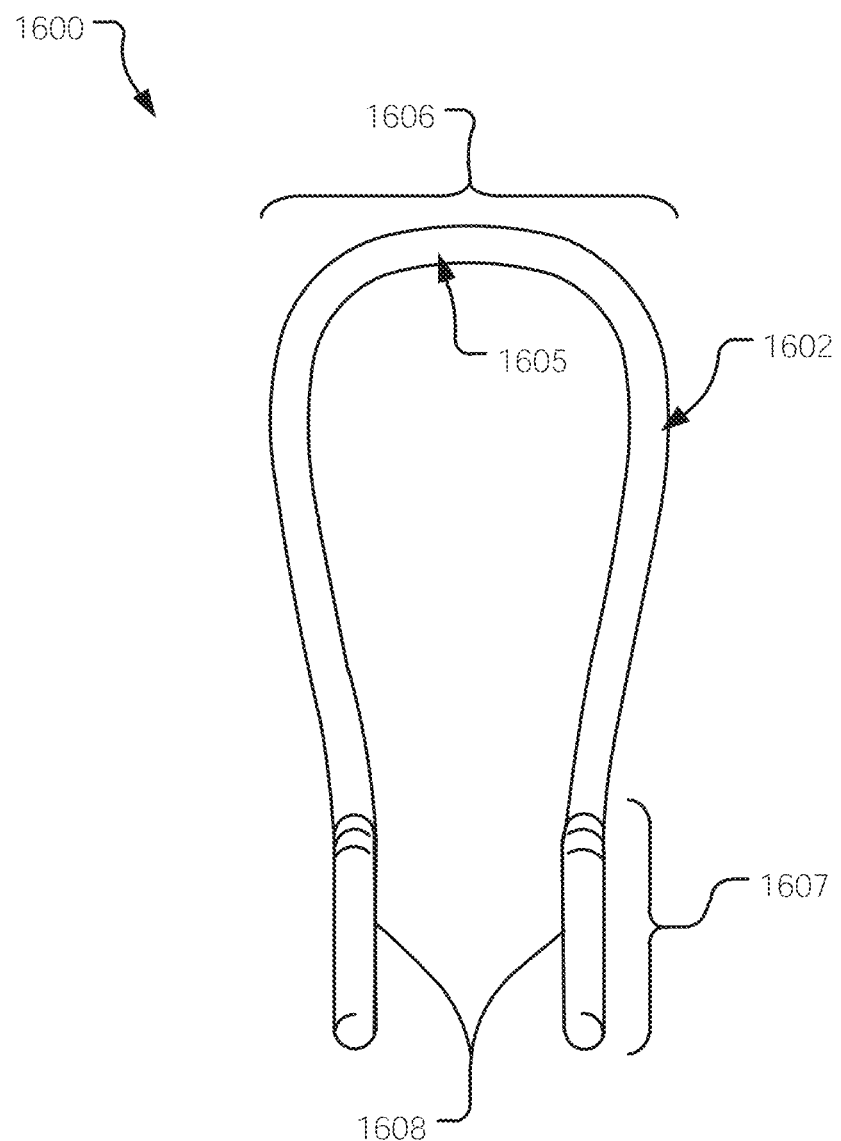

In some embodiments, a FIG. 16 series of figures, a FIG. 17 series of figures, a FIG. 18 series of figures, and a FIG. 19 series of figures may all address and focus on various nose-clip embodiments. Such nose-clips may be intended to be used in conjunction with using various face soaking device embodiments. In some embodiments, a system may comprise a given face soaking device along with a given nose-clip embodiment. Such nose-clips may facilitate use with various breathing apparatus embodiments. For some users 9000, they may desire use of a nose-clip to close their nostrils when otherwise using their mouth to breathe by using a given breathing apparatus embodiment.

In some embodiments of using various face soaking device embodiments (e.g., face soaking device 100), user 9000 may also use a nose-clip 1600, a nose-clip 1700, a nose-clip 1800, a nose-clip 1900, nose-plugs, and/or any other device suitable for closing (e.g. sealing and/or shutting) nostrils off from liquid 101. Closing off the nostrils of user 9000 may facilitate ease of breathing when face 9010 may be immersed in liquid 101. In some embodiments, a system (kit) for soaking face 9010 of user 9000 may comprise face soaking device 100 and at least one of: nose-clip 1600, nose-clip 1700, nose-clip 1800, nose-clip 1900, nose-plugs, and/or any other device suitable for removably closing nostrils off from liquid 101.

In some embodiments, such nose-clip(s) may be constructed from at least one wire that may bend without breaking, such that the at least one wire may be bent into a shape which removably clamps the nostrils shut. When bent to clamp the nostrils shut, the at least one wire may be sufficiently strong to resist forces exerted by the nostrils on the wire.

FIG. 16A may depict an exemplary embodiment of nose-clip 1600, comprising tight coils 1609, shown from a top perspective view. FIG. 16B may depict nose-clip 1600, shown from a bottom perspective view. FIG. 16C may depict nose-clip 1600, shown from a front view. FIG. 16D may depict nose-clip 1600, shown from a side view. FIG. 16E may depict nose-clip 1600, shown from a back view. FIG. 16F may depict nose-clip 1600, shown from a top view. FIG. 16G may depict nose-clip 1600, shown from a bottom view.

In some embodiments, nose-clip 1600 may comprise a wire that may be at least one elongate member 1602 with two disposed opposite terminal ends 1603. In some embodiments, the at least one wire may be bent generally into a "U" shape with a central bend region 1605 forming a major radius 1606 of the "U" shape. See e.g., FIG. 16A. When in use, each terminal end 1603 and/or each terminal end region may be brought towards each other pinching the nostrils shut between to the two terminal ends 1603 and/or the two terminal end regions. When in use, the central bend region 1605 may be either over a bridge of the nose or disposed under the nostrils, i.e. closer to a mouth than to the bridge. To remove such a wire, the two terminal ends 1603 and/or the two terminal end regions may be bent away from each other a distance sufficient to permit the nostrils to open and for the wire to be removed from the nose.

In some embodiments, each terminal end 1603 or each terminal end region may form a terminating structure 1607. See e.g., FIG. 16A. In some embodiments, terminating structure 1607 may comprise one or more of: a series of tight coils 1609 (see e.g., FIG. 16A through FIG. 16G), a series of loose coils 1710 (see e.g., FIG. 17A through FIG. 17G), an ovoid structure, a spherical structure 1811 (see e.g., FIG. 18A through FIG. 18F), a disk structure, a rod structure, and/or the like. Such terminating structures may form a pad 1608. See e.g., FIG. 16C. Pad 1608 may provide additional surface area to exert against each nostril.

In some embodiments, each terminating structure 1607 may be formed by bending the terminal ends 1603 into the terminating structure 1607, e.g. with the series of tight coils 1609 (see e.g., FIG. 13A through FIG. 13G) and/or with the series of loose coils 1710 (see e.g., FIG. 17A through FIG. 17G). A curvature associated with major radius 1606 may be more gentle (less curved) than curvatures associated with tight coils 1609 and/or with loose coils 1710. That is, curvatures associated with tight coils 1609 and/or with loose coils 1710 may be greater (bend sharper) than the curvature associated with major radius 1606. The curvature associated with tight coils 1609 may be greater (bend sharper) than the curvature associated with loose coils 1710 (see e.g., FIG. 17A for loose coils 1710).

In some embodiments, each terminating structure 1607 may be constructed of a same material, such as at least one wire. In some embodiments, each terminating structure 1607 may be constructed of a material different than that of the at least one wire.

In some embodiments, the at least one wire may be a metal wire. In some embodiments, the at least one wire may be a solid metal wire. In some embodiments, the metal may be one or more of: copper, aluminum, steel, stainless steel, brass, various alloys, and the like.

In some embodiments, the at least one metal wire and/or the at least one elongate member 1602 may be coated with a polymer. See e.g., nose-clip 1900 embodiments of FIG. 19A through FIG. 19G. This polymer coating may waterproof the metal wire and/or the at least one elongate member 1602. The polymer may provide durability to the wire, e.g. by minimizing corrosion. The polymer may also promote comfort to user 9000 when being worn. The polymer may also comprise various colorants so the polymer when cured appears in a variety of colors. The polymer may be a plastic and/or an elastomer (e.g. silicone, rubber, etc.). For example, and without limiting the scope of the present invention, the plastic may be a plastisol type of PVC suspension wherein the wire may be dipped into a liquid plastisol and then cured into a plastic covering of the wire. In a similar fashion, the wire may be powder coated with the polymer (plastic).

FIG. 17A through FIG. 17G may depict nose-clip 1700 with loose coils 1710. Aside from loose coils 1710, nose-clip 1700 may be substantially similar to nose-clip 1600. FIG. 17A may depict an exemplary embodiment of nose-clip 1700, comprising loose coils 1710, shown from a top perspective view. FIG. 17B may depict nose-clip 1700, shown from a bottom perspective view. FIG. 17C may depict nose-clip 1700, shown from a front view. FIG. 17D may depict nose-clip 1700, shown from a side view. FIG. 17E may depict nose-clip 1700, shown from a back view. FIG. 17F may depict nose-clip 1700, shown from a top view. FIG. 17G may depict nose-clip 1700, shown from a bottom view.

FIG. 18A through FIG. 18F may depict nose-clip 1800 with spherical structure 1811. In some embodiments, terminating structure 1607 of nose-clip 1800 may comprise spherical structure 1811; otherwise nose-clip 1800 may be substantially similar to nose-clip 1600. FIG. 18A may depict an exemplary embodiment of nose-clip 1800, comprising a pair of spherical terminating structures 1811, shown from a top perspective view. FIG. 18B may depict nose-clip 1800, shown from a bottom perspective view. FIG. 18C may depict nose-clip 1800, shown from a front view. FIG. 18D may depict nose-clip 1800, shown from a side view. FIG. 18E may depict nose-clip 1800, shown from a back view. FIG. 18F may depict nose-clip 1800, shown from a top view.

FIG. 19A may depict an exemplary embodiment of nose-clip 1900, wherein nose-clip 1900 may be coated with a polymer, shown from a top perspective view. FIG. 19B may depict nose-clip 1900, shown from a bottom perspective view. FIG. 19C may depict nose-clip 1900, shown from a front view. FIG. 19D may depict nose-clip 1900, shown from a side view. FIG. 19E may depict nose-clip 1900, shown from a back view. FIG. 19F may depict nose-clip 1900, shown from a top view. FIG. 19G may depict nose-clip 1900, shown from a bottom view.

In some embodiments, nose-clip 1900 may be substantially similar to nose-clip 1600, except elongate member 1602 of nose-clip 1900 may be coated with the polymer. In some embodiments, when the at least one wire may be coated with the polymer, such that surface area of pad 1608 may be increased. See e.g., FIG. 19A. For example, and without limiting the scope of the present invention, when the terminal ends 1603 may be bent into the series of tight coils 1609, that series of tight coils 1609 once coated with the polymer may appear as a disc like pad 1608, with no air gaps remaining between tight coils. See e.g., FIG. 19A.

In some embodiments, the at least one solid metal (e.g., of nose-clip 1600, nose-clip 1700, nose-clip 1800, and/or nose-clip 1900) wire may be 10 gauge to 12 gauge in diameter. In some embodiments, the at least one solid metal (e.g., of nose-clip 1600, nose-clip 1700, nose-clip 1800, and/or nose-clip 1900) wire may be 8 gauge to 16 gauge in diameter. Testing may have determined that copper wire diameters of smaller than 12 gauge, for example 14 gauge, may not have sufficient strength to effectively clamp some nostrils shut. Testing may have determined that copper wire diameters greater than 10 gauge may be difficult for some users (e.g. children and/or elderly users) to bend the wire such that the wire may clamp the nostrils shut.

In some embodiments, the at least one elongate member 1602 may be a plurality of elongate members. For example, and without limiting the scope of the present invention, in some embodiments there may be two or three elongate members, wherein each elongate member may be a metal wire, such the plurality of metal wires, may together be bent into the "U" shape. Such a plurality of metals wires may be generally parallel with each other. Such a plurality of metal wires may be wrapped helically around each other. Such a plurality of metal wires may be twisted around each other. Such a plurality of metal wires may be braided with each other. When a plurality of metal wires may be used, smaller diameters (higher gauges) of metal wire may be used.

In some embodiments, any such nose-clip as noted above may also comprise a leash (i.e., tether), wherein the leash may removably tether the nose-clip to another object of vessel 200 or some subassembly of a given face soaking device (e.g., face soaking device 100), such that the nose-clip may be on hand when user 9000 may want to use the nose-clip. Such a leash may minimize loss of the nose-clip. For example, and without limiting the scope of the present invention, the leash may removably tether the nose-clip to breathing apparatus 400. For example, and without limiting the scope of the present invention, the leash may removably tether the nose-clip to rim 225.

In some embodiments, a given nose-clip embodiment (e.g., of nose-clip 1600, nose-clip 1700, nose-clip 1800, and/or nose-clip 1900) may be kept associated with a given vessel embodiment (e.g., vessel 3400) with a nose-clip holder means. See FIG. 34. In some embodiments, vessel 3400 may be substantially similar to vessel 200, except vessel 3400 may comprise at least one nose-clip holder recessed cavity 3403 and at least one recessed cavity 3412 for receiving at least one recess pocket 3411. For example, vessel 3400 may comprise vessel lining 200*a* and vessel cover 200*b*, as vessel 200 may comprise. In some embodiments, neither nose-clip holder recessed cavity 3403 nor the at least one recessed cavity 3412 for receiving at least one recess pocket 3411 may be protrude into vessel lining 200*a*. In some embodiments, neither nose-clip holder recessed cavity 3403 nor the at least one recessed cavity 3412 for receiving at least one recess pocket 3411 may breach vessel lining 200*a*.

In some embodiments, the nose-clip holder means may comprise a nose-clip holder 3402 and nose-clip holder recessed cavity 3403. In some embodiments, nose-clip holder recessed cavity 3403 may be a recessed cavity located in a surface of a roof 1020. In some embodiments, there may be at least one such nose-clip holder recessed cavity 3403. In some exemplary embodiments, there may be at least two such nose-clip holder recessed cavities 3403. In some embodiments, each nose-clip holder recessed cavity 3403 may be proximate to at least some portion of a membrane switch cover 1001. In some embodiments, this proximate distance may be six inches or less. In some exemplary embodiments, there may be two nose-clip holder recessed cavity 3403, with one located on either side of membrane switch cover 1001. See e.g., FIG. 34.

In some embodiments, each such nose-clip holder recessed cavity 3403 may be sized and shaped to receive at least one nose-clip holder 3402. In some embodiments, each such nose-clip holder recessed cavity 3403 may be sized and shaped to removably receive at least one nose-clip holder 3402. In some embodiments, a nature of fitting between nose-clip holder recessed cavity 3403 and nose-clip holder 3402 may be a frictional fit. In some embodiments, nose-clip holder recessed cavity 3403 may comprise a frictional means 3405 to provide a frictional fit with nose-clip holder 3402. In some embodiments, this frictional means 3405 may be at least one crush rib located on at least one periphery side wall of nose-clip holder recessed cavity 3403. See FIG. 34. In some embodiments, nose-clip holder 3402 may be removable from nose-clip holder recessed cavity 3403; which may facilitate cleaning and/or sanitizing.

In some embodiments, nose-clip holder 3402 may comprise at least one nose-clip cavity 3407. In some embodiments, each nose-clip cavity 3407 may be sized to removably receive a given nose-clip embodiment (e.g., of nose-clip 1600, nose-clip 1700, nose-clip 1800, and/or nose-clip 1900). In some embodiments, nose-clip holder 3402 may be rigid to semi-rigid. In some embodiments, nose-clip holder 3402 may be substantially constructed from EVA (ethylene vinyl acetate) or other similar material.

In some embodiments, a given mouthing portion 403 embodiment may be kept associated with a given vessel embodiment (e.g., vessel 3400) with a mouthing portion holder means. See FIG. 34.

In some embodiments, the mouthing portion holder means may comprise recess pocket 3411 and recessed cavity 3412 for receiving recess pocket 3411. In some embodiments, this recessed cavity 3412 may be a recessed cavity originating on a surface of vessel cover 200*b* of vessel 3400. In some embodiments, this recessed cavity 3412 may be a recessed cavity located in side wall 205 of vessel 3400. In some embodiments, there may be at least one such recessed cavity 3412 in side wall 205. In some exemplary embodiments, there may be at least two such recessed cavities 3412 in side wall 205. In some exemplary embodiments, there may be one such recessed cavity 3412 in first side wall 206 and one such recessed cavity 3412 in third side wall 208 (note third side wall 208, which opposes first side wall 206 may not be shown in FIG. 34). In some embodiments, such a recessed cavity 3412 may be located in any of the side walls 205, including second side wall 207 and/or fourth side wall 209.

In some embodiments, each such recessed cavity 3412 may be sized and shaped to receive at least one recess pocket 3411. In some embodiments, each such recessed cavity 3412 may be sized and shaped to removably receive at least one recess pocket 3411. In some embodiments, a nature of fitting between such recessed cavities 3412 and recess pockets 3411 may be a frictional fit, such as a press fit. In some embodiments, a nature of fitting between such recessed cavities 3412 and recess pockets 3411 may be a permanent connection. Such a permanent connection may be accomplished by one or more of the following: mechanical fasteners, chemical adhesives, ultrasonic welding, heat welding, and/or solvent bonding. In some embodiments, recess pockets 3411 may be substantially constructed of a thermoformed plastic.

In some embodiments, recess pocket 3411 may comprise an internal cavity sized and shaped to receive at least one mouthing portion 403. See FIG. 34. Such internal cavities of recess pockets 3411 may be used to store mouthing portions 403 when not in use. In some embodiments, bottom surfaces of this internal cavity may be sloped to facilitate liquid 101 drainage and not pooling within the internal cavity. In some embodiments, a stem 3415 may be attached via a stem attachment means 3416 to the bottom surface of the internal cavity of recess pocket 3411. See FIG. 34. In some embodiments, stem attachment means 3416 may be a mechanical fastener, such as, but not limited, to a screw. In some embodiments, stem 3415 may be sized and shaped to removably couple with mouthing portion 403, by at least some portion of stem 3415 removably fitting into at least one orifice of mouthing portion 403.

A FIG. 5 series of figures may comprise FIG. 5A through FIG. 5I. This FIG. 5 series of figures may focus on depicting an exemplary embodiment of a head rest subassembly 500, its various component parts, structures, and communicative relationships. In some embodiments, head rest subassembly 500 may physically support a portion of the head of user 9000. For example and without limiting the scope of the present invention, the portion of the head that may be supported by head rest subassembly 500 may be a forehead, or some portion thereof, of user 9000. In some embodiments, head rest subassembly 500 in its various embodiments, may promote comfort of user 9000 (particularly for neck 9020).

Figure 5A:
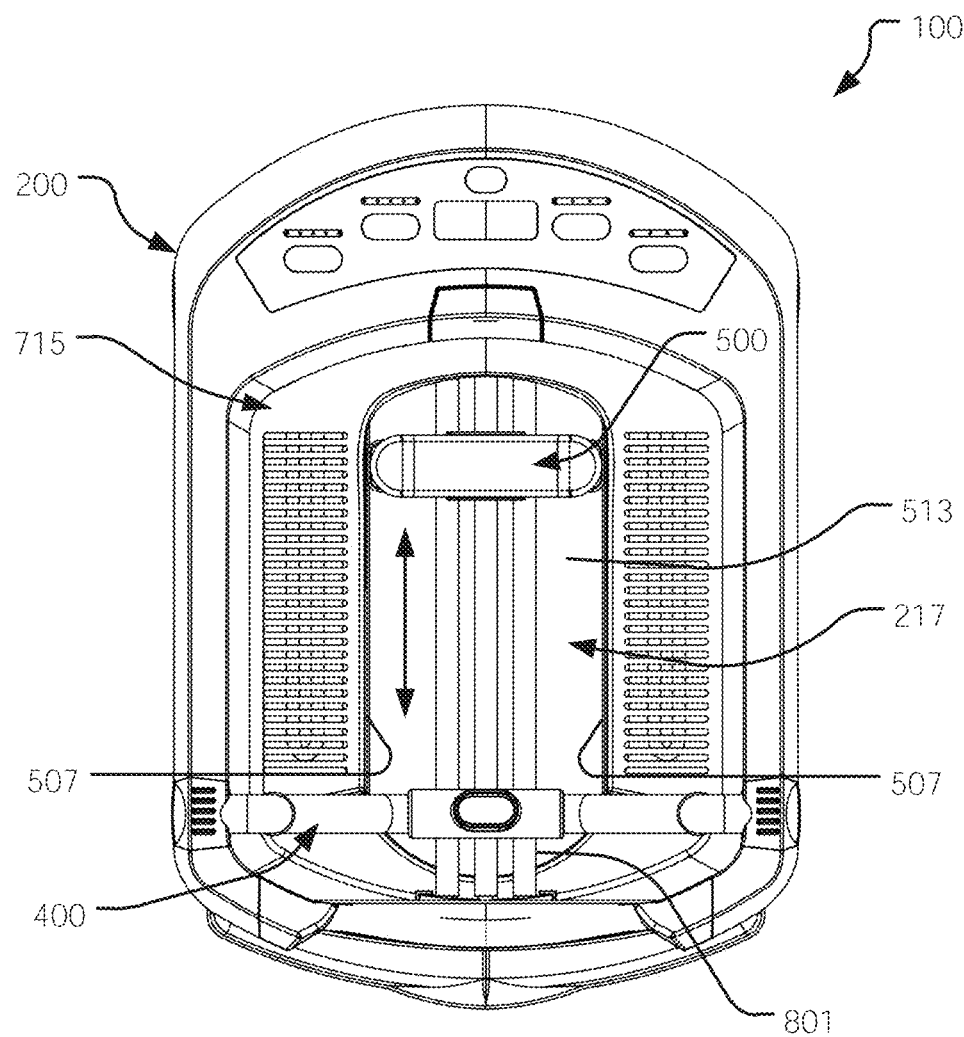
FIG. 5A may depict the face soaking device of FIG. 2A, shown from a top view, wherein a head rest subassembly may be in backwards configuration (i.e., a rear configuration).
Figure 5B:
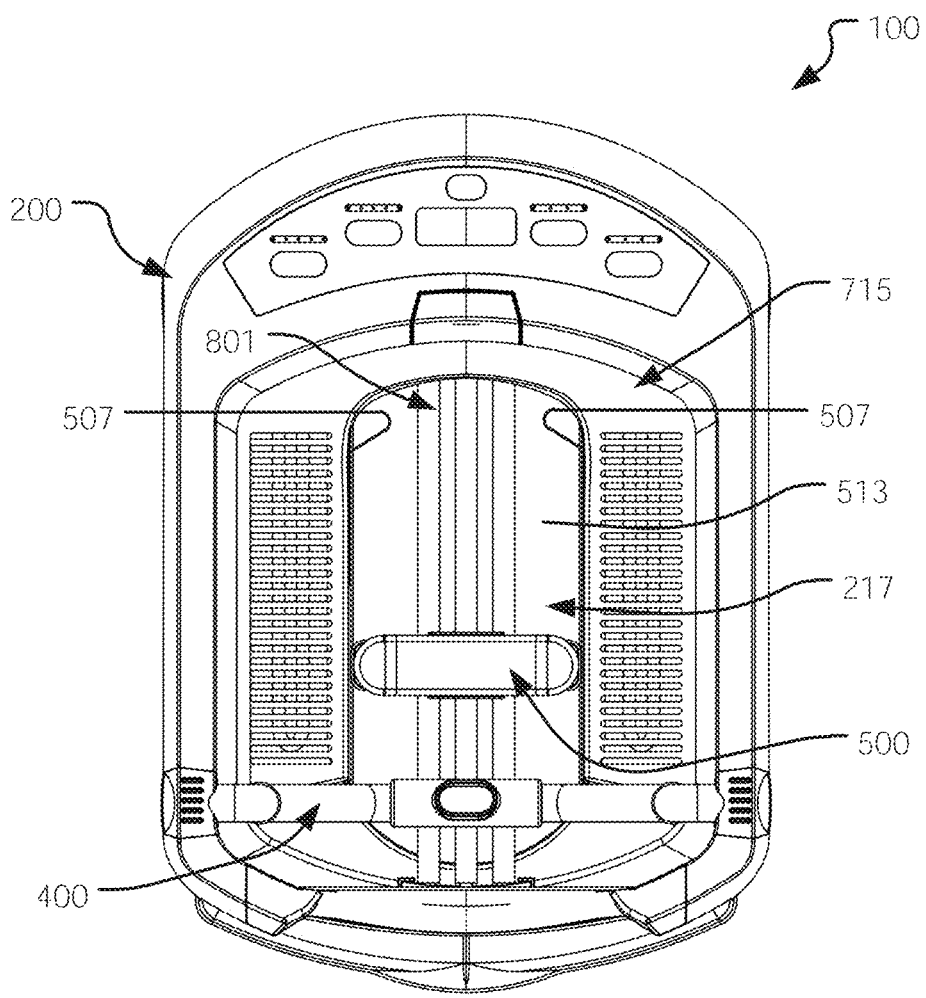
FIG. 5B may depict the face soaking device of FIG. 2A, shown from a top view, wherein the head rest subassembly may be in a forwards configuration.
Figure 5C:
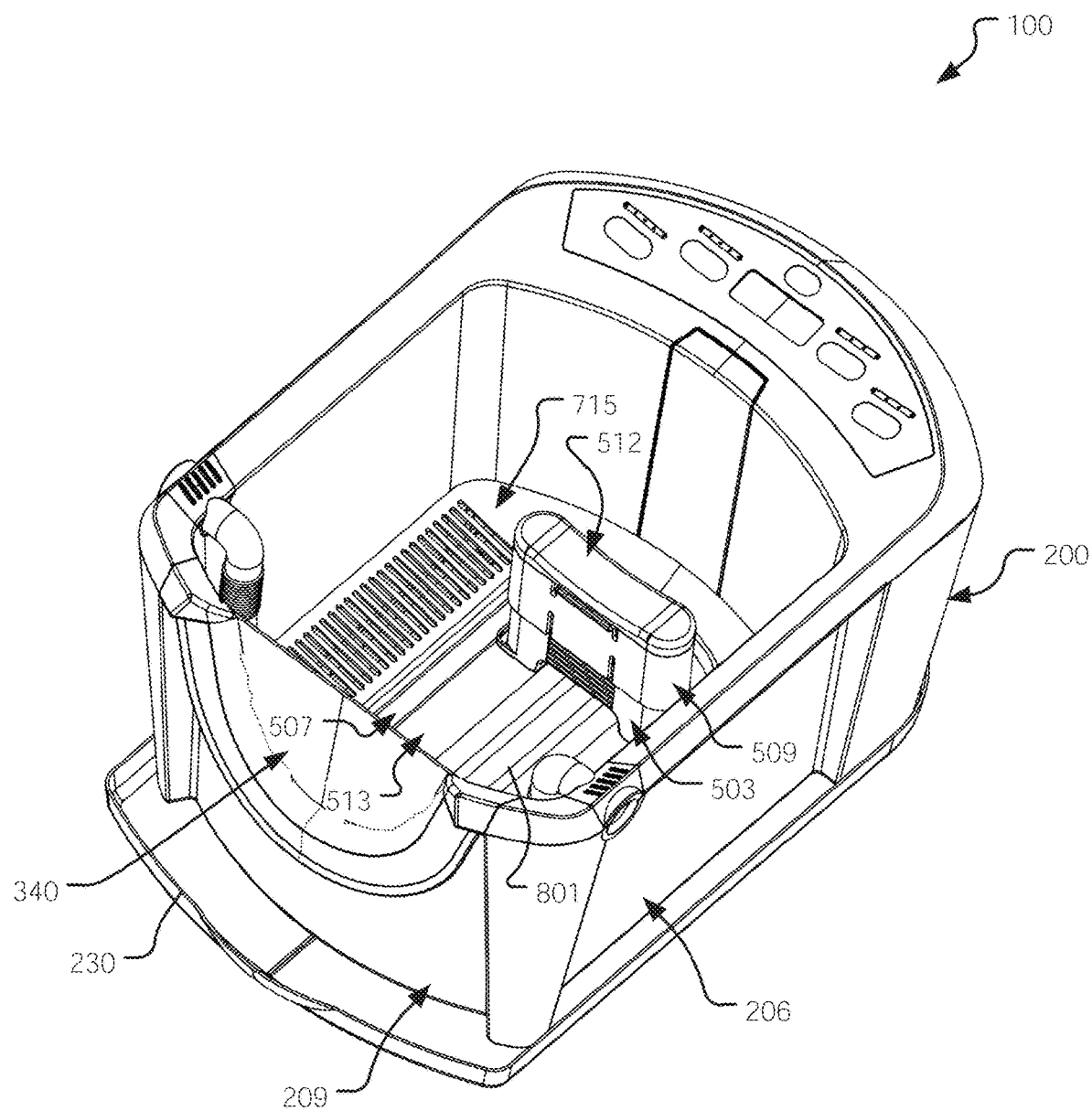
FIG. 5C may depict the face soaking device of FIG. 2A, shown from a top view, wherein the head rest subassembly may be in an up (a raised) configuration (as well as in the backwards configuration).
Figure 5D:
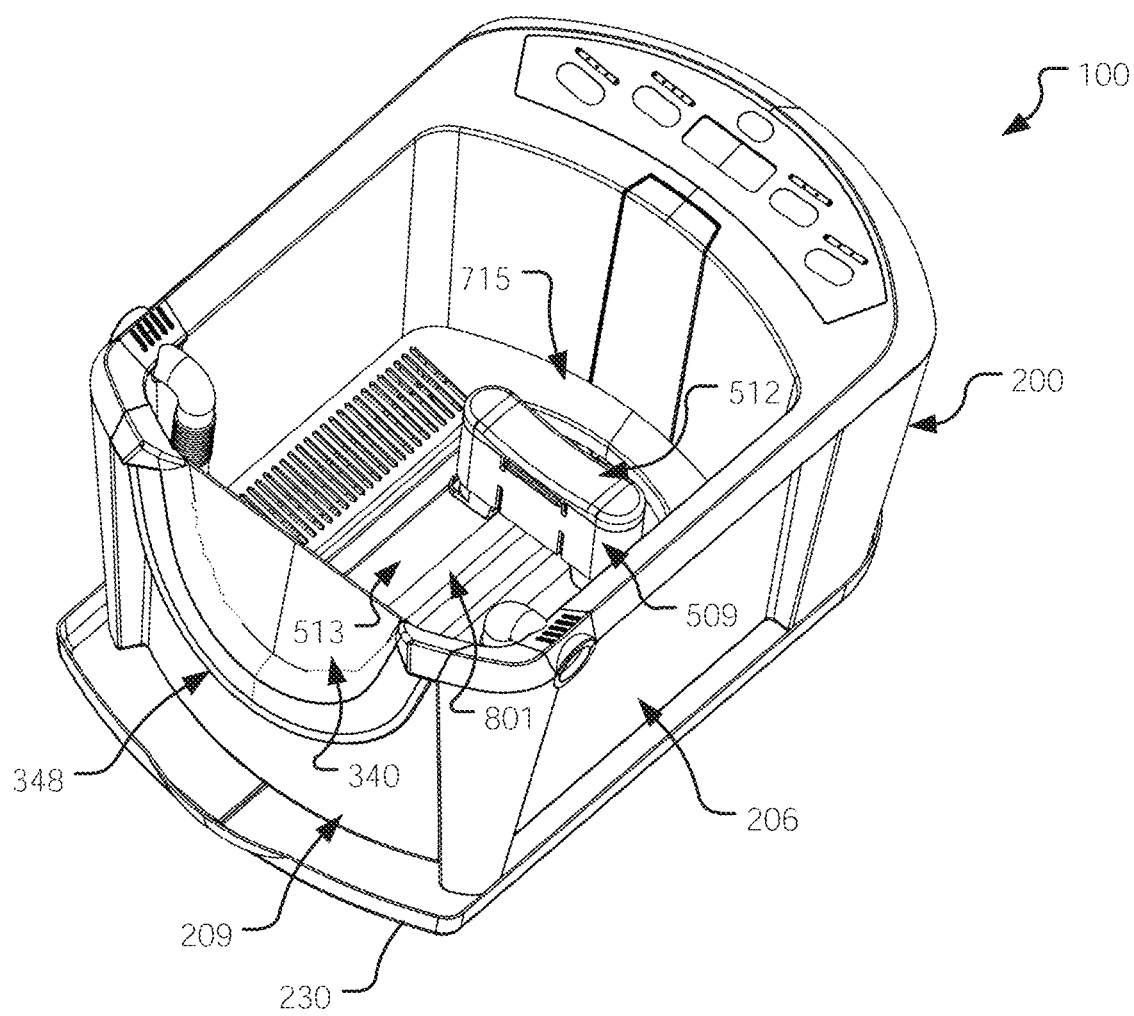
FIG. 5D may depict the face soaking device of FIG. 2A, shown from a top view, wherein the head rest subassembly may be in a down (a lowered) configuration (as well as in the backwards configuration).
Figure 5E:
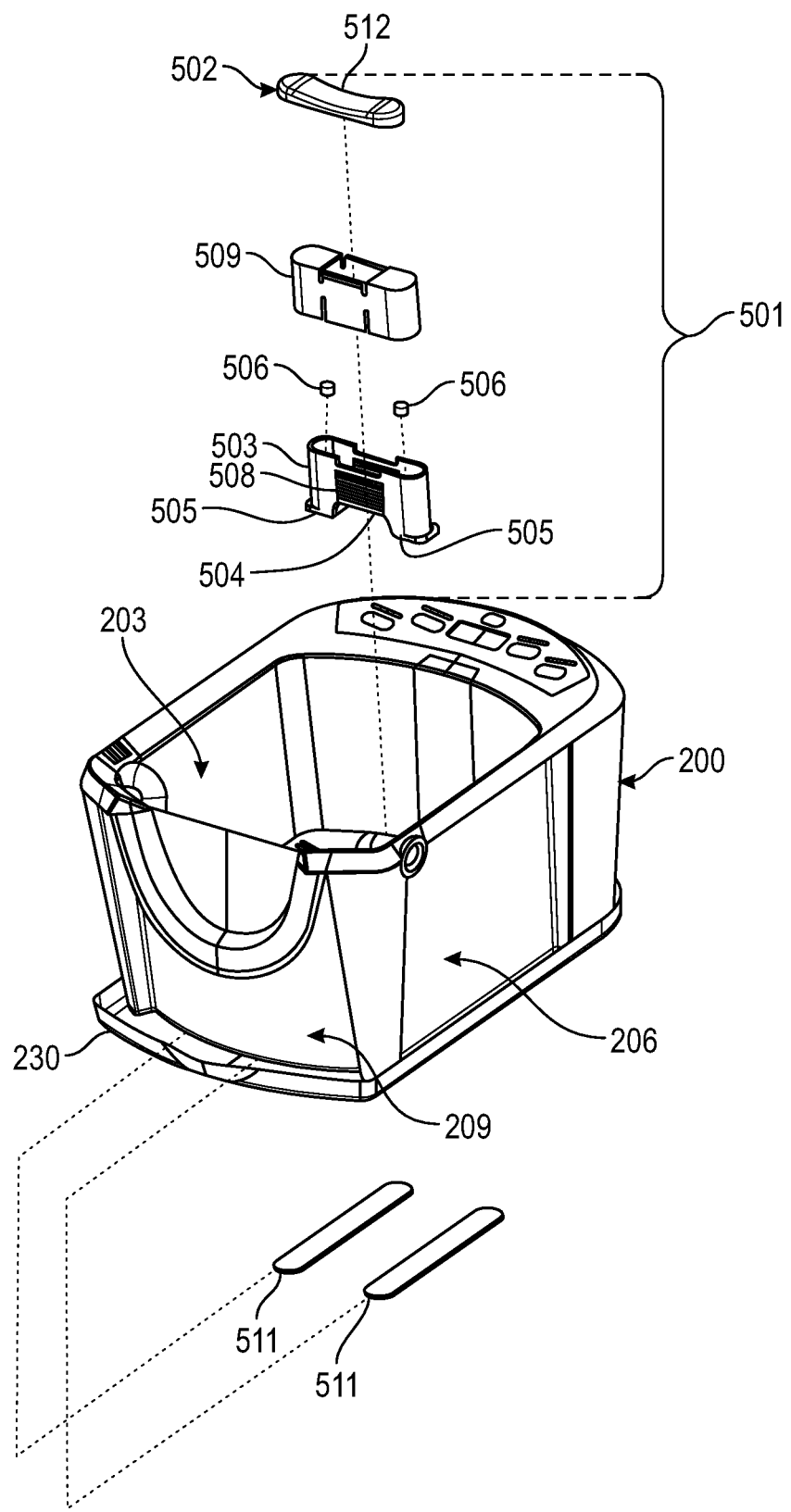
FIG. 5E may depict an exploded top perspective view of the head rest subassembly exploded from the vessel of the face soaking device of FIG. 2A.
Figure 5F:
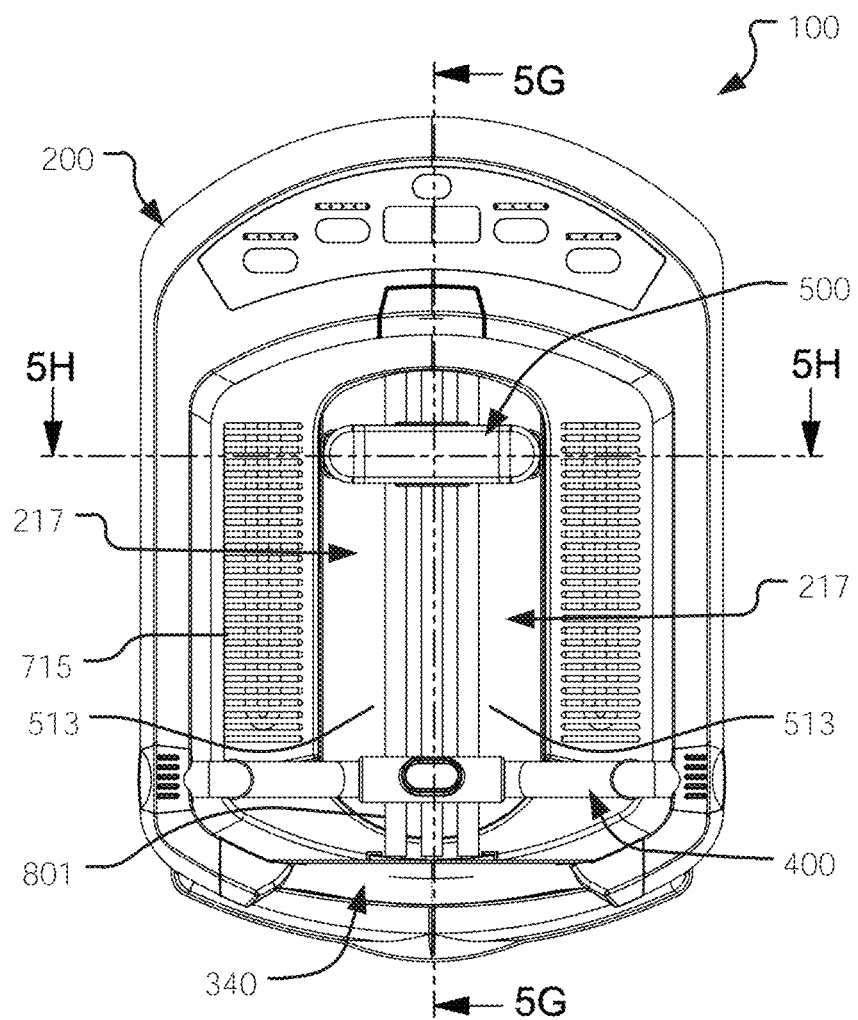
FIG. 5F may depict a top view of the face soaking device of FIG. 2A, wherein FIG. 5F further depicts two sectional lines, sectional line 5G-5G and sectional line 5H-5H; wherein sectional line 5G-5G may be a longitudinal sectional line through the head rest subassembly, and sectional line 5H-5H may a transverse-width sectional line through the head rest subassembly.
Figure 5G:
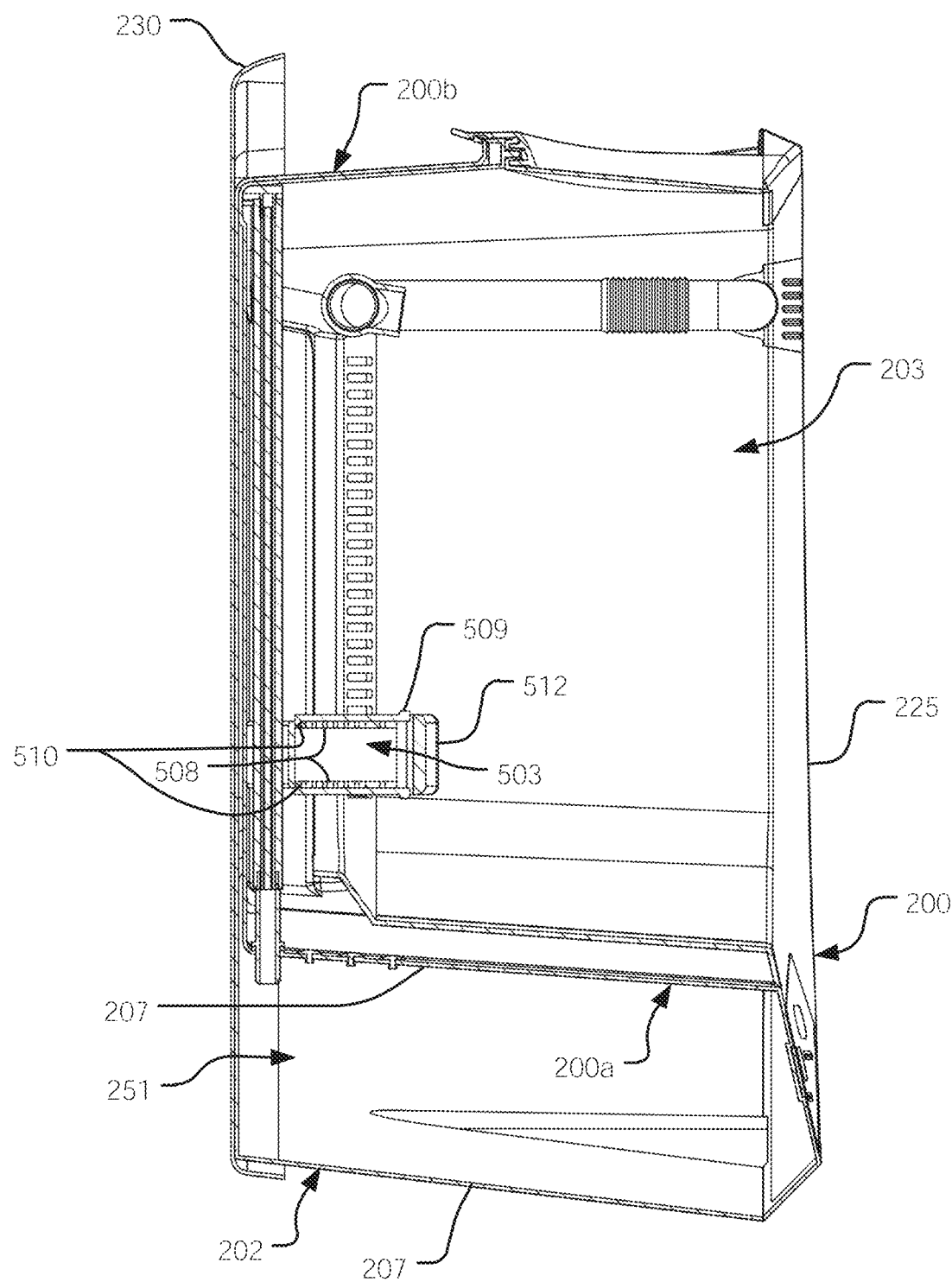
FIG. 5G may depict a longitudinal cross-sectional view along sectional line 5G-5G through the head rest subassembly.
Figure 5H:
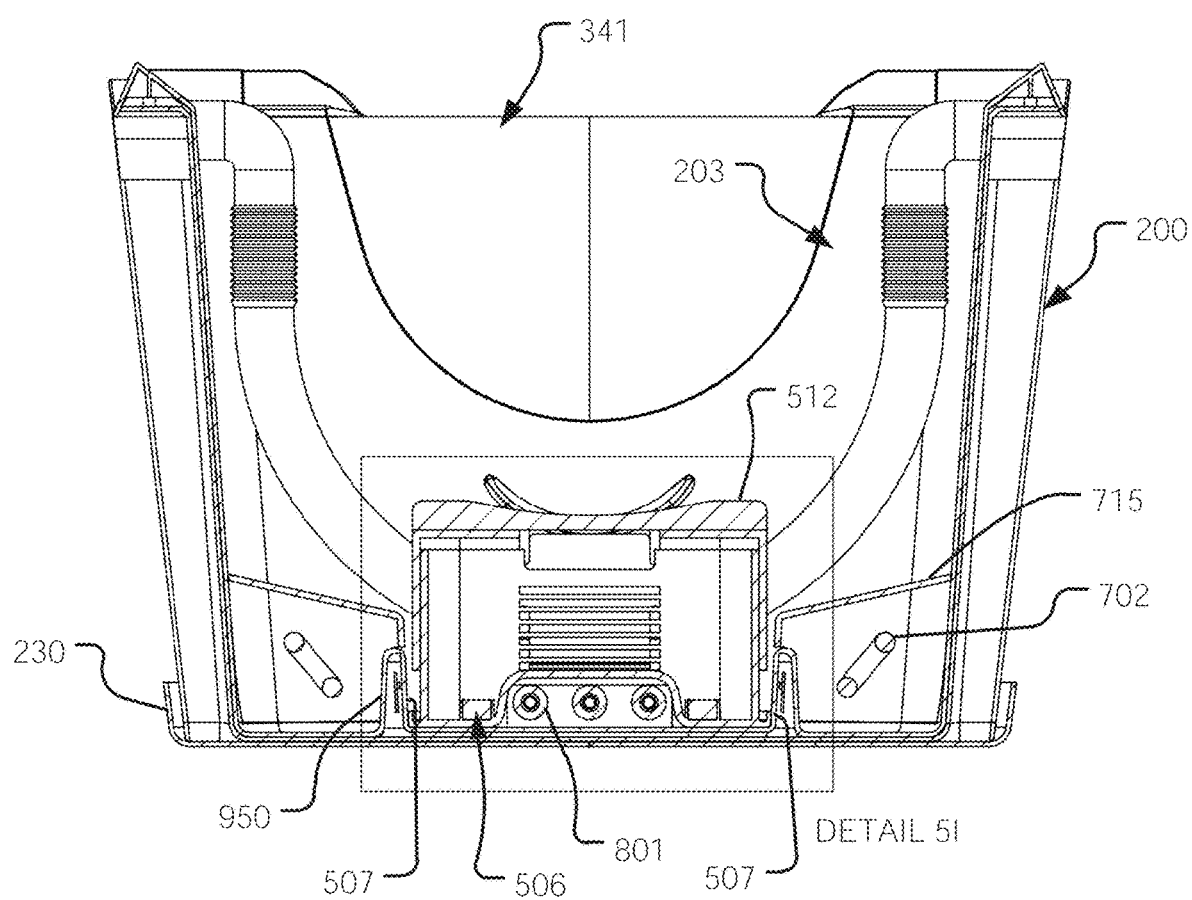
FIG. 5H may depict a transverse-width cross-sectional view along sectional line 5H-5H through the head rest subassembly; wherein a region of Detail 5I may depict the head rest subassembly.
Figure 5I:
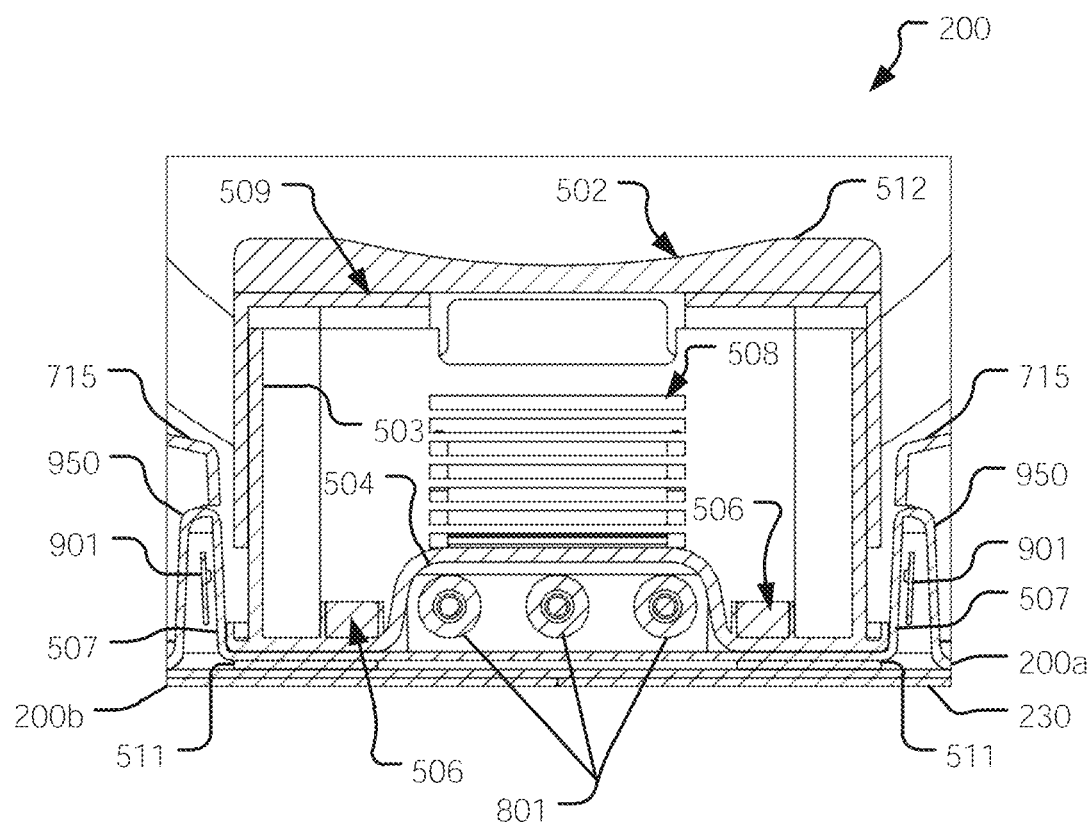
FIG. 5I may depict a close-up view of Detail 5I.

FIG. 5E may depict an exploded top perspective view of head rest subassembly 500 exploded from the vessel (e.g., vessel 200) of face soaking device 100. FIG. 5F may depict a top view of face soaking device 100, wherein FIG. 5F further depicts two sectional lines, sectional line 5G-5G and sectional line 5H-5H; wherein sectional line 5G-5G may be a longitudinal sectional line through head rest subassembly 500, and sectional line 5H-5H may a transverse-width sectional line through head rest subassembly 500. FIG. 5G may depict a longitudinal cross-sectional view along sectional line 5G-5G through head rest subassembly 500. FIG. 5H may depict a transverse-width cross-sectional view along sectional line 5H-5H through head rest subassembly 500; FIG. 5H may further depict a region of Detail 5I that may focus on areas of head rest subassembly 500. FIG. 5I may depict a close-up view of Detail 5I.

In some embodiments, a given face soaking device (e.g., face soaking device 100) may comprise head rest subassembly 500. See e.g., FIG. 5E. In some embodiments, head rest subassembly 500 may be attached to vessel 200. In some embodiments, the nature of the attachment may be removable; whereas, in other embodiments the nature of the attachment may be non-removable. The FIG. 5 series of figures may depict removable attachment embodiments.

In some embodiments, head rest subassembly 500 may comprise a support member 501 (see e.g., FIG. 5E) or a strap (not depicted). Support member 501 or the strap may be configured to physically support a portion of the head of user 9000. For example and without limiting the scope of the present invention, the portion of the head that may be supported by the support member may be a forehead, or portion thereof, of user 9000.

In some embodiments, support member 501 may be semi-rigid to rigid. Support member 501 may be a structural member(s). In some embodiments, an upper surface or a top surface of support member 501 or the strap may be substantially horizontal (i.e. substantially parallel with the substrate) when head rest subassembly 500 may be in physical contact with vessel 200. In some embodiments, the upper surface or the top surface of support member 501 or the strap may be substantially horizontal (i.e. substantially parallel with bottom interior surface 217) when head rest subassembly 500 may be in physical contact with vessel 200.

In some embodiments, support member 501 may comprise a comfortable exterior surface 502. See e.g., FIG. 5E. Comfortable exterior surface 502 may provide comforting support to at least some portion of the head region of user 9000. In some embodiments, comfortable exterior surface 502 may be a compressible foam material. In some embodiments, the compressible foam material may be replaced with a soft elastomeric material, such as silicone or other soft elastomeric materials. In some embodiments, comfortable exterior surface 502 may circumscribe support member 501 along a longitude of support member 501. In some embodiments, comfortable exterior surface 502 may at least partially cover the upper surface or top surface of support member 501.

In some embodiments, the strap may be constructed of flexible material. A length of the strap may be greater than a width of the strap. The strap may comprise two ends. Each end of the strap may be attached to at least two different at least one wall 201. Strap embodiments may not be depicted in the figures.

For example, and without limiting the scope of the present invention, the strap may be configured to act as a sling or a cradle for the forehead. In some embodiments, the strap may be a woven material. In some embodiments, the strap may be water, mildew, and abrasion resistant. The strap may be constructed of natural and/or synthetic materials. Natural materials may comprise one or more of: cotton, wool, hemp, leather, and the like. Synthetic materials may comprise one or more of: nylon, polypropylene, polyester, neoprene, and the like.

In some embodiments, support member 501 may comprise at least one post 503, a cap 509, and comfortable exterior surface 502. See e.g., FIG. 5E. In some embodiments, at least one post 503 may be in physical contact with cap 509. In some embodiments, cap 509 may be a cap covering at least a portion of at least one post 503. In some embodiments, cap 509 may be in physical contact with comfortable exterior surface 502. In some embodiments, comfortable exterior surface 502 may at least cover a portion of an upper surface of cap 509 or at least a portion of an upper surface of at least one post 503. In some embodiments, comfortable exterior surface 502 may be pad 512. In some embodiments, head rest subassembly 500 may also comprise at least one magnet 506 and at least one plate 511, in addition to comprising support member 501. In some embodiments, at least one magnet 506 may be located within at least one post 503 (e.g., at a bottom of at least one post 503). In some embodiments, at least one plate 511 may be disposed between vessel lining 200a and vessel cover 200b (see e.g., FIG. 2G). See e.g., FIG. 5E for at least one plate 511.

In some embodiments, support member 501 may comprise at least one post 503. See e.g., FIG. 5E. In some embodiments, at least one post 503 may be removably located within internal volume 220 of vessel 200. See e.g., FIG. 5G and FIG. 5H. In some embodiments, at least one post 503 may be in removable physical contact with bottom interior surface 217 of at least one base 215 of vessel 200. See e.g., FIG. 5G and FIG. 5H. In some embodiments, at least one post 503 may comprise an upper end disposed opposite of a bottom end. In some embodiments, the bottom end at least one post 503 of may be in removable physical contact with bottom interior surface 217. See e.g., FIG. 5G and FIG. 5H. In some embodiments, at least one post 503 may be rigid to semi-rigid.

In some embodiments, this bottom end may comprise gas-diffuser-tubing-groove 504. In some embodiments, this gas-diffuser-tubing-groove 504 may be one more grooves (i.e., cutouts, indentations, or recesses) at the bottom end of at least one post 503 that may permit the at least one post 503 to straddle one or more gas-diffuser-tubings 801. See e.g., FIG. 5E and FIG. 5I. In some embodiments, this gas-diffuser-tubing-groove 504 may be formed from at least one post 503 with two distinct bottom ends (two legs 505), but still with one upper end (one upper surface). See e.g., FIG. 5E and FIG. 5I.

In some embodiments, at least one post 503 may comprise two legs 505. See e.g., FIG. 5E. Portions of one or more gas-diffuser-tubings 801 may be disposed between these two legs 505. See e.g., FIG. 5I. In some embodiments, the bottom end of each leg 505 may be in removable physical contact with bottom interior surface 217. See e.g., FIG. 5I. In some embodiments, each bottom end of leg 505 may house at least one magnet 506. See e.g., FIG. 5E and FIG. 5I. In some embodiments, each leg 505 may be guided in the forwards-backwards direction by at least one guide 507 that may at least in part be substantially parallel with the forwards-backwards direction. In some embodiments, at least one guide 507 may be a portion of a LED-housing 950 (wherein LED may be an acronym for light emitting diode). In some embodiments, at least one guide 507 may be a structural region of a bottom area of vessel lining 200*a*. See e.g., FIG. 5A.

In some embodiments, two legs 505 may each comprise separate and distinct upper ends (not depicted), i.e., an embodiment of two at least one posts 503. Alternatively, in some embodiments, the two legs 505 may comprise a shared upper end. See e.g., FIG. 5E. A portion of this shared upper end may be located above the one or more gas-diffuser-tubings 801. Or alternatively, in some embodiments, two legs 505 may comprise a shared bridge of material that joins each leg 505, such that a portion of this shared bridge of material spans above the one more gas-diffuser-tubings 801. See e.g., FIG. 5E.

In some embodiments, this shared bridge may comprise opposing dual sets of a plurality of paired slots 508 at one or more different heights. See e.g., FIG. 5E and FIG. 5I. Each pair of slots 508 may be engaged by a pair of opposing tabs 510 located on a bottom of cap 509. Together these paired slots 508 and pair of the opposing tabs 510 may work in a ratchet manner to vary a height of cap 509 and/or a height of pad 512. See e.g., FIG. 5G.

In some embodiments, at least one post 503 (and/or two legs 505) may be substantially hollow. In some embodiments, at least one post 503 (and/or two legs 505) may be rigid to semi-rigid.

In some embodiments, head rest subassembly 500 may comprise a forwards-backwards adjust means. Functionality of the forwards-backwards adjust means may be depicted in FIG. 5A and FIG. 5B. In some embodiments, head rest subassembly 500 may comprise a height adjust means (i.e., a vertical adjust means). Functionality of the height adjust means may be depicted in FIG. 5C and FIG. 5D. Such adjustments in the forwards-backwards directions and/or in the vertical direction may allow a diverse multitude of different sized users 9000 to use a single face soaking device embodiment (e.g., face soaking device 100).

In some embodiments, head rest subassembly 500 may exist in one of two forwards-backwards configurations, or within configurations within those two forwards-backwards configurations. One of the two forwards-backwards configurations may comprise a backwards configuration, wherein head rest subassembly 500 may be located closest to a rear wall (e.g., second side wall 207) of the vessel (e.g., vessel 200) versus a front wall (e.g., fourth side wall 209) of the vessel (e.g., vessel 200). See e.g., FIG. 5A. FIG. 5A may depict face soaking device 100, shown from a top view, wherein head rest subassembly 500 may be the backwards configuration (i.e., a rear configuration).

The other of the two forwards-backwards configurations may comprise a forwards configuration, wherein head rest subassembly 500 may located closest to the front wall (e.g., fourth side wall 209) of the vessel (e.g., vessel 200) versus the rear wall (e.g., second side wall 207) of the vessel (e.g., vessel 200). See e.g., FIG. 5B. FIG. 5B may depict face soaking device 100, shown from a top view, wherein head rest subassembly 500 may be in the forwards configuration.

In some embodiments, head rest subassembly 500 may comprise a forwards-backwards adjust means. In some embodiments, the forwards-backwards adjust means may be for removable setting or determination of a location of at least one post 503 along a longitude of the bottom interior surface 217. In some embodiments, the forwards-backwards adjust means may be configured to vary a location of at least one post 503 along a longitude of the face residing within internal volume 220 of vessel 200. See e.g., FIG. 5A and FIG. 5B.

In some embodiments, the forwards-backwards adjust means comprise a smooth bottom interior surface 217, such that the at least one post 503 may be slideable or moveable along at least some portion of bottom interior surface 217 in a forwards-backwards direction. See e.g., FIG. 5A and FIG. 5B.

In some embodiments, the forwards-backwards adjust means may comprise at least one guide 507. In some embodiments, at least one guide 507 may minimize or may prevent (restrict) translation of at least one post 503 in side-to-side directions (e.g., right-to-left or left-to-right directions). In some embodiments, at least one guide 507 may facilitate linear translation of at least one post 503 in the forwards-backwards direction along at least some portion of the bottom interior surface 217. See e.g., FIG. 5A, FIG. 5B, and FIG. 33D. In some exemplary embodiments, there may be a pair of substantially parallel guides 507.

In some embodiments, at least one guide 507 may be selected from one or more of: at least one rail, at least one length of gas-diffuser-tubing 801, at least one length of at least one heat shield, at least one length of at least one EM emitter 900 (e.g., LED array 901), at least one LED-housing 950, and/or other hardware or structural elements that may be located within internal volume 220. In some embodiments, at least one guide 507 may at least in part be substantially parallel with the forwards-backwards direction. In some embodiments, at least one guide 507 may be a portion of a LED-housing 950. In some embodiments, at least one guide 507 may be a structural region of a bottom area of vessel lining 200*a*. See e.g., FIG. 5A.

In some embodiments, at least one guide 507 may form and/or bound defined channel 513 in bottom interior surface 217, with respect to side to side direction (i.e., left to right). In some embodiments, defined channel 513 may be formed by one or more of: at least one rail, at least one length of gas-diffuser-tubing 801, at least one length of at least one heat shield, or at least one length of at least one EM emitter 900, at least one LED-housing 950 and/or other hardware or structural elements that may be located within internal volume 220. In some embodiments, defined channel 513 may define a region of bottom interior surface 217 where at least one post 503 may translate in the forwards-backwards direction. In some embodiments, defined channel 513 may be substantially flat and/or smooth on its top exterior surface to facilitate sliding of at least one post 503. See e.g., FIG. 5C and FIG. 5D.

See also a pair of guides 507 in FIG. 33D. FIG. 33D may depict a transverse width cross section of face soaking device embodiment (e.g., face soaking device 100), showing a support member 501 of headrest subassembly 500 removably riding two guides 507 (i.e., rails). In FIG. 33D, each leg 505 of the at least one post 503 of headrest subassembly 500 may straddle a given guide 507. In FIG. 33D, each such leg 505 may longitudinally translate in a sliding fashion along a given guide 507. In some embodiments, at least one magnetically attractable member 3311 may be an elongate cylindrical member of ferrous or magnetic materials of construction.

Continuing discussing FIG. 5 series of figures, in some embodiments, the forwards-backwards adjust means may comprises at least one magnet 506. See e.g., FIG. 5E. In some embodiments, at least a portion of at least one magnet 506 may be in removable physical contact with at least a portion of bottom interior surface 217 and/or defined channel 513. In some embodiments, at least a portion of at least one magnet 506 may be in removable physical contact with at least a portion of a bottom of at least one post 503. In some embodiments, at least one magnet 506 may be attached to the bottom end of the at least one post 503. See e.g., FIG. 5I.

In some of head rest subassembly 500 embodiments, at least one magnet 506 may comprise at least two magnets 506. Such magnets 506 may be disposed at opposite sides of gas-diffuser-tubing-groove 504 within at least one post 503. See e.g., FIG. 5E.

In some embodiments, the forwards-backwards adjust means may comprise at least one plate 511 and/or at least one magnetically attractable member 3311 (see e.g., FIG. 33B and FIG. 33D for at least one magnetically attractable member 3311). In some embodiments, at least one plate 511 and/or at least one magnetically attractable member 3311 may be substantially constructed of magnetic or ferrous materials. In some embodiments, at least one plate 511 and/or at least one magnetically attractable member 3311 may be substantially a magnet or a ferrous metal. In some embodiments, at least one plate 511 and/or at least one magnetically attractable member 3311 may be disposed beneath a portion of bottom interior surface 217. See e.g., 2G and FIG. 5I (for at least one plate 511); and see FIG. 33B and FIG. 33D for at least one magnetically attractable member 3311. In some embodiments, at least one plate 511 and/or at least one magnetically attractable member 3311 may be disposed between vessel lining 200a and vessel cover 200b. See e.g., 2G and FIG. 5I (for at least one plate 511); and see FIG. 33B and FIG. 33D for at least one magnetically attractable member 3311. In some embodiments, at least one plate 511 may be located on bottom interior surface 217 (not depicted). A combination of at least one plate 511 and/or at least one magnetically attractable member 3311, below a portion of bottom interior surface 217, but within a magnetic field of at least one magnet 506 located within at least one post 503 may promote removable attachment of at least one post 503 to bottom interior surface 217 (or to defined channel 513 or to guide 507).

Note in embodiments at least one magnet 506 may be replaced with a substantially ferrous material, then at least one plate 511 and/or at least one magnetically attractable member 3311 may be substantially constructed of magnetic materials.

In some embodiments, head rest subassembly 500 may exist in one of two vertical configurations, or within configurations within those two vertical configurations. One of the the two vertical configurations may comprise an up (i.e., a raised) configuration, wherein a top portion of head rest subassembly 500 (e.g., pad 512) may located at a maximum height from a bottom interior surface (e.g., bottom interior surface 217) of the vessel (e.g., vessel 200). See e.g., FIG. 5C. FIG. 5C may depict face soaking device of 100, shown from a top view, wherein head rest subassembly 500 may be in the up (i.e., the raised) configuration (as well as in the backwards configuration).

The other the two vertical configurations may comprise a down (i.e., a lowered) configuration, wherein the top portion of head rest subassembly 500 may located at a minimum height from the bottom interior surface (e.g., bottom interior surface 217) of the vessel (e.g., vessel 200). See e.g., FIG. 5D. FIG. 5D may depict face soaking device 100, shown from a top view, wherein head rest subassembly 500 may be in the down (i.e., the lowered) configuration (as well as in the rear configuration).

In some embodiments, head rest subassembly 500 may comprise the height adjust means for removable setting of a vertical location of the upper end of at least one post 503 or the upper end of cap 509 or the upper end of pad 512 with respect to a ground (i.e., substrate) that the face soaking device may be located upon. In some embodiments, head rest subassembly 500 may comprise the height adjust means for removable setting of a vertical location of an upper end of pad 512 (or an upper end of cap 509) with respect to the ground that the face soaking device may be located upon. See e.g., FIG. 5C and FIG. 5D. For example and without limiting the scope of the present invention, in some embodiments, this vertical height adjust means may permit adjustment down to where the upper end of the at least one post 503 may be two inches above this ground; up to an adjustment to where this upper end may be seven inches above this ground. In some embodiments, head rest subassembly 500 may comprise the height adjust means for removable setting of a vertical location of the upper end of at least one post 503 or the upper end of cap 509 or the upper end of pad 512 with respect to bottom interior surface 217.

In some embodiments, the height adjust means may be configured to vary a height of the upper surface or the top surface of support member 501 (or the strap) within internal volume 220 of vessel 200 with respect to an axis running from at least one base 215 of vessel 200 to top opening 226 of vessel 200. That is, in a vertical direction. In some embodiments, the height adjust means may be in physical contact with support member 501 (or the strap) and with one or more of: at least one base 215, at least one wall 201 (e.g. interior 203, exterior 202, and/or rim 225) of vessel 200. In some embodiments, the height adjust means may be in physical contact with support member 501 (or the strap) and with at least one base 215 (e.g. interior) of vessel 200.

In some embodiments, the height adjust means may comprise cap 509. In some embodiments, this cap 509 may be coupled to at least one post 503. In some embodiments, cap 509 may comprise structure to fit over at least some of two legs 505. In some embodiments, this cap 509 may be coupled to at least one post 503 by a vertically adjustable ratchet mechanism. See e.g., FIG. 5E. In some embodiments this vertically adjustable ratchet mechanism may comprise complimentary structure on at least one post 503 and on cap 509. For example, at least one post 503 may comprise the opposing dual sets of plurality of paired slots 508 at one or more different heights. See e.g., FIG. 5E and FIG. 5I. Each pair of slots 508 may be engaged by a pair of opposing tabs 510 located on a bottom of cap 509. Together these paired slots 508 and pair of the opposing tabs 510 may work in the ratchet manner to vary a height of cap 509 and/or a height of pad 512 with respect to at least one post 503. See e.g., FIG. 5G.

In some embodiments, a projection from a top view of cap 509 may result in a 2D shape of the following: a circle, an oval, an ellipse, a polygon (with or without rounded corners), a regular polygon (with or without rounded corners), an irregular polygon with or without rounded corners, and/or the like.

In some embodiments, head rest subassembly 500 may comprise comfortable exterior surface 502. This comfortable exterior surface 502 may provide comforting support to the head region or portions thereof. This comfortable exterior surface 502 may be configured to removably engage at least some portion of the head of the user. In some embodiments, this comfortable exterior surface 502 may function as padding and/or as cushioning for where the at least the portion of the head of the user may removably physically contact pad 512. In some embodiments, this comfortable exterior surface 502 may be substantially a compressible foam material. In some embodiments, the compressible foam material may be replaced with a soft elastomeric material, such as silicone or other soft elastomeric materials.

In some embodiments, at least one comfortable exterior surface 502 may comprise pad 512. In some embodiments, pad 512 may be attached to an upper end of cap 509. See e.g., FIG. 5E and FIG. 5I. In some embodiments, a nature of this attachment may be permanent; whereas, in other embodiments, this attachment may be removable. In some embodiments, the upper end of cap 509 may comprise pad 512. In some embodiments, cap 509 and pad 512 may be integral. In some embodiments, pad 512 may be attached to the upper end of at least one post 503 (not depicted). In some embodiments, pad 512 may be attached to cap 509; wherein pad 512 may span over portions of one or more gas-diffuser-tubings 801. See e.g., FIG. 5A.

FIG. 6A through FIG. 6F may depict head rest subassembly 600. FIG. 6G through FIG. 6L may depict head rest subassembly 650. Both head rest subassembly 600 and head rest subassembly 650 may be similar but alternative embodiments to head rest subassembly 500. Both head rest subassembly 600 and head rest subassembly 650 may differ from head rest subassembly 500 by both head rest subassembly 600 and head rest subassembly 650 sharing a similar height adjust means using threads to vary heights by screwing up or down, as opposed to the racket mechanism of head rest subassembly 500. Head rest subassembly 600 and head rest subassembly 650 may differ from each other due to differences in one or more of: shape of bottom interior surface 217, shape of at least one guide 507, shape of at least one defined channel 513, number and/or layout of gas-diffuser-tubings 801. For example, and without limiting the scope of the present invention, in head rest subassembly 650, at least one post 503 may be located in between gas-diffuser-tubings 801; whereas, in head rest subassembly 600, at least one post 503 may straddle one or more gas-diffuser-tubings 801.

Figure 6A:
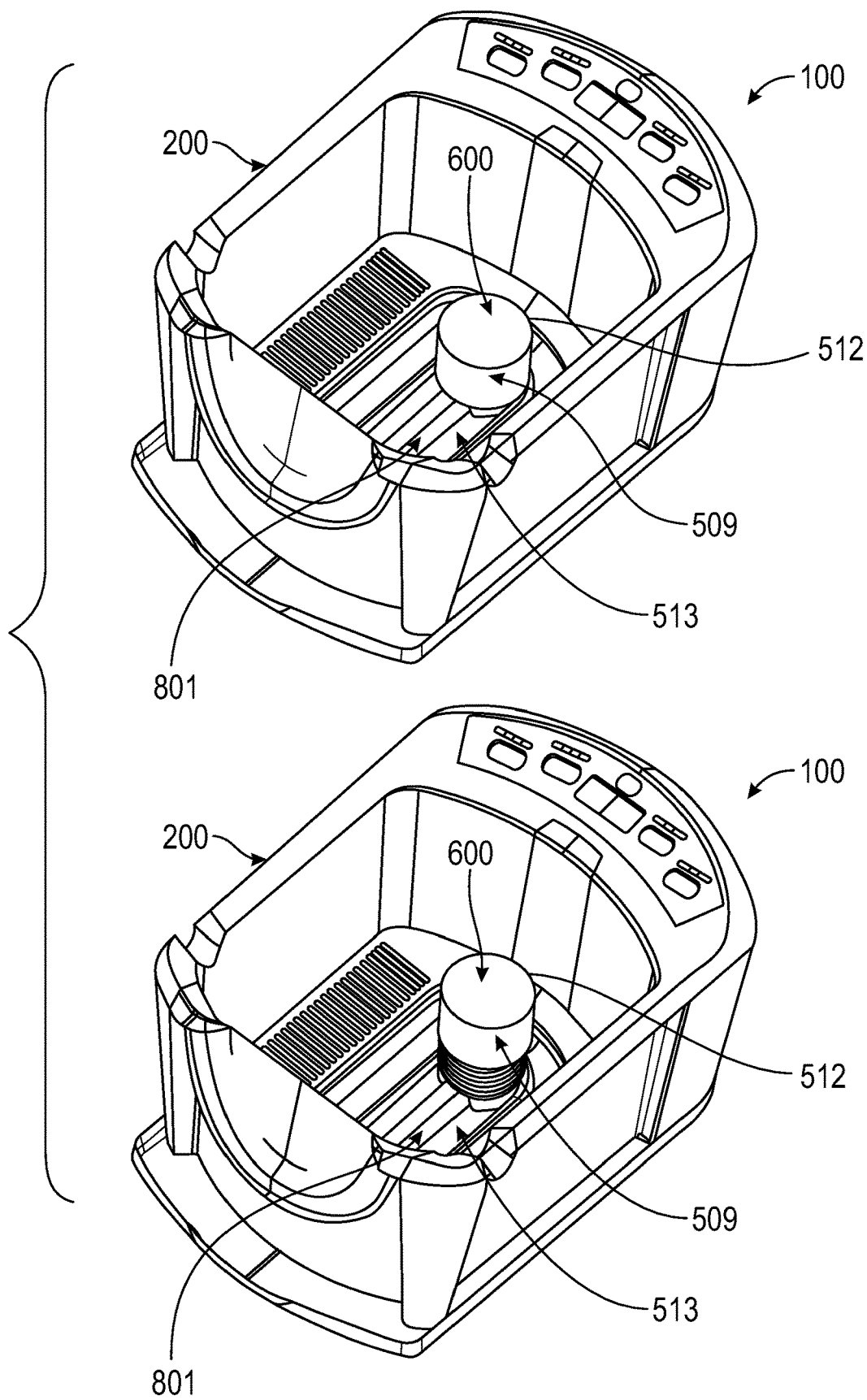
FIG. 6A may depict two face soaking devices, side by side, in two different configurations for the head rest subassemblies depicted, with one head support shown in the down (the lowered) configuration and the other head support shown in the up (the raised) configuration; wherein the head supports depicted may be single post embodiments.

FIG. 6A may depict two face soaking devices, side by side, in two different configurations for the head rest subassemblies 600 depicted, with one head rest subassembly 600 shown in the down (the lowered) configuration and the other head rest subassembly 600 shown in the up (the raised) configuration; wherein head rest subassemblies 600 depicted may be single post 503 embodiments.

Figure 6B:
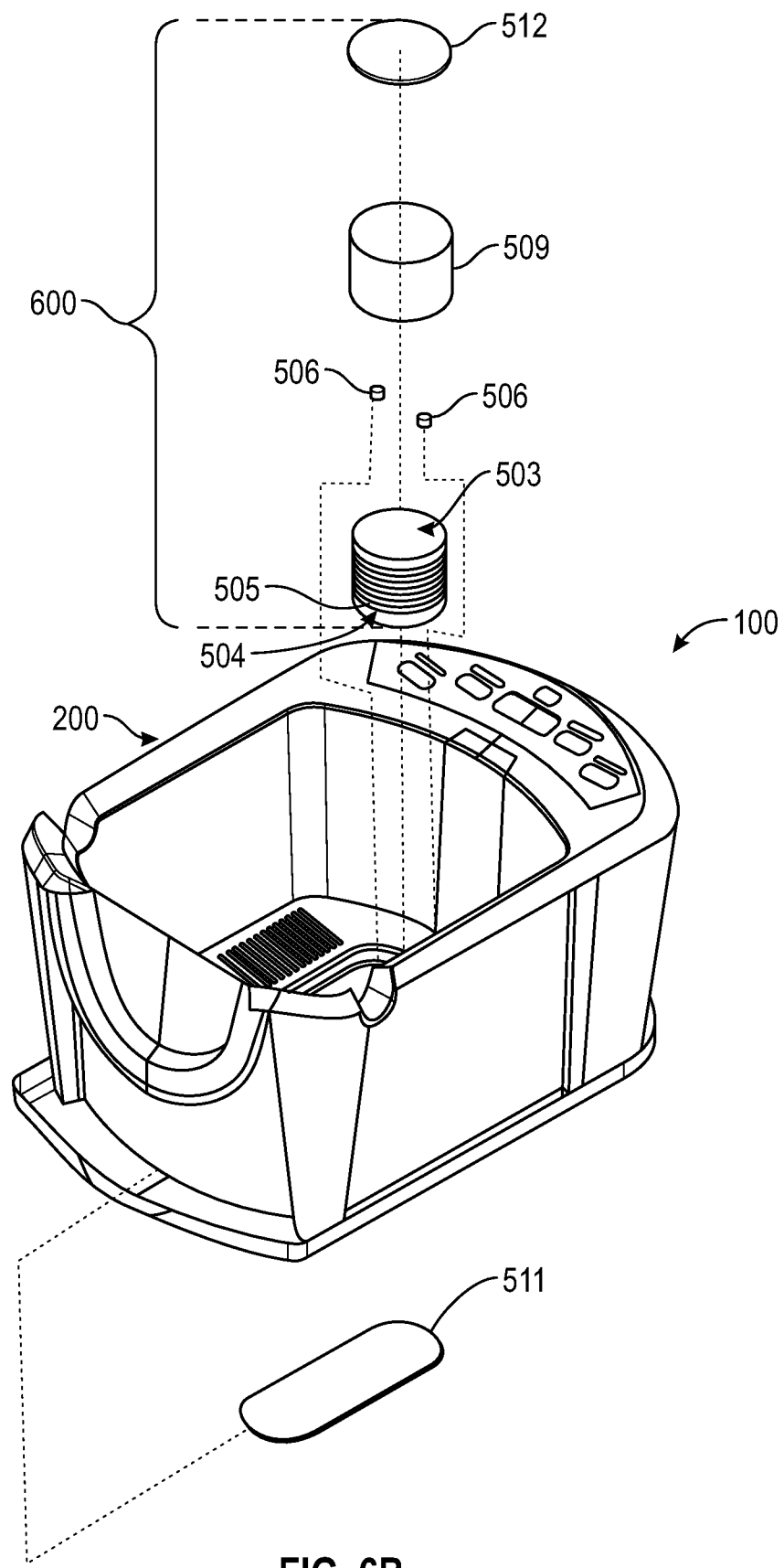
FIG. 6B may depict a top perspective exploded view of one of the head rest subassembly depicted in FIG. 6A; wherein the head rest subassembly is exploded from the vessel.

FIG. 6B may depict a top perspective exploded view of head rest subassembly 600; wherein head rest subassembly 600 is exploded from the vessel.

Figure 6C:
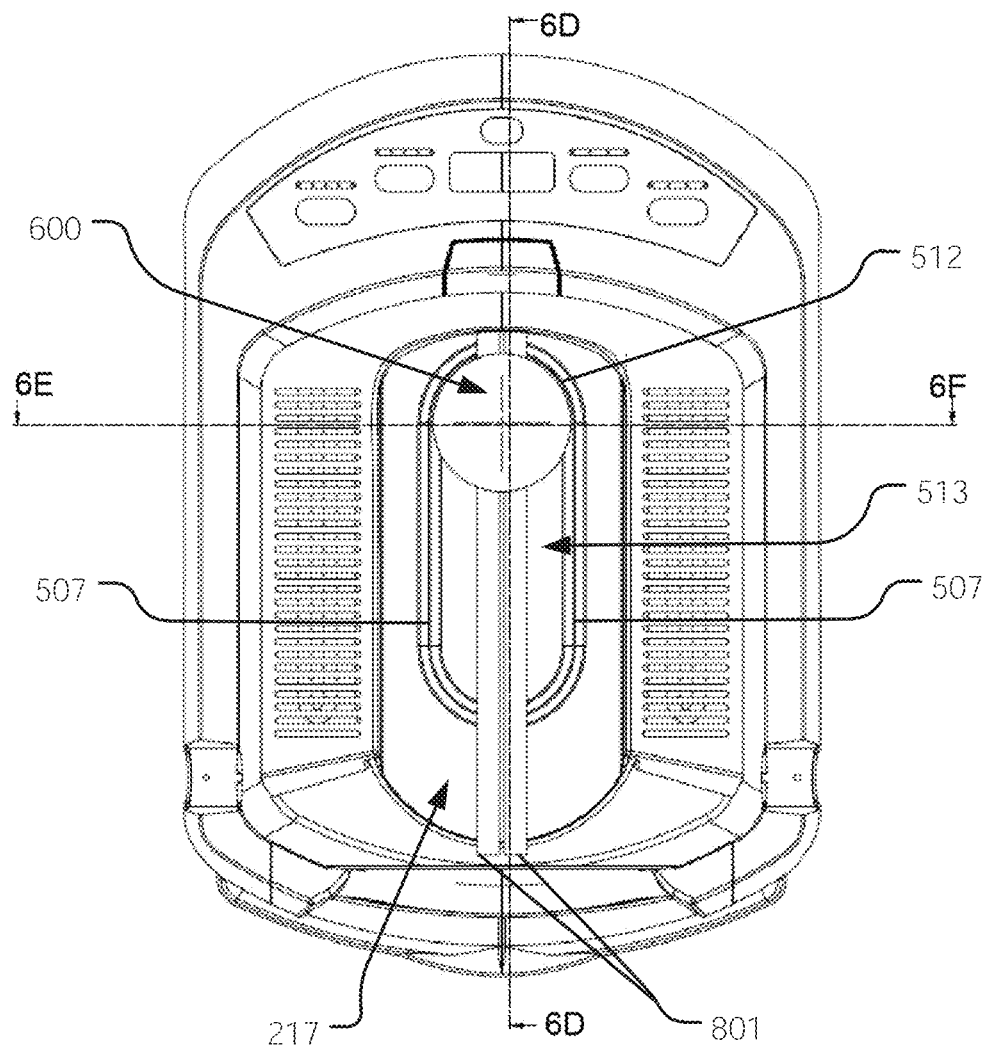
FIG. 6C may depict a top view of one of the head rest subassembly depicted in FIG. 6A; wherein FIG. 6C may depict two sectional lines, sectional line 6D-6D and sectional line 6E-6E; wherein sectional line 6D-6D may a longitudinal sectional line through the head rest subassembly; and wherein sectional line 6E-6E may be a transverse-width sectional line through the head rest subassembly.
Figure 6D:
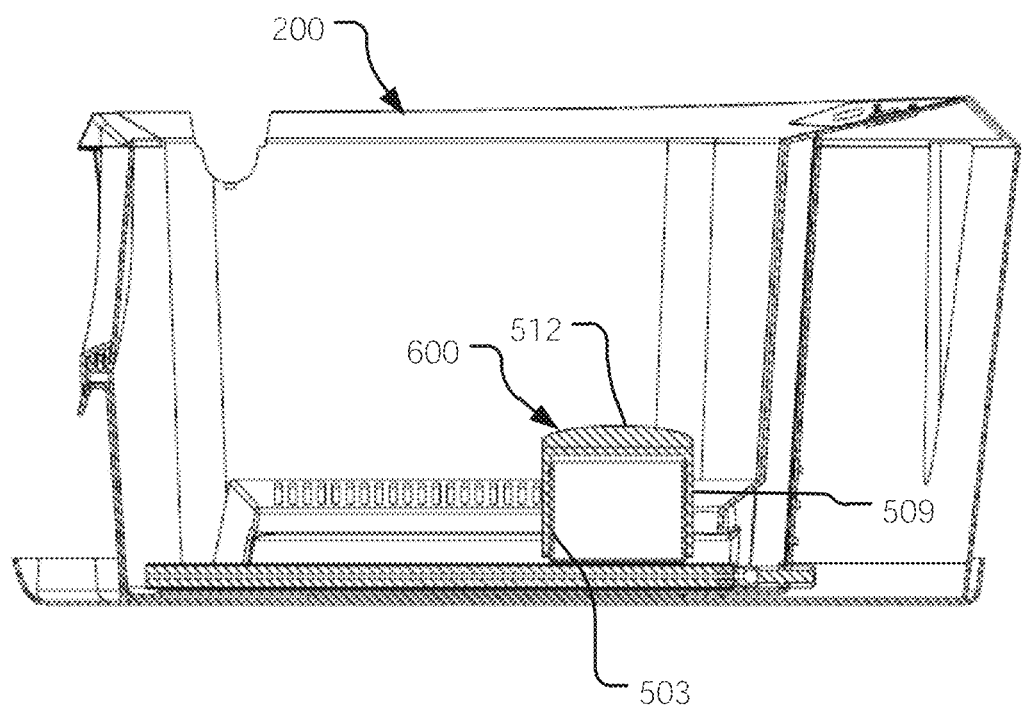
FIG. 6D may depict a longitudinal cross-sectional view along sectional line 6D-6D through the head rest subassembly.

FIG. 6C may depict a top view of head rest subassembly 600; wherein FIG. 6C may depict two sectional lines, sectional line 6D-6D and sectional line 6E-6E; wherein sectional line 6D-6D may be a longitudinal sectional line through head rest subassembly 600; and wherein sectional line 6E-6E may be a transverse-width sectional line through head rest subassembly 600. FIG. 6D may depict a longitudinal cross-sectional view along sectional line 6D-6D through head rest subassembly 600.

Figure 6E:
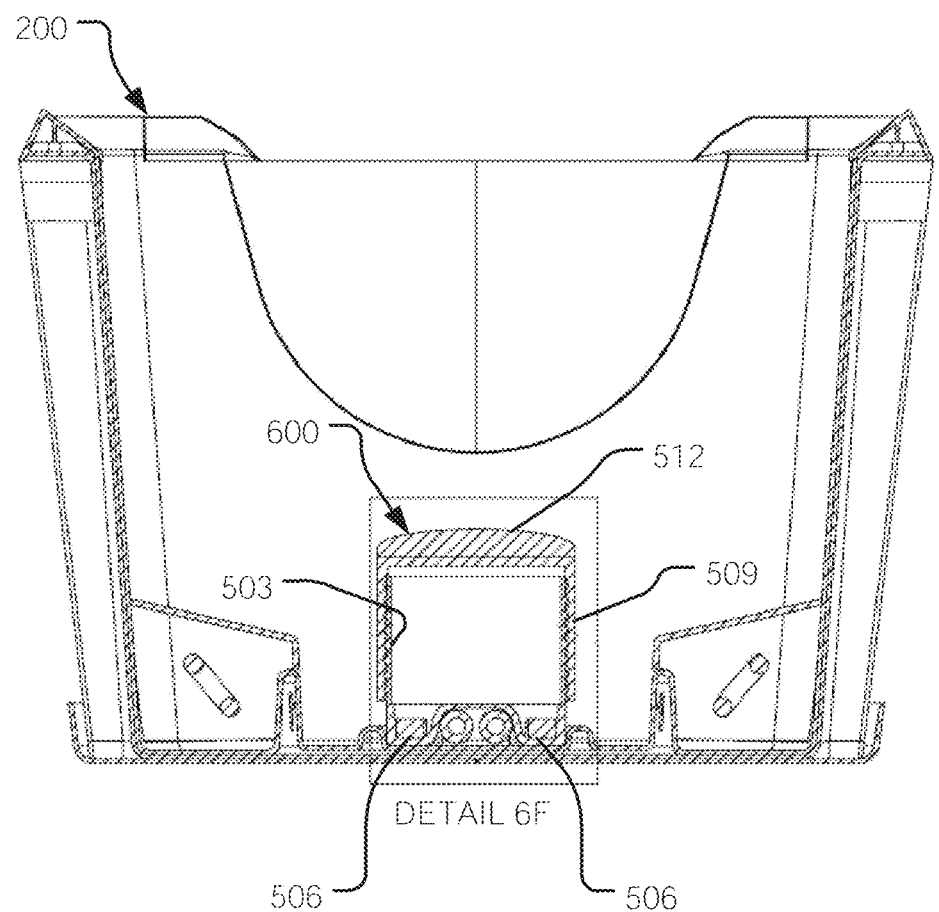
FIG. 6E may depict a transverse-width cross-sectional view along sectional line 6E-6E through the head rest subassembly; wherein a region of Detail 6F may depict the head rest subassembly.
Figure 6F:
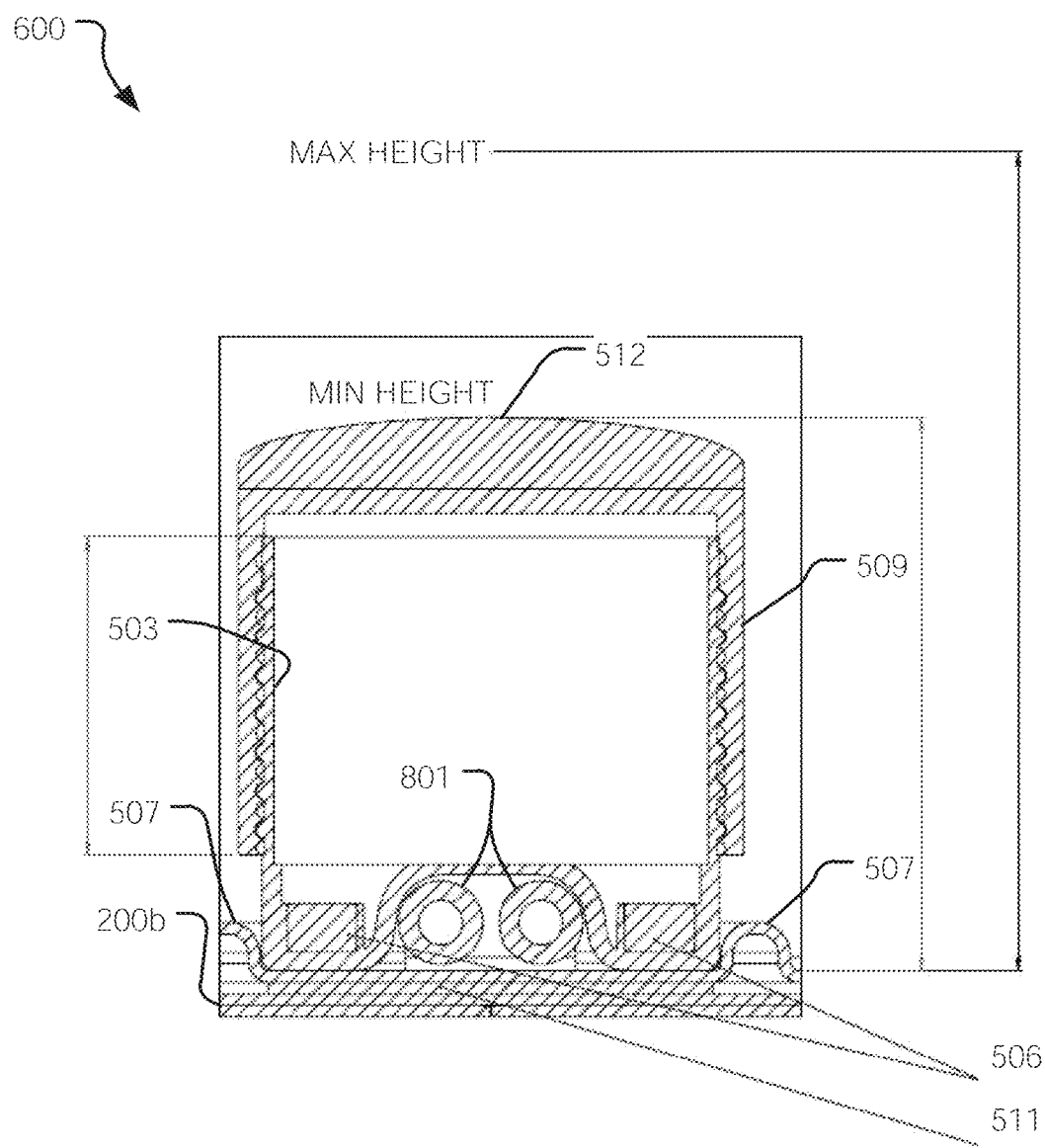
FIG. 6F may depict a close-up view of Detail 6F.

FIG. 6E may depict a transverse-width cross-sectional view along sectional line 6E-6E through head rest subassembly 600. FIG. 6E may further depict a region of Detail 6F may depict head rest subassembly 600. FIG. 6F may depict a close-up view of Detail 6F.

In some embodiments, head rest subassembly 600 may comprise support member 501. In some embodiments, support member 501 may comprise comfortable exterior surface 502. In some embodiments, support member 501 may comprise at least one post 503, cap 509, and comfortable exterior surface 502. See e.g., FIG. 6B. In some embodiments, at least one post 503 may be in physical contact with cap 509. In some embodiments, cap 509 may be a cap covering at least a portion of at least one post 503. In some embodiments, cap 509 may be in physical contact with comfortable exterior surface 502. In some embodiments, comfortable exterior surface 502 may at least cover a portion of an upper surface of cap 509 or at least a portion of the upper surface of at least one post 503. In some embodiments, comfortable exterior surface 502 may be pad 512. In some embodiments, head rest subassembly 600 may also comprise at least one magnet 506 and at least one plate 511, in addition to comprising support member 501. In some embodiments, at least one magnet 506 may be located within at least one post 503. In some embodiments, at least one plate 511 may be disposed between vessel lining 200a and vessel cover 200b (see e.g., FIG. 2G). See e.g., FIG. 6B for at least one plate 511.

However, in head rest subassembly 600, a physical relationship between at least one post 503 and cap 509, may be that cap 509 may screw onto and over at least a portion of at least one post 503. See e.g., FIG. 6B. As depicted in FIG. 6B, at least one post 503 may comprise outside threading, while cap 509 may comprise complimentary inside threading that may be complimentary to the outside threading of at least one post 503.

In some embodiments, the height adjust means may comprise cap 509. In some embodiments, this cap 509 may be coupled to at least one post 503. In some embodiments, this cap 509 may be coupled to at least one post 503 by cap 509 comprising internal inside threads which may removably thread to outside threads of at least one post 503. See e.g., FIG. 6B and FIG. 6F. In this embodiment, vertical positions of the upper end of pad 512 and/or of an upper end of cap 509 may be changed by threading (i.e., screwing or turning) up or down. That is, cap 509 and/or pad 512 may be screwed up or down upon at least on post 503.

In some embodiments, a projection from a top view of cap 509 may result in a 2D shape of the following: a circle, an oval, an ellipse, a polygon (with or without rounded corners), a regular polygon (with or without rounded corners), an irregular polygon with or without rounded corners, and/or the like. Note, in some embodiments, irrespective of this 2D shape of cap 509, an interior shape of cap 509, where the inside threads may be located may be circular as viewed from above. See e.g., FIG. 6C.

Note, in some embodiments of head rest subassembly 600, at least one post 503 may comprise gas-diffuser-tubinggroove 504, such that one or more gas-diffuser-tubings 801 may pass under or through gas-diffuser-tubing-groove 504. Thus because of this structural arrangement, at least post 503 in some head rest subassembly 600 embodiments may comprise two legs 505 at the bottom end of at least post 503, i.e., one leg 505 to each side of gas-diffuser-tubing-groove 504. See e.g., FIG. 6B and FIG. 6A.

In some embodiments, each of the two legs 505 may comprise separate and distinct outside threads for removable complimentary mating with a separate and distinct caps 509, i.e., two such caps 509 (not depicted). This may also require two posts 503, with two caps 509, with one leg 505 per each of the two posts 503 (not depicted). Varying the height in such embodiments, may require adjusting, by screwing, each of the two legs 505 to the two caps 509 (not depicted). In some embodiments, each of the two legs 505 may comprise a shared region of outside threads for removable complimentary mating with a single cap 509. See e.g., FIG. 6A and FIG. 6B.

Figure 6G:
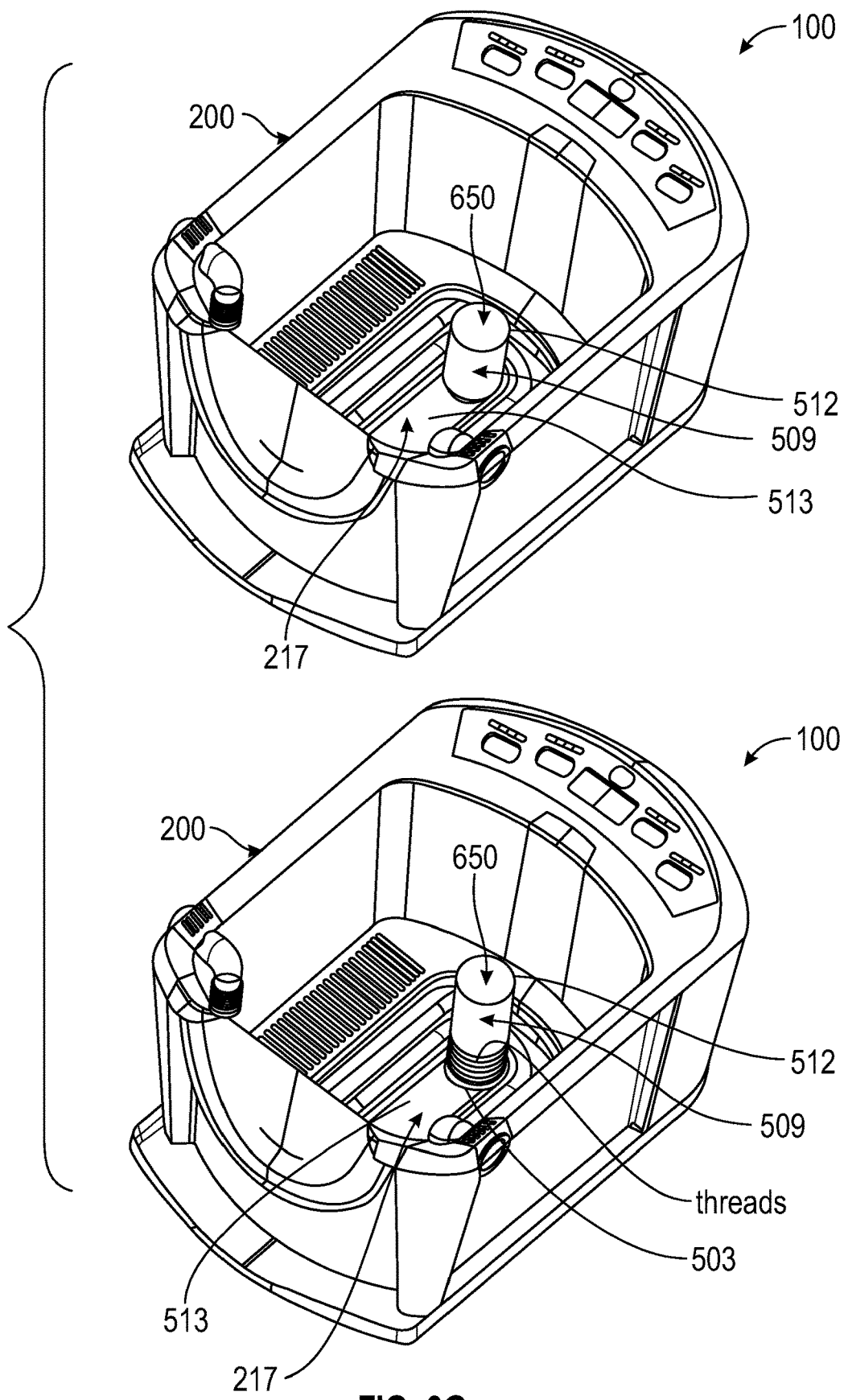
FIG. 6G may depict two face soaking devices, side by side, in two different configurations for the head rest subassemblies depicted, with one head rest subassembly shown in the down (the lowered) configuration and the other head rest subassembly shown in the up (the raised) configuration; wherein the head rest subassemblies depicted may be single post embodiments.

FIG. 6G may depict two face soaking devices, side by side, in two different configurations for head rest subassemblies 650 depicted, with one head rest subassembly 650 shown in the down (the lowered) configuration and the other head rest subassembly 650 shown in the up (the raised) configuration; wherein head rest subassemblies 650 depicted may be single post 503 embodiments.

Figure 6H:
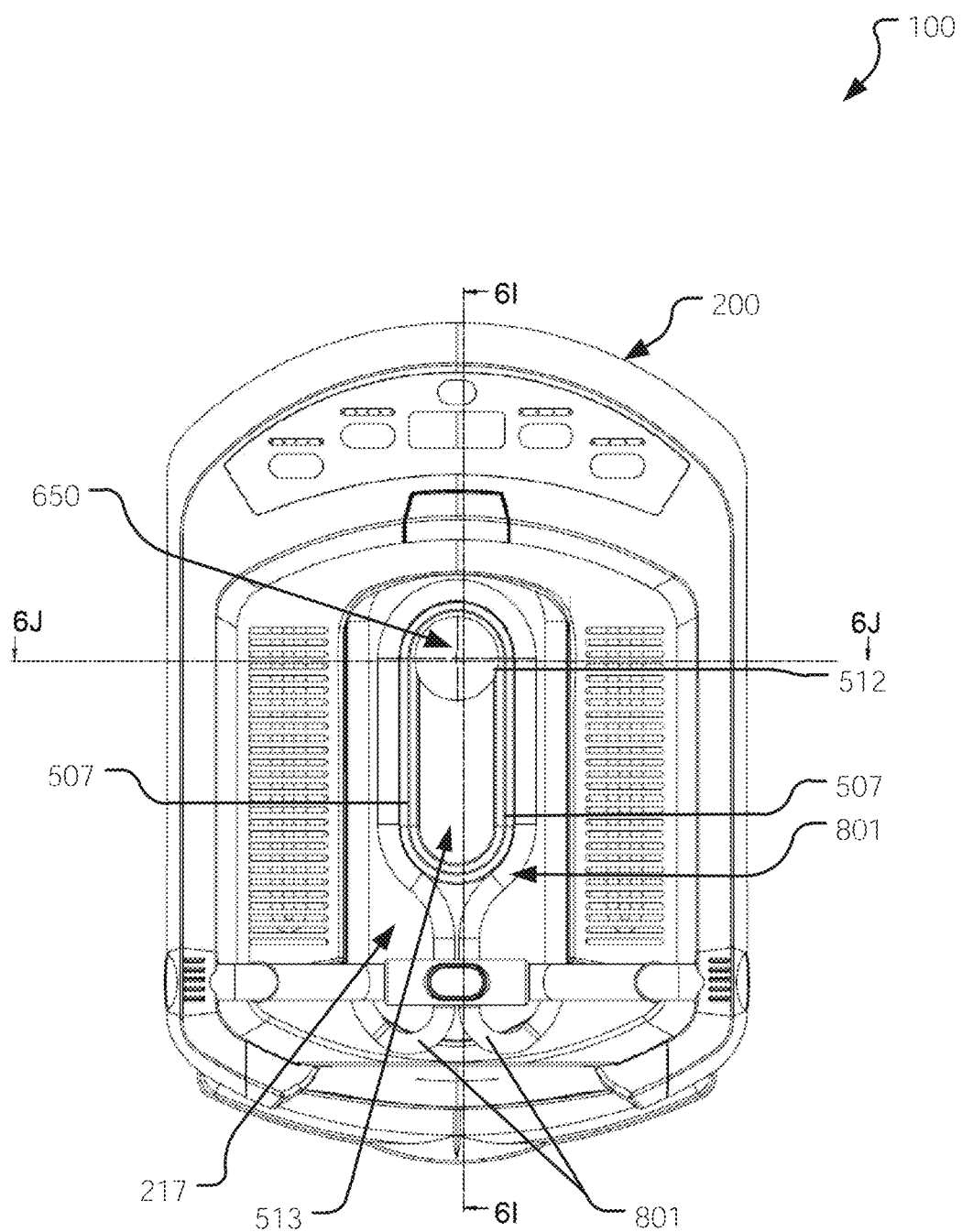
FIG. 6H may depict a top view of one of the head rest subassembly depicted in FIG. 6G; wherein FIG. 6H may depict two sectional lines, sectional line 6I-6I and sectional line 6J-6J; wherein sectional line 6I-6I may a longitudinal sectional line through the head rest subassembly; and wherein sectional line 6J-6J may be a transverse-width sectional line through the head rest subassembly.
Figure 61:
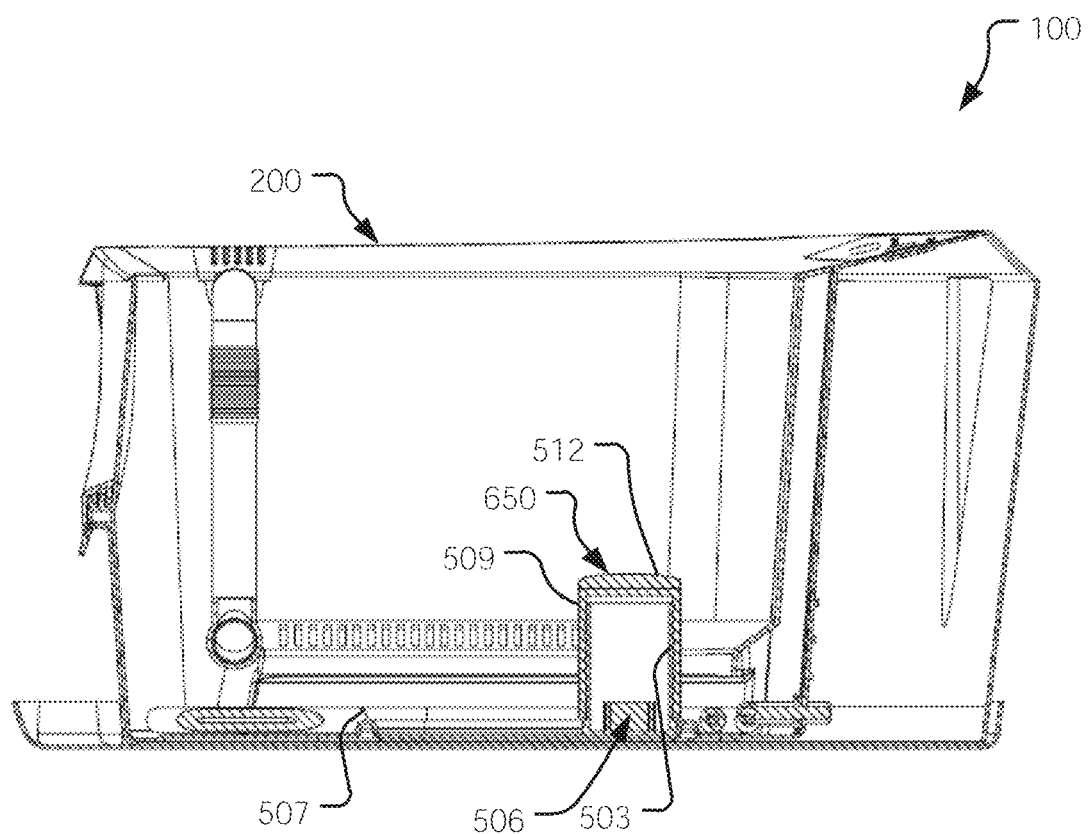

FIG. 6H may depict a top view of head rest subassembly 650; wherein FIG. 6H may depict two sectional lines, sectional line 6I-6I and sectional line 6J-6J; wherein sectional line 6I-6I may a longitudinal sectional line through head rest subassembly 650; and wherein sectional line 6J-6J may be a transverse-width sectional line through head rest subassembly 650.

Figure 6J:
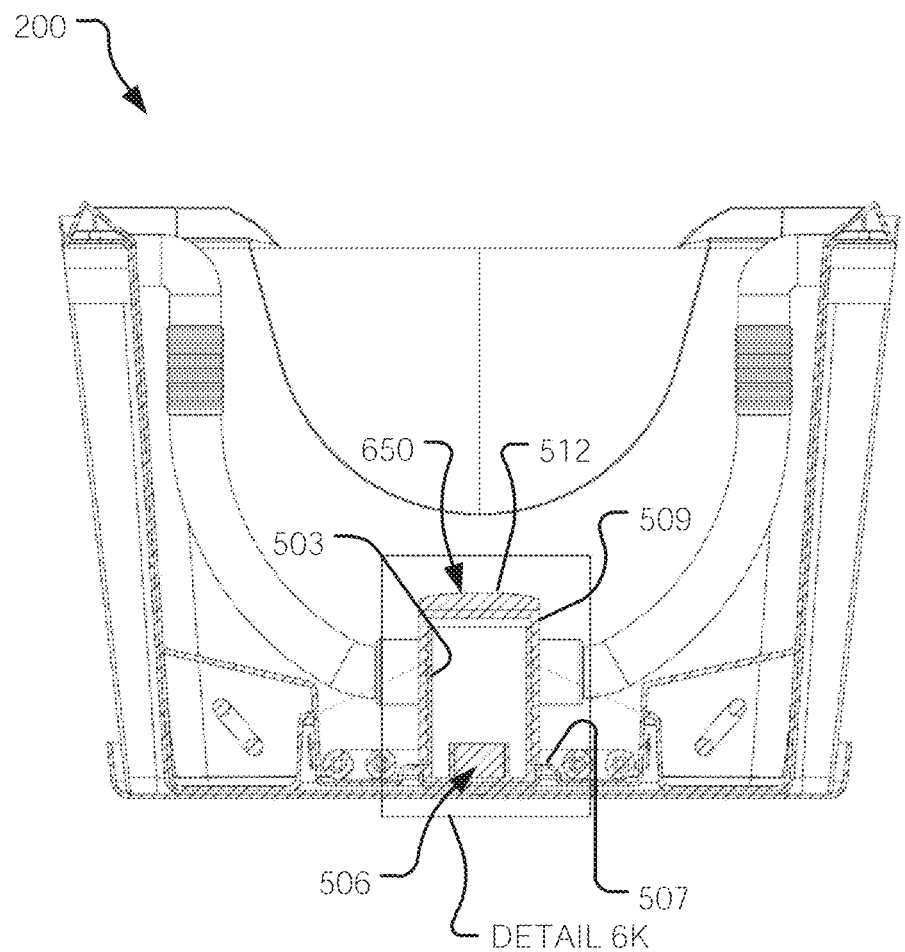
FIG. 6J may depict a transverse-width cross-sectional view along sectional line 6J-6J through the head rest subassembly; wherein a region of Detail 6K may depict the head rest subassembly.
Figure 6K:
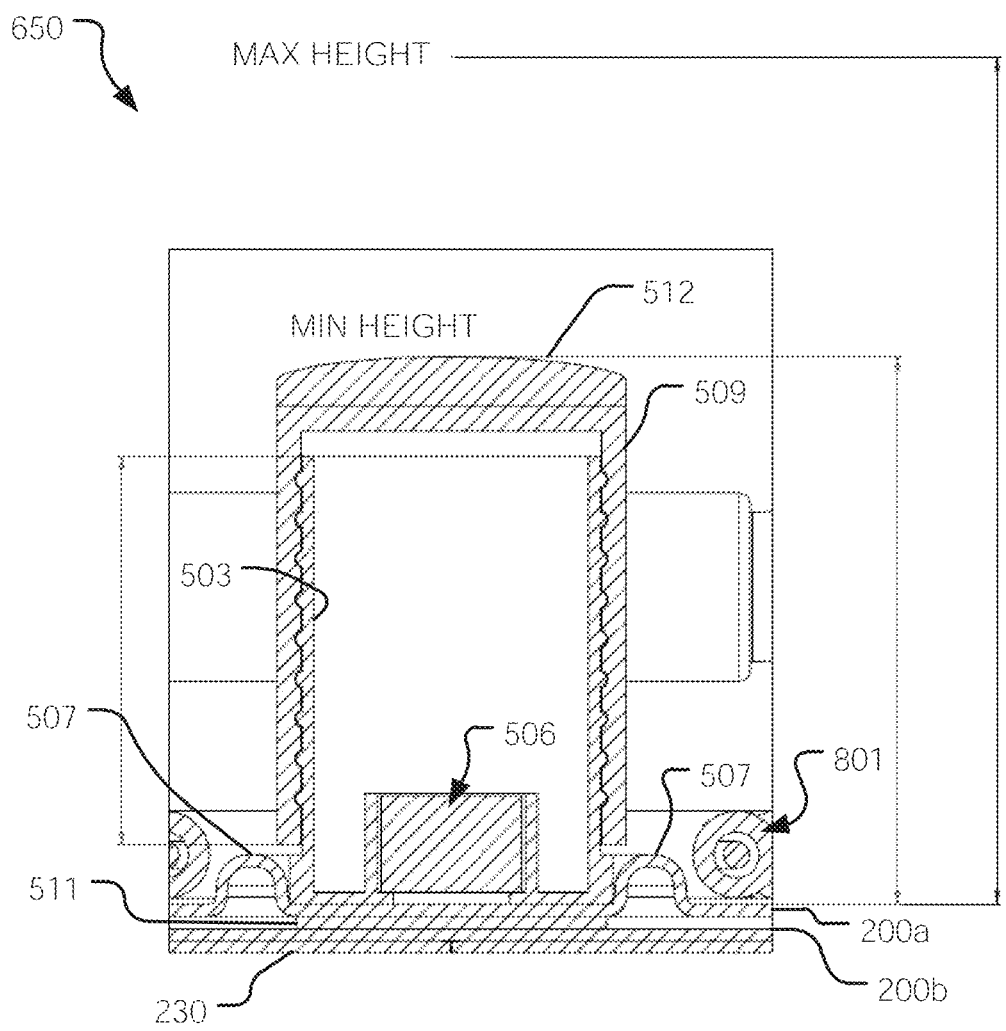
FIG. 6K may depict a close-up view of Detail 6K.

FIG. 6I may depict a longitudinal cross-sectional view along sectional line 6I-6I through head rest subassembly 650. FIG. 6J may depict a transverse-width cross-sectional view along sectional line 6J-6J through head rest subassembly 650. FIG. 6J may depict a region of Detail 6K may depict head rest subassembly 650. FIG. 6K may depict a close-up view of Detail 6K.

In some embodiments, head rest subassembly 650 may comprise support member 501. In some embodiments, support member 501 may comprise comfortable exterior surface 502. In some embodiments, support member 501 may comprise at least one post 503, cap 509, and comfortable exterior surface 502. See e.g., FIG. 6K. In some embodiments, at least one post 503 may be in physical contact with cap 509. In some embodiments, cap 509 may be a cap covering at least a portion of at least one post 503. In some embodiments, cap 509 may be in physical contact with comfortable exterior surface 502. In some embodiments, comfortable exterior surface 502 may at least cover a portion of the upper surface of cap 509 or at least a portion of the upper surface of at least one post 503. In some embodiments, comfortable exterior surface 502 may be pad 512. In some embodiments, head rest subassembly 650 may also comprise at least one magnet 506 and at least one plate 511, in addition to comprising support member 501. In some embodiments, at least one magnet 506 may be located within at least one post 503. In some embodiments, at least one plate 511 may be disposed between vessel lining 200a and vessel cover 200b (see e.g., FIG. 2G). See e.g., FIG. 6K for at least one plate 511.

In head rest subassembly 650, a physical relationship between at least one post 503 and cap 509, may be that cap 509 may screw onto and over at least a portion of at least one post 503. See e.g., FIG. 6G and FIG. 6K. At least one post 503 may comprise outside threading, while cap 509 may comprise complimentary inside threading that may be complimentary to the outside threading of at least one post 503. Also note, in head rest subassembly 650, there may no gas-diffuser-tubing-groove 504, as one or more gas-diffuser-tubings 801 may pass around at least one post 503 and not under or through at least one post 503. Whereas with head rest subassembly 500 and with head rest subassembly 600 one or more gas-diffuser-tubings 801 may pass under or through gas-diffuser-tubing-groove 504. See e.g., 6G and compare against FIG. 5C and FIG. 6A for presence or absence of gas-diffuser-tubing-groove 504 depending upon layout configuration of one or more gas-diffuser-tubings 801.

In some embodiments, the height adjust means may comprise cap 509. In some embodiments, this cap 509 may be coupled to at least one post 503. In some embodiments, this cap 509 may be coupled to at least one post 503 by cap 509 comprising internal inside threads which may removably thread to outside threads of at least one post 503. See e.g., FIG. 6G and FIG. 6K. In this embodiment, vertical positions of the upper end of pad 512 and/or of an upper end of cap 509) may be changed by threading (i.e., screwing or turning) up or down.

In some embodiments, a projection from a top view of cap 509 may result in a 2D shape of the following: a circle, an oval, an ellipse, a polygon (with or without rounded corners), a regular polygon (with or without rounded corners), an irregular polygon (with or without rounded corners), and/or the like. Note, in some embodiments, irrespective of this 2D shape of cap 509, an interior shape of cap 509, where the inside threads may be located may be circular. See e.g., FIG. 6H.

FIG. 23A may depict an exemplary embodiment of a head rest subassembly 2300, shown from a perspective view. FIG. 23B may depict head rest subassembly 2300, but shown from a top view. Two cross-sectionals lines may be shown in FIG. 23B, sectional line 23C-23C and sectional line 23D-23D. FIG. 23C may be a cross-sectional front view of sectional line 23C-23C from FIG. 23B. FIG. 23D may be a cross-sectional side view of sectional line 23D-23D from FIG. 23B. A cross-section of the head of user 9000 may also be shown in FIG. 23D, while resting upon a portion of head rest subassembly 2300. FIG. 23E may depict head rest subassembly 2300, but shown from an exploded perspective view.

Various embodiments of the face soaking devices may comprise head rest subassembly 2300. In some embodiments, head rest subassembly 2300 may be removably attached to a given vessel (e.g., vessel 200). In some embodiments, head rest subassembly 2300 may be configured to support the portion of the head of user 9000 and/or to permit user 9000 to rest their head upon the portion of head rest subassembly 2300. In some embodiments, head rest subassembly 2300 may comprise support member 501. In some embodiments, support member 501 may be configured to physically support the portion of the head of user 9000 and/or to permit user 9000 to rest their head upon the portion of support member 501.

In some embodiments, e.g., head rest subassembly 2300 embodiments, support member 501 may comprise an elongate member. Such an elongate member may have additional structure and/or geometry in various embodiments. For example and without limiting the scope of the present invention, such an elongate member may be selected from a group comprising: a) a flat bar which may be solid; b) a flat bar which may be hollow; c) a rounded bar which may be solid; d) a rounded bar which may be hollow; e) a bar wherein portions may be flat and other portions may be rounded; f) a bar wherein portions may be hollow and other portions may be solid; and/or the like. In various embodiments, such an elongate member of support member 501 may comprise two terminal ends, a fifth terminal end 2301 and a sixth terminal 2302, disposed opposite of each other. See e.g., FIG. 23E.

As shown in the FIG. 23 series of figures, support member 501 may be a flat rod. A flat rod embodiment of support member 501 may comprise the two terminal ends, fifth terminal end 2301 and sixth terminal 2302, disposed opposite of each other. Such a flat rod may further comprise an upper surface 2311 and a lower surface 2312 (see e.g., FIG. 23D) disposed opposite of upper surface 2311. In some exemplary embodiments, upper surface 2311 may not be entirely flat, rather upper surface 2311 may comprise a radius, i.e. a curvature, which may be concave or convex. Such curvature may provide additional structural strength to support member 501 over an entirely flat rod embodiment. In some embodiments, such a curvature may be complimentary to curvature of user 9000's forehead.

In some embodiments, the elongate member of support member 501 may be constructed of a metal and/or constructed of a thermoformed plastic. In some embodiments, the elongate member of support member 501 may be extruded, 3D printed, and/or machined. In some embodiments, the elongate member of support member 501 may be molded, e.g. injection molded, from one or more thermoformed plastics. In some embodiments, such thermoformed plastic formulations may comprise additional ingredients, e.g., glass fiber to increase rigidity and/or structural strength. In some embodiments, the elongate member of support member 501 may be molded with various additional structural reinforcement geometry, such as longitudinal ribs and/or transverse width ribs, and the like. In some embodiments, the elongate member of support member 501 may be hollow (see e.g., FIG. 21 series of figures discussion above). In such embodiments, portions of various embodiments of breathing apparatus may pass through such a hollow elongate member. See e.g., the FIG. 21 series of figures discussed above.

In some embodiments, support member 501 comprise may comfortable exterior surface 502. Comfortable exterior surface 502 may be configured to removably engage the portion of the head of user 9000. Comfortable exterior surface 502 may function as padding and/or as cushioning for where the portion of the head of user 9000 may removably physically contact support member 501. See e.g., the FIG. 23 series of figures.

In some embodiments, the elongate member of support member 501 and comfortable exterior surface 502 may be integral with each other; whereas, in other embodiments, comfortable exterior surface 502 may a separate part which may be attached to the elongate member of of support member 501. In some embodiments, the flat rod and comfortable exterior surface 502 may be integral with each other; whereas, in other embodiments, comfortable exterior surface 502 may a separate part which may be attached to the flat rod. Such attachment may be mechanical fastener, ultrasonic welding, heat welding, solvent bonding, and/or chemical adhesive. For example, and without limiting the scope of the present invention, such mechanical fasteners may be selected from snap fittings, VELCRO or VELCRO like fasteners (plurality of hooks and complimentary plurality of loops), buttons, friction fits, screws, bolts, rivets, quick release buckle, strapping, zipper, and/or the like.

In some embodiments, comfortable exterior surface 502 may be located on upper surface 2311 of the flat rod (or upper surface 2311 of the elongate member), proximate to sixth terminal end 2302. For example, and without limiting the scope of the present invention, comfortable exterior surface 502 may be located on upper surface 2311 closer to sixth terminal end 2302 than to fifth terminal end 2301.

In some embodiments, comfortable exterior surface 502 may extend on upper surface 2311 from sixth terminal end 2302 a distance away from sixth terminal end 2302. In some embodiments, such a distance may vary from 0.25 inch to 13 inches. In other embodiments, this distance may be other dimensions. In some embodiments, comfortable exterior surface 502 may substantially cover upper surface 2311. In some embodiments, comfortable exterior surface 502 may partially cover upper surface 2311.

In some embodiments, comfortable exterior surface 502 may be a length of tubing, wherein the length of tubing may be slid over sixth terminal end 2302. Such a length of tubing may be the same or less than a length of the elongate member of support member 501. Such a length of tubing may be constructed of a foam material (e.g., closed or open celled polyethylene, although closed cell may be exemplary over open celled), an elastomeric material (e.g. rubber and/or silicone), and/or a soft thermoformed (e.g., extruded) plastic (e.g., PVC). Such a length of tubing may be attached to the elongate member of support member 501 (e.g., the flat rod), by one or more of: friction fit, heat shrinking, heat welding, ultrasonic welding, solvent bonding, chemical adhesive bonding, and the like.

In some embodiments, comfortable exterior surface 502 may comprise a complimentary shape to sixth terminal end 2302 and a region proximate to sixth terminal end 2302. In some embodiments, such a region proximate to sixth terminal end 2302 may vary from 0.25 inch to 13 inches extending away from sixth terminal end 2302. In other embodiments, this region proximate to sixth terminal end 2302 may be other dimensions. For example, and without limiting the scope of the present invention, sixth terminal end 2302 and the region proximate to sixth terminal end 2302 may comprise a spoon and/or a spatula shape, wherein surface curvature may be complimentary to a curvature of the portion of the head of user 9000. In some embodiments, comfortable exterior surface 502 may be complimentary shaped to the curvature of the portion of the head of the user 9000.

In some embodiments, support member 501 may comprise the height adjust means and at least a portion of the forwards-backwards adjust means (e.g. slot 2320). In some embodiments, the height adjust means may be located disposed between the two terminal ends of support member 501 (e.g. fifth terminal end 2301 and sixth terminal end 2302). In some embodiments, the at least the portion of the forwards-backwards adjust means may be located proximate to fifth terminal end 2301. For example, and without limiting the scope of the present invention, the at least the portion of the forwards-backwards adjust means may be located closer to fifth terminal end 2301 than to sixth terminal end 2302. See e.g., FIG. 23E.

In some embodiments, the height adjust means may comprise a bend 2315 in the flat rod (or elongate member of support member 501), such that when the support member 501 may be removably attached to the vessel 200, sixth terminal end 2302 may angle towards at least one base 215 (or down towards bottom interior surface 217). See e.g., FIG. 23D. Bend 2315 may be characterized (defined) by angle 2380. Note, such a bend 2315, may permit support member 501 to accommodate a plurality of different sized heads. That is, larger heads may rest higher up on support member 501; whereas, smaller heads may rest further down on support member 501, closer to at least one base 215.

In some embodiments, support member 501 may comprise angle 2380. See e.g., FIG. 23D. In some embodiments, angle 2380 may be formed between lower surface 2312 of sixth terminal end 2302 and lower surface 2312 of fifth terminal end 2301, with bend 2315 located at a vertex of angle 2380. In some embodiments, angle 2380 may be measured from less than 180 degrees and more than 90 degrees between the lower surface of sixth terminal end 2302 and the lower surface of fifth terminal end 2301.

Alternatively, a corresponding angle may be measured of less than 90 degrees, wherein the corresponding angle may be measured as between upper surface 2311 proximate to sixth terminal end 2302 and a plane which may be collinear with a portion of upper surface 2311 proximate to fifth terminal end 2301. For example, and without limiting the scope of the present invention, if the corresponding angle may be 60 degrees, then angle 1580 may be 120 degrees.

In some embodiments, the at least the portion of the forwards-backwards adjust means may comprise slot 2320 located in the flat rod (or in the elongate member of support member 501). In some embodiments, not only may slot 2320 be an element of the forwards-backwards adjust means, but slot 2320 may also be a structural element of support member 501. In some embodiments, slot 2320 may run parallel with a longitude of the flat rod (or in the elongate member of support member 501). In some embodiments, slot 2320 may be proximate to fifth terminal end 2301, i.e. slot 2320 may be closer fifth terminal end 2301 than to sixth terminal end 2302. See e.g., FIG. 23E. In some embodiments (not depicted), slot 2320 may run substantially along a length of support member 501. In some embodiments, the forwards-backwards adjust means may also comprise friction clamp 2322. In some embodiments, a portion of friction clamp 2322 may be configured to pass through an opening of slot 2320 to attach support member 501 to the vessel. See e.g., FIG. 23A and FIG. 23E.

In some embodiments, friction clamp 2322 may comprise a threaded bolt 2321 (or threaded screw 2321) attached to a user engagement flange 2323. In some embodiments, threaded bolt 2321 (or threaded screw 2321) and user engagement flange 2323 may be integral to each other. In some embodiments, threaded bolt 2321 (or threaded screw 2321) may comprise outside threading. In some embodiments, threaded bolt 2321 (or threaded screw 2321) or portions thereof, may be configured to pass through the opening of slot 2320. In some embodiments, user engagement flange 2323 may be configured to be gripped by user 9000. In some embodiments, user engagement flange 2323 may be configured to be rotated by user 9000 gripping user engagement flange 2323, which may then rotate threaded bolt 2321 (or threaded screw 2321). In some embodiments, user engagement flange 2323 may comprise a pair of wings (e.g., as in a wing bolt), and/or undulations around a circumference of the flange of user engagement flange 2323, wherein the undulations may facilitate gripping.

In some embodiments, the forwards-backwards adjust means may further comprise a location of attachment to the vessel (e.g., vessel 200). In some embodiments, the location of attachment to the vessel may comprise a threaded hole 2330 into the vessel (e.g., vessel 200). In some embodiments, threaded hole 2330 may comprise complimentary inside threading that may be complimentary to the outside threading of threaded bolt 2321. See e.g., FIG. 23E. In some embodiments, threaded hole 2330 may be configured to receive threaded bolt 2321, such that threaded bolt 2321 may be screwed into and out of threaded hole 2330.

In some embodiments, the location of attachment to the vessel may be on a roof 2340 of rim 225 of at least one side wall 205 of the vessel (e.g., vessel 200). See e.g., FIG. 23E. In some embodiments, roof 2340 may be an upper exterior surface of rim 225 or portion thereof. In some embodiments, roof 2340 may be a substantially horizontal flat structure in reference to bottom interior surface 217 of internal volume 220 of vessel 200. In some embodiments, roof 2340 may comprise a slope.

In some embodiments, roof 2340 may be a roof to mechanical compartment 251. See e.g., FIG. 23E. In some embodiments, mechanical compartment 251 may be a compartment disposed between exterior wall surface 202 and interior wall surface 203. In some embodiments, mechanical compartment 251 may be a compartment disposed between vessel lining 200*a* and vessel cover 200*b*. In some exemplary embodiments, mechanical compartment 251 may be disposed opposite of neck-gasket-accommodator 335, disposed between vessel lining 200*a* and vessel cover 200*b*. In some embodiments, mechanical compartment 251 may be formed between exterior portions of second side wall 207 of vessel cover 200*b* and interior portions of second side wall 207 of vessel lining 200*a*. See e.g., FIG. 1B and FIG. 5G. In some embodiments, this mechanical compartment 251 may house at least some portions of electronics (e.g., controller 1100 and compressor 1110) and some portions of airline tubing 819 of face soaking device 100. In some embodiments, mechanical compartment 251 may comprise an access door located in exterior wall surface 202 (this access door is not depicted).

In some embodiments, roof 2340 may comprise recessed channel 2350. See e.g., FIG. 23E. In some embodiments, recessed channel 2350 may be configured to receive a portion of the support member 501 which may include slot 2320. In some embodiments, recessed channel 2350 may comprise a transverse width configured to fit a transverse width of support member 501, e.g., a transverse width of support member 501 proximate to fifth terminal end 2301. In some embodiments, recessed channel 2350 may include threaded hole 2330. See e.g., FIG. 23E. In some embodiments, recessed channel 2350 may be molded integrally with roof 2340. In some embodiments, a longitude of recessed channel 2350 may be parallel with a line running straight center from neck-gasket-accommodator 335 to at least one wall 201 (e.g., at least one side wall 205) directly opposite of neck-gasket-accommodator 335. In some embodiments, when support member 501 may be attached to recessed channel 2350 by threaded bolt 2321 passing through slot 2320 and into threaded hole 2330, support member 501 may slide either forwards or backwards within recessed channel 2350 to a desired position for user 9000. When friction clamp 2322 may be loose, support member 501 may be adjustable in the forwards-backwards directions. Because of bend 2315 and/or angle 2380 in support member 501, adjustments in the forwards-backwards directions may also function to adjust for head height preferences of user 9000. User 9000 may make a single adjustment (e.g., using slot 2320 and friction clamp 2322) that may result in both a forwards-backwards adjustment and a height adjustment; that may allow different sized heads of various user 9000s to support and/or rest their respective different sized heads onto various locations of upper surface 2311 and/or comfortable exterior surface 502. When friction clamp 2322 may be tightened, support member 501 may be secured in place in a particular desired position for a given user 9000. In some embodiments, tightening or loosening of friction clamp 2322 may be accomplished by user 9000 turning (rotating) user engagement flange 2323. In some embodiments, turning user engagement flange 2323 clockwise may tighten friction clamp 2322, while turning user engagement flange 2323 counterclockwise may loosen friction clamp 2322. In some embodiments, turning user engagement flange 2323 counterclockwise may tighten friction clamp 2322, while turning user engagement flange 2323 clockwise may loosen friction clamp 2322.

In some embodiments, the forwards-backwards adjust means may further comprise cover 2370. See e.g., FIG. 23E and FIG. 23A. When assembled, cover 2370 may be disposed between friction clamp 2322 and support member 501. Cover 2370 may cover slot 2320. Cover 2370 may fixedly attach to recessed channel 2350. In some embodiments, cover 2370 may also be configured to fit over recessed channel 2350. Cover 2370 may comprise a center hole 2375 large enough to permit passage of threaded bolt 2321. Center hole 2375 may be threaded (e.g., inside threaded) in some embodiments to accept threaded bolt 2321. Center hole 2375 may not be threaded in some embodiments, but may accept threaded bolt 2321 passing through center hole 2375 by center hole 2375 having an inside diameter larger than an outside diameter of threaded bolt 2321. In some embodiments, tightening friction clamp 2322, may cause cover 2370 to push against support member 501 to secure support member 501 into a given desired position for user 9000.

In some embodiments, roof 2340 may comprise a sleeve. This sleeve may be located where recessed channel 2350 may have otherwise been located in roof 2340. This sleeve may function as recessed channel 2350 and cover 2370 may function together. This sleeve may combine both the structures and the functionality of recessed channel 2350 and cover 2370. This sleeve may be configured to circumscribe a portion of support member 501, which may include slot 2320. This sleeve may comprise threaded hole 2330 and an opposing upper hole in the sleeve. In some embodiments, threaded hole 2330 and the opposing upper hole may be collinear. Fifth terminal end 2301 and portions of support member 501, with slot 2320, may pass slidingly into a main cavity of this sleeve. A longitude of this main cavity may be perpendicular to a collinear line passing through threaded hole 2330 and the opposing upper hole.

In some embodiments, this sleeve may be a single molded part that may be attached to roof 2340 or attached to recessed channel 2350. In some embodiments, this sleeve may comprise recessed channel 2350 and cover 2370, wherein the opposing upper hole and center hole 2375 may be collinear. In some embodiments, this sleeve may be molded integrally with vessel 200, e.g., an as an integral component of roof 2340.

In some embodiments, a longitude of this sleeve may be parallel with a line running straight center from neck-gasket-accommodator 335 to at least one wall 201 (e.g., at least one side wall 205) directly opposite of neck-gasket-accommodator 335. When support member 501 may be attached to this sleeve by threaded bolt 2321 passing through the opposing upper hole, and then into slot 2320, and then finally threaded into threaded hole 2330, support member 501 may be slid either forwards or backwards to the desired position of user 9000. When friction clamp 2322 may be loose, support member 501 may be adjustable in the forwards-backwards directions. Because of bend 2315 and/or angle 2380 in support member 501, adjustments in the forwards-backwards directions may also function to adjust for head height preferences of user 9000. User 9000 may make a single adjustment (e.g., using slot 2320 and friction clamp 2322) that may result in both a forwards-backwards adjustment and a height adjustment, that may allow different sized heads of various user 9000s to support and/or rest their respective different sized heads onto various locations of upper surface 2311 and/or comfortable exterior surface 502. When friction clamp 2322 may be tightened, support member 501 may be secured in place in the desired position. In some embodiments, the opposing upper hole may be large enough to permit frictional pressure to be applied from friction clamp 2322 to support member 501. In some embodiments, tightening or loosening of friction clamp 2322 may be accomplished by user 9000 turning (rotating) user engagement flange 2323. In some embodiments, turning user engagement flange 2323 one direction may tighten friction clamp 2322, while turning user engagement flange 2323 an opposite direction may loosen friction clamp 2322.

Because of the angle of bend 2315, when the head of user 9000 may be removably resting upon upper surface 2311 (and/or comfortable exterior surface 502), it may be possible for the face soaking device to slide away from user 9000. That is, a weight of the head of user 9000 may result in part in a force $f_x$ directed horizontally away from user 9000, which if sufficient to overcome a frictional force and a weight of the face soaking device (including liquid 101), the face soaking device may slide away from user 9000. See e.g., FIG. 23F.

A head rest subassembly 2400 embodiment, depicted in a FIG. 24 series of figures, may provide a solution to this potential sliding problem of head rest subassembly 2300. In some embodiments, head rest subassembly 2400 may replace head rest subassembly 2300. See e.g., FIG. 24A, FIG. 24B, FIG. 24C, and FIG. 24D.

FIG. 24A may depict an assembled overall perspective view of a face soaking device with head rest subassembly 2400. FIG. 24B may depict head rest subassembly 2400, but with a portion of head rest subassembly 2400 tilted upwards. FIG. 24C may depict the head rest subassembly 2400, but from a top view. FIG. 24D may depict the head rest subassembly 2400, but showing a transparent view within mechanical compartment 251.

In some embodiments of face soaking devices the face soaking device may comprise head rest subassembly 2400. In some embodiments, head rest subassembly 2400 may comprise: support member 501 and at least one longitudinal-support 2420. In some embodiments support member 501 may comprise a transverse-head-support-member 2410. In some embodiments, head rest subassembly 2400 may comprise: transverse-head-support-member 2410 and at least one longitudinal-support 2420. See e.g., FIG. 24A. In some embodiments, transverse-head-support-member 2410 may be rigid to semi-rigid. In some embodiments, transverse-head-support-member 2410 may be made from round bar. In some embodiments, at least one longitudinal-support 2420 may be rigid to semi-rigid.

In some embodiments, transverse-head-support-member 2410 may be for supporting at least the portion of the head of user 9000. In some embodiments, transverse-head-support-member 2410 may be substantially perpendicular with respect to a line running from a front to a back of the face soaking device. The front of a given face soaking device may be closer to the vessel neck gasket (e.g., vessel neck gasket 340) than the back and the back may be disposed opposite of the front.

In some embodiments, at least one longitudinal-support 2420 may be coupled to the transverse-head-support-member 2410. See e.g., FIG. 24A. In some embodiments, at least one longitudinal-support 2420 may provide structural support to transverse-head-support-member 2410. In some embodiments, at least one longitudinal-support 2420 may carry loads applied to transverse-head-support-member 2410. In some embodiments, at least one longitudinal-support 2420 may comprise two opposing ends, a first-end 2421 and a second-end 2422, where second-end 2422 may be in physical contact with the at least one wall 201 or may be passing into at least one wall 201. In some embodiments, this second-end 2422 may be anchored in mechanical compartment 251. See FIG. 24D for second-end 2422. In some embodiments, at least one wall 201 (e.g., a back wall) may comprise a vertical slot 2451 that may provide at least one longitudinal-support 2420 with access to mechanical compartment 251. See e.g., FIG. 24A. In some embodiments, head rest subassembly 2400 may be substantially, but not entirely, located within internal volume 220 of a given face soaking device embodiment. For example and without limiting the scope of the present invention, knob 2443 may be located exteriorly of internal volume 220. Or during maintenance and/or adjustments, portions of head rest subassembly 2400 may be tilted out (and/or removed) of internal volume 220. See e.g., FIG. 24B. And second-end 2422 of at least one longitudinal-support 2420 may be located in mechanical compartment 251 (see FIG. 24D).

Turning back to discussing FIG. 24A, in some embodiments, transverse-head-support-member 2410 may be a curved elongate member. In some embodiments, a curve of the curved elongate member of transverse-head-support-member 2410 may curve into internal volume 220 of the vessel of the face soaking device. In some embodiments, transverse-head-support-member 2410 may comprise at least one comfortable exterior surface 502. In some embodiments, at least one comfortable exterior surface 502 may comprise one or more of a cushion or a soft material. In some embodiments, the cushion or the soft material is disposed on an upper surface of the at least one comfortable exterior surface 502 to provide padding to the portion of the head of user 9000. See e.g., FIG. 24A.

In some embodiments, at least one longitudinal-support 2420 may be substantially parallel with the line running from the front to the back of the face soaking device. In some embodiments, at least one longitudinal-support 2420 may be substantially an elongate member. In some embodiments, at least one longitudinal-support 2420 may be substantially an "L" shaped elongate member. In some embodiments, a region proximal to a bend that forms an "L" in the at least one longitudinal-support 2420 may be substantially flat to operate as a spring hinge. In some embodiments, second-end 2422 (of at least one longitudinal-support 2420) may be received in a cavity 2461, in mechanical compartment 251, or cavity 2461 in mechanical compartment 251. See FIG. 24D. In some embodiments, this cavity 2461 may be located in mechanical compartment 251 (or in physical contact with mechanical compartment 251 or proximal to mechanical compartment 251, but closer to the back than to the front) of the vessel of the face soaking device. In some embodiments, a longitude of this cavity 2461 may be oriented substantially vertical with respect to a ground (substrate) upon which the face soaking device may be located on. In some embodiments, this longitude of this cavity 2461 may be oriented substantially vertical with respect to a surface of at least one base 215 (i.e., substantially perpendicular with respect to the surface of at least one base 215). In some embodiments, a size (diameter and longitude) of this cavity 2461 may be sized to form a frictional press fit with second-end 2422 (at least one longitudinal-support 2420) or with a region of at least one longitudinal-support 2420 within a proximate distance of second-end 2422 (at least one longitudinal-support 2420). See e.g., FIG. 24D. In some embodiments, this proximate distance may be within: five inches, six inches, seven inches, eight inches, and the like.

In some embodiments, at least one longitudinal-support 2420 may comprise two longitudinal-supports 2420, a first longitudinal-support 2420 and a second longitudinal-support 2420. See e.g., FIG. 24A. In such embodiments, transverse-head-support-member 2410 may comprise opposing ends, wherein each opposing end may be (slidingly) coupled to a portion of each of the two longitudinal-supports 2420. In some embodiments, the two longitudinal-supports 2420 may be substantially parallel with each other. Note in embodiments with two longitudinal-supports 2420 there may be two couplings 2430, two vertical slots 2451, and two cavities housing the second-end of at least one longitudinal-support 2420. See e.g., FIG. 24A.

In some embodiments, head rest subassembly 2400 may comprise a forwards-backwards adjust means for removable setting of a location of the transverse-head-support-member 2410 along a longitude of at least one longitudinal-support 2420. In some embodiments, this forward-backwards adjust means may comprises a coupling 2430 that may connect at least one longitudinal-support 2420 to transverse-head-support-member 2410. See e.g., FIG. 24A. In some embodiments, an end of transverse-head-support-member 2410 may be attached to coupling 2430. In some embodiments, this point of attachment of the ends of transverse-head-support-member 2410 to coupling 2430, may be a freely rotatable hinge, to permit free swing motion of transverse-head-support-member 2410 with respect to coupling 2430 (and at least one longitudinal-support 2420). In some embodiments, coupling 2430 may comprise a receiving-hole 2431 for receiving a portion of the at least one longitudinal-support 2420. In some embodiments, receiving-hole 2431 may be sized (e.g., diameter) to permit sliding of coupling 2430 along the longitude of the at least one longitudinal-support 2420. In some embodiments, receiving-hole 2431 may be sized to permit frictional sliding of coupling 2430 along the longitude of the at least one longitudinal-support 2420. In some embodiments, coupling 2430 may comprise a set screw 2435 for setting the location by applying removable friction to the portion of at least one longitudinal-support 2420. Tightening set screw 2435 may prevent or minimize sliding of coupling 2430 along the longitude of at least one longitudinal-support 2420. See e.g., FIG. 24A.

In some embodiments, coupling 2430 may comprise a spring loaded set pin (not depicted) for setting the location by applying removable friction to the portion of at least one longitudinal-support 2420. Such a spring loaded set pin may be an alternative to set screw 2435. Such a spring loaded set pin may have two operational states, a resting state and pressed state. In the resting state the spring may cause spring loaded set pin to exert pressure against the portion of at least one longitudinal-support 2420. In the pressed state, an exterior of the spring loaded set pin may be pushed by user 9000, compressing the spring and releasing pressure against the portion of at least one longitudinal-support 2420. In some embodiments, at least one longitudinal-support 2420 may comprise a plurality of holes (not depicted), spaced at various intervals, for removably receiving of the pin of the spring loaded set pin when in the resting state. Note, the spring loaded set pin may not be depicted in the FIG. 24 series drawing (figures).

In some embodiments, head rest subassembly 2400 may comprise a height adjust means for removable setting of a vertical location of transverse-head-support-member 2410 with respect to the ground (i.e., the substrate) that the face soaking device may be located upon. In some embodiments, head rest subassembly 2400 may comprise the height adjust means for removable setting of the vertical location of transverse-head-support-member 2410 with respect to the surface of at least one base 215 (i.e., bottom interior surface 217).

In some embodiments, the height adjust means may comprise a set-bolt 2441 (as part of knob 2443) and a head-rest-brake 2445. See FIG. 24D. In some embodiments, this head-rest-brake 2445 may be located in mechanical compartment 251. In some embodiments, this head-rest-brake 2445 may be a flat bar, with a longitude parallel with a transverse width of the vessel. In some embodiments, this head-rest-brake 2445 may comprise a central threaded hole (inside threaded) sized to receive a threaded portion (outside threading) of the set-bolt of knob 2443. In some embodiments, this head-rest-brake 2445 may be comprise an upper surface 2446 to support a region of at least one longitudinal-support 2420 disposed away from first-end 2421. In some embodiments, turning knob 2443 may raise or lower, depending upon a direction of rotation, this head-rest-brake 2445 in a vertical direction with respect to the surface of at least one base 215; which in turn may raise or lower, at least one longitudinal-support 2420, since portions of at least one longitudinal-support 2420 may resting on ends of this head-rest-brake 2445. See e.g., FIG. 24D.

In some embodiments, this set-bolt 2441 may comprise knob 2443 located outside of mechanical compartment 251 exteriorly of roof 2340. In some embodiments, some of threaded portion 2442 of this set-bolt may pass through the center hole of roof 2340, such that knob 2443 remains exterior to mechanical compartment 251. See FIG. 24D. In some embodiments, knob 2443 may comprise perimeter geometry that provides friction when gripped by user 9000. For example, and without limiting the scope of the present invention this perimeter geometry may comprise finger indentations, alternating ridges, undulations, and the like. This set-bolt 2441 may be substantially similar to the structure of friction clamp 2322.

A FIG. 25 series of figures may comprise FIG. 25A through FIG. 25H. These FIG. 25 series of figures may depict various head rest subassembly embodiments (e.g., 2500, 2540, 2550, and 2560).

FIG. 25A may depict a face soaking device with an alternative embodiment head rest subassembly 2500; shown from a top perspective view. FIG. 25B may depict head rest subassembly 2500, shown from a top perspective view. FIG. 25C may depict head rest subassembly 2500, but shown from an exploded top perspective view.

In some embodiments, head rest subassembly 2500 may comprise support member 501 (or a strap) and comfortable exterior surface 502 in communication with support member 501. In some embodiments, head rest subassembly 2500 may comprise a height adjust means. In some embodiments, the height adjust means may comprise at least one strut 2511. Each strut 2511 may comprise a third terminal end 2512 and a fourth terminal end 2513 disposed opposite of third terminal end 2512. Third terminal end 2512 may be connected to support member 501 or to the strap. Fourth terminal end 2513 may be connected to at least one wall 201 or the at least one base 215. In some embodiments, at least one strut 2511 may be two struts 2511. In some embodiments, at least one strut 2511 may be vertical or substantially vertical, when installed in internal volume 220. In some embodiments, at least one strut 2511 may be horizontal or substantially horizontal, when installed in internal volume 220.

In some embodiments, fourth terminal end 2513 of a given strut 2511 may connect to exterior wall surface 202, to interior wall surface 203, and/or to bottom interior surface 217. For example, and without limiting the scope of the present invention, fourth terminal end 2513 may connect to interior surface of at least one base 215 (bottom interior surface 217) or to one of interior side wall surfaces 203. In some embodiments, where fourth terminal end 2513 may connect to one of interior side wall surfaces 203, at least one strut 2511 may be horizontal or substantially horizontal.

For example, and without limiting the scope of the present invention, the fourth terminal end 2513 may connect to at least one exterior side wall(s) 202.

In some embodiments, a point of connection of fourth terminal end 2513 and of wall 201 of vessel 200, whether to interior wall surface 203 or to exterior wall surface 202, may be via a strut attachment means 2530.

In some embodiments, head rest subassembly 2500 may comprise strut attachment means 2530. Strut attachment means 2530 may be configured to connect fourth terminal end 2513 to at least one wall 201 of vessel 200. In some embodiments, strut attachment means 2530 may comprise wing bolt 2531 and an inside threaded hole through at least one strut 2511 for accepting this wing bolt 2531. See e.g., FIG. 25B and FIG. 25C.

In some embodiments, strut attachment means 2530 may be configured to connect fourth terminal end 2513 to at least one base 215 of vessel 200.

In some embodiments strut attachment means 2530 may comprise a track and complimentary flange system. For example, the track may be located on exterior wall surface 202 or interior wall surface 203 and the flange may be at fourth terminal end 2513. The flange may be received and captured by the track and slide along a groove of the track. See FIG. 26A and FIG. 26E for track and flange embodiments.

In some embodiments strut attachment means 2530 may comprise a pivotable locking means 2520. In some embodiments, wing bolt 2531 may be the same component as the wing bolt of friction clamp 2522. See FIG. 25F through FIG. 25H discussed below after the FIG. 25D discussion.

FIG. 25D may depict an alternative embodiment of a head rest subassembly 2540, shown from an exploded top perspective view. A support member 501 may be adjusted vertically, wherein the support member 501 may be a component of head rest subassembly 2540.

In some embodiments, head rest subassembly 2540 may comprise support member 501 and comfortable exterior surface 502 in communication with support member 501. In some embodiments, head rest subassembly 2540 may comprise a height adjust means. In some embodiments, the height adjust means may comprise at least one strut 2511. Each strut 2511 may comprise third terminal end 2512 and fourth terminal end 2513 disposed opposite of third terminal end 2512.

Here in FIG. 25D with head rest subassembly 2540, support member 501 (or the strap) may be adjusted vertically by use of height adjustment slots 2514. Each strut 2511 may comprise at least one height adjustment slot 2514. Each height adjustment slot 2514 may run in parallel or substantially parallel with a longitude of a respective strut 2511, as depicted in FIG. 25D. Such slots 2514 may permit support member 501 (or the strap) to be varied in height with respect to the ground (the substrate) or at least one base 215. A height adjust pin 2515 may secure strut 2511 to each terminal end of support member 501 (or the strap), by height adjust pin 2515 passing through slot 2514 and into the terminal end of support member 501 (or the strap). In some embodiments, height adjust pin 2515 may be a screw, a bolt, a screw/bolt with a washer, and the like.

FIG. 25E may depict an alternative embodiment of a head rest subassembly 2550, shown from side (right and left) view. A support member 501 may be adjusted vertically and/or adjusted in a forwards-backwards direction with respect to a front of the face soaking device. FIG. 25F may depict head rest subassembly 2550, but shown as a cross-sectional view along sectional line 25F-25F shown in FIG. 25E. This cross-sectional view may depict how support member 501 may be pivoted to achieve vertical adjustment and/or forwards-backwards adjustments.

In some embodiments, head rest subassembly 2550 may comprise support member 501 and comfortable exterior surface 502 in communication with support member 501. In some embodiments, head rest subassembly 2550 may comprise a height adjust means. In some embodiments, the height adjust means may comprise at least one strut 2511. Each strut 2511 may comprise third terminal end 2512 and fourth terminal end 2513 disposed opposite of third terminal end 2512.

In some embodiments, fourth terminal end 2513 may be configured to attach to a region at or near top opening 226 of vessel 200. For example, and without limiting the scope of the present invention, in some embodiments, near to top opening 226 may be five inches or less from top opening 226. In other embodiments, near to top opening 226 may be other distances. In some embodiments, fourth terminal end 2513 may comprise a pivotable locking means 2520. Pivotable locking means 2520 may attach fourth terminal end 2513 to the region. Pivotable locking means 2520 may comprise a rotatable axle member 2521 which rests upon top opening 226 (or upon rim 225). In FIG. 25F, rotatable axle member 2521 may be depicted as a pulley member with a short rod passing through a center of the pulley member. This short rod may be captured on each side by fourth terminal end 2513, as fourth terminal end 2513 bends around the pulley member, forming a pocket for the pulley member to reside within. See e.g., FIG. 25F.

When rotatable axle member 2521 pivots on top of top opening 226, support member 501 (or the strap) may move both in height and with respect to moving forwards-backwards within internal volume 220 of vessel 200. Pivotable locking means 2520 also may comprise a friction clamp 2522 for locking desired adjustments. When the desired adjustment may be made by pivoting rotatable axle member 2521, the desired adjustment may be locked in place with friction clamp 2522. As depicted, friction clamp 2522 may be a wing bolt or some other frictional clamping means.

FIG. 25G may depict an alternative embodiment of a head rest subassembly 2560, shown from side rear view. A support member 501 may be adjusted vertically and/or adjusted in a forwards-backwards direction with respect to the front of the face soaking device. FIG. 25G may also depict sectional line 25H-25H. FIG. 25H may depict head rest subassembly 2560, but shown as a cross-sectional view along sectional line 25H-25H. This cross-sectional view may depict how support member 501 may be pivoted to achieve vertical adjustment and/or forwards-backwards adjustment.

In some embodiments, head rest subassembly 2560 may comprise support member 501 and comfortable exterior surface 502 in communication with support member 501. In some embodiments, head rest subassembly 2560 may comprise a height adjust means. In some embodiments, the height adjust means may comprise at least one strut 2511. Each strut 2511 may comprise third terminal end 2512 and fourth terminal end 2513 disposed opposite of third terminal end 2512.

In some embodiments, fourth terminal end 2513 may be configured to attach to the region at or near top opening 226 of vessel 200. For example, and without limiting the scope of the present invention, in some embodiments, near to top opening 226 may be five inches or less from top opening 226. In other embodiments, near to top opening 226 may be other distances. In some embodiments, fourth terminal end 2513 may comprise pivotable locking means 2520. Pivotable locking means 2520 may attach fourth terminal end 2513 to the region. Pivotable locking means 2520 may comprise rotatable axle member 2521 which may rest upon top opening 226 (or upon rim 225).

When rotatable axle member 2521 pivots on top of top opening 226, support member 501 (or the strap) may move both in height and with respect to moving forwards-backwards within internal volume 220 of vessel 200. Pivotable locking means 2520 also may comprise friction clamp 2522 for locking desired adjustments. When the desired adjustment may be made by pivoting rotatable axle member 2521, the desired adjustment may be locked in place with friction clamp 2522. As depicted, friction clamp 2522 may be the wing bolt or some other frictional clamping means.

For example, and without limiting the scope of the present invention, the pivotable locking means 2520 may be assembled from a cylindrical elongate member acting as rotatable axle member 2521.

In some embodiments, head rest subassembly 2500, 2540, 2550, and/or 2560 may comprise a forwards-backwards adjust means. The forwards-backwards adjust means may be configured to vary a location of the support member 501 (or the strap) along a longitude of face 9010 residing within internal volume 220 of vessel 200. In some embodiments, a longitude of support member 501 (or the strap) may be perpendicular to the longitude of face 9010 residing within internal volume 220. The forwards-backwards adjust means may be in physical contact with at least one wall 201 of vessel 200 or with at least one base 215 of vessel 200.

In some embodiments, the forwards-backwards adjust means further may comprise friction clamp 2522 and/or strut attachment means 2530 (e.g. wing bolt 2531). For example, see FIG. 25E and FIG. 25H, where a double-headed straight arrow may indicate that friction clamp 2522 may be slid in the forwards-backwards directions.

In some embodiments, the forwards-backwards adjust means further may comprise at least one track. The at least one track may be located on an exterior wall surface 202, an interior wall surface 203 of vessel 200, or an interior surface at least one base 215 (e.g., bottom interior surface 217). The at least one track may be configured to receive and capture the fourth terminal end 2513. Fourth terminal end 2513 may slide within a groove of the at least one track to vary the longitude of support member 501 (or the strap) along the longitude of the face residing within internal volume 220. See FIG. 26A and FIG. 26E for track and flange embodiments.

A FIG. 26 series of figures may comprise FIG. 26A through FIG. 26F. These FIG. 26 series of figures may depict additional head rest subassemblies that may focus on one or more of: different forwards-backwards adjustment means, different height adjust means, and/or different ways support member 501 may be in communication with the vessel (e.g., vessel 200).

In some embodiments, the forwards-backwards adjust means and/or the height adjust means may further comprise at least one track 2671. The at least one track 2671 may be located on exterior wall surface 202 (see e.g., FIG. 26A), interior wall surface 203 (see e.g., FIG. 26E), or an interior of at least one base 215 (e.g., bottom interior surface 217). The at least one track 2671 may be configured to receive and capture fourth terminal end 2513. Fourth terminal end 2513 may slide within a groove of at least one track 2671 to vary the height and/or forwards-backwards location of support member 501 (or the strap). Fourth terminal end 2513 may comprise a flange geometry, wherein the flange geometry may be configured to be (removably, in some embodiments) captured by the groove of at least one track 2671. See e.g., FIG. 26A and FIG. 26E.

FIG. 26A may depict one or more of a forwards-backwards adjust means and/or a height adjust means for support member 501, using a track and flange embodiment, shown from a cross-sectional view from right to left (i.e., a transverse-width cross-sectional view). FIG. 26E may depict may depict one or more of a forwards-backwards adjust means and/or a height adjust means for support member 501, using a track and flange embodiment, shown from a cross-sectional view from right to left (i.e., a transverse-width cross-sectional view).

In some embodiments, a length of at least one track 2671 may extend vertically, to allow for height adjustments of support member 501 (or the strap). In some embodiments, the length of at least one track 2671 may extend horizontally along at least one side wall, to allow for forwards-backwards (i.e., front-back) adjustment of support member 501 (or the strap). In some embodiments, the length of at least one track 2671 may extend both in a vertical manner and in a horizontal manner along at least one side wall 201, to allow for both adjustments in height and in forwards-backwards positioning of support member 501 (or the strap). For example, a diagonal track, an ovoid track, or a semi-ovoid track may be used wherein such a track may allow for both adjustments in height and in front to back positioning of support member 501 (or the strap).

In some embodiments, fourth terminal end 2513 may be locked into various positions along at least one track 2671 by a system of a spring loaded pin with complimentary plurality of holes along the groove.

In some embodiments, fourth terminal end 2513 may be locked into various positions along at least one track 2671 by fourth terminal end 2513 having a resting state causing a friction fit within the groove that when depressed, with a spring loaded button, a reduction in the resting state friction fit may occur such that fourth terminal end 2513 may be slid to a different position along at least one track 2671.

In some embodiments, each at least one strut may 2511 may be comprised of two sub-struts. These two sub-struts may be complimentary to each other in that one of the two sub-struts may fit into a cavity of the other sub-strut. These two sub-struts may configured to linearly translate with respect to each other in a telescoping fashion. The height of support member 501 (or the strap) may be varied according to this telescoping function. See e.g., FIG. 26B, FIG. 26C, and FIG. 26D.

FIG. 26B may depict a height adjust means for support member 501, using a telescoping strut embodiment, shown from a cross-sectional view from right to left (i.e., a transverse-width cross-sectional view).

FIG. 26C may depict a height adjust means for support member 501, using a telescoping strut embodiment, shown from a cross-sectional view from right to left (i.e., a transverse-width cross-sectional view). At least two different struts may be in communication with at least one base 215 (e.g., bottom interior surface 217).

FIG. 26D may depict a height adjust means for support member 501, using a telescoping strut embodiment, shown from a cross-sectional view from right to left (i.e., a transverse-width cross-sectional view). At least one of these struts may be in communication with at least one base 215 (e.g., bottom interior surface 217).

In some embodiments, the telescoping function of the two sub-struts may be accomplished by at least portions of one such sub-strut fitting into portions of an inside diameter (or inside cavity) of the other sub-strut. In such embodiments, using a spring loaded pin mechanism with a complimentary plurality of holes to vary the telescoping height along a longitude of at least one strut may 2511 may be used to set or lock various positions of varying height. In some embodiments, the sub-strut with a larger diameter may also house at least one spring.

FIG. 26F may depict a height adjust means and a forwards-backwards adjust means for support member 501, using a pivotable locking means, shown from a cross-sectional view from right to left (i.e., a transverse-width cross-sectional view). The pivotable locking means depicted in FIG. 26F may similar structurally and functionally to pivotable locking means 2520 shown in FIG. 25G and FIG. 25H. FIG. 26F may include "J" hook 2681. "J" hook 2681 may provide a means for support member 501 to be in communication with the vessel (e.g., vessel 200). "J" hook 2681 may provide a place of attachment to the vessel. A lower terminal portion of the "J" in "J" hook 2681 may attach or hook onto a downward facing upper exterior lip of the vessel. See e.g., FIG. 26F. "J" hook 2681 along with friction clamp 2522 may provide a means for securing different forwards-backwards and/or different height adjustments of support member 501. A top portion of "J" hook 2681 may be attached to rotatable axle member 2521, where rotatable axle member 2521 may rest upon rim 225. Friction clamp 2522 may engage rotatable axle member 2521. "J" hook 2681 may be complimentary with friction clamp 2522. This embodiment may be employed when rim 225 of the vessel (e.g., vessel 200) may comprise the downward facing upper exterior lip.

In some embodiments, at least one strut 2511 may be hollow with a solid and waterproof exterior, such that this at least one strut 2511 may act as hose 420 or tubing 420; or as a conduit for housing portions of hose 420 or tubing 420. In such embodiments, the given head rest subassembly and the breathing apparatus embodiments may be attached to each other. In some such embodiments, second terminal end 422 may connect to the hollow strut 2511, such that respiratory gasses may pass freely within the hollow interior of such a strut 2511. In such embodiment, fourth terminal end 2513 may be located outside of liquid 101, such that at least one vessel-tube-hose-connector (e.g., 430) may be located at fourth terminal end 2513.

In some embodiments, structural head rest subassemblies (e.g., 500, 2300, 2400, 2500, 2540, 2550, and/or 2560) and/or support member 501 may be replaced (and/or augmented) with liquid 101 being sufficiently buoyant (dense)

to support the head of user 9000. For example, and without limiting the scope of the present invention, liquid 101 may be a saline with a salinity in about the range of 5% to about 35%.

Figure 7A:
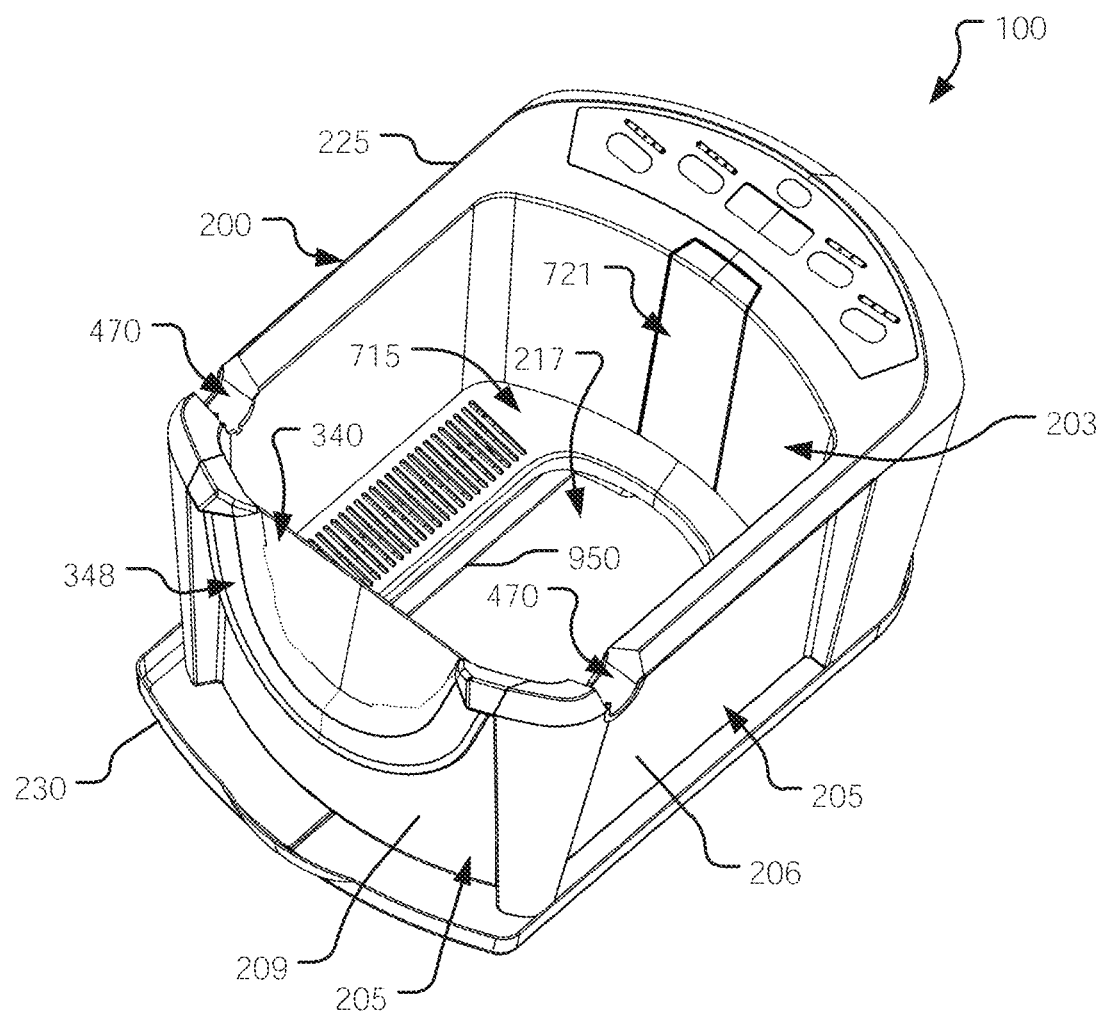
FIG. 7A may depict an assembled heater subassembly, while in communication with the vessel, shown from a top perspective view, but with the breathing apparatus, the head rest subassembly, and portions of a gas diffuser removed.
Figure 7B:
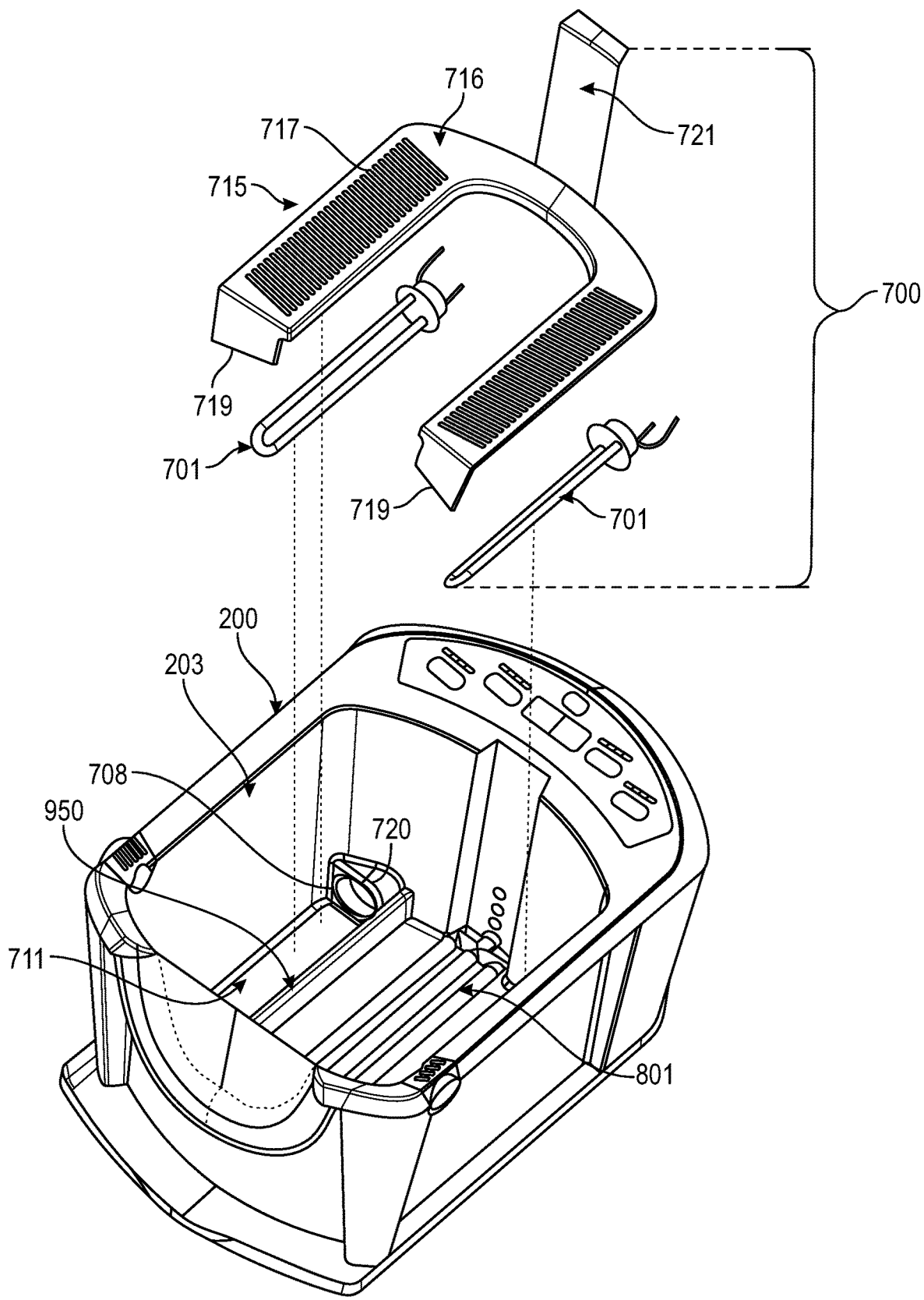
FIG. 7B may depict the heater subassembly of FIG. 7A, but shown in a top perspective exploded view, wherein the heater subassembly is exploded from the vessel.
Figure 7C:
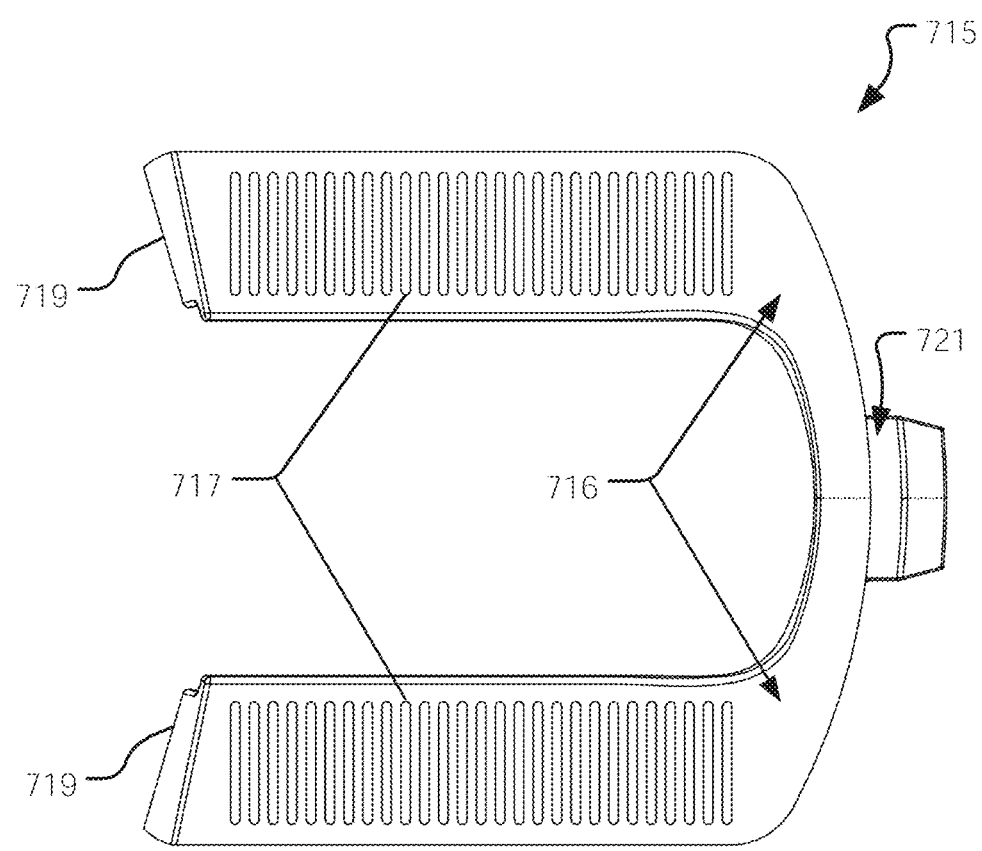
FIG. 7C may depict a heat shield (shield) of the heater subassembly, shown from a top view.
Figure 7D:
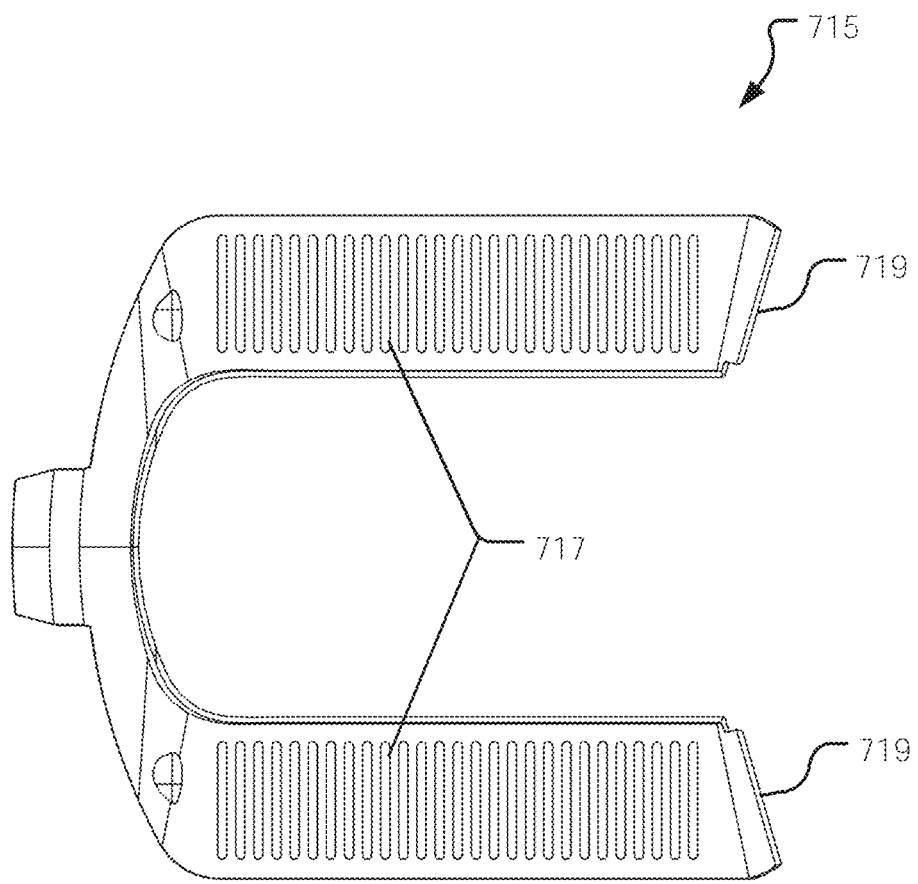
FIG. 7D may depict the shield of the heater subassembly, shown from a bottom view.
Figure 7E:
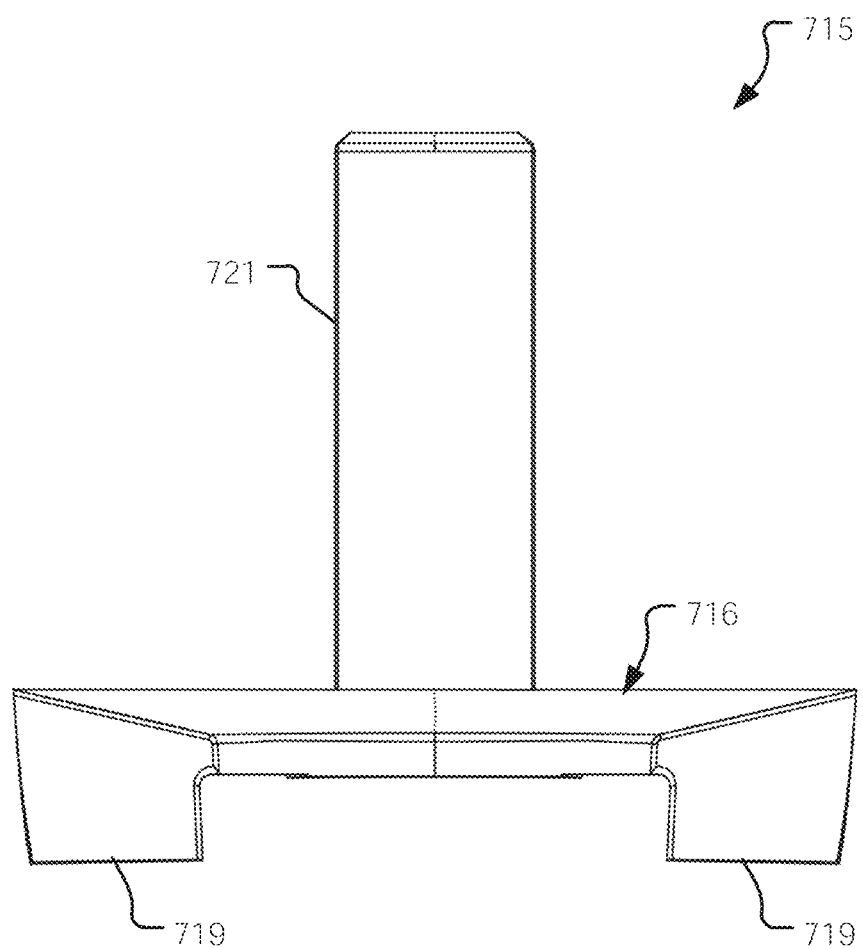
FIG. 7E may depict the shield of the heater subassembly, shown from a front view.
Figure 7F:
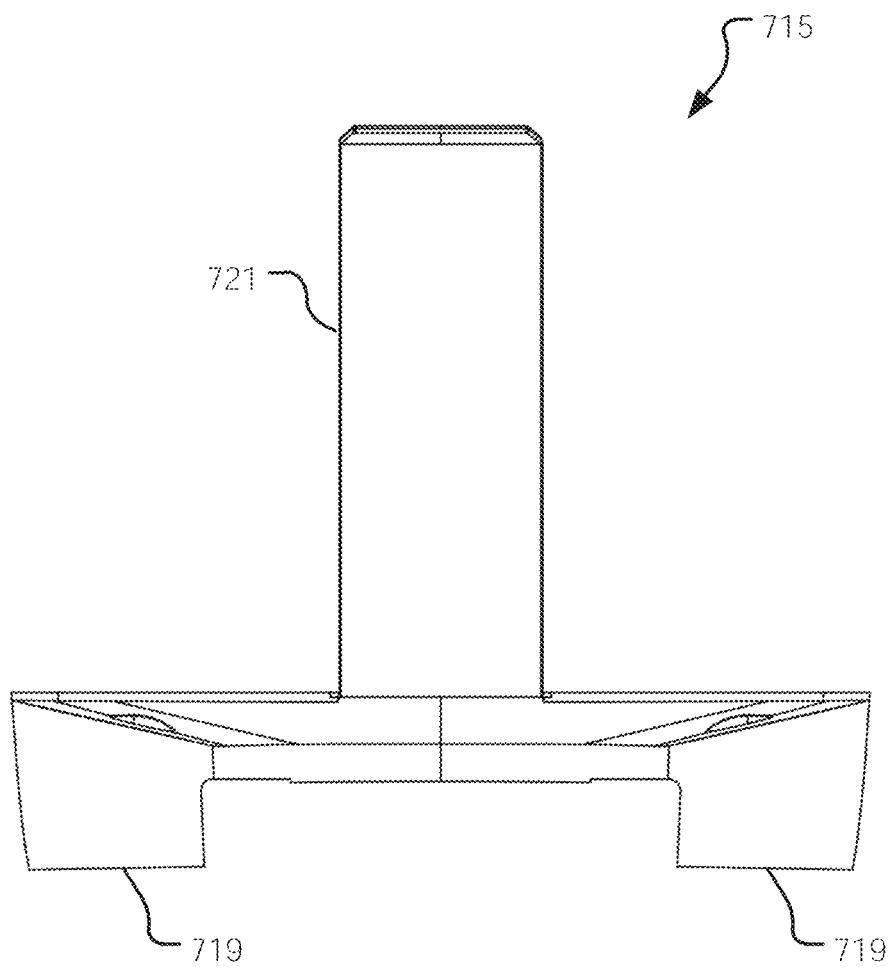
FIG. 7F may depict the shield of the heater subassembly, shown from a back view.
Figure 7G:
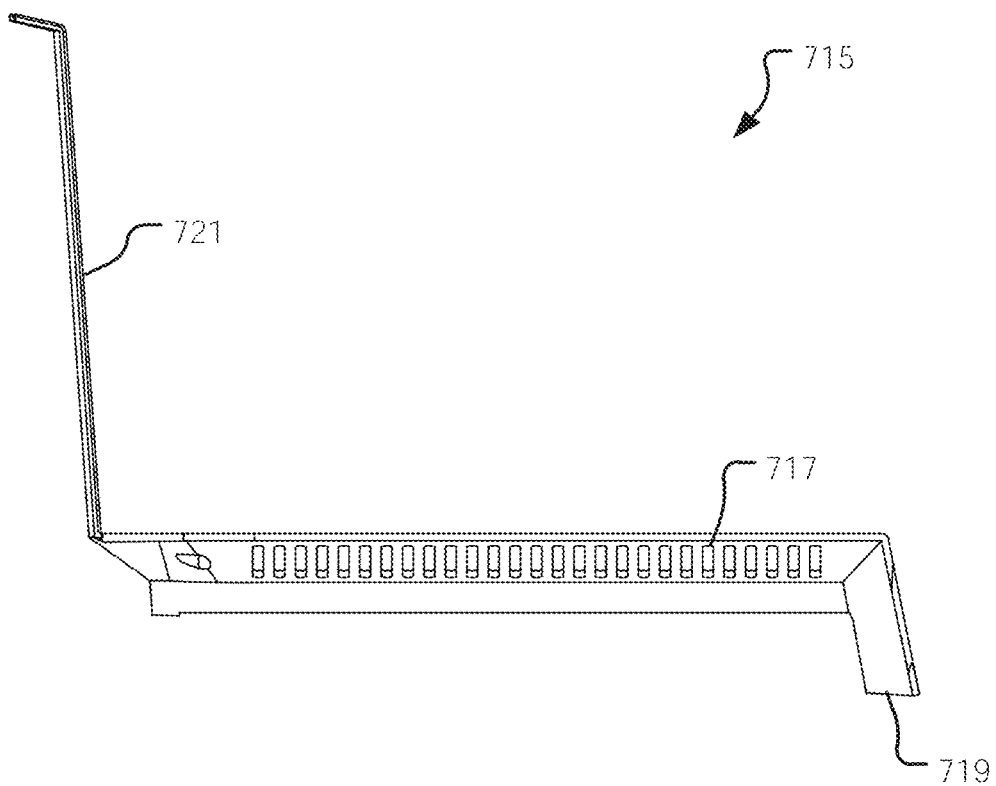
FIG. 7G may depict the shield of the heater subassembly, shown from a longitudinal side view.
Figure 7H:
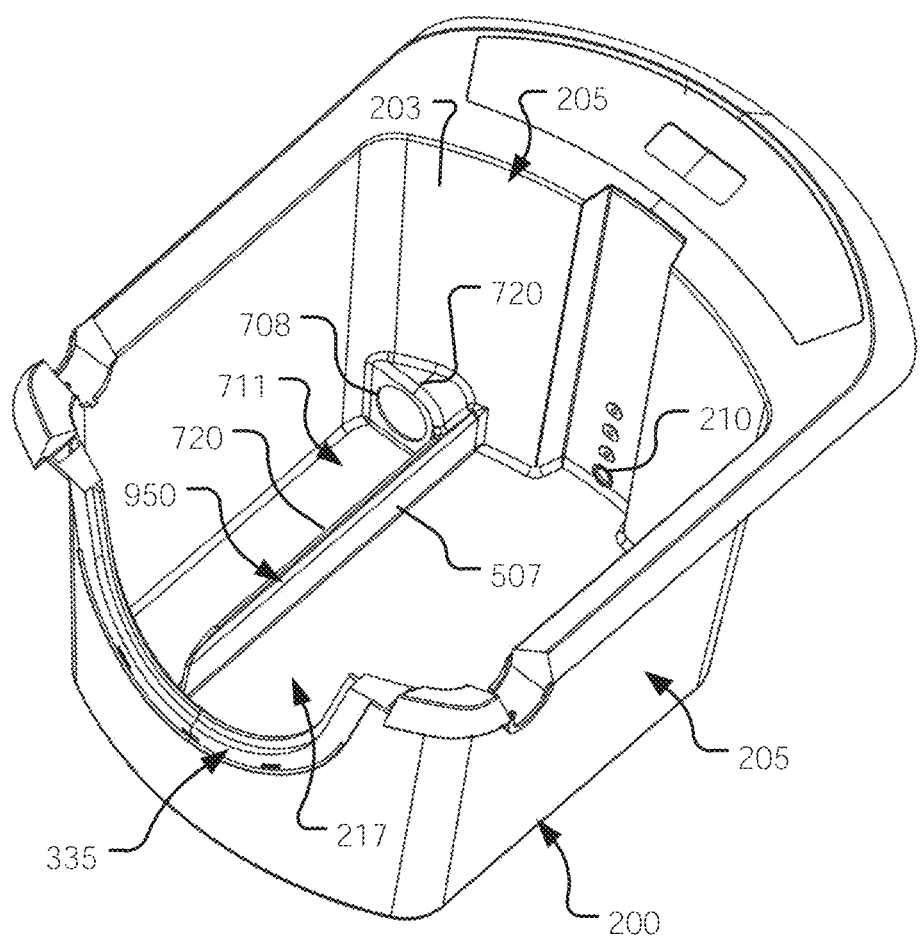
FIG. 7H may depict a top perspective view of the vessel, showing a partial interior view of the vessel, but with the heater subassembly, the breathing apparatus, and the head rest subassembly, and portions of the gas diffuser removed.
Figure 71:
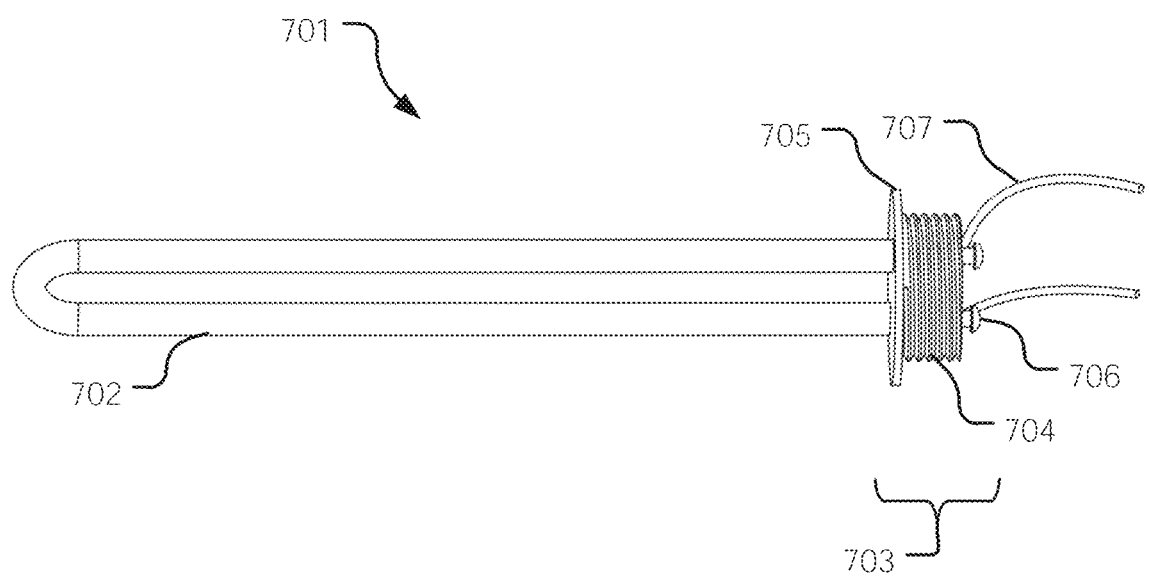
Figure 7J:
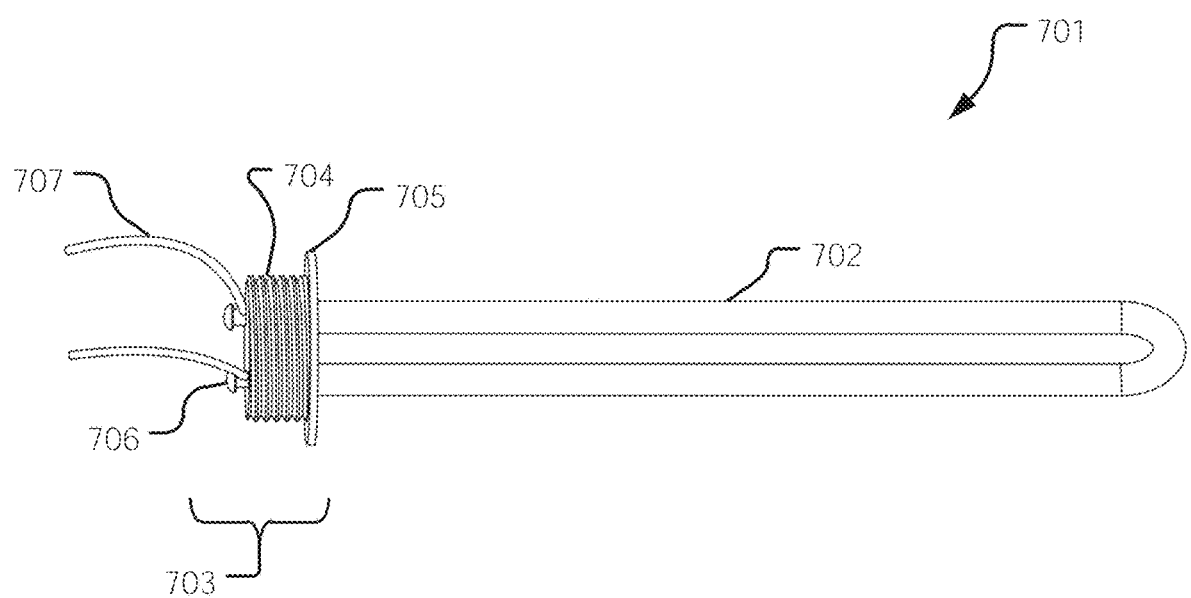
FIG. 7J may depict the at least one heating element of the heater subassembly, shown from a bottom view.
Figure 7K:
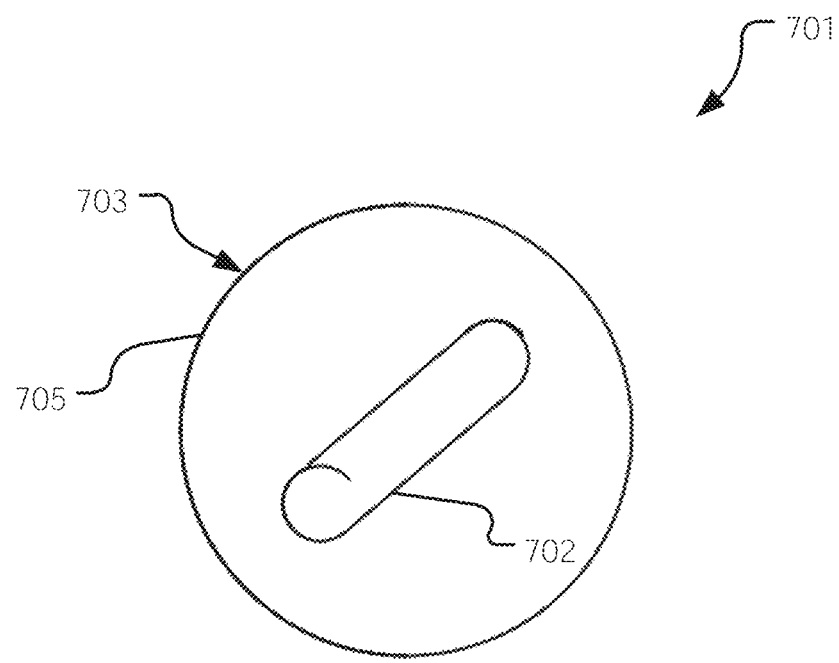
FIG. 7K may depict the at least one heating element of the heater subassembly, shown from a front view.
Figure 7L:
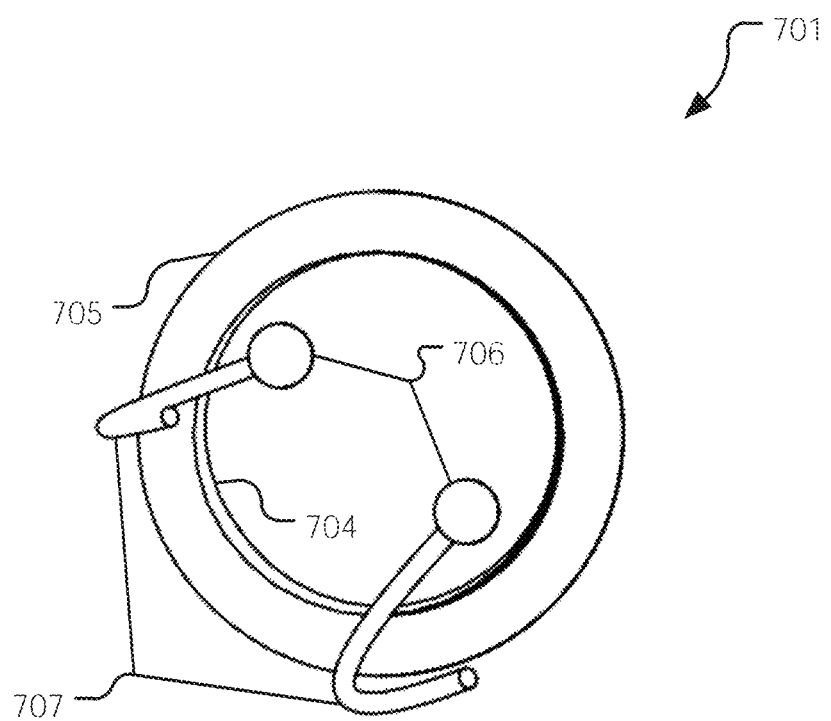
FIG. 7L may depict the at least one heating element of the heater subassembly, shown from a back view.
Figure 7M:
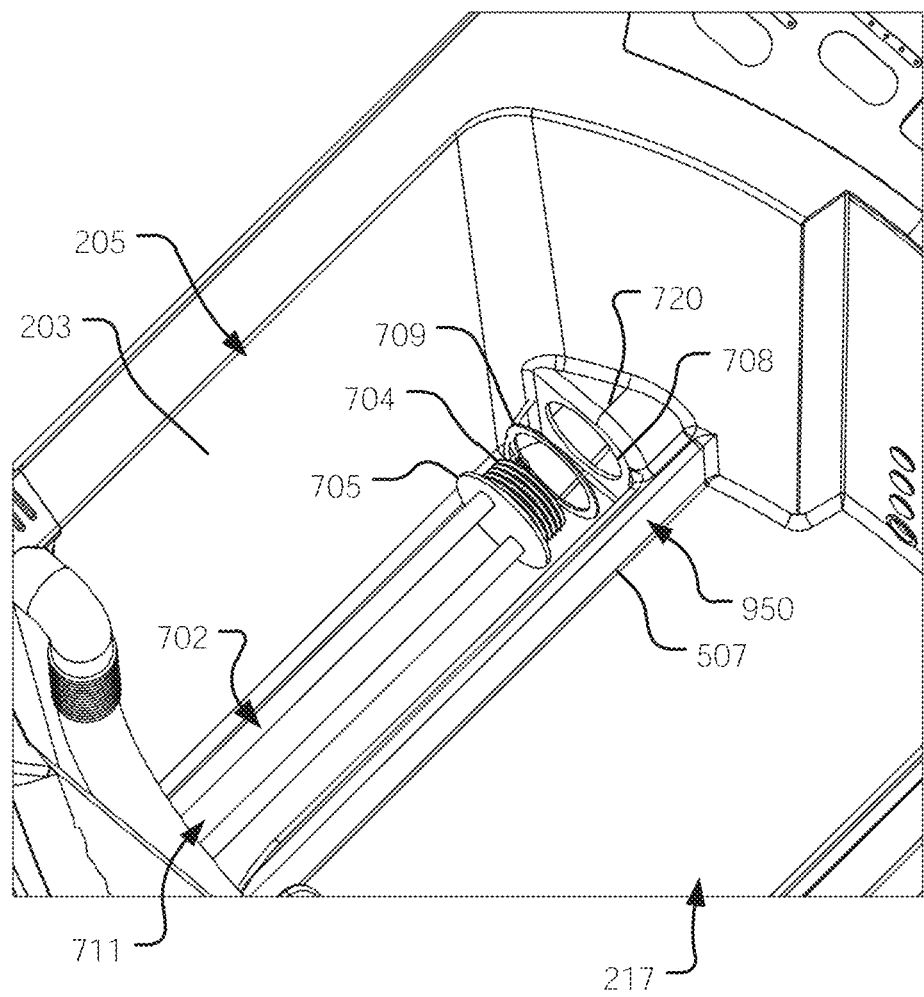
FIG. 7M may depict the at least one heating element disposed within an interior volume of the vessel, but while exploded from a back interior wall of the vessel, shown from a top perspective view.
Figure 7N:
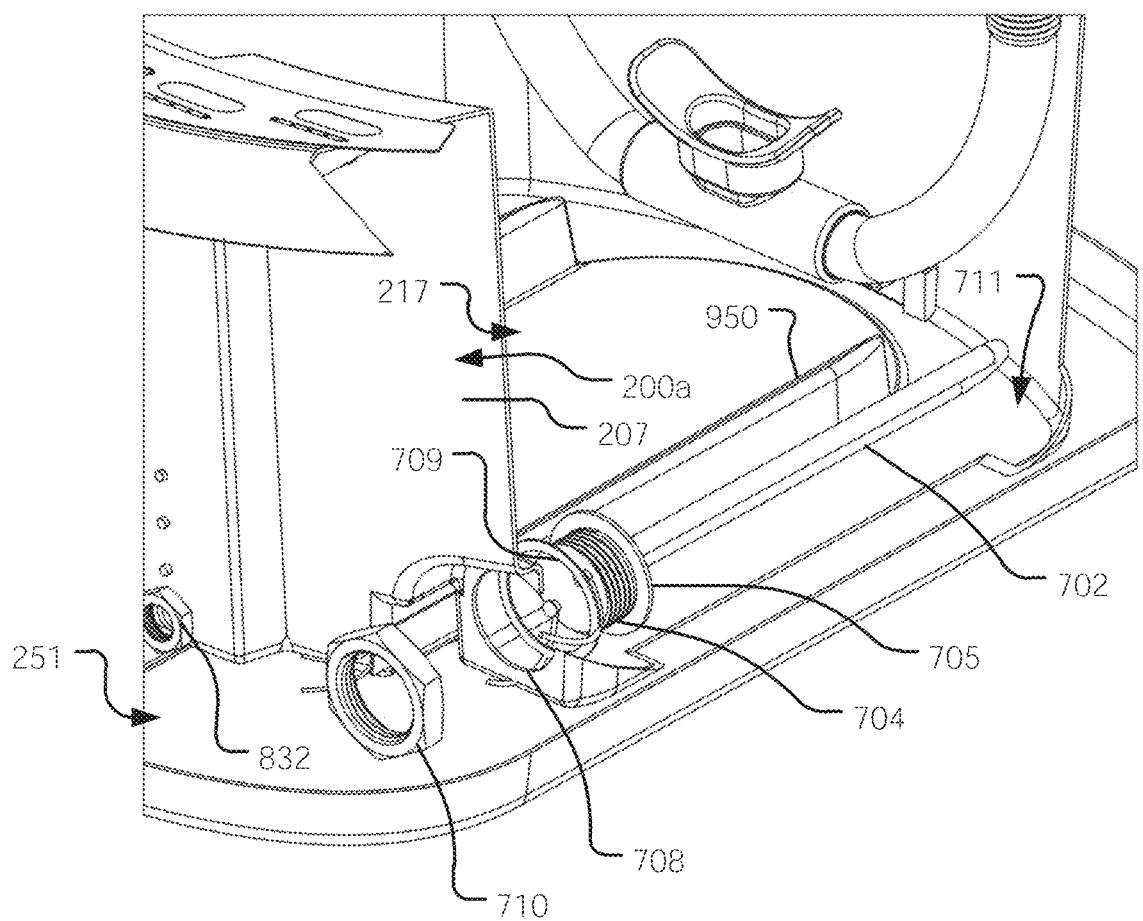
FIG. 7N may depict the at least one heating element disposed within an interior volume of the vessel, but while exploded from a back interior wall of the vessel, shown from a back perspective cut-away view that also shows a partial interior view of a mechanical compartment.

A FIG. 7 series of figures may comprise FIG. 7A through FIG. 7N. This FIG. 7 series of figures may focus on depicting exemplary embodiments of heater subassembly 700, its corresponding parts, structures, and communicative relationships thereof.

In some embodiments, face soaking device 100 may comprise heater subassembly 700. Heater subassembly 700 may also be known more simply as heater 700. Heater 700 may be configured to heat liquid 101. Some portions of heater 700 may be in removable physical contact with some portions of liquid 101. Heater 700 may comprise a means to heat liquid 101. In some embodiments, this means to head liquid 101 may be at least one heating element 701. Heater 700 may comprise at least one heating element 701. Heating element 701 may be configured to receive electrical power to produce heat from a heating element, i.e., element 702 (e.g., through electrical resistance and/or through magnetic induction).

In some embodiments, at least some portions of heater 700 may be removable from internal volume 220. In some embodiments, at least one heating element 701 subassembly may be removably located within internal volume 220. See e.g., FIG. 7M and FIG. 7N. In some embodiments, at least some portion of heater 700 may removably attach to at least one interior wall surface 203 or the interior surface of at least one base 215 (e.g., bottom interior surface 217). In some embodiments, at least one heating element 701 subassembly may comprise one of more of: an electrical power cord 1116 in communication with a power source 1115, electrical wiring in communication with power source 1115, and/or electrical terminals 706 for connecting to electrical wiring in communication with power source 1115. The electrical power cord 1116 may pass through at least one port 210 of vessel 200. See e.g., FIG. 2B and FIG. 2E. In some embodiments, at least one heating element 701 may be permanently attached to at least one interior wall surface 203 or the interior surface of at least one base 215 (e.g., bottom interior surface 217). In some embodiments, at least one heating element 701 may be integral with the at least one interior wall surface 203 or the interior surface of at least one base 215.

FIG. 7B may depict heater subassembly 700, but shown in a top perspective exploded view, wherein heater subassembly 700 may be exploded from the vessel (e.g., vessel 200). In this exploded view at least one heating element 701 may be depicted in relation to shield 715 and the vessel. In some embodiments, substantially all of at least one heating element 701 may be disposed between shield 715 and some portion of at least one base 215 (e.g., some portion of bottom interior surface 217). See e.g., FIG. 7B. In some embodiments, connection bushing 704, electrical terminals 706, and electrical wiring 707 may not be disposed between shield 715 and some portion of at least one base 215 (e.g., some portion of bottom interior surface 217). See e.g., FIG. 7I for connection bushing 704, electrical terminals 706, and electrical wiring 707 components of at least one heating element 701.

FIG. 7I through FIG. 7L may depict different views of at least one heating element 701. FIG. 7I may depict at least one heating element 701 of heater subassembly 700, shown from a top view. FIG. 7J may depict at least one heating element 701, shown from a bottom view. FIG. 7K may depict at least one heating element 701, shown from a front view. FIG. 7L may depict at least one heating element 701, shown from a back view.

In some embodiments, at least one heating element 701 may comprise element 702 and bushing 703. Element 702 may be physically and electrically connected to bushing 703. Bushing 703 may comprise structure for connecting to the vessel (e.g., vessel 200) and structure for electrical connections via electrical terminals 706. For example, in some embodiments, bushing 703 may comprise flange 705, connection bushing 704, electrical terminals 706, and electrical wiring 707. Whereas, element 702, when electrically powered, may give off heat, which may heat liquid 101 and/or the gas released into liquid 101.

In some embodiments, element 702 may be at least substantially constructed of a metal. In some embodiments, the metal may be one or more of: steel, stainless steel, copper, and/or incoloy. Stainless steel (e.g. type 316, 321L, etc.) and incoloy (e.g. type 840, 800, etc.) may be appropriate for when liquid 101 may be various saline solutions. When electrical current may be delivered to one of electrical terminals 706, e.g. a positive electrical terminal, said electrical current may pass through the metal and out of the remaining electrical terminal, e.g. a negative electrical terminal, to form a complete circuit, wherein the metal may heat up and discharge heat into liquid 101 that may be physically contacting element 702.

In some embodiments, element 702 may comprise a coating to protect element 702 from corrosion and/or impacts. In some embodiments, such a coating may be a sheath of non-electrically conductive material. In some embodiments, the coating may be waterproof. In some embodiments, this coating may be a silicone elastomer.

In some embodiments, there may be one bushing 703 per one element 702. See e.g., FIG. 7I, and FIG. 7J. Element 702 may comprise an overall shape when an entirety of element 702 may be viewed from above, such that the overall shape may be selected from the group comprising: a "T" shape (see e.g., FIG. 27F and FIG. 28C), a "L" shape (see e.g., FIG. 17B), an "I" shape, a "J" shape, a linear shape with one bend (see e.g., FIG. 7I and FIG. 7J), and/or the like. In some embodiments, where there may be one bushing 703 per one element 702, both electrical terminals 706 (positive and negative) may be located on one side of connection bushing 704, i.e. on one side of flange 705. See e.g., FIG. 7L.

In some embodiments, where there may be one bushing 703 per one element 702, installment of at least one heating element 701 may occur from inside internal volume 220 (e.g., when the overall shape may be the linear shape with one bend), e.g. by passing at least a portion of connection bushing 704 into bushing hole 708 from internal volume 220 side. See e.g., FIG. 7M and FIG. 7N.

In some embodiments, where there may be one bushing 703 per one element 702, installment of at least one heating element 701 may occur from outside internal volume 220 (e.g., from mechanical compartment 251), e.g. by passing element 702 into bushing hole 708 and then into internal volume 220. This installment embodiment is not depicted in the FIG. 7 series of figures.

In some embodiments, at least one heating element 701 may comprise low watt density (LWD) consumption and/or high watt density (HWD) consumption in other embodiments. In some embodiments, LWD may be about 55 watts per square inch or less; and HWD may be greater than 55 watts per square inch. Whereas, in some embodiments, LWD may be about 60 watts per square inch or less; and HWD may be greater than 60 watts per square inch.

("About" as used in this paragraph may mean plus or minus two watts in some embodiments.) The more element 702 surface area, the lower the wattage per square inch needed to heat liquid 101, and the less concern for plastic parts melting and/or deforming. Increasing such surface area may accomplished by using longer (lengthwise) element(s) 702 and/or by coiling element(s) 702. Also, the lower the wattage per square inch of at least one heating elements 701, the longer (temporally) at least one heating elements 701 may last.

For example, and without limiting the scope of the present invention, each at least one heating element 701 depicted in the FIG. 7 series of embodiments may be LWD. For example, and without limiting the scope of the present invention, each at least one heating element 701 depicted in the FIG. 7 series of embodiments may be HWD.

In some embodiments, element(s) 702 may comprise a close-up shape (versus the overall shape) when less than an entirety of element(s) 702 may be viewed, such that the close-up shape may be selected from the group comprising: coils, spirals, zig-tags, bends, curves, linear runs, and/or the like.

In some embodiments, bushing 703 may comprise flange 705, connection bushing 704, and electrical terminals 706. In some embodiments, electrical wiring 707 may be attached to the electrical terminals 706. In some embodiments, bushing 703 may comprise electrical wiring 707 that may be attached to electrical terminals 706. Flange 705 may be separate element 702 from connection bushing 704, electrical terminals 706, and from electrical wiring 707. See e.g., FIG. 7I and FIG. 7J. Flange 705 may have an outside diameter that may be greater than an inside diameter of bushing hole 708, such that flange 705 and element 702 remain in interior volume 220, when at least one heating element 701 may be attached to the vessel (e.g., vessel 200). See e.g., FIG. 7M. FIG. 7M may depict flange 705 and element 702 remaining disposed within interior volume 220 of vessel 200, but while exploded from a back interior wall (e.g., interior wall surface 203 of second side wall 207) of vessel 200, shown from a top perspective view. Bushing hole 708 may be a hole through a portion of the back interior wall (e.g., interior wall surface 203 of second side wall 207), providing passage from interior volume 220 into mechanical compartment 251. In some embodiments, bushing hole 708 may be a hole through a portion of vessel lining 200a. In some embodiments, bushing hole 708 may comprise inside threading that may be complimentary to outside threading of connection bushing 704. See e.g., FIG. 7M and FIG. 7N.

FIG. 7M and FIG. 7N together may depict how at least one heating element 701 may be attached to the vessel (e.g., vessel 200). FIG. 7N may depict element 702, flange, 705, and gasket/washer 709 disposed within interior volume 220 of vessel 200, but while exploded from the back interior wall of vessel 200 (e.g., interior wall surface 203 of second side wall 207), shown from a back perspective cut-away view that also shows a partial interior view of a mechanical compartment. Once at least one heating element 701 may be secured to the vessel (e.g., vessel 200); element 702, flange, 705, and gasket/washer 709 may be disposed within interior volume 220 of vessel 200. See e.g., FIG. 7M and FIG. 7N. Once at least one heating element 701 may be secured to the vessel (e.g., vessel 200); portions of connection bushing 704, electrical terminals 706, electrical wiring 707, other gasket/washer 709, and at least one nut 710 may be disposed within mechanical compartment 251 of vessel 200. See e.g., FIG. 7N. At least one nut 710 may be have inside threading that may be complimentary to outside threading of connection bushing 704. At least one nut 710 may thread onto outside threading of connection bushing 704, and may secure, by friction, a portion of at least one wall 201 (or of at least one side wall 205 or of second side wall 207) disposed between at least one nut 710 and flange 705. Inclusion of one or more gasket/washers 709 on either or both sides (of mechanical compartment 251 side and/or of interior volume 220 side) may prevent and/or minimize liquid 101 leakage. The one or more gasket/washer 709 may have an inside hole with a diameter sized to fit around the outside threading of connection bushing 704. The one or more gasket/washer 709 may be substantially constructed from one or more plastics or elastomers, including silicones and/or rubbers, and with various durometers.

Note, while FIG. 7M and FIG. 7N may depict at least one heating element 701 attached to the vessel (e.g., vessel 200) at the back wall (e.g., interior wall surface 203 of second side wall 207); in other embodiments, at least one heating element 701 may be attached to any other at least one wall 201 and/or at least one base 215. Such embodiments may not be depicted. Such attachment may still utilize connection bushing 704 (with outside threading), flange 705, gasket/washers 709, and at least one nut 710 (with complimentary inside threading).

In some embodiments, at least one heating element 701 may comprise at least one element support means. The at least one element support means may be configured to keep element 702 from physically contacting interior wall surface 203 and/or bottom interior surface 217. The at least one element support means may comprise bushing 703 and bushing hole 708. In some embodiments, the at least one element support means may further comprise one or more gasket/washers 709 and at least one nut 710. The at least one nut 710 may be have inside threading that may be complimentary to outside threading of connection bushing 704. See e.g., FIG. 7N. The one or more gasket/washer 709 may have an inside hole with a diameter sized to fit around the outside threading of connection bushing 704. See e.g., FIG. 7M.

FIG. 7H may depict a top perspective view of vessel lining 200a, showing a partial interior view of vessel lining 200a, but with heater subassembly 700, the breathing apparatus (e.g., breathing apparatus 400), and the head rest subassembly (e.g., head rest subassembly 500), and portions of the gas diffuser (e.g., gas diffuser 800) removed. FIG. 7H may depict element receiving channel 711 and bushing hole 708. In some embodiments, bottom interior surface 217 may comprise element receiving channel 711. In some embodiments, element receiving channel 711 may be a region or a portion of bottom interior surface 217; wherein this region or this portion may be configured to accommodate element 702, but without substantially all of bottom interior surface 217 and/or substantially all of at least one wall 201 (or at least one side wall 205 or interior wall surface 203) touching element 702, aside from the at least one element support means. In some embodiments, element receiving channel 711 may be bounded on three sides by three different at least one walls 201 (or three different at least one side wall 205). In some embodiments, element receiving channel 711 may be bounded on one side by LED-housing 950. In some embodiments, element receiving channel 711 may be bounded on four sides as follows: by two sides by two different, but adjacent, at least one walls 201 (or three different at least one side wall 205), bounded one side by bushing hole 708, and bounded the final side by LED-housing 950. See e.g., FIG. 7H.

FIG. 7A may depict an assembled heater subassembly 700, while in communication (e.g., attached) with the vessel (e.g., vessel 200), shown from a top perspective view, but with the breathing apparatus (e.g., breathing apparatus 400), the head rest subassembly (e.g., head rest subassembly 500), and portions of the gas diffuser (e.g., gas diffuser 800) removed. However, when heater subassembly 700 may be assembled and attached to the vessel (e.g., vessel 200), from this top perspective view, only aspects of a shield 715 may be viewable. Shield 715 may be a component of heater subassembly 700. That is, in some embodiments, heater subassembly 700 may comprise shield 715.

FIG. 7C through FIG. 7G may focus on depicting shield 715 from different views. FIG. 7C may depict shield 715, shown from a top view. FIG. 7D may depict shield 715, shown from a bottom view. FIG. 7E may depict shield 715, shown from a front view. FIG. 7F may depict shield 715, shown from a back view. FIG. 7G may depict shield 715, shown from a longitudinal side view.

Shield 715 may be configured to protect user 9000 from physically touching element 702 and/or to protect user 9000 from physically touching a component of at least one heating element 701 which may be hot to touch. Shield 715 may be configured to minimize objects from touching element 702 and/or configured to minimize objects from touching a component of at least one heating element 701 which may be hot. Such objects may be similar sized as a diameter of a human pinky finger. In some embodiments, shield 715 may be substantially constructed from a heat resistant thermoformed plastic. For example, and without limiting the scope of the present invention, shield 715 may be constructed from chlorinated polyvinyl chloride (CPVC) and/or the like. Such materials of construction for shield 715 may also be sufficiently dense to avoid and/or minimize buoyancy in liquid 101; i.e., such that shield 715 tends to sink in liquid 101.

In some embodiments, shield 715 may comprise a planar member, with an upper planar surface 716. This upper planar surface may be physical structure that functions as a barrier to prevent touching of element 702 and/or a component of at least one heating element 701. A shape of upper planar surface 716 may be constrained and/or limited by the overall shape of element 702 and/or location(s) of element 702 within interior volume 220. The shape of upper planar surface 716 may be constrained and/or limited by the location(s) of gas-diffuser-tubing(s) 801 within interior volume 220, such that upper planar surface 716 may not block nor obstruct release of gas bubbles from gas-diffuser-tubing(s) 801. In some exemplary embodiments, gas-diffuser-tubing(s) 801 may be concentrated at a middle and/or a center of bottom interior surface 217, and thus in such embodiments, upper planar surface 716 may not be located over such a center and/or over such a middle of bottom interior surface 217. In some embodiments, there may sufficient upper planar surface 716 to substantially cover all elements 702 that may be located in interior volume 220. See e.g., FIG. 7B, where there may be one shield 715 and one continuous upper planar surface 716, but that may be in a "U" shape with two prongs, when viewed from above, such each of the two prongs covers one element 702. See e.g., FIG. 7C and FIG. 7D. In some embodiments, there may sufficient upper planar surface 716 to substantially cover all elements 702 that may be located in interior volume 220, but without covering nor obstructing gas bubbles from gas-diffuser-tubing(s) 801.

In some embodiments, shield 715 may comprise a liquid passage means 717. See e.g., FIG. 7A, FIG. 7B, FIG. 7C, FIG. 7D, and FIG. 7G. Liquid passage means 717 may comprise at least one opening through upper planar surface 716 of shield 715. Liquid 101 may pass through liquid passage means 717 such that liquid 101 may be in removable physical contact with element 702 (or the coating of element 702). In some embodiments, liquid passage means 717 may comprise a plurality of such openings. See e.g., FIG. 7A, FIG. 7B, FIG. 7C, FIG. 7D, and FIG. 7G. In some embodiments, the plurality of such opening may be selected from one or more of: slots (slits), holes, parallel slots, holes in geometric patterns, slots in geometric patterns, linear slots, curved slots, a mesh, combinations thereof, and/or the like. Parallel linear slots may be depicted in the FIG. 7 series of figures for liquid passage means 717. In some embodiments, the slots may run horizontally (or substantially horizontally). In some embodiments, the slots may be run vertically (or substantially vertically).

In some embodiments, element 702 may be located closer to at least one base 215 than to rim 225, such that heating liquid 101 generates convective current flow of liquid 101, with denser (cooler) liquid 101 moving downwards and less dense (warmer) liquid 101 moving upwards within internal volume 220. In some embodiments, such convective flow of liquid 101 may also not be impeded (significantly) by the structural geometry of liquid passage means 717. In some embodiments, such convective flow of liquid 101 may also be facilitated by the structural geometry of liquid passage means 717. In some embodiments, such convective flow of liquid 101 may for vertically oriented eddies of liquid 101 within internal volume 220. Such vertically oriented eddies of liquid 101 may facilitate substantially uniform temperature of liquid 101.

In some embodiments, shield 715 may comprise shield-attachment-means 718. In some embodiments, shield-attachment-means 718 may be how shield 715 may attach to one or more of: the vessel (e.g., vessel 200), the breathing apparatus, and/or the head rest subassembly. In FIG. 7A and FIG. 7B, shield 715 may attach to vessel 200 via shield-attachment-means 718. Shield-attachment-means 718 may comprise structure which may rest upon complimentary and supportive structure 720 of bottom interior surface 217 (or of at least one base 215). Such complimentary and supportive structure 720 of bottom interior surface 217, may be of vessel lining 200a. See e.g., FIG. 7H. In some embodiments, this complimentary and supportive structure 720 may a top region of bushing hole 708 and/or a top of LED-housing 950, both or either of which may be structure of: bottom interior surface 217, at least one base 215, and/or structure of vessel lining 200a. See e.g., FIG. 7H. In some embodiments, where shield 715 may have the "U" shape when viewed from above, with the two prongs, at a terminal end of each prong may comprise the structure which may rest upon complimentary and supportive structure 720, wherein this structure may be shield-legs 719. Each such prong may terminate in a shield-leg 719. See e.g., FIG. 7B, FIG. 7E, FIG. 7F, and FIG. 7G. Each such shield-leg 719 may rest upon bottom interior surface 217 and/or element receiving channel 711.

In some embodiments, shield 715 may also comprise shield-back-panel 721. When shield 715 may be installed in interior volume 220, shield-back-panel 721 may cover one or more ports 210 in: at least one wall 201, at least one side wall 205, and/or second side wall 207 of vessel 200. See e.g., FIG. 7H for such one or more ports 210. See e.g., FIG. 7E, FIG. 7F, and FIG. 7G for shield-back-panel 721. In some embodiments, shield-back-panel 721 may be disposed between the two prongs of the "U" shaped shield 715.

In some embodiments, heater 700 may comprise a thermostat 1107 (see e.g., FIG. 11A) for controlling the means to heat liquid 101. Thermostat 1107 may turn on or off the means to heat liquid 101 as a temperature of liquid 101 varies by thermostat 1107 sensing liquid 101 temperature via a temperature sensor 1106 (see e.g., FIG. 11A). Thermostat 1107 may be in electrical communication with the means to heat liquid 101. That is, in some embodiments, thermostat 1107 may comprise a liquid temperature sensing means (e.g., temperature sensor 1106). In some embodiments, thermostat 1107 may be configured to maintain liquid 101 at 110 degrees Fahrenheit or less. In some embodiments, thermostat 1107 may be configured to maintain liquid 101 at 116 degrees Fahrenheit or less. In some embodiments, thermostat 1107 may be configured to heat liquid 101 proximate to the means to heat liquid 101 (e.g. at least one heating element 701) at 116 degrees Fahrenheit or less. Here, proximate may be within 20 inches of the means to heat liquid 101 (e.g. at least one heating element 701). In some embodiments, thermostat 1107 may be preset during manufacturing such that liquid 101 may not be heated to a temperature which may be harmful to user 9000. In some embodiments, heater 700 may be turned on or off by controller 1100 similar to a bubble controller that may control gas bubbles 125 production (release). In some embodiments, the means to heat liquid 101 (e.g. at least one heating element 701) may be turned on or off by thermostat 1107. In some embodiments, all functions of an independent thermostat 1107 may be performed by controller 1100 (see e.g., FIG. 11A and FIG. 11A discussion below), in which case there may no independent thermostat 1107. In some embodiments, the bubble controller may also turn on and off heater 700, and when heater 700 may be on, temperature may then be controlled by thermostat 1107.

In some embodiments, heater 700 may comprise power source 1115. In other embodiments, power source 1115 may be independent of a given face soaking device. Power source 1115 may be configured to supply electrical power to one or more of: the means to heat liquid 101, the thermostat 1107, controller 1100, and/or any other electrical components of a given face soaking device. In some embodiments, power source 1115 may be an electrical cord 1116 removably connected to an electrical outlet at one end, and wherein the remaining end may be electrically coupled to one or more of: the means to heat liquid 101, thermostat 1107, controller 1100, and/or the any other electrical components of the given face soaking device.

In some embodiments, the means to heat liquid 101 may comprise a liquid circulation pump (not depicted). In some embodiments, heater 700 may comprise the liquid circulation pump. Note, this embodiment is not depicted in the figures. In such embodiments, heating of liquid 101 may be provided by the liquid circulation pump motor, i.e., heat may be derived from the heat emanating from operation of the liquid circulation pump motor. In such embodiments, at least one interior wall surface 203 or the interior surface of at least one base 215 may comprise at least one intake vent (port) to provide liquid 101 from interior volume 220 to the liquid circulation pump. In such embodiments, at least one interior wall surface 203 or the interior surface of at least one base 215 may also comprise at least one exit jet (return) where liquid 101 may be expelled from the liquid circulation pump back into interior volume 220.

In some embodiments, the means to heat liquid 101 may comprise a heating portion of heater 700 that may be removably located outside of internal volume 220. In such embodiments, this heating portion may be a block heater, wherein liquid 101 may be fed into a chamber external to internal volume 220, wherein this heating portion may be located within this chamber, and then at least some liquid 101, that has been heated, may be returned to internal volume 220. Such flow of liquid 101 may be by various pumping means, various impeller means, convection means, and/or any other means suitable for moving some of liquid 101 from internal volume 220 to the chamber and back to internal volume 220. This embodiment may not be depicted in the figures.

In some embodiments, the means to heat liquid 101 may be selected from one or more of: at least one heating element 701, the liquid circulation pump, block heater, and/or the like.

In some embodiments, the means to heat liquid 101 may operate by heating a gas (e.g. air, oxygen, nitrogen, carbon dioxide, nitrous oxide, and/or the like) that may be released from the gas diffuser (e.g., gas diffuser 800). Such heated gas may then heat liquid 101.

FIG. 27A may depict an exemplary embodiment of an exploded perspective view of a U-shaped heater embodiment 2700 for various embodiments of face soaking devices. Such a configuration may be depicted schematically in FIG. 28D. In such embodiments, element 702 may be U-shaped and shield 715, which may removably cover element 702, may also be U-shaped. Element 702 and shield 715 may each run along three of four interior perimeter sides the vessel (e.g. not along the back wall). Bottom interior surface 217 of base 215 may comprise element receiving channel 2745, which may also run along three of four interior perimeter sides the vessel (e.g. not along the back wall). Each connection bushing 2736 and 2737 may pass through a back wall, via two bushing holes, 2761 and 2762. Each electrical terminal 706 may be connected to each connection bushing 2736 and 2737, such that the electrical connections to thermostat 1107, to controller 1100, and/or power source 1115 may be made in mechanical compartment 251. FIG. 27C may depict the exemplary embodiment of an assembled perspective view of U-shaped heater embodiment 2700 of FIG. 27A.

FIG. 27B may depict an exemplary embodiment of an exploded perspective view of a U-shaped heater embodiment 2705 for various embodiments of face soaking devices. Such a configuration may be depicted schematically in FIG. 28F. In such embodiments, element 702 may be U-shaped and shield 715, which may removably cover element 702, may also be U-shaped. Element 702 and shield 715 may each run along three of four interior perimeter sides the vessel (e.g. not along a front wall). Interior surface 217 of base 215 may comprise element receiving channel 2745, which may also run along three of four interior perimeter sides the vessel (e.g. not along the front wall). Each connection bushing 2736 and 2737 may pass through base 215, via two bushing holes 2761 and 2762 (not depicted in FIG. 27B). In U-shaped heater 2705 embodiment, first bushing hole 2761 and second bushing hole 2762 may be located in at least one base 215 or fourth side wall 209.

FIG. 27D may depict an exemplary embodiment of an exploded perspective view of an O-shaped heater embodiment 2710 for various embodiments of face soaking devices. In such embodiments, element 702 may be O-shaped and shield 715, which may removably cover element 702, may also be O-shaped. Such an "O" shape in some embodiments, may approach an oval, square, and/or rectangular shape, as in a wall picture frame shape. Element 702 and shield 715 may each run along four of four interior perimeter sides the vessel. Interior surface 217 of base 215 may comprise element receiving channel 2745, which may also run along four of four interior perimeter sides the vessel. Each connection bushing 2736 and 2737 may pass through the back wall, via two bushing holes, 2761 and 2762. Each electrical terminal 706 may be connected to each connection bushing 2736 and 2737, such that the electrical connections to thermostat 1107, controller 1100, and/or power source 1115 may be made in the mechanical compartment.

In some embodiments, first edge 2751 of shield 715 of O-shaped heater embodiment 2710 may lock in a gas diffuser membrane when shield 715 may be assembled. O-shaped heater embodiment 2710 may comprise a longer overall element 702 than other heater embodiments, yielding a comparatively lower wattage requirement, which in turn may place a lower heat load upon surrounding materials. Such a four sided shield 715 may be stronger than three sided shield 715 and may be less prone to breakage.

FIG. 27E may depict an exemplary embodiment of an exploded perspective view of a back walled heater embodiment 2715 for various embodiments of face soaking devices. Such a configuration may be depicted schematically in FIG. 28A. In such embodiments, element 702 may be linear or I-shaped and shield 715, which may removably cover element 702, may be a planar member. Element 702 and shield 715 may each run along a bottom back wall of the vessel. Because this back wall heater embodiment 2715 may occupy a shorter linear distance than other heater embodiments, e.g., U-shaped heater embodiment 2700, back wall heater embodiment 2715 may be comparatively higher wattage (compared to U-shape or O-shaped elements 702), which may generate greater heat, and thus element 702 in heater embodiment 2715 may be housed in element receiving tray 2748. Element receiving tray 2748 may be configured to keep element 702 from directly contacting base 215, e.g., bottom interior surface 217, and/or from directly contacting interior surface 203. Element receiving tray 2748 may be constructed of a heat resistant thermoplastic, such as chlorinated polyvinyl chloride (CPVC). Interior surface 217 of base 215 may comprise element receiving channel 2745, which may also run along the bottom back wall of the vessel. Element receiving tray 1648 may be configured to fit within element receiving channel 2745. Connection bushing 2735 may pass through a side wall, via bushing hole 2760. (In other similar embodiments, element 702 may have an overall L-shape, such that connection bushing 2735 may pass through the back wall, via bushing hole 2760, see e.g., FIG. 28B.) A pair of electrical terminals 706 may protrude (or be accessible) from single connection bushing 2735. FIG. 27G may depict the exemplary embodiment of an assembled perspective view of back wall heater embodiment 2715 of FIG. 27E.

FIG. 27F may depict an exemplary embodiment of an exploded perspective view of a T-shaped heater embodiment 2720 for various embodiments of face soaking devices. Such a configuration may be depicted schematically in FIG. 28C. In such embodiments, element 702 may be T-shaped and shield 715, which may removably cover element 702, may be a planar member. Element 702 and shield 715 may each run along a bottom back wall of the vessel. Because this T-shaped heater embodiment 2720 may occupy a shorter linear distance than other heater embodiments, e.g. heater embodiment 2700, heater embodiment 2715 may be comparatively higher wattage (compared to U-shape or O-shaped elements 702), which may generate greater heat, and thus element 702 in heater embodiment 2715 may be housed in element receiving tray 2748. Element receiving tray 2748 may be configured to keep element 702 from directly contacting base 215, e.g. interior surface 217, and/or from directly contacting interior surface 203. Element receiving tray 2748 may be constructed of a heat resistant thermoplastic, such as CPVC. Interior surface 217 of base 215 may comprise element receiving channel 2745, which may also run along the bottom back wall of the vessel. Element receiving tray 2748 may be configured to fit within element receiving channel 2745. Connection bushing 2735 may pass through the side wall, via bushing hole 2760. The pair of electrical terminals 706 may terminate from single connection bushing 2735 and the electrical connection to the two electrical terminals 706 may be made within the mechanical compartment. FIG. 27G may depict the exemplary embodiment of an assembled perspective view of T-shaped heater embodiment 2720 of FIG. 27G.

FIG. 27H may depict an exemplary embodiment of an exploded perspective view of a double heater embodiment 2725 for various embodiments face soaking devices. Such a configuration may be depicted schematically in FIG. 28H. FIG. 27I may depict an exemplary embodiment of an assembled perspective view of double heater embodiment 2725 of FIG. 27H. In double heater embodiment 2725 there may be a pair of separate, distinct, and parallel heating element 701 subassemblies. Each heating element 701 subassembly may run in a direction the front wall to the back wall, with each connection bushing 2735 terminating through the back wall in mechanical compartment 251.

In some embodiments, a given heating element 701 subassembly may comprise at least two electrical terminals 706 (either as a pair per a single connection bushing or with one electrical terminal per connection bushing), at least one connection bushing 2735, and at least one element 702. At least one element 702 may be disposed between each electrical terminal 706 and electrically coupled to each electrical terminal 706. The at least two electrical terminals 706 may be located on one side of at least one connection bushing 2735 with at least one element 702 located on an opposing side of at least one connection bushing 2735. The two electrical terminals 706 may be configured to be electrically coupled to power source 1115, controller 1100, and/or thermostat 1107. At least one connection bushing 2735 may be configured to attach to the vessel or an adapter 2775 attached to the vessel. See e.g., FIG. 27D for adapter 2775.

In some embodiments, the heating element 701 subassembly may comprise a flange 2738. See e.g., FIG. 27A. Flange 2738 may separate at least one element 702 from one or two electrical terminals 706.

In some embodiments, the at least one connection bushing 2735 may comprise a single connection bushing 2735. See e.g., FIG. 27E and FIG. 27F. At least one element 702 may comprise an overall shape when an entirety of at least one element 702 may be viewed, such that the overall shape may be selected from the group comprising: a "T" shape (see e.g., FIG. 27F and FIG. 28C), a "L" shape (see e.g., FIG. 28B), an "I" shape, a "J" shape, and the like. In some embodiments, where there may be one single connection bushing 2735, both electrical terminals 706 (positive and negative) may be located on one side of single connection bushing 2735, i.e. on one side of the flange.

In some embodiments, where there may be one single connection bushing 2735, installment of the heating element 701 subassembly may occur from outside internal volume 220 (e.g., from mechanical compartment 251), e.g. by passing at least one element 702 and at least a portion of the one single connection bushing 2735 into a bushing hole 2760 into internal volume 220.

In some embodiments, where there may be one single connection bushing 2735, installment of the heating element 701 subassembly may occur from inside internal volume 220 (e.g., when the overall shape may be "T" shaped), e.g. by passing at least a portion of the one single connection bushing 2735 into a bushing hole 2760 from internal volume 220 side. See e.g., FIG. 27E and FIG. 27F.

In some embodiments, at least one connection bushing 2735 may comprise two distinct connection bushings, a first connection bushing 2736 and a second connection bushing 2737. See e.g., FIG. 27A, FIG. 27B, and FIG. 27D. The at least one element may comprise an overall shape when an entirety of the at least one element may be viewed, such that the overall shape may be selected from the group comprising: a "U" shape (see e.g., FIG. 27A and FIG. 27B; and FIG. 28D, FIG. 28E, and FIG. 28F), an "O" shape (see e.g., FIG. 27D and FIG. 28G), an ovoid shape, a horseshoe shape, and a semicircle shape, and the like. In some embodiments, where there may be two distinct connection bushings (e.g., first connection bushing 2736 and second connection bushing 2737), one electrical terminal 706 (positive or negative) may be located on one side of each distinct connection bushing. In some embodiments, where there may be two distinct connection bushings, installment of the heating element 701 subassembly may occur from inside internal volume 220, e.g. by passing at least a portion of each connection bushing into two distinct bushing holes from internal volume 220 side. See e.g., FIG. 27A, FIG. 27B, and FIG. 27D.

For example, and without limiting the scope of the present invention, heater embodiments 2700 (see e.g., FIG. 27A), 2705 (see e.g., FIG. 27B), and 2710 (see e.g., FIG. 27D) may be LWD; while heater embodiments 2715 (see e.g., FIG. 27E) and 2720 (see e.g., FIG. 27F) may be HWD.

In some embodiments, a given heater embodiment may comprise shield 715. Shield 715 may comprise a first edge 2751 and an opposing second edge 2752. See e.g., FIG. 27A. Shield 715 may be configured to protect user 9000 from physically touching the heating element 701 subassembly, in particular at least one element 702. In some embodiments, shield 715 may be constructed from a heat resistant thermoformed plastic. For example, and without limiting the scope of the present invention, shield may be constructed from CPVC. Shield 715 may comprise a shield longitude which may be parallel with a longitude of the at least one element 702 (e.g. with the overall shape). First edge 2751 of shield 715 may attach to (or contact) bottom interior surface 217 or may attach closer to bottom interior surface 217 than to interior wall surface 203. Such attachment may be removable in some embodiments. Second edge 2752 may attach to (or contact) interior wall surface 203 or closer to interior wall surface 203 than to bottom interior surface 217.

In some embodiments, shield 715 may be a planar elongate member. The planar elongate member may comprise the shield longitude and a shield transverse width 2753. The shield longitude and shield transverse width 2753 may be substantially perpendicular to each other. First edge 2751 and second edge 2752 may be disposed opposite from each other, separated by shield transverse width 2753. See e.g., FIG. 27A.

In some embodiments, shield 715 may comprise liquid passage means 717. See e.g., FIG. 27A. Liquid passage means 717 may comprise at least one opening through opposing major surfaces of shield 715. Liquid 101 may pass through liquid passage means 717 such that liquid 101 may be in removable physical contact with at least one element 702 or the coating of at least one element 702. In some embodiments, liquid passage means 717 may comprise a plurality of holes. See e.g., FIG. 27B. Some such holes may be located into two groups, with a first group located closer to first edge 2751 than to second edge 2752; and with a second group located closer to second edge 2752 than to first edge 2751. In some embodiments, liquid passage means 717 may comprise a plurality of slots (slits). In some embodiments, the plurality of slots may be parallel. See e.g., FIG. 27A. In some embodiments, the plurality of slots may run horizontally. In some embodiments, such horizontal slots may be grouped into two rows of slits, a first row located closer to first edge 1651 than to second edge 1652; and a second row located closer to second edge 1652 than to first edge 1651. In some embodiments, the plurality of slots may be run vertically. See e.g., FIG. 27A.

In some embodiments, at least one element 702 may be located closer to at least one base 215 than to rim 225, such that heating liquid 101 generates convective current flow of liquid 101, with denser (cooler) liquid 101 moving downwards and less dense (warmer) liquid 101 moving upwards within internal volume 220. Such convective flow of liquid 101 may also be facilitated by the structural geometry of liquid passage means 717, such that relatively cooler liquid 101 may enter liquid passage means 717 closer to first edge 2751 to be heated by at least one element 702, and relatively warmer liquid 101 may leave liquid passage means 717 closer to second edge 2752.

In some embodiments, at least one element 702 may be located in a vertical direction (up/down direction) within the vessel (e.g., vessel 200), closer to at least one base 205 than to rim 225 of the vessel. Such vertical positioning of at least one element 702 may facilitate convective flow of liquid 101. In some exemplary embodiments, at least one element 702 may not be physically touching bottom interior surface 217, nor physically touching any interior wall surface 203. That may be done to avoid increased manufacturing costs that may result if at least one element 702 did physically touch bottom interior surface 217 and/or any interior wall surface 203, because then bottom interior surface 217 and/or interior wall surfaces 203 might require construction from materials (e.g., CPVC) capable of withstanding greater heat loads to avoid deformation under heat produced from the at least element 702. Such heat resistant materials of construction may cost more than corresponding materials with less heat resistance.

In some embodiments, element 702 may be located closer to a back wall of vessel 200 than a front wall of the vessel. See e.g., FIG. 27E and FIG. 27F. In some embodiments, a majority of at least one element(s) 702 may be parallel with the back wall, such as when the overall shape may be linear (e.g. "I" shaped), "T" shaped, "J" shaped, and/or "L" shaped. See e.g., FIG. 27E, FIG. 27F, FIG. 28A, FIG. 28B, and FIG. 28C.

In some embodiments, the at least two electrical terminals 706, when assembled, may protrude from a side wall 205 and/or base 215. See e.g., the FIG. 27 series of figures. For example, and without limiting the scope of the present invention, the overall shape may be linear, "I" shaped, "L" shaped, or "J" shaped. In some embodiments, the at least two electrical terminals 706, when assembled, may protrude into mechanical compartment 251.

In some embodiments, the at least two electrical terminals 706 may protrude from the back wall (e.g., second side wall 207 in FIG. 7N). See e.g., FIG. 27E and FIG. 27F. For example, and without limiting the scope of the present invention, the overall shape may be "L" shaped, "I" shaped, linear shaped, "J" shaped, or "T" shaped.

In some embodiments, the front wall (e.g., fourth side wall 209) may be where neck-gasket-accommodator 335 may be located. In some embodiments, the back wall may oppose the front wall. In some embodiments, there may be two side walls (e.g., first side wall 206 and third side wall 208), where each side wall may run from the front wall to the back wall. In some embodiments, the front wall may be fourth side wall 209, the back wall may second side wall 207, and the side wall may be first side wall 206 and/or third side wall 208.

In some embodiments, at least one element 702 may run around an interior perimeter of the at least one base 215, along three of four sides. See e.g., FIG. 27A, FIG. 27B, FIG. 28D, FIG. 28E, and FIG. 28F. For example, and without limiting the scope of the present invention, the overall shape may be "U" shaped, horseshoe shaped, "W" shaped, "M" shaped, as viewed from above. In some embodiments, the at least two electrical terminals 706 may protrude from a back wall, a front wall, a side wall, or base 215 (see e.g., FIG. 27B). In some such embodiments, there may be two distinct connecting bushings, each with one electrical terminal 706, first connection bushing 1636 and second connection bushing 1637. See e.g., FIG. 27A and FIG. 27B.

In some embodiments, at least one element 702 may run around an interior perimeter of at least one base 215, along four of four sides. See e.g., FIG. 27D and FIG. 28G. For example, and without limiting the scope of the present invention, the overall shape may be "O" shaped, circular shaped, or ovoid shaped. In some embodiments, at least two electrical terminals 706 may protrude from a back wall (see e.g., FIG. 27D), a front wall, a side wall, or base 215. In some such embodiments, there may be two distinct connecting bushings, each with one electrical terminal 706, e.g. first connection bushing 1636 and second connection bushing 1637. See e.g., FIG. 27D.

In some embodiments, the heater may comprise two (distinct) heating element 701 subassemblies. See e.g., FIG. 27H. Each heating subassembly may be parallel with each other (when installed into internal volume 220). Each element 702 may run from the back wall towards the front wall. See e.g., FIG. 27H. In some embodiments, a majority of each at least one element may be parallel with side walls (e.g. first side wall 206 and/or third side wall 208). See e.g., FIG. 27H. In some embodiments, each element 702 may be located closer to a side wall 205 than to an other side wall 205, such that each element 702 may be located proximate to each side wall 205 (right and left). In some embodiments, the at least two electrical terminals 706 of each heating element 701 subassembly may protrude from the back wall (see e.g., FIG. 27H), the front wall, either side wall, or base 215. In some embodiments, the at least two electrical terminals 706 of each heating element 701 subassembly may protrude into mechanical compartment 251.

In some embodiments, at least one connection bushing 2735 (or first connection bushing 2736 and second connection bushing 2737) may be attached to at least one wall 201 (e.g. at least one side wall 205) and/or the at least one base 215. In some embodiments, adapter 2775 may be attached to at least one wall 201 (e.g. at least one side wall 205) and/or at least one base 215. In some exemplary embodiments, at least one connection bushing 2735 (or first connection bushing 2736 and second connection bushing 2737) may be attached to the back wall or attached to adapter 2775, which in turn may be connected to the back wall, such that the at least two electrical terminals 706 may be accessible from mechanical compartment 251. See e.g., FIG. 27A, FIG. 27D, FIG. 27F, and FIG. 27H.

In some embodiments, the heater may comprise a bushing attachment means. The bushing attachment means may be configured to attach a given heating element 701 subassembly to vessel 200. The bushing attachment means may comprise at least one connection bushing 2735 (or first connection bushing 2736 and second connection bushing 2737) and at least one bushing hole 2760 (or a first bushing hole 2761 and a second bushing hole 2762). At least one bushing hole 2760 (or a first bushing hole 2761 and a second bushing hole 2762) may pass through at least one wall 201 (see e.g., FIG. 27A, FIG. 27D, and FIG. 27F) or at least one base 215. At least one bushing hole 2760 (or a first bushing hole 2761 and a second bushing hole 2762) may be located in at least one wall 201 or at least one base 215. In some embodiments, at least one bushing hole 2760 may comprise first bushing hole 2761 and second bushing hole 2762, which may be two distinct and separate holes.

In some embodiments, at least one bushing hole 2760 may be sized to receive at least one connection bushing 2735. In some embodiments, at least one bushing hole 2760 may be sized to receive adapter 2775, such as a bulkhead. In some embodiments, at least one bushing hole 2760 may not be threaded. Note in some embodiments, at least one bushing hole 2760 may be functionally equivalent to bushing hole 708. Note in some embodiments, at least one bushing hole 2760 may be structurally equivalent to bushing hole 708.

In some embodiments, first bushing hole 2761 may be sized to receive first connection bushing 2736. In some embodiments, first bushing hole 2761 may be sized to receive adapter 2775, such as a bulkhead. In some embodiments, first bushing hole 2761 may not be threaded. In some embodiments, second bushing hole 2762 may be sized to receive second connection bushing 2737. In some embodiments, second bushing hole 2762 may be sized to receive adapter 2775, such as a bulkhead. In some embodiments, second bushing hole 2762 may not be threaded.

In embodiments wherein at least one bushing hole 2760 (or first bushing hole 2761 and second bushing hole 2762) may not be threaded (e.g. inside threading or female threading), such embodiments may be exemplary, in that elimination of bushing hole threading may prevent problems of cross threading and/or problems of thread stripping from over tightening, which could necessitate replacement of the entire vessel (e.g. vessel 200). See e.g., FIG. 27F or FIG. 27A.

In some embodiments, at least one bushing hole 2760 (or first bushing hole 2761 and second bushing hole 2762) may be inside threaded (female threaded) to receive complimentary threading (outside threading) of at least one connection bushing 2735 (or first connection bushing 2736 and second connection bushing 2737).

In some embodiments, at least one bushing hole 2760 (or first bushing hole 2761 and second bushing hole 2762) may be inside threaded (female threaded) to receive complimentary threading of exterior outside threading (male threading) of a double threaded adapter. In some embodiment, a sealant, e.g., silicone, may be used in and/or around at least one bushing hole 2760 (or first bushing hole 2761 and second bushing hole 2762).

In some embodiments, the bushing attachment means may comprise at least one nut 2770. See e.g., FIG. 27A or FIG. 27F. At least one nut 2770 may comprise inside threading (female threading) to attach to complimentary outside threading of at least one connection bushing 2735 (or first connection bushing 2736 and second connection bushing 2737). In some embodiments, at least one nut 2770 may be attached to the complimentary threading of at least one connection bushing 2735 (or first connection bushing 2736 and second connection bushing 2737) exteriorly to internal volume 220. Note in some embodiments, at least one nut 2770 may be functionally equivalent to at least one nut 710. Note in some embodiments, at least one nut 2770 may be structurally equivalent to at least one nut 710.

In some embodiments, the bushing attachment means may comprise at least one: gasket 2780, washer 2780, O-ring, and/or the like. At least one gasket 2780, washer 2780, or O-ring may be sized to circumscribe a circumference (e.g., outside diameter) of at least one connection bushing 2735 (or first connection bushing 2736 and second connection bushing 2737). In some embodiments, at least one gasket 2780, washer 2780, or O-ring may be disposed between at least one nut 2770 and a surface of the at least one wall 201 or a surface of the at least one base 215. In some embodiments, at least one gasket 2780, washer 2780, or O-ring may be disposed between flange 2738 of at least one connection bushing 2735 (or first connection bushing 2736 and second connection bushing 2737) and interior wall surface 203 or bottom interior surface 217. When secured, flange 2738 may push up against at least one gasket 2780, washer 2780, and/or the O-ring. At least one gasket 2780, washer 2780, or the O-ring may be used to mitigate against liquid 101 leakage, particularly into mechanical compartment 251. Note in some embodiments, gasket 2780, washer 2780, and/or the O-ring may be functionally equivalent to gasket/washer 709. Note in some embodiments, gasket 2780, washer 2780, and/or the O-ring may be structurally equivalent to gasket/washer 709.

In some embodiments, the bushing attachment means further comprise at least one adapter 2775. See e.g., FIG. 27D. In some embodiments, at least one adapter 2775 may comprise a bulkhead and/or the double threaded adapter (i.e., with outside and inside threading). In some embodiments, at least one adapter 1675 may be substantially constructed from a heat resistant thermoformed plastic. For example, and without limiting the scope of the present invention, at least one adapter 2775 may be substantially constructed from CPVC and/or the like.

In some embodiments, bushing hole 2760 (or first bushing hole 2761 and second bushing hole 2762) may be sized to receive an outside circumference of the bulkhead. The bulkhead may comprises an inside female threaded hole. The inside female threaded hole may be sized to receive complimentary threading of the at least one connection bushing 2735 (first connection bushing 2736 and second connection bushing 2737). In some embodiments, the bulkhead may be permanently attached to bushing hole 2760 (or first bushing hole 2761 and second bushing hole 2762). In some embodiments, the bulkhead may be removably attached to bushing hole 2760 (or first bushing hole 2761 and second bushing hole 2762). In some embodiments, the bulkhead may be an insert, wherein the vessel (e.g. vessel 200) may be molded around the bulkhead as a mold insert. In some embodiments, the bulkhead may be attached to bushing hole 2760 (or first bushing hole 2761 and second bushing hole 2762) by a friction fit, ultrasonic welding, heat welding, solvent bonding, and/or chemical adhesive.

In some embodiments, the double threaded adapter (i.e. another type of bushing) may comprise exterior outside threading (male threading) and interior inside threading (female threading). Bushing hole 2760 (or first bushing hole 2761 and second bushing hole 2762) may be inside threaded (female threaded), sized to receive the exterior outside threading (male threading) of the double threaded adapter. The interior inside threading may be sized to receive complimentary threading of at least one connection bushing 2735 (or first connection bushing 2736 and second connection bushing 2737).

In some exemplary embodiments, adapter 2770 embodiments (e.g. bulkhead or double threaded adapter) may be preferable over a direct connection of at least one connection bushing 2735 (or first connection bushing 2736 and second connection bushing 2737) to the vessel (e.g. vessel 200), because use of adapter 2770 as an intermediary may permit constructing adapter 2770 of a thermoplastic (e.g., CPVC) specifically engineered to take higher heat loads and so a majority of vessel materials need not be engineered to take higher heat loads. Thus, such embodiments would be less expensive to manufacture over an embodiment wherein a majority (or entirety) of the vessel may be constructed of the material able to take higher heat loads.

In some embodiments, any application of threading and complimentary threading for connecting two parts herein, may employ tapered threadings to increase friction and security of such connections. In some embodiments, use of tapered threadings may be used in place of gaskets, washers, and/or O-rings (e.g., gasket 2780, washer 2780, and/or gasket/washer 709).

FIG. 28A through FIG. 28H may depict various element 702 layout configurations, as shown from a top schematic view, depicting various overall shapes of the heater (element 702). These FIG. 28 figures have been noted above in the FIG. 27 series discussion.

FIG. 28A may depict a linear element 702 proximate to the back of the vessel, with element 702 entering the vessel from side wall 205 of the vessel. In some embodiments, elements 702 with an overall shape that may be linear may comprise a single bend, such element 702 loops back on itself, such that there may be one connection bushing with a pair of electrical terminals 706. See e.g., FIG. 7I and FIG. 7J for depictions of such linear elements 702.

FIG. 28B may depict a L-shaped element 702 proximate to the back of the vessel, with element 702 entering the vessel from the back.

FIG. 28C may depict a T-shaped element 702 proximate to the back of the vessel, with element 702 entering the vessel from the back.

FIG. 28D may depict a U-shaped element 702, with element 702 entering the vessel from the back of the vessel.

FIG. 28E may depict a U-shaped element 702, with element 702 entering the vessel from the front of the vessel. For example, FIG. 28E may depict a U-shaped heater embodiment, similar to embodiments 2700 and 2705, except in FIG. 28E, the two connection bushings 2736 and 2737 may extend through the front wall, instead of the back wall or base 215.

FIG. 28F may depict a U-shaped element 702, with element 702 entering the vessel from the bottom of the vessel.

FIG. 28G may depict an approximate O-shaped element 702, with element 702 entering the vessel from the back of the vessel. For example, FIG. 28G may depict an O-shaped heater embodiment, wherein there may be one connection bushing 2735 (with the pair of electrical terminals 706) terminating through the back wall and into the mechanical compartment (not shown).

FIG. 28H may depict a pair of linear element 702, with each proximate to an opposing but parallel side wall 205, with elements 702 entering the vessel from the back of the vessel. FIG. 28H may be representative of the exemplary heater 700 embodiment's element 702 layout configuration as depicted in the FIG. 7 series of figures.

In some embodiments for a given face soaking device, such as, but not limited to face soaking device 100, a given heater embodiment may be heater subassembly 3300 or heater subassembly 3330 as shown in a FIG. 33 series of figures. The FIG. 33 series of figures may comprise FIG. 33A, FIG. 33B, FIG. 33C, and FIG. 33D. FIG. 33A may depict heater subassembly 3300 for the given face soaking device (e.g., face soaking device 100), shown from a top perspective exploded view. FIG. 33B may depict the embodiment of FIG. 33A, but shown simultaneously with from two orthogonal sections, a transverse with cross-section being depicted (and about a front half of the given face soaking device removed) and a bottom perspective section being depicted (and about a top half of the given face soaking device removed). FIG. 33C may depict an embodiment of a heating pad heater subassembly 3330 for the given face soaking device (e.g., face soaking device 100), shown from a top perspective exploded view; wherein at least some portions of a heating pad 3331 may be disposed between vessel lining 200a and vessel cover 200b in at least some side wall 205 portions of the vessel (e.g., vessel 200).

FIG. 33D may depict a transverse width cross section of face soaking device embodiment (e.g., face soaking device 100), showing a support member 501 of a headrest subassembly 500 removably riding two guides 507 (i.e., rails). Note, FIG. 33D may omit showing heating pad 3301, heating pad 3331, insulator 3304, and insulator 3334.

In some embodiments, heater subassembly 3300 may comprise a heating pad 3301. See e.g., FIG. 33A. In some embodiments, heater subassembly 3300 may comprise heating pad 3301 and insulator 3304; wherein insulator 3304 may be disposed beneath heating pad 3301. See e.g., FIG. 33A. As shown in FIG. 33A, heating pad 3301 and/or insulator 3304 may be disposed between vessel lining 200a and vessel cover 200b, such that heating pad 3301 and/or insulator 3304 may be sandwiched between vessel lining 200a and vessel cover 200b in the assembled configuration shown in FIG. 33B. In some such embodiments, such sandwiching may be at bottom portions of vessel lining 200a and vessel cover 200b. In some embodiments, heating pad 3301 may be disposed beneath bottom interior surface 217 of vessel lining 200a. See e.g., FIG. 33A and FIG. 33B. In such arrangements and/or configurations, heating pad 3301 may not be in physical contact with liquid 101, which minimize chances for electrical shorting and/or minimize shocking user 9000. In some embodiments, wiring from heating pad 3301 may lead into mechanical compartment 251. In some embodiments, such wiring may connect to controller 1100, thermostat 1107, and/or temperature sensor 1106. In some embodiments, heating pad 3301 may be waterproof.

In some embodiments, heating pad 3301 may be disposed above bottom interior surface 217, such that at least some portions of heating pad 3301 may be removable physical contact with liquid 101 (such embodiments not depicted in the figures). In such embodiments, heating pad 3301 may be waterproof.

In some embodiments, heating pad 3301 may be a HWD heating pad. In some embodiments, this may be greater than 50 watts per square inch (i.e., about 25 mm) of heating pad. In some embodiments, heating pad 3301 may be a LWD heating pad.

In some embodiments, heating pad 3301 may comprise an upper pad 3302, a lower pad 3303 and at least one element 702 (as in a heating element) disposed between upper pad 3302 and lower pad 3303. See e.g., FIG. 33A. In such embodiments, one or more of: upper pad 3302, lower pad 3303, and/or element 702 may be substantially flat and/or substantially planar members. In some embodiments, such substantially flat and/or such substantially planar members may be flexible. In some embodiments, around peripheral (i.e., perimeter) edges of upper pad 3302 may be sealed to lower pad 3303 peripheral edges. In some embodiments, such sealing of such edges may be accomplished by one or more of: mechanical fasteners, welding, heat welding, ultrasonic welding, solvent bonding, chemical adhesives, and/or injection molding of upper pad 3302 and lower pad 3303 around the at least one element 702. In some embodiments, such sealing of edges may result in a waterproof cavity or space where the at least one element 702 may reside.

In some embodiments, upper pad 3302 and lower pad 3303 may be upper and lower portions of a film or a coating that may encase at least one element 702. In some embodiments, this film may be a thin film.

In some embodiments, upper pad 3302 and/or lower pad 3303 may be substantially constructed of an elastomeric material of construction that may be heat resistant, such as, but not limited to, silicone. In some embodiments, upper pad 3302 and/or lower pad 3303 may be substantially constructed of a heat resistant material, such as, but not limited to, silicone, Teflon, Kapton, and/or the like. In some embodiments, upper pad 3302 may be thinner than lower pad 3303. In some embodiments, there may be no lower pad 3303. Such heat resistant materials of construction for upper pad 3302 and/or lower pad 3303 may be elastomeric and/or thermoplastics. In embodiments where at least one element 702 may be disposed beneath bottom interior surface 217 of vessel lining 200a, heat from the at least one element 702 may conduct and/or dissipate upwards through at least some portions of upper pad 3302, optionally through some portions of insulation 3305, through some portions of bottom interior surface 217; and into liquid 101; resulting in heating of liquid 101.

In some embodiments, at least one element 702 may be a PTC (positive temperature coefficient) heating element; wherein the heating element has a carbon-based ink applied to a plastic film of the heating element wherein the carbon may aggregate away from one another when certain predetermined temperature threshold may be exceeded. This may permit an increase in electrical resistance within the heating element, resulting in a drop in power and providing safety mechanism to the heating element when that certain predetermined temperature threshold may be exceeded. In some embodiments, such PTC heating elements may be located above or beneath bottom interior surface 217 of vessel lining 200a.

In some embodiments, heating pad 3301 may not include upper pad 3302 and at least one element 702 may be in physical contract with a portion of a bottom of bottom interior surface 217 of vessel lining 200a. In some embodiments, at least one element 702 may be attached to the portion of the bottom of bottom interior surface 217 of vessel lining 200a. In some embodiments, such attachment may be by chemical adhesive and/or mechanical fastener.

In some embodiments, heater subassembly may comprise insulator 3304. In some embodiments, insulator 3304 may be disposed beneath heating pad 3301. See e.g., FIG. 33A and FIG. 33B. In some embodiments, insulator 3304 may serve at least one purpose of insulating a bottom of vessel cover 200b (e.g., at least one base 215) from receiving too much heat energy, which may help to assure long term structural integrity of vessel 200. In some embodiments, a two dimensional (2D) shape and size of insulator 3304 may be complimentary to a 2D shape and size of heating pad

3301, when viewed from above. In some embodiments, the 2D shape and size of insulator 3304 may approximate the 2D shape and size of heating pad 3301, when viewed from above. For example, and without limiting the scope of the present invention, in some embodiments wherein the 2D shape of heating pad 3301 may be substantially rectangular, then the 2D shape of insulator may be substantially complimentary rectangle. See e.g., FIG. 33A. In some embodiments, insulator 3304 may be substantially constructed from a heat resistant elastomer, thermoplastic, and/or foam. In some embodiments, insulator 3304 may be substantially constructed from an insulating elastomer, thermoplastic, and/or foam. In some embodiments, insulator 3304 may be rigid to semi-rigid. In some embodiments, insulator 3304 may be a rigid to a semi-rigid sheet (i.e., board) of foam.

In some embodiments, such as, but not limited to, embodiments utilizing heater subassembly 3300, disposed between at least some portions of vessel lining 200a and vessel cover 200b may be insulation 3305. See e.g., FIG. 33B. In some embodiments, insulation 3305 may be one or more of an insulating: air gap, foam, liquid, gel, batting, fiber, wool, vacuum, any other form of thermal insulation, and/or combinations thereof. In some embodiments, such insulating foams that may comprise all or a portion of insulation 3305 may be a spray on foam.

In FIG. 33B, at least one guide 507 and at least one magnetically attractable member 3311, which may relate to various head rest subassemblies, may be depicted. In such embodiments, at least one magnetically attractable member 3311 may be replace at least one plate 511. In such embodiments, at least one post 503's of a given support member 501, may slidingly ride upon at least one guide 507's to vary the given support member 501 in the forwards-backwards direction. See e.g., FIG. 33D. And at least one magnet 506's that may be within at least one post 503's may be magnetically coupled (connected) to at least one magnetically attractable member 3311; which may be located within (i.e., under) the at least one guide 507's. In some embodiments, at least one magnetically attractable member 3311 may be substantially constructed of magnetic and/or ferrous materials. In some embodiments, at least one magnetically attractable member 3311 may be substantially constructed of a substantially ferrous material, such as, but not limited to, irons and/or some steels.

FIG. 33B may also depict cover 3321. Cover 3321 may cover a recessed channel in a back wall of vessel lining 200a. Cover 3321 may cover where one or more gas-diffuser-tubings 801 may connect to connector 813. Cover 3321 may cover temperature sensor 1106.

FIG. 33C may depict an embodiment of heater subassembly 3330 for a face soaking device (e.g., face soaking device 100), shown from a top perspective exploded view; wherein at least some portions of heating pad 3331 may be disposed between vessel lining 200a and vessel cover 200b in at least some side wall 205 portions of the vessel (e.g., vessel 200). The view depicted in FIG. 33C may be substantially similar to the view depicted in FIG. 33A, but of a different embodiment. In some embodiments, heater subassembly 3330 may differ from heater subassembly 3300 (in FIG. 33A and FIG. 33B) by at least some portions of heating pad 3331 and/or insulator 3334 being disposed between at least some portions of vessel lining 200a and vessel cover 200b in at least some side wall 205 portions of the vessel (e.g., vessel 200); otherwise heater subassembly 3330 and heater subassembly 3300 may be substantially similar, such that relevant portions of the heater subassembly 3300 discussion may apply to heater subassembly 3330.

In some embodiments, heater subassembly 3330 may comprise heating pad 3331. See e.g., FIG. 33C. In some embodiments, heater subassembly 3330 may comprise heating pad 3331 and insulator 3334; wherein insulator 3334 may be disposed beneath at least some portions of heating pad 3331. See e.g., FIG. 33C. As shown in FIG. 33C, heating pad 3331 and/or insulator 3334 may be disposed between vessel lining 200a and vessel cover 200b, such that heating pad 3331 and/or insulator 3334 may be sandwiched between vessel lining 200a and vessel cover 200b in the assembled configuration. In some such embodiments, such sandwiching may be at bottom portions of vessel lining 200a and vessel cover 200b. In some such embodiments, such sandwiching may be at side wall 205 portions of vessel lining 200a and vessel cover 200b. With respect to any given side wall 205 (comprised of portions of vessel lining 200a and vessel cover 200b), heating pad 3331 and/or insulator 3334 may be disposed between vessel lining 200a and vessel cover 200b for only some of the given side wall 205 up to an entirety of the given side wall 205. Locating at least some portions of heating pad 3331 between side wall(s) 205 may increase heating efficiency and/or a speed at bringing liquid 101 up to a desirable temperature. In some embodiments, wherever heating pad 3331 may be sandwiched between vessel lining 200a and vessel cover 200b, insulator 3334 may be sandwiched, with insulator 3334 closer to vessel cover 200b than to vessel lining 200a. See e.g., FIG. 33C. In such arrangements and/or configurations, heating pad 3331 may not be in physical contact with liquid 101, which minimize chances for electrical shorting and/or minimize shocking user 9000. In some embodiments, wiring from heating pad 3331 may lead into mechanical compartment 251. In some embodiments, such wiring may connect to controller 1100 and/or thermostat 1107. In some embodiments, heating pad 3331 may be waterproof.

In some embodiments, heating pad 3331 may be disposed above bottom interior surface 217, such that at least some portions of heating pad 3331 may be removable physical contact with liquid 101 (such embodiments not depicted in the figures). In such embodiments, heating pad 3331 may be waterproof.

In some embodiments, heating pad 3331 may be a HWD heating pad. In some embodiments, this may be greater than 50 watts per square inch (i.e., about 25 mm) of heating pad. In some embodiments, heating pad 3331 may be a LWD heating pad.

In some embodiments, heating pad 3331 may comprise an upper pad 3332, a lower pad 3323 and at least one element 702 (as in a heating element) disposed between upper pad 3332 and lower pad 3333. See e.g., FIG. 33C. In such embodiments, one or more of: upper pad 3332, lower pad 3333, and/or element 702 may be substantially flat and/or substantially planar members. In some embodiments, such substantially flat and/or such substantially planar members may be flexible. In some embodiments, around peripheral (i.e., perimeter) edges of upper pad 3332 may be sealed to lower pad 3333 peripheral edges. In some embodiments, such sealing of such edges may be accomplished by one or more of: mechanical fasteners, welding, heat welding, ultrasonic welding, solvent bonding, chemical adhesives, and/or injection molding of upper pad 3332 and lower pad 3333 around the at least one element 702. In some embodiments, such sealing of edges may result in a waterproof cavity or space where the at least one element 702 may reside.

In some embodiments, upper pad 3332 and lower pad 3333 may be upper and lower portions of a film or a coating that may encase at least one element 702. In some embodiments, this film may be a thin film.

In some embodiments, upper pad 3332 and/or lower pad 3333 may be substantially constructed of an elastomeric material of construction that may be heat resistant, such as, but not limited to, silicone. In some embodiments, upper pad 3332 and/or lower pad 3333 may be substantially constructed of a heat resistant material, such as, but not limited to, silicone, Teflon, Kapton, and/or the like. In some embodiments, upper pad 3332 may be thinner than lower pad 3303. In some embodiments, there may be no lower pad 3333. Such heat resistant materials of construction for upper pad 3322 and/or lower pad 3333 may be elastomeric and/or thermoplastics. In embodiments where at least one element 702 may be disposed from exterior surfaces of vessel lining 200*a*, wherein heat from the at least one element 702 may conduct and/or dissipate upwards through at least some portions of upper pad 3332, optionally through some portions of insulation 3305, through some portions of vessel lining 200*a*; and into liquid 101; resulting in heating of liquid 101.

In some embodiments, other than sizing and placement differences as noted, heater subassembly 3300 may be substantially similar to heater subassembly 3330. That is, the following may be substantially similar: heating pad 3301 to heating pad 3331; upper pad 3302 to upper pad 3332; lower pad 3303 to lower pad 3333; and insulator 3304 to insulator 3334.

In some embodiments, temperature sensor 1106 and/or thermostat 1107 may be components of a given heating pad embodiment (e.g., heating pad 3301 and/or heating pad 3331). In some embodiments, temperature sensor 1106 and/or thermostat 1107 may in communication with one or more of: upper pad 3302, upper pad 3332, lower pad 3303, lower pad 3333, and/or element 702.

In some embodiments, in addition to various heating equipment (e.g., heater 700 subassembly), there may be various chilling equipment. Or in other embodiments, an alternative to various heating equipment, may be various chilling equipment. In some embodiments, the face soaking devices (e.g., 100) may comprise a chiller for chilling liquid 101 to a temperature below room temperature. In some embodiments, the face soaking devices (e.g., face soaking devices 100) may comprise the chiller for chilling liquid 101 to a temperature above a freezing point of liquid 101. In addition or alternatively, in some embodiments, liquid 101 may be chilled by introduction of ice, such as water ice. Or liquid 101 may be chilled before introduction into interior volume 220.

Chilling liquid 101 by use of a chiller, chilling equipment, and/or by introduction of ice or chilled liquid 101, may then permit various cold therapy to be used to treat face 9010 or other body part(s) which may be removably immersed into the chilled liquid 101. In some embodiments, liquid 101 may be substantially ice. Additionally or alternatively, warm (or hot) therapy may be alternated with cold therapy; wherein such alternation of warmth and cold may aid in increasing blood flow, facilitating removal of cellular toxins (e.g., but not limited to, lactic acid), and/or promoting healing of burned or traumatized tissue.

Now turning to a discussion of the FIG. 8 figures. The FIG. 8 series of figures may comprise FIG. 8A through FIG. 8G. The FIG. 8 series of figures may depict exemplary embodiments of portions of an aerator. In some embodiments, face soaking device 100 may comprise various aerator embodiments. Such aerators may release gas bubbles 125 into liquid 101 within internal volume 220 of vessel 200. In some embodiments, a given aerator embodiment may by a means of supplying a stream of gas to at least one point near a bottom of the interior space of vessel 200, provide for the stream of gas such that there may be a release of bubbles 125 into liquid 101 when the vessel 200 may contain a sufficient quantity of liquid 101. Some portions of aerator embodiments (e.g., a gas diffuser) may be in physical contact with vessel 200. See e.g., FIG. 8A, FIG. 8C, FIG. 8D, and FIG. 8E.

In some embodiments, the aerator may comprise a gas diffuser and a gas source. In some embodiments, the gas source may be coupled to the gas diffuser, such that gas from the gas source may be provided to the gas diffuser. In some embodiments, the gas diffuser may comprise a porous structure. In some embodiments, the gas diffuser may comprise a plurality of pores. In some embodiments, the porous structure may be the plurality of pores. In some embodiments, the gas diffuser may be located within internal volume 220 or positioned, such that gas bubbles 125 from the gas diffuser are released into internal volume 220. The gas source may provide at least some gas to the gas diffuser. In some embodiments, the gas source may be selected from one or more of a cylinder (e.g., a gas cylinder) containing a compressed gas or an air pump for pumping atmospheric air. In some embodiments, the gas diffuser may then release the at least some of the gas through the plurality of pores and/or through the porous structure. When liquid 101 may be occupying some portion of internal volume 220 of vessel 200, the release of the at least some of the gas through the plurality of pores may result in a release of gas bubbles 125 into liquid 101. This may increase an amount of dissolved gas within liquid 101 (as well as non-dissolved gas), including dissolved oxygen, depending upon the composition of the gas.

In some embodiments, the gas diffuser may be located on an interior surface of at least one base 215 (e.g., to a portion of bottom interior surface 217) of vessel 200. See e.g., FIG. 8A, FIG. 8C, FIG. 8D, and FIG. 8E. In some embodiments, the gas diffuser may be located within internal volume 220. In some embodiments, the gas diffuser may comprise one or more gas-diffuser-tubings 801. For example, gas diffuser 800 may comprise one or more gas-diffuser-tubings 801. See e.g., the FIG. 8 series of figures.

In some embodiments, the gas diffuser may be connected to interior wall surface 203 of vessel 200 and below the maximum liquid level. In some embodiments, the gas diffuser, or a portion thereof, may be located on interior wall surface 203 of vessel 200. In some embodiments, the gas diffuser may be removable from interior wall surface 203 of vessel 200.

In some embodiments, the gas diffuser may be integral with interior wall surface 203 of vessel 200. The plurality of pores (and/or the porous structure) may release air (or some other gas) from at least one interior wall surface 203 of vessel 200. The gas diffuser and interior wall surface 203 of vessel 200 may be a single article of manufacture in some embodiments. In such embodiments, at least one wall 201 and the gas diffuser may be injection molded as the single article of manufacture, with airline plumbing needs molded into space between interior wall surface 203 and exterior wall surface 202. For example, between vessel lining 200*a* and vessel cover 200*b*.

In some embodiments, the gas diffuser may be integral with bottom interior surface 217 of vessel 200. The plurality of pores (and/or the porous structure) may release air (or some other gas) from bottom interior surface 217 of vessel 200. The gas diffuser and bottom interior surface 217 of vessel 200 may be a single article of manufacture in some embodiments. In such embodiments, at least one base 215 and the gas diffuser may be injection molded as the single article of manufacture, with airline plumbing needs molded into space between bottom interior surface 217 and exterior wall surfaces 202. For example, between vessel lining 200*a* and vessel cover 200*b*. For example, and without limiting the scope of the present invention, see e.g., gas diffuser 800 in FIG. 27A, which may be integral with bottom interior surface 217. Note, a 2D view from a top of gas diffuser 800 in FIG. 27A need not be circular in shape, but could be other 2D geometric shapes, such as, but not limited to: linear runs, with or without curves; ellipses; ovals; regular polygons, with or without rounded corners; irregular polygons, with or without rounded corners; and/or the like.

Figure 8A:
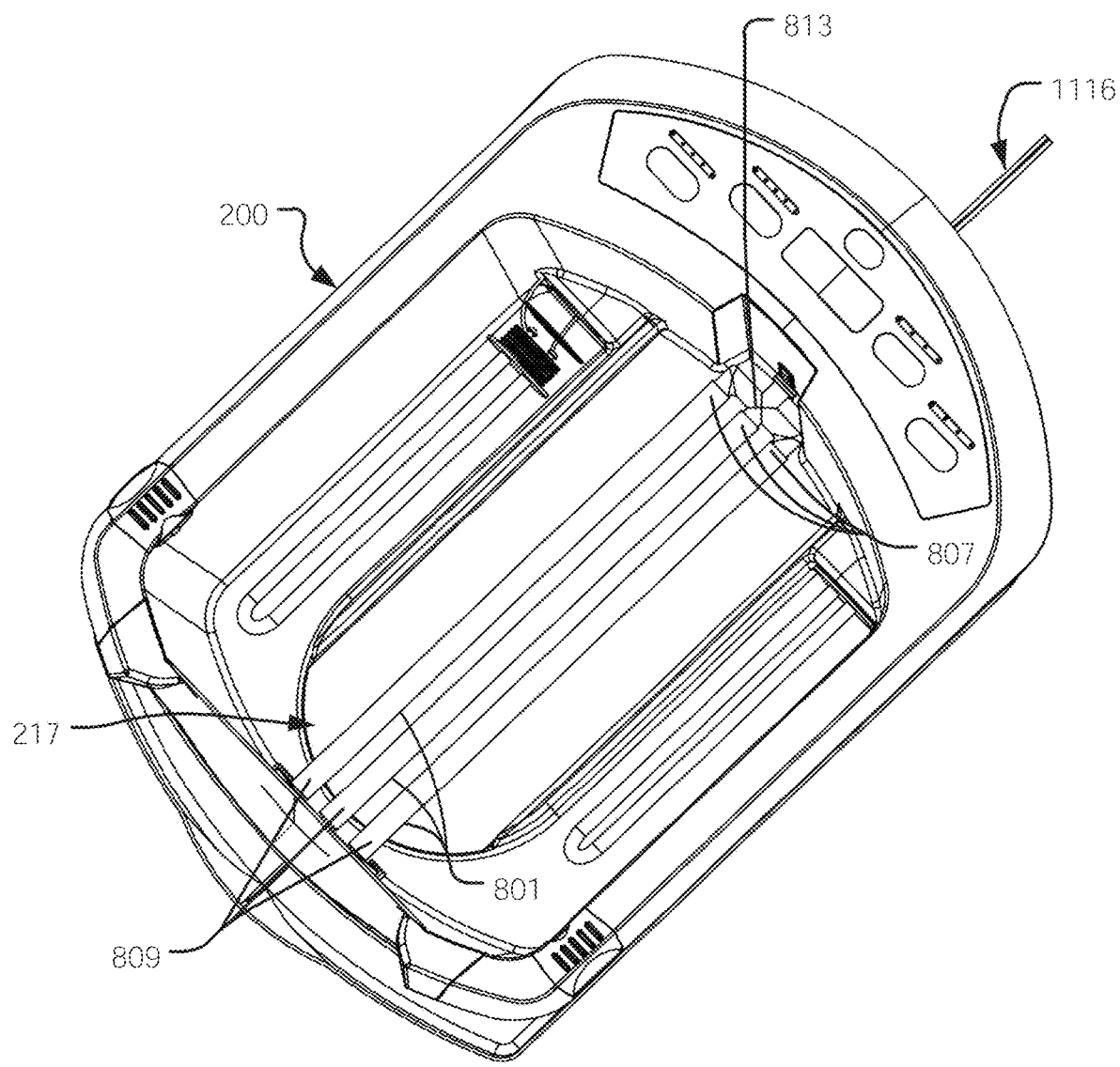
FIG. 8A may depict portions of a gas diffuser of the face soaking device of FIG. 2A, shown from a top perspective view, but with the breathing apparatus, the head rest subassembly, and the (heat) shield removed.
Figure 8B:
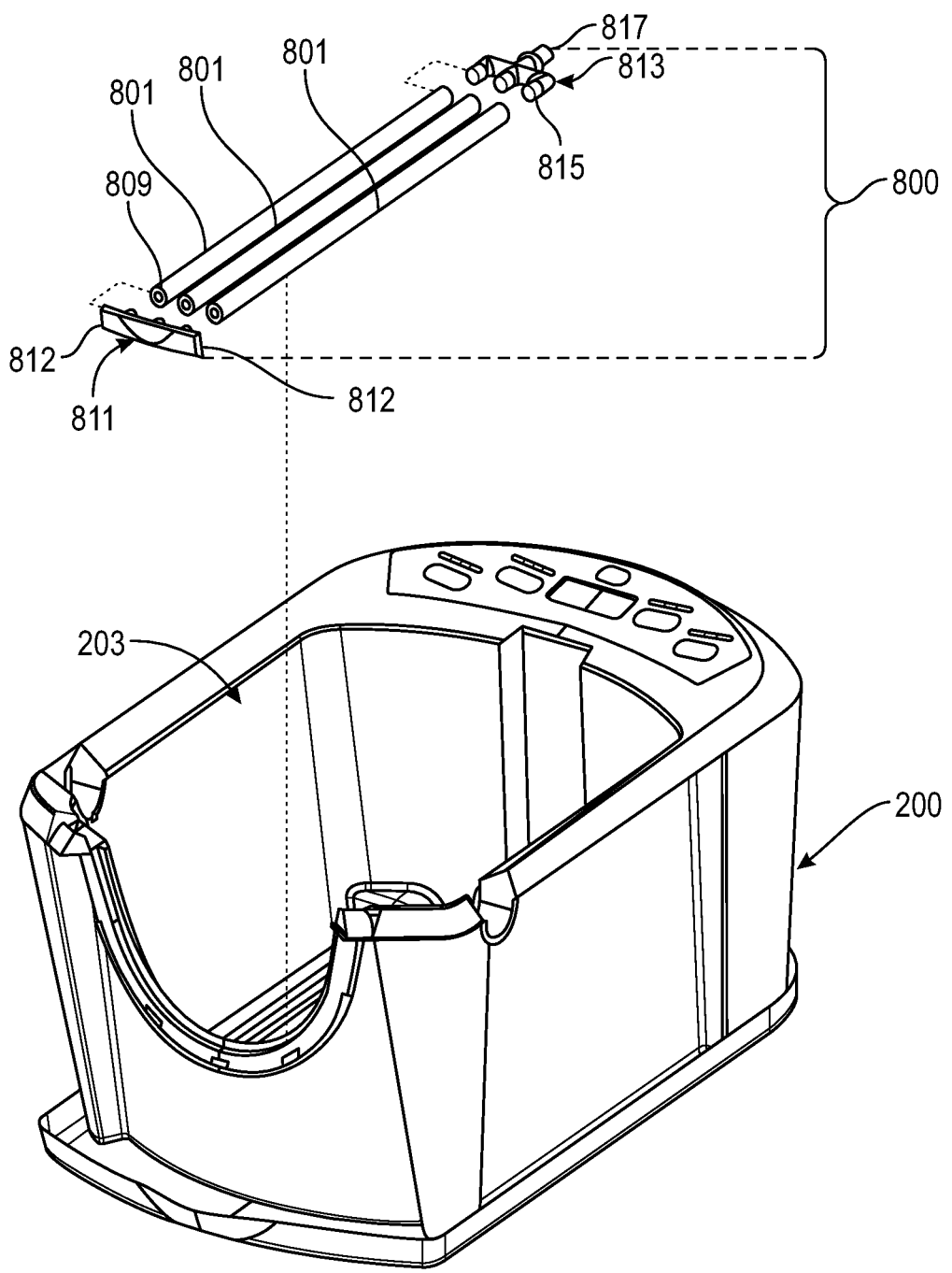
FIG. 8B may depict portions of the gas diffuser from FIG. 8A, shown exploded from the vessel, from a top perspective exploded view.

In some embodiments, the gas diffuser may be gas diffuser 800. See e.g., the FIG. 8 series of figures. FIG. 8A may depict portions of gas diffuser 800 of face soaking device 100, shown from a top view, but with the breathing apparatus (e.g., breathing apparatus 400), the head rest subassembly (e.g., head rest subassembly 500), and shield 715 removed. FIG. 8B may depict portions of gas diffuser 800 exploded from the vessel (e.g., vessel 200), from a top perspective view.

In some embodiments, gas diffuser 800 may comprise one or more gas-diffuser-tubings 801. For example, and without limiting the scope of the present invention, there may be one, two, three, four, five, or six distinct gas-diffuser-tubings 801 in various embodiments. For example, the FIG. 8 series of figures may depict embodiments with three gas-diffuser-tubings 801; and a FIG. 29 series of figures (FIG. 29A through FIG. 29E) may depict different layout configurations of one or two gas-diffuser-tubings 801. Additionally, one gas-diffuser-tubing 801 may be looped (and/or bent) onto layout configurations that may be substantially equivalent to two or more gas-diffuser-tubings 801 layout configurations. See e.g., FIG. 29A through FIG. 29E.

Figure 8C:
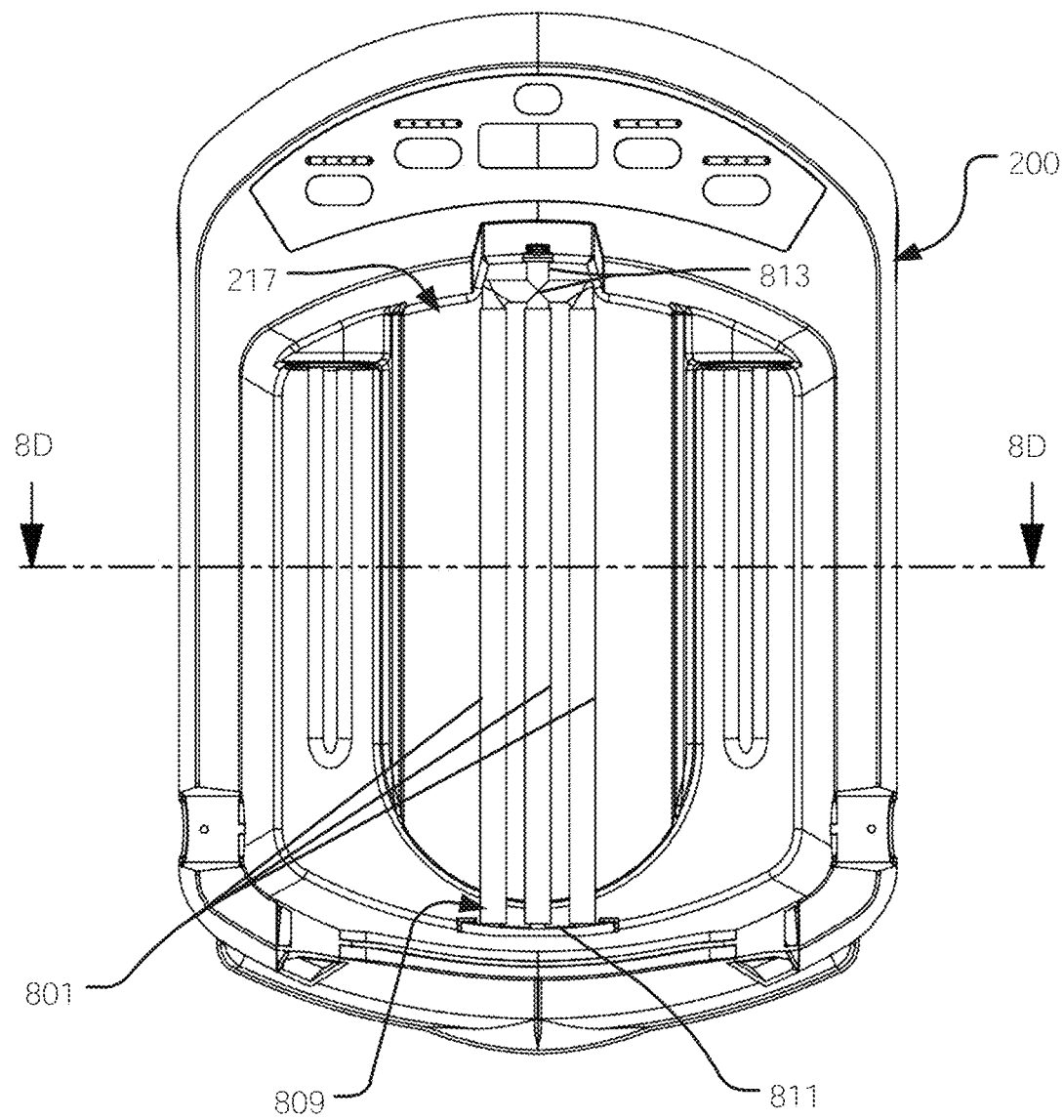
FIG. 8C may depict the portions of the gas diffuser of FIG. 8A, shown from a top view, along with a transverse-width sectional line 8D-8D through gas-diffuser-tubings.
Figure 8D:
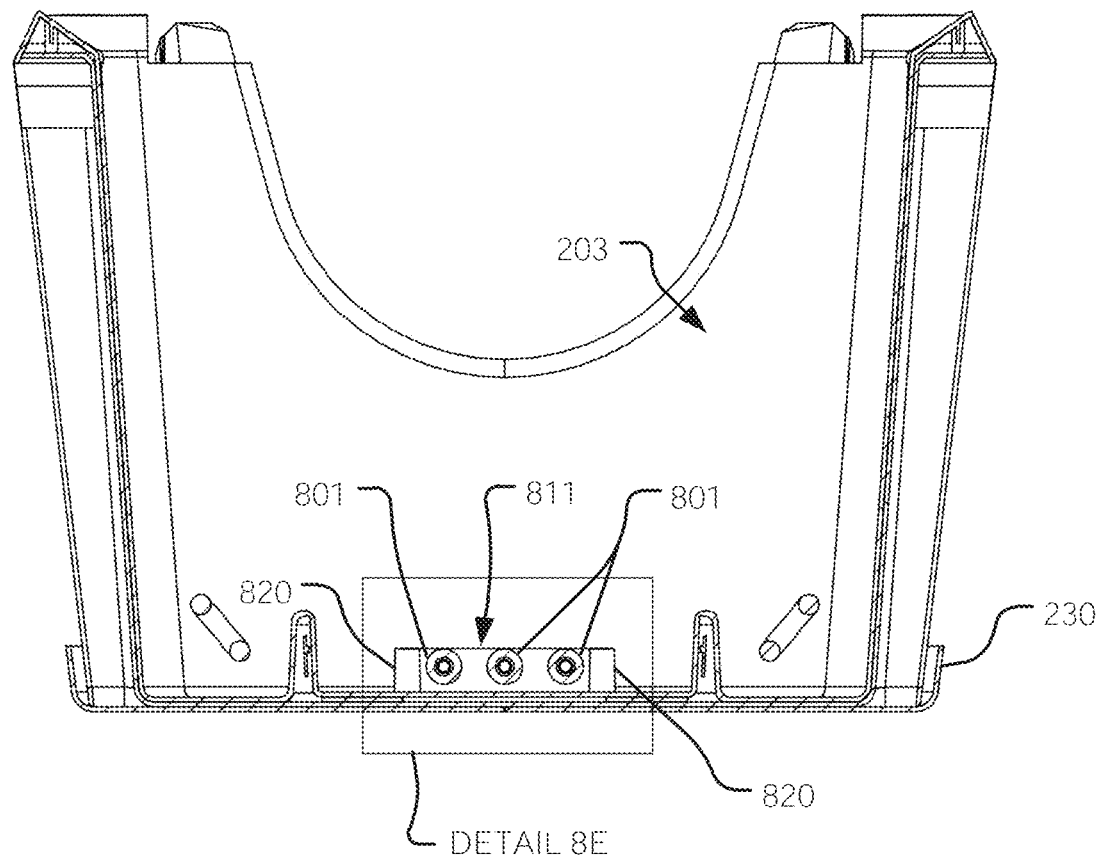
FIG. 8D a transverse-width cross-sectional view along sectional line 8D-8D through the gas-diffuser-tubings; wherein FIG. 8D may also depict a region of Detail 8E.
Figure 8E:
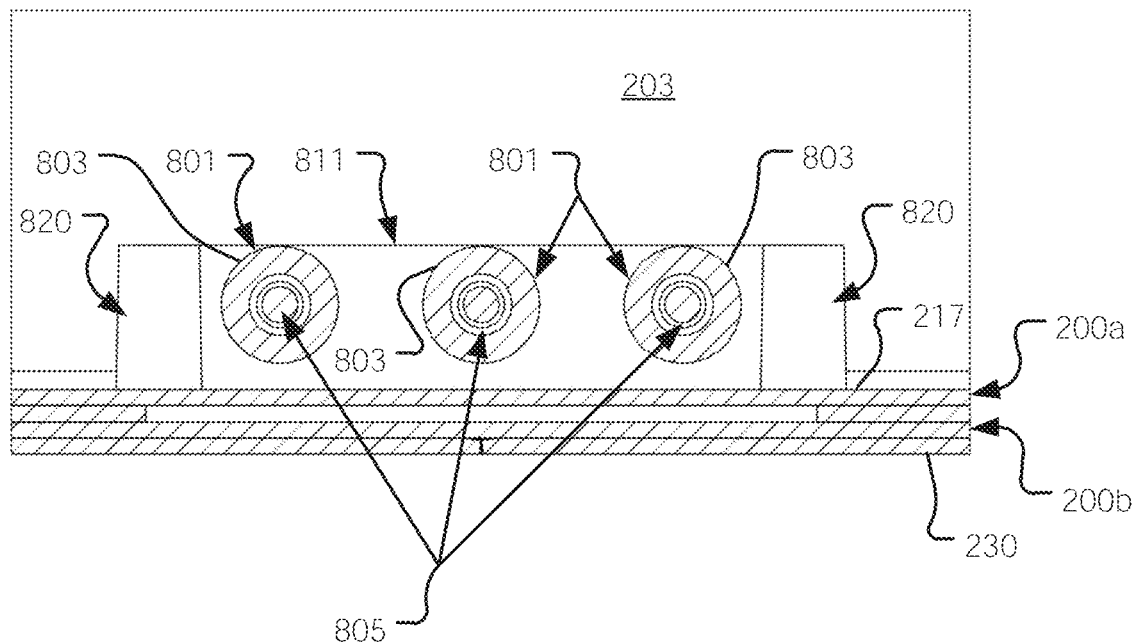
FIG. 8E may depict a close-up view of Detail 8E.

In some embodiments, each gas-diffuser-tubing 801 selected from one or more gas-diffuser-tubings 801 may comprise a porous-elongate-member 803 and a central-elongate member 805. In some exemplary embodiments, porous-elongate-member 803 and the central-elongate-member 805 are coaxial with respect to each other. See e.g., FIG. 8E and FIG. 8D. FIG. 8C may depict the portions of gas diffuser 800, shown from a top view, along with a transverse-width sectional line 8D-8D through gas-diffuser-tubings 801. FIG. 8D a transverse-width cross-sectional view along sectional line 8D-8D through gas-diffuser-tubings 801; wherein FIG. 8D may also depict a region of Detail 8E. FIG. 8E may depict a close-up view of Detail 8E showing close up cross-sectional details of gas-diffuser-tubings 801. This cross-sectional close-up of Detail 8E in FIG. 8E may show porous-elongate-member 803 and a central-elongate member 805 and their coaxial relationship to each other.

In some embodiments, central-elongate-member 805 may be located within a cavity of the porous-elongate-member 803. See e.g., FIG. 8E and FIG. 8D. In some embodiments, central-elongate-member 805 may rigid or semi-rigid, permitting bends in the gas-diffuser-tubing 801 to be retained. See e.g., some the various layout configurations of one or more gas-diffuser-tubings 801 shown in the FIG. 29 series of figures. In some embodiments, central-elongate-member 805 may be substantially constructed of a metal. For example, and without limiting the scope of the present invention, in some embodiments, such metals may be selected from: aluminum, copper, steel, and/or the like. In some embodiments, central-elongate-member 805 may be an insulated metal wire, to minimize corrosion to the metal wire and/or to minimize forming an inadvertent battery. Such insulation may be a thermoplastic and/or an elastomer.

In some embodiments, porous-elongate-member 803 may be substantially constructed of a porous material. In some embodiments, this porous material may comprise the plurality of pores of gas diffuser 800. In some embodiments, this porous material may be an elastomeric material. In some embodiments, this porous material may be an open celled foam material.

In some embodiments, each gas-diffuser-tubing 801 selected from one or more gas-diffuser-tubings 801 may comprises two terminal ends, a first end 807 and disposed opposite a second end 809. See e.g., FIG. 8B. Note, in some embodiments, denoting first end 807 from second end 809 may be arbitrary and only for naming convention, in that first end 807 and second end 809 may be structurally equivalent. In some embodiments, first end 807 may be connected to either the gas source or to an intermediary that may be connected to the gas source. In some embodiments, second end 809 may be connected to an end-cap 811, the gas source, or to the intermediary or a different intermediary. The embodiments shown in the FIG. 8 series of figures may show second end 809 connected to end-cap 811. See e.g., FIG. 8F for end-cap 811. In some embodiments, the intermediary may comprise one or more of a connector 813 (or connector 3013) or airline tubing 819. The embodiments shown in the FIG. 8 series of figures may show first end 807 connected to connector 813. See e.g., FIG. 8G for connector 813.

Figure 8F:
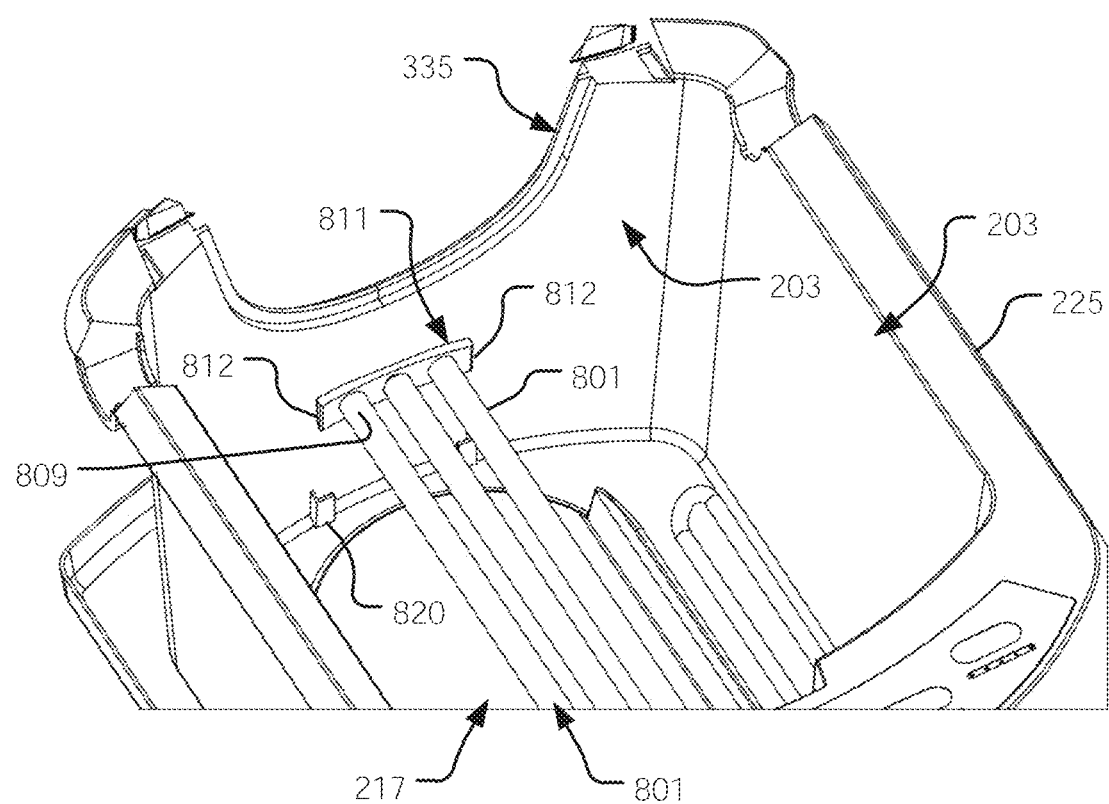
FIG. 8F may depict gas-diffuser-tubings removably coupled with an end-cap, wherein the gas-diffuser-tubings and the end-cap may be exploded from a flange-receiver of the vessel, shown from a partial top perspective view of the interior of the vessel.

In some embodiments, gas diffuser 800 may comprise one or more end-cap(s) 811. See e.g., FIG. 8B and FIG. 8F. In some embodiments, end-cap 811 may attach to at least one of the terminal ends 807 or 809 of gas-diffuser-tubing 801 to prevent gas escape from that terminal end 807 or 809. See e.g., FIG. 8B and FIG. 8F. FIG. 8F may depict gas-diffuser-tubings 801 removably coupled with end-cap 811, wherein the gas-diffuser-tubings 811 and end-cap 811 may be exploded from a flange-receiver 820 of the vessel (e.g., vessel 200), shown from a partial top perspective view of the interior of the vessel. In some embodiments, end-cap 811 may comprise hose barbs for attachment to at least one of the terminal ends, first end 807 and/or second end 809 of gas-diffuser-tubing 801. In some embodiments, end-cap 811 hose barbs may not be hollow. In some embodiments, end-cap 811 hose barbs may be solid. That is, end-caps 811 may have structure to function as plugs to first end 807 or second end 809 of gas-diffuser-tubing 801. This structure may comprise hose barbs for insertion into an inside diameter of porous-elongate-member 803. In some embodiments, only one terminal end, first end 807 or second end 809, of gas-diffuser-tubing 801 may have end-cap 811 attached thereto; and the remaining terminal end may be connected to airline tubing 819 or to airline tubing 819 through the intermediary. See e.g., FIG. 29B, FIG. 29C, FIG. 29E, and FIG. 8G. Note, in some embodiments, both terminal ends, first end 807 and second 809 of gas-diffuser-tubing 801 may be connected to airline tubing 819 or both connected to the intermediary. See e.g., FIG. 29A and FIG. 29D (layout configurations without end-caps 811).

In some embodiments, end-cap 811 may comprise flanges 812, in addition to hose barbs. In some embodiments, end-cap 811 may comprise two opposing flanges 812, wherein the hose barbs may be disposed between both opposing flanges 812. In some embodiments, end-cap 811 may attach to flange-receiver 820. See e.g., FIG. 8F, where flanges 812 may be removably captured by flange-receiver 820. A nature of fit between each flange 812 and each flange-receiver 820 may be a press fit or a frictional fit. Flange-receiver 820 may comprise a pair of oppositely disposed slots sized to receive flanges 812. See e.g., FIG. 8F.

In some embodiments, flange-receiver 820 may be attached to (or integral with): interior wall surface 203 of vessel 200, at least one base 215, bottom interior surface 217, shield 715, or LED-housing 950. In FIG. 8F, flange-receiver 820 may attach to bottom interior surface 217, proximate to interior wall surface 203. In some embodiments, this proximate distance may be four inches or less.

Figure 8G:
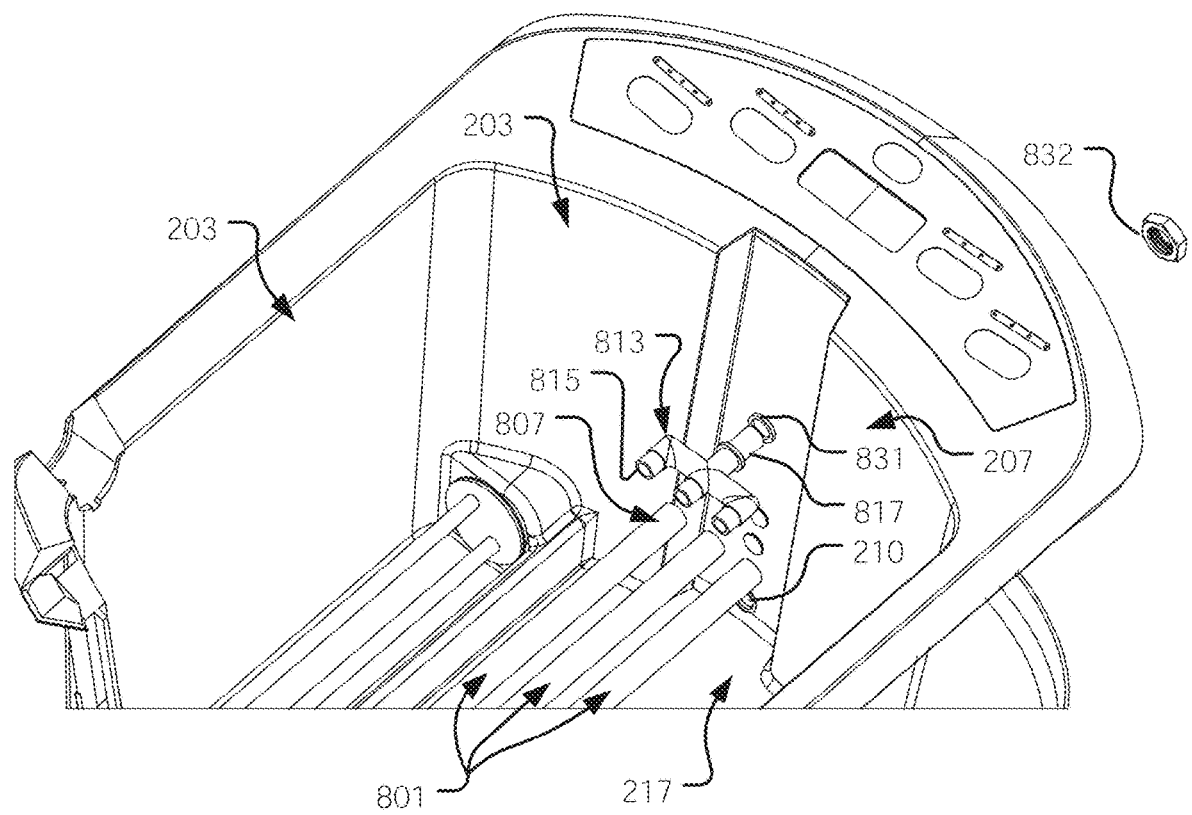
FIG. 8G may depict an opposing view from FIG. 8F, wherein FIG. 8G may depict gas-diffuser-tubings exploded from a connector and from an interior back wall of the vessel, shown from a partial top perspective view of the interior of the vessel.

In some embodiments, gas diffuser 800 may comprise connector 813. See e.g., FIG. 8B and FIG. 8G. Connector 813 may the intermediary. In some embodiments, connector 813 may comprise hollow hose barbs 815 for insertion into the inside diameter of porous-elongate-member 803 of one terminal end, first end 807 and/or second end 809, of gas-diffuser-tubing 801. See e.g., FIG. 8G. FIG. 8G may depict an opposing view from FIG. 8F, wherein FIG. 8G may depict gas-diffuser-tubings 801 exploded from a connector 813 and from an interior back wall of the vessel (e.g., interior wall surface 203 of second side wall 207), shown from a partial top perspective view of the interior of the vessel. As depicted in the FIG. 8 series of figures, it may be first end 807 that may be removably connected to hose barbs 815 of connector 813. See e.g., FIG. 8G. (In some embodiments, connector 3013 may comprise hollow hose barbs 815 for insertion into the inside diameter of porous-elongate-member 803 of one terminal end, first end 807 and/or second end 809, of gas-diffuser-tubing 801. See e.g., FIG. 30A and FIG. 30B.) In some embodiments, the connector (e.g., 813 or 3013) may be for one or more of: connecting at least one of terminal ends, first end 807 and/or second end 809, of gas-diffuser-tubing 801 to a terminal end of airline tubing 819 (see e.g., FIG. 30B); or connecting the least one of the terminal ends, first end 807 and/or second end 809, of gas-diffuser-tubing 801 to the gas source. Thus either connector (e.g., 813 or 3013) may be the intermediary. Note, different sized and/or styled connectors (e.g., 813 and/or 3013) may be used for each of these different connections, e.g., with differences in hose barbs (e.g., 815 or 817). For example, and without limiting the scope of the present invention, hose barbs 815 may be configured for fitting into the inside diameter of porous-elongate-member 803. While hose barbs 817 may be configured for fitting into an inside diameter of airline tubing 819. Both hose barbs (e.g., 815 or 817) may facilitate gas flow within the given hose barb. In some embodiments, other connectors may connect another terminal end of airline tubing 819 to the gas source (not depicted).

Note, in some embodiments, hose barbs 817 may be more broadly characterized as airline tubing connector 817. And in some embodiments, airline tubing connector 817 may comprise hose barbs 817. In some embodiments, airline tubing connector 817 may comprise some portion of threading, such as outside threading for complimentary connection to nut 832 (which may have inside threading). See e.g., FIG. 8G, FIG. 7N, and FIG. 9C for nut 832.

In some embodiments, the connector (e.g., 813 or 3013) may attach to: interior wall surface 203 of vessel 200, at least one base 215, bottom interior surface 217 of vessel 200, the heat shield 715, or LED-housing 950. In some embodiments, the connector (e.g., 813 or 3013) may attach to bottom interior surface 217 of vessel 200 proximate to interior wall surface 203 of vessel 200 (e.g., the back wall). See e.g., FIG. 8G, FIG. 30A, and FIG. 30B. In some embodiments, this proximate distance may be 2 inches or less. In some embodiments, a nature of this attachment is removable; while in other embodiments, this attachment is permanent. FIG. 8G may show connector 813 for connection to interior wall surface 203 of the back wall at at least one port 210.

Connector 813 may differ from connector 3013 in how the connectors may attach to interior wall surface 203 of vessel 200, at least one base 215, bottom interior surface 217 of vessel 200, shield 715, or LED-housing 950. Connector 813 may differ from connector 3013 in how at least some of the gas may be delivered (routed) to one or more gas-diffuser-tubings 801 in internal volume 220 from airline tubing 819. Connector 813 may be used in a bulkhead connection manner via at least one port 210 through interior wall surface 203 (e.g., the back wall) into (substantially dry) mechanical compartment 251. In some embodiments, on internal volume 220 side, there may also be a gasket 831 for sealing up against interior wall surface 203 (e.g., the back wall). See e.g., FIG. 8G. Gasket 831 may removably circumscribe a portion of hose barbs 817. In some embodiments, on mechanical compartment side 251, there may be portions of hose barbs 817 (or threading 817) for connection to a terminal end of airline tubing 819. In some embodiments, connector 813 may comprise hose barbs 817 (and/or threading 817) for connection to a terminal end of airline tubing 819. In some embodiments, on mechanical compartment side 251, there may also be a washer and/or a nut 832 to make sure that connector 813 may be secured against interior wall surface 203 without any (or minimal) liquid 101 leakage into mechanical compartment 251. See e.g., FIG. 8G, FIG. 7N, and FIG. 9C.

Whereas, connector 3013 may be used in an "up and over" configuration, where a portion of airline tubing 819 may be brought over rim 225 (or over top opening 226 or over a top slot in rim 225) and down into liquid 101 within internal volume 220, where connector 3013 may reside. See e.g., FIG. 30A and FIG. 30B. FIG. 30A may depict the "up and over" manner of securing one or more gas-diffuser-tubings 801 located within internal volume 220 of vessel 200 to airline tubing 819. A portion of airline tubing 819 may be located outside of internal volume 220. "Up and over" may be with respect to rim 225 of vessel 200. FIG. 30B may depict a close up detailed view of a connection region of FIG. 30A where the one or more gas-diffuser-tubings 801 may be removably coupled to the airline tubing 819 via connector 3013. In some embodiments, airline tubing 819 that may be in internal volume 220 may be fitted into a groove along the back wall of the vessel (e.g., vessel 200). In some embodiments, this groove may be airline tubing channel 3021. In some embodiments, airline tubing channel 3021 may run from bottom interior surface 217 to rim 225 in a substantially vertical manner. See e.g., FIG. 30A.

In some embodiments, connector 3013 may comprise flange(s) 3019 to be captured (e.g., via a snap fit or frictional fit) by some region of: interior wall surface 203 of vessel 200, at least one base 215, bottom interior surface 217 of vessel 200, shield 715, the LED-housing 950, and/or the like. See e.g., FIG. 30B, where flange(s) 3019 may be removably captured by flange-receiver 3020. In some embodiments, flange-receiver 3020 may be attached to (or integral with): interior wall surface 203 of vessel 200, at least one base 215, bottom interior surface 217 of vessel 200, shield 715, the LED-housing 950, and/or the like. A nature of fit between flange(s) 3019 and flange-receiver 3020 may be a press fit or a frictional fit. Flange-receiver 3020 may comprise a pair of oppositely disposed slots (i.e., grooves) sized to receive flanges 3019. See e.g., FIG. 30B. In FIG.

30B, flange-receiver 3020 may be attached to (or integral with) bottom interior surface 217, proximate to interior wall surface 203 (e.g., the back wall). In some embodiments, this proximate distance may be four inches or less.

In some embodiments, connector 3013 may comprise hollow hose barbs 815 for insertion into the inside diameter of porous-elongate-member 803 of one terminal end, first end 807 and/or second end 809, of gas-diffuser-tubing 801. See e.g., FIG. 30B. In some embodiments, connector 3013 may comprise hollow hose barbs 817 for insertion into the inside diameter of airline tubing 819 of one terminal end. See e.g., FIG. 30B.

In some embodiments, one or more gas-diffuser-tubings 801 may be located in internal volume 220 of vessel 200. See e.g., FIG. 8A, FIG. 8C, FIG. 8D, and FIG. 8E. In some embodiments, one or more gas-diffuser-tubings 801 may be located in physical contact with or proximate to: interior wall surface 203 of vessel 200, at least one base 215, bottom interior surface 217 of vessel 200, shield 715, and/or LED-housing 950. In some embodiments, portions of one or more gas-diffuser-tubings 801 may be located in physical contact with or proximate to bottom interior surface 217 of vessel 200. For example, and without limiting the scope of the present invention, proximate may be within two inches or less. See e.g., FIG. 8A, FIG. 8C, FIG. 8D, and FIG. 8E.

In some embodiments, at least a portion of one gas-diffuser-tubing 801 selected the one or more gas-diffuser-tubings 801 may be located along a portion of a longitudinal center line of at least one base 215 of the vessel 200. See e.g., FIG. 8A and FIG. 8C. In some embodiments, it may be desirable to locate portions of the one or more gas-diffuser-tubings 801 along this longitudinal center line of at least one base 215, such that gas bubble 125 density may be more likely to be released in locations that are more likely to interact with or benefit face 9010 of user 9000, when face 9010 may be immersed within a portion of liquid 101 in vessel 200.

In some embodiments, one or more gas-diffuser-tubings 801 located in internal volume 220 of vessel 200 may be arranged in a layout configuration with first end 807 of each gas-diffuser-tubing 801 selected from one or more gas-diffuser-tubings 801 may be located closer to the back wall of vessel 200 than to the front wall of the vessel 200. In some embodiments, one or more gas-diffuser-tubings 801 located in internal volume 220 of vessel 200 may be arranged in a layout configuration with second end 809 of each gas-diffuser-tubing 801 selected from one or more gas-diffuser-tubings 801 may be located closer to the front wall of vessel 200 than to the back wall of the vessel 200. See e.g., FIG. 8A and FIG. 8C.

In some embodiments, each gas-diffuser-tubing 801 selected from the one or more gas-diffuser-tubings 801 may proceed in a (substantially) straight linear direction from the back wall towards the front wall. See e.g., FIG. 8A and FIG. 8C.

In some embodiments, each gas-diffuser-tubing 801 selected from the one or more gas-diffuser-tubings 801 may proceed in a straight linear direction from the back wall towards the front wall for a first length and then the gas-diffuser-tubing 801 may proceed with one or more bends; but, where a maximum number of bends may be limited and/or constrained by: surface area of bottom interior surface 217; surface area between LED-housings 950; surface area between at least one side wall 205; and/or surface area between longitudinal arms (prongs) of shield 715. See e.g., the FIG. 29 series of figures.

In some embodiments, some layout configurations of one or more gas-diffuser-tubings 801 when viewed from above may resemble: a letter U, a letter W (with rounded corners), a letter I, a letter L, a number 1, an oval, a circle, a rectangle with rounded corners, other patterns capable of fitting between LED-housings 950, other patterns capable of fitting between at least one side wall 205, other patterns capable of fitting between longitudinal arms (prongs) of shield 715, and/or the like. See e.g., the FIG. 29 series of figures. Patterns which may release and/or direct and/or cause a greater amount or density of gas bubbles 125 to contact the face 9010 of the user 900 may be desirable and exemplary.

In some embodiments, airline tubing 819 may provide an enclosed and non-porous path for a delivery of the at least some of the gas from the gas source to the one or more gas-diffuser-tubings 801. A portion of airline tubing 819 may be depicted in FIG. 30B, otherwise, airline tubing 819 may not be depicted.

In some embodiments, airline tubing 819 may run from the gas source to the one or more gas-diffuser-tubings 801. In some embodiments, airline tubing 819 may run from the gas source to connector 813 or connector 3013; wherein connector 813 or connector 3013 may be connected to one or more gas-diffuser-tubings 801. As noted above, some portion of airline tubing 819 may be routed through a port 210 in a back wall of the vessel 200 (see e.g., FIG. 8G). As noted above, some portion of airline tubing 819 may be routed over rim 225 or over top opening 226 of vessel 200 and into internal volume 220. See e.g., FIG. 30A and FIG. 30B.

In some embodiments, the aerator may also comprise airline tubing 819. Airline tubing 819 may connect the gas source to the gas diffuser (e.g., gas diffuser 800), providing an enclosed path (and non-porous path) for a delivery of the gas or at least some of the gas from the gas source to the gas diffuser. In some embodiments, disposed along a length of airline tubing 819 may be one or more check valves. The check valve may prevent the liquid 101 from traveling within airline tubing 819 towards the gas source.

In some embodiments, the air pump may be replaced with one or more cylinders (gas cylinders) as a supply source for the gas to the gas diffuser (e.g., gas diffuser 800). The gasses within these one or more cylinders may be selected from gasses which may be safe to human skin or safe to terrestrial vertebrate skin. The one or more gas cylinders may be selected from compressed air cylinders, oxygen cylinders, nitrogen cylinders, carbon dioxide cylinders, nitrous oxide, and/or the like. In such embodiments, appropriate pressure regulators may be used in between the cylinders and/or the gas diffuser.

In some embodiments, the air pump may receive atmospheric air and force such air into the gas diffuser (e.g., gas diffuser 800). In some embodiments, the air pump may comprise electrical power cord 1116. Electrical power cord 1116 may receive electrical power from an electrical power source 1115, such as an electrical outlet. The electrical power received by the air pump may provide necessary power to pump (and compress) air with sufficient force to deliver the air to the gas diffuser.

In some embodiments, the air pump may be located outside of internal volume 220. In some embodiments, the air pump may be located inside or partially inside mechanical compartment 251. In some embodiments, the air pump may be located outside of vessel 200. In some embodiments, the gas diffuser may be located in internal volume 220, such that the plurality of pores may release air into internal volume 220.

In some embodiments, the air pump may be housed on exterior wall surface 202. In some embodiments, the air pump may be housed within at least one base 215.

Figure 11A:
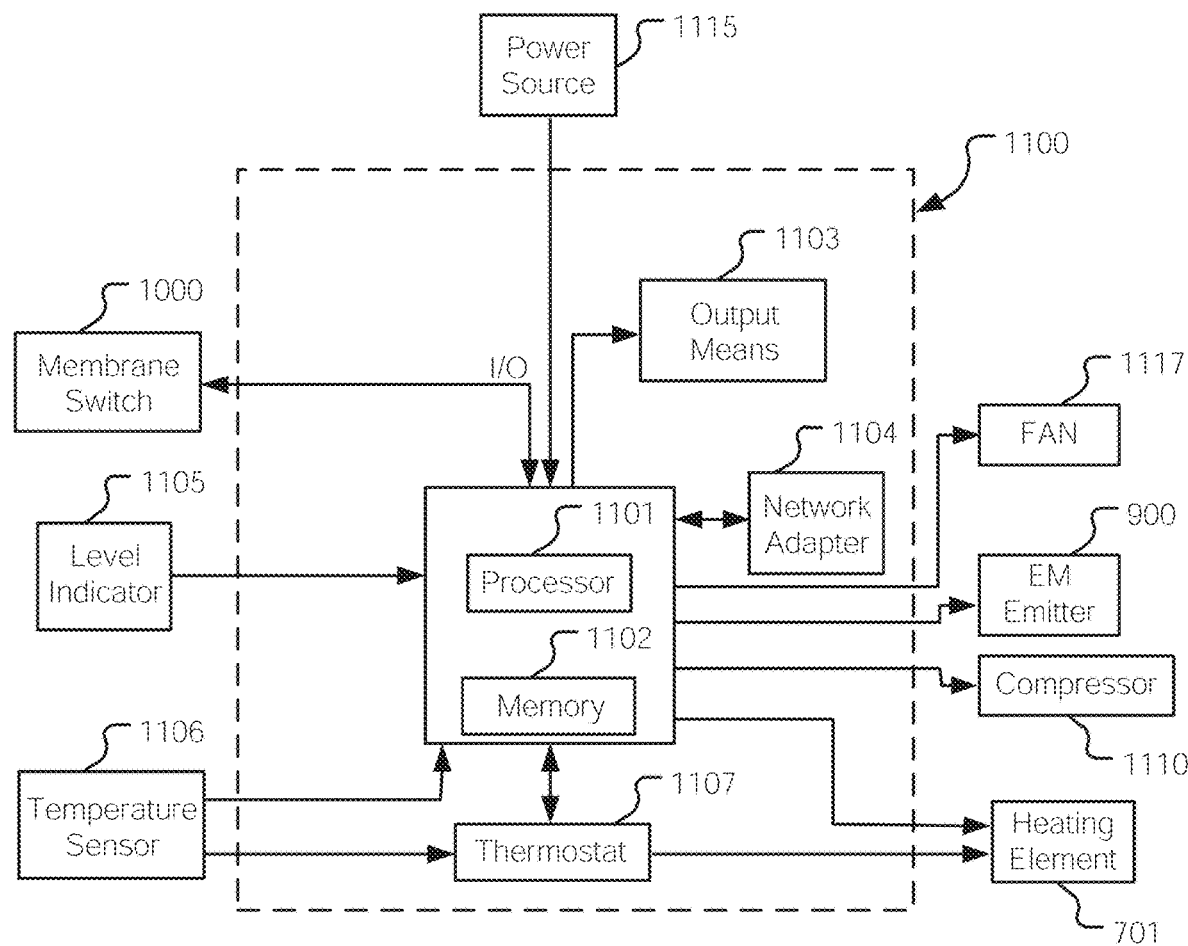
FIG. 11A may depict an exemplary embodiment of a controller of a face soaking device, shown as a block diagram.

In some embodiments, the air pump may be replaced with compressor 1110 (see e.g., FIG. 11A). In some embodiments, the air pump may be compressor 1110. In such embodiments, compressor 1110 may be configured to supply air to more than one face soaking device 100. One or more compressor(s) 1110 may be used to operate a plurality of face soaking devices 100. When compressor 1110 may be used to supply air to any face soaking device 100, additional plumbing components may also be included, such as manifolds, check valves, valves, filters, oil traps, and/or pressure regulators.

In some embodiments, the aerator may comprise a bubble controller. In some embodiments, the bubble controller may be a pressure regulator and in communication with the gas source or the airline tubing 819. In some embodiments, the bubble controller may be in electrical communication with the air pump or compressor 1110. The bubble controller may control an intensity (density) of bubbles 125 produced from the gas diffuser by controlling an intensity of how hard the air pump or compressor 1110 may work (e.g., as measured by output pressure). The bubble controller may be configured to be engaged by user 9000.

In some embodiments, the bubble controller may be a dial type controller, of either analog or digital design. In such embodiments, user 9000 may rotate the dial to increase or decrease the intensity of produced bubbles. In such embodiments, user 9000 may also turn on or off the air pump.

In some embodiments, the bubble controller may be mounted on one of the exterior wall surfaces 202 of vessel 200. In such embodiments, wiring from the bubble controller to the air pump or compressor 1110 may at least in part be run through and within at least one wall 201 and/or at least one base 215. For example, at least in part between vessel lining 200a and vessel cover 200b.

In some embodiments, the bubble controller may be mounted on the air pump or compressor 1110. In some embodiments the bubble controller may be free standing and in electrical communication with the air pump or compressor 1110 via at least one wire disposed between the bubble controller and the air pump or compressor 1110.

In some embodiments, all of the bubble controller's functionality may be performed by controller 1100, wherein there may be no independent bubble controller.

In some embodiments, a given face soaking device (e.g., face soaking device 100) may comprise at least one electromagnetic (EM) emitter 900. See e.g., the FIG. 9 series of figures. In some embodiments, at least one EM emitter 900 may emit EM radiation of a wavelength selected from a range of about 1 picometre (pm) to about 100 megametre (Mm). Note, unless otherwise stated, "about" may mean plus or minus 10% in this context. In some embodiments, at least one EM emitter 900 may emit EM radiation of a wavelength selected from a range of gamma rays to extremely low frequency. In some embodiments, at least one EM emitter 900 may emit EM radiation of a wavelength selected from one or more of the group comprising: gamma rays, hard x-rays, soft x-rays, extreme ultraviolet (UV), near UV, visible light, near infrared (IR), mid IR, far IR, microwave, radio waves, ultra low frequency, super low frequency, extremely low frequency, and/or the like.

Note, at least one EM emitter 900 may not necessarily be a single device capable of emitting across the entire EM spectrum (since different technologies may be required to produce a given range of wavelengths), but rather at least one EM emitter 900 may be a multitude of EM emitting devices wherein each different EM emitting device may be capable of emitting a particular range of wavelengths, such that these different EM emitting devices may collectively as a group be able to cover the entire EM spectrum or a portion thereof.

For example, and without limiting the scope of the present invention, in embodiments wherein treatment of human skin, mammalian skin, and/or terrestrial vertebrate skin may be receive a benefit to such treated skin, wavelengths in the visible light spectrum (about 380 nanometers (nm) to about 770 nm), near UV, UV, and/or near IR may be emitted from at least one EM emitter 900. Treating such skin at such wavelengths may be known as "light therapy" with skin tissue and/or the organism receiving a benefit. However, until this invention, such light therapy was not conducted in combination with simultaneous removable soaking of the skin in liquid 101, and/or in combination with exposures to bubbles 125. Bubbles 125 may enhance the efficacy of such light therapy via optical chain reaction (OCR) as discussed further in the FIG. 12 series of figures discussion below, and/or wherein liquid 101 itself (with additives in some embodiments) may also enhance the efficacy of such light therapy.

In some embodiments, at least one EM emitter 900 may comprise one or more of: a light emitting diode (LED), an incandescent light bulb (including a halogen light source), a fluorescent light source, a high intensity discharge (HID) light source, a mercury lamp, a metal halide lamp, a high pressure sodium (HPS) light source, a laser, a maser, a transducer, a magnetron, a klystron, a traveling-wave tube (TWT), a gyrotron, a field-effect transistor (at least at lower EM frequencies), a tunnel diode, a Gunn diode (transferred electron device (TED)), an IMPATT diode (an impact ionization avalanche transit-time diode), and/or the like.

In some embodiments, at least one EM emitter 900 may be configured to emit light within the visible spectrum (visible to humans). In some embodiments, at least one EM emitter 900 may be configured to emit light within the non-visible spectrum, such as infrared (IR), near infrared, ultraviolet (UV), and the like. In some embodiments, at least one EM emitter 900 may be at least one LED. Various LEDs may be currently available to emit light from the UV spectrum through the visible spectrum and into the IR spectrum. In some embodiments, at least one EM emitter 900 may be at least one incandescent light source and/or at least one fluorescent lamp source.

In some embodiments, at least one EM emitter 900 may be removably attached to one or more of: the vessel (e.g., vessel 200), the breathing apparatus (e.g., breathing apparatus 400), the head rest subassembly (e.g., head rest subassembly 500), the heater subassembly (e.g., shield 715), and/or the gas diffuser (e.g., gas diffuser 800). In some embodiments, at least one EM emitter 900 may be configured to emit electromagnetic radiation (EM) within internal volume 220 such that the emitted EM may irradiate (i.e., shine) upon face 9010 of user 9000 through liquid 101. A portion of at least one EM emitter 900 where the EM may emit from, may be directed towards internal volume 220.

In some embodiments, at least one EM emitter 900 may be a standalone component which may be removable and placed into internal volume 220. In some embodiments, at least one EM emitter 900 may be constructed as component(s) of at least one wall 201 and/or at least one base 215, such that the EM emitted may be directed towards internal volume 220. For example, and without limiting the scope of the present invention, in some embodiments, at least one EM emitter 900 may be constructed as insert(s) where at least one wall 201 and/or at least one base 215 may be molded around such insert(s).

In some embodiments, at least one EM emitter 900 may comprise power source 1115. In some embodiments, at least one EM emitter 900 may receive electrical power from power source 1115, either directly or indirectly via controller 1110. Power source 1115 may be a battery, and in some embodiments at least one battery may be rechargeable. In some embodiments, power source 1115 may be independent from a given face soaking device. In some embodiments, power source 1115 may be wired, such as to an electrical cord 1116 connected to a wall electrical outlet. Such an electrical cord 1116 may pass through at least one port 210 and may be sealed by an electrical cord gasket to prevent leakage of liquid 101.

In some embodiments, such EM emitted from at least one EM emitter 900 may be used for various light therapy treatments of user 9000. Numerous studies have shown significant skin benefits from light therapy. Such skin benefits may comprise: promoting skin tissue repair for faster acne healing; reducing pain associated with skin problems; reducing redness associated with acne; decreasing skin inflammation; reducing pore size and/or minimizing enlarged pores; reducing post acne scarring; promoting a healthier skin tone; promoting a smoother skin complexion, and/or the like. In addition to light therapy having a direct benefit to skin, light therapy may provide indirect benefits, such as the light therapy may be soothing and relaxing to user 9000. Such soothing and relaxing light therapy may then release stress and mitigate against headaches. Release of stress may promote lowering of blood pressure, healing of damaged skin, and a stronger immune system. In some embodiments, various face soaking devices (e.g., face soaking device 100) may be used with or without liquid 101 for light therapy purposes.

In some embodiments, where powerful EM may be emitted from at least one EM emitter 900, various safety mechanisms may be employed to protect user 9000, such as timers and/or filters that may limit EM exposure to user 9000. Powerful EM may include IR, UV, and even visible light of sufficient brightness. Powerful EM may be EM which may harm user 9000 given sufficient exposure time and/or EM with sufficient intensity to be unpleasant to user 9000.

In some embodiments, emitted UV EM from at least one EM emitter 900 may be used for skin tanning purposes, e.g., facial tanning.

In some embodiments, emitted UV EM (or more energetic EM) from at least one EM emitter 900 may be used to sterilize or reduce a microbial load within liquid 101 and/or on the interior (internal) surfaces in internal volume 220 receiving the emitted UV EM (or more energetic EM).

In some embodiments, at least one EM emitter 900 may be shielded and/or insulated from liquid 101, such that liquid 101 may not wet electronics of at least one EM emitter 900. Such shielding and/or insulation may be to mitigate against unintentional short circuiting and/or to mitigate against unintentional electrocution of user 9000. Such embodiments may utilize low voltage and/or a leak detection means. The leak detection means may, upon detecting a leak of liquid 101 into the electronics of any electrical component of the various face soaking device embodiments (e.g., face soaking device 100), terminate electrical flow to such electrical component.

Figure 9A:
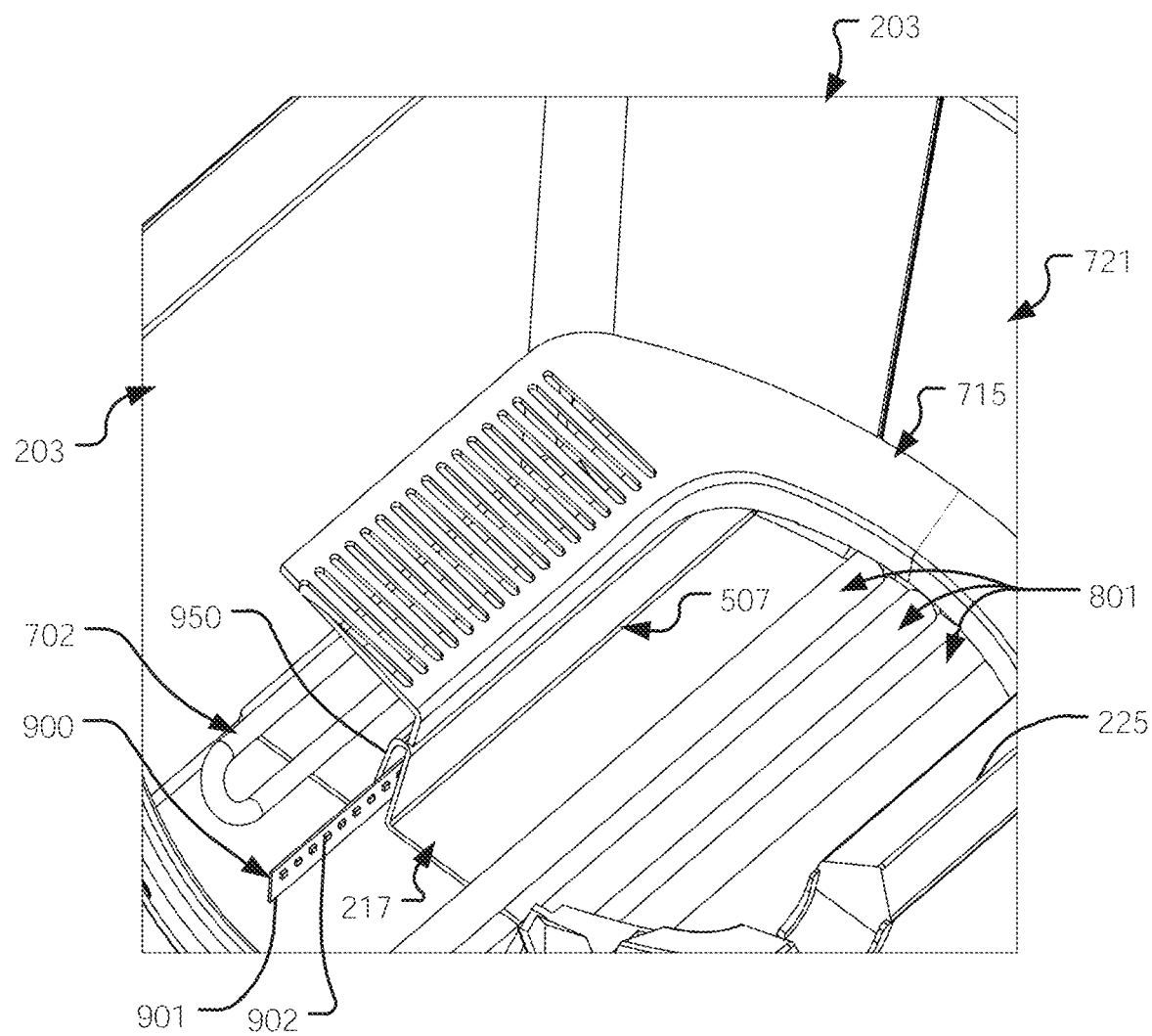
FIG. 9A may depict a partial view of at least one electromagnetic (EM) radiation emitters shown inserted in a LED-housing of a vessel lining, shown from a top perspective view showing a partial interior view of the vessel; and wherein the LED-housing is shown in a cutaway view.
Figure 9B:
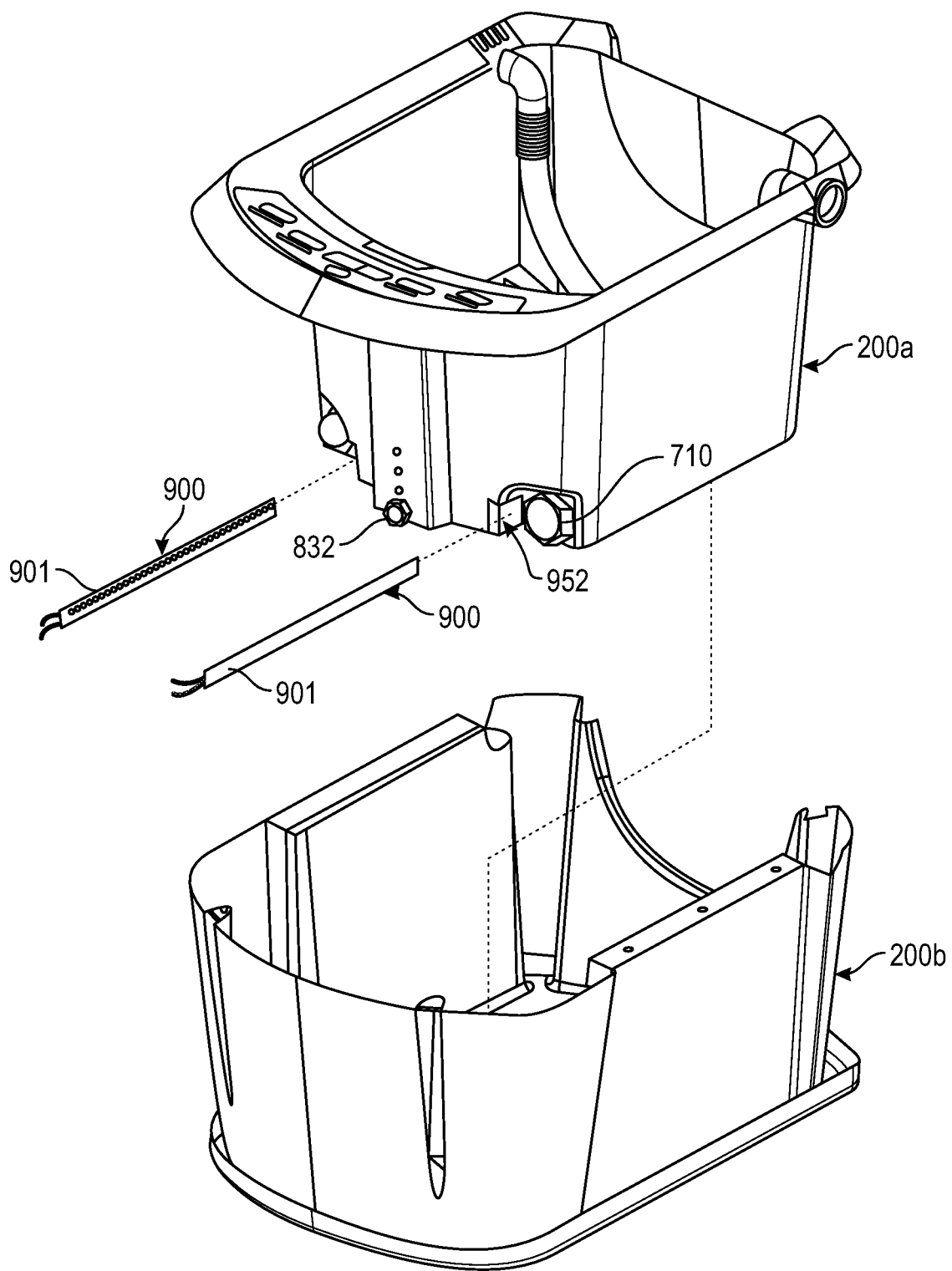
FIG. 9B may depict the at least one EM radiation emitters exploded and disposed between the vessel lining and a vessel cover, wherein the vessel lining and the vessel cover may form the vessel.
Figure 9C:
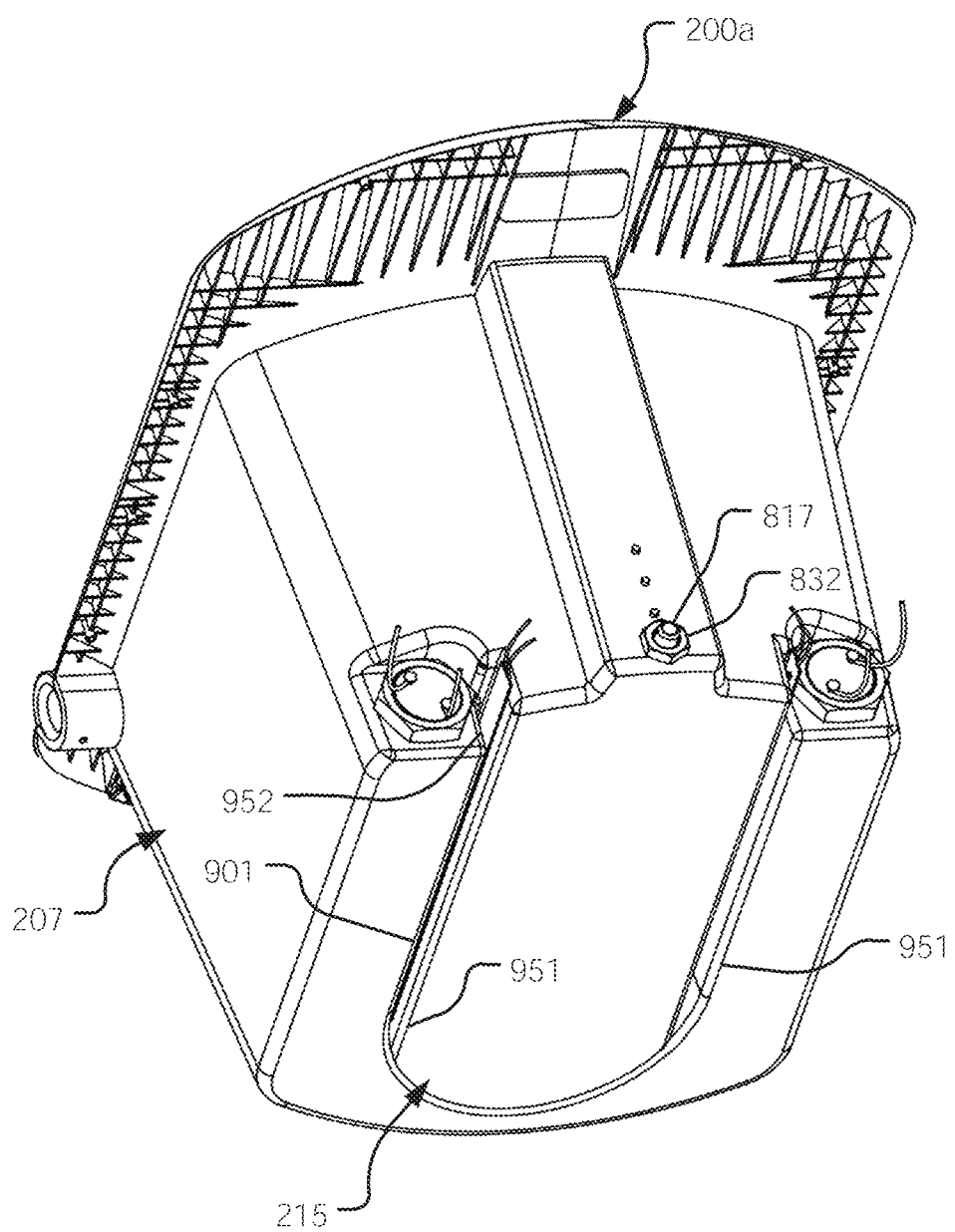
FIG. 9C may depict a bottom perspective view of the vessel lining of the vessel of a face soaking device.

Now turning to at least one EM emitter 900 embodiments depicted in the FIG. 9 series of figures. In some embodiments, at least one EM emitter 900 may comprise at least one LED array 901. The FIG. 9 series of figures may comprise FIG. 9A through FIG. 9C. FIG. 9A may depict a partial view of at least one LED array 901 shown inserted in a given LED-housing 950 of vessel lining 200a, shown from a top perspective view showing a partial interior view of the vessel (e.g., vessel 200). LED-housing 950 shown in FIG. 9A may be cutaway. FIG. 9B may depict at least one LED array 901 exploded and disposed between vessel lining 200a and vessel cover 200b, wherein vessel lining 200a and vessel cover 200b may form the vessel (e.g., vessel 200). FIG. 9C may depict a bottom perspective view of vessel lining 200a of the vessel (e.g., vessel 200) of face soaking device (e.g., face soaking device 100). FIG. 9C may depict access to LED-housing 950 for at least one LED array 901.

In some embodiments, at least one LED array 901 may be comprise two LED array 901. See e.g., FIG. 2G, FIG. 9B, and FIG. 9C. In some embodiments, at least one LED array 901 may be comprise one, two, three, four, five, six, seven, eight, nine, or ten LED arrays 901.

In some embodiments, a given at least one LED array 901 may be an elongate member. In some embodiments this elongate member may comprise at least one LED 902 along a longitude of that elongate member. See e.g., FIG. 9A. In some embodiments, at least one LED 902 may comprise a plurality of LEDs (light emitting diodes) along the longitude of that elongate member. That plurality of LEDs or at least one LED 902 may be configured to outwardly emit EM and/or light (as noted above with respect to at least one EM emitter 900). In some embodiments, the plurality of LEDs or at least one LED 902 may be disposed on only one side of that elongate member, such that EM may be emitted towards face 9010 when face 9010 may be removably within a portion of internal volume 220. See e.g., FIG. 2G and FIG. 9A. On at least one end of such an elongate member may be electrical connections and/or electrical wires protruding. Such electrical wires may connect to controller 1100 (e.g., within the mechanical compartment) and/or to power source 1115. See e.g., FIG. 9B and FIG. 9C. In some embodiments, at least one LED array 901 may be rigid to semi-rigid. In some embodiments, at least one LED array 901 may be flexible.

In some embodiments, at least one LED array 901 may be housed within LED-housing 950. See e.g., FIG. 9A. In some embodiments, there may be one LED-housing 950 per each at least one LED array 901. In some embodiments, LED-housing 950 may be a component of at least one base 215. In some embodiments, LED-housing 950 may be a component of a bottom of vessel lining 200a. In some embodiments, LED-housing 950 may protrude into internal volume 220 from bottom interior surface 217. See e.g., FIG. 9A. In some embodiments, LED-housing 950 may comprise a cavity, i.e., a LED-housing-cavity 951, that may be sized to fit substantially all off at least one LED array 901. In some embodiments, LED-housing-cavity 951 may be accessible from a bottom of at least one base 215. In some embodiments, LED-housing-cavity 951 may be accessible from a bottom of vessel lining 200a. In some embodiments, LED-housing-cavity 951 may be a slot. See e.g., FIG. 9C. In some embodiments, LED-housing 950 may also comprise an opening 952 that may be accessible from a back wall of vessel lining 200a. In some embodiments, opening 952 may provide access to LED-housing-cavity 951. See e.g., FIG. 9C. The electrical wires connected to at least one LED array 901 may protrude from opening 952. These electrical wires may protrude into mechanical compartment 251. These electrical wires may connect to controller 1100 and/or to power source 1115.

In some embodiments, at least some portions of each LED-housing 950 may be optically transparent to permit EM emission from at least one EM emitter 900 (or from at least one LED array 901) into internal volume 220. In some embodiments, at least some portions of each LED-housing 950 may comprise at least window, which may be optically transparent.

Figure 10A:
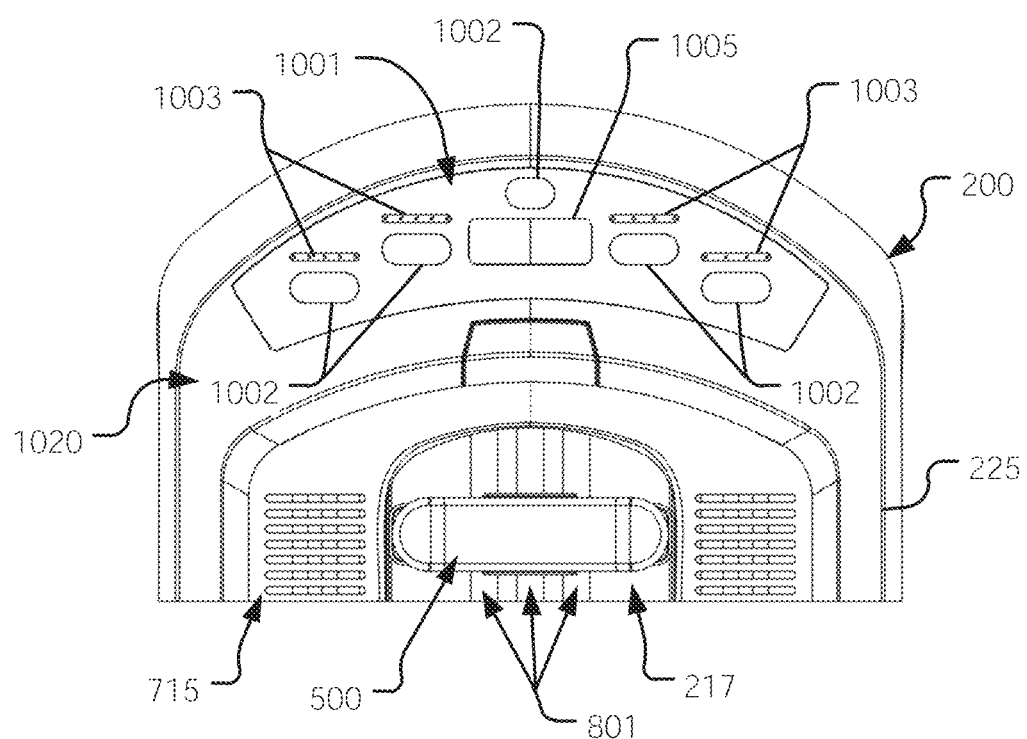
FIG. 10A may depict a top view of a membrane of a membrane switch subassembly, shown from a partial top view of the face soaking device of FIG. 2A.
Figure 10B:
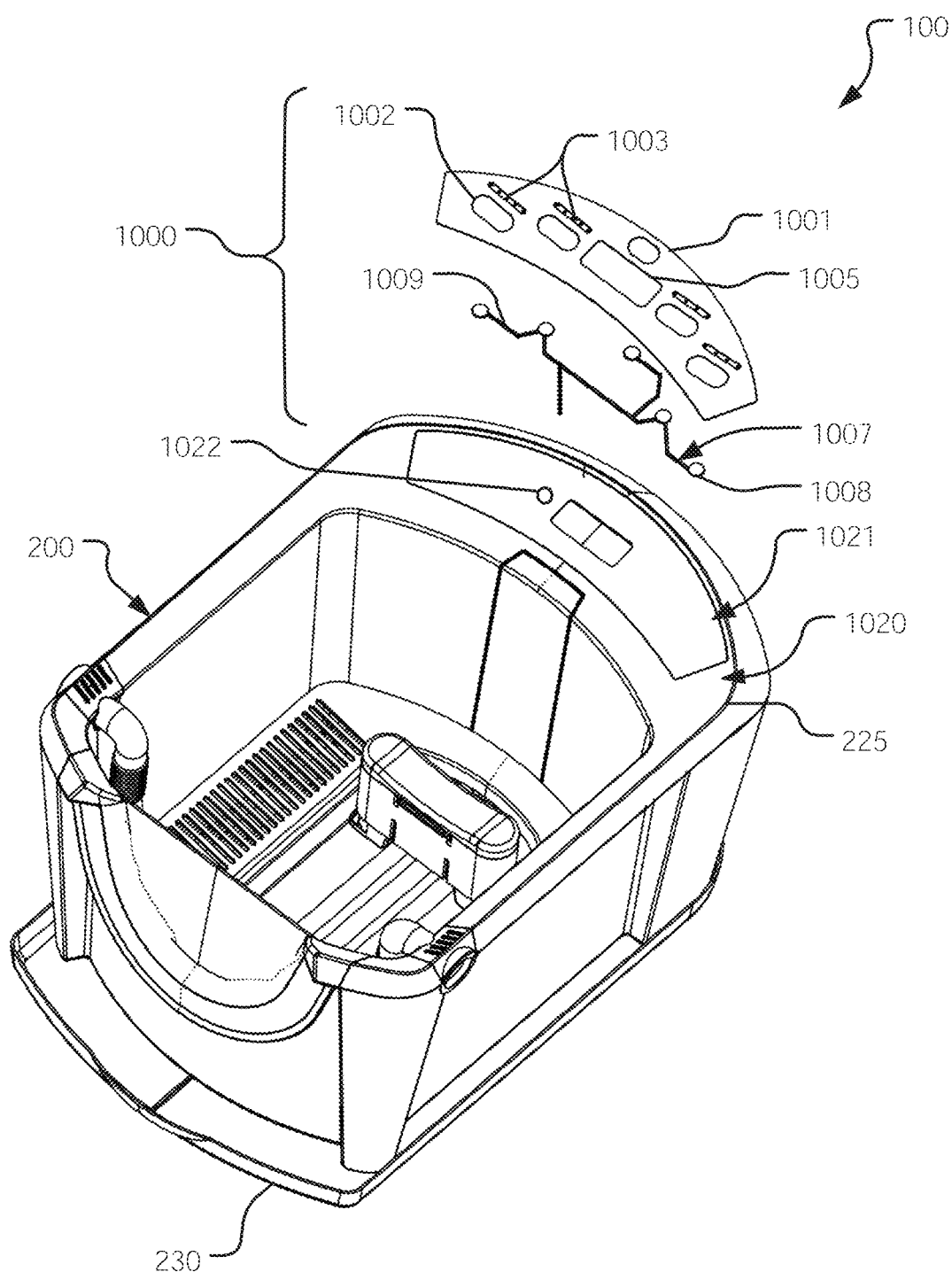
FIG. 10B may depict portions of the membrane switch subassembly exploded from the vessel, shown from a top perspective exploded view.

A FIG. 10 series of figures may comprise FIG. 10A and FIG. 10B. These FIG. 10 figures may depict views of a membrane switch subassembly 1000. In some embodiments, this membrane switch subassembly 1000 may be at least one local means for user 9000 to use, control, operate, update, program, and/or troubleshoot controller 1100 housed in mechanical compartment 251. Local may mean the membrane switch subassembly 1000 may be attached to a given face soaking device embodiment (e.g., face soaking device 100). In some embodiments, this membrane switch subassembly 1000 may be at least one local means for user 9000 to use, control, operate, update, and/or troubleshoot various electronic components of a given face soaking device embodiment (e.g., face soaking device 100). In some embodiments, these various electronic components may comprise one or more of: the heater subassembly (e.g., heater subassembly 700), the gas diffuser (e.g., the gas pump, compressor 1110, and/or a solenoid valve), the at least one EM emitter (e.g., at least one LED array 901), controller 1100, a fan 1117 for cooling mechanical compartment 251, thermostat 1107, the bubble controller, and/or the like.

FIG. 10A may depict a top view of a membrane switch cover 1001 of membrane switch subassembly 1000, shown from a partial top view of the face soaking device (e.g., face soaking device 100). FIG. 10B may depict portions of membrane switch subassembly 1000 exploded from the vessel (e.g., vessel 200), shown from a top perspective exploded view.

In some embodiments, a given face soaking device may comprise membrane switch subassembly 1000. In some embodiments, membrane switch subassembly 1000 may comprise membrane switch cover 1001 and membrane switch electronics 1007. See e.g., FIG. 10B.

In some embodiments, membrane switch cover 1001 may be a substantially planar member. However, membrane switch cover 1001 may comprise one or more regions of raised or recessed upper surface geometry for where user 9000 may be engage membrane switch cover 1001. These regions of raised or recessed upper surface geometry may be one or more areas of engagement 1002 and/or area of engagement and/or status indicator 1005. That is, in some embodiments, membrane switch cover 1001 may comprise one or more areas of engagement 1002 and/or area of engagement and/or status indicator 1005. See e.g., FIG. 10A. In some embodiments, proximate to at least one of the one or more areas of engagement 1002 may be a region of membrane switch cover 1001 configured to permit or relay a status indicator from a display means, such as a LED disposed beneath membrane switch cover 1001. In some embodiments, this region may be at least one status indicator 1003. In some embodiments, proximate may be one inch or less. In some embodiments, membrane switch cover 1001 may be waterproof. In some embodiments one or more areas of engagement 1002, at least one status indicator 1003 and/or area of engagement and/or status indicator 1005 may be substantially transparent. In some embodiments one or more areas of engagement 1002, at least one status indicator 1003 and/or area of engagement and/or status indicator 1005 may be transparent.

In some embodiments, area of engagement and/or status indicator 1005 may be flat. In some embodiments, area of engagement and/or status indicator 1005 may be substantially flat. In some embodiments area of engagement and/or status indicator 1005 may be configured to permit or relay status indications from a display means, such as a screen (monitor) disposed beneath membrane switch cover 1001. This screen (monitor) may be a LED screen and/or a LCD (liquid crystal display) screen.

In some embodiments, membrane switch electronics 1007 may comprise one or more sensors 1008 and wiring 1009 connecting one or more sensors 1008. See e.g., FIG. 10B. In some embodiments, membrane switch electronics 1007 may be disposed beneath membrane switch cover 1001. In some embodiments, membrane switch electronics 1007 may be in physical contact with at least some of a bottom surface of membrane switch cover 1001. In some embodiments, there may be one sensor 1008 for each area of engagement 1002. See e.g., FIG. 10B. In some embodiments there may be a sensor disposed beneath area of engagement and/or status indicator 1005 (not depicted). In some embodiments, each sensor 1008 may receive user 9000 pressure exerted directly on a given area of engagement 1002 that may then be conferred upon sensor 1008. In some embodiments, at least some of wiring 1009 may pass through a passage 1022 leading to controller 1100. See e.g., FIG. 10B.

Note, while FIG. 10A and FIG. 10B, depict five areas of engagement 1002 and five sensors 1008, in some embodiments there may be more or less areas of engagement 1002 and sensors 1008. For example, and without limiting the scope of the present invention, identical or equivalent functionality could also be achieved with one area of engagement and one sensor disposed beneath and in communication with that one area of engagement.

In terms of functionality, membrane switch subassembly 1000 may be used to initiate inputs to controller 1100 for one or more of: turning on or off any electronic component of a given face soaking device embodiment; turning on or off a given heater subassembly; setting a maximum liquid 101 temperature; setting a minimum liquid 101 temperature; setting a desired liquid 101 temperature; warming or cooling liquid 101; setting alarms; turning alarms off; setting timers (for any electronic component); controlling right electronics separately from left electronics (e.g., right LED array 901 versus left LED array 901); turning on or off a fan 1117 in mechanical compartment 251; turning on or off a gas pump; turning on or off compressor 1110; opening or closing solenoid valves; varying an intensity of gas bubble 125 production from the gas diffuser; turning on or off the at least one EM emitter 900; dimming or intensifying the at least one EM emitter 900; selecting a light color pattern from LED arrays 901, and/or the like. Some outputs, such as status indications may be displayed at at least one status indicator 1003 and/or at area of engagement and/or status indicator 1005.

In some embodiments, membrane switch subassembly 1000 may be located on a roof 1020 of vessel 200. See e.g., FIG. 10A and FIG. 10B. In some embodiments, vessel 200 may comprise roof 1020. In some embodiments, roof 1020 may be located proximate to rim 225 along a back portion of vessel 200 (e.g., above second side wall 207). See e.g., FIG. 10A and FIG. 10B. In some embodiments, proximate may be three inches or less.

In some embodiments, roof 1020 may be an upper exterior surface of rim 225 or portion thereof or proximate to rim 225. In some embodiments, roof 1020 may be a substantially flat upper surface. In some embodiments, roof 1020 may be a substantially horizontal flat structure in reference to bottom interior surface 217 of internal volume 220 of vessel 200. In some embodiments, roof 1020 may comprise a slope. In some embodiments, roof 1020 may be a roof to mechanical compartment 251. In some embodiments, roof 1020 may be disposed above at least some portion of mechanical compartment 251.

In some embodiments, roof 1020 may comprise a flat recess configured to receive membrane switch cover 1001 and substantially all of membrane switch electronics 1007 (minus the portion of wiring 1009 that may pass through passage 1022). See e.g., FIG. 10B. This flat recess may be membrane-switch-receiving-recess 1021. In some embodiments, substantially all of membrane switch electronics 1007 (minus the portion of wiring 1009 that may pass through passage 1022) may be disposed between membrane switch cover 1001 and membrane-switch-receiving-recess 1021. See e.g., FIG. 10B. In some embodiments, membrane-switch-receiving-recess 1021 may comprise passage 1022. See e.g., FIG. 10B. In some embodiments passage 1022 may be a hole from membrane-switch-receiving-recess 1021 into mechanical compartment 251. Passage 1022 may permit some of wiring 1009 to pass into mechanical compartment 251. Such some of wiring 1009 may connect to controller 1100 in some embodiments. In some embodiments, passage 1022 may comprise a sealer, such as silicone and/or a gasket or an O-ring to minimize fluid leakage into mechanical compartment 251.

FIG. 11A may depict an exemplary embodiment of controller 1100 of a face soaking device (e.g., for face soaking device 100), shown as a block diagram. In some embodiments, controller 1100 may control operational functionality of one or more electrical components of a given face soaking device embodiment. In some embodiments, controller 1100 may be in communication with the one or more electrical components of a given face soaking device embodiment. In some embodiments, the one or more electrical components of a given face soaking device embodiment may comprise one or more of: the heater subassembly (e.g., heater subassembly 700, e.g., heating element 701), the gas diffuser (e.g., the air pump, compressor 1110, and/or the solenoid valve), the at least one EM emitter (e.g., at least one LED array 901), membrane switch subassembly 1000, a level indicator 1105, temperature sensor 1106, thermostat 1107, output means 1103, network adapter 1104, power source 1115, fan 1117 for cooling mechanical compartment 251, and/or the like.

In some embodiments, controller 1100 may comprise processor 1101 and memory 1102. See e.g., FIG. 11A. In some embodiments, memory 1102 and processor 1101 may be in communication with each other. In some embodiments, such communication may be via electrical wiring, optical wiring, circuit wiring, via one or more integrated (printed) circuit boards (PCBs), and/or chips. In some embodiments, memory 1102 may non-transitorily store software (e.g., code), wherein processor 1101 may execute the software to control the one or more electronic components.

In some embodiments, membrane switch subassembly 1000 may be in electrical communication with processor 1101 (either directly [e.g., via some wiring 1009] or via a bus). See e.g., FIG. 11A. In some embodiments, such electrical communication may be via electrical wiring, e.g., via some wiring 9000. In some embodiments, membrane switch subassembly 1000 may receive user 9000 inputs. In some embodiments, membrane switch subassembly 1000 may direct or convey those received user 9000 inputs to processor 1101 (for interpretation according to the software and/or code non-transitorily stored within memory 1102).

In some embodiments, user 9000 inputs (e.g., from membrane switch subassembly 1000) that processor 1101 may be capable of interpreting may be selected from one or more of the following: turning on or off any electronic component of a given face soaking device embodiment; turning on or off a given heater subassembly; setting a maximum liquid 101 temperature; setting a minimum liquid 101 temperature; setting a desired liquid 101 temperature; warming or cooling liquid 101; setting alarms; turning alarms off; setting timers (for any electronic component); controlling right electronics separately from left electronics (e.g., right LED array 901 versus left LED array 901); turning on or off a fan 1117 in mechanical compartment 251; turning on or off a gas pump; turning on or off compressor 1110; opening or closing solenoid valves; varying an intensity of gas bubble 125 production from the gas diffuser; turning on or off the at least one EM emitter 900; dimming or intensifying the at least one EM emitter 900; selecting a light color pattern from LED arrays 901, and/or the like.

In some embodiments, input means for controller 1100 may comprise one or more of the following: membrane switch subassembly 1000, a microphone, at least one button, at least one switch, at least one lever, at least one dial, at least one slide, a touch screen, a keyboard, a joystick, a mouse, a payment receiving device, and/or the like. In some embodiments, input means for controller 1100 may also come from one or more mobile computing devices 1150 (see e.g., FIG. 11B).

In some embodiments, one or more of methods and/or one or more of steps described and disclosed herein may be implemented as computer program(s), software, firmware, including codes executable by a processor (e.g., processor 1101 of controller 1100). Such computer program(s), software, firmware, and/or code may be non-transitorily stored in computer-readable media, such as memory 1102.

Various aspects of systems and methods for practicing features of the present invention may be implemented on one or more computer systems. For example, the various controller 1100 components, may comprise, but may not be limited to: processor 1101, memory 1102, output means 1103, network adapter 1104, thermostat 1107, temperature sensor 1106, and level indicator 1105; anyone of which may be coupled, directly or indirectly, via interconnection mechanisms, which may comprise electrical wiring, optical wiring, one or more buses, switches, networks, cloud, and/or any other suitable interconnection. Membrane switch subassembly 1000 and/or one or more mobile computing devices 1150 may receive input(s) from user 9000. At least one status indicator 1003 and/or area of engagement and/or status indicator 1005 may display outputs and/or status indications that relate to a given face soaking device (e.g., face soaking device 100). In some embodiments, controller 1100 (via network adapter 1104) may transmit information (e.g., outputs and/or status indications) to user 9000 via one or more mobile computing devices 1150.

Processors (e.g., processor 1101 of controller 1100) may also execute one or more computer programs, such as software, firmware, and/or code to implement various methods and/or steps. These computer programs may be written in any type of computer program language, including a procedural programming language, object-oriented programming language, macro language, or combinations thereof.

These computer programs may be non-transitorily stored in computer-readable media, such as memory 1102. Such non-transitorily storage in computer-readable media may be in volatile or non-volatile medium, and may be fixed or removable. Such computer-readable media may include a tangible computer readable and computer writable non-volatile recording medium, on which signals are stored non-transitorily that define a computer program or information to be used by the program. The recording medium for the computer-readable media may, for example, be disk memory, flash memory, and/or any other article(s) of manufacture usable to record and store information. Typically, in operation, the processor(s) (e.g., processor 1101) may cause data to be read from the nonvolatile recording medium into a volatile memory (e.g., a random access memory, or RAM) that allows for faster access to the data and/or information by the processers than from the nonvolatile recording medium. The processors may generally manipulate the data and/or information within the RAM memory and then copy the manipulated data and/or information to the nonvolatile recording medium after processing is completed. A variety of mechanisms are known for managing data movement between the medium and the integrated circuit memory element, and the invention is not limited to any mechanism, whether now known or later developed. Various embodiments of the invention are also not limited to a particular processor nor to particular computer readable media (whether volatile or non-volatile).

In some embodiments, controller 1100 may comprise output means 1103. In some embodiments, output means 1103 may be in electrical communication with processor 1101. See e.g., FIG. 11A. In some embodiments, output means 1103 may be selected from one or more: a speaker, a buzzer, a noise maker, display screens, LEDs, lights, and/or the like. In some embodiments, output means 1103 may comprise the screen (monitor) associated with membrane switch subassembly 1000, wherein this screen (monitor) may be the LED screen and/or the LCD (liquid crystal display) screen that displays beneath area of engagement and/or status indicator 1005. In some embodiments, output means 1103 may comprise the LEDs that display(s) beneath at least one status indicator 1003.

In some embodiments, controller 1100 may comprise network adapter 1104. In some embodiments, network adapter 1104 may in electrical communication with processor 1101. In some embodiments, such electrical communication may be via electrical wiring, bus, circuitry, via one or more integrated (printed) circuit boards (PCBs), and/or chips. In some embodiments, network adapter 1104 may comprise one or more of a modem and/or a router. In some embodiments, network adapter 1104, the modem, and/or the router may each comprise at least one radio or at least one antenna. In some embodiments, the at least one radio and/or the at least one antenna may be configured for one or more of the following: to receive radio transmissions and/or to broadcast radio transmissions. In some embodiments, one or more of network adapter 1104, the modem, or the router may provide wireless communication via a wireless communication protocol utilizing the at least one radio or the at least one antenna.

In some embodiments, the one or more of the network adapter 1104, the modem, and/or the router via the at least one radio or the at least one antenna may operate as one or more gateways to facilitate communications with one or more mobile computing devices 1150. See e.g., FIG. 11B. In some embodiments, one or more mobile computing devices 1150 may be selected from smart phones, tablet computing devices, laptop computers, desktop computers, servers, smart watches, smart wearables, remote controls, and the like. For example, and without limiting the scope of the present invention, communication between the one or more mobile computing devices 1150 and controller 1100 (of e.g., face soaking device 100) may be direct via a compatible wireless communication protocol. For example, and without limiting the scope of the present invention, communication between the one or more mobile computing devices 1150 and controller 1100 (of e.g., face soaking device 100) may be indirect over network 1160 (see e.g., FIG. 11B). In some embodiments, network 1160 may be one or more of a LAN (local area network), a WAN (wide area network), the internet, combinations thereof, and/or the like. Thus, network adapter 1104 may permit remote use, control, operation, updating (e.g., updating software, firmware, code, and/or the like), and/or troubleshooting of a given face soaking device from one or more mobile computing devices 1150.

In some embodiments, controller 1100 may comprise level indicator 1105. In some embodiments, vessel 200 may comprise level indicator 1105. In some embodiments, level indicator 1105 may be in electrical communication with processor 1101. See e.g., FIG. 11A. In some embodiments, level indicator 1105 may be in electrical communication with controller 1100. See e.g., FIG. 11A. In some embodiments, level indicator 1105 may indicate a height level of liquid 101 in internal volume 220. In some embodiments, level indicator 1105 may indicate if liquid 101 is above or below some threshold height level, e.g., the maximum liquid level. In some embodiments, level indicator 1105 may be an optical sensor. In some embodiments, level indicator 1105 may be a float sensor. In some embodiments, level indicator 1105 may be attached to some portion of interior wall surface 203. In some embodiments, level indicator 1105 may be located behind shield-back-panel 721 and attached to some portion of interior wall surface 203.

In some embodiments, controller 1100 may be in electrical communication with one or more of heating element 701, temperature sensor 1106, and thermostat 1107. See e.g., FIG. 11A. In some embodiments, controller 1100 may be in electrical communication with one or more of heating element 701, temperature sensor 1106, and thermostat 1107. See e.g., FIG. 11A. In some embodiments, controller 1100 may comprise thermostat 1107. In some embodiments, there may be no independent thermostat 1107 and all such thermostat functions may be performed entirely by processor 1101 using appropriate software non-transitorily stored in memory 1102. In some embodiments, controller 1100 may control a temperature (or temperatures) of liquid 101 by controlling at least one heating element 701 and/or by controlling at least one chiller. In some embodiments, controller 1100 may comprise temperature sensor 1106. In some embodiments, temperature sensor 1106 may measure heat of liquid 101. In some embodiments, temperature sensor 1106 may measure a temperature of liquid 101. In some embodiments, temperature sensor 1106 may be a thermometer, an optical thermometer, and/or a thermocouple. In some embodiments, there may be a plurality of temperature sensors 1106. In some embodiments, temperature sensor 1106 may be attached to interior wall surface 203, bottom interior surface 217, at least one heating element 701, shield 715, a surface or structure in internal volume 220, and/or the like.

In some embodiments, controller 1100 may be in electrical communication with one or more of: compressor 1110, the air pump, and/or the solenoid valve. See e.g., FIG. 11A. In some embodiments, controller 1100 may control whether the gas diffuser (e.g., gas diffuser 800) is on or off. In some embodiments, controller 1100 may control the intensity (e.g., density) of gas bubbles 125 being produced (released) by the gas diffuser (e.g., gas diffuser 800). In some embodiments, both controller 1100 and compressor 1110 may be located within the mechanical compartment. In some embodiments, compressor 1110 may be located outside of the mechanical compartment.

In some embodiments, controller 1100 may be in electrical communication with at least one EM emitter 900. See e.g., FIG. 11A. In some embodiments, controller 1100 may control whether at least one EM emitter 900 may be on or off. In some embodiments, controller 1100 may control the intensity (e.g., density) of emitted EM produced by at least one EM emitter 900. For example, and without limiting the scope of the present invention, controller 1100 may comprise dimmer functionality for at least one EM emitter 900 and at least one EM emitter 900 may include functionality that permits dimming. In some embodiments, controller 1100 may control light color patterns from LED arrays 901.

In some embodiments, controller 1100 may receive electrical power from power source 1115. See e.g., FIG. 11A. Controller 1100 may be in electrical communication with power source 1115. Power source 1115 may be in electrical communication with all electrical components of a given face soaking device embodiment, either directly or indirectly. Power source 1115 may provide electrical power to the given face soaking device. Power source 1115 may provide electrical power to one or more of the electrical components of the given face soaking device.

Power source 1115 may be independent of a given face soaking device, i.e., not part of the invention in some embodiments. For example, and without limiting the scope of the present invention, power source 115 may be a standard electrical wall outlet. Power source 1115 may be located externally of mechanical compartment 251. Electrical power cord 1116 may run be removably connected to such standard electrical wall outlet; and may run from the standard electrical wall outlet to a given face soaking device (e.g., face soaking device 100) where electrical power cord 1116 may enter mechanical compartment 251 (and then interconnect with controller 1100 and/or electronic components) at an exterior port, such at least one port 210. See e.g., FIG. 2E, showing a back view of face soaking device 100 and electrical power cord 1116 emerging from the exterior back wall (e.g., second side wall 207).

In some embodiments, power source 1115 may a component of a given face soaking device, e.g., when power source 1115 may be a battery, a rechargeable battery, and/or a backup power supply. In such embodiments, power source 1115 may be located in mechanical compartment 251.

In some embodiments, controller 1100 may be in electrical communication with fan 1117. In some embodiments, controller 1100 may comprise fan 1117. See e.g., FIG. 11A. In some embodiments, controller 1100 may control fan 1117. In some embodiments, face soaking device 100 may comprise fan 1117. In some embodiments, vessel 200 may comprise fan 1117. In some embodiments, mechanical compartment 251 may comprise fan 1117. In some embodiments, fan 1117 may be located within mechanical compartment 251. In some embodiments, fan 1117 may cool electrical components in mechanical compartment 251.

Figure 11B:
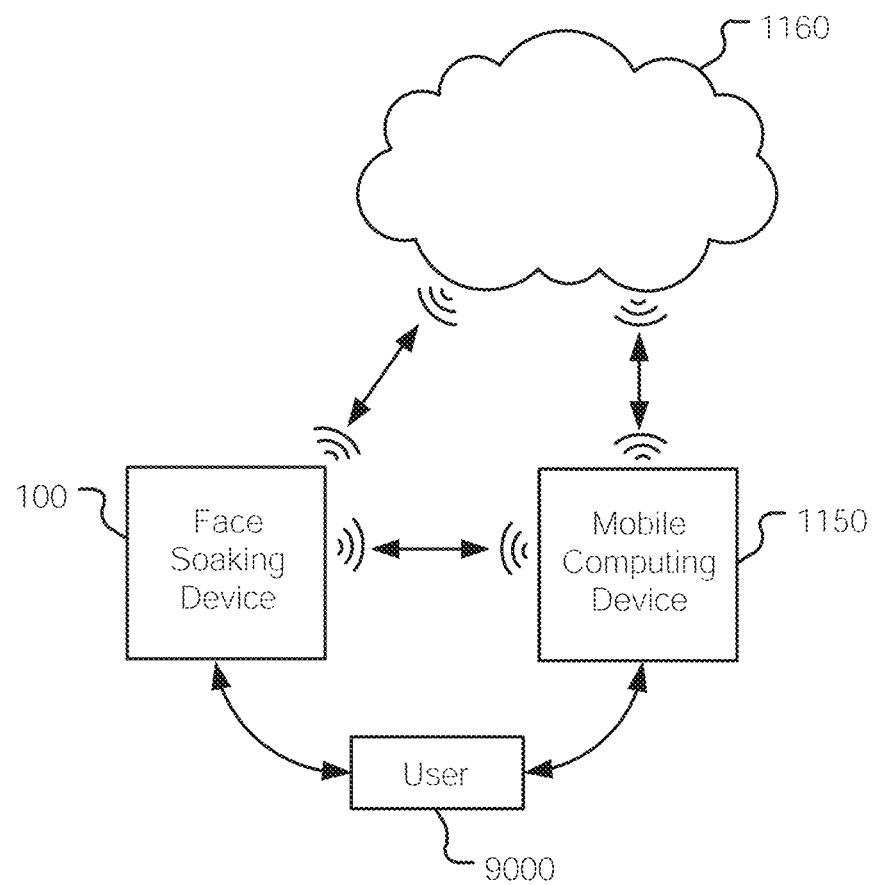
FIG. 11B may depict an operational environment of a face soaking device, showing how a user may operate and/or program the face soaking device.

FIG. 11B may depict an operational environment of a given face soaking device (e.g., face soaking device 100). FIG. 11B may show how user 9000 may use, control, operate, update, program, and/or troubleshoot the given face soaking device. User 9000 may use, control, operate, update, program, and/or troubleshoot a given face soaking device embodiment directly, e.g., via membrane switch subassembly 1000. User 9000 may use, control, operate, update, program, and/or troubleshoot a given face soaking device embodiment via one or more mobile computing device 1150 that may communicate directly with network adapter 1104 or indirectly with network adapter 1104 via network 1160.

Figure 12A:
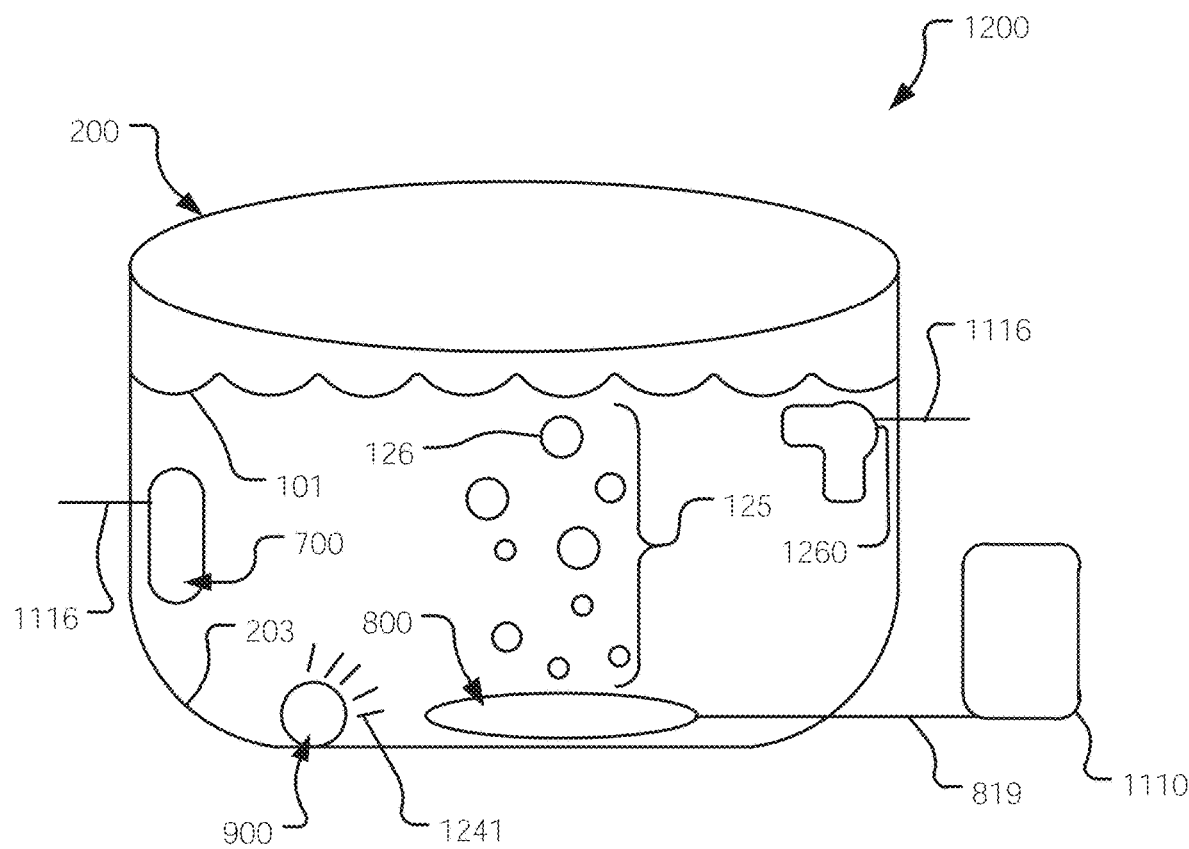
FIG. 12A may depict an exemplary embodiment of a device, such as a vessel, for treating an article (such as skin); wherein a method for treating the article may also utilize this device, shown from a perspective view.

FIG. 12A may depict an exemplary embodiment of a device 1200 (e.g., face soaking device 100), which may comprise vessel 200, for treating an article; wherein a method for treating the article may also utilize device 1200, shown from a perspective view. In some exemplary embodiments, device 1200 may comprise vessel 200 and at least one aerator. In some exemplary embodiments, device 1200 may comprise vessel 200 and at least one electromagnetic (EM) emitter 900 (at least one EM emitter 900). In some exemplary embodiments, device 1200 may comprise vessel 200, the at least one aerator, and at least one EM emitter 900.

In some embodiments, vessel 200 may comprise interior wall surface 203 and an interior volume 220. In some embodiments, interior wall surface 203 may substantially bound interior volume 220, i.e. interior wall surface 203 may form interior volume 220. Note, "substantially," as used in the preceding sentence may denote that vessel 200 may have at least one opening (e.g., top opening 226) providing access to interior volume 220, i.e. interior wall surface 203 does not entirely bound interior volume 220, as where the opening may be located. In some embodiments, interior volume 220 may be sized to removably house at least a portion of the article. In some embodiments, interior volume 220 may be sized to removably house an entirety of the article. In some embodiments, interior volume 220 may be removably fillable with liquid 101 to or below a liquid fill level. The liquid fill level may be predetermined and may be indicated at a location on interior wall surface 203 in some embodiments.

In some embodiments, vessel 200 may comprise at least one window 1203. In some embodiments, at least one window 1203 may be substantially transparent and/or translucent. In some embodiments, at least a portion of vessel 200 may be substantially transparent, translucent, or opaque; or some portions may be substantially transparent and/or translucent, while other portions may be opaque. Note, transparency and/or translucency may be respect to particular wavelengths of EM radiation, such as, but not limited to visible light. And use of "substantially" in this paragraph may note that the transparence and/or translucency need not be perfect. (Note, at least one window 1203 may be depicted in FIG. 12B.)

In some embodiments, at least a portion of interior wall surface 203 may be electromagnetic (EM) radiation reflective for some predetermined wavelength of EM radiation. For example, and without limiting the scope of the present invention, the at least the portion of interior wall surface 203 may be optically mirrored to reflect visible light, near ultraviolet, near infrared, and the like. For example, and without limiting the scope of the present invention, the at least the portion of interior wall surface 203 may be substantially constructed of a metal to reflect microwaves, and the like.

In some embodiments, the article may be selected from the group comprising: an animal or at least one part thereof the animal; a vertebrate animal or at least one part thereof the vertebrate animal; a terrestrial vertebrate animal or at least one part thereof the terrestrial vertebrate animal; an invertebrate animal or at least one part thereof the invertebrate animal; a mammalian animal or at least one part thereof of the mammalian animal; a human or at least one part thereof the human. For example, at least one part of the human may be a face, a finger, a hand, an arm, an elbow, a shoulder, a toe, a foot, an ankle, a lower leg, an upper leg, and the like. In exemplary applications, the article may be face 9010.

In some embodiments, liquid 101 may be selected from one or more of the group comprising: water, oil, gel, a slurry, peroxide, alcohol, bleach, inorganic solvents, organic solvents, polar solvents, weak acids, weak bases, combinations thereof, and the like.

In some embodiments, liquid 101 may comprise at least one additive. In some embodiments, the at least one additive may be selected from one or more of the group comprising: inorganic salts, mineral salts, organic salts, a pharmaceutically active compound, at least one herb, at least one moistener, at least one surfactant, at least one dye, at least one oxidizer, at least one fragrance, combinations thereof, and the like. In some exemplary embodiments, liquid 101 may be various water based saline solutions.

In some embodiments, device 100 may further comprise liquid 101.

In some embodiments, when the at least the portion of the article (or any other portion of the article) may be removably submerged within liquid 101, wherein liquid 101 may be removably residing within internal volume 220; the article may be exposed to liquid 101 and liquid 101 may treat the article. In some embodiments, wherein device 1200 comprises the at least one aerator, when the at least the portion of the article (or any other portion of the article) may be removably submerged within liquid 101 and exposed to liquid 101 and a plurality of bubbles 125 from the at least one aerator, both liquid 101 and bubbles 125 may treat the portion of the article removably submerged. In some embodiments, wherein device 1200 comprises at least one EM emitter 900, when the at least the portion of the article (or any other portion of the article) may be removably submerged within liquid 101 and exposed to liquid 101 and EM radiation 1241 from at least one EM emitter 900; then both liquid 101 and EM radiation 1241 may treat the portion of the article removably submerged. In some embodiments, wherein device 1200 comprises the at least one aerator and at least one EM emitter 900, when the at least the portion of the article (or any other portion of the article) may be removably submerged within liquid 101 and exposed to liquid 101, plurality of bubbles 125, and at least portions of EM radiation 1241; then liquid 101, bubbles 125, and the at least portions of EM radiation 1241 may treat the portion of the article removably submerged.

Note, "treat," "treatment," and/or "treating" as used herein may mean: a benefit may be provided to the article; a detriment may be provided to the article; that the article might be physically changed by the treatment; that the article might be chemically changed by the treatment; and the like.

For example, and without limiting the scope of the present invention, examples of the benefit may be using the device and/or the method for therapeutic treatment of humans, animals, and/or portions thereof. For example, and without limiting the scope of the present invention, examples of the benefit may be using the device and/or the method to treat the article with oxygen therapy, light therapy, combined oxygen therapy with light therapy, enhanced light therapy by use of bubbles 125, enhanced light therapy by use of oxygen bubbles which also provide oxygen therapy, and combinations thereof. For example, and without limiting the scope of the present invention, examples of the benefit may be using device 1200 and/or method(s) to treat the skin of the article using soaking in liquid 101 (either by itself in combination with bubbles 125, oxygen, light therapy, and the like) to address acne, wrinkles, bruising, lacerations, cuts, burns, and the like.

For example, and without limiting the scope of the present invention, examples of the detriment or of the physical change or of the chemical change may be using the device and/or the method(s) to treat the article with ionizing radiation. For example, ionizing radiation may be used for sterilization purposes of the article. For example, ionizing radiation may be used to induce chemical changes in the article.

For example, and without limiting the scope of the present invention, examples of the detriment or of the physical change or of the chemical change may be using the device and/or the method to sterilize, induce mutations, dye, oxidize, and the like to the article and/or portions of the article, such as a treated surface of the article.

In some embodiments, at least one aerator may comprise at least one gas source (e.g., compressor 1110) and at least one gas diffuser 800. In some embodiments, at least one compressor 1110 may be connected to at least one gas diffuser 800 (e.g., via airline tubing 819). See e.g., FIG. 12A. In some embodiments, at least one compressor 1110 may provide a gas to at least one gas diffuser 800. In some embodiments, at least one gas diffuser 800 may be disposed within interior volume 220 or may be located on interior wall surface 203. In some embodiments, the gas exiting at least one gas diffuser 800 into liquid 101 may form the plurality of bubbles 125. In some embodiments, at least one compressor 1110 may be replaced with one or more of a gas cylinder comprising the gas. In some embodiments, at least one gas diffuser 800 may be connected to at least one compressor 1110 via at least one length of gas line tubing or gas line piping, such as airline tubing 819, which in some embodiments, may comprise at least one; check valve, flow sensor, pressure sensor, shutoff valve, solenoid valve, and the like. In some embodiments, at least one gas diffuser 800 may comprises a plurality of gas exit ports. For example, and without limiting the scope of the present invention, the plurality of gas exit ports may be a porous structure. In some embodiments, the gas may be selected from one or more of group comprising: air, oxygen, air enriched with oxygen, nitrogen, carbon dioxide, nitrous oxide, combinations thereof, and the like. In some embodiments, wherein the gas may comprise oxygen (including air), exposing the article to such gas may be "oxygen therapy."

In embodiments where bubbles 125 may derive from at least gas diffuser 800, such bubbles 125 may be gas bubbles, wherein contents of the gas bubbles may be substantially the gas. In some embodiments, bubbles 125 may derive from agitating liquid 101 wherein liquid 101 may comprise one or more surfactants. In such embodiments, bubbles 125 may comprise whatever gas was at a gas-liquid surface interface, such as atmospheric air. In some embodiments, such agitation may be imparted by at least one jet 1260 with flow from at least one jet 1260 directed at the gas-liquid surface interface. In some embodiments, such agitation may be imparted by stirring action of at least some of liquid 101. Such stirring may be done manually by user 900. Such stirring may be done automatically by a spinnable impeller mounted in interval volume 220 (not shown).

In some embodiments, device 1200 may comprise at least one heater 700 for heating liquid 101. See e.g., FIG. 12A. In some embodiments, at least one heater 700 may be located: within the interior volume 220, on interior wall surface 203, or in a chamber that may be in communication with liquid 101. In some embodiments, heating of liquid 101 with at least one heater 700 may create convective current movements of liquid 101 within internal volume 220. In some embodiments, at least one heater 700 may comprise a means to prevent overheating of liquid 101, e.g. a thermostat and/or temperature sensing means (e.g., temperature sensor 1106). In some embodiments, such a means to prevent overheating of liquid 101 may be such as to prevent or minimize burns to the article being treated.

In some embodiments, at least one heater 700 may also be a chiller, allowing liquid 101 to be cooled. Or alternatively, in some embodiments, device 1200 may comprise at least one chiller for chilling liquid 101. Such a chiller may be located in the same locations as for at least one heater 700. In some embodiments, device 1200 may comprise a controller (e.g., controller 1100) for alternating heating and cooling cycles. Such a controller may be in communication with at least one heater 700 and/or at least one chiller. Alternating heating and cooling cycles may provide therapeutic benefits to the article being treated, such as promoting healing to injured tissue.

In some embodiments, water ice may be added to liquid 101 as well to accomplish cooling treatments for the article.

In some embodiments, device 1200 may comprise at least one jet 1260 for circulating liquid 101 and/or for directing at least one stream of liquid 101 at the submerged article. See e.g., FIG. 12A. In some embodiments, at least one jet 1260 may be located: within interior volume 220, on interior wall surface 203, or in a chamber that may be in communication with liquid 101 (this chamber may be the same or different than the chamber housing at least one heater 700 in some embodiments). In some embodiments, at least one jet 1260 may comprise a pump and/or an impeller.

In some embodiments, device 1200 may comprise at least one EM emitter 900 for emitting at least some emitted EM 1241 into liquid 101. See e.g., FIG. 12A. In some embodiments, at least one EM emitter 900 may be located: within interior volume 220 and/or on interior wall surface 203. See e.g., FIG. 12A.

Figure 12B:
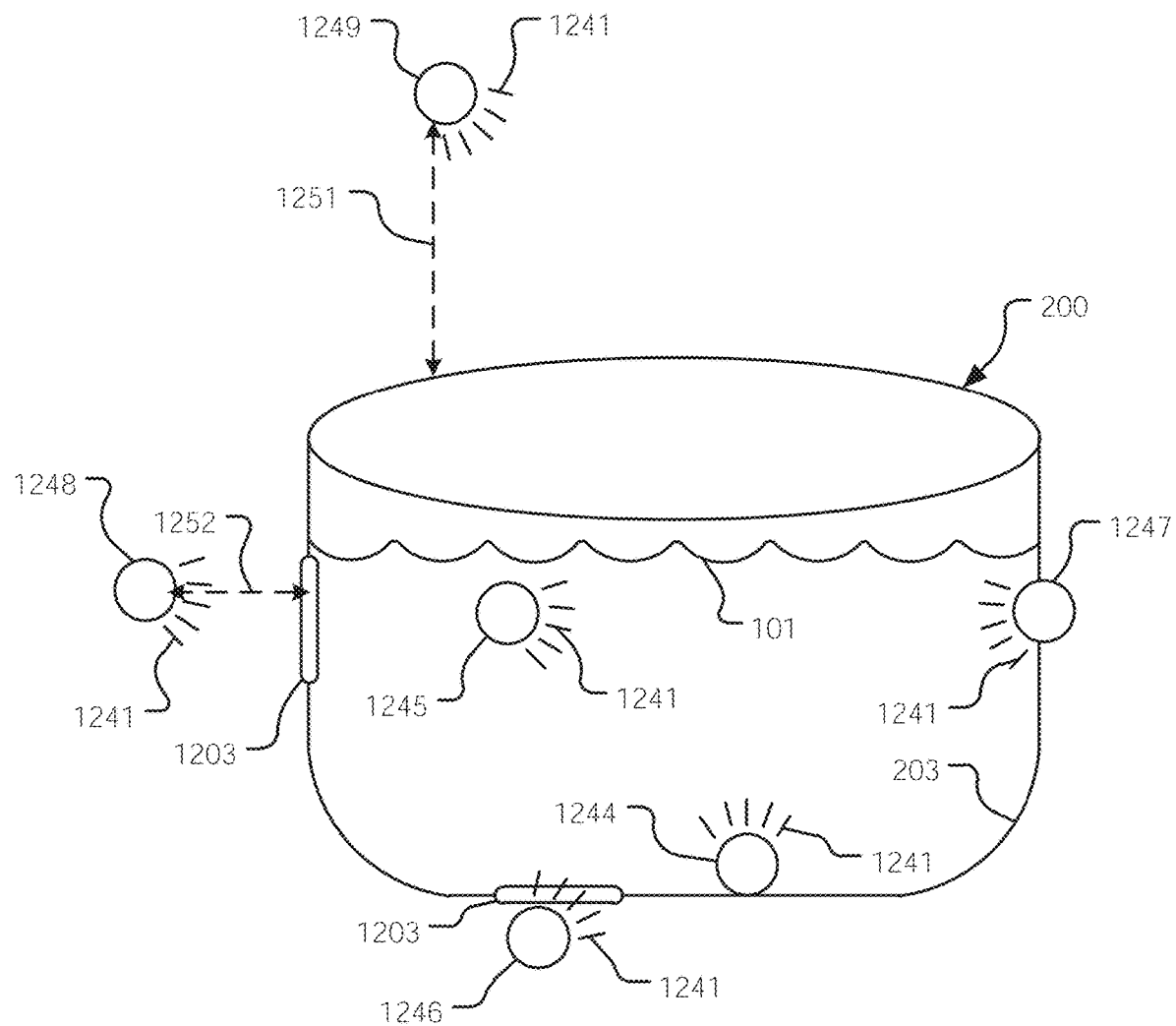
FIG. 12B may depict the device of FIG. 12A, but wherein the at least one EM emitter may be depicted at various locations with respect to the device, shown from a perspective view.

FIG. 12B may depict device 1200 of FIG. 12A, but wherein at least one EM emitter 900 may be depicted at various different locations with respect to device 1200 (e.g. vessel 200), shown from the same perspective view. In some embodiments, at least one EM emitter 900 may be located within interior volume 220, on interior wall surface 203, exteriorly from vessel 200 within a proximate distance 1251 or 1252, or on an exterior surface of vessel 200 that may be disposed opposite of interior wall surface 203.

In some embodiments, at least one EM emitter 900 may comprise one or more of: at least one EM emitter 1244, at least one EM emitter 1245, at least one EM emitter 1246, at least one EM emitter 1247, at least one EM emitter 1248, at least one EM emitter 1249, and the like. See e.g., FIG. 12B.

In some embodiments, at least one EM emitter 1244 may be on interior wall surface 203. In some embodiments, at least one EM emitter 1245 may be located in interior volume 220. In some embodiments, at least one EM emitter 1246 may be located on the exterior surface of vessel 200 (e.g., exterior wall surface 202) that may be disposed opposite of interior wall surface 203. In some embodiments, at least one EM emitter 1247 may be located partially embedded within a wall of vessel 200, wherein a portion of the wall may form interior wall surface 203. In some embodiments, at least one EM emitter 1248 may be located exteriorly from vessel 200 within proximate distance 1252 from at least one window 203. In some embodiments, at least one EM emitter 1249 may be located exteriorly from vessel 200 within proximate distance 1251 from vessel 200.

In some embodiments, proximate distance 1252 may be thirty feet or less. In some embodiments, proximate distance 1251 may be thirty feet or less. In some exemplary embodiments, proximate distance 1252 may be five feet or less. In some exemplary embodiments, proximate distance 1251 may be five feet or less. Whereas, in some embodiments, proximate distance 1251 may be substantially greater, such as when at least one EM emitter 1249 may be the Sun, by the Sun providing natural daylight to the article or portion of the article removably submerged within liquid 101 within interior volume 220 of vessel 200.

Note, in some embodiments, at least one EM emitter 900 may be waterproof. In some embodiments, at least one EM emitter 900 may be direct physical contact with liquid 101. Such embodiments, may comprise one or more of: at least one EM emitter 1244, at least one EM emitter 1245, and/or at least one EM emitter 1247.

Each at least one EM emitter 900 may emit at least some emitted EM 1241 into liquid 101. Each at least one EM emitter may emit at least some emitted EM 1241 into liquid 101. See e.g., FIG. 12A and FIG. 12B.

Figure 12C:
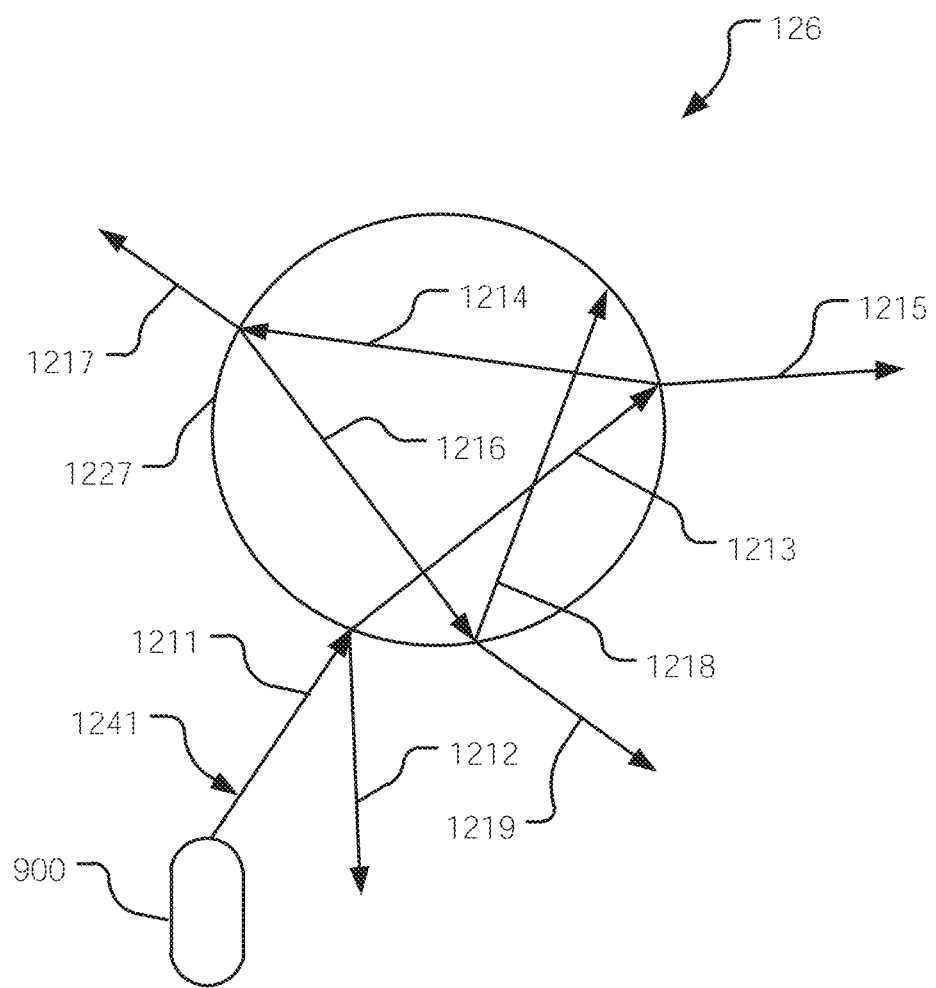
FIG. 12C may depict a diagram of an optical chain reaction from electromagnetic (EM) radiation interacting with at least one bubble.
Figure 12D:
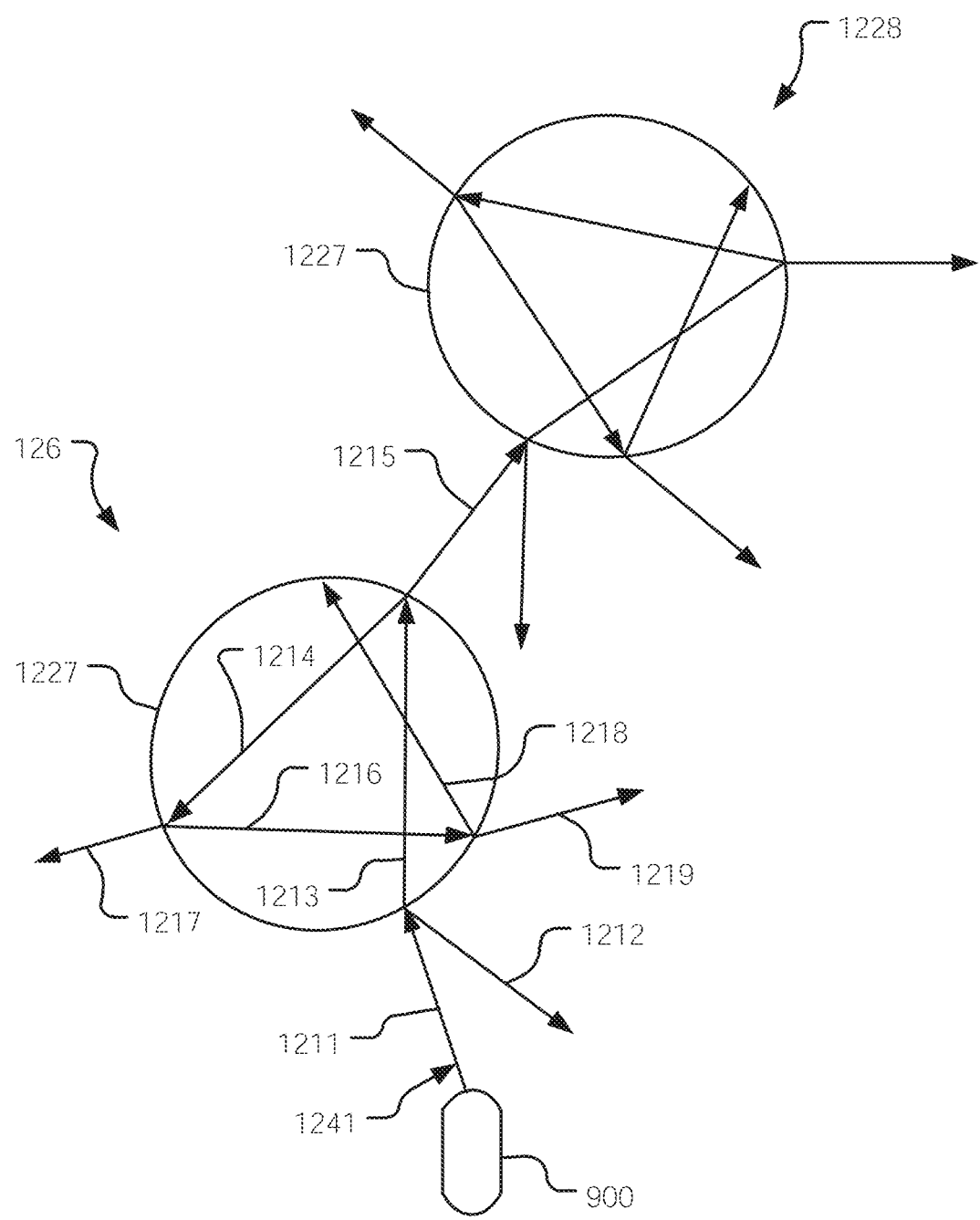
FIG. 12D may depict a diagram of the optical chain reaction from EM radiation interacting with a plurality of bubbles.

FIG. 12C may depict a diagram of a phenomenon of an optical chain reaction (OCR) from emitted EM radiation 1241 interacting with at least one bubble 126 from plurality of bubbles 125. FIG. 12D may depict a diagram of the OCR from EM radiation 1241 interacting with plurality of bubbles 125, such as, but not limited to, at least one bubble 126 and another bubble 1228. That is, FIG. 12D may depict how the OCR from one bubble 126 may continue to occur in other bubbles 1228 derived from EM from bubble 126. Bubble 1228 may also be receiving emitted EM 1241 from at least one EM emitter 900 in addition to receiving EM from bubble 126. In some embodiments, OCR interactions may require liquid 101, at least one bubble 126 in liquid 101, and emitted EM radiation 1241 in liquid 101.

In some embodiments, device 1200 and/or the method(s) may comprise an OCR interaction in each bubble 126/1228 that may receive EM radiation (such as emitted EM radiation 1241). A product from the one or more OCR interactions may provide enhanced EM radiation coverage of an exterior of the at least the portion of the article submerged in liquid 101, as compared to if there were no bubbles 125 present in liquid 101. In some embodiments, each OCR may be formed by EM radiation passing through liquid 101 and interacting with at least some of the bubbles from plurality of bubbles 125. EM passing out of such bubbles may further interact with more bubbles. This EM radiation may originally derive from at least one EM emitter 900 (e.g., emitting EM radiation 1241). In some embodiments, such emitted EM 1241 may comprise at least a first beam 1211. In some embodiments, upon first beam 1211 hitting a surface 1227 of at least one bubble 126 from plurality of bubbles 125, first beam 1211 may reflect into a first reflected beam 1212 and may refract into a first refracted beam 1213. In some embodiments, first refracted beam 1213 may continue within at least one bubble 126 until hitting surface 1227 at a different location. In some embodiments, at this different location first refracted beam 1213 may reflect into a second reflected beam 1214 and may refract into a second refracted beam 1215. In some embodiments, second reflected beam 1214 may continue within at least one bubble 126 until hitting surface 1227 at another different location. In some embodiments, second reflected beam 1214 at this another different location may reflect and refract again and continue on this iterative fashion $n^{th}$ times (stated as "n-th" in the claims) producing $n^{th}$ reflected beams 1216 moving interiorly of the at least one bubble 126 and $n^{th}$ refracted beams 1217 moving exteriorly of at least one bubble 126. In some embodiments, first reflected beam 1212, second refracted beam 1215, and/or $n^{th}$ refracted beams 1217 may interact with another bubble 1228 forming another OCR at bubble 1228, and/or may interact with the exterior of the at least the portion of the article, and/or may interact with interior wall surface 203.

In some embodiments, OCR may attenuate, magnify, and/or amplify EM radiation received at the exterior of the at least the portion of the article as compared to EM radiation received at the exterior of the at least the portion of the article if no bubbles 125 were present in liquid 101. In some embodiments, OCR may be occurring in and on more than one bubble 126/1228 resulting in an additive combined attenuation, magnification, and/or amplification of the EM radiation received at the exterior of the at least the portion of the article. For example, and without limiting the scope of the present invention, in embodiments where the emitted EM radiation 1241 may be in the visible light spectrum, this OCR phenomena may be seen visually as the liquid 101 and bubbles 125 appearing to glow, which may manifest in enhanced EM radiation coverage of the exterior of the at least the portion of the article submerged in the liquid, as compared to if there were no bubbles 125 present in liquid 101.

In some embodiments, at each location of interaction of the EM radiation with surface 1227, the EM radiation passing through surface 1227 that may result in the refracted beams, may also result in lensing of those refracted beams. For example, and without limiting the scope of the present invention, EM interactions (e.g. reflections) occurring exteriorly of a given bubble 126/1228 may be convex lensing; whereas, EM radiation interactions (e.g. reflections) occurring interiorly of the given bubble 126/1228 may be concave lensing. For example, EM radiation hitting surface 1227 of the given bubble 126/1228, a portion of such EM radiation may then continue moving interiorly of the given bubble 126/1228 and then exit the given bubble 126/1228 may result in magnification.

Note, OCR occurring on and/or in the one or more bubbles 126/1228 may continue to occur while at least one EM emitter 900 may be emitting EM 1241 into liquid 101 and while plurality of bubbles 125 may be present. Also, note an energy level associated with the EM in a single OCR phenomena may dissipate over time due to EM interactions (reflections and refractions) along surface 1227 and because of EM particle (photon) collisions both interiorly and/or exteriorly of any given bubble 126/1228, and/or article EM absorption; however, when there may be at least one EM emitter 900 emitting EM 1241, and plurality of bubbles 125 may be present, the additive (cumulative) of many OCR interactions may be the enhanced EM radiation coverage of the exterior of the at least the portion of the article submerged in liquid 101, as compared to if there were no bubbles 125 present in liquid 101. Additionally, because bubbles 125 are moving in liquid 101, enhanced light therapy provided by OCR tends to provide for very uniform exposure to submerged surfaces of the article being treated. For example, and without limiting the scope of the present invention, this may provide for increased efficacy, greater efficiency, and/or less of a duration of treatment in the case of light therapy as compared to light therapy not using bubbles 125.

In some embodiments, a method for treating the article using bubbles 125 within liquid 101 may comprise the steps:

Step (a): (removably) filling interior volume 220 of vessel 200 with liquid 101 to or below the liquid fill level of interior volume 220;

Step (b): removably receiving at least a portion of the article within interior volume 220 such that the at least the portion of the article may be removably submerged within liquid 101;

Step (c): releasing plurality of bubbles 125 into liquid 101;

Step (d): exposing the at least the portion of the article to liquid 101; and

Step (e): exposing the at least the portion of the article to plurality of bubbles 125.

In some embodiments, Step (a), Step (b), and Step (c) in any order may precede Step (d) and Step (e). (Of course, step (c) occurring before step (a) will first result in releasing bubbles 125 into atmospheric air in interior volume 220, until liquid 101 may be added in step (a).) In some embodiments, the exposing of the at least the portion of the article to liquid 101 and plurality of bubbles 125 may treat the article and/or may treat the portion of the article exposed, particularly the surface submerged and exposed.

In some embodiments, this method may further comprise the step of emitting EM radiation 1241 into liquid 101 and irradiating at least some of the exterior of the at least the portion of the article. In some embodiments, this emitted EM radiation 1241 may be from at least one EM emitter 900. In some embodiments, at least some of the bubbles 126/1228 from plurality of bubbles 125 may be disposed between at least one EM emitter 900 emitting emitted EM radiation 1241 and the at least the portion of the article. This may result in enhanced light therapy from OCR.

In some embodiments, a method for treating the article using emitted EM radiation 1241 within liquid 101, may comprise the steps of (note this method may be different from the preceding method disclosed above):

Step (a): (removably) filling interior volume 220 of vessel 200 with liquid 101 to or below the liquid fill level of interior volume 220;

Step (b): removably receiving at least a portion of the article within interior volume 220 such that the at least the portion of the article may be removably submerged within liquid 101;

Step (c): emitting EM radiation 1241 into liquid 101 and irradiating at least some of the exterior of the at least the portion of the article; wherein the emitted EM radiation 1241 may be from at least one EM emitter 900;

Step (d): exposing the at least the portion of the article to liquid 101; and

Step (e): exposing the at least some of the exterior of the at least the portion of the article to the emitted EM radiation 1241.

In some embodiments, Step (a), Step (b), and Step (c) in any order precede Step (d) and Step (e). In some embodiments, the exposing of the at least the portion of the article to liquid 101 and the emitted EM radiation 1241 may treat the article.

In some embodiments, this method may further comprise the step of releasing plurality of bubbles 125 into liquid 101. In some embodiments, at least some of bubbles 125 (e.g. 126 and/or 1228) from plurality of bubbles 125 may be disposed between at least one EM emitter 900 and the at least the portion of the article. This may result in enhanced light therapy from OCR.

In some embodiments, a method for treating the article using bubbles 125 and emitted EM radiation 1241 within liquid 101, may comprise the steps of:

Step (a): (removably) filling interior volume 220 of vessel 200 with liquid 101 to or below liquid 101 fill level of interior volume 220;

Step (b): removably receiving at least a portion of the article within interior volume 220 such that the at least the portion of the article may be removably submerged within liquid 101;

Step (c): releasing plurality of bubbles 125 into liquid 101;

Step (d): emitting EM radiation 1241 (e.g., from at least one EM emitter 900) into liquid 101 and irradiating at least some of the exterior of the at least the portion of the article;

Step (e): exposing the at least the portion of the article to liquid 101; and Step (f): exposing the at least the portion of the article to at least some of the bubbles (e.g. 126 and/or 1228) from plurality of bubbles 125; and Step (g): exposing the at least some of the exterior of the at least the portion of the article to at least some of the emitted EM radiation 1241.

In some embodiments, Step (a), Step (b), Step (c), Step (d) in any order precede Step (e), Step (f), and Step (g). (Of course, step (c) occurring before step (a) will first result in releasing bubbles 125 into atmospheric air in interior volume 220, until liquid 101 may be added in step (a).) In some embodiments, the exposing of the at least the portion of the article to liquid 101, plurality of bubbles 125, and to the emitted EM radiation 1241 may treat the article.

In some embodiments, this method (as well as other methods that may comprise the step of emitting EM radiation 1241 into liquid 101 and irradiating the at least some of the exterior of the at least the portion of the article) may further comprise the step of causing at least a portion of the emitted EM radiation 1241 to interact with at least some of bubbles 125 (e.g. 126 and/or 1228) from plurality of bubbles 125 in one or more OCR interactions as depicted in FIG. 12C and FIG. 12D.

In some embodiments, face soaking device 100 may comprise a liquid jet means. The liquid jet means may be configured to direct a stream of liquid 101 at a portion of the face immersed within liquid 101. In some embodiments, the liquid jet means may be at least one jet 1260 (see e.g., FIG. 12A). The liquid jet means may comprise at least one intake vent, at least one liquid circulation pump, and at least one exit jet. The at least one liquid circulation pump may be in physical contact with the at least one vent via tubing or a hose. The at least one liquid circulation pump may be in physical contact with the at least one exit jet via a different tubing or a different hose. The at least one liquid circulation pump may take in liquid from the at least one intake vent and then expel the liquid through the at least one exit jet. The at least one vent may be located on at least one interior wall surface 203 or the interior surface of at least one base 215 (bottom interior surface 217). The at least one exit jet may be located on at least one interior wall surface 203 or the interior surface of at least one base 215 (bottom interior surface 217). The at least one exit jet may comprise an adjustable nozzle. The adjustable nozzle may be movable to change a direction of the expelled liquid from the at least one exit jet. The liquid circulation pump may be located externally of internal volume 220.

In some embodiments, the face soaking device (e.g. 100, 1200, 1300, 1351, and 1370) may comprise the at least one vibrations means. A purpose of the at least one vibrations means may be to impart a vibration massage upon user 9000. Vibration massage may provide benefits, such as leaving user 9000 soothed and relaxed.

In some embodiments, the at least one vibration means may be a motor configured to vibrate. In some embodiments, this motor may be housed within mechanical compartment 251. In some embodiments, this motor may be in electrical communication with controller 1100. In some embodiments, this motor may be controlled by controller 1110. The at least one vibration means may be removably attached to a component of the face soaking devices (e.g. 100, 1200, 1300, 1351, and 1370), such that vibrations of the at least one vibration means may be imparted to the component. For example, and without limiting the scope of the present invention, the component may be from head rest subassembly 500, 600, 650, 2100, 2300, 2400, 2500, 2540, 2550, and 2560; vessel 200, 1360, and 1372; and heater 700, 2700, 2705, 2710, 2720, and 2725. In some exemplary embodiments, the component which the at least one vibration means may be removably attached to may be support member 501 or comfortable exterior surface 502 because the forehead of user 9000 may be in removable contact with support member 501 or comfortable exterior surface 502. In such embodiments, the at least one vibration means may be within internal volume 220 (and/or internal volume 1320). In some embodiments, the at least one vibration means may be located externally to internal volume 220 (and/or internal volume 1320), for example, in embodiments where at least one vibration means may be removably attached to vessel 200, vessel 1360, and/or vessel 1372.

In some embodiments, the at least one vibration means may comprise power source 1115. In some embodiments, the at least one vibration means may receive electrical power from power source 1115. Power source 1115 may be a battery, and in some embodiments such a battery may be rechargeable. In some embodiments, power source 1115 may be wired, such as to electrical cord 1116 connected to a standard electrical wall outlet. Such an electrical cord 1116 may pass through at least one port 210 into mechanical compartment 251 and may be sealed by an electrical cord gasket to prevent or minimize moisture ingress into mechanical compartment 251.

Note it is contemplated that components, including subassemblies, of one face soaking device embodiment may be combined with different components of other face soaking device embodiments to arrive at yet other face soaking device embodiments—all within the scope of the present invention. For example, and without limiting the scope of the present invention, various embodiments of breathing apparatus (such as, but not limited to 400, 2000, 2050, and 2100—as depicted in the FIG. 4 series of figures, FIG. 20 series of figures, FIG. 21 series of figures, FIG. 22 series of figures, and FIG. 23 series of figures) may be used with various embodiments of vessels, including vessel 200, 1360, and 1372. Likewise, embodiments which may employ breathing apparatus 400, may instead utilize independent breathing apparatus 2000 or 2050 as depicted in the FIG. 20 series of figures. For example, and without limiting the scope of the present invention, breathing apparatus 400 as depicted in the FIG. 4 series of figures may be used with various embodiments of vessels, including vessel 200 and vessel 1372. For example, and without limiting the scope of the present invention, various embodiments of head rest subassemblies (500, 600, 650, 2100, 2300, 2400, 2500, 2540, 2550, and 2560—as depicted in the FIG. 5 series of figures, FIG. 6 series of figures, FIG. 21 series of figures, FIG. 23 series of figures, FIG. 24 series of figures, FIG. 25 series of figures, and FIG. 26 series of figures) may be used with various embodiments of vessels, including vessel 200, 1360, and 1372. For example, and without limiting the scope of the present invention, embodiments which may employ head rest subassembly 500, may instead utilize head rest subassembly 600, 650, or 2300. For example, and without limiting the scope of the present invention, various embodiments of the gas diffusers (e.g., gas diffuser 800) may be used with various embodiments of vessels, including vessel 200, 1360, and 1372. For example, and without limiting the scope of the present invention, various embodiments of at least one EM emitter 900 may be used with various embodiments of vessels, including vessel 200, 1360, and 1372. For example, and without limiting the scope of the present invention, various embodiments of the at least one vibration means may be used with various embodiments of vessels, including vessel 200, 1360, and 1372.

In some embodiments, the face soaking device (e.g., 100, 1200, 1300, 1351, and 1370) may comprise: (1) the vessel with the vessel-neck-gasket accommodator and the vessel neck gasket; (2) the vessel and the head rest subassembly; (3) the vessel and the breathing apparatus; (4) the vessel with the vessel-neck-gasket accommodator, the vessel neck gasket, and the head rest subassembly; (5) the vessel with the vessel-neck-gasket accommodator, the vessel neck gasket, and the breathing apparatus; (6) the vessel, the head rest subassembly, and the breathing apparatus; and/or (7) the vessel with the vessel-neck-gasket accommodator, the vessel neck gasket, the breathing apparatus, and the head rest subassembly. The vessel may be 200, 1360, 1372, and the like. The vessel neck gasket may be 340 or the like. The head rest subassembly may be 500, 600, 650, 2300, 2400, 2500, 2540, 2550, 2560, or the like. The breathing apparatus may be 400, 2000, 2050, 2100 or the like.

Each face soaking device embodiment (e.g., 100, 1200, 1300, 1351, and 1370) may also comprise one or more additional structures, components, and/or elements. For example, and without limiting the scope of the present invention, such additional structures, components and/or elements may be selected from one or more of the following: aerator(s), bubble source(s), gas diffuser(s), gas source(s), air pump(s), compressor(s), heater(s), thermostat(s), electromagnetic (EM) radiation sources/emitters, light(s), vibrator(s), jet(s), control(s), means for receiving user input(s), mechanical compartment(s), drain(s), plug(s), and/or the like. Various embodiments of the vessel (e.g., 200, 1360, and 1372) may be used with various combinations of such one or more additional structures, components and/or elements.

The various embodiments of a given face soaking device (e.g., 100, 1200, 1300, 1351, and 1370) may be a standalone device. The various embodiments of a given face soaking device (e.g., 100, 1200, 1300, 1351, and 1370) may be a portable (mobile) device. The various embodiments of a given face soaking device (e.g., 100, 1200, 1300, 1351, and 1370) may be integrated (built-in) into other structures. Such other structures, may comprise: counters, countertops, tables, tabletops, work stations, desks, chairs, furniture, pedestals, bathtubs, hot tubs, shower stalls, wash basins, mounted on wheels, combinations thereof, and the like. Various embodiments of face soaking devices may be used in: medical exam rooms, medical treatment rooms, salons, beauty salons, hair salons, nail salons, facial salons, home use, office use, bathrooms, steam rooms, saunas, and the like.

A face soaking device and a flexible detachable vessel cover have been described in various embodiments, including exemplary embodiments. Method(s) of using face soaking devices and article soaking devices have been described in various embodiments, including exemplary embodiments. The foregoing description of the various exemplary embodiments of the present invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A vessel having a top opening and capable of holding a liquid, the vessel having a gasket-accommodator; wherein the vessel comprises:
    a flexible sheet, the flexible sheet having a bottom portion functioning as a gasket to cover at least some top portion of the gasket-accommodator of the vessel;
    a breathing apparatus, with a mouth piece, configured to permit a user to breathe while a face of the user is submerged within the liquid in the vessel; wherein the breathing apparatus is attached to two opposing side walls of the vessel with the mouth piece disposed in between;
    wherein the bottom portion of the flexible sheet and the at least some top portion of the gasket-accommodator of the vessel are arranged to mate tightly with one another to form a primary water tight seal;
    wherein a different portion of the flexible sheet, disposed away from the bottom portion, is configured to removably receive a front portion of a neck of the user to form a secondary water tight seal between this different portion of the flexible sheet and the front portion of the neck of the user; and
    wherein the flexible sheet and the vessel, in use, do not directly support a weight of the neck of the user.

2. The vessel according to claim 1, wherein a top of the flexible sheet is higher than a rim of the vessel the vessel.

3. A soaking device comprising:
    a vessel having a top opening and capable of holding a liquid in an interior space of the vessel;
    a means of supplying a stream of gas to at least one point near a bottom of the interior space, such that the stream of gas results in released bubbles when the vessel contains a sufficient quantity of the liquid; and
    at least one electromagnetic emitter for emitting electromagnetic radiation into the interior space of the vessel, whereby the electromagnetic radiation emitted into the interior space of the vessel is emitted into and through the liquid to interact with at least some of the bubbles in the liquid held in the vessel;
    a breathing apparatus configured to permit a user to breathe while a face of the user is submerged within the liquid in the vessel; wherein the breathing apparatus is attached to a side wall of the vessel, wherein the side wall is substantially vertical; and
    a head rest located inside the interior space that extends from a region that is closer to the bottom of the interior space than to the top opening of the vessel, wherein a portion of the head rest is adapted to removably support a forehead of the user, wherein the portion of the head rest is movable.

4. The soaking device according to claim 3, wherein the at least one electromagnetic emitter is selected from one or more of a light-emitting diode, an incandescent light source, and another source of therapeutic electromagnetic radiation.

5. A face soaking device, comprising:

a vessel with an internal volume sized to fit a whole face of a user or a portion thereof; wherein the internal volume is sized to hold a liquid in a sufficient volume to submerge the whole face or the portion thereof; wherein the vessel comprises at least one wall and at least one base; wherein the at least one wall and the at least one base are in physical contact with each other; wherein the at least one wall and the least one base together substantially bound the internal volume with a top opening to the internal volume disposed opposite from the at least one base; wherein the at least one wall comprises a neck-gasket-accommodator; wherein the neck-gasket-accommodator accommodates a vessel neck gasket;

the vessel neck gasket, wherein the vessel neck gasket is joined to the vessel, forming a primary water tight seal at the neck-gasket-accommodator; wherein when the vessel neck gasket receives a first portion of a neck region of the user when the whole face or the portion thereof is submerged a secondary water tight seal is formed between the first portion of the neck region and the vessel neck gasket; wherein the vessel neck gasket is adapted to be in removable contact with the first portion of the neck region; and a breathing apparatus, wherein the breathing apparatus is physically attached to the vessel; wherein the breathing apparatus comprises a mouth piece, at least one vessel-tube-hose-connector, and at least one hose or at least one tubing, wherein the at least one hose or the at least one tubing connects to the mouth piece and connects to the at least one vessel-tube-hose-connector providing a sealed pathway for respiratory gas movement; wherein the mouth piece is configured to be holdable by a mouth of the user; wherein the at least one vessel-tube-hose-connector attaches to the vessel providing a physical link between the breathing apparatus and the vessel; wherein the user is able to breathe using the breathing apparatus when the mouth of the user is holding the mouth piece; wherein at least a majority of the at least one hose or at least a majority of the at least one tubing resides from within the internal volume to above a rim of the vessel via swivel rotational communication between the at least one vessel-tube-hose-connector and the at least one hose or the at least one tubing;

a head rest subassembly with at least a majority located inside the internal volume, wherein the head rest subassembly comprises a support member that a portion of the is adapted to removably support a forehead of the user, which during use prevents the neck-gasket-accommodator from digging into a neck of the user;

wherein when the vessel is filled with the liquid to a level at or less than a maximum liquid level of the vessel, the user soaks the whole face or the portion thereof for a time period, such that skin being soaked in the liquid for the time period receives a health, an aesthetic, and/or a soothing benefit.

6. The face soaking device according to claim 5, wherein the neck-gasket-accommodator comprises a contour, wherein the contour is located below the rim of the vessel; wherein the rim substantially circumscribes the top opening; wherein the contour begins where a surface of the contour first runs below the rim and the contour continues until ending where the surface of the contour runs back up to the rim; wherein where the contour begins and where the contour ends is separated by a horizontal width; wherein the contour has a maximum vertical length from a height of the rim to a lowest point on the contour.

7. The face soaking device according to claim 6, wherein the horizontal width is sized to be greater than or equal to a diameter of the neck of the user.

8. The face soaking device according to claim 6, wherein the maximum vertical length is sized to be greater than or equal to half of a diameter of the neck of the user.

9. The face soaking device according to claim 6, wherein a shape of the contour as viewed from a front of the face soaking device is selected from the group consisting of: one third to three thirds of a circle, one third to three thirds of an oval, one third to three thirds of an ellipse, a "U" shape, a horseshoe shape, a regular polygon, an irregular polygon, and a semi-polygon.

10. The face soaking device according to claim 5, wherein the vessel neck gasket comprises a top edge accommodative to receiving the first portion of the neck region of the user.

11. The face soaking device according to claim 5, wherein the vessel neck gasket is a flexible member; wherein the vessel neck gasket is planar with an internal surface and an external surface disposed opposite of the internal surface; wherein the external surface or the internal surface is adapted to form the secondary water tight seal with the first portion of the neck region.

12. The face soaking device according to claim 5, wherein the vessel neck gasket is constructed of a material of construction that comprises one or more elastomers selected from the group consisting of: silicone, rubber, neoprene, nitrile, vinyl, polyethylene, and polypropylene.

13. The face soaking device according to claim 5, wherein the vessel neck gasket comprises a mating edge that is complimentary to a shape and surfaces of a contour of the neck-gasket-accommodator.

14. The face soaking device according to claim 13, wherein the mating edge of the vessel neck gasket is attached in one of three arrangements:

(a) to the contour of the neck-gasket-accommodator by a vessel neck gasket attachment means; or (b) to an exterior wall surface of the at least one wall at a first fixed distance from the contour, wherein this attachment is by the vessel neck gasket attachment means; or (c) to an interior wall surface of the at least one wall at a second fixed distance from the contour, wherein this attachment is by the vessel neck gasket attachment means.

15. The face soaking device according to claim 14, wherein the vessel neck gasket attachment means is selected from one or more of: heat welding, ultrasonic welding, solvent bonding, chemical adhesives, sealants, and mechanical fasteners.

16. The face soaking device according to claim 14, wherein the vessel neck gasket attachment means from attachment arrangement (a) comprises at least one mechanical fastener that is a clamp; wherein the vessel neck gasket is attached to the neck-gasket-accommodator by use of the clamp, wherein such an attachment forms the primary water tight seal; wherein the clamp is shaped to complimentary fit by a friction fit to the neck-gasket-accommodator, with a portion of the vessel neck gasket sandwiched between the clamp and the contour of the neck-gasket-accommodator, forming the primary water tight seal.

17. The face soaking device according to claim 16, wherein the portion of the vessel neck gasket comprises the mating edge.

18. The face soaking device according to claim 16, wherein the clamp is rigid.

19. The face soaking device according to claim 5, wherein the vessel neck gasket is removably joined to the vessel.

20. The face soaking device according to claim 5, wherein the neck-gasket-accommodator and the vessel neck gasket are integral with each other and integral with the at least one wall; wherein the vessel neck gasket is a region of flexible side wall with a thin wall thickness that is less than a surrounding wall thickness of the at least one wall that is semi-rigid to rigid; wherein the neck-gasket-accommodator is a transitional region around some portions of the region of flexible side wall where the thin wall thickness transitions into the surrounding wall thickness.

21. The face soaking device according to claim 5, wherein at least some portion of the head rest subassembly is attached to the vessel; wherein the support member is configured to support the forehead of the user when the whole face or portion thereof of the user is removably located in the internal volume.

22. The face soaking device according to claim 5, wherein the head rest subassembly comprises a height adjust means; wherein the height adjust means varies a height of the support member within the internal volume of the vessel, with respect to an axis running vertically from the at least one base of the vessel to the top opening of the vessel; and wherein the height adjust means is in physical contact with the support member.

23. The face soaking device according to claim 5, wherein the head rest subassembly comprises a forwards-backwards adjust means; wherein the forwards-backwards adjust means varies a location of the support member along a longitude of the face soaking device running from a front to a back of the face soaking device; and wherein the forwards-backwards adjust means is in physical contact with the vessel.

24. The face soaking device according to claim 5, wherein the face soaking device further comprises a heater subassembly; wherein at least a portion of the heater subassembly is attached to the vessel; wherein the heater subassembly comprises a heating element that heats at least a portion of the liquid within the internal volume.

25. The face soaking device according to claim 5, wherein the face soaking device further comprises an aerator; wherein the aerator comprises a gas diffuser and a gas source in physical communication with the gas diffuser; wherein the gas diffuser is attached to the vessel; wherein the gas source provides gas to the gas diffuser; wherein the gas diffuser releases at least some of the gas received through a porous structure of the gas diffuser into the internal volume.

26. The face soaking device according to claim 25, wherein the gas source is selected from one or more of: a cylinder containing a compressed gas, an air pump for pumping atmospheric air, or a compressor for compressing the gas.

27. The face soaking device according to claim 5, wherein the face soaking device further comprises at least one electromagnetic emitter; wherein the at least one electromagnetic emitter emits electromagnetic radiation across a predetermined range of wavelengths; wherein at least some portion of the at least one electromagnetic emitter is attached to the vessel; wherein at least some of emitted electromagnetic radiation is emitted into the internal volume.

28. The face soaking device according to claim 27, wherein the at least one electromagnetic emitter is at least one light emitting diode.

* * * * *